United States Patent
Andresen et al.

(10) Patent No.: US 11,685,761 B2
(45) Date of Patent: Jun. 27, 2023

(54) CYCLIC DI-NUCLEOTIDE COMPOUNDS AS STING AGONISTS

(71) Applicants: Merck Sharp & Dohme Corp., Rahway, NJ (US); Brian M. Andresen, Sharon, MA (US); Frank Bennett, Cranford, NJ (US); Wonsuk Chang, Princeton, NJ (US); Matthew Lloyd Childers, Medfield, MA (US); Jared N. Cumming, Winchester, MA (US); Jongwon Lim, Lexington, MA (US); Min Lu, Brookline, MA (US); Benjamin Wesley Trotter, Medfield, MA (US); Wen-Lian Wu, Green Brook, NJ (US)

(72) Inventors: Brian M. Andresen, Sharon, MA (US); Frank Bennett, Cranford, NJ (US); Wonsuk Chang, Princeton, NJ (US); Matthew Lloyd Childers, Medfield, MA (US); Jared N. Cumming, Winchester, MA (US); Jongwon Lim, Lexington, MA (US); Min Lu, Brookline, MA (US); Benjamin Wesley Trotter, Medfield, MA (US); Wen-Lian Wu, Green Brook, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 254 days.

(21) Appl. No.: 16/771,814

(22) PCT Filed: Dec. 17, 2018

(86) PCT No.: PCT/US2018/065902
§ 371 (c)(1),
(2) Date: Jun. 11, 2020

(87) PCT Pub. No.: WO2019/125974
PCT Pub. Date: Jun. 27, 2019

(65) Prior Publication Data
US 2021/0206796 A1 Jul. 8, 2021

Related U.S. Application Data

(60) Provisional application No. 62/608,154, filed on Dec. 20, 2017.

(51) Int. Cl.
*C07H 21/00* (2006.01)
*A61P 37/04* (2006.01)
(Continued)

(52) U.S. Cl.
CPC .......... *C07H 21/00* (2013.01); *A61K 31/7084* (2013.01); *A61P 37/04* (2018.01);
(Continued)

(58) Field of Classification Search
CPC .................................................. A61K 31/7084
See application file for complete search history.

(56) References Cited

U.S. PATENT DOCUMENTS

| 7,488,802 B2 | 2/2009 | Collins et al. |
| 7,521,051 B2 | 4/2009 | Collins et al. |

(Continued)

FOREIGN PATENT DOCUMENTS

| EP | 3135290 A1 | 1/2018 |
| WO | 2001002369 A2 | 1/2001 |

(Continued)

OTHER PUBLICATIONS

U.S. Appl. No. 16/904,888, filed Jun. 2020, Altman, Michael D.*
Ablasser et al., Cell intrinsic immunity spreads to bystander cells via the intercellular transfer of cGAMP, Nature, Nov. 28, 2013, 530-546, 503.
Ablasser et al., cGAS produces a 2'-5'-linked cyclic dinucleotide second messenger that activates STING, Nature, Jun. 20, 2013, 380-385, 498.
Ausmees et al., Genetic Data Indicate that Proteins Containing the GGDEF Domain Possess Diguanylate Cyclase Activity, FEMS Microbiology, 2001, 163-167, Letters 204.
Berge, S.M., et al., "Pharmaceutical Salts", J. Pharm. Sci, 1977, pp. 1-19, vol. 66, No. 1.
(Continued)

*Primary Examiner* — Eric Olson
(74) *Attorney, Agent, or Firm* — Julie M. Lake; Catherine D. Fitch

(57) ABSTRACT

A class of polycyclic compounds of general formula (I), wherein Base$^1$, Base$^2$, Y, Z$^a$, X$^a$, X$^{a1}$, X$^b$, X$^{b1}$, X$^c$, X$^{c1}$, X$^d$, X$^{d1}$, R$^1$, R$^{1a}$, R$^2$, R$^{2a}$, R$^3$, R$^4$, R$^{4a}$, R$^5$, R$^6$, R$^{6a}$, R$^7$, R$^{7a}$, R$^8$, R$^{8a}$, and R$^9$ are defined herein, that may be useful as inductors of type I interferon production, specifically as STING active agents, are provided. Also provided are processes for the synthesis and use of compounds.

(I)

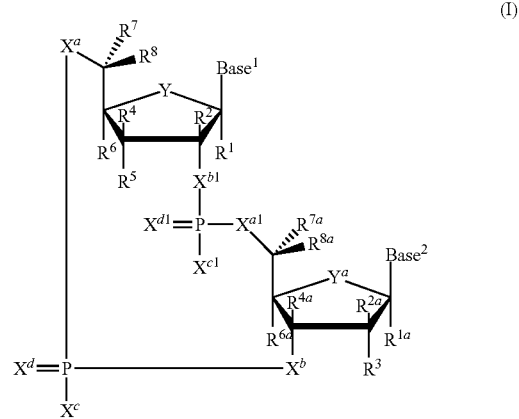

20 Claims, No Drawings
Specification includes a Sequence Listing.

(51) Int. Cl.
  *C07H 21/02* (2006.01)
  *A61K 31/7084* (2006.01)
  *C07H 21/04* (2006.01)
(52) U.S. Cl.
  CPC ............. *C07H 21/02* (2013.01); *C07H 21/04* (2013.01); *C07B 2200/07* (2013.01)

(56) References Cited

U.S. PATENT DOCUMENTS

| | | | |
|---|---|---|---|
| 7,595,048 | B2 | 9/2009 | Honjo et al. |
| 8,008,449 | B2 | 8/2011 | Korman et al. |
| 8,168,757 | B2 | 5/2012 | Finnefroch et al. |
| 8,354,509 | B2 | 1/2013 | Carven et al. |
| 8,383,796 | B2 | 2/2013 | Korman et al. |
| 9,724,408 | B2 | 8/2017 | Dubensky, Jr. et al. |
| 10,106,574 | B2 * | 10/2018 | Altman .................. A61P 35/00 |
| 10,738,074 | B2 * | 8/2020 | Altman .................. C07H 21/04 |
| 10,759,825 | B2 * | 9/2020 | Altman .................. C07H 19/20 |
| 10,766,919 | B2 * | 9/2020 | Altman .................. C07H 21/02 |
| 2006/0040887 | A1 | 2/2006 | Karaolis |
| 2006/0167241 | A1 | 7/2006 | Hayakawa et al. |
| 2008/0025979 | A1 | 1/2008 | Honjo et al. |
| 2008/0286296 | A1 | 11/2008 | Ebensen et al. |
| 2011/0271358 | A1 | 11/2011 | Freeman et al. |
| 2014/0206640 | A1 | 7/2014 | Girijavallabhan et al. |
| 2014/0329889 | A1 | 11/2014 | Vance et al. |
| 2014/0341976 | A1 | 11/2014 | Dubensky, Jr. et al. |
| 2015/0056224 | A1 | 2/2015 | Dubensky, Jr. et al. |
| 2015/0158886 | A1 | 6/2015 | Jones et al. |
| 2016/0074507 | A1 | 3/2016 | Manel et al. |
| 2016/0287698 | A1 | 10/2016 | Yan et al. |
| 2016/0362441 | A1 | 12/2016 | Vemnejoul et al. |
| 2017/0044206 | A1 | 2/2017 | Altman et al. |
| 2017/0050967 | A1 | 2/2017 | Burai et al. |
| 2017/0158724 | A1 | 6/2017 | Adams et al. |
| 2020/0062798 | A1 * | 2/2020 | Wu .......... C07H 21/00 |
| 2022/0024964 | A1 * | 1/2022 | Altman .................. C07H 21/00 |
| 2022/0033431 | A1 * | 2/2022 | Altman .................. C07H 19/14 |
| 2022/0033435 | A1 * | 2/2022 | Altman .................. A61P 35/00 |
| 2022/0175811 | A1 * | 6/2022 | Brunell .................. A61K 47/20 |

FOREIGN PATENT DOCUMENTS

| | | | |
|---|---|---|---|
| WO | 2001002369 | A3 | 1/2001 |
| WO | 2002010192 | A2 | 2/2002 |
| WO | 2002057245 | A1 | 7/2002 |
| WO | 2002068470 | A2 | 9/2002 |
| WO | 2004004771 | A1 | 1/2004 |
| WO | 2004056875 | A1 | 7/2004 |
| WO | 2004072286 | A1 | 8/2004 |
| WO | 2010027827 | A2 | 3/2010 |
| WO | 2010047774 | A2 | 4/2010 |
| WO | 2010077634 | A1 | 7/2010 |
| WO | 2011066342 | A2 | 6/2011 |
| WO | 2013019906 | A1 | 2/2013 |
| WO | 2013185052 | A1 | 12/2013 |
| WO | 2014093936 | A1 | 6/2014 |
| WO | 2014099824 | A1 | 6/2014 |
| WO | 2014099941 | A1 | 6/2014 |
| WO | 2014179335 | A1 | 11/2014 |
| WO | 2014179760 | A1 | 11/2014 |
| WO | 2014189805 | A1 | 11/2014 |
| WO | 2014189806 | A1 | 11/2014 |
| WO | 2015017652 | A1 | 2/2015 |
| WO | 2015074145 | A1 | 5/2015 |
| WO | 2015077354 | A1 | 5/2015 |
| WO | 2015148746 | A1 | 10/2015 |
| WO | 2015161137 | A1 | 10/2015 |
| WO | 2015185565 | A1 | 12/2015 |
| WO | 2015189117 | A1 | 12/2015 |
| WO | 2016096174 | A1 | 6/2016 |
| WO | 2016096577 | A1 | 6/2016 |
| WO | 2016100261 | A2 | 6/2016 |
| WO | 2016120305 | A1 | 8/2016 |
| WO | 2016120605 | A1 | 8/2016 |
| WO | 2016145102 | A1 | 9/2016 |
| WO | 2017011522 | A1 | 1/2017 |
| WO | 2017011622 | A1 | 1/2017 |
| WO | 2017011920 | A1 | 1/2017 |
| WO | 2017027645 | A1 | 2/2017 |
| WO | 2017027646 | A1 | 2/2017 |
| WO | 2017075477 | A1 | 5/2017 |
| WO | 2017093933 | A1 | 6/2017 |
| WO | 2017100305 | A2 | 6/2017 |
| WO | 2017123657 | A1 | 7/2017 |
| WO | 2017123669 | A1 | 7/2017 |
| WO | 2017161349 | A1 | 9/2017 |
| WO | 2017175147 | A1 | 10/2017 |
| WO | 2017175156 | A1 | 10/2017 |
| WO | 2017186711 | A1 | 11/2017 |
| WO | 2017216726 | A1 | 12/2017 |
| WO | 2018009466 | A1 | 1/2018 |
| WO | 2018100558 | A2 | 6/2018 |
| WO | 2018156625 | A1 | 8/2018 |
| WO | 2018198084 | A1 | 11/2018 |
| WO | 2018208667 | A1 | 11/2018 |
| WO | WO-2019046500 A1 * | 3/2019 | ........... A61K 31/708 |

OTHER PUBLICATIONS

Bhattacharya et al., Total Synthesis of 2'-deoxy-2'-arafluoro-tubericidin, -toyocamycin, -sangivamycin and certain related molecules, J. Chem. Soc., Perkin Trans. 1; Organic and Bio-Organic Chemistry, 1995, 1543-1550, 12.

Boehr et al., Establishing the Principles of Recognition in the Adenine-Binding Region of an Aminoglycoside Antibiotic Kinase [APH(3')-IIIa], Biochemistry, 2005, 12445-12453, 44(37).

Bookser et al., High-Throughput Five Minute Microwave Accelerated Glycosylation Approach to the Synthesis of Nucleoside Libraries, JOC Article, 2007, 173-179, 72.

Bruno et al., N-Substituted 2-aminobiphenylpalladium Methanesulfonate Precatalysts and Their Use in C—C and C—N Cross Couplings, The Journal of Organic Chamistry, 2014, 4161-4166, 79.

Burdette, Dara L., STING and the innate immune response to nucleic acids in the cytosol, Nature Immunology, Jan. 2013, 19-26, 14(1).

Burdette, Dara L., STING is a direct innate immune sensor of cyclic di-GMP, Nature, Oct. 27, 2011, 515-519, 478.

Dande et al., Improving RNA Interference in Mammalian Cells by 4'-Thio-Modified Small Interfering RNA (siRNA) Effect on siRNA Activity and Nuclease Stability When Used in Combination with 2'-0-Alkyl Modifications, Journal of Medicinal Chemistry, 2006, 1624-1634, 49(5).

Diner et al., The Innate Immune DNA Sensor cGAS Produces a Noncanonical Cyclic Dinucleotide that Activates Human STING, 3 Cell Reports, Cell Reports, 2013, 1355-1361, 3.

Downey et al., DMXAA Causes Tumor Site-Specific Vascular Disruption in Murine Non-Small Molecule Lung Cancer, and Like the Endogenous Non-Canonical Cyclic Dinucleotide STING Agonist, 2'3'-cGAMP, Induces M2 Macrophage Repolarization, PLOS ONE, 2014, 1-14, 9-6-e99988.

Dubensky, et al., Rationale, progress and development of vaccines utilizing STING-activating cyclic dinucleotide adjuvants, Therapeutic Advances in Vaccines, 2013, 131-143, 1(4).

Ertem et al., Synthesis of RNA oligomers on heterogeneous templates, Nature, 1996, 238-240, 379-18.

Fagundes et al., Building unique bonds to fight misplaced DNA, Cell Research, 2013, 1065-1066, 2-9.

Fu, Juan, et al., STING agonist formulated cancer vaccines can cure established tumors resistant to PD-1 blockade. Science Translational Medicine, 2015, 1-13, 7.

Gadthula et al., Synthesis and Anti-HIV Activity of β-D-3'-Azido-2',3'-unsaturated Nucleosides and β-D-3'-Azido-3'deoxyribofuranosylnucleosides, Nucleoside, Nucleotides, Nucleic Acids, 2005, 1707-1727, 24.

Gaffney et al., One-Flask Syntheses of c-di-GMP and the [Rp,Rp] and [Rp,Sp] Thiophosphate Analogues, Organic Letters, 2010, 3269-3271, 12-14.

(56) References Cited

OTHER PUBLICATIONS

Gao et al., Cyclic [G(2',5')pA(3',5")p] Is the Metazoan Second Messenger Produced by DNA-Activated Cyclic GMP-AMP Synthase, Cell, 2013, 1094-1107, 153.
Gao et al., Structure-Function Ananlysis of STING Activation by c[G(2',5')pA(3',5')p] and Targeting by Antiviral DMXAA, Cell, 2013, 748-762, 154.
Goerlitzer, et al., 1,3-Dicarbonyl Compounds. XIV: 4-Oxo-4H-[1]benzofuro[3,2-b]pyrans, Archiv der Pharmazie, 1980, 385-398, vol. 313; Issue 5.
Gosselin et al., Systematic Synthesis and Biological Evaluation of α- and β-D-lyxofuranosyl Nucleosides of the Five Naturally Occurring Nucleic Acid Bases, J. Med. Chem, 1987, 982-991, 30.
Gould, Salt Selections for Basic Drugs, Intl. J. Pharmaceutics, 1986, pp. 201-217, vol. 33.
Guanghui Yi et al., Single Nucleotide Polymorphisms of Human STING Can Affect Innate Immune Response to Cyclic Dinucleotides, PLOS ONE, 2013, 1-16, 8-10-e77846.
Heping Shi, et al., Molecular basis for the specific recognition of the metazoan cyclic GMP-AMP by the innate immune adaptor protein STING, PNAS, 2015, 8947-8952, vol. 112/No. 29.
Ikeuchi et al., Practical synthesis of natural plant-growth regulator 2-azahypoxanthine, its derivatives, and biotin-abeled probes, Organic & Biomolecular Chemistry, 2014, 3813, 12(23).
Joshi et al., Selectivity of montmorillonite catalyzed prebiotic reactions of D, L-nucleotides, Orig Life Evol Biosph, 2007, 3-26, 37-3.
Kim et al., A Convenient and Versatile Syntheses of 2' (and 3') amino (and azido)-2'(and 3') deoxyadenosine as Diverse Synthetic Precursors of Cyclic Adenosine Diphosphate Ribose (cADPR), Bull. Korean Chem. Soc., 2004, 243, 25-2.
Kobayashi et al., Bacterial c-di-GMP Affects Hematopoietic Stem/Progenitors and their Niches through STING, Cell Reports, 2015, 71-84, 11.
Kranzusch et al., Structure-Guided Reporgramming of Human cGAS Dinucleotide Linkage Specificity, Cell Inc., Elsevier Inc., 2014, 1011-1021, 158.
Li et al., Cyclic GMP-AMP Synthase is Activated by Double-Stranded DNA-Induced Oligomerization, Immunity, 2013, 1019-1031, 39.
Li et al., Hydrolysis of 2'3'-cGAMP by ENPPI and Design of Nonhydrolyzable Analogs, 10 Nature Chemical Biology 1043 (Dec. 2014); Li et al., Hydrolysis of 2'3'-cGAMP by ENPPI and Design of Nonhydrolyzable Analogs Erratum, Nature Chemical Biology, 2014, 1043, 10.
Li et al., Synthesis of 2'-Deoxy-2'- C-a-methylpurine Nucleosides, Synthesis, 2005, 2865-2870, 2005(17).
Liu et al., Activated STING in a Vascular and Pulmonary Syndrome, The New England Journal of Medicine, 2015, 507, 371-6.
Liu et al., Hepatitis B Virus Polymerase Disrupts K63-Linked Ubiquitination of STING to Block Inate Cytosolic DNA-Sensing Pathways, Journal of Virology, 2015, 2287, 89-4.
Lolicato et al., Cyclic Dinucleotides Bind the C-Linker of HCN4 to Control Channel cGAMP Responsiveness, 10 Nature Chemical Biology 457 (Jun. 2014); Lolicato et al., Cyclic Dinucleotides Bind the C-Linker of HCN4 to Control Channel cGAMP Responsiveness, Nature Chemical Biology, 2014, 457, 10.
Mikhailov et al., Conformational Peculiarities of 5'-C-methylnucleosides, Bioorganicheskaya Khimiya, 1989, 969-975, 15(7).
Minakawa et al., Nucleosides and nucleotides. 116. Convenient syntheses of 3-deazaadenosine, 3-deazaguanosine, and 3-deazainosine via ring closure of 5-ethynyl-1-B-D-ribofuranosylimidazole-4-carboxamide or-carbonitrile. Tetrahedron, 1993, 557-570, 49(3).
Minakawa et al., Nucleosides and Nucleotides. 143. Synthesis of 5-Amino-4-imidazolecarboxamide (AICA) Deoxyribosides from Deoxyinosines and Their Conversion into 3-Deazapurine Derivatives, Chemical & Pharmaceutical Bulletin, 1996, 288-295, 44(2).
O'Neill et al., Sensing the Dark Side of DNA, Sceince, 2013, 763, 339.
Ora et al., Hydrolytic reactions of cyclic bis(3'-5') diadenylic acid (c-di-AMP), J. Phys. Org. Chem, 2013, 218-225, 26.
Panne et al., Cytosolic DNA sensing unraveled, Nature Chemical Biology, 2013, 533, 9.
Patil et al., 4-aza-7,9-dideazaadenosine, a new cytotoxic synthetic C-nucleoside analogue of adenosine, Tetrahedron Letters, 1994, 5339-5342, 35(30).
Pubchem, Substance Record for CID 126584781, Create Date: Apr. 22, 2017 [retrieved on Feb. 13, 2019], 12 pages.
Puech et al., Synthesis of 9-(3-deoxy- and 2,3-dideoxy-3-fluoro-β-D-xylofuranosyl)guanines as potential antiviral agents, Tetrahedron Letters, 1989, 3171-3174, 30-24.
Ramesh et al., A convenient synthesis of 1-(β-D-ribofuranosyl)imidazo[4,5-d]pyridazin-4(5H)-one (2-aza-3-deazainosine) and its 2'-deoxy counterpart by ring closure of imidazole nucleosides, Journal of the Chemical Society, Perkin Transaction 1, 1989, 1769-1774, 10.
Ren et al., Structural Basis for Molecular Discrimination by a 3',3'-cGAMP Sensing Riboswitch, Cell Reports, 2015, 1-12, 11.
Robins et al., Nucleic acid related compounds. 74. Synthesis and biological activity of 2'(and 3')-deoxy-2'(and 3')-methylenenucleoside analogs that function as mechanism-based inhibitors of S-adenosyl-L-homocysteine hydrolase and/or ribonucleotide reductase, Journal of Medicinal Chemistry, 1992, 2283-2293, 35(12).
Robins et al., Nucleic Acid-Related Compounds. 91. Biomimetic Reactions Are in Harmony with Loss of 2'-Substituents as Free Radicals (Not Anions) during Mechanism-Based Inactivation of Ribonucleotide Reductases. Differential Interactions of Azide, Halogen, and Alkylthio, J. Am. Chem. Soc., 1996, pp. 11341-11348, 118(46).
Roembke et al., A cyclic dinucleotide contianing 2-aminopurine is a general fluorescent sensor for c-di-GMP and 3'-3'-cGAMP, Molecular BioSystems, 2014, 1568-1575, 10.
Sawai et al., Preparation and Properties of Oligocytidylates with 2'-5' Internucleotide Linkage, Chem. Pharm. Bull. Jpn, 1985, 361-366, 58.
Sawai et al., Synthesis of 2'-5' Linked Oligouridylates in Awueous Medium using the Pd2+ Ion, Chem. Pharm. Bull, 1981, 2237-2245, 29(8).
Seela et al., Fluorinated Pyrrolo[2,3-d]pyrimidine Nucleosides: 7-Fluoro-7-deazapurine 2'-Deoxyribofuranosides and 2'-Deoxy-2'-fluoroarabinofuranosyl Derivatives, Synthesis, 2006, 2005-2012, (12).
Sheridan, Cormac, Drug Developers Switch Gears to Inhibit STING, Nature Biotechnology, Mar. 4, 2019, 199-208, 37.
Simm et al., Phenotypic Convergence Mediated by GGDEF-Domain-Containing Proteins, Journal of Bacteriology, 2005, 6816-6823, 187(19).
Stahl et al., Aminoquinazoline Compounds as A2A Antagonist, Handbook of Pharmaceutical Salts Properties, Selection, and Use, 2002, 330-331.
Sun et al., Cyclic GMP-AMP Synthase Is a Cytosolic DNA Sensor That Activates the Type 1 Interferon Pathway, Science, 2013, 786, 339.
Tezuka, T. et al, Synthesis of 2'-Modified Cyclic Bis(3'-5')diadenylic Acids (c-di-AMPs) and Their Promotion of Cell Division in a Freshwater Green Alga, Chem. Lett., 2012, 1723-1725, 41.
Tosolini et al., Human Monocyte Recognition of Adenosine-Based Cyclic Dinucleotides Unveils the A2a G∞s Protein-Coupled Receptor Tonic Inhibition of Mitochondrially Induced Cell Death, Molecular and Cellular Biology, 2015, 479-495, 35-2.
Urata et al., Regio- and Diastereo-Selectivity of Montmorillonite-Catalyzed Oligomerization of Racemic Adenosine 5'-Phosphorimidazolide, Nucleosides, Nucleotides and Nucleic Acids, Nucleosides, Nucleotides and Nucleic Acids, 2008, 421-430, 27.
Wang et al., Synthesis and Biological Activity of 5-Fluorotubercidin, Nucleosides, Nucleotides and Nucleic Acids, 2004, 161-170, 23(1).
Wu et al., Cyclic GMP-AMP Is an Endogenous Second Messenger in Innate Immune Signaling by Cytosolic DNA, Science 826, 2013, 826-830, 339.
Zeng et al., MAVS, cGAS, and Endogenous Retroviruses in T-Independent B Cell Responses, Science, 2014, 1486-1492, 346-6216.

(56) References Cited

OTHER PUBLICATIONS

Zhang et al., Cyclic GMP-AMP Containing Mixed Phosphodiester Linkages Is an Endogenous High-Affinity Ligand for STING, Molecular Cell, 2013, 226-235, 51.

Zhou et al., The ER-Associated Protein ZDHHC1 Is a Positive Regulator of DNA Virus-Triggered, MITA/STING-Dependent Innate Immune Signaling, Cell Host & Microbe, 2014, 450-461, 16.

Kumar, A. et al., Conformational Rigidity Introduced by 2',5'-Phosphodiester Links in DNA, Nucleosides, Nucleotides & Nucleic Acids, 2001, 1783-1796, 20.

Wexselblatt, E. et al., ppGpp analogues inhibit synthetase activity of Rel proteins from Gram-negative and Gram-positive bacteria, Bioorganic & Medicinal Chemistry, 2010, 4485-4497, 18.

\* cited by examiner

CYCLIC DI-NUCLEOTIDE COMPOUNDS AS STING AGONISTS

CROSS-REFERENCE TO RELATED APPLICATIONS

This application is a National Stage of International Patent Application No. PCT/US2018/065902, filed Dec. 17, 2018, which claims priority to U.S. Provisional Patent Application No. 62/608,154, filed Dec. 20, 2017.

FIELD OF THE INVENTION

The present disclosure relates to cyclic di-nucleotide compounds and derivatives thereof that may be useful as STING (Stimulator of Interferon Genes) agonists that activate the STING pathway. The present disclosure also relates to processes for the synthesis and to uses of such cyclic di-nucleotide compounds.

REFERENCE TO SEQUENCE LISTING SUBMITTED ELECTRONICALLY

The sequence listing of the present application is submitted electronically via EFS-Web as an ASCII-formatted sequence listing, with a file name of "24556_SEQLIST_14NOV2018", a creation date of Nov. 14, 2018, and a size of 25 KB. This sequence listing submitted via EFS-Web is part of the specification and is herein incorporated by reference in its entirety.

BACKGROUND OF THE INVENTION

The immune system has evolved to recognize and neutralize different types of threats in order to maintain the homeostasis of the host, and it is generally broken down into two arms: adaptive and innate. The adaptive immune system is specialized to recognize as foreign those antigens not naturally expressed in the host and to mount an anti-antigen response through the coordinated actions of many leukocyte subsets. The hallmark of adaptive immune responses is their ability to provide "memory" or long-lasting immunity against the encountered antigen. While this specific and long-lasting effect is critical to host health and survival, the adaptive immune response requires time to generate a full-blown response.

The innate immune system compensates for this time delay and is specialized to act quickly against different insults or danger signals. It provides the first line of defense against bacteria, viruses, parasites and other infectious threats, but it also responds strongly to certain danger signals associated with cellular or tissue damage. The innate immune system has no antigen specificity but does respond to a variety of effector mechanisms. Opsonization, phagocytosis, activation of the complement system, and production of soluble bioactive molecules such as cytokines or chemokines are all mechanisms by which the innate immune system mediates its response. By responding to these damage-associated molecular patterns (DAMPs) or pathogen-associated molecular patterns (PAMPs) described above, the innate immune system is able to provide broad protection against a wide range of threats to the host.

Free cytosolic DNA and RNA are among these PAMPs and DAMPs. It has recently been demonstrated that the main sensor for cytosolic DNA is cGAS (cyclic GMP-AMP synthase). Upon recognition of cytosolic DNA, cGAS catalyzes the generation of the cyclic-dinucleotide 2'3'-cGAMP, an atypical second messenger that strongly binds to the ER-transmembrane adaptor protein STING. A conformational change is undergone by cGAMP-bound STING, which translocates to a perinuclear compartment and induces the activation of critical transcription factors IRF-3 and NF-κB. This leads to a strong induction of type I interferons and production of pro-inflammatory cytokines such as IL-6, TNF-α and IFN-γ.

The importance of type I interferons and pro-inflammatory cytokines on various cells of the immune system has been very well established. In particular, these molecules strongly potentiate T-cell activation by enhancing the ability of dendritic cells and macrophages to uptake, process, present and cross-present antigens to T-cells. The T-cell stimulatory capacity of these antigen-presenting cells is augmented by the up-regulation of critical co-stimulatory molecules, such as CD80 or CD86. Finally, type I interferons can rapidly engage their cognate receptors and trigger the activation of interferon-responsive genes that can significantly contribute to adaptive immune cell activation.

From a therapeutic perspective, type I interferons are shown to have antiviral activities by directly inhibiting human hepatitis B virus and hepatitis C virus replication, and by stimulating immune responses to virally infected cells. Compounds that can induce type I interferon production are used in vaccines, where they act as adjuvants, enhancing specific immune responses to antigens and minimizing side effects by reducing dosage and broadening the immune response.

In addition, interferons, and compounds that can induce interferon production, have potential use in the treatment of human cancers. Such molecules are potentially useful as anti-cancer agents with multiple pathways of activity. Interferons can inhibit human tumor cell proliferation directly and may be synergistic with various approved chemotherapeutic agents. Type I interferons can significantly enhance anti-tumor immune responses by inducing activation of both the adaptive and innate immune cells. Finally, tumor invasiveness may be inhibited by interferons by modulating enzyme expression related to tissue remodeling.

In view of the potential of type I interferons and type I interferon-inducing compounds as anti-viral and anti-cancer agents, there remains a need for new agents that can induce potent type I interferon production. With the growing body of data demonstrating that the cGAS-STING cytosolic DNA sensory pathway has a significant capacity to induce type I interferons, the development of STING activating agents is rapidly taking an important place in to day's anti-tumor therapy landscape.

SUMMARY OF THE INVENTION

The present disclosure relates to novel compounds of general formula (I). In particular, the present disclosure relates to compounds having the general structural formula (I):

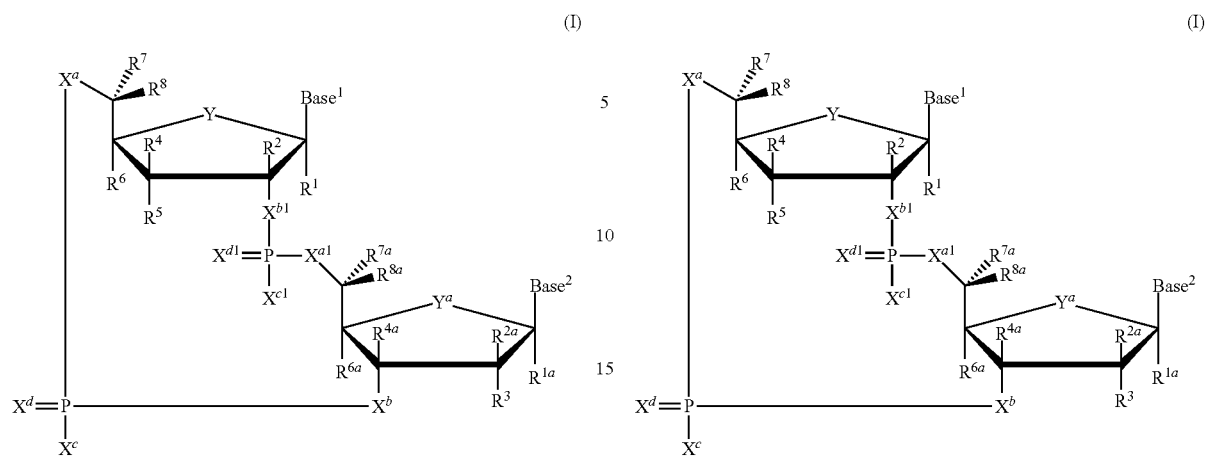
(I)

or pharmaceutically acceptable salts, hydrates, solvates, or prodrugs thereof, as described herein. Embodiments of the disclosure include compounds of general formula (I), and pharmaceutically acceptable salts, hydrates, solvates, or prodrugs thereof, as well as synthesis and isolation of compounds of general formula (I), and pharmaceutically acceptable salts, hydrates, solvates, or prodrugs thereof. The compounds of general formula (I), and their pharmaceutically acceptable salts, hydrates, solvates, and/or prodrugs, may be useful as agents to induce immune responses, to induce STING-dependent type I interferon production, and/or to treat a cell proliferation disorders, such as cancers, in a subject. The compounds of general formula (I) could further be used in combination with other therapeutically effective agents, including but not limited to, other drugs useful for the treatment of cell proliferation disorders, such as cancers. The invention further relates to processes for preparing compounds of general formula (I), and pharmaceutical compositions that comprise compounds of general formula (I) and pharmaceutically acceptable salts thereof.

Other embodiments, aspects and features of the present invention are either further described in or will be apparent from the ensuing description, examples and appended claims.

BRIEF DESCRIPTION OF THE DRAWINGS

Not Applicable

DETAILED DESCRIPTION OF THE INVENTION

The present disclosure includes compounds of general formula (I), and pharmaceutically acceptable salts, hydrates, solvates, or prodrugs thereof. These compounds and their pharmaceutically acceptable salts, hydrates, solvates, and/or prodrugs may be useful as agents to induce immune responses, to induce STING-dependent type I interferon production, and/or to treat a cell proliferation disorder.

Embodiments disclosed herein relate to compounds of general formula (I):

The present disclosure includes compounds of general formula (I), and pharmaceutically acceptable salts, hydrates, solvates, or prodrugs thereof. These compounds and their pharmaceutically acceptable salts, hydrates, solvates, and/or prodrugs may be useful as agents to induce immune responses, to induce STING-dependent type I interferon production, and/or to treat a cell proliferation disorder.

Embodiments disclosed herein relate to compounds of general formula (I) or pharmaceutically acceptable salts, hydrates, solvates, or prodrugs thereof, wherein Base$^1$ and Base$^2$ are each independently selected from the group consisting of

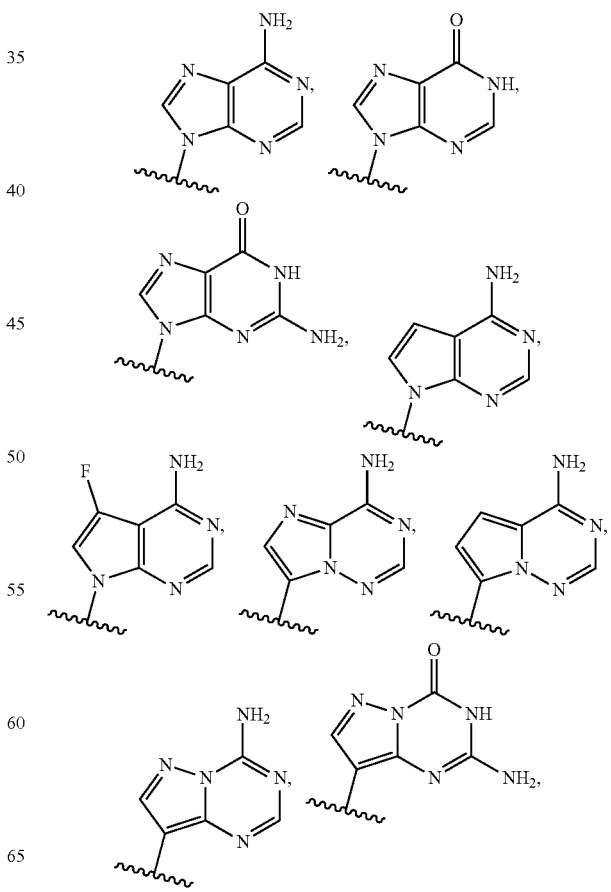

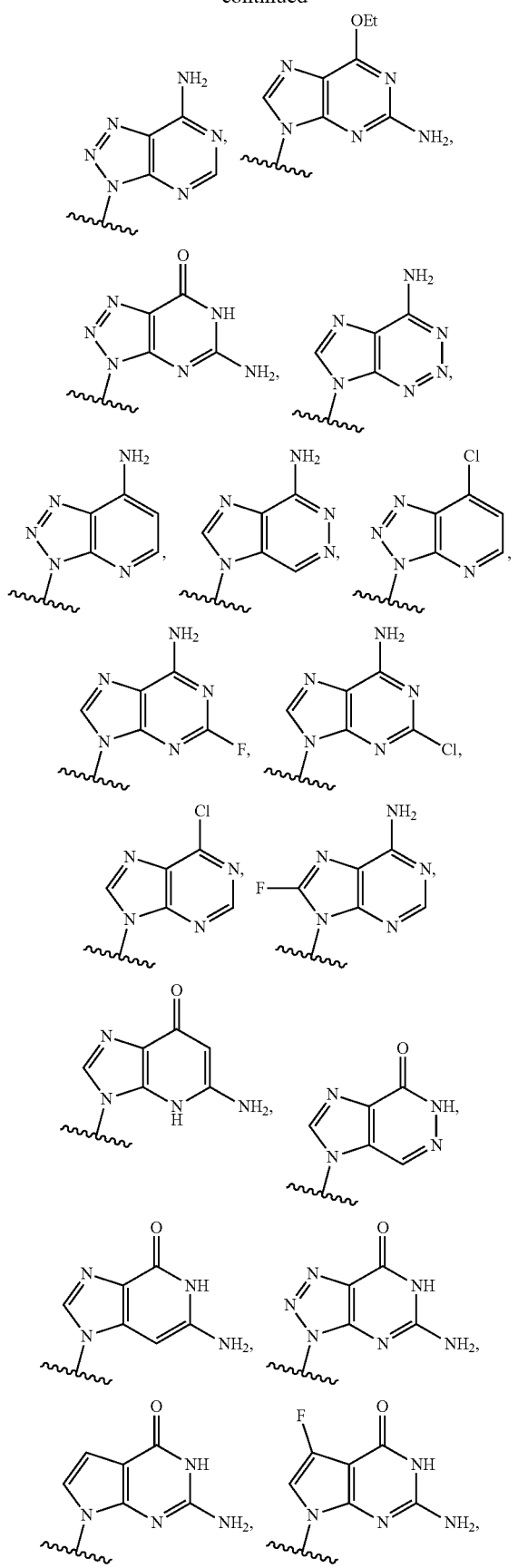
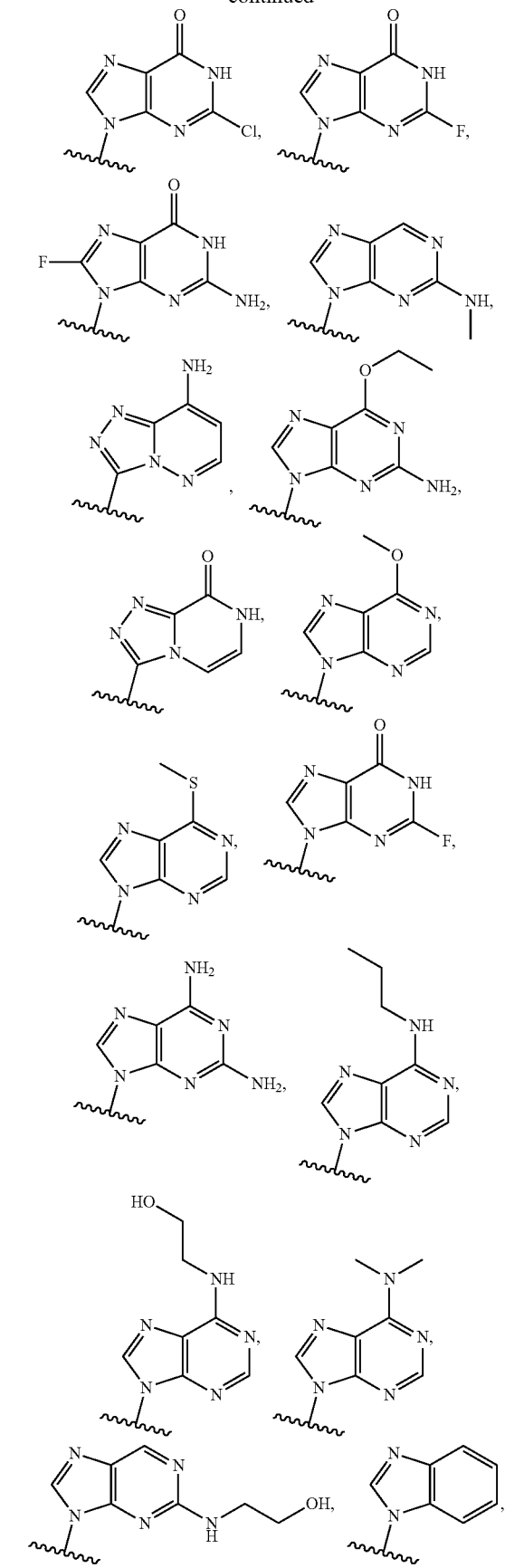

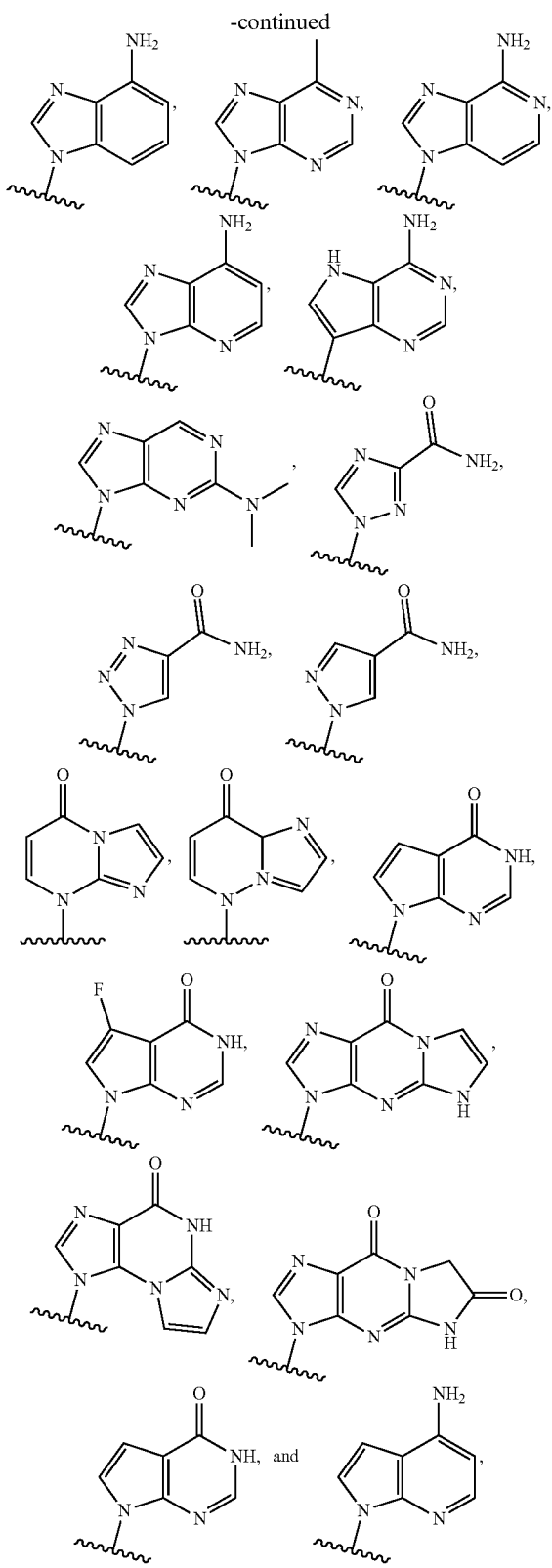

where Base[1] and Base[2] each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O—, —S—, —$SO_2$—, —$CH_2$—, and —$CF_2$—; $X^a$ and $X^{a1}$ are each independently selected from the group consisting of —O—, —S—, and —$CH_2$—; $X^b$ and $X^{b1}$ are each independently selected from the group consisting of —O—, —S—, and —$CH_2$—; $X^c$ and $X^{c1}$ are each independently selected from the group consisting of —$SR^9$, —$OR^9$, and —$NR^9R^9$; $X^d$ and $X^{d1}$ are each independently selected from the group consisting of O and S; $R^1$ and $R^{1a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^1$ and $R^{1a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^2$ and $R^{2a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^2$ and $R^{2a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^3$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^3$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^4$ and $R^{4a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^4$ and $R^{4a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^5$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^5$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^6$ and $R^{6a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^6$ and $R^{6a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^7$ and $R^{7a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^7$ and $R^{7a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^8$ and $R^{8a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^8$ and $R^{8a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; each $R^9$ is independently selected from the group consisting of H, $C_1$-$C_{20}$ alkyl,

[structures shown]

, and where each $R^9$ $C_1$-$C_{20}$ alkyl is optionally substituted by 0 to 3 substituents independently selected from the group consisting of OH, —O—$C_1$-$C_{20}$ alkyl, —S—C(O)$C_1$-$C_6$ alkyl, and C(O)O$C_1$-$C_6$ alkyl; optionally $R^{1a}$ and $R^3$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^{1a}$ and $R^3$ are connected to form —O—$C_1$-$C_6$ alkylene, or —O—$C_2$-$C_6$ alkenylene, said O is bound at the $R^3$ position; optionally $R^{2a}$ and $R^3$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^{2a}$ and $R^3$ are connected to form —O—$C_1$-$C_6$ alkylene, or —O—$C_2$-$C_6$ alkenylene, said O is bound at the $R^3$ position; optionally $R^3$ and $R^{6a}$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^3$ and $R^{6a}$ are connected to form —O—$C_1$-$C_6$ alkylene, or —O—$C_2$-$C_6$ alkenylene, said O is bound at the $R^3$ position; optionally $R^4$ and $R^5$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^4$ and $R^5$ are connected to form —O—$C_1$-$C_6$ alkylene, or —O—$C_2$-$C_6$ alkenylene, said O is bound at the $R^5$ position; optionally $R^5$ and $R^6$ are connected to form —O—$C_1$-$C_6$ alkylene, —O—$C_2$-$C_6$ alkenylene, or —O—$C_2$-$C_6$ alkynylene, such that where $R^5$ and $R^6$ are connected to form —O—$C_1$-$C_6$ alkylene, —O—$C_2$-$C_6$ alkenylene, or —O—$C_2$-$C_6$ alkynylene, said O is bound at the $R^5$ position; optionally $R^7$ and $R^8$ are connected to form $C_1$-$C_6$ alkylene or $C_2$-$C_6$ alkenylene; and optionally $R^{7a}$ and $R^{8a}$ are connected to form $C_1$-$C_6$ alkylene or $C_2$-$C_6$ alkenylene.

In embodiments, at least one of Base$^1$ and Base$^2$ is each independently selected from the group consisting of

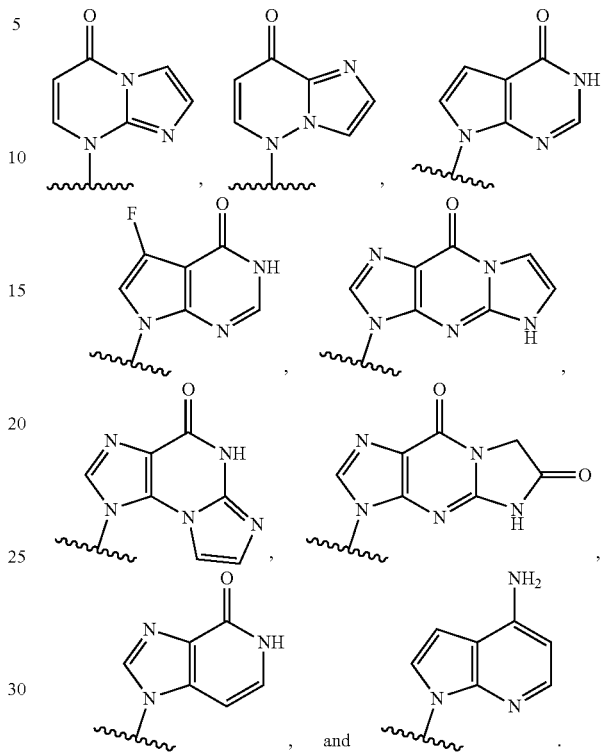

In each embodiment described herein, variables Base$^1$, Base$^2$, Y, Y$^a$, X$^a$, X$^{a1}$, X$^b$, X$^{b1}$, X$^c$, X$^{c1}$, X$^d$, X$^{d1}$, R$^1$, R$^{1a}$, R$^2$, R$^{2a}$, R$^3$, R$^4$, R$^{4a}$, R$^5$, R$^6$, R$^{6a}$, R$^7$, R$^{7a}$, R$^8$, R$^{8a}$, and R$^9$ of general formula (I), and the various aspects thereof, are each selected independently from each other.

In a first embodiment, Base$^1$ and Base$^2$ are each independently selected from the group consisting of

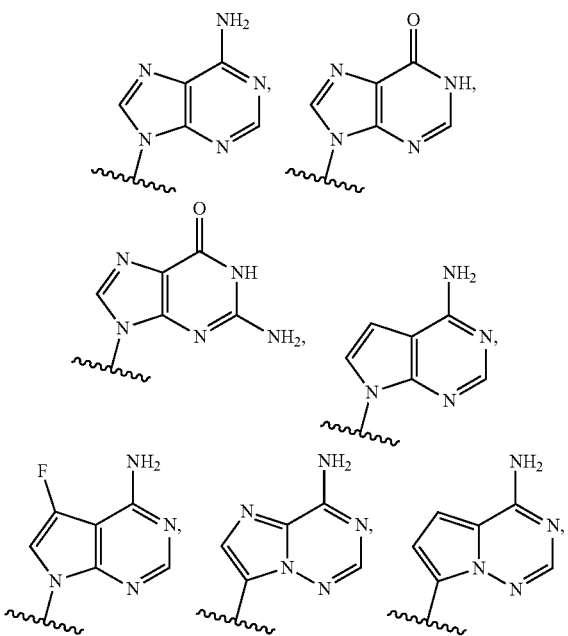

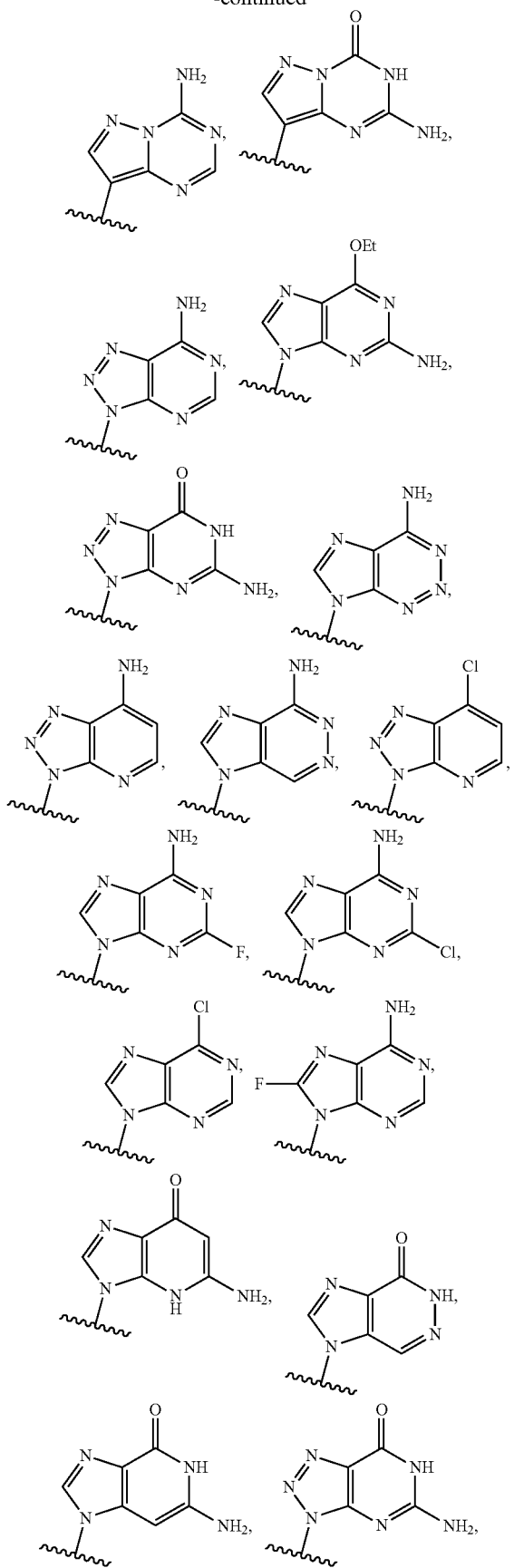
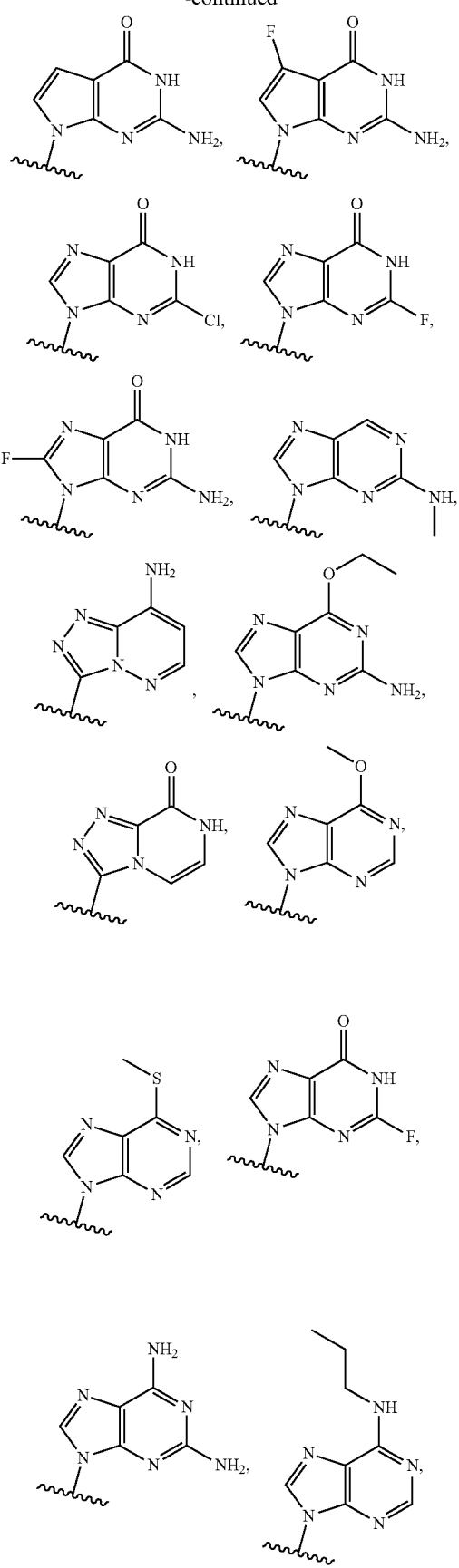

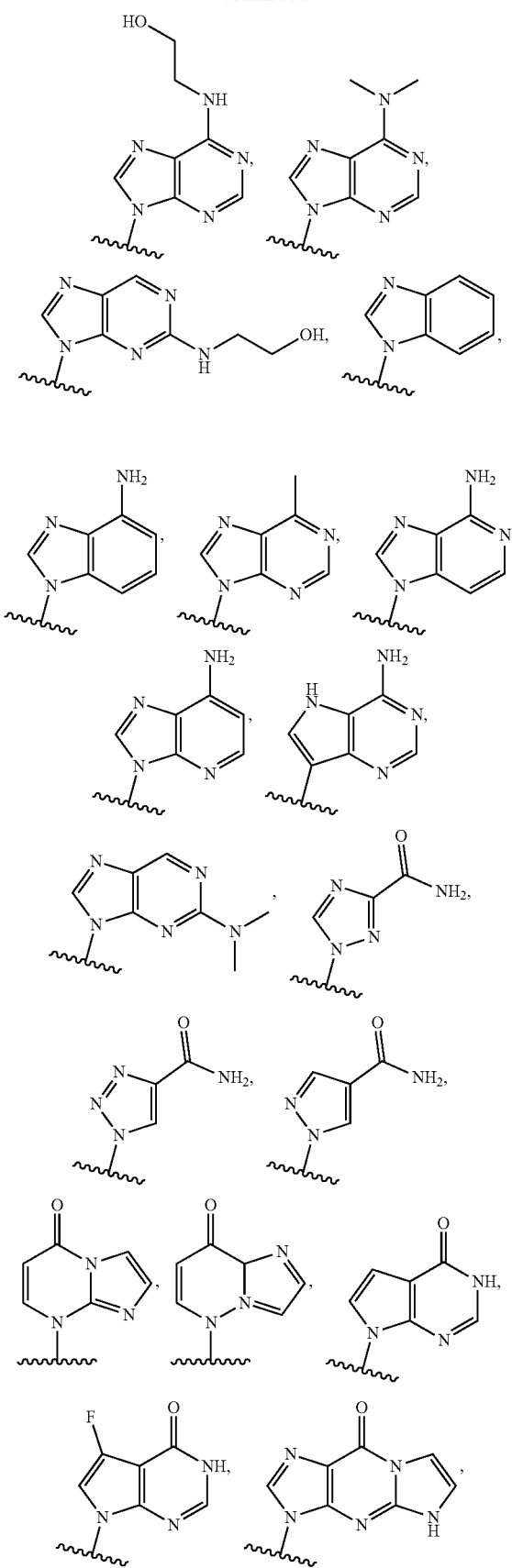

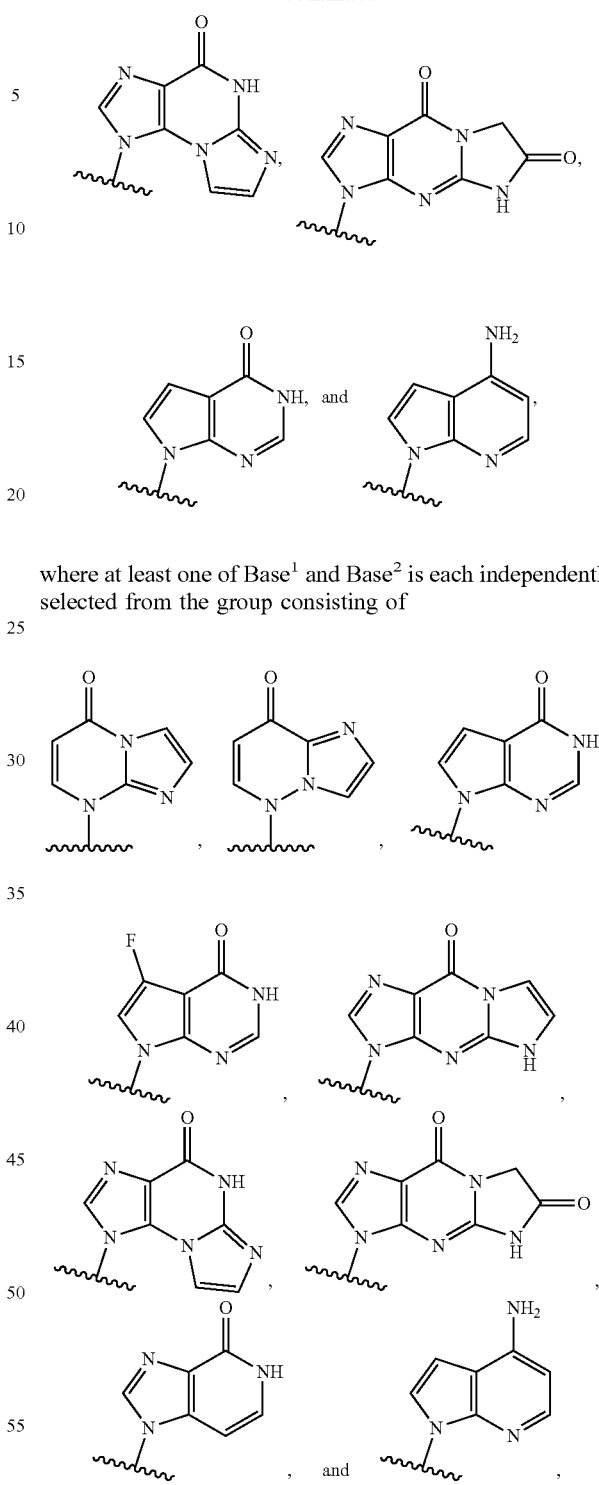

where at least one of Base¹ and Base² is each independently selected from the group consisting of and where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In particular aspects, Base¹ and Base² are each independently selected from the group consisting of

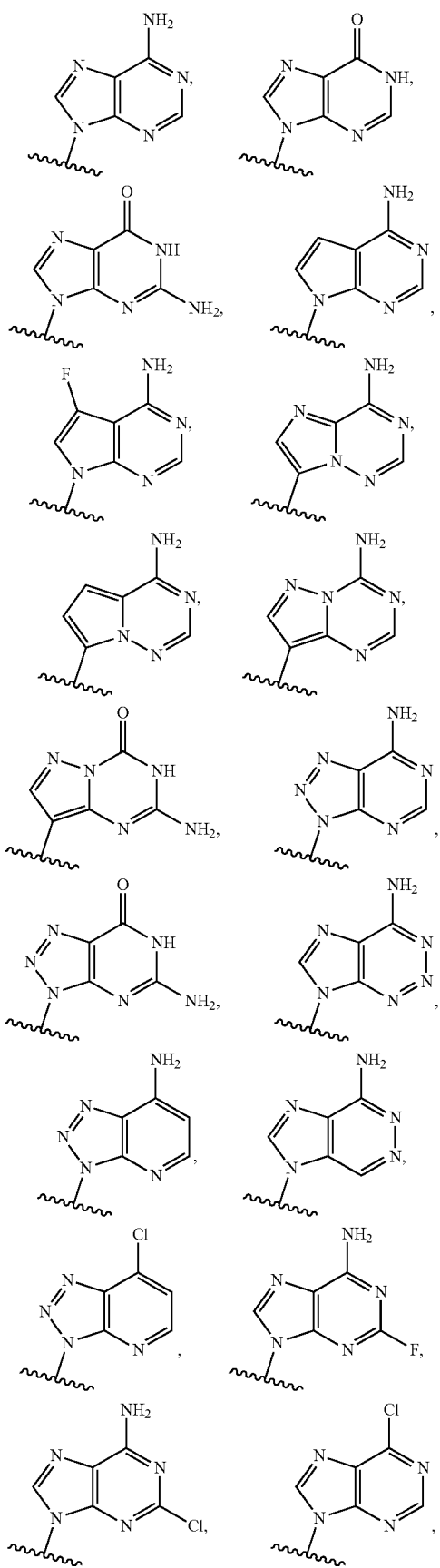
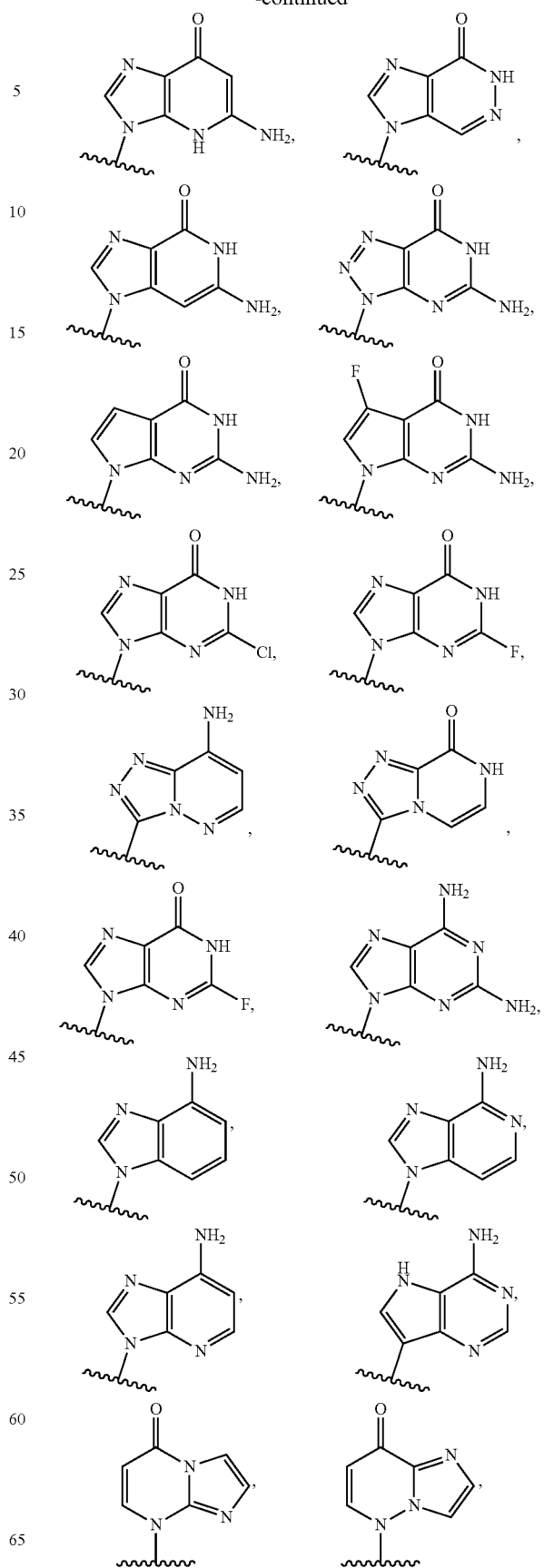

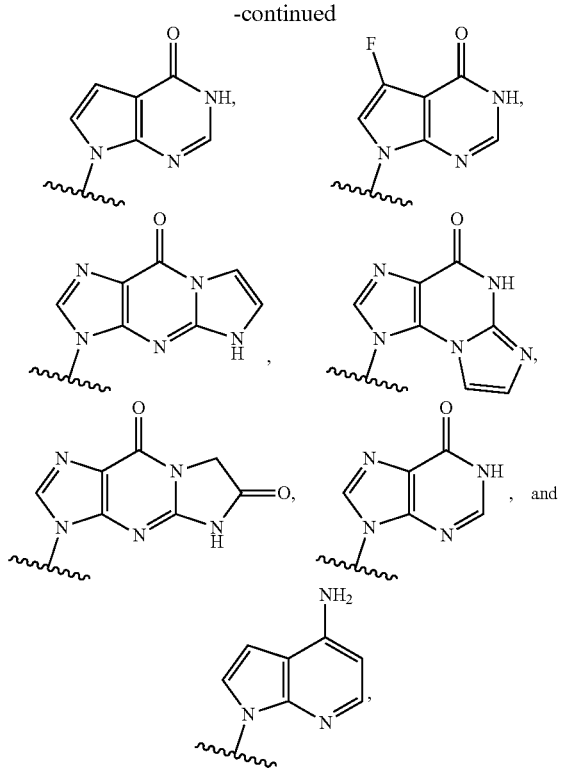

where at least one of Base¹ and Base² is each independently selected from the group consisting of

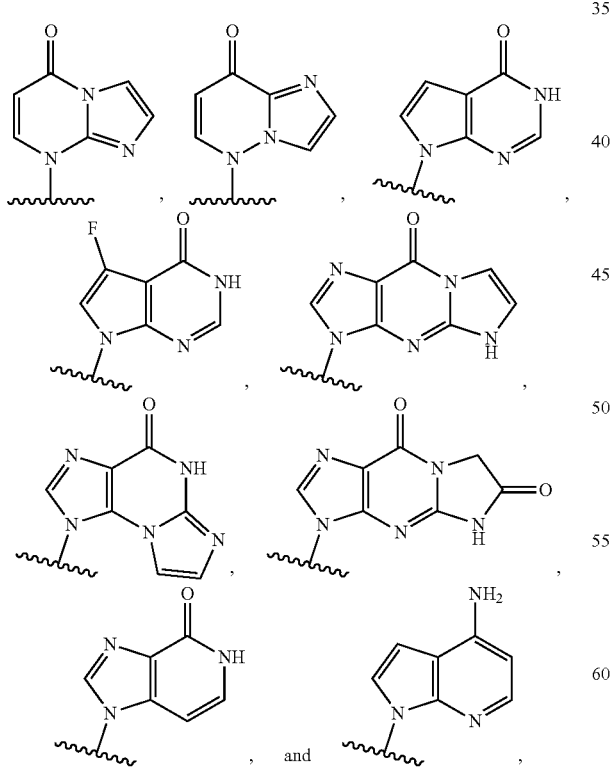

and where Base¹ and Base² each may be independently substituted by 0-3 substituents R¹⁰, where each R¹⁰ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In even more particular aspects, Base¹ and Base² are each independently selected from the group consisting of

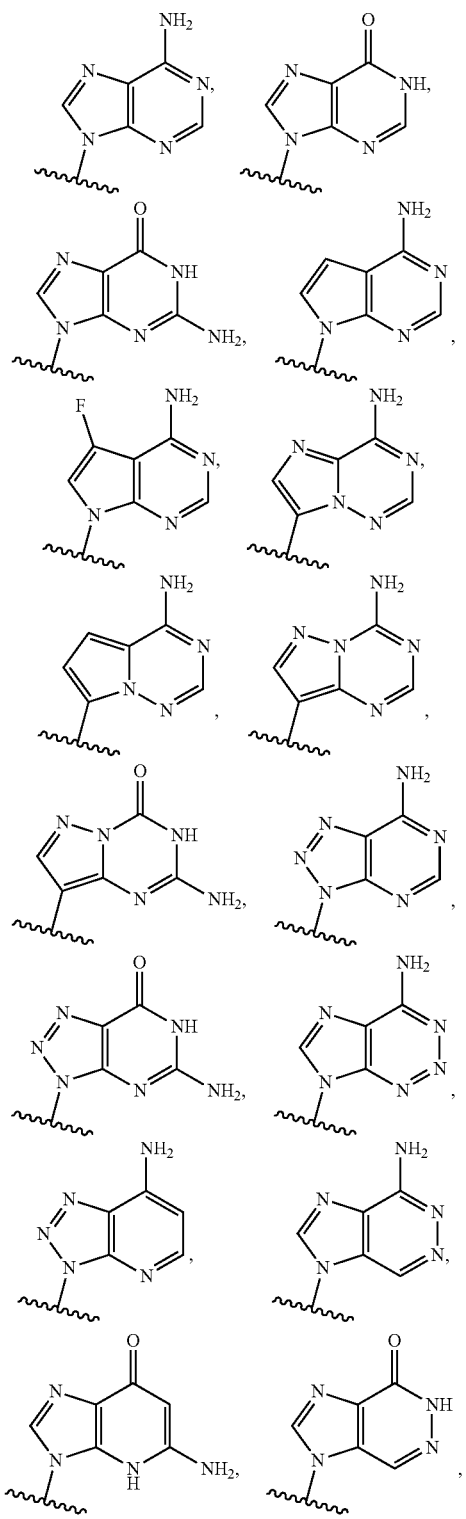

-continued

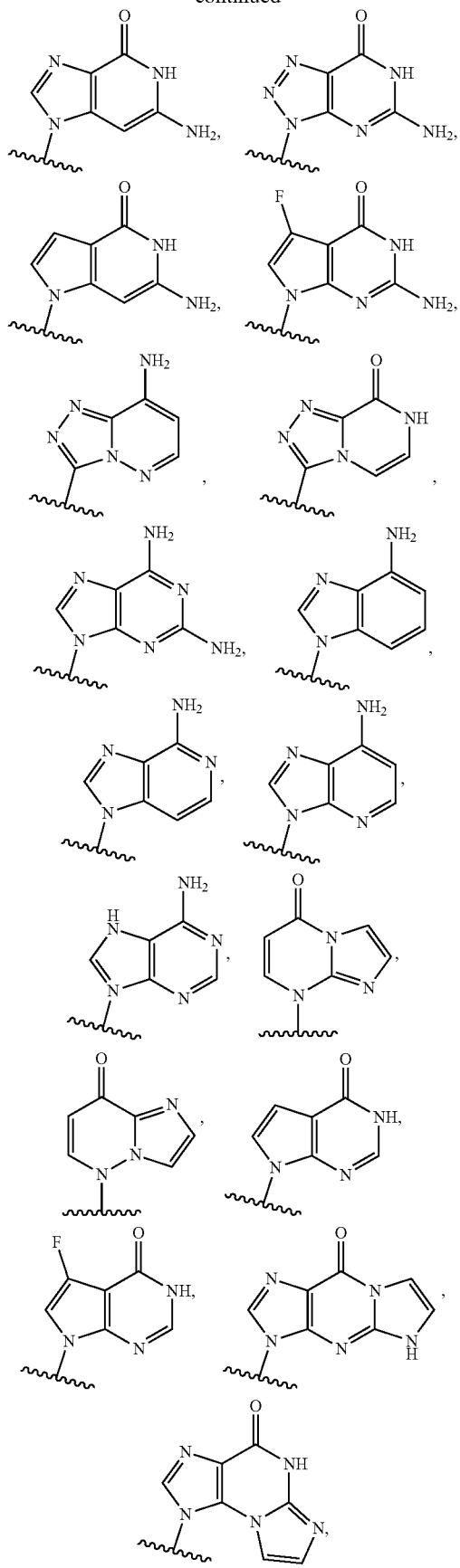

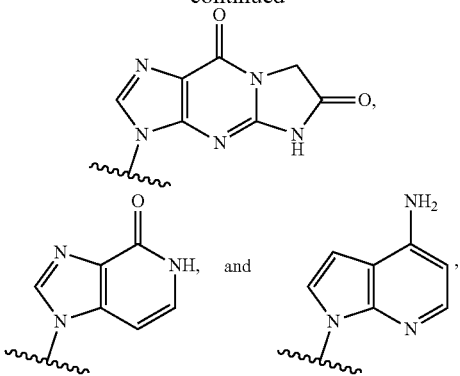

where at least one of Base¹ and Base² is each independently selected from the group consisting of

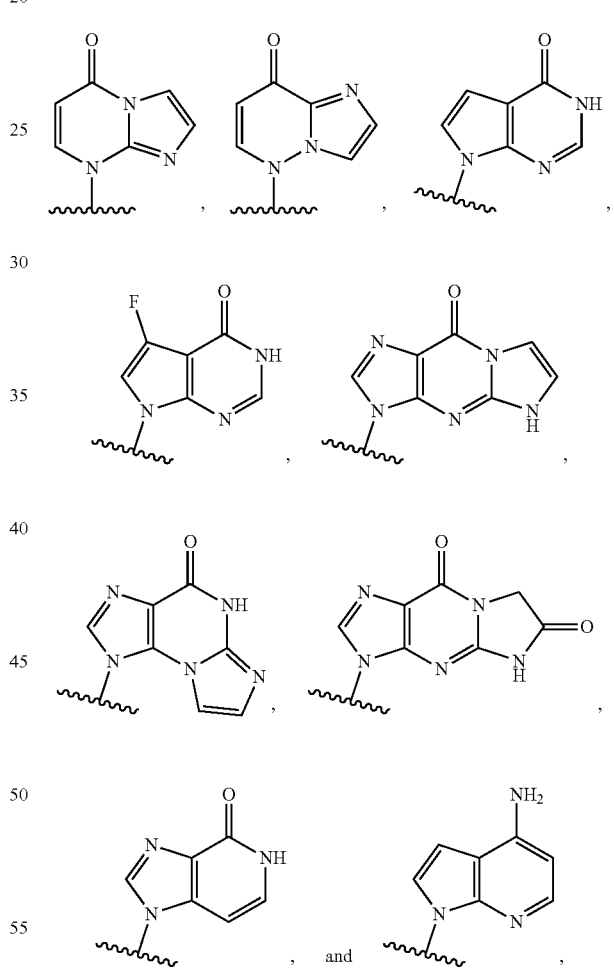

and where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In even more particular aspects, Base¹ and Base² are each independently selected from the group consisting of

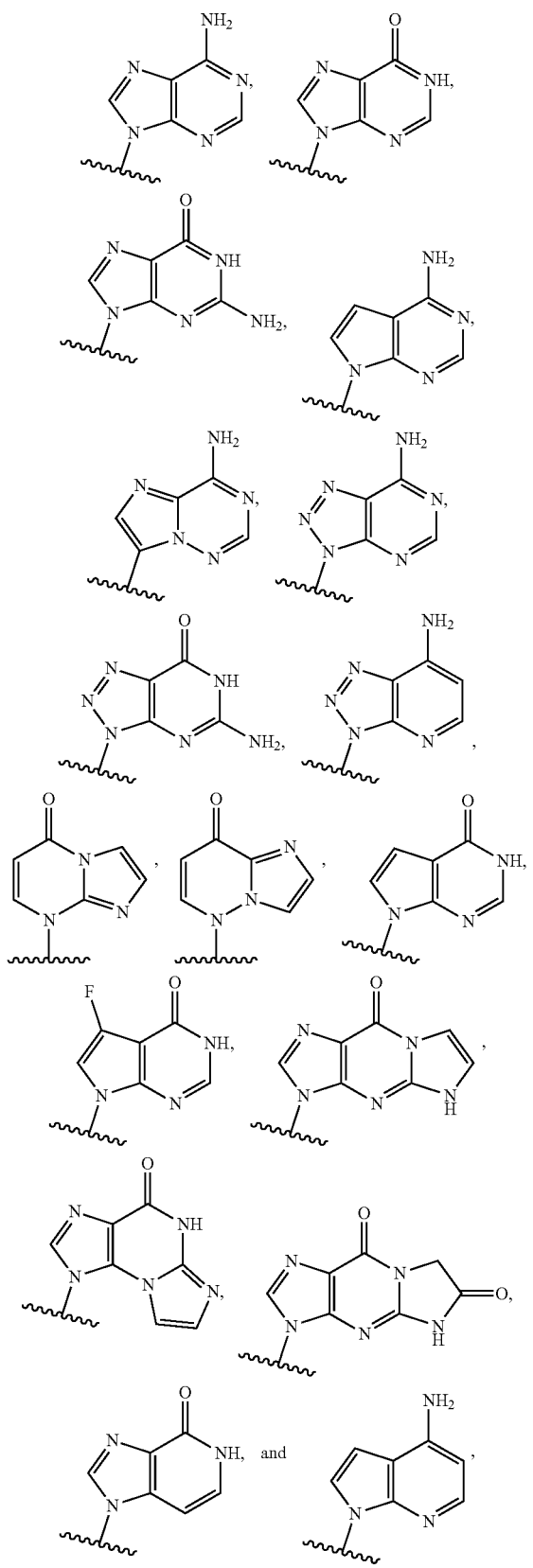

where at least one of Base[1] and Base[2] is each independently selected from the group consisting of

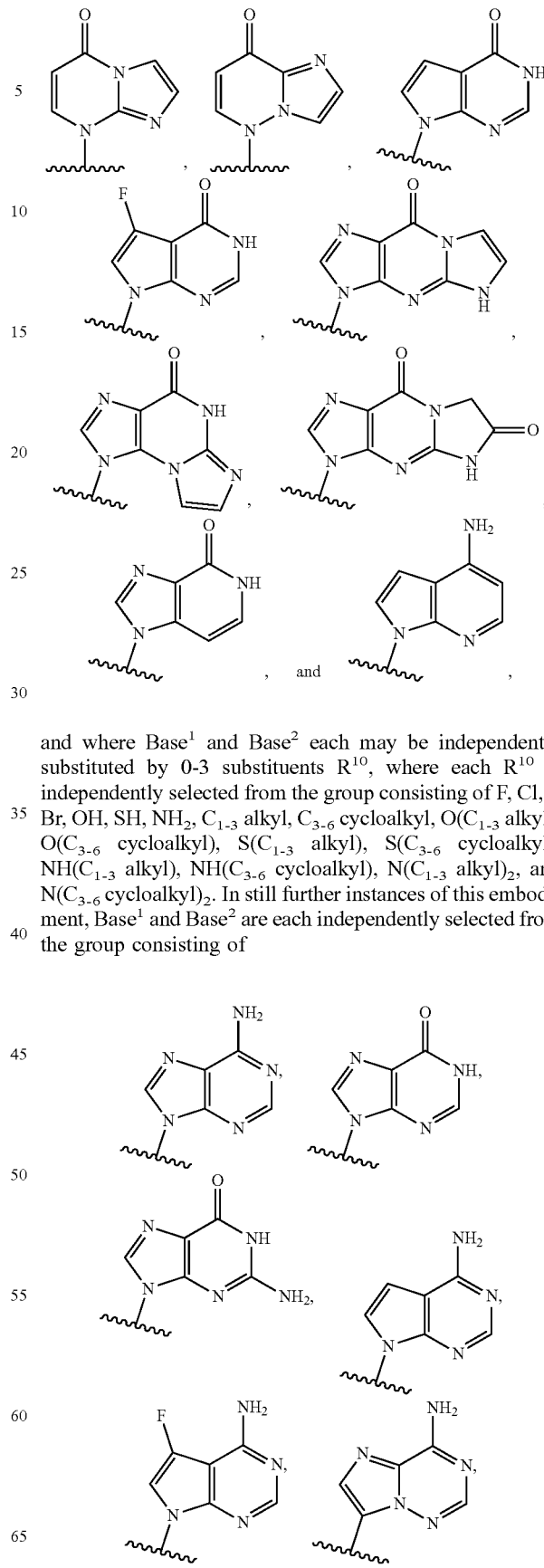

and where Base[1] and Base[2] each may be independently substituted by 0-3 substituents R[10], where each R[10] is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In still further instances of this embodiment, Base[1] and Base[2] are each independently selected from the group consisting of

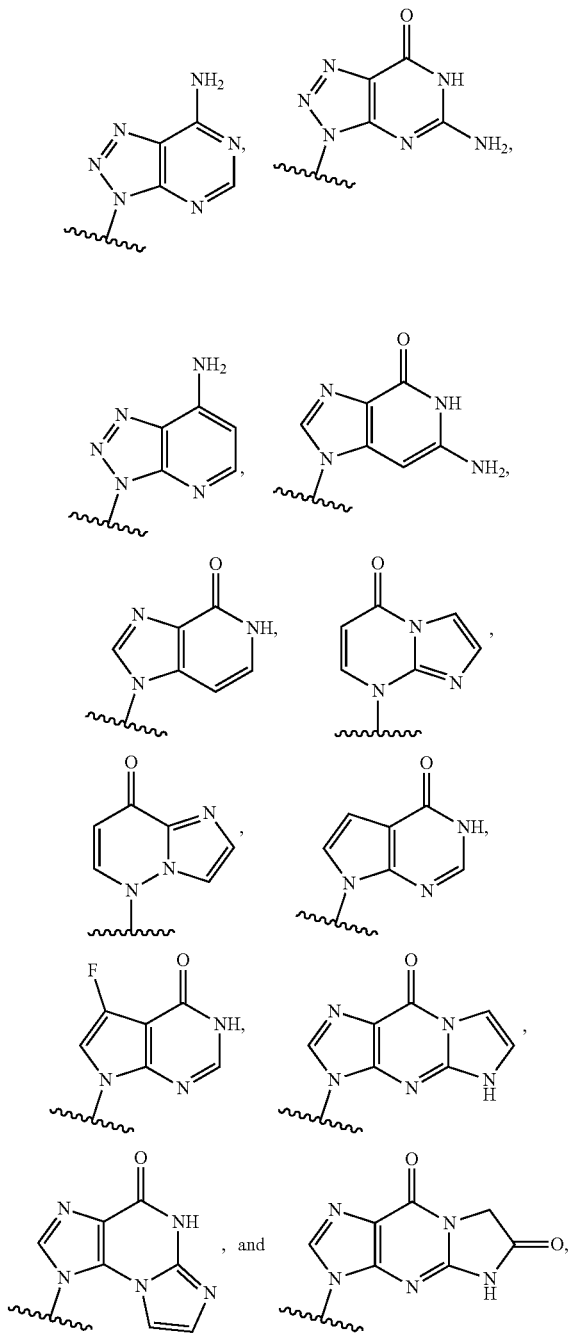

where at least one of Base[1] and Base[2] is each independently selected from the group consisting of

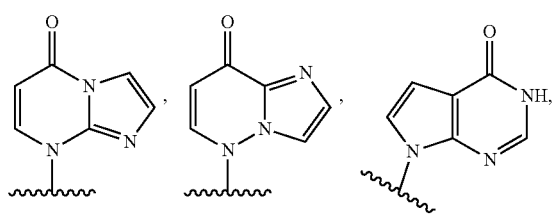

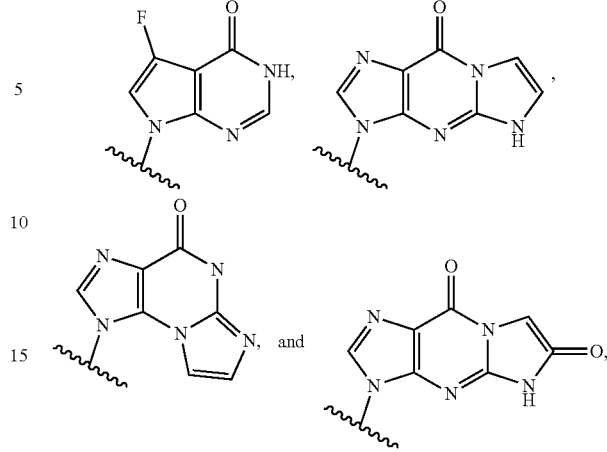

and where Base[1] and Base[2] each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In even more particular instances of this embodiment, Base[1] is selected from the group consisting of

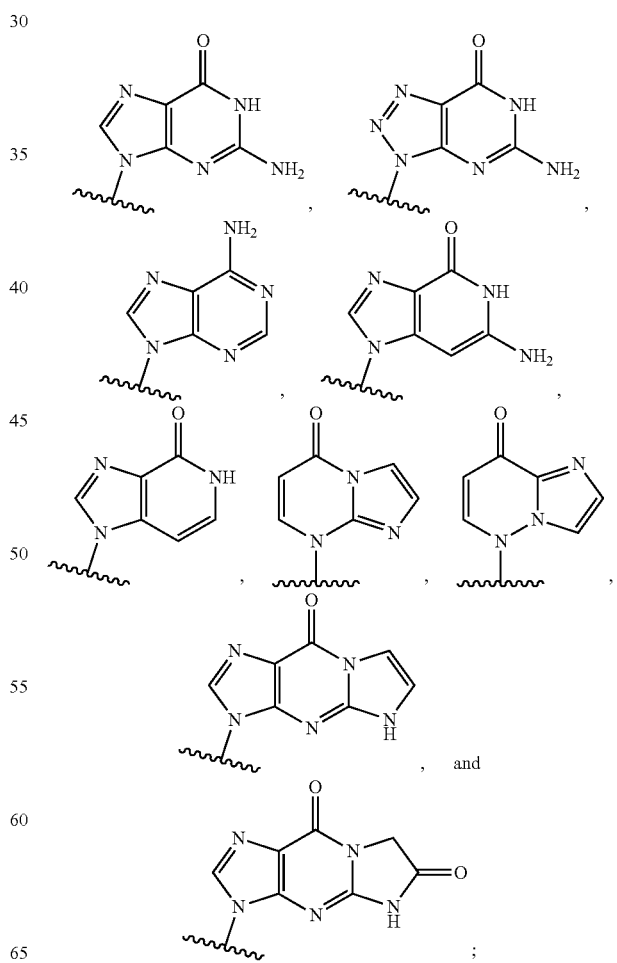

Base² is selected from the group consisting of

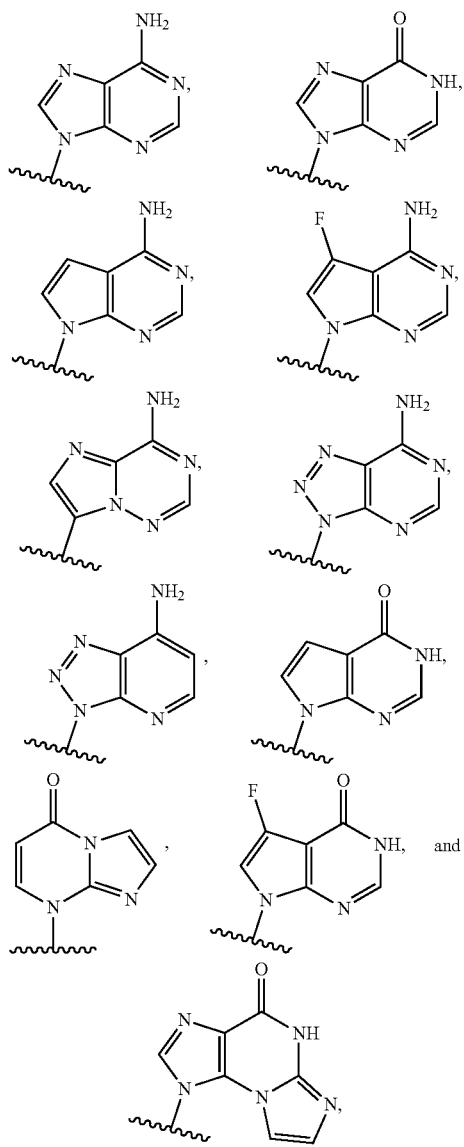

where at least one of Base¹ and Base² is each independently selected from the group consisting of

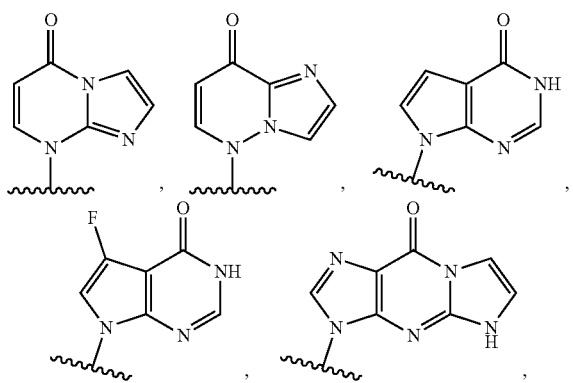

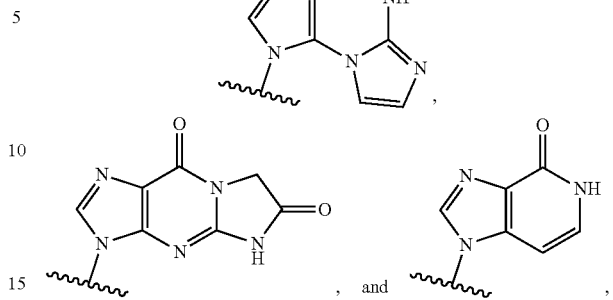

, and and where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In this embodiment, all other groups are as provided in the general formula (I) above.

In a second embodiment, Y and $Y^a$ are each independently selected from the group consisting of —O— and —S—. In this embodiment, all other groups are as provided in the general formula (I) above or in the first embodiment described above.

In a third embodiment, $X^a$ and $X^{a1}$ are each independently selected from the group consisting of —O— and —S—. In this embodiment, all other groups are as provided in the general formula (I) above or in the first through second embodiments described above.

In a fourth embodiment, $X^b$ and $X^{b1}$ are each independently selected from the group consisting of —O— and —S—. In this embodiment, all other groups are as provided in the general formula (I) above or in the first through third embodiments described above.

In a fifth embodiment, $X^c$ and $X^{c1}$ are each independently selected from the group consisting of —$OR^9$, —$SR^9$, and —$NR^9R^9$, where each $R^9$ is independently selected from the group consisting of H, $C_1$-$C_{20}$ alkyl,

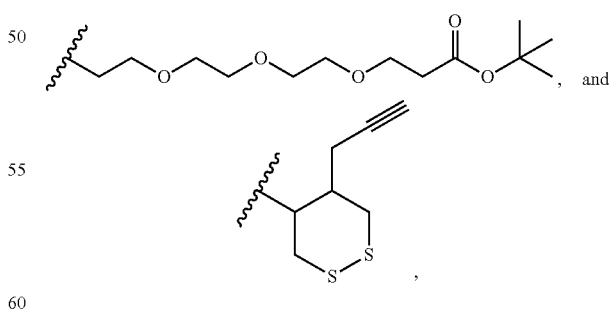

where each $R^9$ $C_1$-$C_{20}$ alkyl is optionally substituted by 0 to 3 substituents independently selected from the group consisting of —OH, alkyl, —S—C(O)$C_1$-$C_6$ alkyl, and —C(O)O$C_1$-$C_6$ alkyl. In particular aspects, $X^c$ and $X^{c1}$ are each independently selected from the group consisting of —OH, —SH,

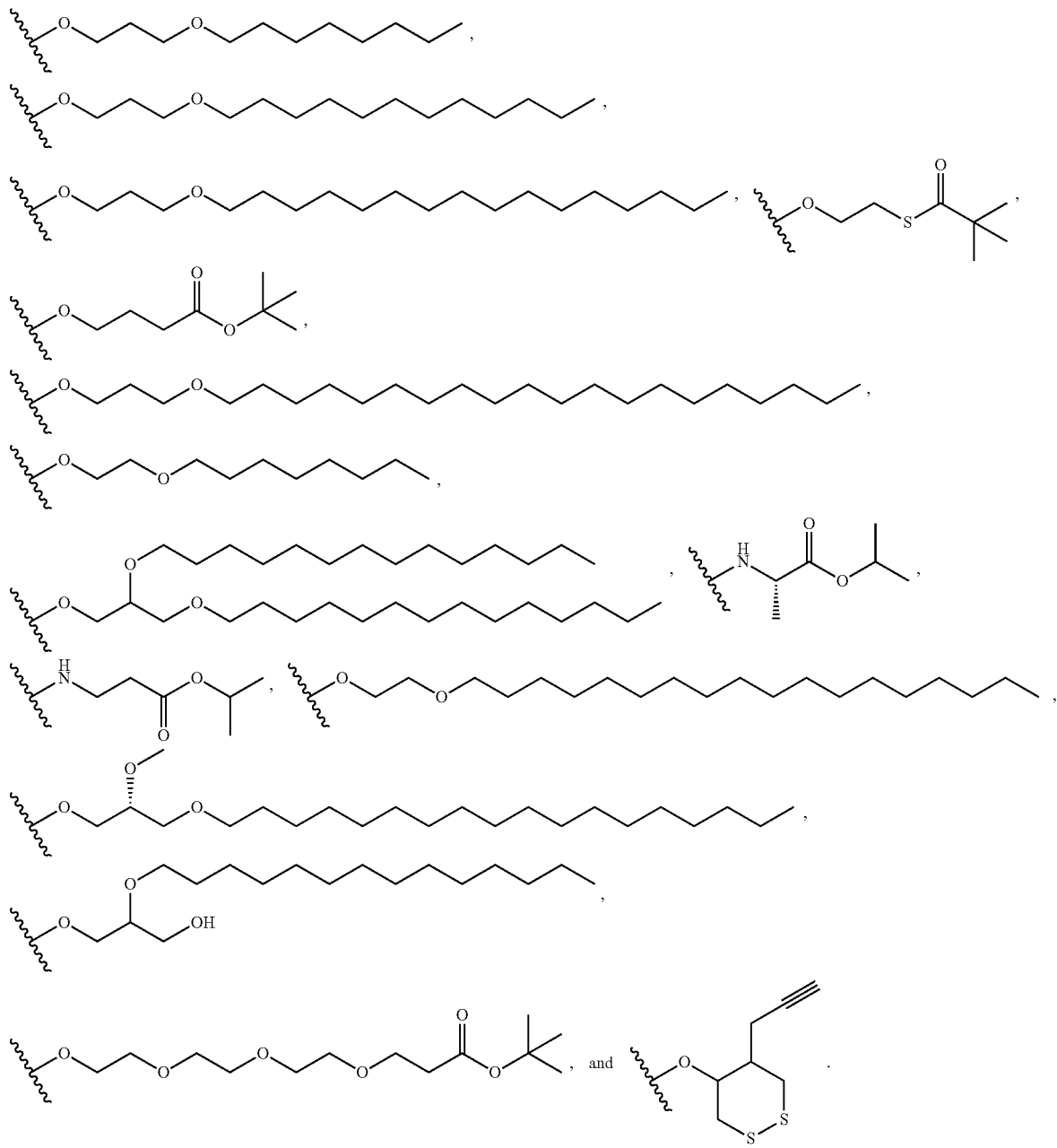

In more particular aspects, $X^c$ and $X^{c1}$ are each independently selected from the group consisting of —OH and —SH. In all aspects of this embodiment, all other groups are as provided in the general formula (I) above or in the first through fourth embodiment described above.

In a sixth embodiment, $X^d$ and $X^{d1}$ are each independently selected from the group consisting of O and S. In this embodiment, all other groups are as provided in the general formula (I) above or in the first through fifth embodiments described above.

In a seventh embodiment, $R^1$ and $R^{1a}$ are each H. In this embodiment, all other groups are as provided in the general formula (I) above or in the first through sixth embodiments described above.

In an eighth embodiment, $R^2$ and $R^{2a}$ are each independently selected from the group consisting of H, F, Cl, I, Br, OH, CN, $N_3$, $C_1$-$C_6$ alkyl, and $C_1$-$C_6$ haloalkyl, where said $R^2$ and $R^{2a}$ $C_1$-$C_6$ alkyl or $C_1$-$C_6$ haloalkyl are substituted by 0 to 3 substituents selected from the group consisting of OH, CN, and $N_3$. In particular aspects, $R^2$ and $R^{2a}$ are each independently selected from the group consisting of H, F, Cl, I, Br, OH, CN, $N_3$, —$CF_3$, —$CH_3$, —$CH_2OH$, and —$CH_2CH_3$. In more particular aspects, $R^2$ and $R^{2a}$ are each independently selected from the group consisting of H, F, Cl, OH, CN, $N_3$, and —$CH_3$. In even more particular aspects, $R^2$ and $R^{2a}$ are each independently selected from the group consisting of H, F, and OH. In all aspects of this embodiment, all other groups are as provided in the general formula (I) above or in the first through seventh embodiments described above.

In a ninth embodiment, $R^3$ is selected from the group consisting H, F, Cl, I, Br, OH, CN, $N_3$, $C_1$-$C_6$ alkyl, and $C_1$-$C_6$ haloalkyl, where said $R^3$ $C_1$-$C_6$ alkyl or $C_1$-$C_6$ haloalkyl are substituted by 0 to 3 substituents selected from the group consisting of OH, CN, and $N_3$. In particular aspects, $R^3$ is selected from the group consisting of H, F, Cl, I, Br, OH, CN, $N_3$, —$CF_3$, —$CH_3$, —$CH_2OH$, and —$CH_2CH_3$. In more particular aspects, $R^3$ is selected from the group consisting of H, F, Cl, OH, CN, $N_3$, and —$CH_3$. In even more particular aspects, $R^3$ is selected from the group consisting of H, F, and OH. In all aspects of this embodiment, all other groups are as provided in the general formula (I) above or in the first through eighth embodiments described above.

In a tenth embodiment, $R^4$ and $R^{4a}$ are each independently selected from the group consisting of H, F, Cl, I, Br, CN, OH, $N_3$, $C_1$-$C_6$ alkyl, and $C_1$-$C_6$ haloalkyl, where said $R^4$ and $R^{4a}$ $C_1$-$C_6$ alkyl or $C_1$-$C_6$ haloalkyl are substituted by 0 to 3 substituents selected from the group consisting of OH, CN, and $N_3$. In particular aspects, $R^4$ and $R^{4a}$ are each independently selected from the group consisting of H, F, Cl, I, Br, OH, CN, $N_3$, —$CF_3$, —$CH_3$, —$CH_2OH$, and —$CH_2CH_3$. In more particular aspects, $R^4$ and $R^{4a}$ are each independently selected from the group consisting of H, F, Cl, OH, CN, $N_3$, and —$CH_3$. In even more particular aspects, $R^4$ and $R^{4a}$ are each independently selected from the group consisting of H, F, and OH. In all aspects of this embodiment, all other groups are as provided in the general formula (I) above or in the first through ninth embodiments described above.

In an eleventh embodiment, $R^5$ is selected from the group consisting of H, F, Cl, I, Br, OH, CN, $N_3$, $C_1$-$C_6$ alkyl, and $C_1$-$C_6$ haloalkyl, where said $R^5$ $C_1$-$C_6$ alkyl or $C_1$-$C_6$ haloalkyl are substituted by 0 to 3 substituents selected from the group consisting of OH, CN, and $N_3$. In particular aspects, $R^5$ is selected from the group consisting of H, F, Cl, I, Br, OH, CN, $N_3$, —$CF_3$, —$CH_3$, —$CH_2OH$, and —$CH_2CH_3$. In more particular aspects, $R^5$ is selected from the group consisting of H, F, Cl, OH, CN, $N_3$, and $CH_3$. In even more particular aspects, $R^5$ is selected from the group consisting of H, F, and OH. In all aspects, all other groups are as provided in the general formula (I) above or in the first through tenth embodiments described above.

In a twelfth embodiment, $R^6$ and $R^{6a}$ are each independently selected from the group consisting of H, F, Cl, I, Br, OH, CN, $N_3$, $C_1$-$C_6$ alkyl, $C_2$-$C_6$ alkenyl, and $C_2$-$C_6$ alkynyl, where said $R^6$ and $R^{6a}$ $C_1$-$C_6$ alkyl, $C_2$-$C_6$ alkenyl, and $C_2$-$C_6$ alkynyl are substituted by 0 to 3 substituents selected from the group consisting of F, Cl, Br, I, OH, CN, and $N_3$. In particular aspects, $R^6$ and $R^{6a}$ are each independently selected from the group consisting of H, F, Cl, I, Br, OH, CN, $N_3$, —$CF_3$, —$CH_3$, —$CH_2OH$, —$CH_2CH_3$, —$CH=CH_2$, —$C\equiv CH$, and —$C\equiv C$—$CH$. In more particular aspects, $R^6$ and $R^{6a}$ are each independently selected from the group consisting of H, F, CN, $N_3$, —$CH_3$, —$CH=CH_2$, and —$C\equiv H$. In even more particular aspects, $R^6$ and $R^{6a}$ are each H. In all aspects of this embodiment, all other groups are as provided in the general formula (I) above or in the first through eleventh embodiments described above.

In a thirteenth embodiment, $R^7$ and $R^{7a}$ are each independently selected from the group consisting of H, $C_1$-$C_6$ alkyl, and $C_1$-$C_6$ haloalkyl, where said $R^7$ and $R^{7a}$ $C_1$-$C_6$ alkyl or $C_1$-$C_6$ haloalkyl are substituted by 0 to 3 substituents selected from the group consisting of OH, CN, and $N_3$. In particular aspects, $R^7$ and $R^{7a}$ are each independently selected from the group consisting of H, —$CF_3$, —$CH_3$, and —$CH_2CH_3$. In more particular aspects, $R^7$ and $R^{7a}$ are each H. In all aspects of this embodiment, all other groups are as provided in the general formula (I) above or in the first through twelfth embodiments described above.

In a fourteenth embodiment, $R^8$ and $R^{8a}$ are each independently selected from the group consisting of H, $C_1$-$C_6$ alkyl, and $C_1$-$C_6$ haloalkyl, where said $R^8$ and $R^{8a}$ $C_1$-$C_6$ alkyl or $C_1$-$C_6$ haloalkyl are substituted by 0 to 3 substituents selected from the group consisting of OH, CN, and $N_3$. In particular aspects, $R^8$ and $R^{8a}$ are each independently selected from the group consisting of H, —$CF_3$, —$CH_3$, and —$CH_2CH_3$. In more particular aspects, $R^8$ and $R^{8a}$ are each H. In all aspects of this embodiment, all other groups are as provided in the general formula (I) above or in the first through thirteenth embodiments described above.

In a fifteenth embodiment, $R^{1a}$ and $R^3$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^{1a}$ and $R^3$ are connected to form —O—$C_1$-$C_6$ alkylene or —O—$C_2$-$C_6$ alkenylene, said O is bound at the $R^3$ position. In this embodiment, all other groups are as provided in the general formula (I) above or in the first through fourteenth embodiments described above.

In a sixteenth embodiment, $R^{2a}$ and $R^3$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^{2a}$ and $R^3$ are connected to form —O—$C_1$-$C_6$ alkylene or —O—$C_2$-$C_6$ alkenylene, said O is bound at the $R^3$ position. In this embodiment, all other groups are as provided in the general formula (I) above or in the first through fourteenth embodiments described above.

In a seventeenth embodiment, $R^3$ and $R^{6a}$ are connected to form $C_2$-$C_6$ alkylene, $C_2$-$C_6$ alkenylene, —O—$C_1$-$C_6$ alkylene, or —O—$C_2$-$C_6$ alkenylene such that where $R^3$ and $R^{6a}$ are connected to form —O—$C_1$-$C_6$ alkylene or —O—$C_2$-$C_6$ alkenylene, said O is bound at the $R^3$ position. In this embodiment, all other groups are as provided in the general formula (I) above or in the first through fourteenth embodiments described above.

In an eighteenth embodiment, $R^4$ and $R^5$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^4$ and $R^5$ are connected to form —O—$C_1$-$C_6$ alkylene or —O—$C_2$-$C_6$ alkenylene, said O is bound at the $R^5$ position. In this embodiment, all other groups are as provided in the general formula (I) above or in the first through fourteenth embodiments described above.

In a nineteenth embodiment, $R^5$ and $R^6$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^5$ and $R^6$ are connected to form —O—$C_1$-$C_6$ alkylene or —O—$C_2$-$C_6$ alkenylene, said O is bound at the $R^5$ position. In this embodiment, all other groups are as provided in the general formula (I) above or in the first through fourteenth embodiments described above.

In a twentieth embodiment, $R^7$ and $R^8$ are connected to form $C_1$-$C_6$ alkylene or $C_2$-$C_6$ alkenylene. In this embodiment, all other groups are as provided in the general formula (I) above or in the first through fourteenth embodiments described above.

In a twenty-first embodiment, $R^{7a}$ and $R^{8a}$ are connected to form $C_1$-$C_6$ alkylene or $C_2$-$C_6$ alkenylene. In this embodiment, all other groups are as provided in the general formula (I) above or in the first through fourteenth embodiments described above.

In a twenty-second embodiment, Base[1] and Base[2] are each independently selected from the group consisting of

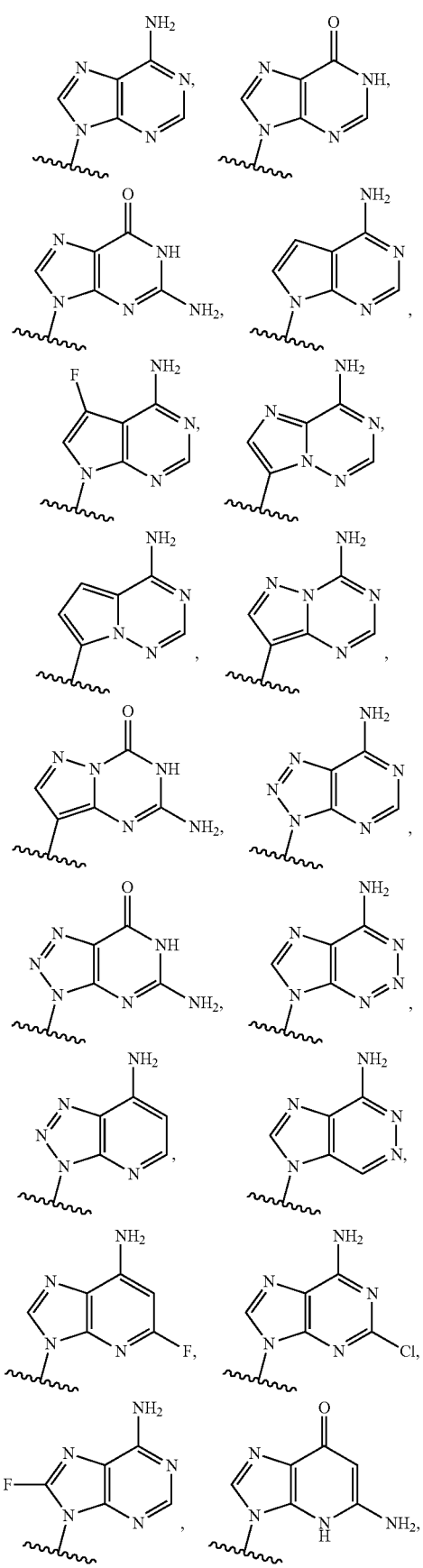
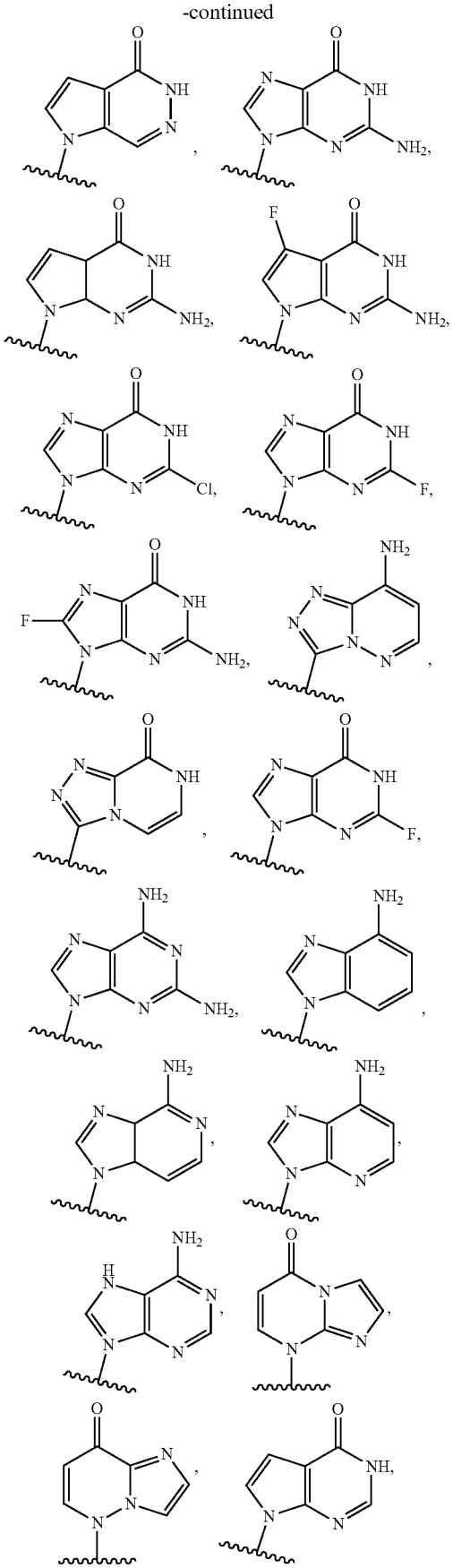

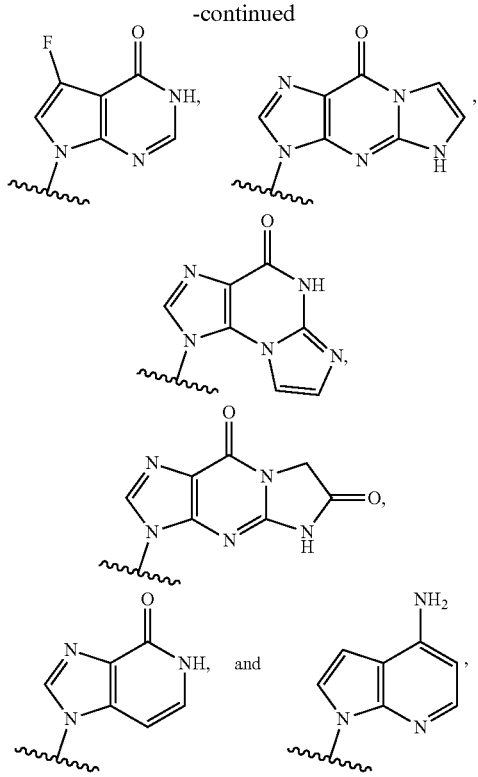

where at least one of Base¹ and Base² is each independently selected from the group consisting of

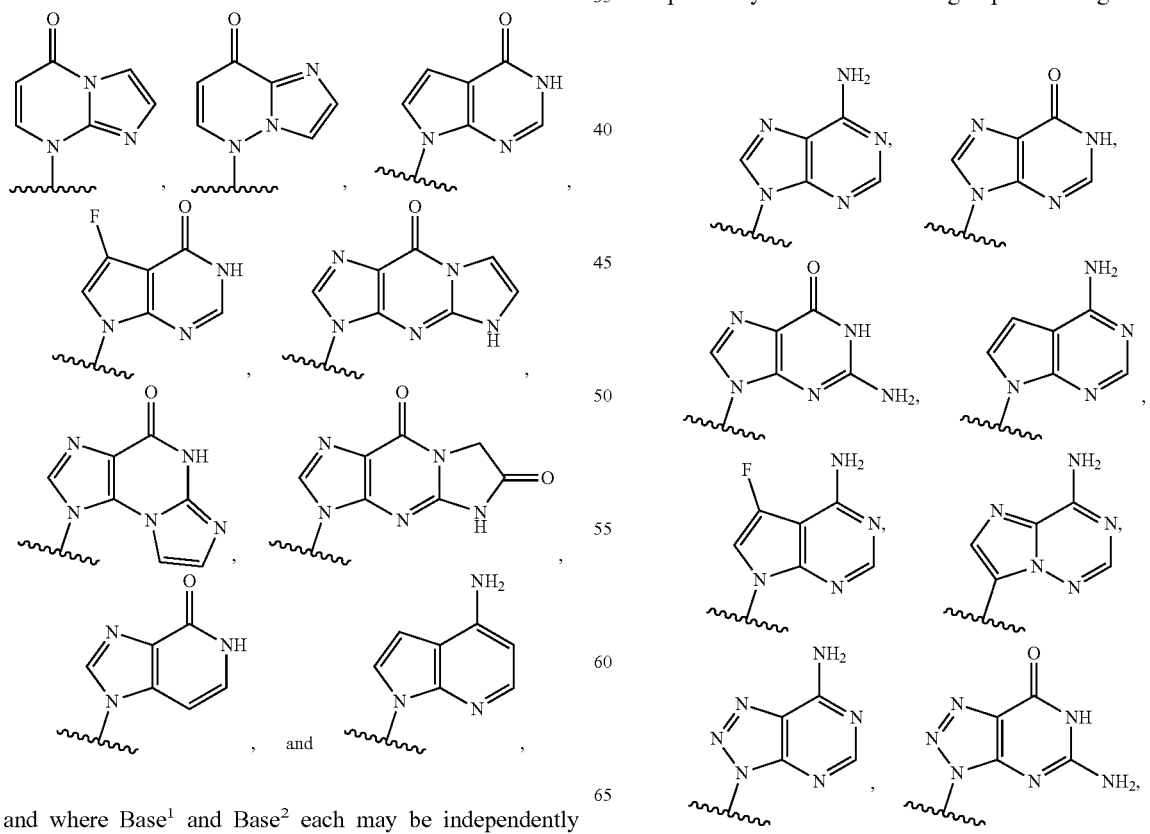

and where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O— and —S—; $X^a$ and $X^{a1}$ are each —O—; $X^b$ and $X^{b1}$ are each —O—; $X^c$ and $X^{c1}$ are each independently selected from the group consisting of —OH and —SH; $X^d$ and $X^{d1}$ are each independently selected from the group consisting of O and S; $R^1$ and $R^{1a}$ are each H; $R^2$ and $R^{2a}$ are each independently selected from the group consisting of H, F, Cl, OH, CN, $N_3$, and —$CH_3$; $R^3$ is selected from the group consisting of H, F, Cl, OH, CN, $N_3$, and —$CH_3$; $R^4$ and $R^{4a}$ are each independently selected from the group consisting of H, F, Cl, OH, CN, $N_3$, and —$CH_3$; $R^5$ is selected from the group consisting of H, F, Cl, OH, CN, $N_3$, and —$CH_3$; $R^6$ and $R^{6a}$ are each independently selected from the group consisting of H, F, CN, $N_3$, —$CH_3$, —$CH=CH_2$, and —C≡CH; $R^7$ and $R^{7a}$ are each H; $R^8$ and $R^{8a}$ are each H; optionally $R^3$ and $R^{6a}$ are connected to form —O—$C_1$-$C_6$ alkylene or —O—$C_2$-$C_6$ alkenylene, such that where $R^3$ and $R^{6a}$ are connected to form —O—$C_1$-$C_6$ alkylene or —O—$C_2$-$C_6$ alkenylene, said O is bound at the $R^3$ position; and optionally $R^5$ and $R^6$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^5$ and $R^6$ are connected to form —O—$C_1$-$C_6$ alkylene or —O—$C_2$-$C_6$ alkenylene, said O is bound at the $R^5$ position. In this embodiment, all other groups are as provided in the general formula (I) above or in the first through fourteenth embodiments described above.

In a twenty-third embodiment, Base¹ and Base² are each independently selected from the group consisting of -continued

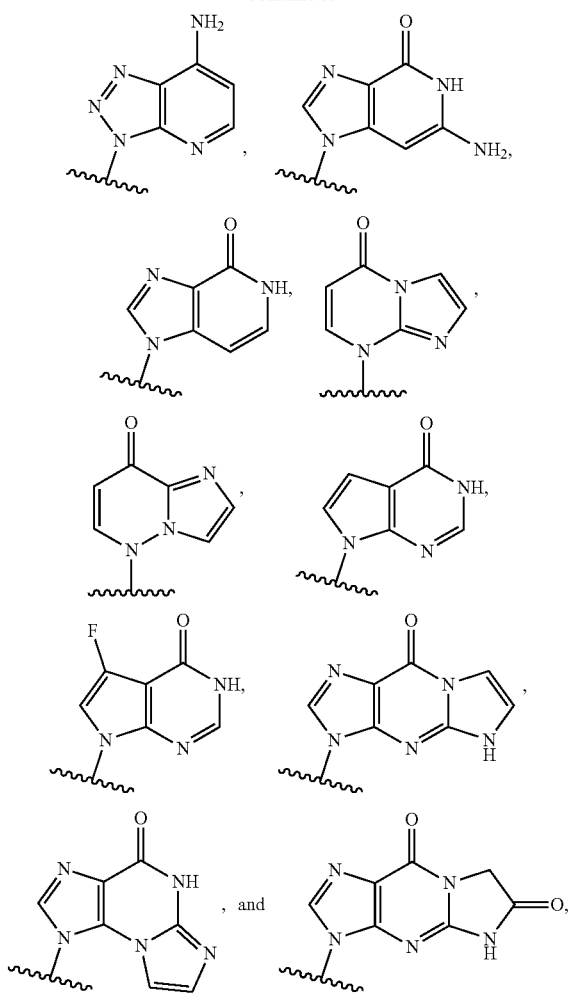

where at least one of Base[1] and Base[2] is each independently selected from the group consisting of

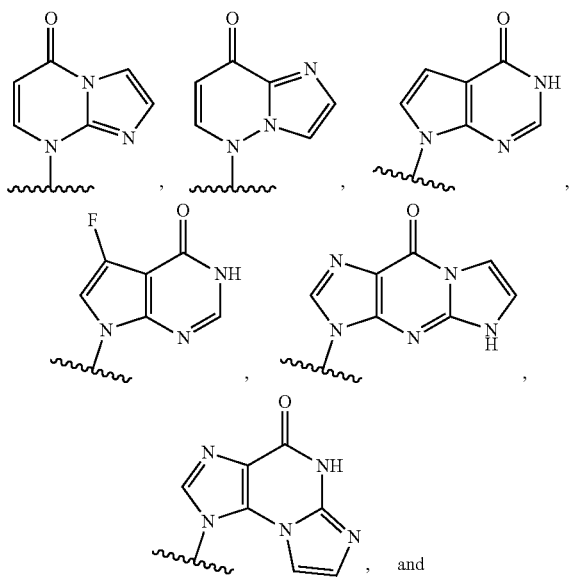

-continued

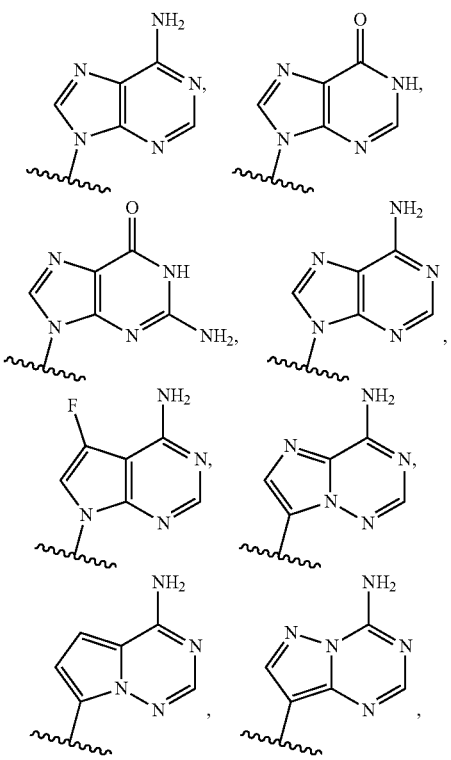

and where Base[1] and Base[2] each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O— and —S—; $X^a$ and $X^{a1}$ are each —O—; $X^b$ and $X^{b1}$ are each —O—; $X^c$ and $X^{c1}$ are each independently selected from the group consisting of —SH and —OH; $X^d$ and $X^{d1}$ are each independently selected from the group consisting of O and S; $R^1$ and $R^{1a}$ are each H; $R^2$ is H; $R^{2a}$ is selected from the group consisting of H, F, and OH; $R^3$ is selected from the group consisting of H, F, and OH; $R^4$ is selected from the group consisting of H, F, and OH; $R^{4a}$ is H; $R^5$ is selected from the group consisting of H, F, and OH; $R^6$ and $R^{6a}$ are each H; $R^7$ and $R^{7a}$ are each H; and $R^8$ and $R^{8a}$ are each H; and optionally $R^3$ and $R^{6a}$ are connected to form —O—$C_1$-$C_6$ alkylene, such that where $R^3$ and $R^{6a}$ are connected to form —O—$C_1$-$C_6$ alkylene, said O is bound at the $R^3$ position. In this embodiment, all other groups are as provided in the general formula (I) above or in the first through fourteenth embodiments described above.

In a twenty-fourth embodiment, Base[1] and Base[2] are each independently selected from the group consisting of -continued
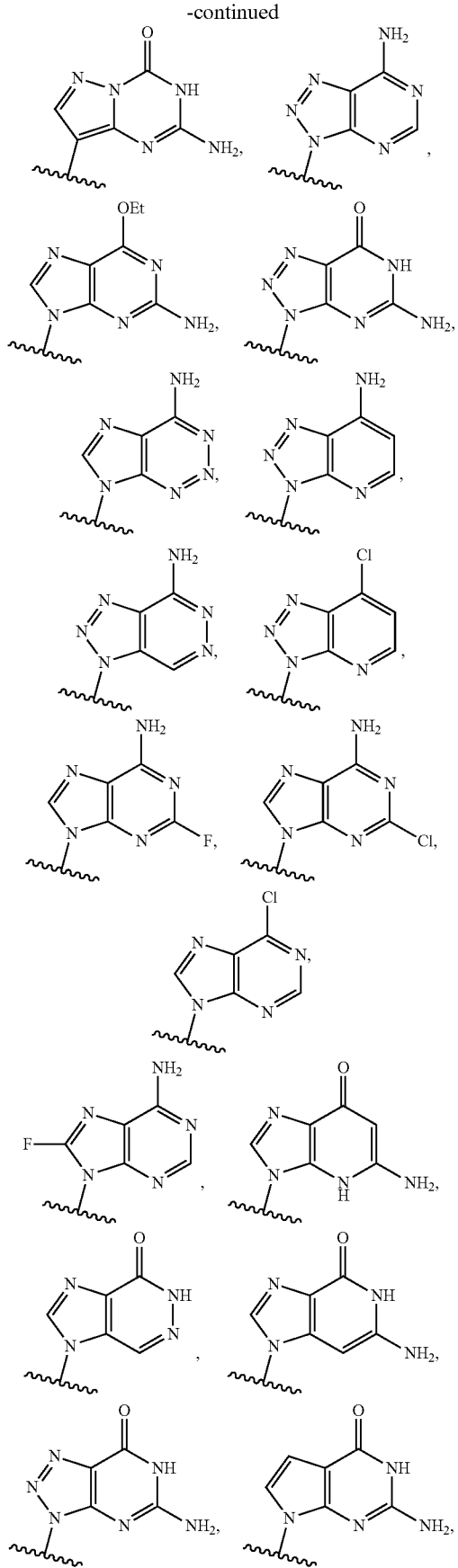
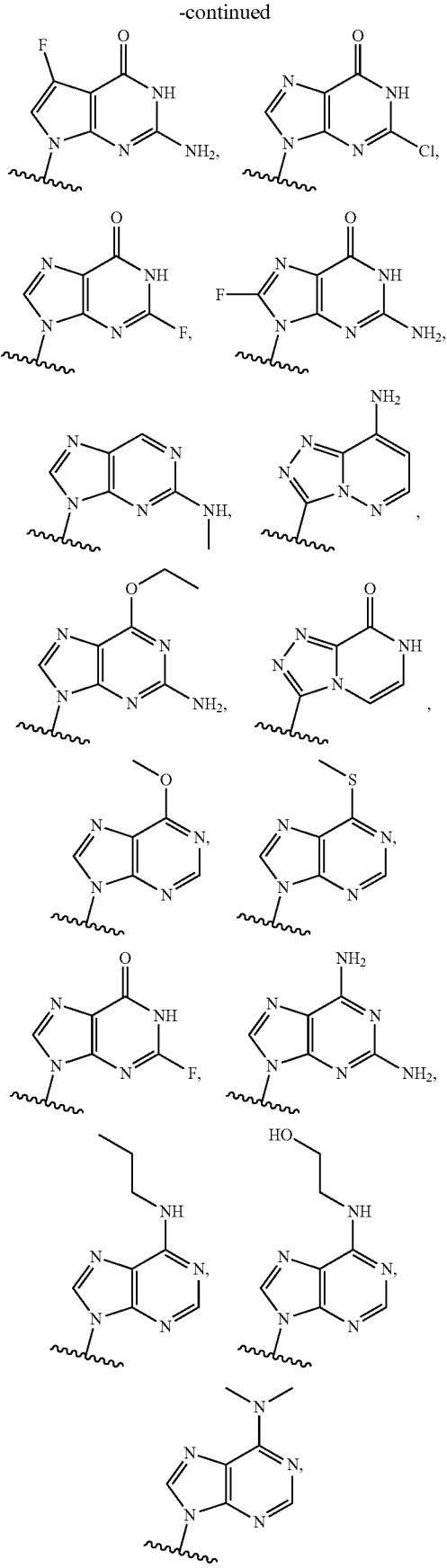

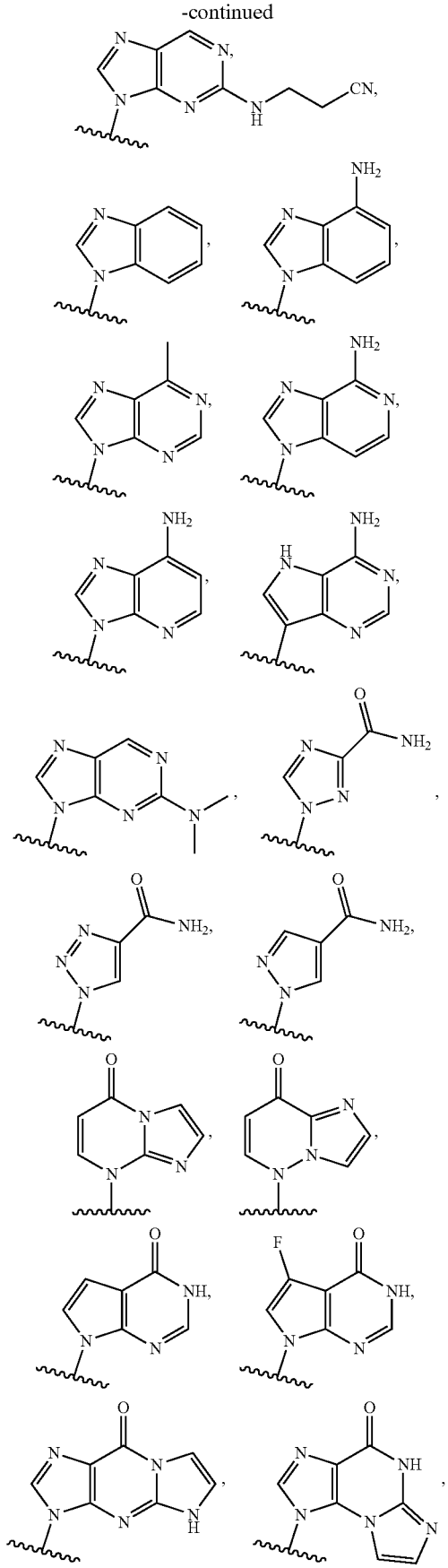

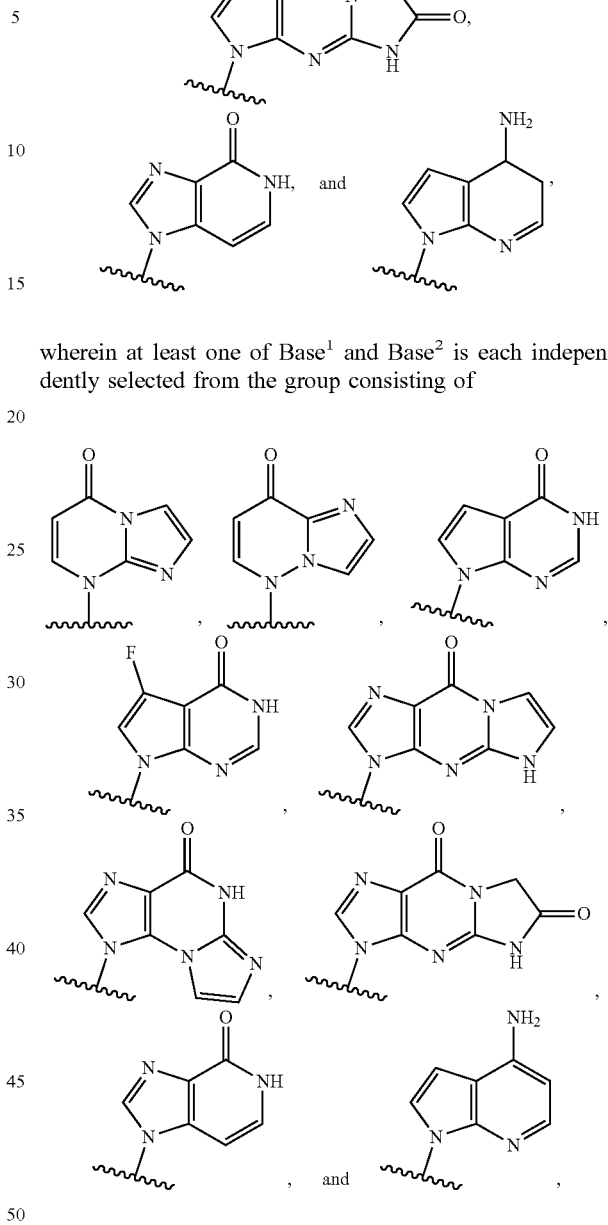

wherein at least one of Base¹ and Base² is each independently selected from the group consisting of and Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O— and —S—; $X^a$ and $X^{a1}$ are each independently selected from the group consisting of —O— and —S—; $X^b$ and $X^{b1}$ are each independently selected from the group consisting of —O— and —S—; $X^c$ and $X^{c1}$ are each independently selected from the group consisting of —$SR^9$, —$OR^9$, and $NR^9R^9$; $X^d$ and $X^{d1}$ are each independently selected from the group consisting of O and S; $R^1$ and $R^{1a}$ are each H; $R^2$ and $R^{2a}$ are each independently selected from the group consisting of H, F, Cl, Br, I, OH, CN, N₃, C₁-C₆ alkyl, and C₁-C₆ haloalkyl, where said R² and R²ᵃ C₁-C₆ alkyl or C₁-C₆ haloalkyl are substituted by 0 to 3 substituents selected from the group consisting of OH, CN, and N₃; R³ is selected from the group consisting of H, F, Cl, Br, I, OH, CN, N₃, C₁-C₆ alkyl, and C₁-C₆ haloalkyl, where said R³ C₁-C₆ alkyl or C₁-C₆ haloalkyl are substituted by 0 to 3 substituents selected from the group consisting of OH, CN, and N₃; R⁴ and R⁴ᵃ are each independently selected from the group consisting of H, F, Cl, I, Br, CN, OH, N₃, C₁-C₆ alkyl, and C₁-C₆ haloalkyl, where said R⁴ and R⁴ᵃ C₁-C₆ alkyl or C₁-C₆ haloalkyl are substituted by 0 to 3 substituents selected from the group consisting of OH, CN, and N₃; R⁵ is selected from the group consisting of H, F, Cl, Br, I, OH, N₃, C₁-C₆ alkyl, and C₁-C₆ haloalkyl, where said R⁵ C₁-C₆ alkyl or C₁-C₆ haloalkyl are substituted by 0 to 3 substituents selected from the group consisting of F, Cl, Br, I, OH, CN, and N₃; R⁶ and R⁶ᵃ are each independently selected from the group consisting of H, F, Cl, I, Br, OH, CN, N₃, C₁-C₆ alkyl, C₂-C₆ alkenyl, and C₂-C₆ alkynyl, where said R⁶ and R⁶ᵃ C₁-C₆ alkyl, C₂-C₆ alkenyl, and C₂-C₆ alkynyl are substituted by 0 to 3 substituents selected from the group consisting of F, Cl, Br, I, OH, CN, and N₃; R⁷ and R⁷ᵃ are each independently selected from the group consisting of H, C₁-C₆ alkyl, and C₁-C₆ haloalkyl, where said R⁷ and R⁷ᵃ C₁-C₆ alkyl or C₁-C₆ haloalkyl are substituted by 0 to 3 substituents selected from the group consisting of OH, CN, and N₃; R⁸ and R⁸ᵃ are each independently selected from the group consisting of H, C₁-C₆ alkyl, and C₁-C₆ haloalkyl, where said R⁸ and R⁸ᵃ C₁-C₆ alkyl or C₁-C₆ haloalkyl are substituted by 0 to 3 substituents selected from the group consisting of OH, CN, and N₃; each R⁹ is independently selected from the group consisting of H, C₁-C₆ alkyl,

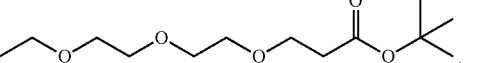

, and

, where each R⁹ C₁-C₆ alkyl is optionally substituted by 1 to 2 substituents independently selected from the group consisting of OH, —O—C₁-C₂₀ alkyl, —S—C(O)C₁-C₆ alkyl, and —C(O)OC₁-C₆ alkyl; optionally R³ and R⁶ᵃ are connected to form C₂-C₆ alkylene, C₂-C₆ alkenylene, —O—C₁-C₆ alkylene, or —O—C₂-C₆ alkenylene, such that where R³ and R⁶ᵃ are connected to form —O—C₁-C₆ alkylene or —O—C₂-C₆ alkenylene, said O is bound at the R³ position; and optionally R⁵ and R⁶ are connected to form C₁-C₆ alkylene, C₂-C₆ alkenylene, —O—C₁-C₆ alkylene, or —O—C₂-C₆ alkenylene, such that where R⁵ and R⁶ are connected to form —O—C₁-C₆ alkylene or —O—C₂-C₆ alkenylene, said O is bound at the R⁵ position. In this embodiment, all other groups are as provided in the general formula (I) above or in the first through fourteenth embodiments described above.

In a twenty-fifth embodiment, Base¹ and Base² are each independently selected from the group consisting of

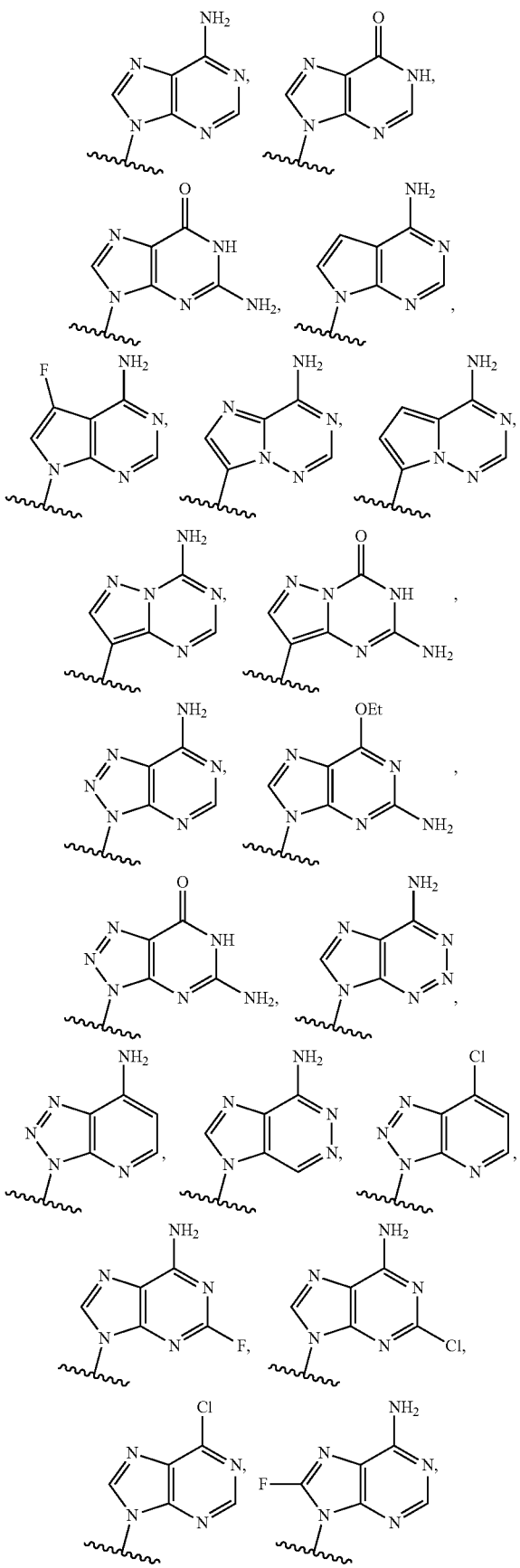

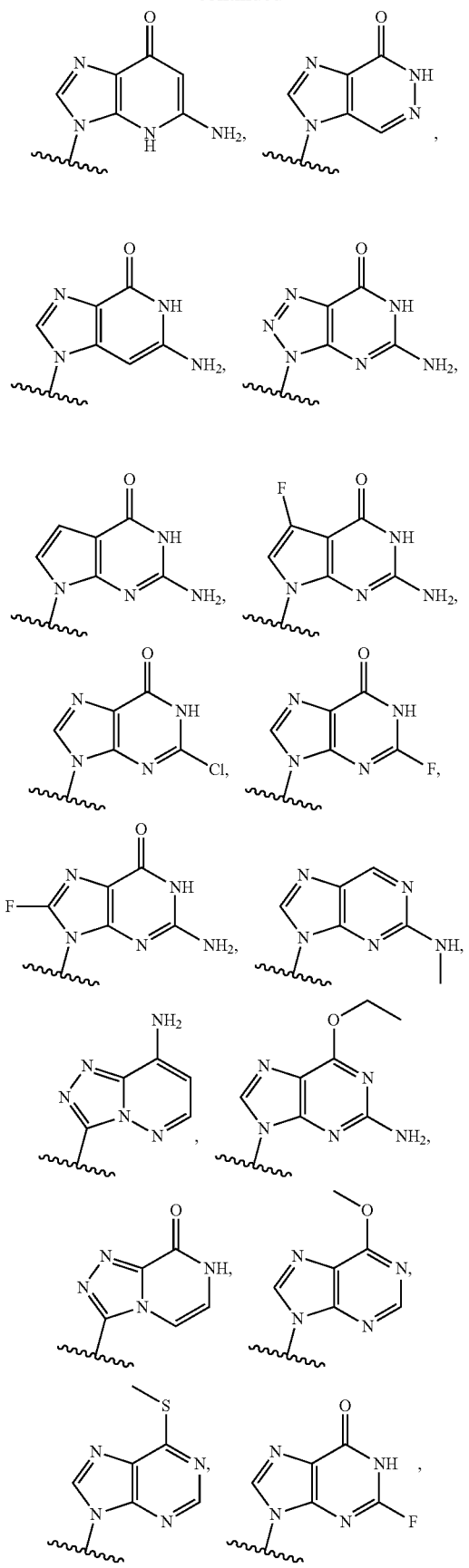
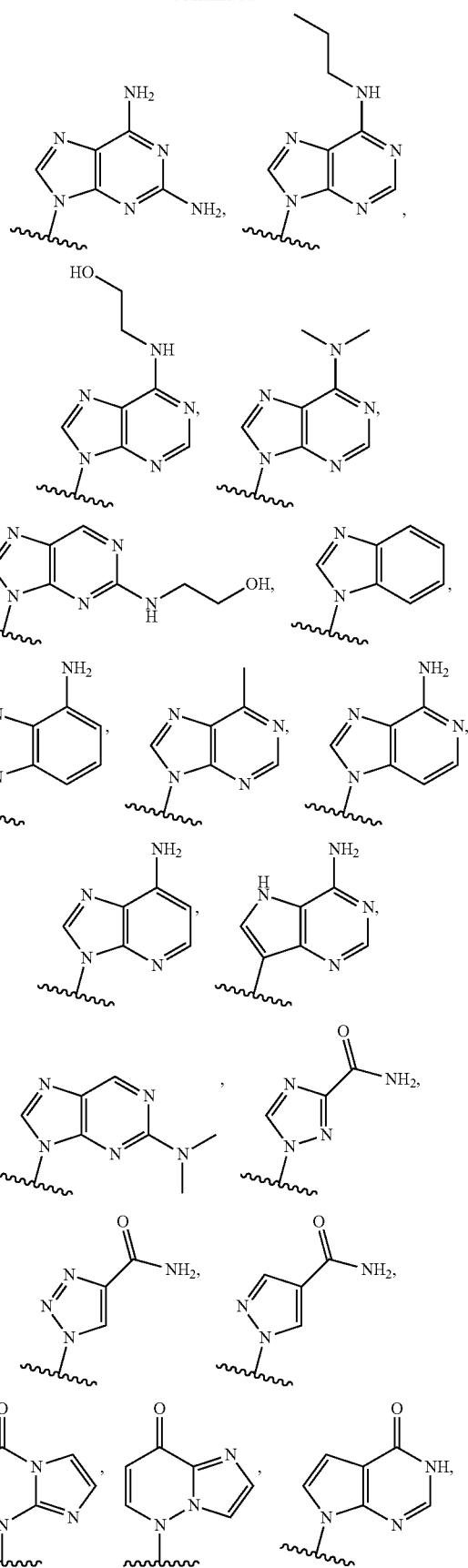

-continued

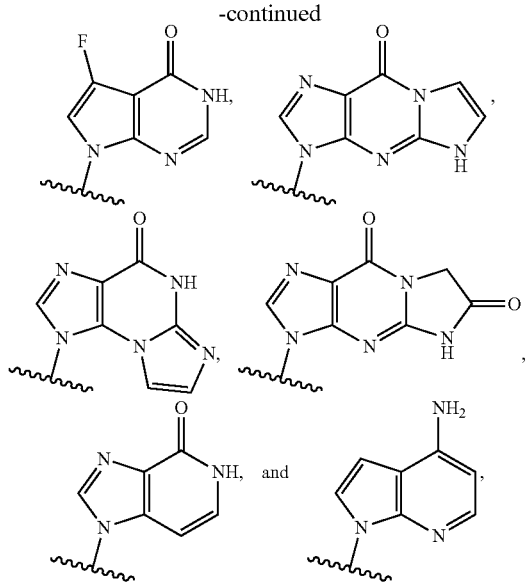

wherein at least one of Base¹ and Base² is each independently selected from the group consisting of and Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O— and —S—; $X^a$ and $X^{a1}$ are each independently selected from the group consisting of —O— and —S—; $X^b$ and $X^{b1}$ are each independently selected from the group consisting of —O— and —S—; $X^c$ and $X^{c1}$ are each independently selected from the group consisting of —OH, —SH,

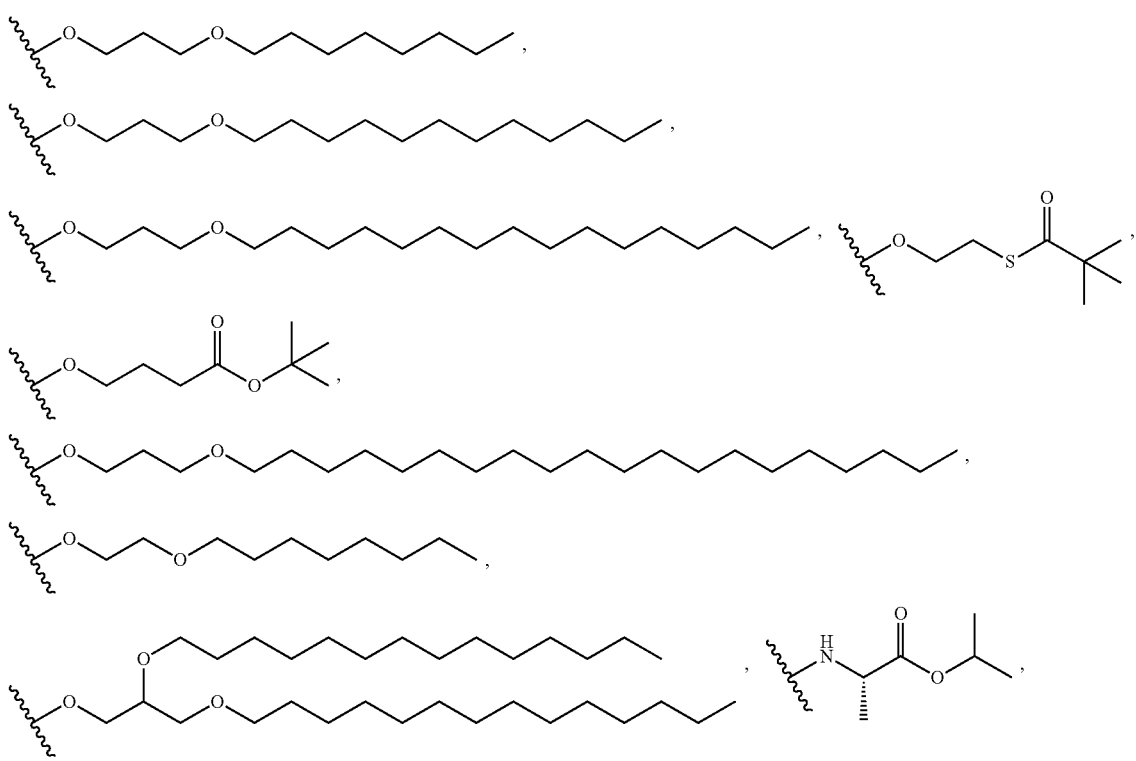

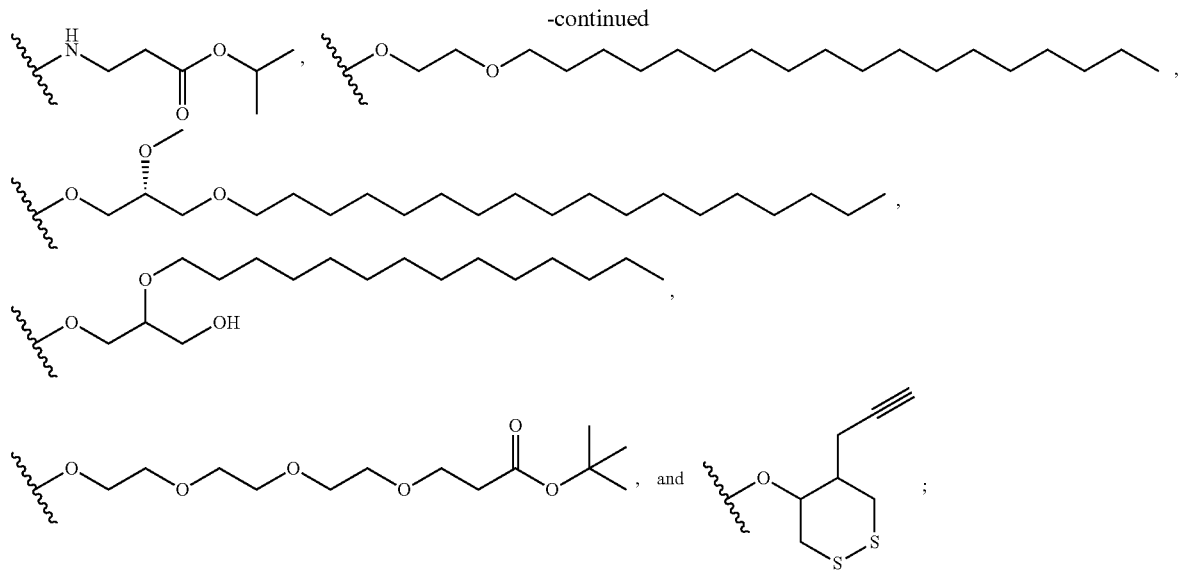

$X^d$ and $X^{d1}$ are each independently selected from the group consisting of O and S; $R^1$ and $R^{1a}$ are each H; $R^2$ and $R^{2a}$ are each independently selected from the group consisting of H, F, Cl, I, Br, OH, CN, $N_3$, —$CF_3$, —$CH_3$, —$CH_2OH$, and —$CH_2CH_3$; $R^3$ is selected from the group consisting of H, F, Cl, I, Br, OH, CN, $N_3$, —$CF_3$, —$CH_3$, —$CH_2OH$, and —$CH_2CH_3$; $R^4$ and $R^{4a}$ are each independently selected from the group consisting of H, F, Cl, I, Br, OH, CN, $N_3$, —$CF_3$, —$CH_3$, —$CH_2OH$, and —$CH_2CH_3$; $R^5$ is selected from the group consisting of H, F, Cl, I, Br, OH, CN, $N_3$, —$CF_3$, —$CH_3$, —$CH_2OH$, and —$CH_2CH_3$; $R^6$ and $R^{6a}$ are each independently selected from the group consisting of H, F, Cl, I, Br, OH, CN, $N_3$, —$CF_3$, —$CH_3$, —$CH_2OH$, —$CH_2CH_3$, —CH=$CH_2$, —C≡CH, and —C≡C—$CH_3$; $R^7$ and $R^{7a}$ are each independently selected from the group consisting of H, —$CF_3$, —$CH_3$, and —$CH_2CH_3$; $R^8$ and $R^{8a}$ are each independently selected from the group consisting of H, —$CF_3$, —$CH_3$, and —$CH_2CH_3$; optionally $R^3$ and $R^{6a}$ are connected to $C_2$-$C_6$ alkylene, $C_2$-$C_6$ alkenylene, —O—$C_1$-$C_6$ alkylene, or —O—$C_2$-$C_6$ alkenylene, such that where $R^3$ and $R^{6a}$ are connected to form —O—$C_1$-$C_6$ alkylene or —O—$C_2$-$C_6$ alkenylene, said O is bound at the $R^3$ position; and optionally $R^5$ and $R^6$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^5$ and $R^6$ are connected to form —O—$C_1$-$C_6$ alkylene or —O—$C_2$-$C_6$ alkenylene, said O is bound at the $R^5$ position. In this embodiment, all other groups are as provided in the general formula (I) above or in the first through fourteenth embodiments described above.

In a twenty-sixth embodiment, Base$^1$ and Base$^2$ are each independently selected from the group consisting of

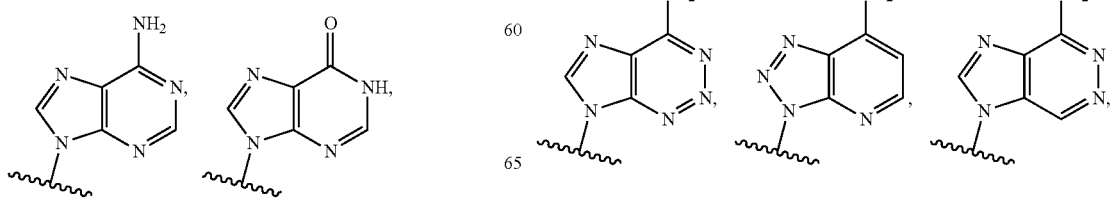

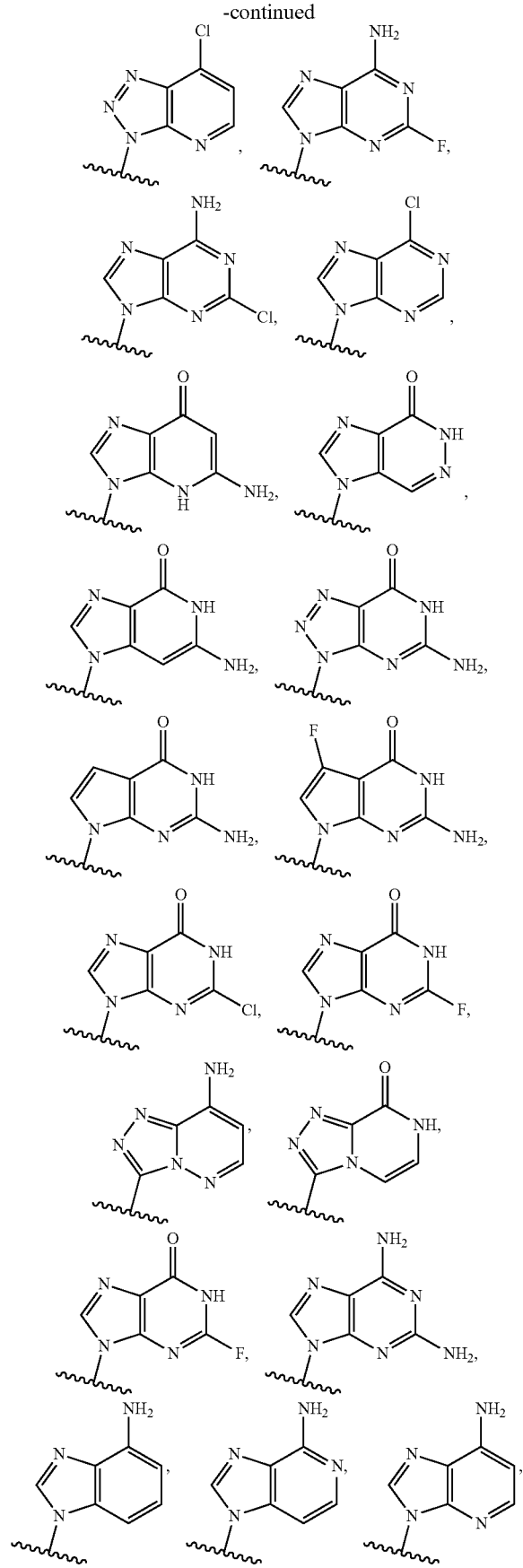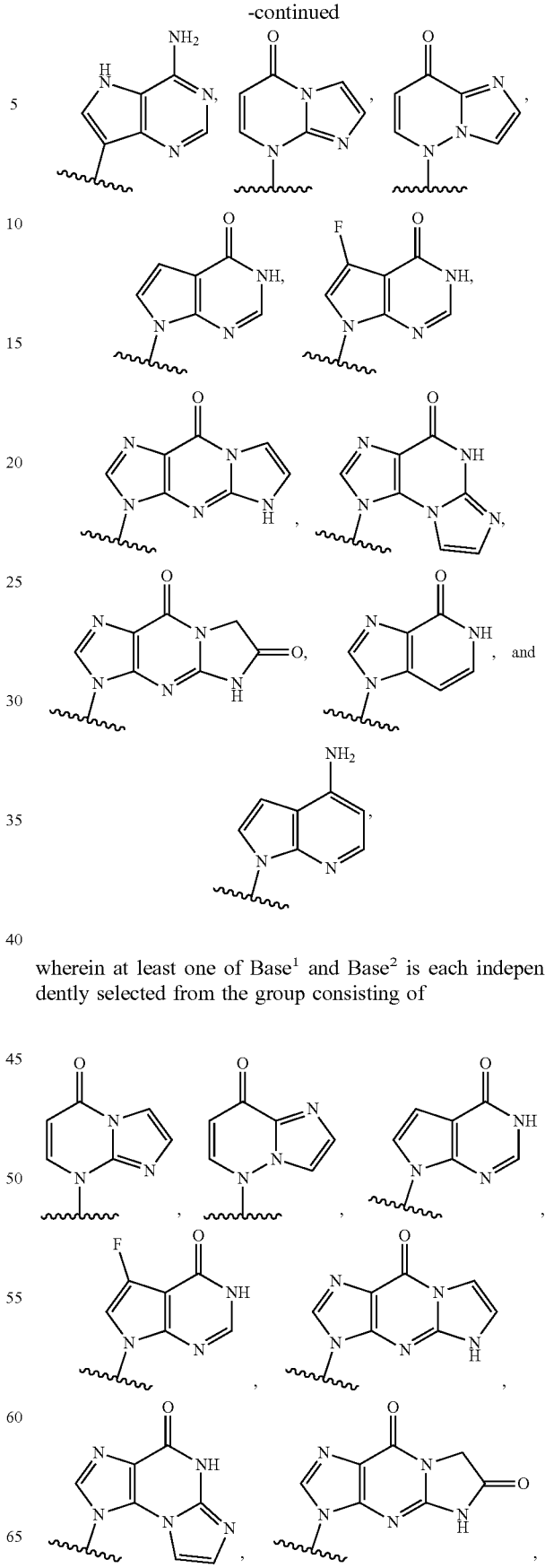
wherein at least one of Base[1] and Base[2] is each independently selected from the group consisting of

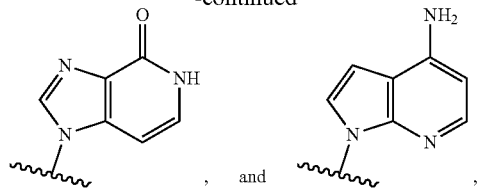
, and and Base¹ and Base² each may be independently substituted by 0 to 3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O— and —S—; $X^a$ and $X^{a1}$ are each —O—; $X^b$ and $X^{b1}$ are each —O—; $X^c$ and $X^{c1}$ are each independently selected from the group consisting of —OH and —SH; $X^d$ and $X^{d1}$ are each independently selected from the group consisting of O and S; $R^1$ and $R^{1a}$ are each H; $R^2$ and $R^{2a}$ are each independently selected from the group consisting of H, F, Cl, OH, CN, $N_3$, and —$CH_3$; $R^3$ is selected from the group consisting of H, F, Cl, OH, CN, $N_3$, and —$CH_3$; $R^4$ and $R^{4a}$ are each independently selected from the group consisting of H, F, Cl, OH, CN, $N_3$, and —$CH_3$; $R^5$ is selected from the group consisting of H, F, Cl, OH, CN, $N_3$, and —$CH_3$; $R^6$ and $R^{6a}$ are each independently selected from the group consisting of H, F, CN, $N_3$, —$CH_3$, —CH=$CH_2$, and —C≡CH; $R^7$ and $R^{7a}$ are each H; $R^8$ and $R^{8a}$ are each H; optionally $R^3$ and $R^{6a}$ are connected to form —O—$C_1$-$C_6$ alkylene or —O—$C_2$-$C_6$ alkenylene, such that O is bound at the $R^3$ position; and optionally $R^5$ and $R^6$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^5$ and $R^6$ are connected to form —O—$C_1$-$C_6$ alkylene or —O—$C_2$-$C_6$ alkenylene, said O is bound at the $R^5$ position. In this embodiment, all other groups are as provided in the general formula (I) above or in the first through fourteenth embodiments described above.

In a twenty-seventh embodiment, Base¹ and Base² are each independently selected from the group consisting of

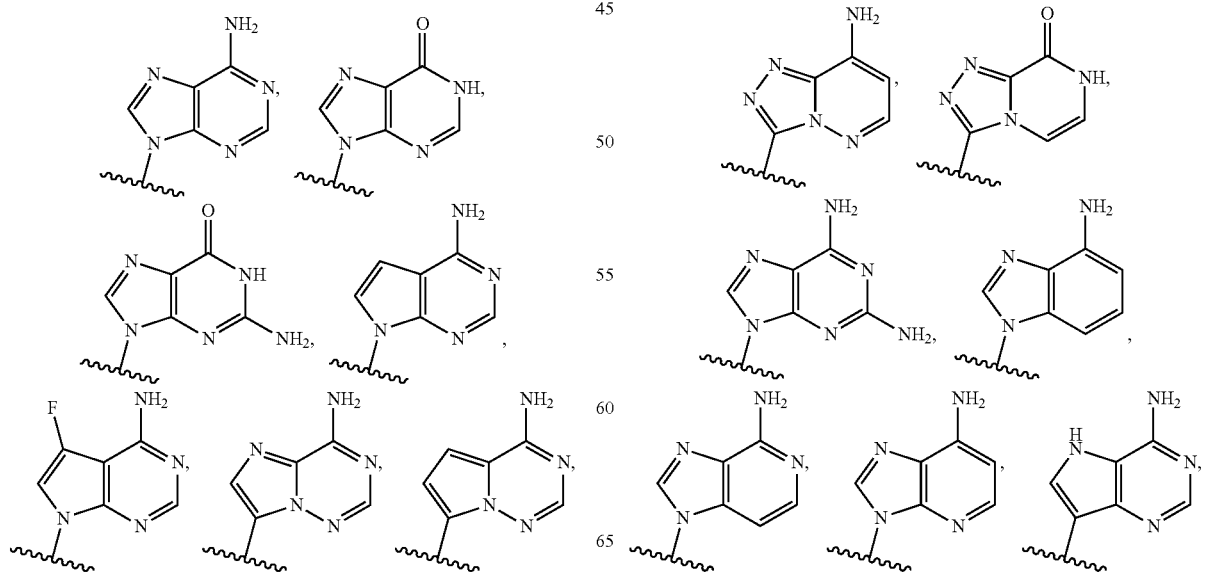

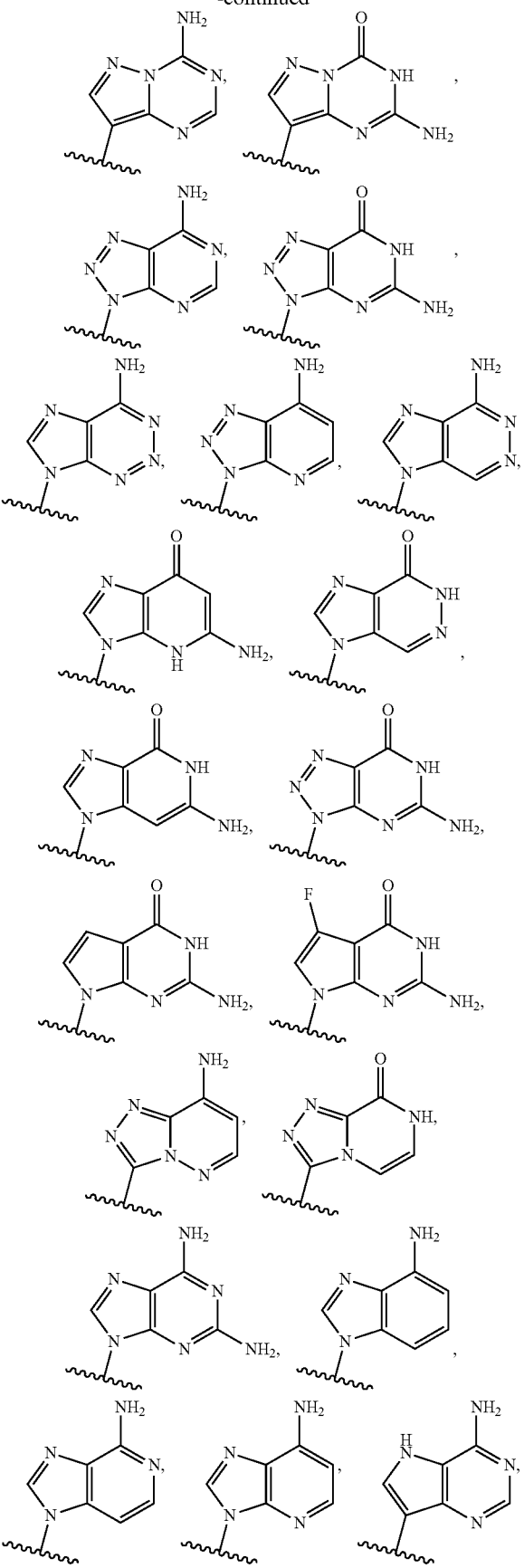

-continued

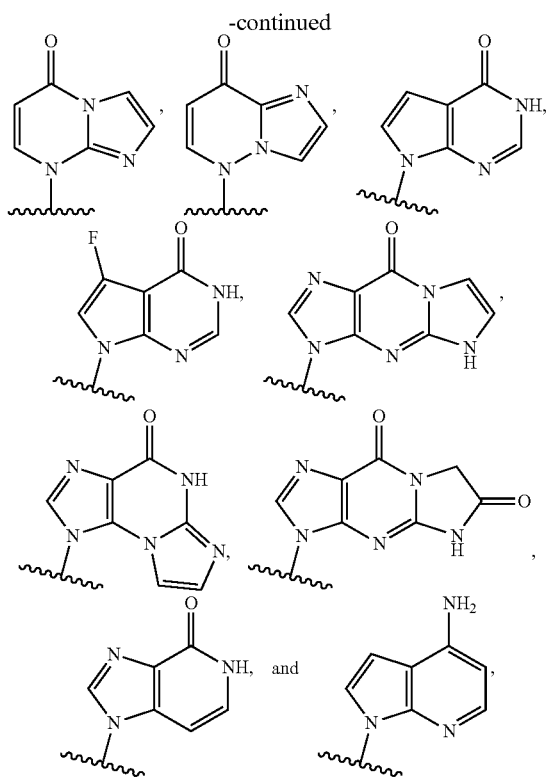

wherein at least one of Base¹ and Base² is each independently selected from the group consisting of

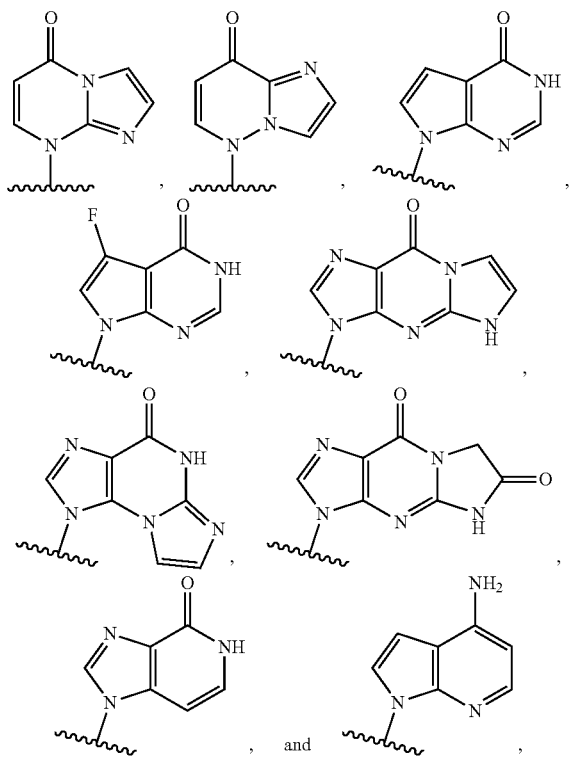

and Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O— and —S—; $X^a$ and $X^{a1}$ are each —O—; $X^b$ and $X^{b1}$ are each —O—; $X^c$ and $X^{c1}$ are each independently selected from the group consisting of —OH and —SH; $X^d$ and $X^{d1}$ are each independently selected from the group consisting of O and S; $R^1$ and $R^{1a}$ are each H; $R^2$ and $R^{2a}$ are each independently selected from the group consisting of H, F, Cl, OH, CN, $N_3$, and —$CH_3$; $R^3$ is selected from the group consisting of H, F, Cl, OH, CN, $N_3$, and —$CH_3$; $R^4$ and $R^{4a}$ are each independently selected from the group consisting of H, F, Cl, OH, CN, $N_3$, and $CH_3$; $R^5$ is selected from the group consisting of H, F, Cl, OH, CN, $N_3$, and —$CH_3$; $R^6$ and $R^{6a}$ are each independently selected from the group consisting of H, F, CN, $N_3$, —$CH_3$, —$CH=CH_2$, and —C≡CH; $R^7$ and $R^{7a}$ are each H; $R^8$ and $R^{8a}$ are each H; optionally $R^3$ and $R^{6a}$ are connected to form —O—$C_1$-$C_6$ alkylene or —O—$C_2$-$C_6$ alkenylene, such that where $R^3$ and $R^{6a}$ are connected to form —O—$C_1$-$C_6$ alkylene or —O—$C_2$-$C_6$ alkenylene, said O is bound at the $R^3$ position; and optionally $R^5$ and $R^6$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^5$ and $R^6$ are connected to form —O—$C_1$-$C_6$ alkylene or —O—$C_2$-$C_6$ alkenylene, said O is bound at the $R^5$ position. In this embodiment, all other groups are as provided in the general formula (I) above or in the first through fourteenth embodiments described above.

In a twenty-eighth embodiment, Base¹ and Base² are each independently selected from the group consisting of

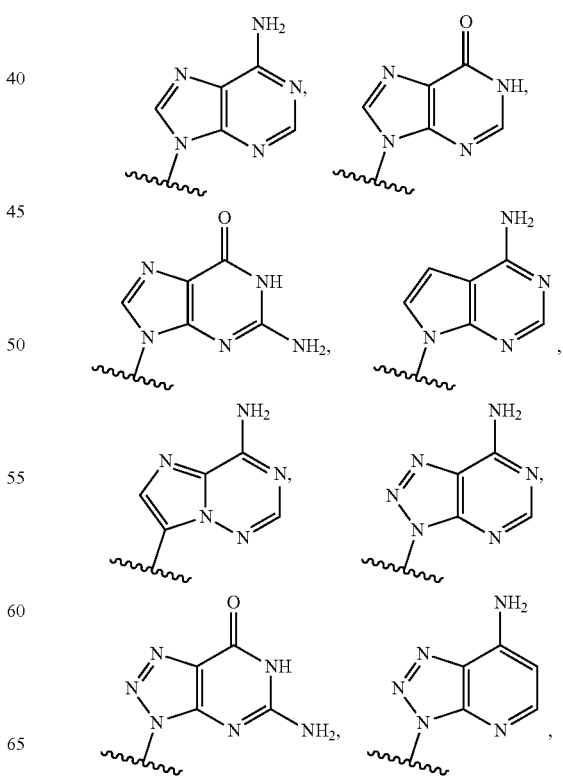

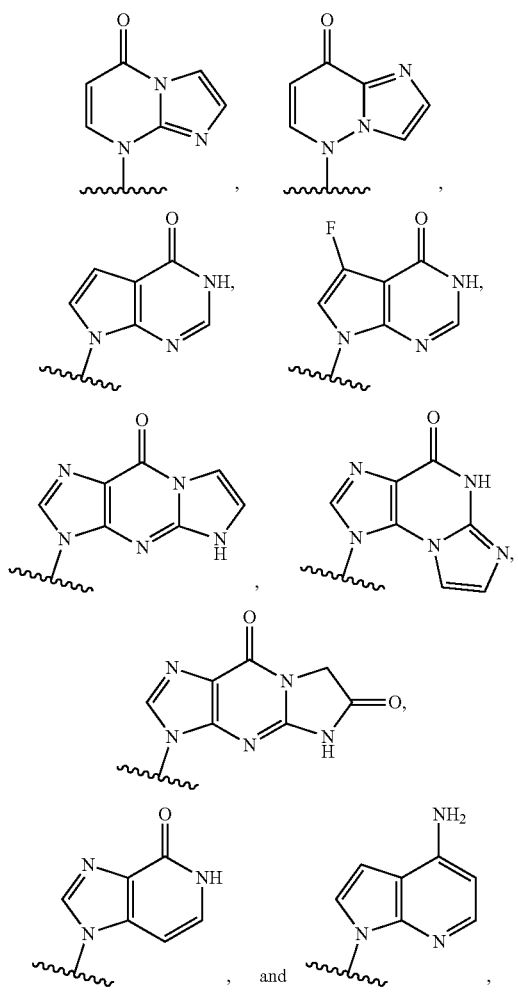

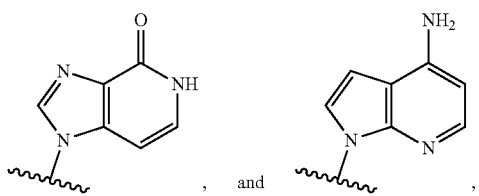

wherein at least one of Base¹ and Base² is each independently selected from the group consisting of

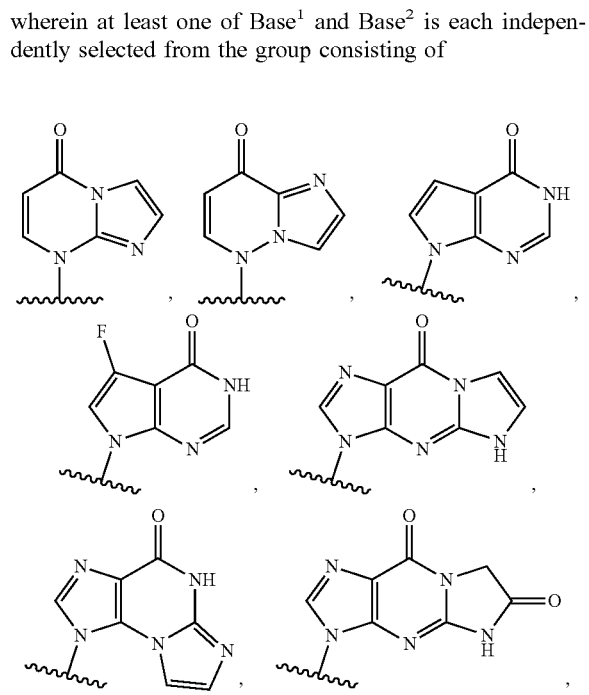

and Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O— and —S—; $X^a$ and $X^{a1}$ are each —O—; $X^b$ and $X^{b1}$ are each —O—; $X^c$ and $X^{c1}$ are each independently selected from the group consisting of —SH and —OH; $X^d$ and $X^{d1}$ are each independently selected from the group consisting of O and S; $R^1$ and $R^{1a}$ are each H; $R^2$ and $R^{2a}$ are each independently selected from the group consisting of H, F, and OH; $R^3$ is selected from the group consisting of H, F, and OH; $R^4$ and $R^{4a}$ are each independently selected from the group consisting of H, F, and OH; $R^5$ is selected from the group consisting of H, F, and OH; $R^6$ and $R^{6a}$ are each H; $R^7$ and $R^{7a}$ are each H; $R^8$ and $R^{8a}$ are each H; and optionally $R^3$ and $R^{6a}$ are connected to form —O—$C_1$-$C_6$ alkylene or —O—$C_2$-$C_6$ alkenylene, such that where $R^3$ and $R^{6a}$ are connected to form —O—$C_1$-$C_6$ alkylene or —O—$C_2$-$C_6$ alkenylene, said O is bound at the $R^3$ position. In this embodiment, all other groups are as provided in the general formula (I) above or in the first through fourteenth embodiments described above.

In a twenty-ninth embodiment, Base¹ and Base² are each independently selected from the group consisting of

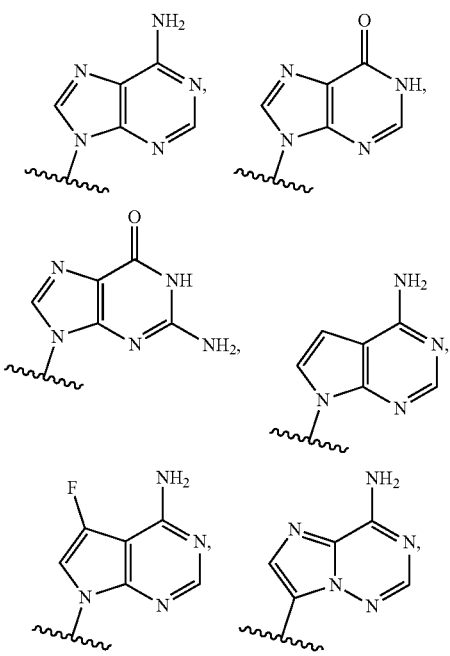

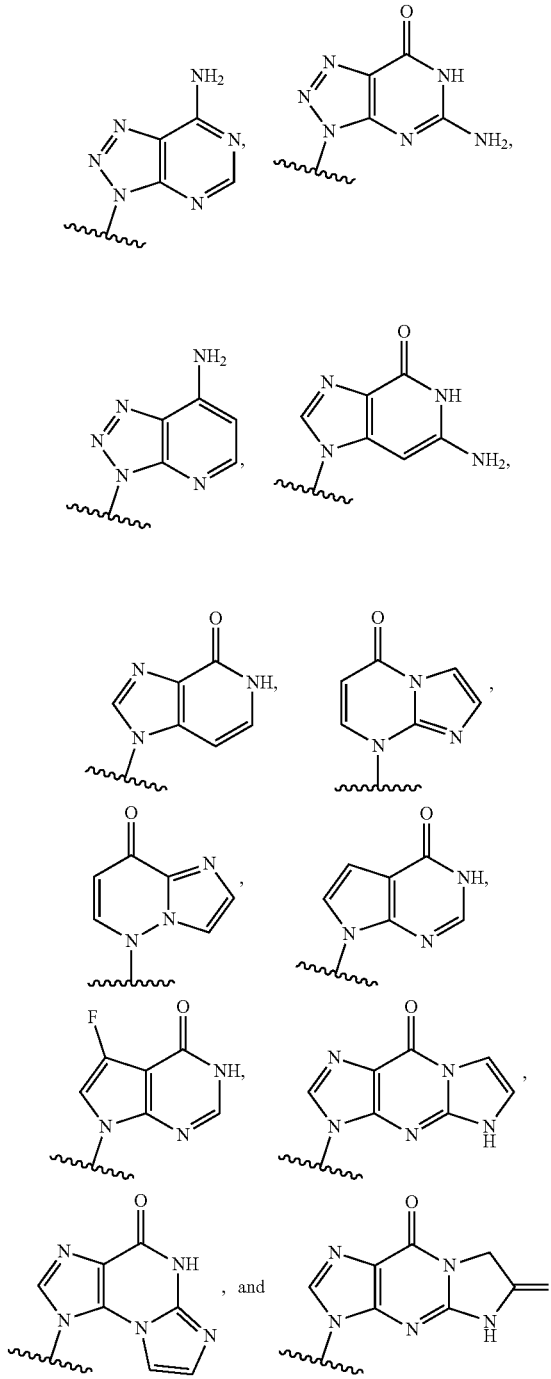

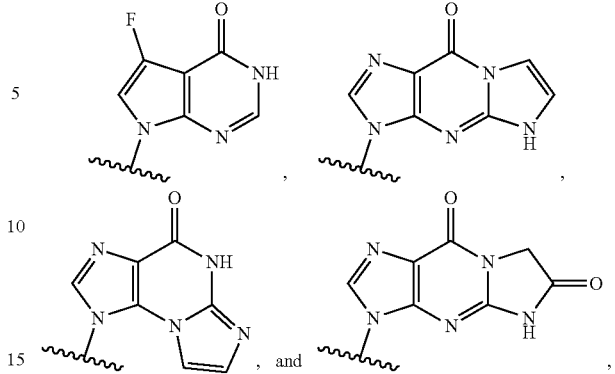

and Base¹ and Base² each may be independently substituted by 0 to 3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O— and —S—; $X^a$ and $X^{a1}$ are each —O—; $X^b$ and $X^{b1}$ are each —O—; $X^c$ and $X^{c1}$ are each independently selected from the group consisting of —SH and —OH; $X^d$ and $X^{d1}$ are each independently selected from the group consisting of O and S; $R^1$ and $R^{1a}$ are each H; $R^2$ is H; $R^{2a}$ is selected from the group consisting of H, F, and OH; $R^3$ is selected from the group consisting of H, F, and OH; $R^4$ is selected from the group consisting of H, F, and OH; $R^{4a}$ is H; $R^5$ is selected from the group consisting of H, F, and OH; $R^6$ and $R^{6a}$ are each H; $R^7$ and $R^{7a}$ are each H; $R^8$ and $R^{8a}$ are each H; and optionally $R^3$ and $R^{6a}$ are connected to form —O—$C_1$-$C_6$ alkylene, such that where $R^3$ and $R^{6a}$ are connected to form —O—$C_1$-$C_6$ alkylene, said O is bound at the $R^3$ position. In this embodiment, all other groups are as provided in the general formula (I) above or in the first through fourteenth embodiments described above.

In a thirtieth embodiment, Base¹ and Base² are each independently selected from the group consisting of

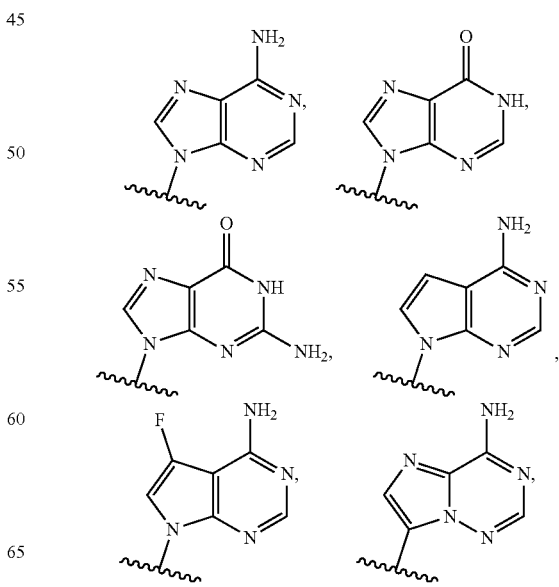

wherein at least one of Base¹ and Base² is each independently selected from the group consisting of

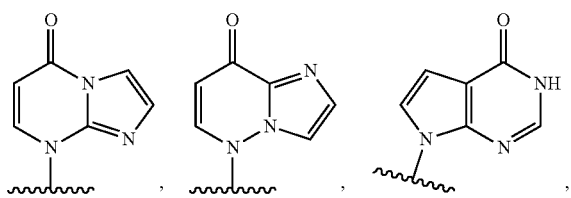

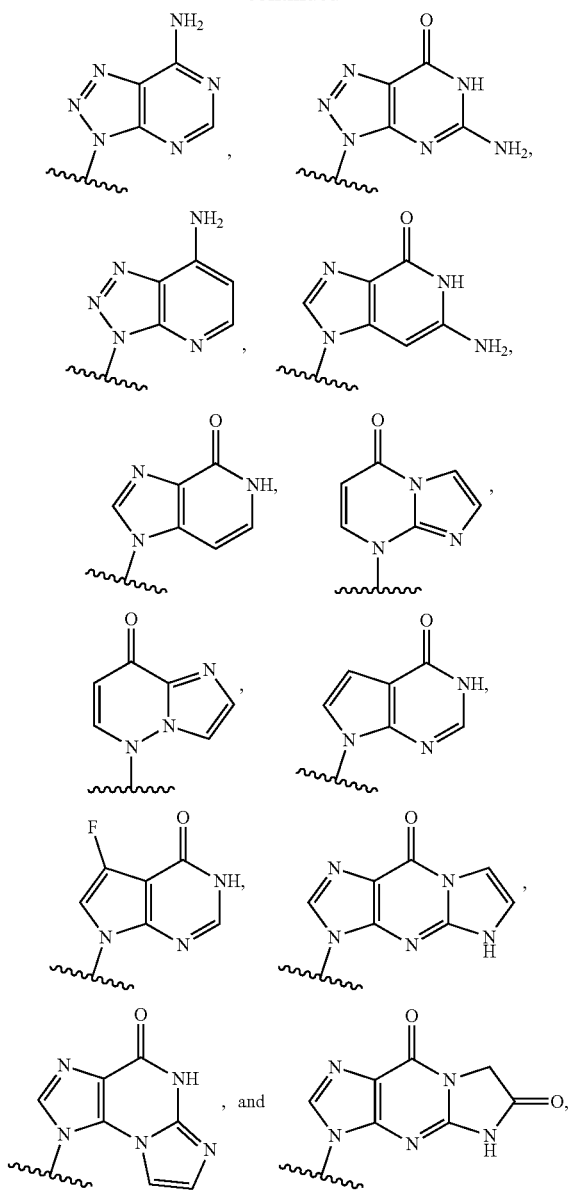

wherein at least one of Base[1] and Base[2] is each independently selected from the group consisting of

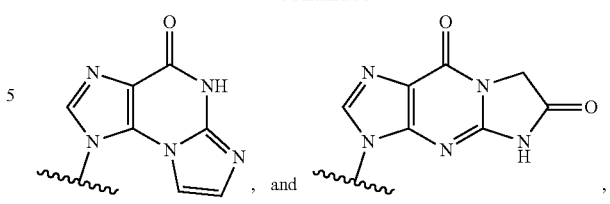

and Base[1] and Base[2] each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O— and —S—; $X^a$ and $X^{a1}$ are each —O—; $X^b$ and $X^{b1}$ are each —O—; $X^c$ and $X^{c1}$ are each independently selected from the group consisting of —SH and —OH; $X^d$ and $X^{d1}$ are each independently selected from the group consisting of O and S; $R^1$ and $R^{1a}$ are each H; $R^2$ is H; $R^{2a}$ is selected from the group consisting of H, F, and OH; $R^3$ is selected from the group consisting of H, F, and OH; $R^4$ is selected from the group consisting of H, F, and OH; $R^{4a}$ is H; $R^5$ is selected from the group consisting of H, F, and OH; $R^6$ and $R^{6a}$ are each H; $R^7$ and $R^{7a}$ are each H; and $R^8$ and $R^{8a}$ are each H. In this embodiment, all other groups are as provided in the general formula (I) above or in the first through fourteenth embodiments described above.

In a thirty-first embodiment, Base[1] is selected from the group consisting of

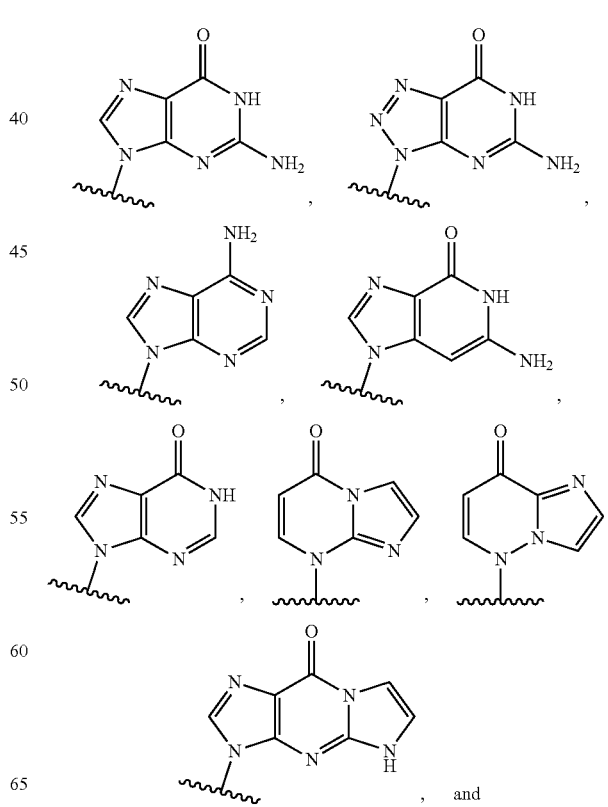

-continued

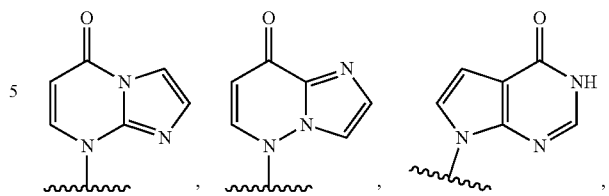

Base² is selected from the group consisting of

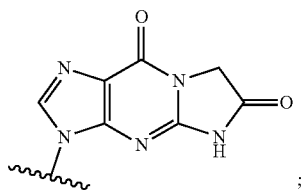

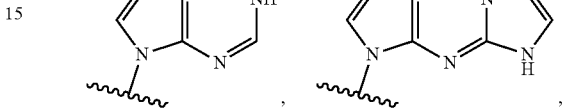

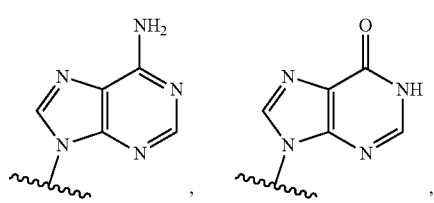

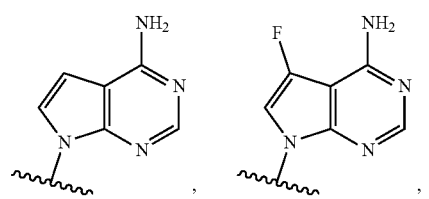

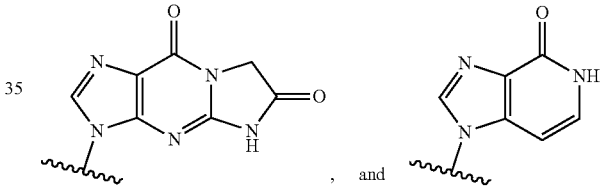

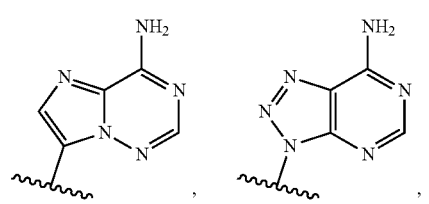

, and

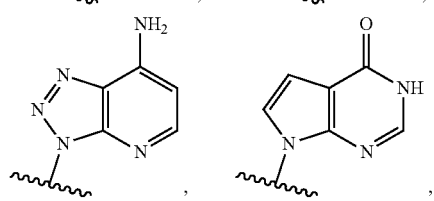

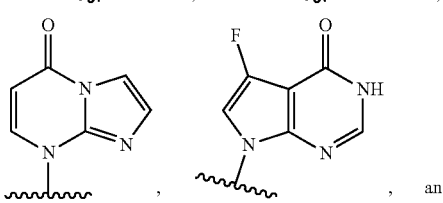

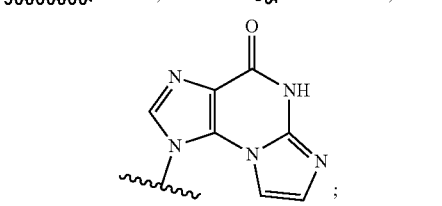

where at least one of Base¹ and Base² is each independently selected from the group consisting of and where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O— and —S—; $X^a$ and $X^{a1}$ are each —O—; $X^b$ and $X^{b1}$ are each —O—; $X^c$ and $X^{c1}$ are each independently selected from the group consisting of —SH and —OH; $X^d$ and $X^{d1}$ are each independently selected from the group consisting of O and S; $R^1$ and $R^{1a}$ are each H; $R^2$ is H; $R^{2a}$ is selected from the group consisting of H, F, and OH; $R^4$ is selected from the group consisting of H, F, and OH; $R^{4a}$ is H; $R^5$ is selected from the group consisting of H, F, and OH; $R^6$ is H; $R^7$ and $R^{7a}$ are each H; and $R^8$ and $R^{8a}$ are each H; and optionally $R^3$ and $R^{6a}$ are connected to form —O—$C_1$-$C_6$ alkylene, such that where $R^3$ and $R^{6a}$ are connected to form —O—$C_1$-$C_6$ alkylene, said O is bound at the $R^3$ position. In this embodiment, all other groups are as provided in the general formula (I) above or in the first through fourteenth embodiments described above.

A thirty-second embodiment relates to a compound selected from the group consisting of 63
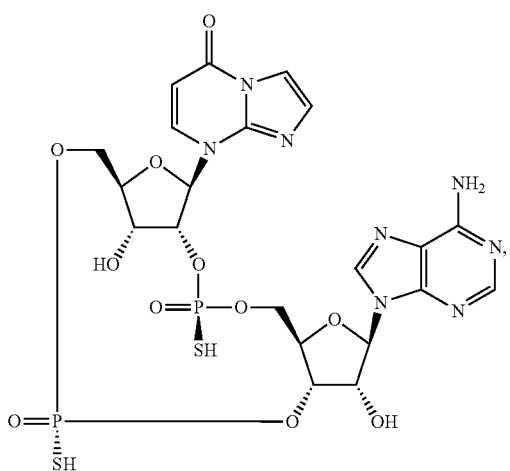
64
-continued
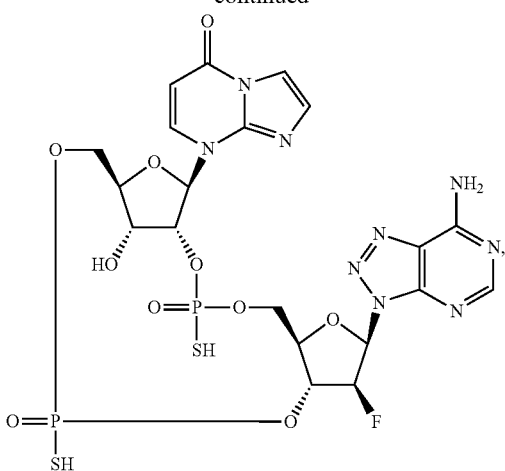
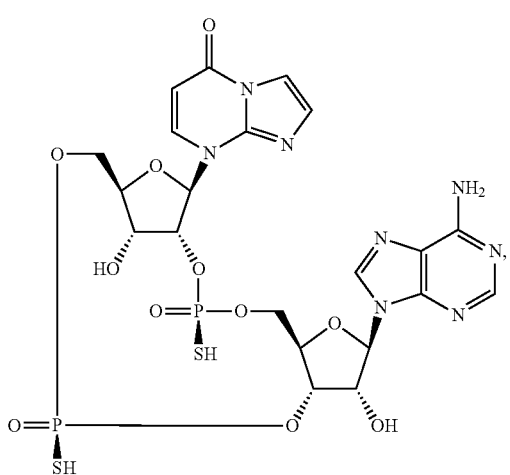
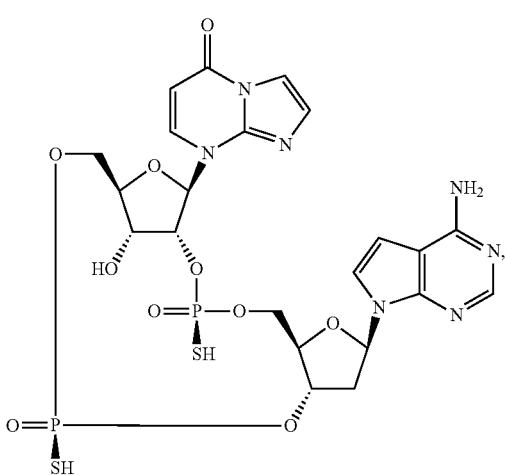
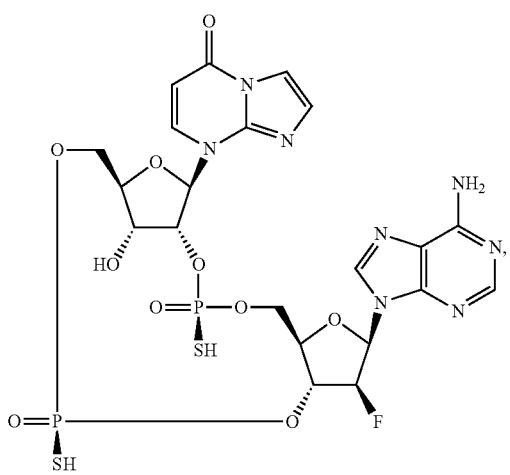
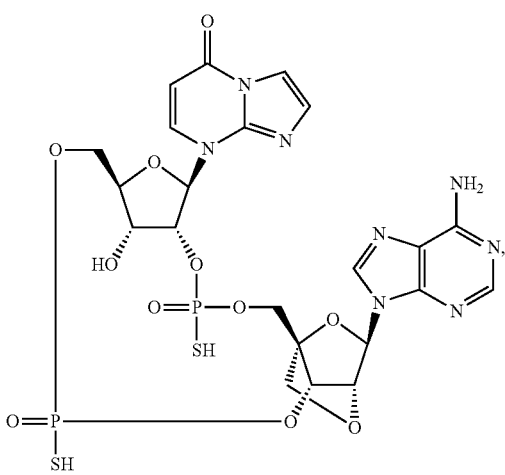

65
-continued
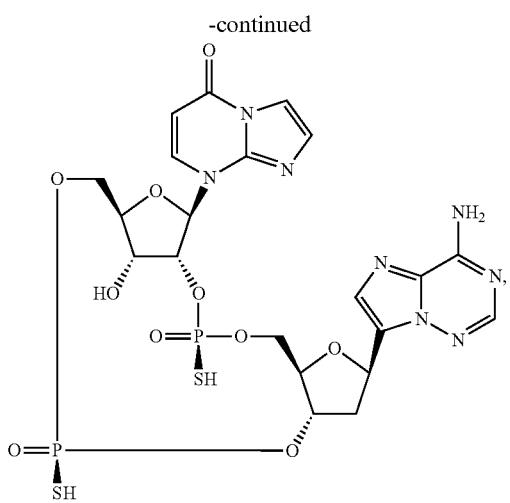
66
-continued
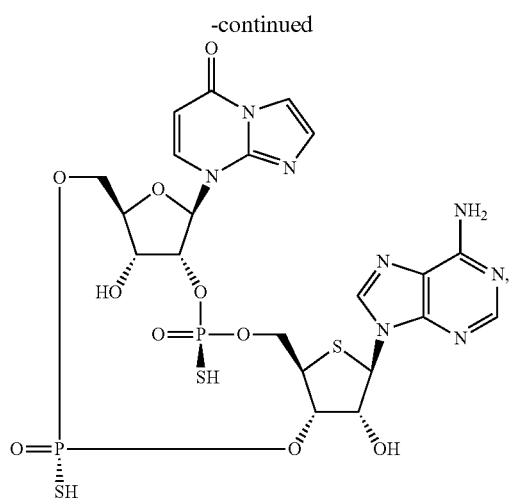
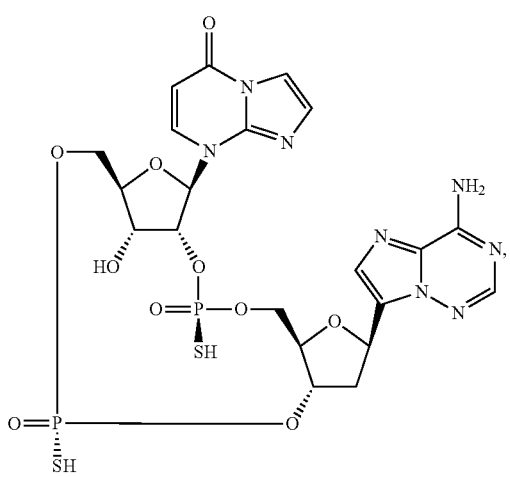
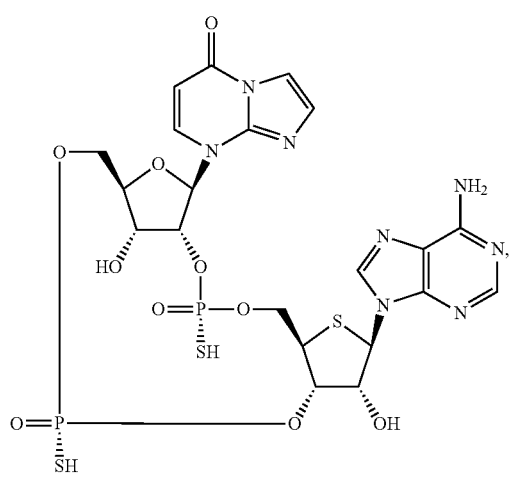
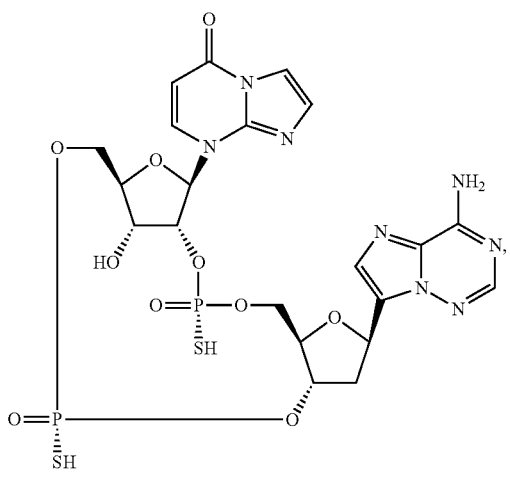
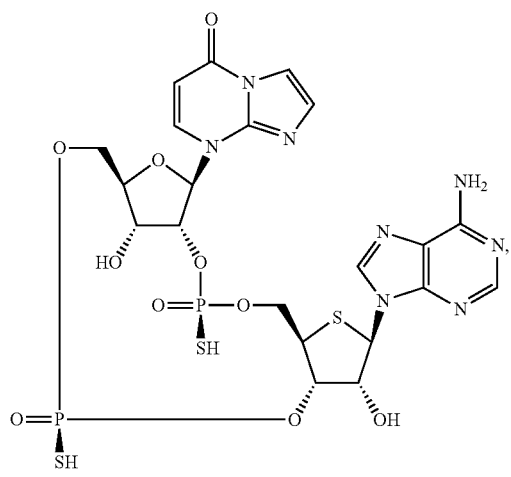

67
-continued
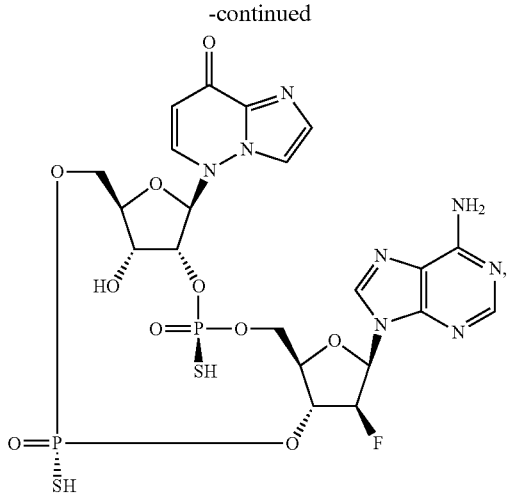
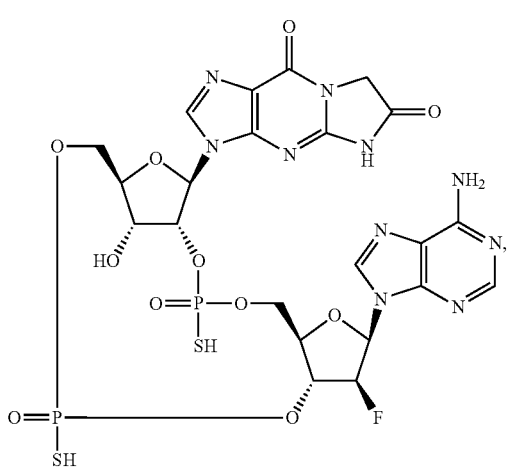
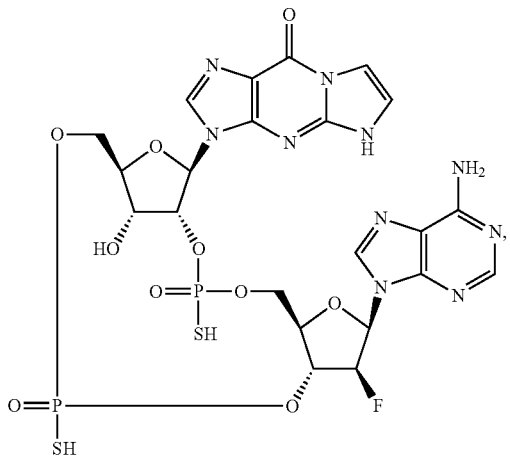
68
-continued
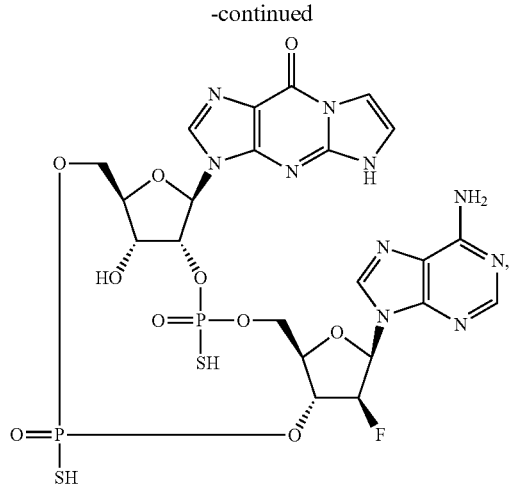
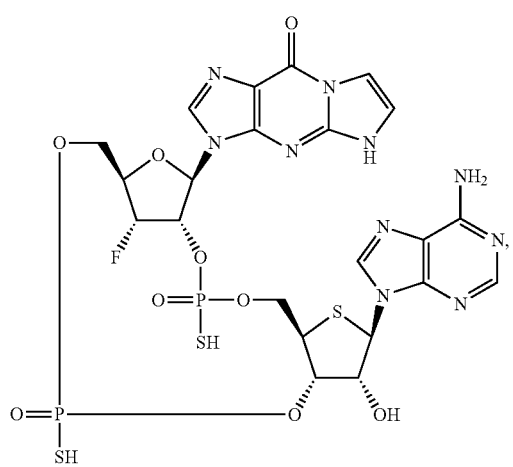
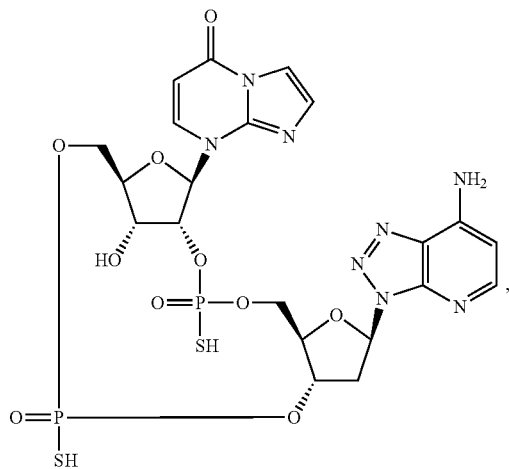

69
-continued
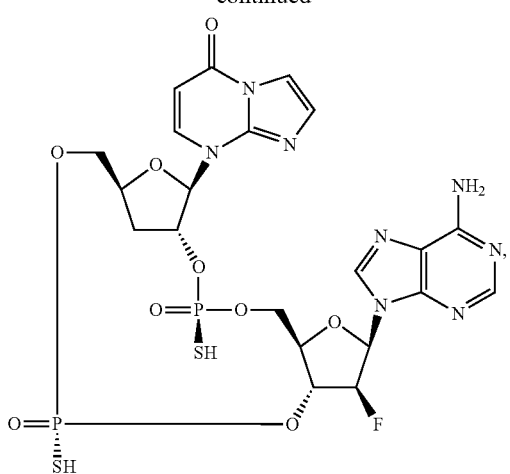
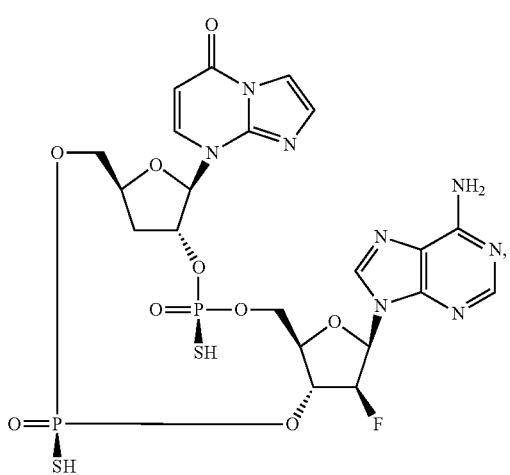
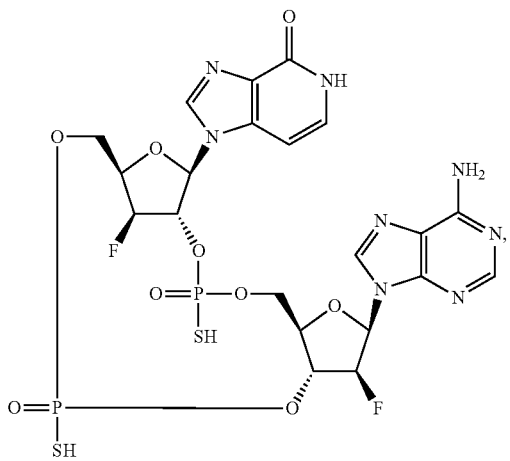
70
-continued
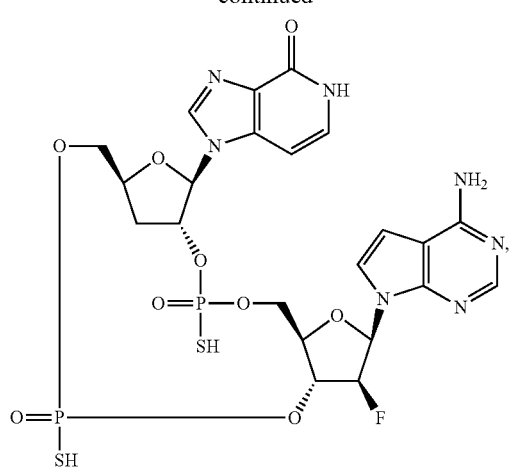
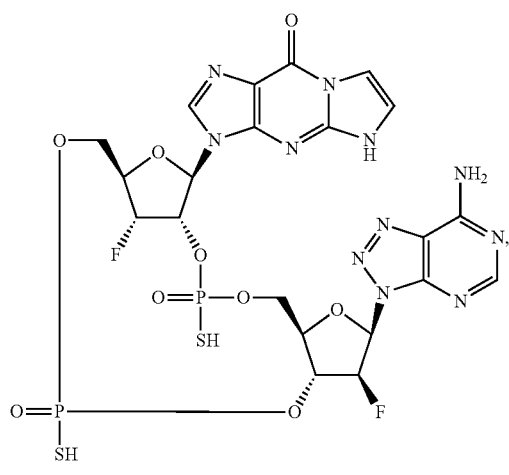
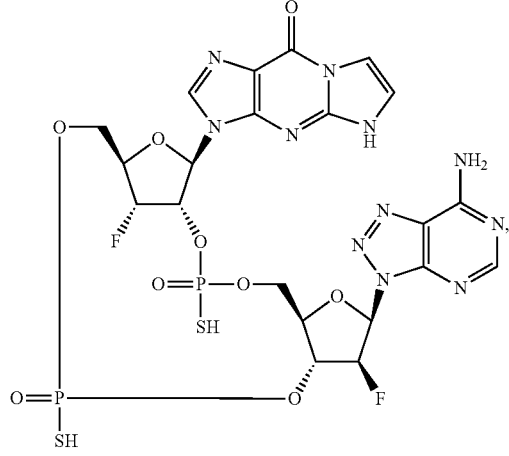

71
-continued
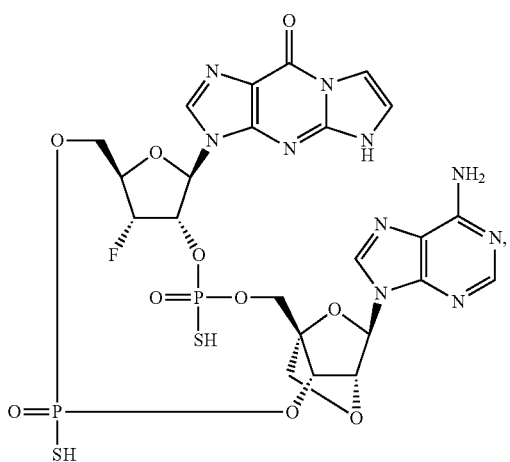
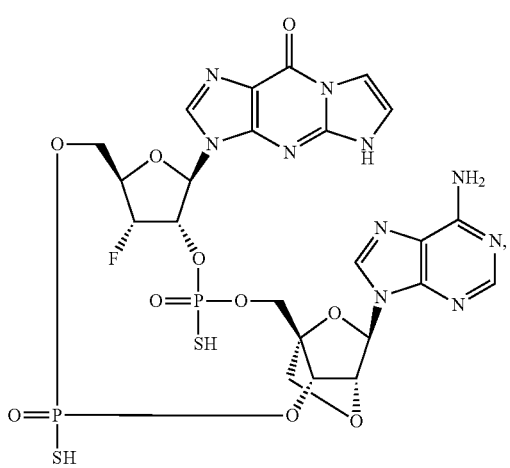
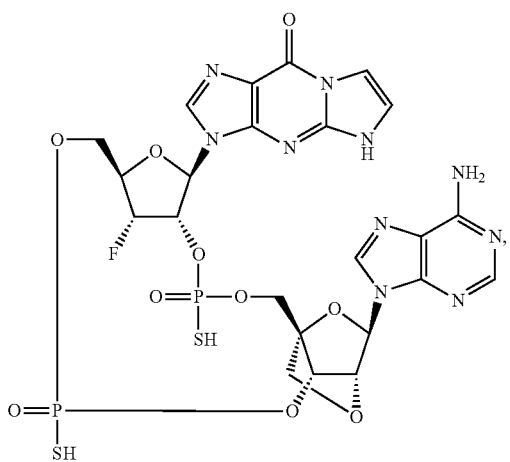
72
-continued
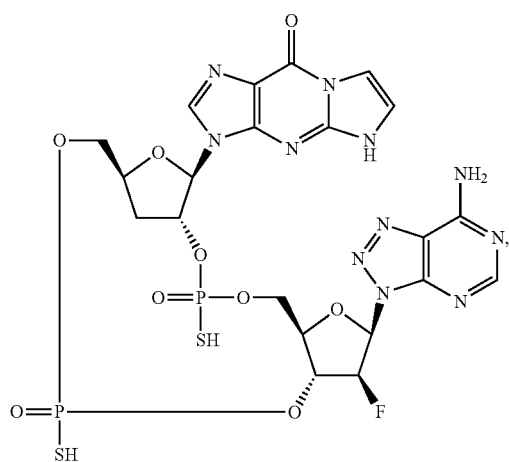
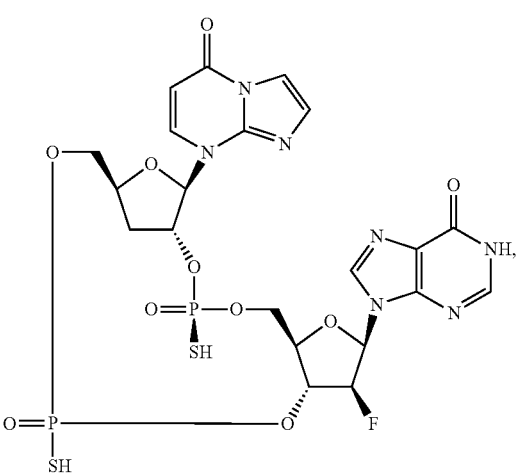
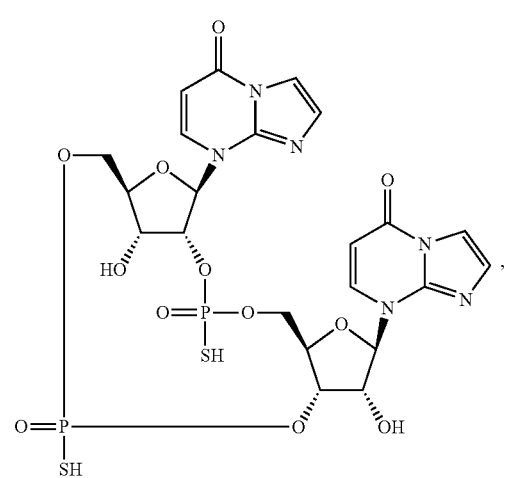

73
-continued
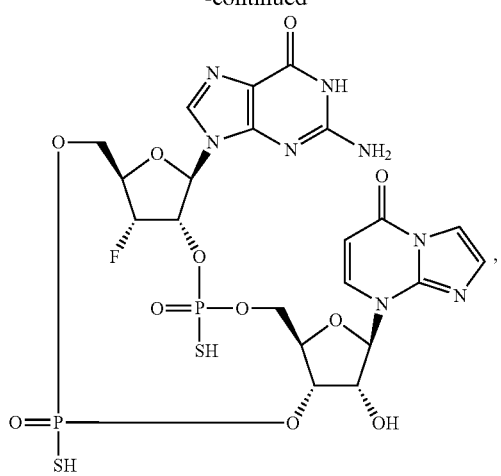
74
-continued
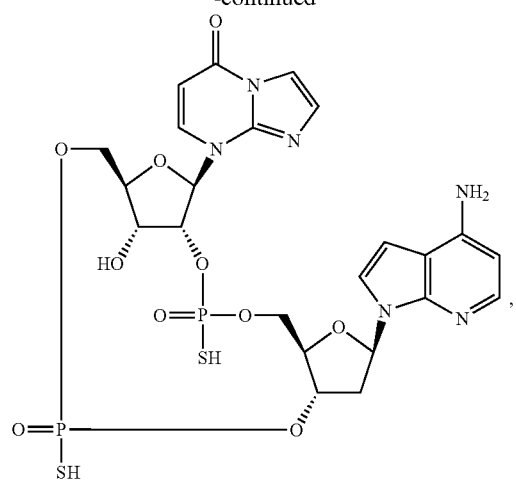
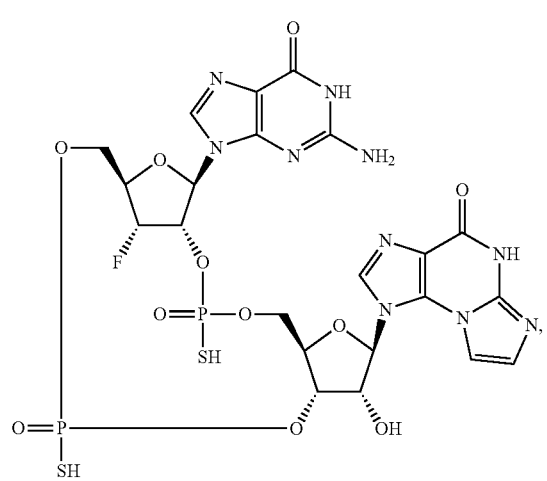
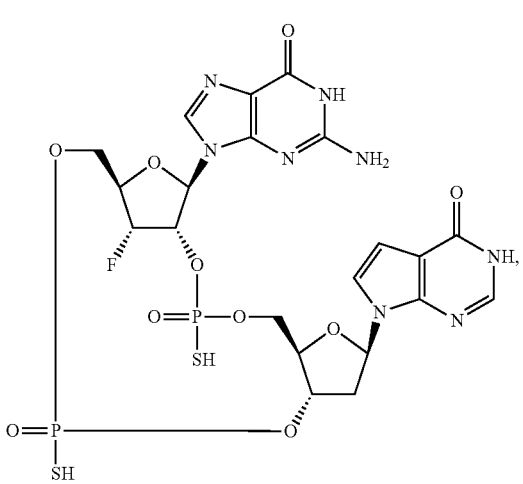
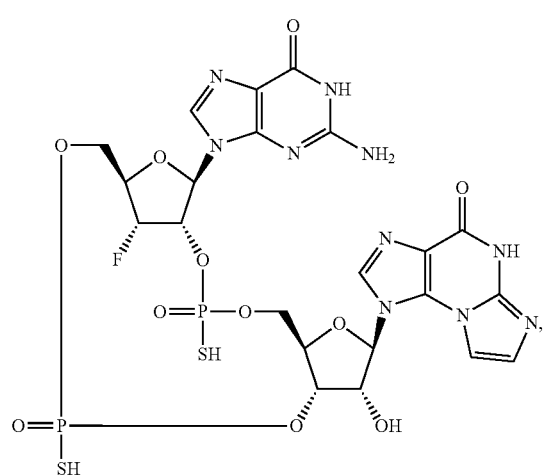
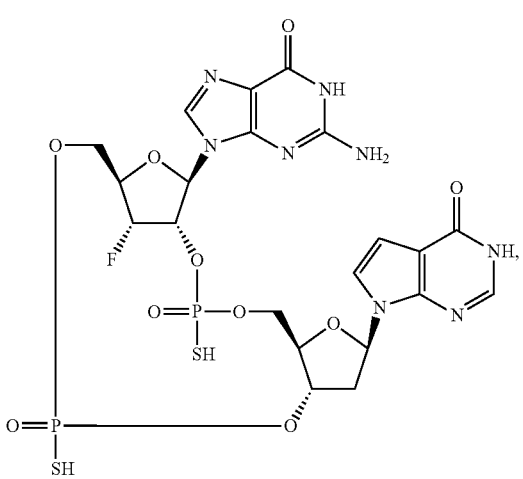

75
-continued
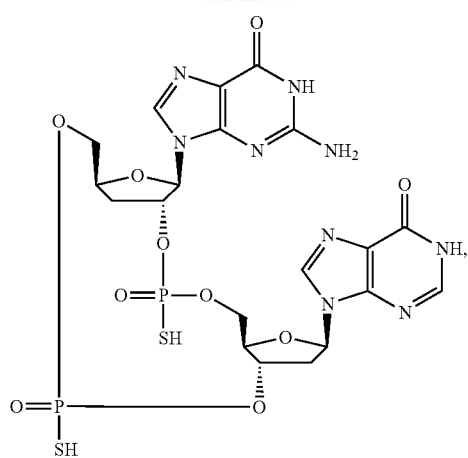
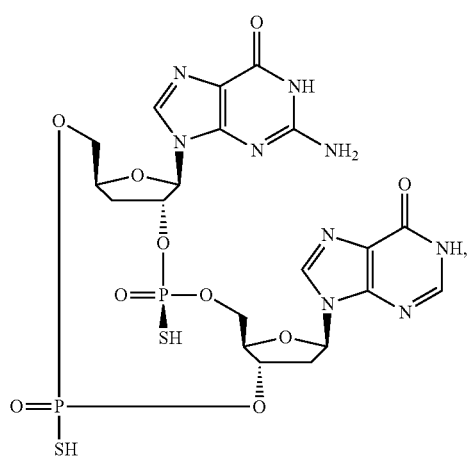
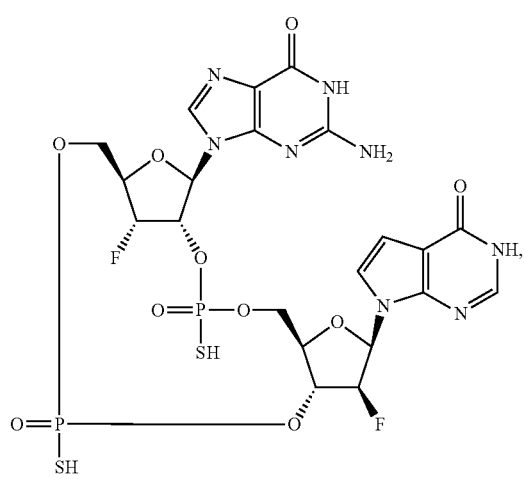
76
-continued
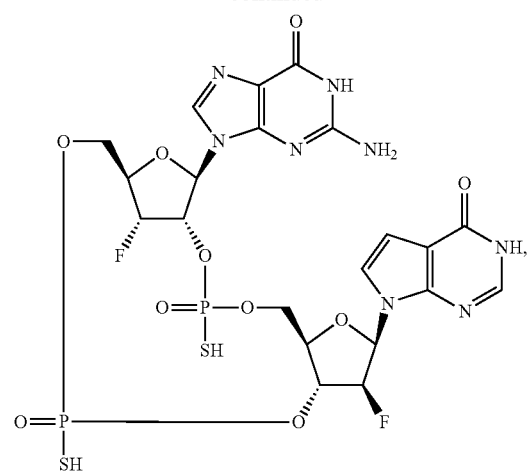
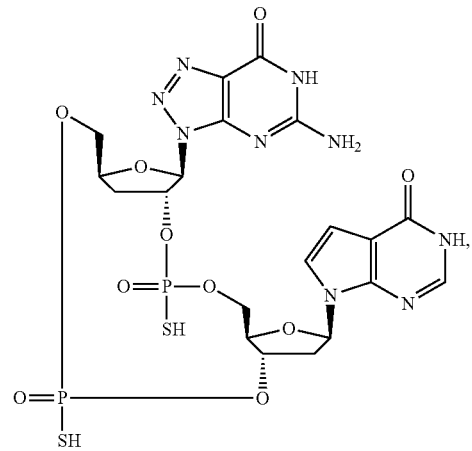

77
-continued
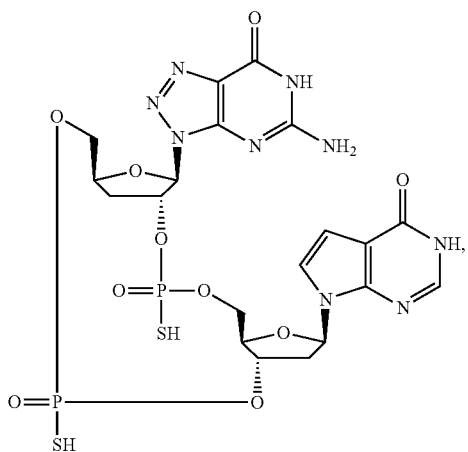
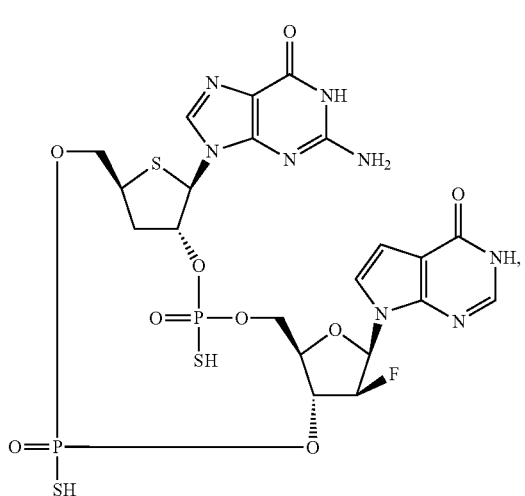
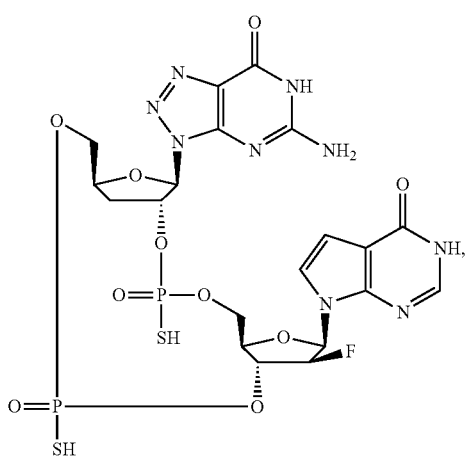
78
-continued
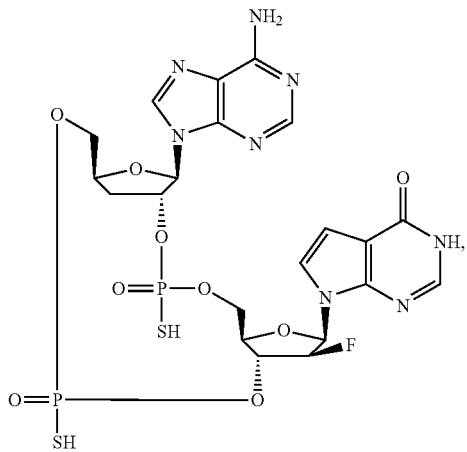
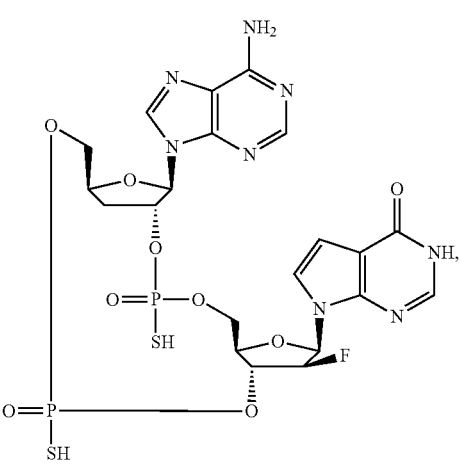
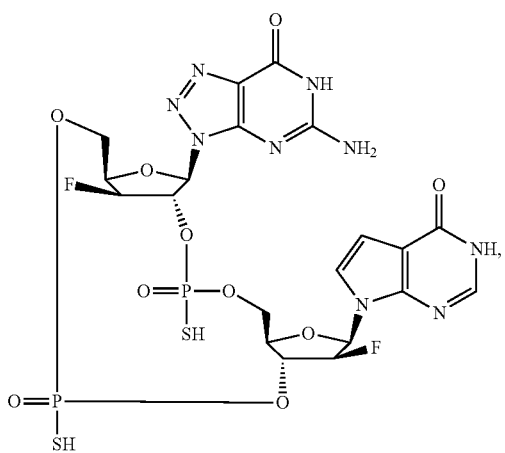

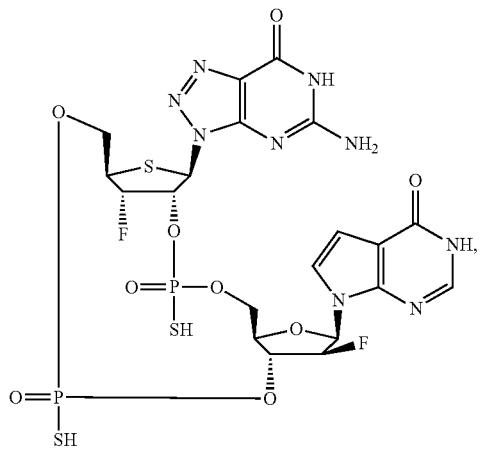
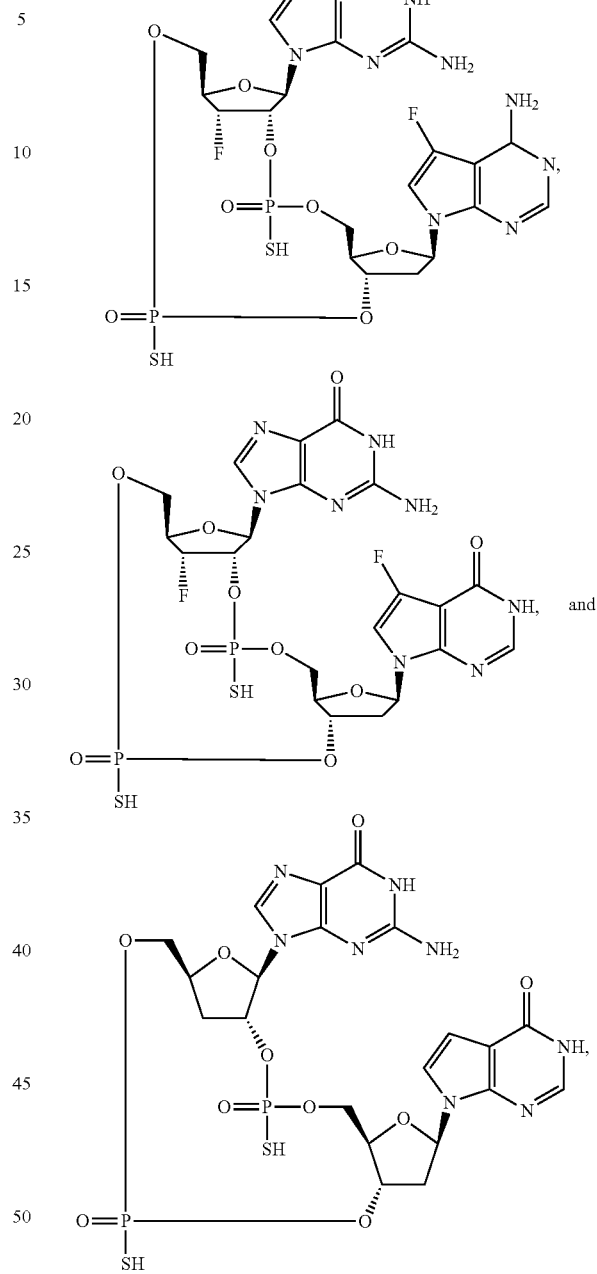

and pharmaceutically acceptable salts thereof.

A thirty-third embodiment relates to a pharmaceutical composition, said pharmaceutical composition comprising (a) a compound according to any one of general formula (I) above or the first through thirty-second embodiments above or a pharmaceutically acceptable salt thereof; and (b) a pharmaceutically acceptable carrier.

A thirty-fourth embodiment relates to methods of inducing an immune response in a subject, comprising administering a therapeutically effective amount of a compound according to any one of general formula (I) above or the first through thirty-second embodiments above or a pharmaceutically acceptable salt thereof to the subject.

A thirty-fifth embodiment relates to methods of inducing an immune response in a subject, comprising administering a therapeutically effective amount of a composition according to the thirty-third embodiment above to the subject.

A thirty-sixth embodiment relates to methods of inducing STING-dependent type I interferon production in a subject, comprising administering a therapeutically effective amount of a compound according to any one of general formula (I) above or the first through thirty-second embodiments above or a pharmaceutically acceptable salt thereof to the subject.

A thirty-seventh embodiment relates to methods of inducing STING-dependent type I interferon production in a subject, comprising administering a therapeutically effective amount of a composition according to the thirty-third embodiment above to the subject.

A thirty-eighth embodiment relates to methods of inducing STING-dependent cytokine production in a subject, comprising administering a therapeutically effective amount of a compound according to any one of general formula (I) above or the first through thirty-second embodiments above or a pharmaceutically acceptable salt thereof to the subject.

A thirty-ninth embodiment relates to methods of inducing a STING-dependent cytokine production in a subject, comprising administering a therapeutically effective amount of a composition according to the thirty-third embodiment above to the subject.

A fortieth embodiment relates to a compound selected from the exemplary species depicted in Examples 1 through 54 shown below.

A forty-first embodiment relates to a pharmaceutical composition, said pharmaceutical composition comprising (a) a compound according to the fortieth embodiment above or a pharmaceutically acceptable salt thereof; and (b) a pharmaceutically acceptable carrier.

A forty-second embodiment relates to methods of inducing an immune response in a subject, comprising administering a therapeutically effective amount of a compound according to the fortieth embodiment above or a pharmaceutically acceptable salt thereof to the subject.

A forty-third embodiment relates to methods of inducing an immune response in a subject, comprising administering a therapeutically effective amount of a composition according to the forty-first embodiment above to the subject.

A forty-fourth embodiment relates to methods of inducing STING-dependent type I interferon production in a subject, comprising administering a therapeutically effective amount of a compound according to the fortieth embodiment above or a pharmaceutically acceptable salt thereof to the subject.

A forty-fifth embodiment relates to methods of inducing STING-dependent type I interferon production in a subject, comprising administering a therapeutically effective amount of a composition according to the forty-first embodiment above to the subject.

A forty-sixth embodiment relates to methods of inducing STING-dependent cytokine production in a subject, comprising administering a therapeutically effective amount of a compound according to the fortieth embodiment above or a pharmaceutically acceptable salt thereof to the subject.

A forty-seventh embodiment relates to methods of inducing STING-dependent cytokine production in a subject, comprising administering a therapeutically effective amount of a composition according to the forty-first embodiment above to the subject.

Other embodiments of the present disclosure include the following:

(a) A pharmaceutical composition comprising an effective amount of a compound of general formula (I), or a pharmaceutically acceptable salt thereof, and a pharmaceutically acceptable carrier.

(b) The pharmaceutical composition of (a), further comprising an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents.

(c) A pharmaceutical combination that is (i) a compound of general formula (I), or a pharmaceutically acceptable salt thereof, and (ii) an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents; wherein the compound of general formula (I), or pharmaceutically acceptable salt thereof, and the active agent are each employed in an amount that renders the combination effective for inducing an immune response in a patient.

(d) A method of inducing an immune response in a patient, which comprises administering to the subject a therapeutically effective amount of a compound of general formula (I), or a pharmaceutically acceptable salt thereof.

(e) A method of inducing an immune response in a patient, which comprises administering to the subject a therapeutically effective amount of a composition of (a), a composition of (b), or a combination of (c).

(f) A method of inducing STING-dependent type I interferon production in a patient, which comprises administering to the subject a therapeutically effective amount of a compound of general formula (I), or a pharmaceutically acceptable salt thereof.

(g) A method of inducing STING-dependent type I interferon production in a patient, which comprises administering to the subject a therapeutically effective amount of a composition of (a), a composition of (b), or a combination of (c).

(h) A method of inducing STING-dependent cytokine production in a patient, which comprises administering to the subject a therapeutically effective amount of a compound of general formula (I), or a pharmaceutically acceptable salt thereof.

(i) A method of inducing STING-dependent cytokine production in a patient, which comprises administering to the subject a therapeutically effective amount of a composition of (a), a composition of (b), or a combination of (c).

(j) A method of treating a cell proliferation disorder in a subject, said method comprising administering a therapeutically effective amount of a compound of general formula (I), or a pharmaceutically acceptable salt thereof to the subject;

(k) The method of (j), wherein the cell proliferation disorder is cancer.

(l) A method of treating a cell proliferation disorder in a subject, said method comprising administering a therapeutically effective amount of a composition of (a), a composition of (b), or a combination of (c) to the subject.

The present disclosure also includes a compound of the present disclosure for use (i) in, (ii) as a medicament for, or (iii) in the preparation of a medicament for: (a) inducing an immune response in a patient, or (b) inducing STING-dependent cytokine production in a patient. In these uses, the compounds of the present disclosure can optionally be employed in combination with one or more active agents selected from STING agonist compounds, anti-viral compounds, antigens, adjuvants, CTLA-4 and PD-1 pathway antagonists and other immunomodulatory agents, lipids, liposomes, peptides, anti-cancer agents, and chemotherapeutic agents.

Additional embodiments of the disclosure include the pharmaceutical compositions, combinations and methods set forth in (a) through (l) above and the uses set forth in the preceding paragraph, wherein the compound of the present disclosure employed therein is a compound of one of the embodiments, aspects, instances, occurrences, or features of the compounds described above. In all of these embodiments, the compound may optionally be used in the form of a pharmaceutically acceptable salt, as appropriate.

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (l) above are understood to include all embodiments of the compounds, including such embodiments as result from combinations of embodiments.

The term "subject" (alternatively "patient") as used herein refers to a mammal that has been the object of treatment, observation, or experiment. The mammal may be male or female. The mammal may be one or more selected from the group consisting of humans, bovine (e.g., cows), porcine (e.g., pigs), ovine (e.g., sheep), capra (e.g., goats), equine (e.g., horses), canine (e.g., domestic dogs), feline (e.g., house cats), *lagomorpha* (rabbits), rodents (e.g., rats or mice), *Procyon lotor* (e.g., raccoons). In particular embodiments, the subject is human.

As used herein, the term "immune response" relates to any one or more of the following: specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, a compound of general formula (I), or a pharmaceutically acceptable salt of the foregoing, is administered in conjunction with one or more additional therapeutic agents including anti-viral compounds, vaccines intended to stimulate an immune response to one or more predetermined antigens, adjuvants, CTLA-4 and PD-1 pathway antagonists and other immunomodulatory agents, lipids, liposomes, peptides, anti-cancer agents, and chemotherapeutic agents, etc. In certain embodiments, a compound of general formula (I), or a pharmaceutically acceptable salt of the foregoing, is administered in conjunction with one or more additional compositions including anti-viral compounds, vaccines intended to stimulate an immune response to one or more predetermined antigens, adjuvants, CTLA-4 and PD-1 pathway antagonists and other immunomodulatory agents, lipids, liposomes, peptides, anti-cancer agents, and chemotherapeutic agents, etc.

Compounds

The term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and tert-butyl, n- and iso-propyl, ethyl, and methyl. As another example, "$C_{1-4}$ alkyl" refers to n-, iso-, sec- and tert-butyl, n- and isopropyl, ethyl, and methyl.

As used herein, the term "alkylene" refers to a bivalent straight chain, saturated aliphatic hydrocarbon radical having a number of carbon atoms in the specified range.

As used herein, the term "alkenyl" refers to a monovalent straight or branched chain, unsaturated aliphatic hydrocarbon radical having a number of carbon atoms in the specified range and including one or more double bond.

As used herein, the term "alkenylene" refers to a bivalent straight chain, unsaturated aliphatic hydrocarbon radical having a number of carbon atoms in the specified range and including one or more double bond.

As used herein, the term "alkynyl" refers to a monovalent straight or branched chain, unsaturated aliphatic hydrocarbon radical having a number of carbon atoms in the specified range and including one or more triple bond.

As used herein, the term "alkynylene" refers to a bivalent straight chain, unsaturated aliphatic hydrocarbon radical having a number of carbon atoms in the specified range and including one or more triple bond. The term "halogen" (or "halo") refers to fluorine, chlorine, bromine, and iodine (alternatively referred to as fluoro, chloro, bromo, and iodo or F, Cl, Br, and I).

The term "haloalkyl" refers to an alkyl group as defined above in which one or more of the hydrogen atoms have been replaced with a halogen. Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

As used herein, the term "haloalkenyl" refers to an alkenyl group as defined above in which one or more of the hydrogen atoms have been replaced with a halogen.

As used herein, the term "haloalkynyl" refers to an alkynyl group as defined above in which one or more of the hydrogen atoms have been replaced with a halogen.

As used herein, the term "alkoxy" as used herein, alone or in combination, includes an alkyl group connected to the oxy connecting atom. The term "alkoxy" also includes alkyl ether groups, where the term "alkyl" is defined above, and "ether" means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as "dimethyl ether"), and methoxyethane (also referred to as "ethyl methyl ether").

As used herein, the term "cycloalkyl" refers to a saturated hydrocarbon containing one ring having a specified number of carbon atoms. Examples of cycloalkyl include cyclopropyl, cyclobutyl, cyclopentyl, and cyclohexyl.

As used herein, the term "heterocycle", "heterocyclyl", or "heterocyclic", as used herein, represents a stable 3- to 6-membered monocyclic that is either saturated or unsaturated, and that consists of carbon atoms and from one to two heteroatoms selected from the group consisting of N, O, and S. The heterocyclic ring may be attached at any heteroatom or carbon atom which results in the creation of a stable structure. The term includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, triazolyl, and thienyl.

As used herein, the term "spirocycle" or "spirocyclic ring" refers to a pendant cyclic group formed by substituents on a single atom.

The term "compound" refers to the compound and, in certain embodiments, to the extent they are stable, any hydrate or solvate thereof. A hydrate is the compound complexed with water, and a solvate is the compound complexed with a solvent, which may be an organic solvent or an inorganic solvent.

A "stable" compound is a compound that can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by general formula (I), or pharmaceutically acceptable salts thereof.

Unless expressly stated to the contrary, all ranges cited herein are inclusive; i.e., the range includes the values for the upper and lower limits of the range as well as all values in between. As an example, temperature ranges, percentages, ranges of equivalents, and the like described herein include the upper and lower limits of the range and any value in the continuum there between. Numerical values provided herein, and the use of the term "about", may include variations of ±1%, ±2%, ±3%, ±4%, ±5%, ±10%, ±15%, and ±20% and their numerical equivalents. As used herein, the term "one or more" item includes a single item selected from the list as well as mixtures of two or more items selected from the list.

In the compounds of general formula (I), and pharmaceutically acceptable salts of the foregoing, the atoms may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds of general formula (I), and pharmaceutically acceptable salts of the foregoing. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within general formula (I), and the pharmaceutically acceptable salts of the foregoing, can be prepared without undue experimentation by conventional techniques well known to those skilled in the art or by processes analogous to those described in the Schemes and Examples herein using appropriate isotopically-enriched reagents and/or intermediates.

In particular embodiments of the compounds of general formula (I), and/or pharmaceutically acceptable salts of the foregoing, the compounds are isotopically enriched with deuterium. In aspects of these embodiments, one or more of Base$^1$, Base$^2$, Y, Y$^a$, X$^a$, X$^{a1}$, X$^b$, X$^{b1}$, R$^1$, R$^{1a}$, R$^2$, R$^{2a}$, R$^3$, R$^4$, R$^{4a}$, R$^5$, R$^6$, R$^{6a}$, R$^7$, R$^{7a}$, R$^8$, R$^{8a}$, and R$^9$ may include deuterium.

As shown in the general structural formulas and the structures of specific compounds as provided herein, a straight line at a chiral center includes both (R) and (S) stereoisomers and mixtures thereof.

Recitation or depiction of a specific compound in the claims (i.e., a species) without a specific stereoconfiguration designation, or with such a designation for less than all chiral centers, is intended to encompass, for such undesignated chiral centers, the racemate, racemic mixtures, each individual enantiomer, a diastereoisomeric mixture and each individual diastereomer of the compound where such forms are possible due to the presence of one or more asymmetric centers.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism, the invention includes both the cis form and the trans form, as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of general formula (I), or a pharmaceutically acceptable salt of the foregoing, or it can be done on a final racemic product. Absolute stereochemistry may be determined by X-ray crystallography of crystalline products or crystalline intermediates that are derivatized, if necessary, with a reagent containing a stereogenic center of known configuration. Unless a particular isomer, salt, solvate (including hydrates) or solvated salt of such racemate, enantiomer, or diastereomer is indicated, the present invention includes all such isomers, as well as salts, solvates (including hydrates), and solvated salts of such racemates, enantiomers, diastereomers, and mixtures thereof.

Those skilled in the art will recognize that chiral compounds, and in particular sugars, can be drawn in a number of different ways that are equivalent. Those skilled in the art will further recognize that the identity and regiochemical position of the substituents on ribose can vary widely and that the same principles of stereochemical equivalence apply regardless of substituent. Non-limiting examples of such equivalence include those exemplified below.

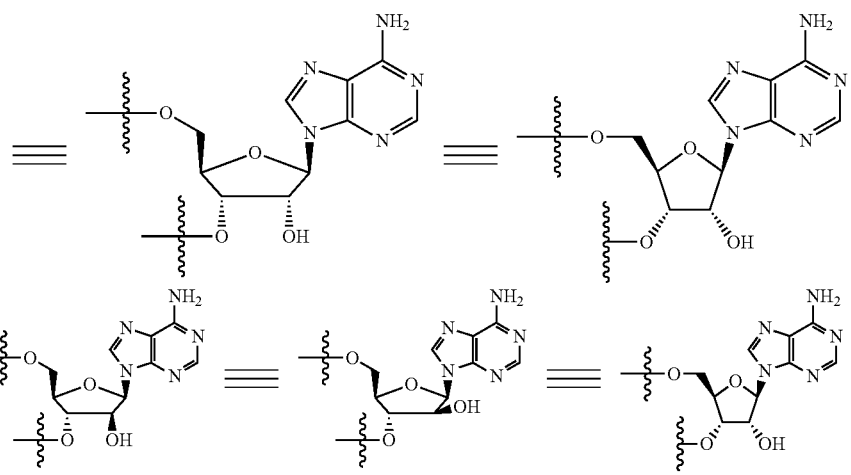

Salts

As indicated above, the compounds of the present invention can be employed in the form of pharmaceutically acceptable salts. Those skilled in the art will recognize those instances in which the compounds of the invention may form salts. Examples of such compounds are described herein by reference to possible salts. Such reference is for illustration only. Pharmaceutically acceptable salts can be used with compounds for treating patients. Non-pharmaceutical salts may, however, be useful in the preparation of intermediate compounds.

The term "pharmaceutically acceptable salt" refers to a salt (including an inner salt such as a zwitterion) that possesses effectiveness similar to the parent compound and that is not biologically or otherwise undesirable (e.g., is neither toxic nor otherwise deleterious to the recipient thereof). Thus, an embodiment of the invention provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Additionally, acids that are generally considered suitable for the formation of pharmaceutically useful salts from basic pharmaceutical compounds are discussed, for example, by P. Stahl et al, Camille G. (eds.), *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (such as —COOH) or alcohol group being present, pharmaceutically acceptable esters can be employed to modify the solubility or hydrolysis characteristics of the compound.

All such acid salts and base salts are intended to be pharmaceutically acceptable salts within the scope of the invention and all acid and base salts are considered equivalent to the free forms of the corresponding compounds for purposes of the invention.

In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the terms "salt(s)" as used herein. It is understood that certain compounds of the invention may exist in zwitterionic form, having both anionic and cationic centers within the same compound and a net neutral charge. Such zwitterions are included within the invention.

Methods of Preparing Compounds

Several methods for preparing the compounds of general formula (I), and pharmaceutically acceptable salts of the foregoing, are described in the following Schemes and Examples. Starting materials and intermediates are purchased from commercial sources, made from known procedures, or are otherwise illustrated. In some cases the order of carrying out the steps of the reaction schemes may be varied to facilitate the reaction or to avoid unwanted reaction products.

In the following Methods and Schemes, $PG_1$ or $PG_2$ represents a protecting group for an amino group in a nucleobase, which may be a phenyl carbonyl group including benzoyl group, an alkyl carbonyl group including isobutyl carbonyl group and 2-(4-(tert-butyl)phenoxy) acetyl group or a formamidine group including N,N-dimethyl-formamidine. All other variables have the same meaning as provided above.

Method 1

One method for the preparation of examples of Formula (I) of the instant invention is detailed in Scheme 1. This procedure was adequately modified from the previously reported procedure for cyclic dinucleotide synthesis (Barbara L. Gaffney et al., *One-Flask Syntheses of c-di-GMP and the [Rp,Rp] and [Rp,Sp] Thiophosphate Analogues,* 12 ORG. LETT. 3269-3271 (2010)). The sequence starts with modified ribo-nucleoside with DMTr ether at 5'-O position and a nucleobase of which amino group was appropriately protected as described above if necessary. It was treated with diphenyl phosphite and then, aqueous trimethylamine to introduce an H-phosphonate group. Then, DMTr ether was removed under acidic condition. The resulting 5'-hydroxyl group was reacted with 3'-phosphoramidites of fully protected second modified ribo-nucleoside to give a linear dimer compound. It was immediately treated with (E)-N,N-dimethyl-N'-(3-thioxo-3H-1,2,4-dithiazol-S-yl)formimidamide or tert-butyl hydroperoxide. Then, the 5'-hydroxyl group of the second ribo-nucleoside was deprotected with dichloroacetic acid. Using diphenyl chlorophosphate as a coupling reagent, the H-phosphonate at 2'-O of the first ribo-nucleoside was reacted with 5'-OH of the second ribo-nucleoside to give a cyclic product. It was immediately sulfurized with 3H-1,2-benzodithiol-3-one. Treatment with ammonium hydroxide, t-butylamine, or methylamine plus fluoride anion in case silyl protection was used provided the desired cyclic dinucleotide 1G.

Scheme 1

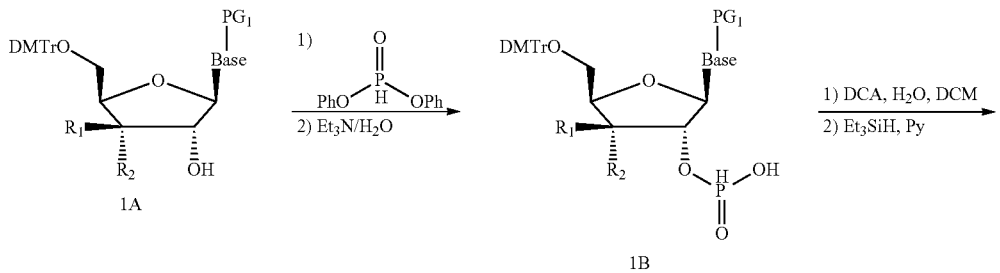

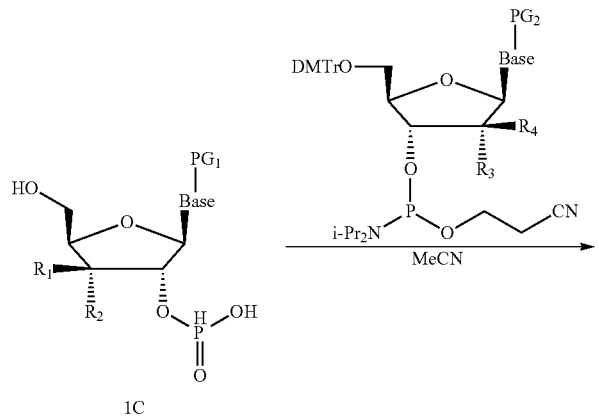

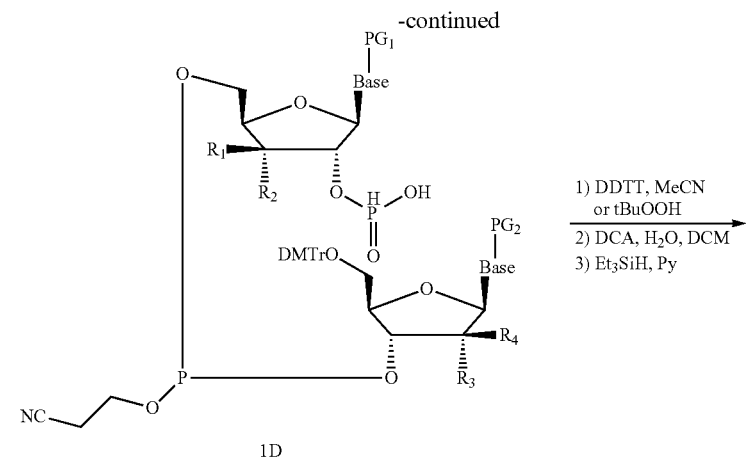

1D

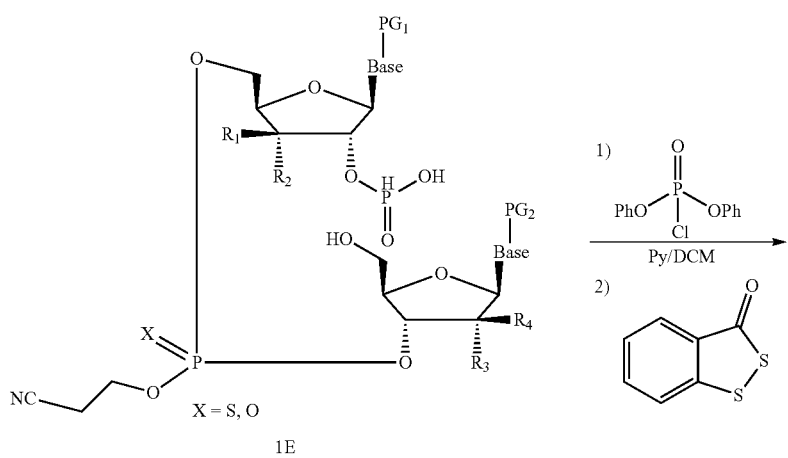

1E

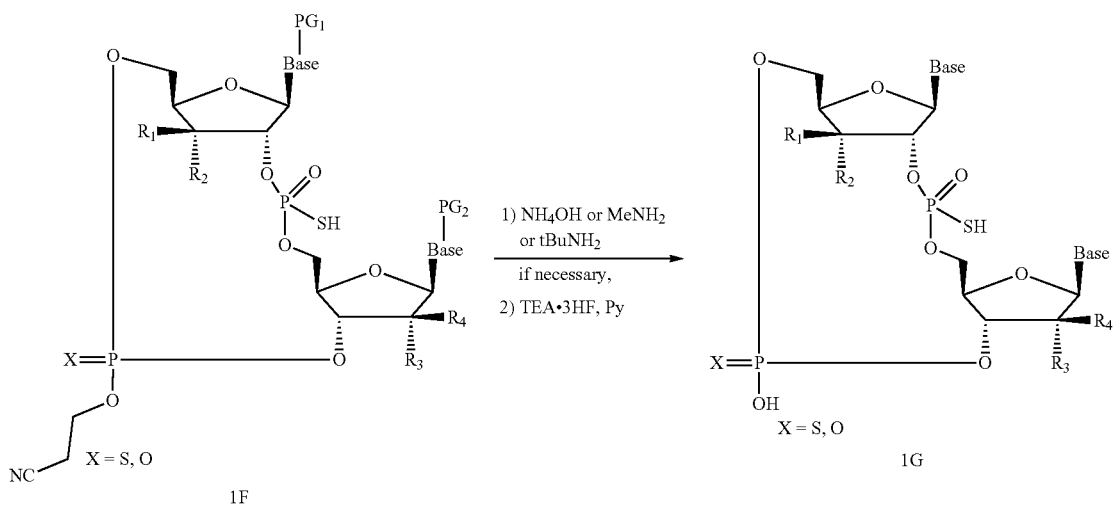

1F                               1G

Method 2

One method for the preparation of examples of Formula (I) of the instant invention is detailed in Scheme 2. The sequence starts with a cyclic dinucleotide with 6-amino moiety in a nucleobase prepared from a sequence similar to Scheme 1. It was treated with adenosine monophosphate deaminase in an appropriate aqueous buffer solution to give cyclic dinucleotide 2B with 6-oxo moiety in the nucleobase.

Scheme 2

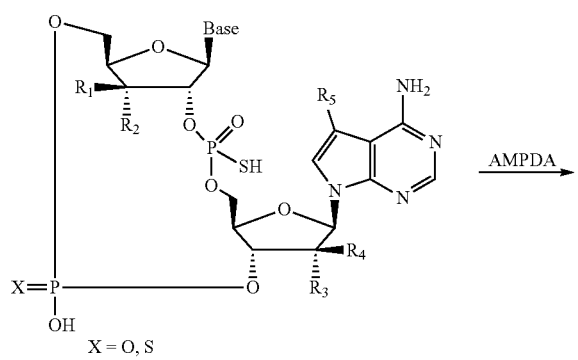

2A

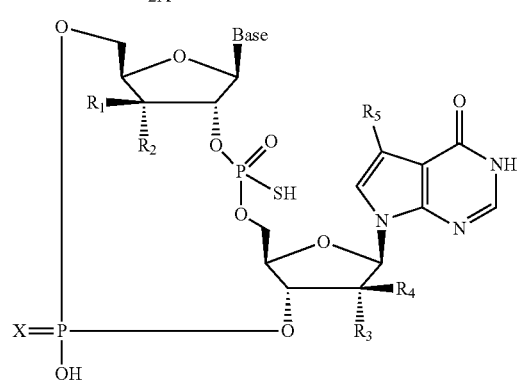

2B

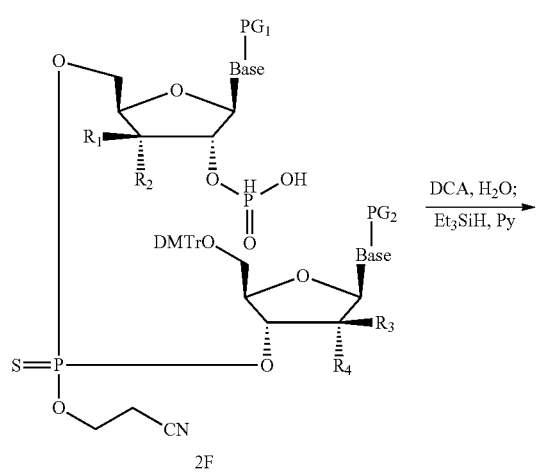

2F

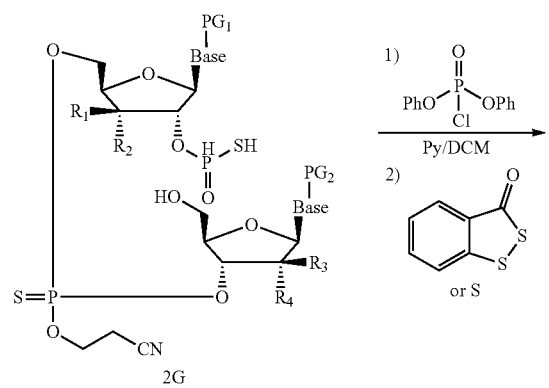

2G

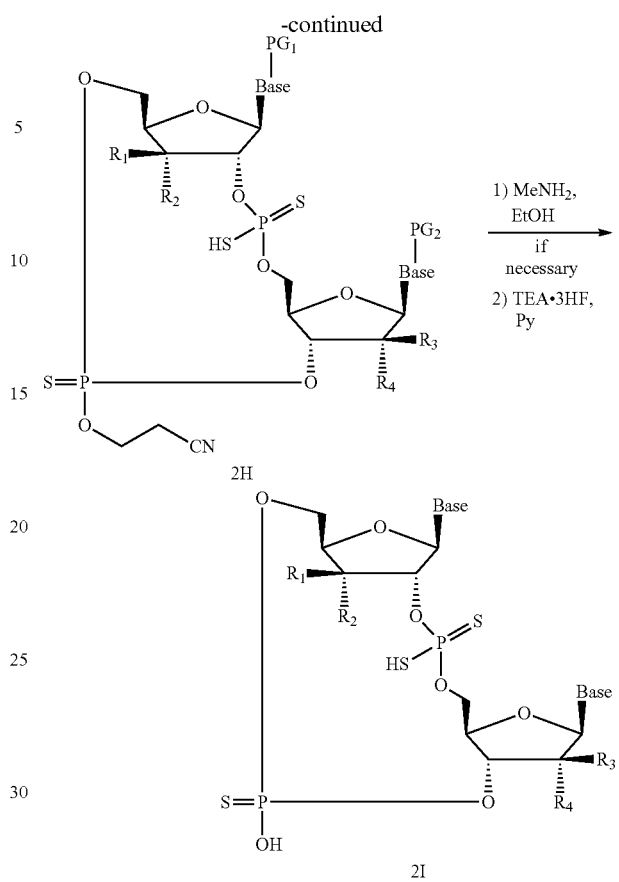

2H

2I

Methods of Use

Compounds described herein having therapeutic applications, such as the compounds of general formula (I), the compounds of the Examples 1 through 54, and pharmaceutically acceptable salts of the foregoing, may be administered to a patient for the purpose of inducing an immune response, inducing STING-dependent cytokine production and/or inducing anti-tumor activity. The term "administration" and variants thereof (e.g., "administering" a compound) means providing the compound to the individual in need of treatment. When a compound is provided in combination with one or more additional active agents (e.g., antiviral agents useful for treating HCV infection or anti-tumor agents for treating cancers), "administration" and its variants are each understood to include concurrent and sequential provision of the compound or salt and other agents.

The compounds disclosed herein may be STING agonists. These compounds are potentially useful in treating diseases or disorders including, but not limited to, cell proliferation disorders. Cell-proliferation disorders include, but are not limited to, cancers, benign papillomatosis, gestational trophoblastic diseases, and benign neoplastic diseases, such as skin papilloma (warts) and genital papilloma.

In specific embodiments, the disease or disorder to be treated is a cell proliferation disorder. In certain embodiments, the cell proliferation disorder is cancer. In particular embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary (i.e., cancers in which a metastasized cancer is found but the original cancer site is not known). In particular embodiments, the cancer is present in an adult patient; in additional embodiments, the cancer is present in a pediatric patient. In particular embodiments, the cancer is AIDS-related.

In specific embodiments, the cancer is selected from brain and spinal cancers. In particular embodiments, the cancer is selected from the group consisting of anaplastic astrocytomas, glioblastomas, astrocytomas, and estheosioneuroblastomas (also known as olfactory blastomas). In particular embodiments, the brain cancer is selected from the group consisting of astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma), oligodendroglial tumor (e.g., oligodendroglioma, and anaplastic oligodendroglioma), oligoastrocytic tumor (e.g., oligoastrocytoma, and anaplastic oligoastrocytoma), ependymoma (e.g., myxopapillary ependymoma, and anaplastic ependymoma); medulloblastoma, primitive neuroectodermal tumor, schwannoma, meningioma, atypical meningioma, anaplastic meningioma, pituitary adenoma, brain stem glioma, cerebellar astrocytoma, cerebral astorcytoma/malignant glioma, visual pathway and hypothalmic glioma, and primary central nervous system lymphoma. In specific instances of these embodiments, the brain cancer is selected from the group consisting of glioma, glioblastoma multiforme, paraganglioma, and suprantentorial primordial neuroectodermal tumors (sP-NET).

In specific embodiments, the cancer is selected from cancers of the head and neck, including nasopharyngeal cancers, nasal cavity and paranasal sinus cancers, hypopharyngeal cancers, oral cavity cancers (e.g., squamous cell carcinomas, lymphomas, and sarcomas), lip cancers, oropharyngeal cancers, salivary gland tumors, cancers of the larynx (e.g., laryngeal squamous cell carcinomas, rhabdomyosarcomas), and cancers of the eye or ocular cancers. In particular embodiments, the ocular cancer is selected from the group consisting of intraocular melanoma and retinoblastoma.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In specific embodiments, the cancer is selected from skin cancers. In particular embodiments, the skin cancer is selected from the group consisting of melanoma, squamous cell cancers, and basal cell cancers.

In specific embodiments, the cancer is selected from cancers of the reproductive system. In particular embodiments, the cancer is selected from the group consisting of breast cancers, cervical cancers, vaginal cancers, ovarian cancers, prostate cancers, penile cancers, and testicular cancers. In specific instances of these embodiments, the cancer is a breast cancer selected from the group consisting of ductal carcinomas and phyllodes tumors. In specific instances of these embodiments, the breast cancer may be male breast cancer or female breast cancer. In specific instances of these embodiments, the cancer is a cervical cancer selected from the group consisting of squamous cell carcinomas and adenocarcinomas. In specific instances of these embodiments, the cancer is an ovarian cancer selected from the group consisting of epithelial cancers.

In specific embodiments, the cancer is selected from cancers of the gastrointestinal system. In particular embodiments, the cancer is selected from the group consisting of esophageal cancers, gastric cancers (also known as stomach cancers), gastrointestinal carcinoid tumors, pancreatic cancers, gallbladder cancers, colorectal cancers, and anal cancer. In instances of these embodiments, the cancer is selected from the group consisting of esophageal squamous cell carcinomas, esophageal adenocarcinomas, gastric adenocarcinomas, gastrointestinal carcinoid tumors, gastrointestinal stromal tumors, gastric lymphomas, gastrointestinal lymphomas, solid pseudopapillary tumors of the pancreas, pancreatoblastoma, islet cell tumors, pancreatic carcinomas including acinar cell carcinomas and ductal adenocarcinomas, gallbladder adenocarcinomas, colorectal adenocarcinomas, and anal squamous cell carcinomas.

In specific embodiments, the cancer is selected from liver and bile duct cancers. In particular embodiments, the cancer is liver cancer (also known as hepatocellular carcinoma). In particular embodiments, the cancer is bile duct cancer (also known as cholangiocarcinoma); in instances of these embodiments, the bile duct cancer is selected from the group consisting of intrahepatic cholangiocarcinoma and extrahepatic cholangiocarcinoma.

In specific embodiments, the cancer is selected from kidney and bladder cancers. In particular embodiments, the cancer is a kidney cancer selected from the group consisting of renal cell cancer, Wilms tumors, and transitional cell cancers. In particular embodiments, the cancer is a bladder cancer selected from the group consisting of urethelial carcinoma (a transitional cell carcinoma), squamous cell carcinomas, and adenocarcinomas.

In specific embodiments, the cancer is selected from bone cancers. In particular embodiments, the bone cancer is selected from the group consisting of osteosarcoma, malignant fibrous histiocytoma of bone, Ewing sarcoma, chordoma (cancer of the bone along the spine).

In specific embodiments, the cancer is selected from lung cancers. In particular embodiments, the lung cancer is selected from the group consisting of non-small cell lung cancer, small cell lung cancers, bronchial tumors, and pleuropulmonary blastomas.

In specific embodiments, the cancer is selected from malignant mesothelioma. In particular embodiments, the cancer is selected from the group consisting of epithelial mesothelioma and sarcomatoids.

In specific embodiments, the cancer is selected from sarcomas. In particular embodiments, the sarcoma is selected from the group consisting of central chondrosarcoma, central and periosteal chondroma, fibrosarcoma, clear cell sarcoma of tendon sheaths, and Kaposi's sarcoma.

In specific embodiments, the cancer is selected from lymphomas. In particular embodiments, the cancer is selected from the group consisting of Hodgkin lymphoma (e.g., Reed-Sternberg cells), non-Hodgkin lymphoma (e.g., diffuse large B-cell lymphoma, follicular lymphoma, mycosis fungoides, Sezary syndrome, primary central nervous system lymphoma), cutaneous T-cell lymphomas, primary central nervous system lymphomas. In specific embodiments, the cancer is selected from glandular cancers. In particular embodiments, the cancer is selected from the group consisting of adrenocortical cancer (also known as adrenocortical carcinoma or adrenal cortical carcinoma), pheochromocytomas, paragangliomas, pituitary tumors, thymoma, and thymic carcinomas.

In specific embodiments, the cancer is selected from thyroid cancers. In particular embodiments, the thyroid cancer is selected from the group consisting of medullary thyroid carcinomas, papillary thyroid carcinomas, and follicular thyroid carcinomas.

In specific embodiments, the cancer is selected from germ cell tumors. In particular embodiments, the cancer is selected from the group consisting of malignant extracranial germ cell tumors and malignant extragonadal germ cell tumors. In specific instances of these embodiments, the malignant extragonadal germ cell tumors are selected from the group consisting of nonseminomas and seminomas.

In specific embodiments, the cancer is selected from heart tumors. In particular embodiments, the heart tumor is selected from the group consisting of malignant teratoma, lymphoma, rhabdomyosacroma, angiosarcoma, chondrosarcoma, infantile fibrosarcoma, and synovial sarcoma.

In specific embodiments, the cell-proliferation disorder is selected from benign papillomatosis, benign neoplastic diseases and gestational trophoblastic diseases. In particular embodiments, the benign neoplastic disease is selected from skin papilloma (warts) and genital papilloma. In particular embodiments, the gestational trophoblastic disease is selected from the group consisting of hydatidiform moles, and gestational trophoblastic neoplasia (e.g., invasive moles, choriocarcinomas, placental-site trophoblastic tumors, and epithelioid trophoblastic tumors).

As used herein, the terms "treatment" and "treating" refer to all processes in which there may be a slowing, interrupting, arresting, controlling, or stopping of the progression of a disease or disorder described herein. The terms do not necessarily indicate a total elimination of all disease or disorder symptoms.

The terms "administration of" and or "administering" a compound should be understood to include providing a compound described herein, or a pharmaceutically acceptable salt thereof, and compositions of the foregoing to a subject.

The amount of a compound administered to a subject is an amount sufficient to induce an immune response and/or to induce STING-dependent type I interferon production in the subject. In an embodiment, the amount of a compound can be an "effective amount" or "therapeutically effective amount," such that the subject compound is administered in an amount that will elicit, respectively, a biological or medical (i.e., intended to treat) response of a tissue, system, animal, or human that is being sought by a researcher, veterinarian, medical doctor, or other clinician. An effective amount does not necessarily include considerations of toxicity and safety related to the administration of a compound.

An effective amount of a compound will vary with the particular compound chosen (e.g., considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, intratumoral, and subcutaneous injection or infusion.

The compounds disclosed herein may be administered once or according to a dosing regimen where a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life, which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen.

One embodiment of the present disclosure provides for a method of treating a cell proliferation disorder comprising administration of a therapeutically effective amount of a compound of general formula (I), or a pharmaceutically acceptable salt of the foregoing, to a subject in need of treatment thereof. In embodiments, the disease or disorder to be treated is a cell proliferation disorder. In aspects of these embodiments, the cell proliferation disorder is cancer. In further aspects of these embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary.

In one embodiment, disclosed herein is the use of a compound of general formula (I), or a pharmaceutically acceptable salt of the foregoing, in a therapy. The compound may be useful in a method of inducing an immune response and/or inducing STING-dependent type I interferon production in a subject, such as a mammal in need of such inhibition, comprising administering an effective amount of the compound to the subject.

In one embodiment, disclosed herein is a pharmaceutical composition comprising at least one compound of general formula (I), or at least one pharmaceutically acceptable salt of the foregoing, for use in potential treatment to induce an immune response and/or to induce STING-dependent type I interferon production.

One embodiment disclosed herein is the use of a compound of general formula (I), or a pharmaceutically acceptable salt of the foregoing, in the manufacture of a medicament to induce an immune response and/or to induce STING-dependent type I interferon production. In embodiments, the disease or disorder to be treated is a cell proliferation disorder. In aspects of these embodiments, the cell proliferation disorder is cancer. In further aspects of these embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary.

Compositions

The term "composition" as used herein is intended to encompass a dosage form comprising a specified compound in a specified amount, as well as any dosage form that results, directly or indirectly, from combination of a specified compound in a specified amount. Such term is intended to encompass a dosage form comprising a compound of general formula (I), or a pharmaceutically acceptable salt, hydrate, solvate, or prodrug of the foregoing, and one or more pharmaceutically acceptable carriers or excipients. In embodiments, the dosage form comprises compounds of general structural formula (I), or a pharmaceutically acceptable salt, hydrate, or solvate thereof, and one or more pharmaceutically acceptable carriers or excipients. In specific embodiments, the dosage form comprises compounds of general structural formula (I), or a pharmaceutically acceptable salt thereof, and one or more pharmaceutically acceptable carriers or excipients. Accordingly, the compositions of the present disclosure encompass any composition made by admixing a compound of the present disclosure and one or more pharmaceutically acceptable carrier or excipients. By "pharmaceutically acceptable", it is meant the carriers or excipients are compatible with the compound disclosed herein and with other ingredients of the composition.

For the purpose of inducing an immune response and/or inducing STING-dependent type I interferon production, the compounds of general formula (I), or pharmaceutically acceptable salts of the foregoing, can be administered by means that produces contact of the active agent with the agent's site of action. The compounds can be administered by conventional means available for use in conjunction with pharmaceuticals, either as individual therapeutic agents or in a combination of therapeutic agents. The compounds can be administered alone, but typically are administered with a pharmaceutical carrier selected on the basis of the chosen route of administration and standard pharmaceutical practice.

In one embodiment, disclosed herein is a composition comprising a compound of general formula (I), or a pharmaceutically acceptable salt of the foregoing, and one or more pharmaceutically acceptable carriers or excipients. The composition may be prepared and packaged in bulk form in which a therapeutically effective amount of a compound of the disclosure can be extracted and then given to a subject, such as with powders or syrups. Alternatively, the composition may be prepared and packaged in unit dosage form in which each physically discrete unit contains a therapeutically effective amount of a compound of general formula (I), or a pharmaceutically acceptable salt of the foregoing.

The compounds disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the compositions of the disclosure. In addition, there are a number of resources available to the skilled artisan, which describe pharmaceutically acceptable carriers and excipients and may be useful in selecting suitable pharmaceutically acceptable carriers and excipients. Examples include REMINGTON'S PHARMACEUTICAL SCIENCES (Mack Publishing Company), THE HANDBOOK OF PHARMACEUTICAL ADDITIVES (Gower Publishing Limited), and THE HANDBOOK OF PHARMACEUTICAL EXCIPIENTS (the American Pharmaceutical Association and the Pharmaceutical Press).

The compositions of the disclosure are prepared using techniques and methods known to those skilled in the art. Some methods commonly used in the art are described in REMINGTON'S PHARMACEUTICAL SCIENCES (Mack Publishing Company).

In one embodiment, the disclosure is directed to a solid oral dosage form such as a tablet or capsule comprising a therapeutically effective amount of a compound of general formula (I), or a pharmaceutically acceptable salt of the foregoing, and a diluent or filler. Suitable diluents and fillers include lactose, sucrose, dextrose, mannitol, sorbitol, starch (e.g., corn starch, potato starch, and pre-gelatinized starch), cellulose and its derivatives, (e.g., microcrystalline cellulose), calcium sulfate, and dibasic calcium phosphate. The solid oral dosage form may further comprise a binder. Suitable binders include starch (e.g., corn starch, potato starch, and pre-gelatinized starch) gelatin, acacia, sodium alginate, alginic acid, tragacanth, guar gum, povidone, and cellulose and its derivatives (e.g., microcrystalline cellulose). The solid oral dosage form may further comprise a disintegrant. Suitable disintegrants include crospovidone, sodium starch glycolate, croscarmelose, alginic acid, and sodium carboxymethyl cellulose. The solid oral dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the disclosure may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates, and cross-linked or amphipathic block copolymers of hydrogels.

In one embodiment, the disclosure is directed to a liquid oral dosage form. Oral liquids such as solutions, syrups, and elixirs can be prepared in dosage unit form so that a given quantity contains a predetermined amount of a compound or a pharmaceutically acceptable salt thereof disclosed herein. Syrups can be prepared by dissolving the compound of the disclosure in a suitably flavored aqueous solution; elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil, or other natural sweeteners or saccharin or other artificial sweeteners and the like can also be added.

In one embodiment, the disclosure is directed to compositions for parenteral administration. Compositions adapted for parenteral administration include aqueous and non-aqueous sterile injection solutions that may contain antioxidants, buffers, bacteriostats, and solutes that render the formulation isotonic with the blood of the intended recipient; and aqueous and non-aqueous sterile suspensions that may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

Combinations

The compounds of general formula (I), and/or pharmaceutically acceptable salts of the foregoing, may be administered in combination with one or more additional active agents. In embodiments, one or more compounds of general formula (I), or one or more pharmaceutically acceptable salts of the foregoing, and the one or more additional active agents may be co-administered. The additional active agent(s) may be administered in a single dosage form with the compound of general formula (I), or pharmaceutically acceptable salt of the foregoing, or the additional active agent(s) may be administered in separate dosage form(s) from the dosage form containing the compound of general formula (I), or pharmaceutically acceptable salt of the foregoing. The additional active agent(s) may be one or more agents selected from the group consisting of STING agonist compounds, anti-viral compounds, antigens, adjuvants, anti-cancer agents, CTLA-4, LAG-3, and PD-1 pathway antagonists, lipids, liposomes, peptides, cytotoxic agents, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, anti-metabolites, retinoids, and immunomodulatory agents including but not limited to anti-cancer vaccines. It will be understood the descriptions of the above additional active agents may be overlapping. It will also be understood that the treatment combinations are subject to optimization, and it is understood that the best combination to use of the compounds of general formula (I), or pharmaceutically acceptable salts of the foregoing, and one or more additional active agents will be determined based on the individual patient needs.

A compound disclosed herein may be used in combination with one or more other active agents, including but not limited to, other anti-cancer agents that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present disclosure.

When a compound disclosed herein is used contemporaneously with one or more other active agents, a composition containing such other active agents in addition to the compound disclosed herein is contemplated. Accordingly, the compositions of the present disclosure include those that also contain one or more other active ingredients, in addition to a compound disclosed herein. A compound disclosed herein may be administered either simultaneously with, or before or after, one or more other active agent(s). A compound disclosed herein may be administered separately, by the same or different route of administration, or together in the same pharmaceutical composition as the other agent(s).

Products provided as combinations may include a composition comprising a compound of general formula (I), or a pharmaceutically acceptable salt of the foregoing, and one or more other active agent(s) together in the same pharmaceutical composition, or may include a composition comprising a compound of general formula (I), or a pharmaceutically acceptable salt of the foregoing, and a composition comprising one or more other active agent(s) in separate form, e.g. in the form of a kit or in any form designed to enable separate administration either concurrently or on separate dosing schedules.

The weight ratio of a compound of general formula (I), or a pharmaceutically acceptable salt of the foregoing, to a second active agent may be varied and will depend upon the therapeutically effective dose of each agent. Generally, a therapeutically effective dose of each will be used. Combinations of a compound disclosed herein and other active agents will generally also be within the aforementioned range, but in each case, a therapeutically effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, this disclosure provides a composition comprising a compound of general formula (I), or a pharmaceutically acceptable salt thereof, and at least one other active agent as a combined preparation for simultaneous, separate or sequential use in therapy. In one embodiment, the therapy is the treatment of a cell proliferation disorder, such as cancer.

In one embodiment, the disclosure provides a kit comprising two or more separate pharmaceutical compositions, at least one of which contains a compound of general formula (I), or a pharmaceutically acceptable salt of the foregoing. In one embodiment, the kit comprises means for separately retaining said compositions, such as a container, divided bottle, or divided foil packet. An example of such a kit is a blister pack, as typically used for the packaging of tablets, capsules, and the like.

A kit of this disclosure may be used for administration of different dosage forms, for example, oral and parenteral, for administration of the separate compositions at different dosage intervals, or for titration of the separate compositions against one another. To assist with compliance, a kit of the disclosure typically comprises directions for administration.

Disclosed herein is a use of a compound of general formula (I), or a pharmaceutically acceptable salt of the foregoing, for treating a cell proliferation disorder, where the medicament is prepared for administration with another active agent. The disclosure also provides the use of another active agent for treating a cell proliferation disorder, where the medicament is administered with a compound of general formula (I), or a pharmaceutically acceptable salt of the foregoing.

The disclosure also provides the use of a compound of general formula (I), or a pharmaceutically acceptable salt of the foregoing, for treating a cell proliferation disorder, where the patient has previously (e.g., within 24 hours) been treated with another active agent. The disclosure also provides the use of another active agent for treating a cell proliferation disorder, where the patient has previously (e.g., within 24 hours) been treated with a compound of general formula (I), or a pharmaceutically acceptable salt of the foregoing. The second agent may be administered a week, several weeks, a month, or several months after the administration of a compound disclosed herein.

STING agonist compounds that may be used in combination with the compounds of general formula (I), or pharmaceutically acceptable salts of the foregoing, disclosed herein include but are not limited to cyclic di-nucleotide compounds.

Anti-viral compounds that may be used in combination with the compounds of general formula (I), or pharmaceutically acceptable salts of the foregoing, disclosed herein include hepatitis B virus (HBV) inhibitors, hepatitis C virus (HCV) protease inhibitors, HCV polymerase inhibitors, HCV NS4A inhibitors, HCV NS5A inhibitors, HCV NS5b inhibitors, and human immunodeficiency virus (HIV) inhibitors.

Antigens and adjuvants that may be used in combination with the compounds of general formula (I), or the pharmaceutically acceptable salts of the foregoing, include B7 costimulatory molecule, interleukin-2, interferon-y, GM-CSF, CTLA-4 antagonists, OX-40/0X-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryllipid A, lipoteichoic acid, imiquimod, resiquimod, and in addition retinoic acid-inducible gene I (RIG-I) agonists such as poly I:C, used separately or in combination with the described compositions are also potential adjuvants.

CLTA-4 and PD-1 pathways are important negative regulators of immune response. Activated T-cells up-regulate CTLA-4, which binds on antigen-presenting cells and inhibits T-cell stimulation, IL-2 gene expression, and T-cell proliferation; these anti-tumor effects have been observed in mouse models of colon carcinoma, metastatic prostate cancer, and metastatic melanoma. PD-1 binds to active T-cells and suppresses T-cell activation; PD-1 antagonists have demonstrated anti-tumor effects as well. CTLA-4 and PD-1 pathway antagonists that may be used in combination with the compounds of general formula (Ia), the compounds of general formula (Ib), the compounds of general formula (I), or the pharmaceutically acceptable salts of the foregoing, disclosed herein, include ipilimumab, tremelimumab, nivolumab, pembrolizumab, CT-011, AMP-224, and MDX-1106.

"PD-1 antagonist" or "PD-1 pathway antagonist" means any chemical compound or biological molecule that blocks binding of PD-L1 expressed on a cancer cell to PD-1 expressed on an immune cell (T-cell, B-cell, or NKT-cell) and preferably also blocks binding of PD-L2 expressed on a cancer cell to the immune-cell expressed PD-1. Alternative names or synonyms for PD-1 and its ligands include: PDCD1, PD1, CD279, and SLEB2 for PD-1; PDCD1L1, PDL1, B7H1, B7-4, CD274, and B7-H for PD-L1; and PDCD1L2, PDL2, B7-DC, Btdc, and CD273 for PD-L2. In any of the treatment method, medicaments and uses of the present disclosure in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present disclosure include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody, or a chimeric antibody and may include a human constant region. In some embodiments, the human constant region is selected from the group consisting of IgG1, IgG2, IgG3, and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv, and Fv fragments.

Examples of mAbs that bind to human PD-1, and useful in the treatment method, medicaments and uses of the present disclosure, are described in U.S. Pat. Nos. 7,488,802, 7,521,051, 8,008,449, 8,354,509, and 8,168,757, PCT International Patent Application Publication Nos. WO2004/

004771, WO2004/072286, and WO2004/056875, and U.S. Patent Application Publication No. US2011/0271358.

Examples of mAbs that bind to human PD-L1, and useful in the treatment method, medicaments and uses of the present disclosure, are described in PCT International Patent Application Nos. WO2013/019906 and WO2010/077634 A1 and in U.S. Pat. No. 8,383,796. Specific anti-human PD-L1 mAbs useful as the PD-1 antagonist in the treatment method, medicaments and uses of the present disclosure include MPDL3280A, BMS-936559, MEDI4736, MSB0010718C, and an antibody that comprises the heavy chain and light chain variable regions of SEQ ID NO:24 and SEQ ID NO:21, respectively, of WO2013/019906.

Other PD-1 antagonists useful in any of the treatment method, medicaments, and uses of the present disclosure include an immune-adhesion that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immune-adhesion molecules that specifically bind to PD-1 are described in PCT International Patent Application Publication Nos. WO2010/027827 and WO2011/066342. Specific fusion proteins useful as the PD-1 antagonist in the treatment method, medicaments, and uses of the present disclosure include AMP-224 (also known as B7-DCIg), which is a PD-L2-FC fusion protein and binds to human PD-1.

Examples of cytotoxic agents that may be used in combination with the compounds of general formula (I) or pharmaceutically acceptable salts thereof, include, but are not limited to, arsenic trioxide (sold under the tradename TRISENOX®), asparaginase (also known as L-asparaginase, and Erwinia L-asparaginase, sold under the tradenames ELSPAR® and KIDROLASE®).

Chemotherapeutic agents that may be used in combination with the compounds of general formula (I), or pharmaceutically acceptable salts of the foregoing, disclosed herein include abiraterone acetate, altretamine, anhydrovinblastine, auristatin, bexarotene, bicalutamide, BMS 184476, 2,3,4,5, 6-pentafluoro-N-(3-fluoro-4-methoxyphenyl)benzene sulfonamide, bleomycin, N,N-dimethyl-L-valyl-L-valyl-N-methyl-L-valyl-L-prolyl-1-Lproline-t-butylamide, cachectin, cemadotin, chlorambucil, cyclophosphamide, 3',4'-didehydro-4'deoxy-8'-norvin-caleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyurea andtaxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onapristone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine.

Examples of vascular endothelial growth factor (VEGF) receptor inhibitors include, but are not limited to, bevacizumab (sold under the trademark AVASTIN by Genentech/Roche), axitinib (described in PCT International Patent Publication No. WO01/002369), Brivanib Alaninate ((S)—((R)-1-(4-(4-Fluoro-2-methyl-1H-indol-S-yloxy)-S-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4- pyridinylmethyl)amino]-3-pyridinecarboxamide. and described in PCT International Patent Application Publication No. WO02/068470), pasireotide (also known as SO 230, and described in PCT International Patent Publication No. WO02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID, and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX® and MYLERAN®), carboplatin (sold under the tradename PARAPLATIN®), lomustine (also known as CCNU, sold under the tradename CEENU®), cisplatin (also known as CDDP, sold under the tradenames PLATINOL® and PLATINOL®-AQ), chlorambucil (sold under the tradename LEUKERAN®), cyclophosphamide (sold under the tradenames CYTOXAN® and NEOSAR®), dacarbazine (also known as DTIC, DIC and imidazole carboxamide, sold under the tradename DTIC-DOME®), altretamine (also known as hexamethylmelamine (HMM) sold under the tradename HEXALEN®), ifosfamide (sold under the tradename IFEX®), procarbazine (sold under the tradename MATULANE®), mechlorethamine (also known as nitrogen mustard, mustine and mechloroethamine hydrochloride, sold under the tradename MUSTARGEN®), streptozocin (sold under the tradename ZANOSAR®), thiotepa (also known as thiophosphoamide, TESPA and TSPA, and sold under the tradename THIOPLEX®.

Examples of anti-tumor antibiotics include, but are not limited to, doxorubicin (sold under the tradenames ADRIAMYCIN® and RUBEX®), bleomycin (sold under the tradename LENOXANE®), daunorubicin (also known as dauorubicin hydrochloride, daunomycin, and rubidomycin hydrochloride, sold under the tradename CERUBIDINE®), daunorubicin liposomal (daunorubicin citrate liposome, sold under the tradename DAUNOXOME®), mitoxantrone (also known as DHAD, sold under the tradename NOVANTRONE®), epirubicin (sold under the tradename ELLENCE™), idarubicin (sold under the tradenames IDAMYCIN®, IDAMYCIN PFS®), and mitomycin C (sold under the tradename MUTAMYCIN®).

Examples of anti-metabolites include, but are not limited to, claribine (2-chlorodeoxyadenosine, sold under the tradename LEUSTATIN®), 5-fluorouracil (sold under the tradename ADRUCIL®), 6-thioguanine (sold under the tradename PURINETHOL®), pemetrexed (sold under the tradename ALIMTA®), cytarabine (also known as arabinosylcytosine (Ara-C), sold under the tradename CYROSAR-U®), cytarabine liposomal (also known as Liposomal Ara-C, sold under the tradename DEPOCYT™), decitabine (sold under the tradename DACOGEN®), hydroxyurea and (sold under the tradenames HYDREA®, DROXIA™ and MYLOCEL™) fludarabine (sold under the tradename FLUDARA®), floxuridine (sold under the tradename FUDR®), cladribine (also known as 2-chlorodeoxyadenosine (2-CdA) sold under the tradename LEUSTA- TIN™), methotrexate (also known as amethopterin, methotrexate sodium (MTX), sold under the tradenames RHEUMATREX® and TREXALL™), and pentostatin (sold under the tradename NIPENT®).

Examples of retinoids include, but are not limited to, alitretinoin (sold under the tradename PANRETIN®), tretinoin (all-trans retinoic acid, also known as ATRA, sold under the tradename VESANOID®), Isotretinoin (13-c/s-retinoic acid, sold under the tradenames ACCUTANE®, AMNESTEEM®, CLARAVIS®, CLARUS®, DECUTAN®, ISOTANE®, IZOTECH®, ORATANE®, ISOTRET®, and SOTRET®), and bexarotene (sold under the tradename TARGRETIN®).

Activity: STING Biochemical [3H]cGAMP Competition Assay

The individual compounds described in the Examples herein are defined as STING agonists by (i) binding to the STING protein as evidenced by a reduction in binding of tritiated cGAMP ligand to the STING protein by at least 20% at 20 uM (concentration of compound being tested) in a STING Biochemical [3H]cGAMP Competition Assay and (ii) demonstrating interferon production with a 6% or greater induction of IFN-β secretion at 30 uM in the THP1 cell assay (where induction caused by cGAMP at 30 uM was set at 100%).

The ability of compounds to bind STING is quantified by the ability to compete with tritiated cGAMP ligand for human STING receptor membrane using a radioactive filter-binding assay. The binding assay employs STING receptor obtained from Hi-Five cell membranes overexpressing full-length HAQ STING prepared in-house and tritiated cGAMP ligand also purified in-house.

The following experimental procedures detail the preparation of specific examples of the instant disclosure. The compounds of the examples are drawn in their neutral forms in the procedures and tables below. In some cases, the compounds were isolated as salts depending on the method used for their final purification and/or intrinsic molecular properties. The examples are for illustrative purposes only and are not intended to limit the scope of the instant disclosure in any way.

ABBREVIATIONS $A^{Bz}$ 6-N-benzoyladenine
AcOH Acetic acid
AIBN Azobisisobutyronitrile, 2,2'-azobis(2-methylpropionitrile)
AMPDA Adenosine monophosphate deaminase
atm Atmosphere, a unit of pressure defined as 101325 Pa (1.01325 bar)
$BCl_3$ Boron trichloride
$BF_3$—$OEt_2$, $BF_3$-$Et_2O$ Boron trifluoride diethyl etherate
$BrCH_2CHO$ Bromoacetaldehyde
BSA Trimethylsilyl N-(trimethylsilyl)acetimidate
Bz Benzoyl
BzCl Benzoyl chloride
$CD_3OD$ Deuterium-enriched methyl alcohol, deuterium-enriched methanol
Ci Curie, a non-standard unit of radioactivity; 1Ci=3 0.7× $10^{10}$ Bq, where Bq is Becquerel, the SI unit of radioactivity, equivalent to 1 disintegration per second (dps)
$ClCH_2CHO$ Chloroacetaldehyde
d Doublet
$D_2O$ Deuterium-enriched water
DCA Dichloroacetic acid
DCE Dichloroethane
DCM, $CH_2Cl_2$ Dichloromethane
ddd Doublet of doublet of doublet
ddt Doublet of doublet of triplet
DDTT (E)-N,N-dimethyl-N'-(3-thioxo-3H-1,2,4-dithiazol-5-yl)formimidamide, N'-(3-thioxo-3H-1,2,4-dithiazol-S-yl)-N,N-dimethylmethanimidamide
DEAD Diethyl azodicarboxylate
DIEA N-ethyl-N-isopropylpropan-2-amine
DIEA HCl N-ethyl-N-isopropylpropan-2-amine hydrochloride
DiPEA N,N-Diisopropylethylamine
DiPEA-HCl 2-chloro-N,N-diisopropylethylamine hydrochloride
DMA N,N-dimethylacetamide
DMAP Dimethylaminopyridine
DMF N,N-dimethylformamide
DMF-DMA N,N-Dimethylformamide dimethyl acetal
DMOCP 2-chloro-5,5-dimethyl-1,3,2-dioxaphosphineane 2-oxide
DMTr 4,4'-dimethoxytrityl
DMTrCl 4,4'-(chloro(phenyl)methylene)bis(methoxybenzene), 4,4'-dimethoxytrityl chloride
dq Doublet of quartet
$EC_{50}$ half maximal effective concentration, concentration of a drug, antibody or toxicant that induces a response halfway between the baseline and maximum after a specified exposure time
eq Equivalents
ES Electron spray
$Et_2O$ Diethyl ether
EtOAc Ethyl acetate
EtOH Ethyl alcohol, ethanol
g Gram
h Hour
$H_2$ Hydrogen (gas)
HEPES 2-[4-(2-hydroxyethyl)piperazin-1-yl]ethanesulfonic acid, a zwitterionic organic chemical buffering agent
hept Heptet
Hex Hexanes
HPLC High performance liquid chromatography
Hz Hertz
i-PrMgCl Isopropylmagnesium chloride
i-PrMgCl—LiCl Isopropylmagnesium chloride-lithium chloride
i-PrOH Isopropanol, isopropyl alcohol
$K_2CO_3$ Potassium carbonate
LCMS Liquid chromatography-mass spectroscopy
m Multiplet
M Molar, moles per liter
m/e Mass/charge
mCi Millicurie
Me Methyl
MeCN, ACN Acetonitrile
MeCOOH, $CH_3COOH$ Acetic acid
MeMgBr, $CH_3MgBr$ Methylmagnesium bromide
MeNH, $CH_3NH_2$ Methylamine
MeOH, $CH_3OH$ Methyl alcohol, methanol
$MgCl_2$ Magnesium chloride
$MgSO_4$ Magnesium sulfate
MOI Multiplicity of infection
MPLC Medium pressure liquid chromatography
MTBE Methyl t-butyl ether, methyl tertiary butyl ether
$Na_2CO_3$ Sodium carbonate
$Na_2SO_4$ Sodium sulfate
NaH Sodium hydride
$NaHCO_3$ Sodium bicarbonate
$NaHSO_3$ Sodium bisulfate
NaOMe Sodium methoxide nBu₃SnH Tri-n-butyltin hydride, tributyl stannane
NH₄HCO₃ Ammonium bicarbonate
NH₄OAc Ammonium acetate
NMP N-methyl-2-pyrrolidone
P₂O₅ Phosphorus pentoxide
Pd(OH)₂/C Palladium hydroxide on carbon
Pd/C Palladium on charcoal
PPh₃ Triphenylphosphine
Py Pyridine
q Quartet
RPM, rpm Revolutions per minute
RT, rt Room temperature, approximately 25° C.
s Singlet
sat Saturated
SnCl₄ Tin(IV) chloride
t Triplet
TBAF, Bu₄NF, Tetra-n-butylammonium fluoride (CH₃CH₂CH₂CH₂)₄NF
TBDPSCl tert-Butylchlorodiphenylsilane
TBS t-Butyldimethylsilyl
TBSCl t-Butyldimethylsilyl chloride
t-BuNH₂ tert-Butylamine
t-BuO₂H tert-Butyl peroxide
TEA, Et₃N Triethylamine
TEA.3HF, Et₃N.3HF Triethylamine trihydrofluoride
TEA.HF Triethylamine hydrofluoride
TEAA Triethylammonium acetate
TES, Et₃SiH Triethylsilane
TFA Trifluoroacetic acid
TFA.Py Pyridine 2,2,2-trifluoroacetate
THF Tetrahydrofuran
TIPSOTf Triisopropylsilyl trifluoromethanesulfonate
TLC Thin layer chromatography
TMA Trimethylamine
TMSCl Trimethylsilyl chloride
(TMS)₃ SiH Tris(trimethylsilyl)silane
$T_R$ Retention time
TrisCl Tris(hydroxymethyl)aminomethane hydrochloride
v/v Volume/volume
$\lambda_{em}$ Emission wavelength
$\lambda_{ex}$ Excitation wavelength Preparations The following experimental procedures detail the preparation of specific examples of the instant disclosure. The compounds of the examples are drawn in their neutral forms in the procedures and tables below. In some cases, the compounds were isolated as salts depending on the method used for their final purification and/or intrinsic molecular properties. The examples are for illustrative purposes only and are not intended to limit the scope of the instant disclosure in any way.

Preparation 1: 8-((2R,3R,4S,5R)-3,4-dihydroxy-S-(hydroxymethyl) tetrahydrofuran-2-yl)imidazo[1,2-a]pyrimidin-5(8H)-one

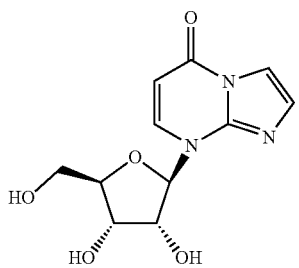 [SMILES: O=c1ccn([C@@H]2O[C@H](CO)[C@@H](O)[C@H]2O)c2nccn12]

Step 1: (3aR,4R,12R,12aR)-2,2,2-triphenyl-3a,4,12,12a-tetrahydro-5H,8H-2l5-4,12-epoxy[1,3,2]dioxaphospholo[4,5-e]pyrimido[2,1-b][1,3]oxazocin-8-one

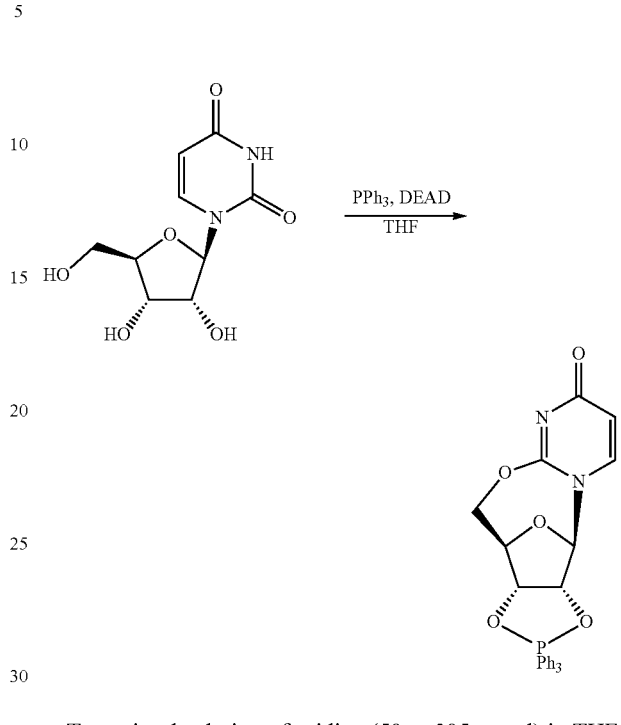

To a stirred solution of uridine (50 g, 205 mmol) in THF (500 mL) was added PPh₃ (161 g, 614 mmol). DEAD (107 g, 614 mmol) was added to the mixture dropwise. The reaction mixture was left to stir for 12 h and filtered. The product was recrystallized from DMF (2 L) at 80° C. ¹H-NMR (400 MHz, DMSO-d₆): δ 8.05 (br d, J=7.5 Hz, 1H), 7.67-7.51 (m, 2H), 7.47-7.17 (m, 15H), 5.96-5.85 (m, 2H), 4.84 (br dd, J=6.6, 13.2 Hz, 1H), 4.73 (s, 1H), 4.60-4.46 (m, 2H), 4.16 (br d, J=12.7 Hz, 1H).

Step 2: (6R,7R,8S,9R)-7,8-dihydroxy-7,8,9,10-tetrahydro-2H,6H-6,9-epoxypyrimido[2,1-b][1,3]oxazocin-2-one

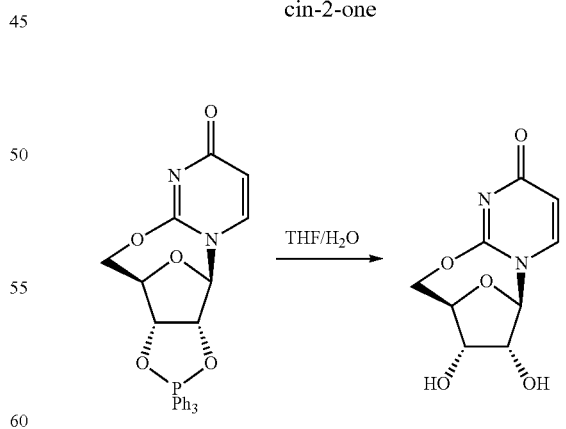

A mixture of (3aR,4R,12R,12aR)-2,2,2-triphenyl-3a,4,12,12a-tetrahydro-5H,8H-2l5-4,12-epoxy[1,3,2]dioxaphospholo[4,5-e]pyrimido[2,1-b][1,3]oxazocin-8-one (50 g, 103 mmol) in THF (500 mL) and H₂O (500 mL) was heated to 60° C. for 12 h. The mixture was cooled to RT and concentrated. To the residue was added acetone (200 mL).

The mixture was allowed to stir for 10 min, filtered, and washed with acetone. The filter cake was dried in vacuo to give the product. ¹H-NMR (400 MHz, DMSO-$d_6$): δ 8.02 (br d, J=7.0 Hz, 1H), 5.93 (br d, J=7.0 Hz, 1H), 5.58 (s, 1H), 5.42 (br s, 2H), 4.57-4.43 (m, 2H), 4.43-4.26 (m, 2H), 4.10 (br d, J=12.7 Hz, 1H).

Step 3: 2-amino-1-(β-D-ribofuranosyl)pyrimidin-4(1H)-one

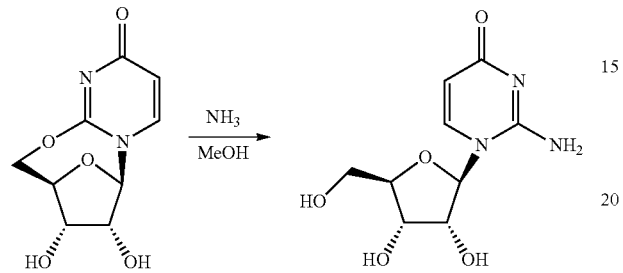

A mixture of (6R,7R,8S,9R)-7,8-dihydroxy-7,8,9,10-tetrahydro-2H,6H-6,9-epoxypyrimido[2,1-b][1,3]oxazocin-2-one (5.0 g, 22 mmol) in sat $NH_3$ in MeOH (60 mL) in autoclave was heated to 60° C. for 12 h. The mixture was cooled to RT and concentrated to give the product. LCMS (ES, m/z): 244 [M+H]⁺. ¹H-NMR (400 MHz, DMSO-$d_6$): δ 7.62 (br d, J=7.1 Hz, 1H), 6.95 (br s, 2H), 5.58 (br d, J=7.5 Hz, 1H), 5.54-5.37 (m, 2H), 5.37-5.16 (m, 2H), 4.12 (br s, 2H), 4.04-3.89 (m, 2H), 3.60 (br s, 2H), 3.17 (br s, 3H).

Step 4: 8-(β-D-ribofuranosyl)-8,8a-dihydroimidazo[1,2-a]pyrimidin-5(1H)-one

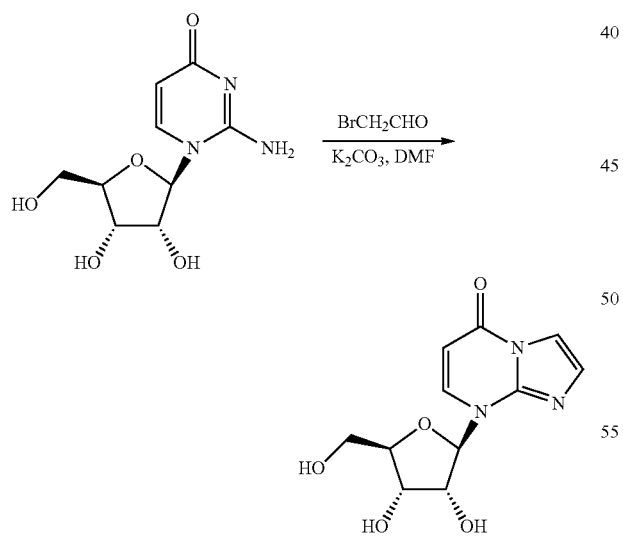

To a stirred solution of 2-amino-1-(β-D-ribofuranosyl)pyrimidin-4(1H)-one (8.0 g, 33 mmol) in DMF (80 mL) were added $K_2CO_3$ (13.6 g, 99 mmol) and $BrCH_2CHO$ (32 g, 260 mmol). The reaction mixture was heated to 40° C. for 4 h, cooled to RT, and filtered. The filtrate was purified by reverse phase chromatography eluted with 1-25% ACN in aq $NH_4OH$ (0.05% v/v) to give the product. LCMS (ES, m/z): 268 [M+H]⁺. ¹H-NMR (400 MHz, DMSO-$d_6$): δ 8.19 (br d, J=7.5 Hz, 1H), 7.65 (br s, 1H), 7.26 (br s, 1H), 6.10 (br s, 1H), 6.02 (br d, J=7.5 Hz, 1H), 4.59 (br s, 1H), 4.27 (br d, J=15.9 Hz, 2H), 3.99-3.90 (m, 1H), 3.88-3.79 (m, 1H).

Preparation 2: (2R,3R,4R,5R)—5-(hydroxymethyl)-2-(8-oxoimidazo[1,2-b]pyridazin-5(8H)-yl)-4-((triisopropylsilyl)oxy)tetrahydrofuran-3-yl hydrogen phosphonate

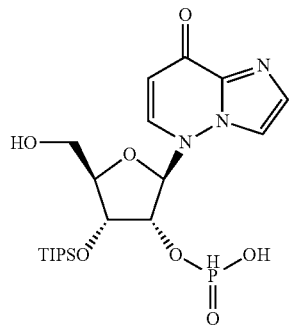

Step 1: 6-chloropyridazin-3-amine

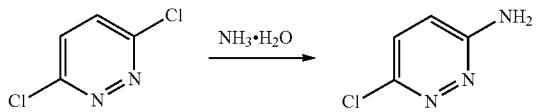 [SMILES: Clc1ccc(Cl)nn1 ; "NH3·H2O" ; Nc1ccc(Cl)nn1]

A mixture of 3,6-dichloropyridazine (100 g, 671 mmol) and $NH_4OH$ (47 g, 50%, 671 mmol) was heated to 120° C. for 16 h, cooled to RT, and filtered to give the product. ¹H-NMR (400 MHz, DMSO-$d_6$): δ 7.35 (s, 1H), 6.84 (s, 1H), 6.63 (s, 2H).

Step 2: 4-bromo-6-chloropyridazin-3-amine

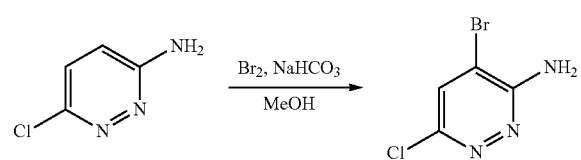

To a stirred solution of 6-chloropyridazin-3-amine (179 g, 1.38 mol) in MeOH (2 L) was added $NaHCO_3$ (232 g, 2.76 mol). $Br_2$ (265 g, 1.66 mol) was added to the mixture dropwise. The reaction mixture was left to stir at RT for 16 h and concentrated to give the crude product. The residue was used in the next step without further purification.

Step 3: 8-bromo-6-chloroimidazo[1,2-b]pyridazine

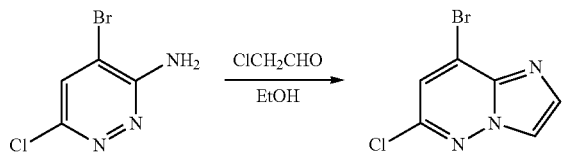

To the crude 4-bromo-6-chloropyridazin-3-amine (120 g, 576 mmol) was added EtOH (1.2 L). ClCH₂CHO (600 g, 7.65 mol) was added to the mixture over 30 min. The reaction mixture was heated to 90° C. for 3 h, cooled to RT, and concentrated. The residue was purified by silica gel column chromatography eluted with 9-50% EtOAc in petroleum ether to give the product. ¹H-NMR (400 MHz, DMSO-d₆): δ 8.01 (s, 1H), 7.68 (brs, 1H), 6.03 (s, 1H).

Step 4: 6-chloroimidazo[1,2-b]pyridazin-8(5H)-one

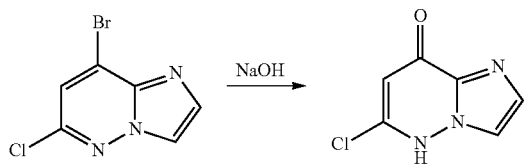

To 8-bromo-6-chloroimidazo[1,2-b]pyridazine (70 g, 301 mmol) were added H₂O (700 mL) and NaOH (26 g, 647 mmol). The reaction mixture was heated to 100° C. for 16 h, cooled to RT, and neutralized to pH 6-7 with HCl. The product was collected by filtration.

Step 5: imidazo[1,2-b]pyridazin-8(5H)-one

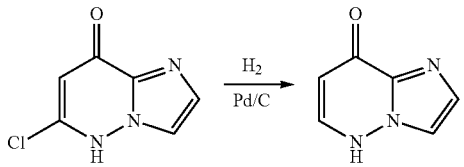

A flask containing 6-chloroimidazo[1,2-b]pyridazin-8 (5H)-one (36 g, 212 mmol) and Pd/C (13 g) in MeOH was degassed and purged with H₂ for three times. The reaction mixture was left to stir under H₂ (50 psi) at 40° C. for 16 h, cooled to RT, and filtered. The filtrate was concentrated to give the product. ¹H-NMR (400 MHz, DMSO-d₆): δ 8.60 (d, 1H), 8.57 (d, 1H), 8.23 (d, 1H), 7.17 (d, 1H).

Step 6: 5-[2,3,5-tris-O-(phenylcarbonyl)-β-D-ribofuranosyl]imidazo[1,2-b]pyridazin-8(5H)-one

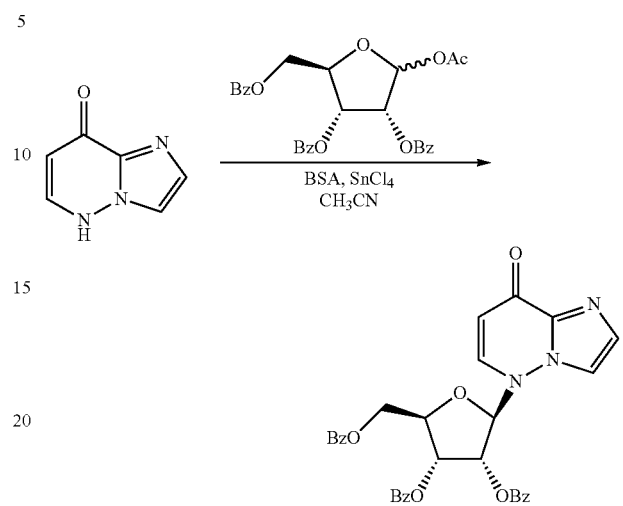

A mixture of imidazo[1,2-b]pyridazin-8(5H)-one (18 g, 133 mmol) and N,O-bis(trimethylsilyl)acetamide (108 g, 532 mmol) in MeCN (200 mL) was heated to 70° C. for 1 h and cooled to RT. To the mixture were added 1-O-acetyl-2,3,5-tri-O-benzoyl-D-ribofuranose (45 g, 89 mmol), CH₃CN (200 mL), and SnCl₄ (45.7 g, 175 mmol). The mixture was heated to 70° C. for 3 h, cooled to RT, and concentrated. The residue was purified by silica gel column chromatography eluted with 9-100% of EtOAc in petroleum ether to give the product. LCMS (ES, m/z): 580 [M+H]⁺. ¹H-NMR (400 MHz, DMSO-d₆): δ 8.26 (s, 1H), 8.18 (s, 1H), 8.01-8.03 (d, J=8 Hz, 3H), 7.92-7.94 (d, J=8 Hz, 2H), 7.84-7.85 (d, J=4 Hz, 2H), 7.74 (s, 1H), 7.60-7.65 (m, 3H), 7.40-7.52 (m, 2H), 6.01-6.07 (m, 3H), 4.81-4.88 (m, 3H).

Step 7: 5-((2R,3R,4S,5R)-3,4-dihydroxy-5-(hydroxymethyl)tetrahydrofuran-2-yl)imidazo[1,2-b]pyridazin-8(5H)-one

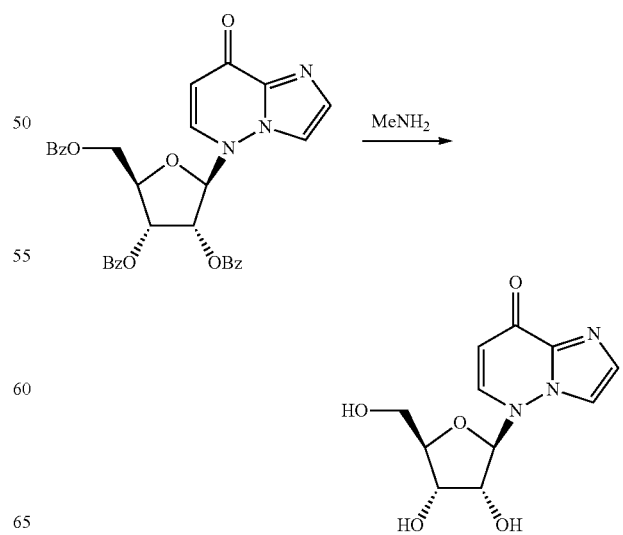

(2R,3R,4R,5R)-2-((benzoyloxy)methyl)-S-(8-oxoimidazo[1,2-b]pyridazin-5(8H)-yl)tetrahydrofuran-3,4-diyl dibenzoate (3.9 g, 5.38 mmol) was dissolved in a solution of MeNH₂ in EtOH (30%, 60 mL), and the resulting solution was stirred at RT for 6 h. Then, the mixture was concentrated under reduced pressure, and the residue was purified by reverse phase (C18) chromatography eluted with 0 to 95% ACN in aq NH₄HCO₃ (0.04%) to give the product. LCMS (ES, m/z): 268.3 [M+H]⁺. ¹H-NMR (400 MHz, DMSO-d₆): δ 8.29 (d, J=2.3 Hz, 1H), 8.21 (d, J=2.3 Hz, 1H), 8.02 (d, J=6.4 Hz, 1H), 7.14 (d, J=4.9 Hz, 1H), 6.05 (d, J=6.4 Hz, 1H), 5.61 (d, J=5.4 Hz, 1H), 5.20 (t, J=5.1 Hz, 1H), 5.15 (d, J=5.0 Hz, 1H), 4.23 (q, J=5.0 Hz, 1H), 4.11 (q, J=4.8 Hz, 1H), 3.96 (q, J=3.6 Hz, 1H), 3.73-3.68 (m, 1H), 3.63-3.58 (m, 1H).

Step 8: 5-((2R,3R,4S,5R)—S-((bis(4-methoxyphenyl)(phenyl)methoxy)methyl)-3,4-dihydroxytetrahydrofuran-2-yl)imidazo[1,2-b]pyridazin-8(5H)-one

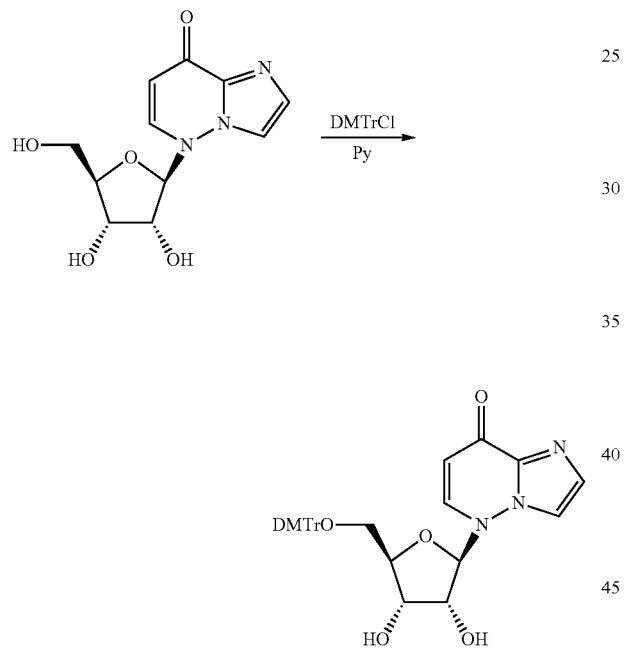

To a solution of 5-((2R,3R,4S,5R)-3,4-dihydroxy-S-(hydroxymethyl) tetrahydrofuran-2-yl)imidazo[1,2-b]pyridazin-8(5H)-one (800 mg, 2.99 mmol) in Py (11 mL) at 0° C. was added 4,4'-(chloro(phenyl)methylene)bis(methoxybenzene) (0.112 g, 3.29 mmol). The mixture was stirred at RT for 2 h. Then, the mixture was concentrated, and the residue was dissolved in CH₂Cl₂ (50 mL). The solution was washed with sat aq NaHCO₃ (10 mL), dried (Na₂SO₄) and concentrated. It was purified by silica gel column chromatography eluted with 0-10% MeOH in DCM (containing 1% Et₃N) to give the product. LCMS (ES, m/z): 568.2 [M–H]⁻. ¹H-NMR (400 MHz, DMSO-d₆): δ 8.17 (d, J=2.2 Hz, 1H), 8.04 (d, J=6.4 Hz, 1H), 7.99 (d, J=2.3 Hz, 1H), 7.43-7.35 (m, 2H), 7.33-7.21 (m, 7H), 7.18 (d, J=4.0 Hz, 1H), 6.93-6.84 (m, 4H), 6.08 (d, J=6.4 Hz, 1H), 5.73 (d, J=5.3 Hz, 1H), 5.20 (d, J=5.9 Hz, 1H), 4.27 (q, J=4.9 Hz, 1H), 4.16 (q, J=5.5 Hz, 1H), 4.07 (dd, J=5.2, 3.5 Hz, 1H), 3.73 (s, 6H), 3.26-3.24 (m, 2H).

Step 9: 5-((2R,3R,4S,5R)—S-((bis(4-methoxyphenyl)(phenyl)methoxy)methyl)-3-hydroxy-4-((triisopropylsilyl)oxy)tetrahydrofuran-2-yl)imidazo[1,2-b]pyridazin-8(5H)-one and 5-((2R,3R,4R,5R)—S-((bis(4-methoxyphenyl)(phenyl)methoxy)methyl)-4-hydroxy-3-((triisopropylsilyl)oxy)tetrahydrofuran-2-yl)imidazo[1,2-b]pyridazin-8(5H)-one

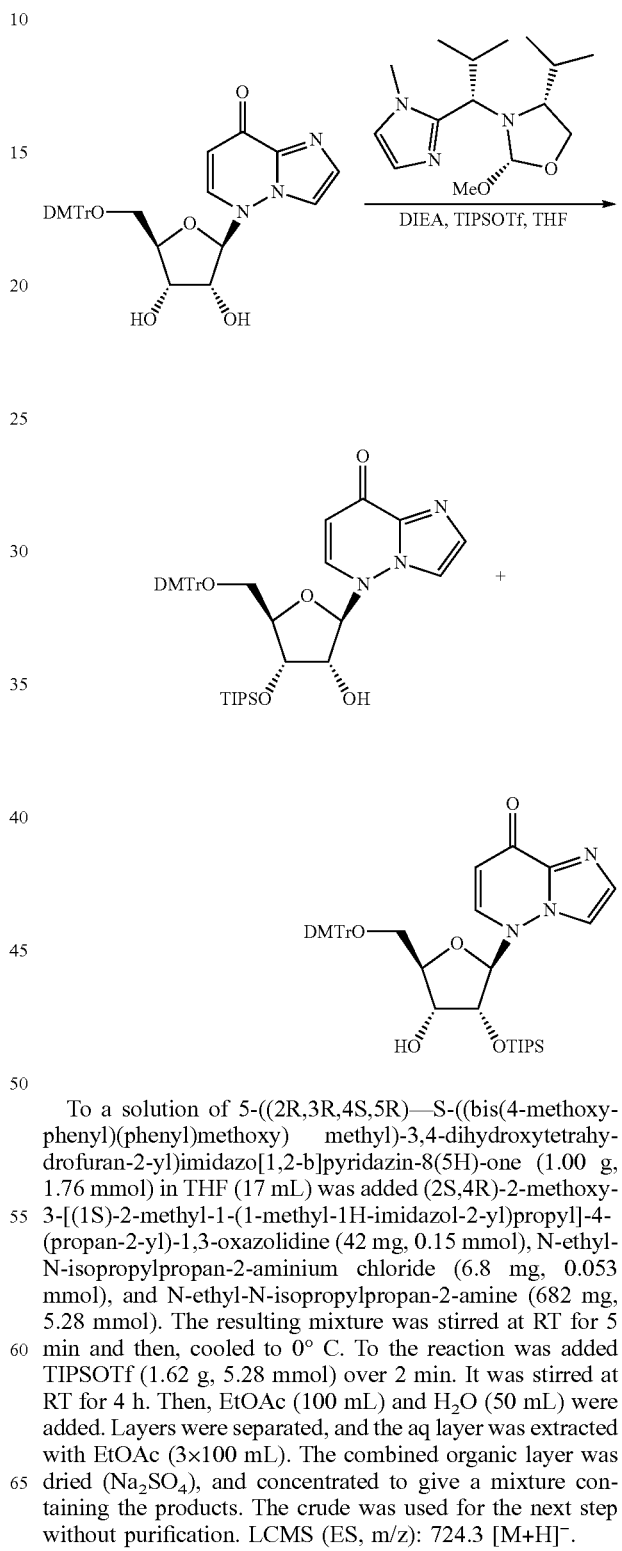

To a solution of 5-((2R,3R,4S,5R)—S-((bis(4-methoxyphenyl)(phenyl)methoxy) methyl)-3,4-dihydroxytetrahydrofuran-2-yl)imidazo[1,2-b]pyridazin-8(5H)-one (1.00 g, 1.76 mmol) in THF (17 mL) was added (2S,4R)-2-methoxy-3-[(1S)-2-methyl-1-(1-methyl-1H-imidazol-2-yl)propyl]-4-(propan-2-yl)-1,3-oxazolidine (42 mg, 0.15 mmol), N-ethyl-N-isopropylpropan-2-aminium chloride (6.8 mg, 0.053 mmol), and N-ethyl-N-isopropylpropan-2-amine (682 mg, 5.28 mmol). The resulting mixture was stirred at RT for 5 min and then, cooled to 0° C. To the reaction was added TIPSOTf (1.62 g, 5.28 mmol) over 2 min. It was stirred at RT for 4 h. Then, EtOAc (100 mL) and H₂O (50 mL) were added. Layers were separated, and the aq layer was extracted with EtOAc (3×100 mL). The combined organic layer was dried (Na₂SO₄), and concentrated to give a mixture containing the products. The crude was used for the next step without purification. LCMS (ES, m/z): 724.3 [M+H]⁻.

Step 10: (2R,3R,4R,5R)—S-((bis(4-methoxyphenyl)(phenyl)methoxy)methyl)-2-(8-oxoimidazo[1,2-b]pyridazin-5(8H)-yl)-4-((triisopropylsilyl)oxy)tetrahydrofuran-3-yl hydrogen phosphonate

Step 11: (2R,3R,4R,5R)—S-(hydroxymethyl)-2-(8-oxoimidazo[1,2-b]pyridazin-5(8H)-yl)-4-((triisopropylsilyl)oxy)tetrahydrofuran-3-yl hydrogen phosphonate

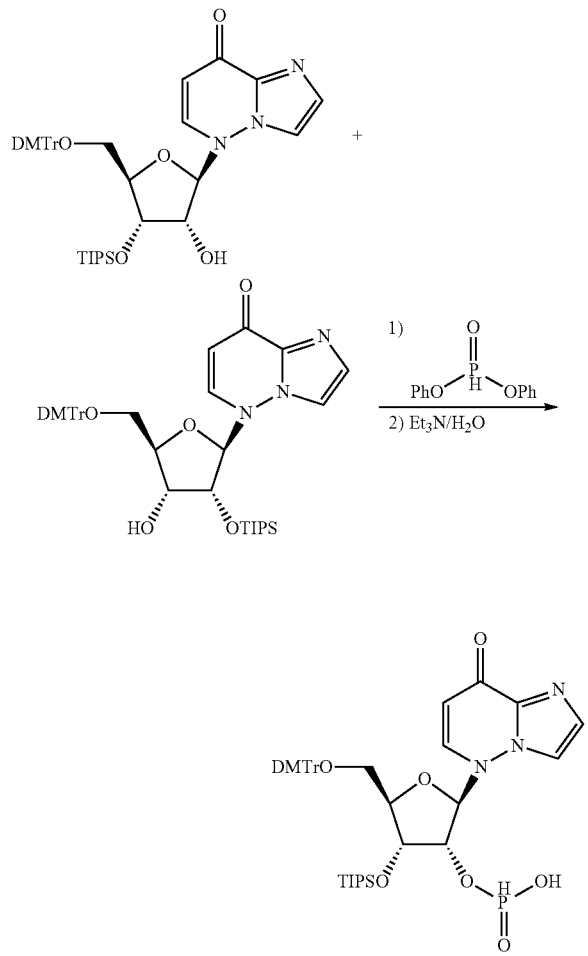

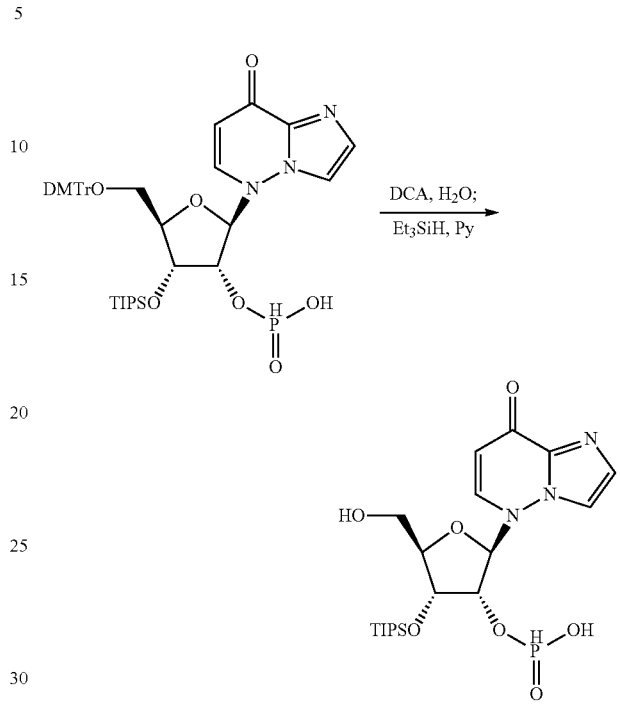

To a solution of the crude from Step 9 (3.5 g, 1.7 mmol) in pyridine (9 mL) at 0° C. under Ar was added diphenyl phosphonate (2.06 g, 8.80 mmol) over 0.5 min. The resulting mixture was warmed to RT for 20 min. To the reaction mixture cooled at 0° C. was added TEA (1.8 mL) in H$_2$O (1.8 mL) dropwise over 0.5 min. It was warmed to RT for 30 min. The mixture was concentrated and then, co-evaporated with toluene (3×20 mL) to give a crude. It was partitioned between CH$_2$Cl$_2$ (300 mL) and aq NaHCO$_3$ (5%, 80 mL). The organic layer was washed with aq NaHCO$_3$ (2×80 mL), dried (Na$_2$SO$_4$) and concentrated. The residue was purified by reverse phase (C18) chromatography eluted with 35 to 55% ACN in aq NH$_4$HCO$_3$ (10 mM) to give the product. LCMS (ES, m/z): 788.3 [M−H]$^−$. $^1$H-NMR (400 MHz, DMSO-d$_6$): δ 8.25 (d, J=2.2 Hz, 1H), 8.09-8.00 (m, 1H), 7.98 (d, J=2.3 Hz, 1H), 7.49-7.35 (m, 3H), 7.34-7.21 (m, 8H), 6.89 (d, J=8.6 Hz, 4H), 6.16-6.06 (m, 1H), 4.71-4.54 (m, 2H), 4.48-4.29 (m, 1H), 3.75 (d, J=2.5 Hz, 6H), 3.72-3.64 (m, 1H), 3.36 (d, J=14.6 Hz, 5H), 3.00 (q, J=7.3 Hz, 2H), 1.34-1.19 (m, 5H), 1.03-0.87 (m, 12H), 0.81 (d, J=6.7 Hz, 8H). $^{31}$P-NMR: (162 MHz, DMSO-d$_6$) δ 0.80 (s).

To a stirred solution of (2R,3R,4R,5R)—S-((bis(4-methoxyphenyl)(phenyl) methoxy)methyl)-2-(8-oxoimidazo[1,2-b]pyridazin-5(8H)-yl)-4-((triisopropylsilyl)oxy) tetrahydrofuran-3-yl hydrogen phosphonate (0.38 g, 0.47 mmol) in CH$_2$Cl$_2$ (6 mL) was added H$_2$O (85 mg, 4.7 mmol), and DCA in CH$_2$Cl$_2$ (6%, 6.0 mL, 4.2 mmol). The mixture was stirred at RT for 15 min, and then Et$_3$SiH (10 mL) was added. After 40 min, Py (0.66 mL) was added to the reaction at 0° C., and the mixture was stirred for 5 min. The reaction was concentrated to provide (2R,3R,4R,5R)—S-(hydroxymethyl)-2-(8-oxoimidazo[1,2-b]pyridazin-5(8H)-yl)-4-((triisopropyl-silyl)oxy)tetrahydrofuran-3-yl hydrogen phosphonate. LCMS (ES, m/z): 488.2 [M+H]$^+$.

Preparation 3: (2R,3S,4R,5R)—S-(6-benzamido-9H-purin-9-yl)-2-((bis(4-methoxyphenyl)(phenyl)methoxy)methyl)-4-((triisopropylsilyl)oxy)tetrahydrothiophen-3-yl (2-cyanoethyl) diisopropylphosphoramidite

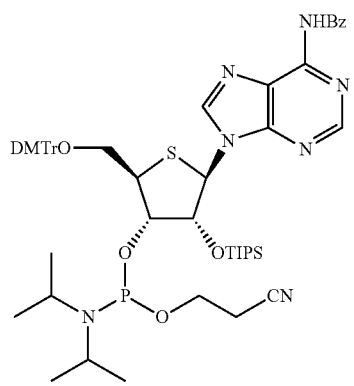

119

Step 1: ((3aS,4R,6R,6aR)-6-(6-amino-9H-purin-9-yl)-2,2-dimethyltetrahydrothieno[3,4-d][1,3]dioxol-4-yl)methanol

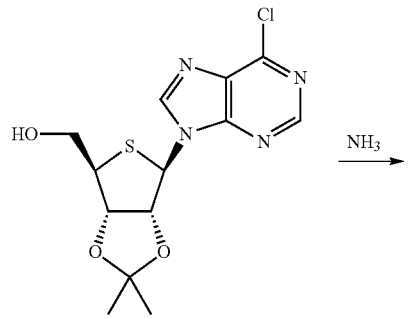

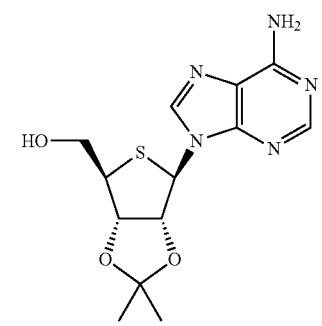

To a tube was added ((3aS,4R,6R,6aR)-6-(6-chloro-9H-purin-9-yl)-2,2-dimethyltetrahydrothieno[3,4-d][1,3]dioxol-4-yl)methanol (3.80 g, 11.1 mmol) in NH₃ in i-PrOH (2.0M, 200 mL). The tube was sealed, and the reaction was stirred at 90° C. for 16 h. The mixture was concentrated. The residue was purified by a silica gel column, eluted with 0-20% MeOH in DCM to give the product. LCMS (ES, m/z): 324.1 [M+H]⁺. ¹H-NMR (400 MHz, DMSO-d₆): δ 8.41 (s, 1H), 8.18 (s, 1H), 7.32 (s, 2H), 6.08 (d, J=2.5 Hz, 1H), 5.43-5.29 (m, 2H), 5.05 (dd, J=5.5, 1.5 Hz, 1H), 3.73-3.55 (m, 3H), 1.54 (s, 3H), 1.31 (s, 3H).

Step 2: N-(9-((3aR,4R,6R,6aS)-6-(hydroxymethyl)-2,2-dimethyltetrahydrothieno[3,4-d][1,3]dioxol-4-yl)-9H-purin-6-yl)benzamide

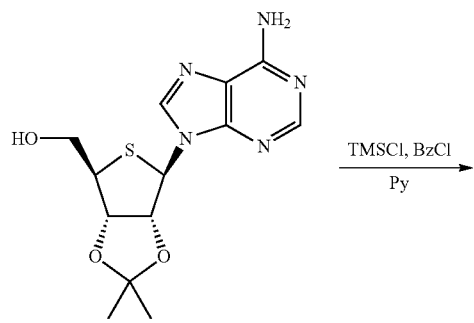

120

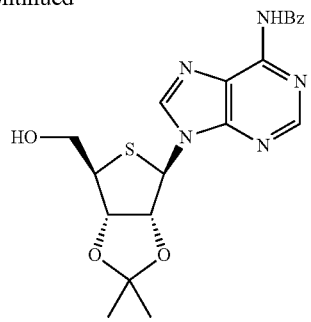

To a solution of ((3aS,4R,6R,6aR)-6-(6-amino-9H-purin-9-yl)-2,2-dimethyltetrahydrothieno[3,4-d][1,3]dioxol-4-yl)methanol (2.60 g, 8.04 mmol) in Py (30 mL) at 0° C. was added TMSCl (8.7 g, 80 mmol) dropwise. The mixture was warmed to RT and continued to stir for 2 h. Then, BzCl (1.70 g, 12.1 mmol) was added, and the resulting mixture was stirred at RT for 2 h. NH₄OH (28%, 2 mL) was added to the mixture, and it was stirred for 2 h. Then, the reaction was concentrated under reduced pressure, and the residue was purified by a silica gel column chromatography eluted with 0-20% MeOH in DCM to give the product. LCMS (ES, m/z): 428.1 [M+H]⁺. ¹H-NMR (400 MHz, DMSO-d₆): δ 11.22 (s, 1H), 8.79 (s, 1H), 8.76 (s, 1H), 8.10-8.02 (m, 2H), 7.80-7.70 (m, 1H), 7.71-7.50 (m, 3H), 6.21 (d, J=2.2 Hz, 1H), 5.46 (dd, J=5.5, 2.3 Hz, 1H), 5.42-5.30 (m, 1H), 5.08 (dd, J=5.5, 1.4 Hz, 1H), 3.74-3.58 (m, 2H), 1.57 (s, 3H), 1.33 (s, 3H).

Step 3: N-(9-((2R,3R,4S,5R)-3,4-dihydroxy-S-(hydroxymethyl)tetrahydrothiophen-2-yl)-9H-purin-6-yl)benzamide

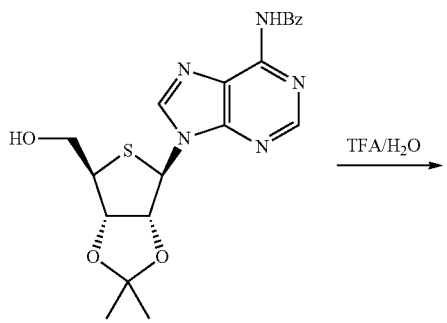

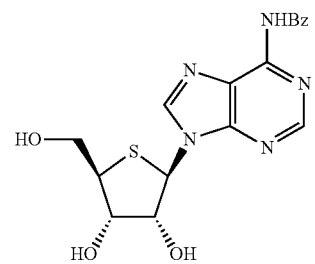

To a solution N-(9-((3aR,4R,6R,6aS)-6-(hydroxymethyl)-2,2-dimethyltetra-hydrothieno[3,4-d][1,3]dioxol-4-yl)-9H-purin-6-yl)benzamide (2.7 g, 6.3 mmol) in H₂O (75 mL) at 0° C. was added TFA (75 mL). The solution was stirred at RT for 30 min. The mixture was concentrated and the, co-evaporated with toluene (4×100 mL). The residue was purified by a silica gel column eluted with 0-20% MeOH in DCM to give the product. LCMS (ES, m/z): 388.2 [M+H]+. 1H-NMR (400 MHz, DMSO-d6): δ 11.16 (br, s, 1H), 8.78 (s, 1H), 8.72 (s, 1H), 8.07-7.97 (m, 2H), 7.68-7.46 (m, 3H), 5.97 (d, J=6.8 Hz, 1H), 4.71 (dd, J=6.8, 3.4 Hz, 1H), 4.21 (t, J=3.4 Hz, 1H), 3.80 (dd, J=11.3, 6.9 Hz, 1H), 3.62 (dd, J=11.4, 5.8 Hz, 1H), 3.41-3.26 (m, 1H).

Step 4: N-(9-((2R,3R,4S,5R)—S-((bis(4-methoxyphenyl)(phenyl)methoxy)methyl)-3,4-dihydroxytetrahydrothiophen-2-yl)-9H-purin-6-yl)benzamide

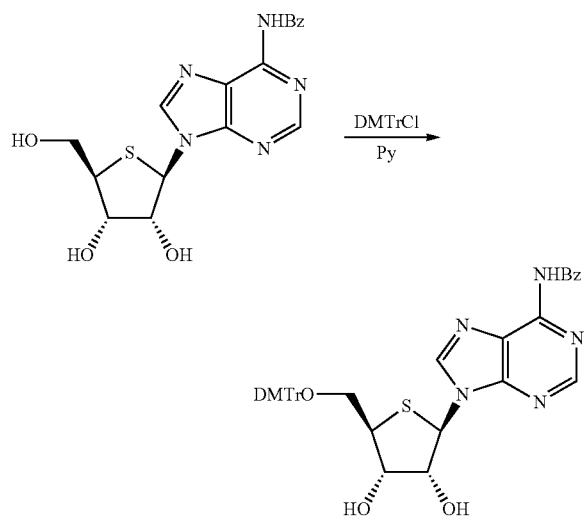

To a solution of N-(9-((2R,3R,4S,5R)-3,4-dihydroxy-S-(hydroxymethyl) tetrahydrothiophen-2-yl)-9H-purin-6-yl) benzamide (2 g, 5.16 mmol) in pyridine (5 mL) at 0° C. was added 4,4'-(chloro(phenyl)methylene)bis(methoxybenzene) (1.92 g, 5.68 mmol). The solution was stirred at RT for 3 h. Then, MeOH (3 mL) was added, and it was concentrated. The residue was purified by a silica gel column chromatography eluted with 0-20% MeOH in DCM to give the product. LCMS (ES, m/z): 690.2 [M+H]+. 1H-NMR (400 MHz, DMSO-d6): δ 11.23 (br, s, 1H), 8.64 (s, 1H), 8.58 (s, 1H), 8.09-8.02 (m, 2H), 7.71-7.61 (m, 1H), 7.61-7.52 (m, 2H), 7.51-7.38 (m, 2H), 7.38-7.22 (m, 7H), 6.97-6.82 (m, 4H), 5.99 (d, J=5.9 Hz, 1H), 5.73 (d, J=5.6 Hz, 1H), 5.43 (d, J=5.0 Hz, 1H), 4.70 (q, J=4.9 Hz, 1H), 4.28 (q, J=3.7 Hz, 1H), 3.76-3.75 (m, 7H), 3.59-3.36 (m, 2H).

Step 5: N-(9-((2R,3R,4S,5R)—S-((bis(4-methoxyphenyl)(phenyl)methoxy)methyl)-4-hydroxy-3-((triisopropylsilyl)oxy)tetrahydrothiophen-2-yl)-9H-purin-6-yl)benzamide

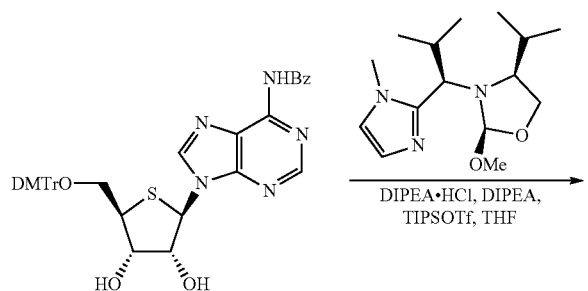

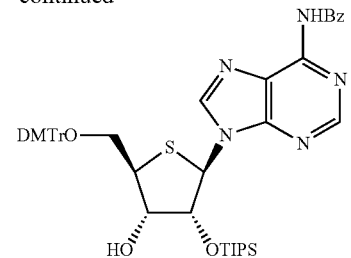

N-(9-((2R,3R,4S,5R)—S-((bis(4-methoxyphenyl)(phenyl)methoxy)methyl)-3,4-dihydroxytetrahydrothiophen-2-yl)-9H-purin-6-yl)benzamide (1.23 g, 1.78 mmol), (2R,4S)-4-isopropyl-2-methoxy-3-((R)-2-methyl-1-(1-methyl-1H-imidazol-2-yl)propyl)oxazolidine (0.753 g, 2.67 mmol), and N-ethyl-N-isopropylpropan-2-aminium chloride (8.9 mg, 0.053 mmol) were co-evaporated with THF (3×10 mL) and then re-dissolved in THF (80 mL) under Ar. To the mixture at 0° C. was added N-ethyl-N-isopropylpropan-2-amine (0.691 g, 5.35 mmol). It was stirred at RT for 5 min, and then TIPSOTf (1.64 g, 5.35 mmol) was added dropwise. The mixture was stirred at RT for 16 h. Then, the solution was diluted with EtOAc (50 mL) and washed with Na2CO3 (3×50 mL). The organic layer was dried (MgSO4) and concentrated to give a crude containing the product. The residue was used for the next reaction step without further purification. LCMS (ES, m/z): 846.3 [M+H]+.

Step 6: (2R,3S,4R,5R)—S-(6-benzamido-9H-purin-9-yl)-2-((bis(4-methoxyphenyl)(phenyl)methoxy)methyl)-4-((triisopropylsilyl)oxy)tetrahydrothiophen-3-yl (2-cyanoethyl) diisopropylphosphoramidite

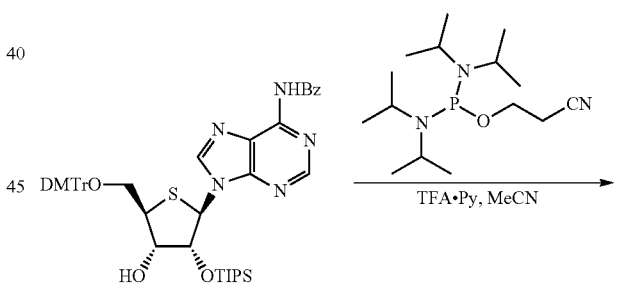

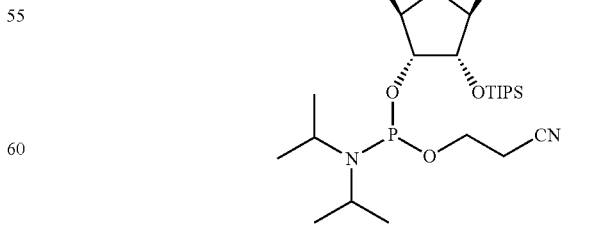

To a stirred solution of 3-((bis(diisopropylamino)phosphino)oxy)propanenitrile (1.43 g, 4.76 mmol) in MeCN (15 mL) under Ar was added pyridin-1-ium 2,2,2-trifluoroacetate (688 mg, 3.57 mmol) and a solution of the crude from Step 5 (~2.0 g, 2.4 mmol) in MeCN (15 mL) over 2 min. It was stirred at RT for 1 h. Then, it was concentrated, and the residue was dissolved in EtOAc (100 mL). The solution was washed with aq NaHCO$_3$ (1%, 2×100 mL), H$_2$O (100 mL) and brine (100 mL), dried (Na$_2$SO$_4$), and purified by reverse phase (C18) chromatography eluted with 40 to 100% ACN in H$_2$O to give the product. LCMS (ES, m/z): 1046.5 [M+H]$^+$. $^1$H-NMR (400 MHz, DMSO-d$_6$): δ 11.17 (s, 1H), 8.60 (d, J=1.5 Hz, 1H), 8.50-8.43 (m, 1H), 8.09-7.99 (m, 2H), 7.72-7.62 (m, 1H), 7.57-7.54 (m, 2H), 7.47-7.44 (m, 2H), 7.40-7.23 (m, 7H), 6.95-6.92 (m, 4H), 6.05-5.97 (m, 1H), 5.30-5.26 (m, 1H), 4.71-4.67 (m, 1H), 3.94-3.82 (m, 2H), 3.76 (d, J=1.5 Hz, 6H), 3.70 (t, J=3.6 Hz, 1H), 3.61-3.58 (m, 1H), 3.50-3.38 (m, 1H), 2.77-2.67 (m, 2H), 2.53-2.49 (m, 2H), 1.18 (dt, 6.9 Hz, 12H), 0.94-0.72 (m, 21H). $^{31}$P-NMR (162 MHz, DMSO-d$_6$): δ 149.66, 149.23.

Preparation 4: (2R,3S,5R)—S-(7-amino-3H-[1,2,3]triazol[4,5-b]pyridin-3-yl)-2-(hydroxymethyl)tetrahydrofuran-3-ol

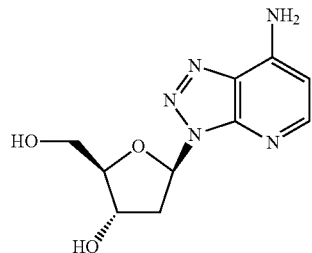 [SMILES: Nc1ccnc2c1nnn2[C@H]1C[C@H](O)[C@@H](CO)O1]

The title compound was prepared according to published procedure (*Nucleoside & Nucleotides* 1992, 11, 1059-1076).

Preparation 5: 1-((3S,4R,5R)—S-((bis(4-methoxyphenyl)(phenyl)methoxy)methyl)-4-fluoro-3-hydroxytetrahydrofuran-2-yl)-1,5-dihydro-4H-imidazo[4,5-c]pyridin-4-one

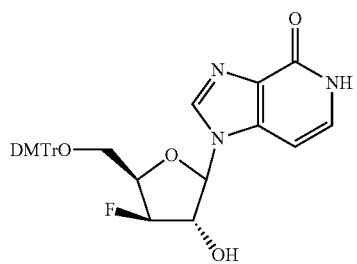

Step 1: ((2R,3S,4S)-4-acetoxy-3-fluoro-S-(4-oxo-4,5-dihydro-1H-imidazo[4,5-c]pyridin-1-yl)tetrahydrofuran-2-yl)methyl benzoate

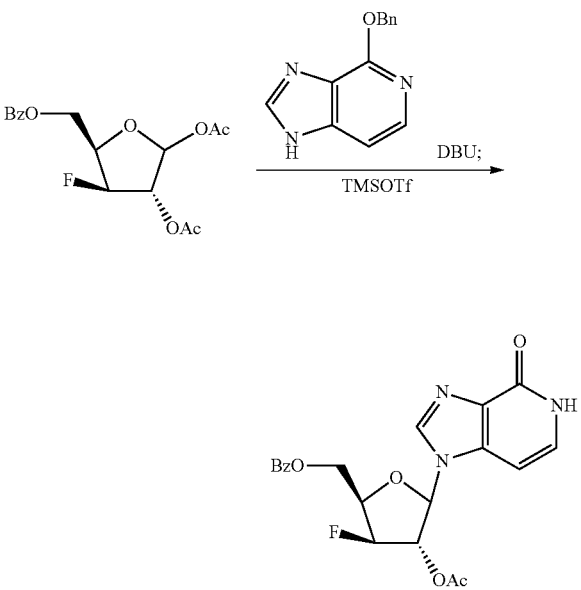

To a suspension of 4-(benzyloxy)-1H-imidazo[4,5-c]pyridine (0.795 g, 3.53 mmol) and (3S,4S,5R)—S-((benzoyloxy)methyl)-4-fluorotetrahydrofuran-2,3-diyl diacetate (1.00 g, 2.94 mmol) in MeCN (20 mL) and DCE (10 mL) at 0° C. under Ar was added 3,4,6,7,8,9,10-octahydropyrimido[1,2-a]azepine (1.34 g, 8.82 mmol). The resulting mixture was stirred at 0° C. for 30 min. Then, TIPSOTf (3.92 g, 17.7 mmol) was added to the solution, and it was stirred at 0° C. for 30 min. Then, the solution was heated to 80° C. for 16 h. Then, the reaction mixture was cooled to 0° C., and sat aq NaHCO$_3$ (10 mL) and H$_2$O (30 mL) were added. Layers were separated, and the aq layer was extracted with EtOAc (3×50 mL). The combined organic layers were washed with brine (100 mL), dried (Na$_2$SO$_4$), and concentrated. The residue was purified by silica gel column chromatography, eluted with 1 to 10% MeOH in DCM to afford the product. LCMS (ES, m/z): 416.3 [M+H]$^+$.

Step 2: 1-((3S,4R,5R)-4-fluoro-3-hydroxy-S-(hydroxymethyl)tetrahydrofuran-2-yl)-1,5-dihydro-4H-imidazo[4,5-c]pyridin-4-one

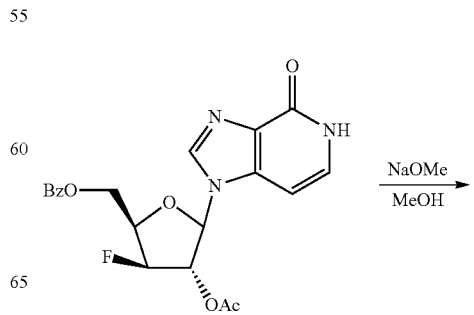

-continued

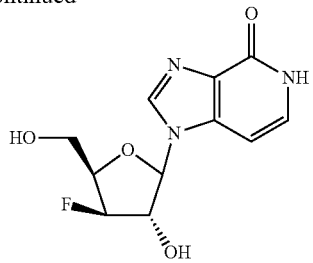

To a stirred solution of ((2R,3S,4S)-4-acetoxy-3-fluoro-S-(4-oxo-4,5-dihydro-1H-imidazo[4,5-c]pyridin-1-yl)tetrahydrofuran-2-yl)methyl benzoate (2.5 g, 5.3 mmol) in MeOH (10 mL) was added NaOMe (3.47 g, 21.2 mmol). The mixture was stirred at RT for 1 h. Then, it was neutralized by addition of CH₃COOH. The solution was concentrated under reduced pressure, and the residue was purified by reverse phase (AQ-C18) chromatography eluted with 0 to 30% ACN in aq NH₄HCO₃ (5 mM) to give the product. LCMS (ES, m/z): 270.0 [M+H]⁺. ¹H-NMR (400 MHz, DMSO-d₆): δ 11.31 (s, 1H), 8.06 (s, 1H), 7.23 (d, J=7.1 Hz, 1H), 6.62 (d, J=7.1 Hz, 1H), 6.37 (d, J=2.9 Hz, 1H), 5.85 (d, J=2.8 Hz, 1H), 5.22-4.98 (m, 2H), 4.54 (d, J=17.7 Hz, 1H), 4.28 (dtd, J=29.6, 6.0, 3.1 Hz, 1H), 3.93-3.62 (m, 2H).

Step 3: 1-((3S,4R,5R)—S-((bis(4-methoxyphenyl)(phenyl)methoxy)methyl)-4-fluoro-3-hydroxytetrahydrofuran-2-yl)-1,5-dihydro-4H-imidazo[4,5-c]pyridin-4-one

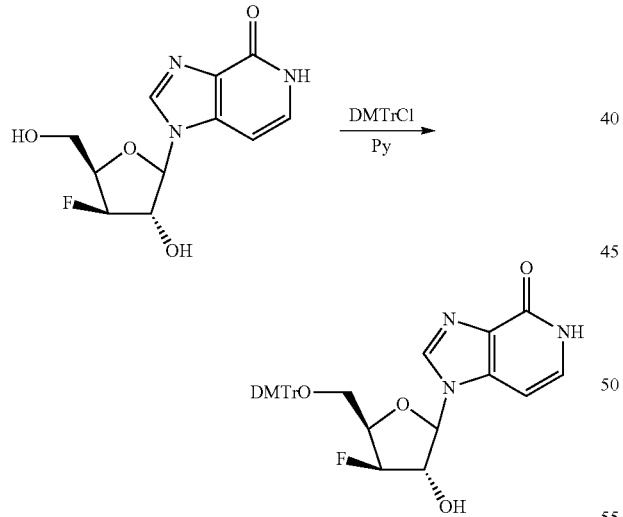

To a solution of 1-((3S,4R,5R)-4-fluoro-3-hydroxy-S-(hydroxymethyl) tetrahydrofuran-2-yl)-1,5-dihydro-4H-imidazo[4,5-c]pyridin-4-one (340 mg, 1.26 mmol) in Py (0.5 mL) was added 4,4'-(chloro(phenyl)methylene)bis(methoxybenzene) (0.43 g, 1.1 mmol). The solution was stirred at RT for 4 h. Then, the mixture was concentrated under reduced pressure, and the residue was purified by silica gel column chromatography eluted with 1 to 10% MeOH in DCM (0.5% Et₃N) to afford the product. LCMS (ES, m/z): 572.3 [M+H]⁺. ¹H-NMR (400 MHz, DMSO-d₆): δ δ 11.32 (d, J=5.9 Hz, 1H), 7.95 (s, 1H), 7.41 (d, J=7.8 Hz, 2H), 7.37-7.15 (m, 8H), 6.86 (dd, J=10.5, 8.6 Hz, 4H), 6.60 (d, J=7.1 Hz, 1H), 6.50-6.36 (m, 1H), 5.92 (d, J=2.6 Hz, 1H), 5.77 (s, 1H), 5.27-5.06 (m, 1H), 4.65-4.42 (m, 2H), 3.73 (d, J=2.6 Hz, 6H), 3.30-3.24 (m, 1H).

Preparation 6: 1-((2R,3R,5S)—S-((bis(4-methoxyphenyl)(phenyl)methoxy) methyl)-3-hydroxytetrahydrofuran-2-yl)-1,5-dihydro-4H-imidazo[4,5-c]pyridin-4-one

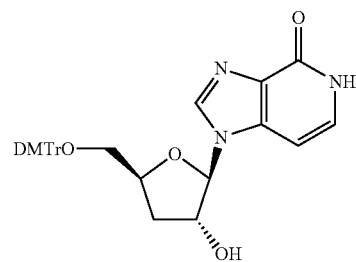

Step 1: ((2S,4R,5R)-4-acetoxy-S-(4-(benzyloxy)-1H-imidazo[4,5-c]pyridin-1-yl)tetrahydrofuran-2-yl)methyl 4-methylbenzoate and ((2S,4R,5R)-4-acetoxy-S-(4-oxo-4,5-dihydro-1H-imidazo[4,5-c]pyridin-1-yl)tetrahydrofuran-2-yl)methyl 4-methylbenzoate

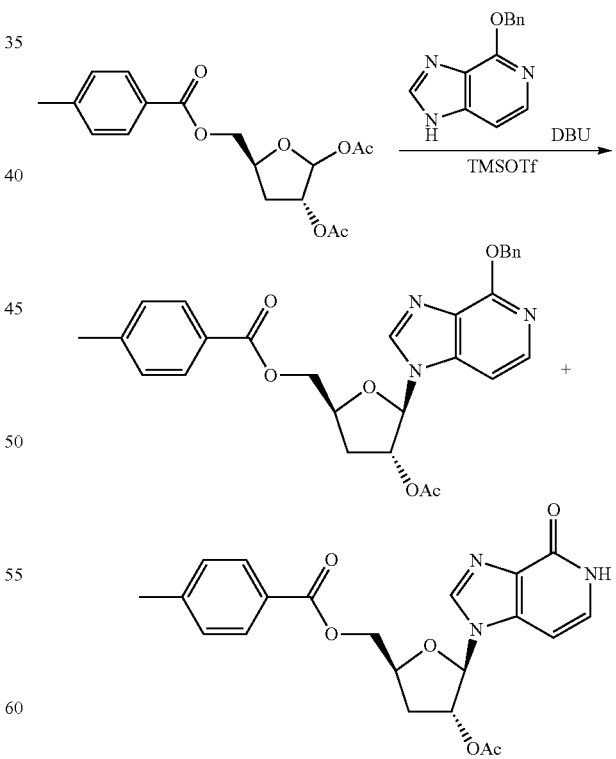

A mixture of (3R,5S)—S-(((4-methylbenzoyl)oxy)methyl)tetrahydrofuran-2,3-diyl diacetate (2.69 g, 8.00 mmol) and 4-(benzyloxy)-1H-imidazo[4,5-c]pyridine (1.98 g, 8.80 mmol) was co-evaporated with MeCN (5×15 mL)

and then, re-dissolved in MeCN (64 mL) under Ar. To the mixture was added 2,3,4,6,7,8,9,10-octahydropyrimido[1,2-a]azepine (1.32 mL, 8.80 mmol) and TIPSOTf (3.05 mL, 16.8 mmol). It was stirred at 80° C. for 1 h. Then, it was cooled to RT, and sat aq NaHCO$_3$ (40 mL) and H$_2$O (150 mL) were added. Layers were separated, and the aq layer was extracted with EtOAc (3×100 mL). The combined organic phase was washed with brine (300 mL), dried (Na$_2$SO$_4$) and concentrated. The residue was purified by silica gel column chromatography eluted with 0-10% MeOH in DCM to give ((2S,4R,5R)-4-acetoxy-S-(4-(benzyloxy)-1H-imidazo[4,5-c]pyridin-1-yl)tetrahydrofuran-2-yl)methyl 4-methylbenzoate. LCMS (ES, m/z): 502.2 [M+H]$^+$. $^1$H NMR (300 MHz, DMSO-d$_6$): δ 8.41 (s, 1H), 7.88-7.75 (m, 3H), 7.56-7.45 (m, 2H), 7.42-7.28 (m, 6H), 6.26 (d, J=1.7 Hz, 1H), 5.59-5.47 (m, 3H), 4.76-4.41 (m, 3H), 2.62-2.54 (m, 1H), 2.41-2.22 (m, 4H), 2.12 (s, 3H). Later fractions gave ((2S,4R,5R)-4-acetoxy-S-(4-oxo-4,5-dihydro-1H-imidazo[4,5-c]pyridin-1-yl)tetrahydrofuran-2-yl)methyl 4-methylbenzoate: LCMS (ES, m/z): 412.1 [M+H]$^+$. $^1$H NMR (300 MHz, DMSO-d$_6$): δ 11.23 (s, 1H), 8.20 (s, 1H), 7.81 (d, J=8.0 Hz, 2H), 7.33 (d, J=7.9 Hz, 2H), 7.12 (t, J=6.4 Hz, 1H), 6.65 (d, J=7.1 Hz, 1H), 6.16 (d, J=1.5 Hz, 1H), 5.45 (d, J=5.8 Hz, 1H), 4.75-4.39 (m, 3H), 2.39 (s, 3H), 2.33-2.22 (m, 2H), 2.11 (s, 3H).

Step 2: ((2S,4R,5R)-4-acetoxy-S-(4-oxo-4,5-dihydro-1H-imidazo[4,5-c]pyridin-1-yl)tetrahydrofuran-2-yl)methyl 4-methylbenzoate

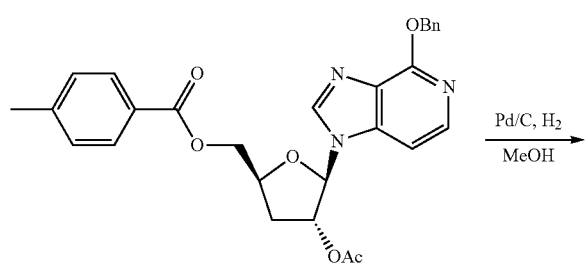

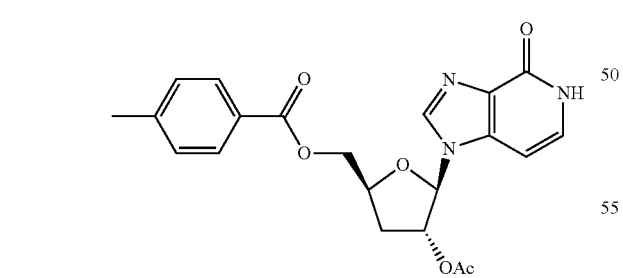

To a solution of ((2S,4R,5R)-4-acetoxy-S-(4-(benzyloxy)-1H-imidazo[4,5-c]pyridin-1-yl)tetrahydrofuran-2-yl)methyl 4-methylbenzoate (1.86 g, 3.70 mmol) in MeOH (40 mL) was added Pd/C (10%, 0.80 g). It was hydrogenated (1 atm) at RT for 5 h. Then, the mixture was filtered, and the filtrate was concentrated. The residue was purified by silica gel column chromatography eluted with 0-10% MeOH in DCM to give the product.

Step 3: 1-((2R,3R,5S)-3-hydroxy-S-(hydroxymethyl)tetrahydrofuran-2-yl)-1,5-dihydro-4H-imidazo[4,5-d]pyridin-4-one

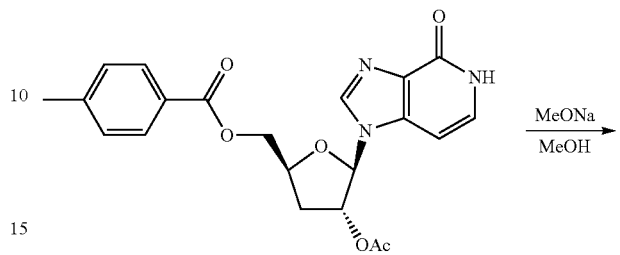

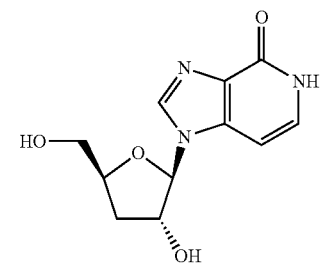

To a solution of ((2S,4R,5R)-4-acetoxy-S-(4-oxo-4,5-dihydro-1H-imidazo[4,5-c]pyridin-1-yl)tetrahydrofuran-2-yl)methyl 4-methylbenzoate (1.60 g, 3.88 mmol) in MeOH (60 mL) was added MeONa (0.52 g, 9.7 mmol). It was stirred at RT for 5 h. Then, it was neutralized with diluted aq HCl. The resulting mixture was concentrated under reduced pressure, and the residue was purified by reverse phase (C18) chromatography eluted with 0 to 95% ACN in aq NH$_4$HCO$_3$ (5 mM) to give the product. LCMS (ES, m/z): 251.9 [M+H]$^+$. $^1$H-NMR (300 MHz, DMSO-d$_6$): δ 8.25 (s, 1H), 7.15 (d, J=7.1 Hz, 1H), 6.65 (d, J=7.1 Hz, 1H), 5.72 (d, J=2.1 Hz, 1H), 4.35-4.28 (m, 2H), 3.67 (dd, J=12.1, 3.2 Hz, 1H), 3.50 (dd, J=12.0, 3.8 Hz, 1H), 2.16-2.07 (m, 1H), 1.88-1.81 (m, 1H).

Step 4: 1-((2R,3R,5S)—S-((bis(4-methoxyphenyl)(phenyl)methoxy)methyl)-3-hydroxytetrahydrofuran-2-yl)-1,5-dihydro-4H-imidazo[4,5-c]pyridin-4-one

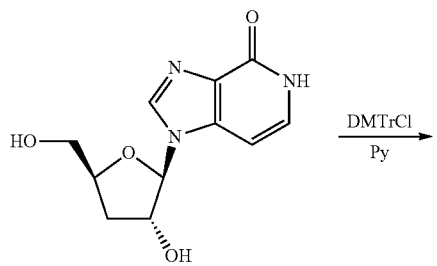

-continued

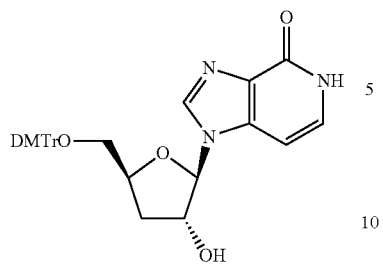

To a solution of 1-((2R,3R,5S)-3-hydroxy-S-(hydroxymethyl)tetrahydrofuran-2-yl)-1,5-dihydro-4H-imidazo[4,5-c]pyridin-4-one (0.90 g, 3.6 mmol) in pyridine (23 mL) was added 4,4'-(chloro(phenyl)methylene)bis(methoxybenzene) (1.21 g, 3.58 mmol). The resulting mixture was stirred at rt for 2 h. Then, MeOH (8 mL) was added, and the mixture was concentrated under reduced pressure. The residue was purified by reverse phase (C18) chromatography eluted with 0 to 95% ACN in aq NH$_4$HCO$_3$ (5 mM) to give the product. LCMS (ES, m/z): 554.2 [M+H]$^+$. $^1$H-NMR (300 MHz, DMSO-d$_6$): δ 11.35-10.99 (m, 1H), 8.10 (s, 1H), 7.33-7.11 (m, 11H), 6.86-6.77 (m, 4H), 6.69 (d, J=7.0 Hz, 1H), 5.81 (d, J=1.8 Hz, 1H), 5.76 (d, J=3.8 Hz, 1H), 3.72 (s, 6H), 3.23-3.02 (m, 2H), 2.27-2.17 (m, 1H), 1.98-1.91 (m, 1H).

Preparation 7: 3-((2R,3R,4S,5R)-3,4-dihydroxy-5-(hydroxymethyl)tetrahydrofuran-2-yl)-3,5-dihydro-9H-imidazo[1,2-a]purine-6,9(7H)-dione

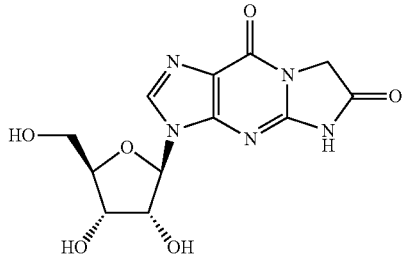 [SMILES: O=C1Cn2c(nc3c(ncn3[C@@H]3O[C@H](CO)[C@@H](O)[C@H]3O)c2=O)N1]

Step 1: N-(9-((2R,3R,4R,5R)-3,4-bis((tert-butyldimethylsilyl)oxy)-S-(((tert-butyldimethylsilyl)oxy)methyl)tetrahydrofuran-2-yl)-6-oxo-6,9-dihydro-1H-purin-2-yl)-2-chloroacetamide

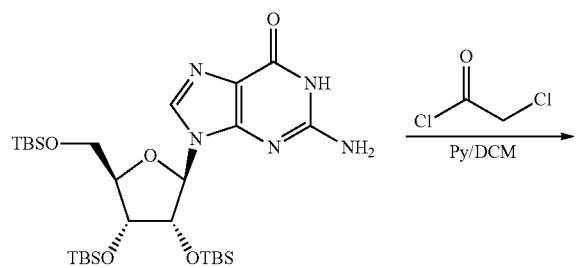

To a solution of 2-amino-9-((2R,3R,4R,5R)-3,4-bis((tert-butyldimethylsilyl)oxy)-5-(((tert-butyldimethylsilyl)oxy)methyl)tetrahydrofuran-2-yl)-1,9-dihydro-6H-purin-6-one (19.0 g, 30.4 mmol) in DCM (190 mL) at 0° C. under Ar was added 2-chloroacetyl chloride (4.11 g, 36.4 mmol) and Py (5.8 g, 73 mmol). The mixture was stirred at 0° C. for 2 h. Then, the volatile components were removed under reduced pressure, and the residue was co-evaporated with toluene (3×50 mL) to give the crude product. LCMS (ES, m/z): 702.3 [M+H]$^+$.

Step 2: 3-((2R,3R,4R,5R)-3,4-bis((tert-butyldimethylsilyl)oxy)-S-(((tert-butyldimethylsilyl)oxy)methyl)tetrahydrofuran-2-yl)-3,5-dihydro-9H-imidazo[1,2-a]purine-6,9(7H)-dione

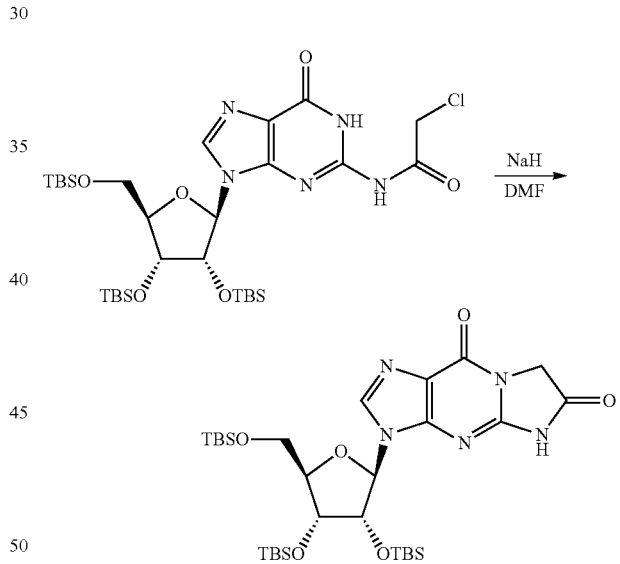

To a solution of the crude from Step 1 in DMF (350 mL) at 0° C. under Ar was added sodium hydride (60%, 2.2 g, 91 mmol), and the mixture was stirred at RT for 2 h. Then, the reaction was quenched with AcOH (25 mL). After 30 min, the reaction mixture was concentrated under reduced pressure. To the residue was added DCM (80 mL) and H$_2$O (40 mL). Layers were separated, and the aq layer was extracted with DCM (4×80 mL). The combined organic solution was washed with brine (50 mL), dried (Na$_2$SO$_4$), and concentrated under reduced pressure. The residue was purified by silica gel column chromatography eluted with 0-10% MeOH in DCM to give the product. LCMS (ES, m/z): 666.3 [M+H]$^+$. $^1$H-NMR: (400 MHz, DMSO-d$_6$): δ 8.16 (s, 1H), 5.81 (d, J=6.6 Hz, 1H), 4.62 (m, J=6.6, 4.4 Hz, 1H), 4.51 (d, J=9.7 Hz, 2H), 4.22 (m, 1.9 Hz, 1H), 4.05-3.98 (m, 1H), 3.89

(m, J=11.3, 5.6 Hz, 1H), 3.74 (dd, J=11.3, 3.7 Hz, 1H), 3.33 (s, 2H), 2.51 (m, J=1.8 Hz, 15H), 0.92 (d, J=1.9 Hz, 21H), 0.17-0.06 (m, 14H).

Step 3: 3-((2R,3R,4S,5R)-3,4-dihydroxy-S-(hydroxymethyl)tetrahydrofuran-2-yl)-3,5-dihydro-9H-imidazo[1,2-a]purine-6,9(7H)-dione

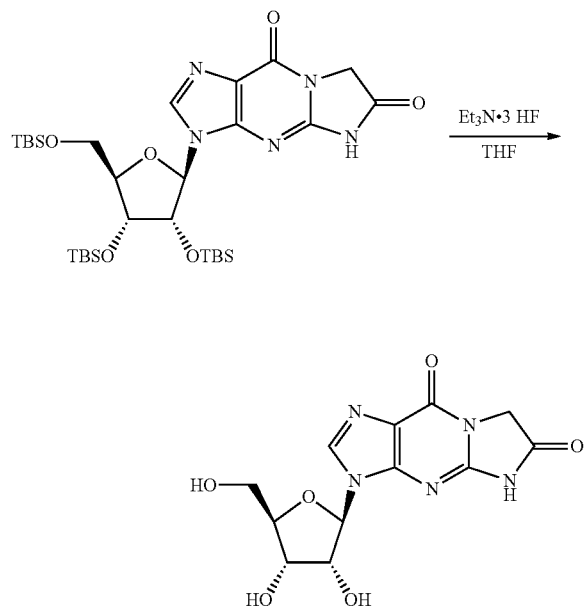

To a solution of 34(2R,3R,4R,5R)-3,4-bis((tert-butyldimethylsilyl)oxy)-S-(((tert-butyldimethylsilyl)oxy)methyl)tetrahydrofuran-2-yl)-3,5-dihydro-9H-imidazo[1,2-a]purine-6,9(7H)-dione (8.80 g, 13.2 mmol) in THF (88 mL) was added Et₃N.3HF (1.66 g, 21.1 mmol), and the mixture was stirred at RT for 24 h. Then, it was concentrated, and the residue was purified by silica gel column chromatography using 0-20% MeOH in DCM to give the product. LCMS (ES, m/z): 324.0 [M+H]⁺. ¹H NMR (400 MHz, DMSO-d₆): δ 8.09 (s, 1H), 5.76 (d, J=5.9 Hz, 1H), 4.45 (t, J=5.5 Hz, 1H), 4.32 (s, 2H), 4.11 (t, J=4.2 Hz, 1H), 3.92 (m, J=3.8 Hz, 1H), 3.64 (dd, J=12.0, 4.0 Hz, 1H), 3.54 (dd, J=12.0, 4.0 Hz, 1H).

Preparation 8: 3-((2R,3R,4S,5R)-3,4-dihydroxy-5-(hydroxymethyl)tetrahydrofuran-2-O)-3,5-dihydro-9H-imidazo[1,2-a]purin-9-one Step 1: 2-amino-1-(2,2-diethoxyethyl)-9-((2R,3R,4S,5R)-3,4-dihydroxy-5-(hydroxymethyl)tetrahydrofuran-2-yl)-1,9-dihydro-6H-purin-6-one

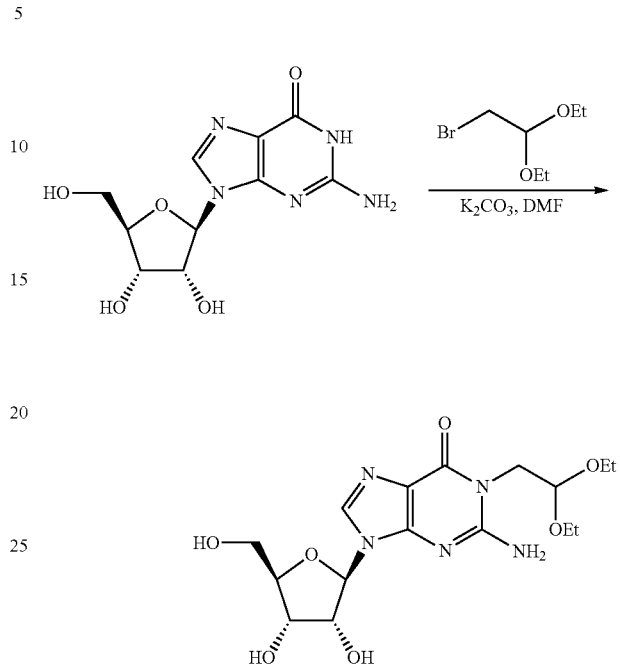

To a suspension of guanosine (15.0 g, 53.0 mmol) in DMF (150 mL) was added K₂CO₃ (11.0 g, 79.0 mmol), and it was heated at 90° C. After 15 min, 2-bromo-1,1-diethoxyethane (12.3 mL, 79.0 mmol) was added over 10 min. The reaction was heated at 90° C. for 72 h. Then, additional K₂CO₃ (7.32 g, 52.7 mmol) and 2-bromo-1,1-diethoxyethane (8.22 mL, 52.7 mmol) were added. After 48 h, the reaction mixture was filtered through a layer of CELITE, and the filtrate was concentrated. The residue was purified by silica column chromatography eluted with 0 to 5.2% MeOH in DCM to give the product. LCMS (ES, m/z): 400.2 [M+H]⁺. ¹H-NMR (400 MHz, DMSO-d₆): δ 7.97 (s, 1H), 6.85 (br s, 2H), 5.70 (d, J=6.1 Hz, 1H), 5.40 (d, J=6.0 Hz, 1H), 5.13 (d, J=4.6 Hz, 1H), 5.01 (t, J=5.5 Hz, 1H), 4.72 (t, J=5.3 Hz, 1H), 4.41 (q, J=5.8 Hz, 1H), 4.13-4.01 (m, 3H), 3.86 (q, J=4.0 Hz, 1H), 3.74-3.56 (m, 3H), 3.56-3.40 (m, 3H), 1.07 (td, J=7.0, 1.9 Hz, 6H).

Step 2: 3-((2R,3R,4S,5R)-3,4-dihydroxy-S-(hydroxymethyl)tetrahydrofuran-2-yl)-3,5-dihydro-9H-imidazo[1,2-a]purin-9-one

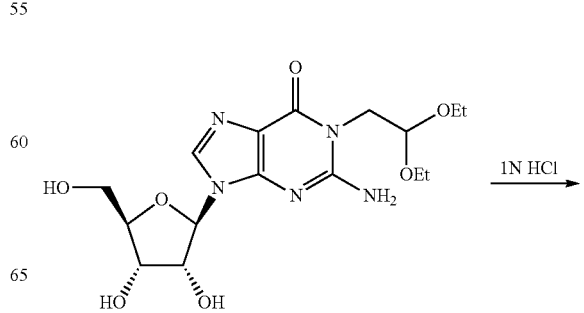

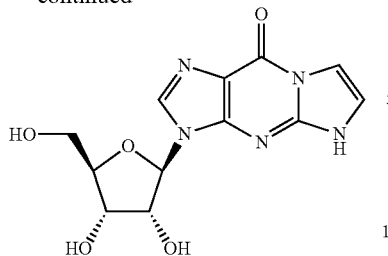

2-amino-1-(2,2-diethoxyethyl)-9-((2R,3R,4S,5R)-3,4-dihydroxy-5-(hydroxymethyl)tetrahydrofuran-2-yl)-1,9-dihydro-6H-purin-6-one (2.4 g, 3.6 mmol) was dissolved in aq HCl (1N, 24 mL, 24 mmol), and the mixture was stirred at RT for 24 h. Then, it was neutralized with concentrated NH$_4$OH and concentrated. The crude was washed with cold H$_2$O and purified by reverse phase (C18) chromatography eluted with 0 to 95% ACN in aq NH$_4$HCO$_3$ (5 mM) to give the product. LCMS (ES, m/z): 308.1 [M+H]$^+$. $^1$H-NMR (300 MHz, DMSO-d$_6$): δ 12.49 (s, 1H), 8.17 (s, 1H), 7.64 (t, J=2.2 Hz, 1H), 7.45 (t, J=2.5 Hz, 1H), 5.84 (d, J=5.7 Hz, 1H), 5.44 (d, J=6.0 Hz, 1H), 5.18 (d, J=4.8 Hz, 1H), 5.07 (t, J=5.5 Hz, 1H), 4.49 (q, J=5.5 Hz, 1H), 4.14 (q, J=4.2 Hz, 1H), 3.93 (q, J=3.9 Hz, 1H), 3.67 (dt, J=11.8, 4.2 Hz, 1H), 3.62-3.51 (m, 1H).

Preparation 9: (2R,3R,4S,5R)-2-(4-(benzyloxy)-1H-imidazo[2,1-b]purin-1-yl)-5-(hydroxymethyl)tetrahydrofuran-3,4-diol

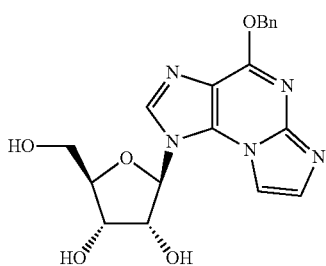 [SMILES: OC[C@H]1O[C@@H](n2cnc3c(OCc4ccccc4)nc4nccn4c32)[C@H](O)[C@@H]1O]

The title compound was prepared according to published procedure (J. Org. Chem. 1987, 52, 2374-2378).

Preparation 10: (2R,3S,4R,5R)—S-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl (2-cyanoethyl) diisopropylphosphoramidite

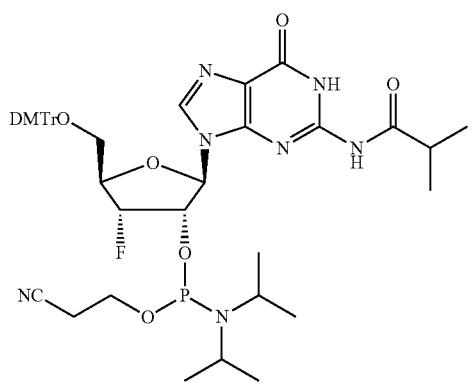

Step 1: N-(9-((2R,3S,4S,5R)-4-fluoro-3-hydroxy-S-(hydroxymethyl)tetrahydrofuran-2-yl)-6-oxo-6,9-dihydro-1H-purin-2-yl)isobutyramide

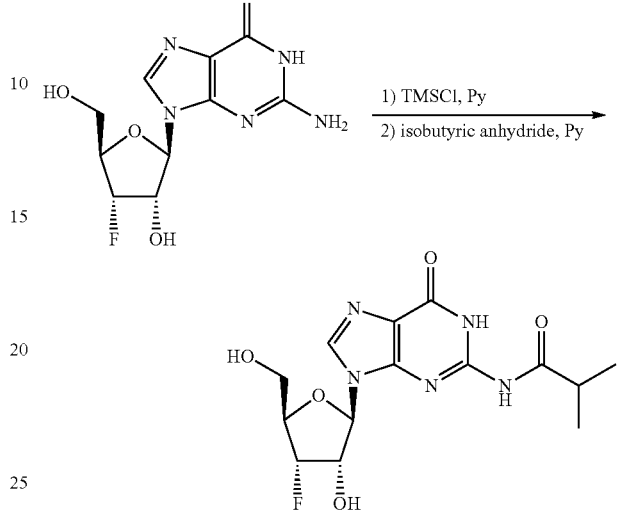

To a suspension of 2-amino-9-((2R,3S,4S,5R)-4-fluoro-3-hydroxy-5-(hydroxymethyl)tetrahydrofuran-2-yl)-1,9-dihydro-6H-purin-6-one (CARBOSYNTH catalog #ND10826, 1.50 g, 5.26 mmol) in Py (30 mL) at 0-5° C. was added TMSCl (2.86 g, 26.3 mmol), and the mixture was stirred at RT for 30 min. Then, isobutyric anhydride (2.50 g, 15.8 mmol) was added dropwise, and it was stirred for an additional for 2 h. Then, MeOH (5.3 mL) was added. After 5 min, NH$_4$OH (10.5 mL) was added dropwise and stirring was continued for 30 min. The reaction mixture was concentrated under reduced pressure, and MeOH (2 mL) in CH$_2$Cl$_2$ (18 mL) was added to the residue. Solids were filtered off, and the filtrate was concentrated and purified by flash column chromatography with 2-10% MeOH in CH$_2$Cl$_2$ to give the product. LCMS (ES, m/z): 356.1 [M+H]$^+$. $^1$H-NMR: (400 MHz, DMSO-d$_6$): δ 12.11 (s, 1H), 11.68 (s, 1H), 8.28 (s, 1H), 5.98 (d, J=6.1 Hz, 1H), 5.85 (d, J=8.0 Hz, 1H), 5.24 (t, J=5.4 Hz, 1H), 5.14 (d, J=4.1 Hz, 0.5H), 5.01 (d, J=4.2 Hz, 0.5H), 4.87-4.69 (m, 1H), 4.26 (t, J=4.4 Hz, 0.5H), 4.19 (t, J=4.4 Hz, 0.5H), 3.61 (t, J=4.9 Hz, 2H), 2.77 (hept, J=6.8 Hz, 1H), 1.13 (d, J=6.7 Hz, 6H). $^{19}$F-NMR: (376 MHz, DMSO-d$_6$): δ−197.5 (s).

Step 2: N-(9-((2R,3S,4S,5R)—S-((bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide

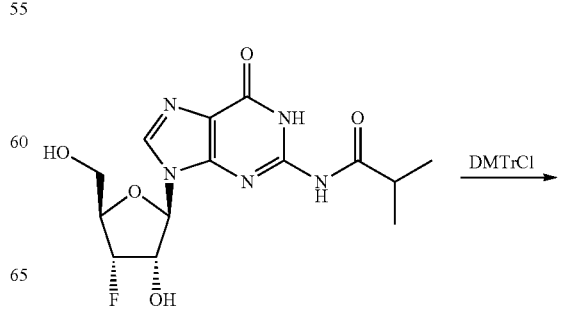

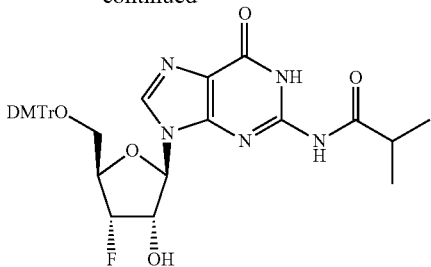

N-(9-((2R,3S,4S,5R)-4-fluoro-3-hydroxy-5-(hydroxymethyl)tetrahydrofuran-2-yl)-6-oxo-6,9-dihydro-1H-purin-2-yl)isobutyramide (1.30 g, 3.66 mmol) was co-evaporated with Py (3×10 mL) and re-dissolved in Py (26 mL). To the solution at 0° C.-5° C. was added DMTrCl (1.36 g, 4.02 mmol). It was stirred at RT for 3 h and then concentrated. CH$_2$Cl$_2$ (40 mL, with 1% Et$_3$N) was added, and it was washed with sat aq NaHCO$_3$ (15 mL), H$_2$O (10 mL) and brine (10 mL). The organic solution was dried (Na$_2$SO$_4$), concentrated and purified by silica gel column chromatography using 0-10% MeOH in CH$_2$Cl$_2$ (1% Et$_3$N) to give the product. LCMS (ES, m/z): 656.2 [M−H]$^+$. $^1$H-NMR: (400 MHz, DMSO-d$_6$): δ 12.10 (s, 1H), 11.61 (s, 1H), 8.14 (s, 1H), 7.40-7.31 (m, 2H), 7.31-7.19 (m, 7H), 6.89-6.78 (m, 4H), 6.08 (d, J=6.1 Hz, 1H), 5.87 (d, J=7.3 Hz, 1H), 5.23 (dd, J=4.1, 1.8 Hz, 0.5H), 5.10 (d, J=4.4 Hz, 0.5H), 4.96 (dq, J=22.4, 5.9 Hz, 1H), 4.30 (dt, J=26.1, 4.6 Hz, 1H), 3.74 (d, J=1.1 Hz, 6H), 3.39 (dd, J=10.6, 5.7 Hz, 1H), 3.22 (dd, J=10.6, 3.8 Hz, 1H), 2.76 (p, J=6.8 Hz, 1H), 1.13 (d, J=6.8 Hz, 6H). $^{19}$F-NMR: (376 MHz, DMSO-d$_6$): δ−198.1 (s, 1F).

Step 3: (2R,3S,4R,5R)—S-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl (2-cyanoethyl) diisopropylphosphoramidite

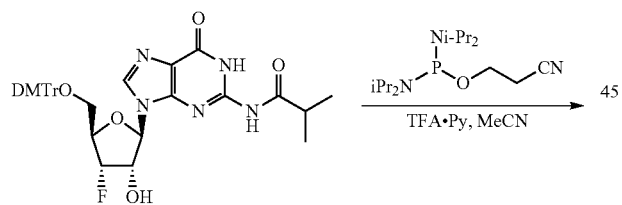

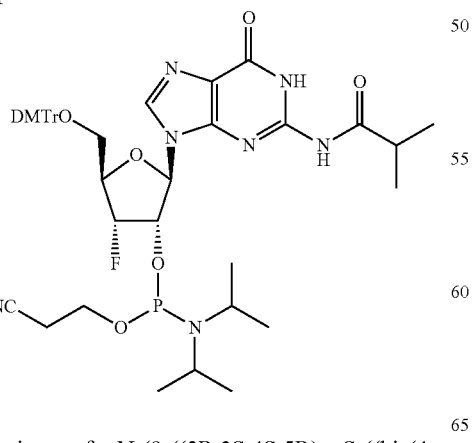

To a solution of N-(9-((2R,3S,4S,5R)—S-((bis(4-methoxyphenyl)(phenyl)methoxy)methyl)-4-fluoro-3-hy-droxytetrahydrofuran-2-yl)-6-oxo-6,9-dihydro-1H-purin-2-yl)isobutyramide (2.10 g, 3.19 mmol) in MeCN (30 mL) at 0° C. under Ar was added pyridin-1-ium 2,2,2-trifluoroacetate (0.678 g, 3.51 mmol) and 3-((bis(diisopropylamino)phosphino)oxy)-propanenitrile (1.16 g, 3.83 mmol) in MeCN (2 mL) over 5 min. The resulting mixture was stirred at RT for 5 h. Then, TEA in CH$_2$Cl$_2$ (2%, 300 mL) and H$_2$O (100 mL) was added. Layers were separated, and the organic layer was washed with H$_2$O (3×100 mL) and brine (2×100 mL). The organic layer was dried (Na$_2$SO$_4$), concentrated, and purified by flash column chromatography eluted with 10% DCM in EtOAc/Hex (2/3) to give the product. LCMS (ES, m/z): 858.3 [M+H]$^+$. $^1$H-NMR: (400 MHz, DMSO-d$_6$): δ 12.07 (s, 1H), 11.55 (s, 1H), 8.08 (d, J=4.2 Hz, 1H), 7.44-7.08 (m, 9H), 6.83 (ddd, J=8.9, 6.2, 2.1 Hz, 4H), 5.99 (t, J=6.8 Hz, 1H), 5.42-5.03 (m, 2H), 4.48-4.22 (m, 1H), 3.71 (s, 7H), 3.59-3.35 (m, 3H), 3.28-3.24 (m, 3H), 2.83-2.61 (m, 2H), 1.09 (s, 12H), 1.03 (d, J=6.8 Hz, 3H), 0.74 (d, J=6.7 Hz, 3H). $^{19}$F-NMR: (376 MHz, DMSO-d$_6$): δ−195.8 (s), −197.1 (s). $^{31}$P-NMR: (162 MHz, DMSO-d$_6$): δ 151.55 (d), 151.35 (d).

Preparation 11: (2R,3S,4R,5R)-4-fluoro-5-(hydroxymethyl)-2-(9-oxo-5,9-dihydro-3H-imidazo[1,2-a]purin-3-yl)tetrahydrofuran-3-yl hydrogen phosphonate

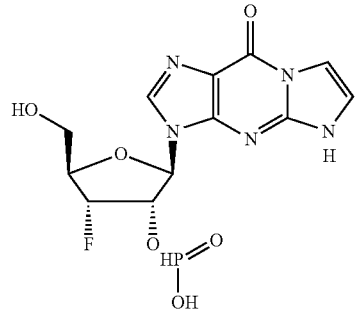

Step 1: 2-amino-1-(2,2-diethoxyethyl)-9-((2R,3S,4S,5R)-4-fluoro-3-hydroxy-5-(hydroxymethyl)tetrahydrofuran-2-yl)-1,9-dihydro-6H-purin-6-one

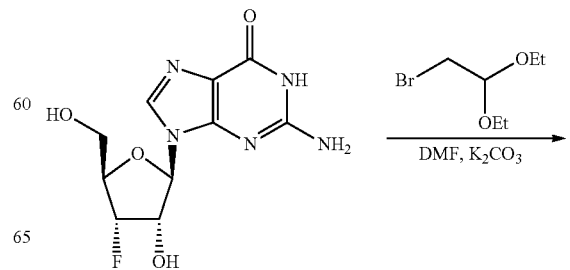

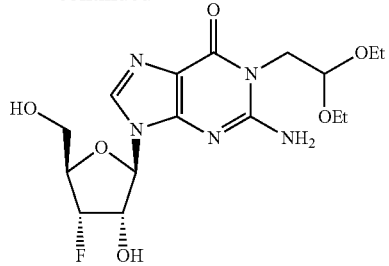

To a stirred suspension of 2-amino-9-((2R,3S,4S,5R)-4-fluoro-3-hydroxy-5-(hydroxymethyl)tetrahydrofuran-2-yl)-1,9-dihydro-6H-purin-6-one (2.36 g, 8.19 mmol) in DMF (50 mL) was added K₂CO₃ (2.29 g, 16.6 mmol) and 2-bromo-1,1-diethoxyethane (3.26 g, 16.6 mmol). It was stirred at 90° C. for 3 days. Then, additional K₂CO₃ (0.572 g, 4.14 mmol) and 2-bromo-1,1-diethoxyethane (0.815 g, 4.14 mmol) were added. After 48 h, the reaction mixture was then filtered through a pad of CELITE. The filtrate was concentrated, and the residue was purified by reverse phase (C18) chromatography eluted with 0 to 95% ACN in aq NH₄HCO₃ (5 mM) to give the product. LCMS (ES, m/z): 402.3 [M+H]⁺. ¹H-NMR (400 MHz, DMSO-d₆): δ 7.99 (s, 1H), 6.89 (s, 2H), 5.91 (d, J=6.4 Hz, 1H), 5.76 (d, J=8.1 Hz, 1H), 5.21 (t, J=5.5 Hz, 1H), 5.11 (d, J=4.1 Hz, 0.5H), 4.98 (d, J=4.2 Hz, 0.5H), 4.84-4.68 (m, 2H), 4.23 (t, J=4.4 Hz, 0.5H), 4.16 (t, J=4.4 Hz, 0.5H), 4.07 (d, J=5.9 Hz, 2H), 3.69 (dq, J=9.7, 7.0 Hz, 2H), 3.60 (t, J=5.0 Hz, 2H), 3.50 (dtd, J=9.4, 7.4, 6.5 Hz, 2H), 1.09 (td, J=7.1, 1.7 Hz, 6H).

Step 2: 3-((2R,3S,4S,5R)-4-fluoro-3-hydroxy-5-(hydroxymethyl)tetrahydrofuran-2-yl)-3,5-dihydro-9H-imidazo[1,2-a]purin-9-one

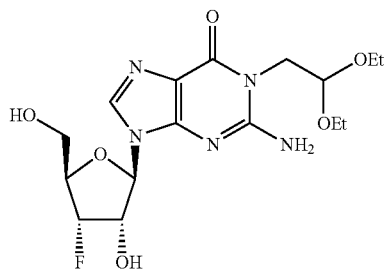

2-amino-1-(2,2-di ethoxyethyl)-9-((2R,3 S,4S,5R)-4-fluoro-3-hydroxy-5-(hydroxymethyl)tetrahydrofuran-2-yl)-1,9-dihydro-6H-purin-6-one (1.10 g, 2.74 mmol) was dissolved in aq HCl (27.4 mL, 54.8 mmol), and it was stirred for 24 h. Then, the solution was neutralized with concentrated NH₄OH and concentrated. The residue was purified by reverse phase (C18) chromatography eluted with 0 to 95% ACN in aq NH₄HCO₃ (5 mM) to give the product. LCMS (ES, m/z): 310.2 [M+H]⁺. ¹H-NMR (300 MHz, DMSO-d₆): δ 8.13 (s, 1H), 7.60 (d, J=2.6 Hz, 1H), 7.41 (d, J=2.6 Hz, 1H), 5.86 (dd, 7.3 Hz, 2H), 5.25 (t, J=5.6 Hz, 1H), 5.13 (d, J=4.2 Hz, 0.5H), 4.95 (d, J=4.3 Hz, 0.5H), 4.25 (t, J=4.5 Hz, 0.5H), 4.16 (s, 0.5H), 3.60 (t, J=5.0 Hz, 2H).

Step 3: 3-((2R,3S,4S,5R)—S-((bis(4-methoxyphenyl)(phenyl)methoxy)methyl)-4-fluoro-3-hydroxytetrahydrofuran-2-yl)-S-(bis(4-methoxyphenyl)(phenyl)methyl)-3,5-dihydro-9H-imidazo[1,2-a]purin-9-one

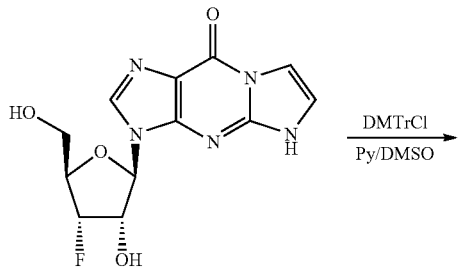

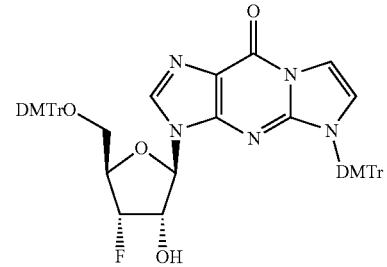

To a solution of 3-((2R,3S,4S,5R)-4-fluoro-3-hydroxy-S-(hydroxymethyl) tetrahydrofuran-2-yl)-3,5-dihydro-9H-imidazo[1,2-a]purin-9-one (600 mg, 1.94 mmol) in Py (12 mL) and DMSO (24 mL) was added a solution of 4,4'-(chloro(phenyl)methylene)bis (methoxybenzene) (1.64 g, 4.85 mmol) in Py (6 mL) over 30 min. It was stirred at RT for 4 h. Then, the reaction mixture was concentrated under reduced pressure, and the residue was purified by reverse phase (C18) chromatography eluted with 0 to 95% ACN in aq NH₄HCO₃ (5 mM) to give the product. LCMS (ES, m/z): 914.3 [M+H]⁺. ¹H-NMR (400 MHz, DMSO-d₆): δ 7.97 (s, 1H), 7.70 (d, J=2.9 Hz, 1H), 7.34-7.08 (m, 19H), 6.83 (ddt, J=8.7, 6.9, 2.9 Hz, 8H), 5.63 (d, J=4.9 Hz, 1H), 5.45 (d, J=4.3 Hz, 1H), 4.44 (t, J=5.1 Hz, 1H), 4.32 (dd, J=9.4, 4.6 Hz, 1H), 4.09-3.97 (m, 1H), 3.71 (d, J=7.3 Hz, 6H), 3.65 (s, 6H), 3.03 (d, J=5.7 Hz, 2H).

Step 4: (2R,3S,4R,5R)—S-((bis(4-methoxyphenyl)(phenyl)methoxy)methyl)-2-(5-(bis(4-methoxyphenyl)(phenyl)methyl)-9-oxo-5,9-dihydro-3H-imidazo[1,2-a]purin-3-yl)-4-fluorotetrahydrofuran-3-yl phenyl phosphonate

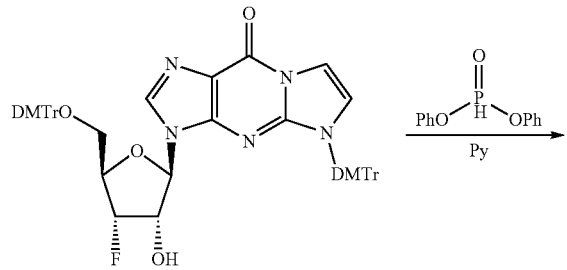

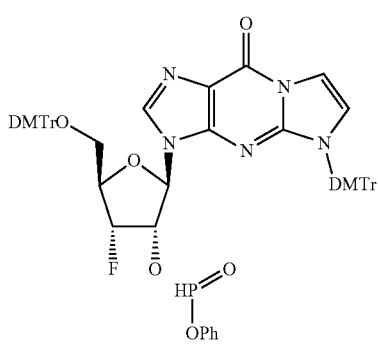

To a solution of 3-((2R,3S,4S,5R)—S-((bis(4-methoxyphenyl)(phenyl)methoxy) methyl)-4-fluoro-3-hydroxytetrahydrofuran-2-yl)-S-(bis(4-methoxyphenyl)(phenyl)methyl)-3,5-dihydro-9H-imidazo[1,2-a]purin-9-one (0.65 g, 0.71 mmol) in Py (3 mL) under Ar was added diphenyl phosphonate (1.16 g, 4.98 mmol), and it was stirred at RT for 20 min. The reaction mixture was used for the next step without purification. LCMS (ES, m/z): 1054.4 [M+H]$^+$.

Step 5: (2R,3S,4R,5R)—S-((bis(4-methoxyphenyl)(phenyl)methoxy)methyl)-2-(5-(bis(4-methoxyphenyl)(phenyl)methyl)-9-oxo-5,9-dihydro-3H-imidazo[1,2-a]purin-3-yl)-4-fluorotetrahydrofuran-3-yl hydrogen phosphonate

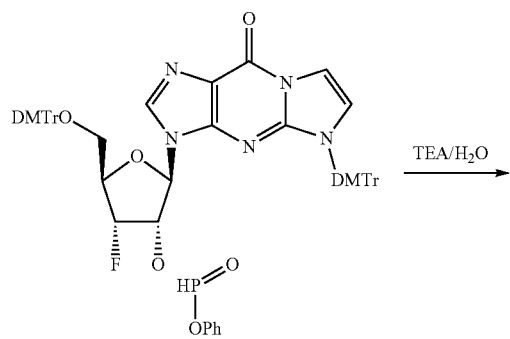

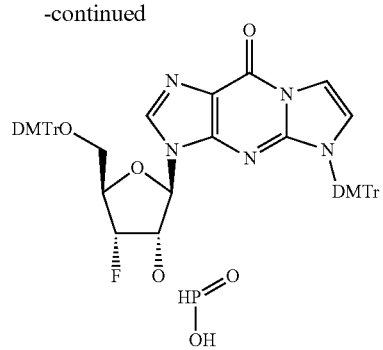

To the reaction mixture from Step 4 at 0° C. was added H$_2$O (3.0 mL, 0.17 mol) and TEA (3.0 mL, 33 mmol). The mixture was stirred at RT for 20 min. Then, it was concentrated and purified by reverse phase (C18) chromatography eluted with 0 to 95% ACN in aq NH$_4$HCO$_3$ (5 mM) to give the product. LCMS (ES, m/z): 978.3 [M+H]$^+$. $^{31}$P NMR (162 MHz, DMSO): δ −0.07 (s).

Step 6: (2R,3S,4R,5R)-4-fluoro-S-(hydroxymethyl)-2-(9-oxo-5,9-dihydro-3H-imidazo[1,2-a]purin-3-yl)tetrahydrofuran-3-yl hydrogen phosphonate

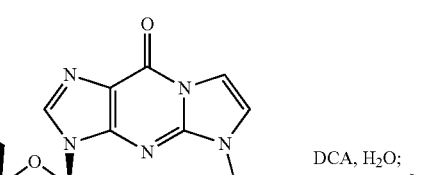

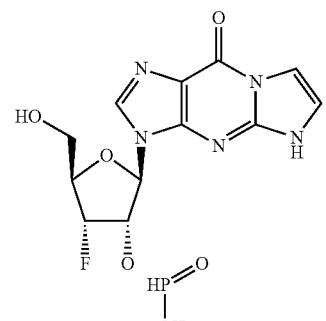

To the solution of (2R,3S,4R,5R)—S-((bis(4-methoxyphenyl)(phenyl)methoxy) methyl)-2-(5-(bis(4-methoxyphenyl)(phenyl)methyl)-9-oxo-5,9-dihydro-3H-imidazo[1,2-a]purin-3-yl)-4-fluorotetrahydrofuran-3-yl hydrogen phosphonate (0.60 g, 0.60 mmol) in DCM (17 mL) were added DCA in DCM (17.4 mL, 10.8 mmol) and H$_2$O (0.20 mL, 11 mmol). It was stirred at rt for 20 min and then Et$_3$SiH (34.0 mL, 212 mmol) was added. The solution was stirred at rt for 60 min. Py (6.4 mL, 80 mmol) was added, and the solution was stirred for 10 min. The mixture was concentrated and co-evaporated with MeCN (3×15 mL) to give the crude product, which was used for next step without purification. LCMS (ES, m/z): 374.0 [M+H]⁺.

Preparation 12: (2R,3S,5R)—S-(4-amino-1H-pyrrolo[2,3-b]pyridin-1-yl)-2-(hydroxymethyl)tetrahydrofuran-3-ol

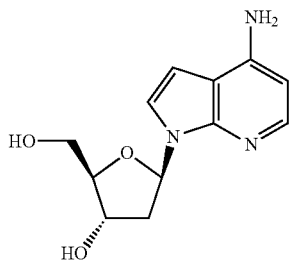 [SMILES: Nc1ccnc2c1ccn2[C@H]1C[C@H](O)[C@@H](CO)O1]

The title compound was prepared according to published procedure (Heterocycles 1989, 29, 795-805).

Preparation 13: (2R,3R,4S,5R)—S-(7-benzamido-3H-[1,2,3]triazolo[4,5-d]pyrimidin-3-yl)-2-((bis(4-methoxyphenyl)(phenyl)methoxy)methyl)-4-fluorotetrahydrofuran-3-yl (2-cyanoethyl) diisopropylphosphoramidite

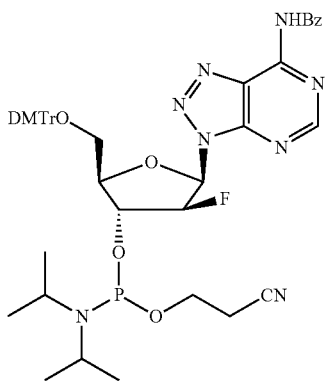

Step 1: (2R,3R,4S,5R)—S-(7-amino-3H-[1,2,3]triazolo[4,5-d]pyrimidin-3-yl)-2-((benzoyloxy)methyl)-4-fluorotetrahydrofuran-3-yl benzoate

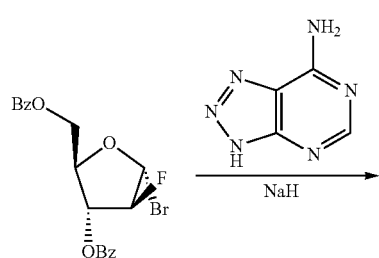

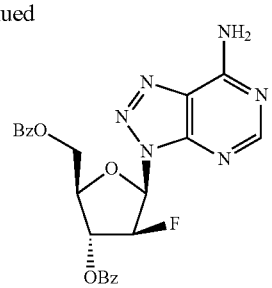

To a mixture of 3H-[1,2,3]triazolo[4,5-d]pyrimidin-7-amine (2.36 g, 17.4 mmol) in NMP (50 mL) was added NaH (60%, 0.744 g, 18.6 mmol). The mixture was vigorously stirred, and after 1 h, generation of bubbles had completely ceased. The mixture was added to ((2R,3R,4S,5R)-3-(benzoyloxy)-S-bromo-4-fluorotetrahydrofuran-2-yl)methyl benzoate (neat, 5.25 g, 12.4 mmol) in one portion. It was stirred for 18 h. LCMS showed several peaks with the desired mass (m/e=479). EtOAc (70 mL) and H₂O (70 mL) were added to the reaction. Layers were separated, and the organic layer was washed with half saturated brine (3×10 mL) and brine (1×10 mL), dried (MgSO₄), and concentrated. The crude was purified via silica column eluting with 0 to 50% EtOAc in Hex to give the product. LCMS (ES, m/z): 479.3 [M+H]⁺. ¹H-NMR (500 MHz, DMSO-d₆): δ 8.62 (s, 1H), 8.34 (s, 1H), 8.28 (s, 1H), 8.10-8.04 (m, 2H), 7.97-7.90 (m, 2H), 7.77-7.69 (m, 1H), 7.67-7.55 (m, 3H), 7.49-7.42 (m, 2H), 6.97 (dd, J=6.5, 3.1 Hz, 1H), 6.49 (dt, J=17.6, 6.9 Hz, 1H), 6.16 (dt, J=56, 6.6 Hz, 1H), 4.76-4.62 (m, 3H).

Step 2: (2R,3R,4S,5R)—S-(7-amino-3H-[1,2,3]triazolo[4,5-d]pyrimidin-3-yl)-4-fluoro-2-(hydroxymethyl)tetrahydrofuran-3-ol

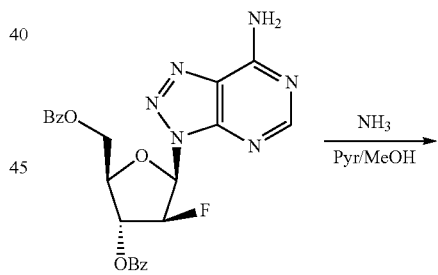

To a solution of (2R,3R,4S,5R)—S-(7-amino-3H-[1,2,3]triazolo[4,5-d]pyrimidin-3-yl)-2-((benzoyloxy)methyl)-4-fluorotetrahydrofuran-3-yl benzoate (2.00 g, 4.18 mmol) in Py (10 mL) at was added NH₃ in MeOH (7N, 20 mL, 140 mmol). It was stirred for 48 h. LCMS showed completion of the reaction (m/e=271). It was concentrated and purified by silica column chromatography eluting with 10% MeOH in CH₂Cl₂ to give the desired product. LCMS (ES, m/z): 271.1 [M+H]⁺. ¹H-NMR (500 MHz, DMSO-d6): δ 8.54 (s, 1H), 8.33 (s, 1H), 8.22 (s, 1H), 6.73 (dd, J=6.5, 2.6 Hz, 1H), 6.00 (d, J=5.4 Hz, 1H), 5.51 (ddd, J=53, 7.2, 6.5 Hz, 1H), 4.93 (t, J=5.8 Hz, 1H), 4.86-4.74 (m, 1H), 3.91-3.83 (m, 1H), 3.77-3.61 (m, 2H).

Step 3: N-(3-((2R,3S,4R,5R)-3-fluoro-4-hydroxy-S-(hydroxymethyl)tetrahydrofuran-2-yl)-3H-[1,2,3]triazolo[4,5-d]pyrimidin-7-yl)benzamide

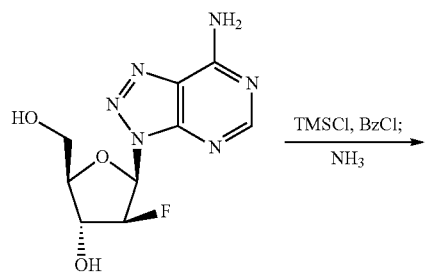

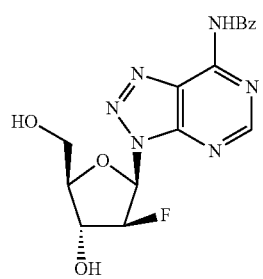

To a solution of (2R,3R,4S,5R)—S-(7-amino-3H-[1,2,3]triazolo[4,5-d]pyrimidin-3-yl)-4-fluoro-2-(hydroxymethyl)tetrahydrofuran-3-ol (1.34 g, 4.96 mmol) in Py (30 mL) at 0° C. was added TMSCl (1.46 mL, 11.4 mmol). It was warmed to RT and stirred for 1 h. Then, it was re-cooled to 0° C., and BzCl (0.921 mL, 7.93 mmol) was added dropwise. The reaction was slowly warmed to RT over 2 h. LCMS showed completion of reaction (m/e=375, 479). H₂O (3 mL) was added. It was cooled to 0° C., and NH₃ in MeOH (7N, 2.8 mL, 20 mmol) was added. After 1 h, the reaction mixture was concentrated. It was purified by silica column chromatography eluting with 0 to 10% MeOH in CH₂Cl₂ to give the product. LCMS (ES, m/z): 375.2 [M+H]⁺. ¹H-NMR (500 MHz, DMSO-d₆): δ 11.95 (s, 1H), 8.98 (s, 1H), 8.10 (d, J=7.6 Hz, 2H), 7.73-7.66 (m, 1H), 7.59 (t, J=7.7 Hz, 2H), 6.91 (d, J=6.2 Hz, 1H), 6.06 (d, J=5.6 Hz, 1H), 5.59 (t, J=53, 6.8 Hz, 1H), 4.90 (t, J=5.8 Hz, 1H), 4.82 (dq, J=19.8, 7.0 Hz, 1H), 3.92 (td, J=7.6, 2.9 Hz, 1H), 3.75 (ddd, J=12.1, 5.6, 3.0 Hz, 1H), 3.66 (dt, J=12.0, 6.6 Hz, 1H).

Step 4: N-(3-((2R,3S,4R,5R)—S-((bis(4-methoxyphenyl)(phenyl)methoxy)methyl)-3-fluoro-4-hydroxytetrahydrofuran-2-yl)-3H-[1,2,3]triazolo[4,5-d]pyrimidin-7-yl)benzamide

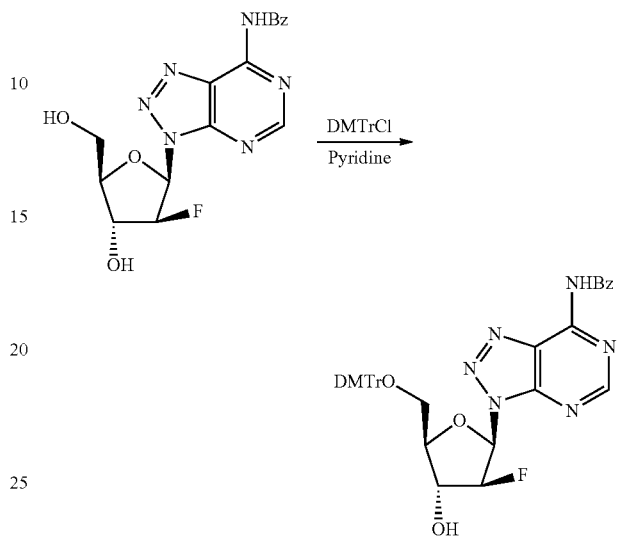

To a solution of N-(3-((2R,3S,4R,5R)-3-fluoro-4-hydroxy-S-(hydroxymethyl)-tetrahydrofuran-2-yl)-3H-[1,2,3]triazolo[4,5-d]pyrimidin-7-yl)benzamide (1.25 g, 3.34 mmol) in Py (15 mL) at 0° C. was added DMTrCl (1.58 g, 4.68 mmol). It was stirred at RT for 1 h. LCMS showed a peak with the desired mass (m/e=677). It was partly concentrated (to 5 mL), and EtOAc (20 mL) and H₂O (10 mL) were added. The layers were separated, and the aq layer was extracted with EtOAc (2×10 mL). The combined organics were washed with brine (5 mL), dried (MgSO₄), concentrated and purified by silica column chromatography eluting with 0 to 60% EtOAc in Hex to give the product. LCMS (ES, m/z): 675.5 [M−H]⁻. ¹H-NMR (500 MHz, DMSO-d₆): δ 8.13-8.07 (m, 2H), 7.69 (t, J=7.4 Hz, 1H), 7.59 (t, J=7.6 Hz, 2H), 7.35-7.29 (m, 2H), 7.23-7.10 (m, 6H), 6.97 (d, J=6.5 Hz, 1H), 6.81-6.74 (m, 2H), 6.74-6.67 (m, 2H), 6.07 (d, J=5.7 Hz, 1H), 5.62 (dt, J=53, 7.0 Hz, 1H), 4.91-4.79 (m, 1H), 4.15-4.07 (m, 1H), 3.69 (s, 3H), 3.67 (s, 3H), 3.44 (dd, J=10.4, 8.0 Hz, 1H), 3.21 (dd, J=10.3, 2.4 Hz, 1H).

Step 5: (2R,3R,4S,5R)—S-(7-benzamido-3H-[1,2,3]triazolo[4,5-d]pyrimidin-3-yl)-2-((bis(4-methoxyphenyl)(phenyl)methoxy)methyl)-4-fluorotetrahydrofuran-3-yl (2-cyanoethyl) diisopropylphosphoramidite

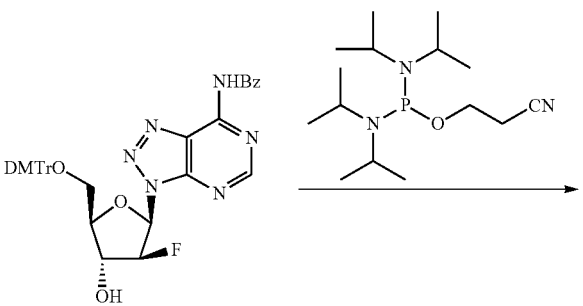

145

-continued

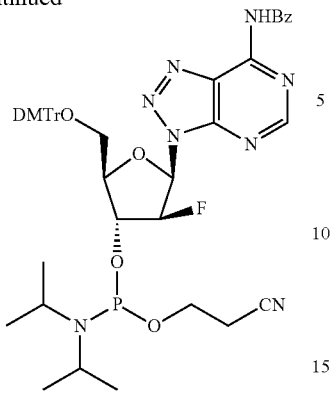

To a solution of 3-((bis(diisopropylamino)phosphino)oxy)propanenitrile (8.02 g, 26.6 mmol) in ACN (90 mL) at RT was added pyridin-1-ium 2,2,2-trifluoroacetate (3.85 g, 19.95 mmol) and a solution of N-(3-((2R,3S,4R,5R)—S-((bis(4-methoxyphenyl)(phenyl)methoxy) methyl)-3-fluoro-4-hydroxytetrahydrofuran-2-yl)-3H-[1,2,3]triazolo[4,5-d]pyrimidin-7-yl) benzamide (9 g, 13.30 mmol) in ACN (90 mL). The resulting mixture was stirred for 1 h. Then, it was concentrated, and the residue was dissolved in CH$_2$Cl$_2$ (1000 mL). It was washed with aq NaHCO$_3$ (1%, 2×300 mL), H$_2$O (300 mL) and brine (300 mL), dried (Na$_2$SO$_4$), concentrated, and purified by reverse phase (C18) chromatography eluting with 0 to 95% ACN in H$_2$O to give the product. LCMS (ES, m/z): 877.5 [M+H]$^+$. $^1$H-NMR: (400 MHz, DMSO-d$_6$): δ 12.01 (s, 1H), 8.92 (s, 1H), 8.11 (d, J=7.6 Hz, 2H), 7.66 (dt, J=42.3, 7.5 Hz, 3H), 7.32 (td J=7.2, 6.6, 2.9 Hz, 2H), 7.22-7.00 (m, 9H), 6.83-6.63 (m, 4H), 5.86 (ddt, J=52.8, 17.6, 6.9 Hz, 1H), 5.16 (td, 17.2, 8.8 Hz, 1H), 3.78-3.63 (m, 7H), 3.59-3.35 (m, 5H), 2.74 (t, J=5.9 Hz, 1H), 2.63 (t, J=5.9 Hz, 1H), 1.23-0.99 (m, 10H), 0.91 (d, J=6.7 Hz, 2H). $^{31}$P-NMR: (162 MHz, DMSO-d$_6$): δ 150.26, 149.60 (2 s, 1P).

Preparation 14: N-(7-((2R,4S,5R)—S-((bis(4-methoxyphenyl)(phenyl)methoxy) methyl)-4-hydroxytetrahydrofuran-2-yl)imidazo[2,1-f][1,2,4]triazin-4-yl)benzamide

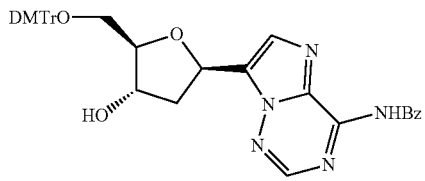

Step 1: (3R,4R,5R)-2-(4-aminoimidazo[2,1-f][1,2,4]triazin-7-yl)-3,4-bis(benzyloxy)-S-((benzyloxy)methyl)tetrahydrofuran-2-ol

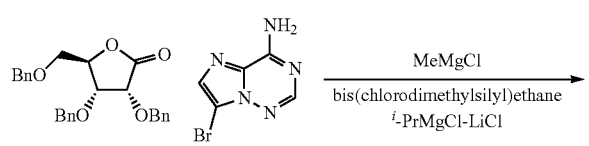

146

-continued

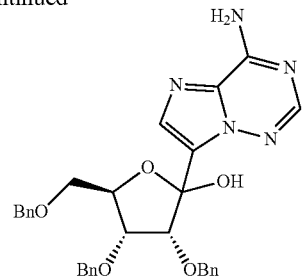

To a stirring mixture of 7-bromoimidazo[2,1-f][1,2,4]triazin-4-amine (41 g, 0.19 mol) in THF (0.50 L) at 0° C. was added MeMgBr (3.0M in THF, 66 mL, 0.19 mol) dropwise to maintain the internal temperature below 10° C. Bis(chlorodimethylsilyl)ethane (41 g, 190 mmol) was added in one portion. MeMgBr (3.0M in diethyl ether, 66 mL, 0.19 mol) was then added dropwise to maintain the internal temperature below 10° C. i-PrMgCl—LiCl (1.3M in THF, 0.16 L, 0.21 mol) was added while maintaining the internal temperature below 10° C. A mixture of (3R,4R,5R)-3,4-bis(benzyloxy)-S-((benzyloxy)methyl)dihydrofuran-2(3H)-one (160 g, 0.38 mol) in THF was added dropwise at 0° C., and the mixture was then allowed to warm to RT and was stirred for 12 h. The mixture was diluted with sat aq NH$_4$Cl (100 mL) and extracted with EtOAc (3×1000 mL). The combined organic layers were dried over Na$_2$SO$_4$ and concentrated under reduced pressure. The resulting residue was purified by column chromatography (column height: 2500 mm, diameter: 1000 mm, 25-75% EtOAc in Hex) to afford (3R,4R,5R)-2-(4-aminoimidazo[2,1-f][1,2,4]triazin-7-yl)-3,4-bis(benzyloxy)-S-((benzyloxy)methyl)-tetrahydrofuran-2-ol.

Step 2: 7-((3S,4R,5R)-3,4-bis(benzyloxy)-S-((benzyloxy)methyl)tetrahydrofuran-2-yl)imidazo[2,1-f][1,2,4]triazin-4-amine

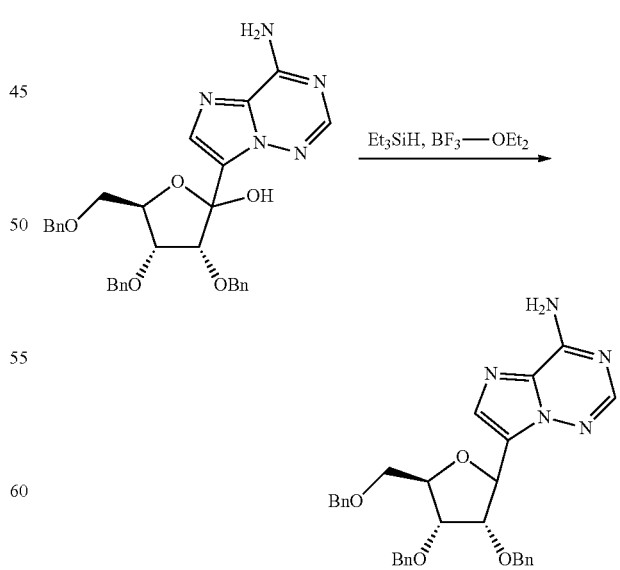

To a stirring mixture of (3R,4R,5R)-2-(4-aminoimidazo[2,1-f][1,2,4]triazin-7-yl)-3,4-bis(benzyloxy)-S-((benzyloxy)methyl)tetrahydrofuran-2-ol (64 g, 0.12 mmol) in DCM (1.3 L) at 0° C. was added TES (81 g, 0.69 mol), and then BF$_3$—OEt$_2$ (21 g, 0.15 mol). The mixture was then allowed to warm to 25° C., and the mixture was stirred for 1 h. More BF$_3$—OEt$_2$ (57 g, 0.40 mol) was added, and the mixture was then heated to 35° C. for 4 h. Upon cooling to RT, the mixture was quenched with sat aq NaHCO$_3$ (200 mL) and then extracted with EtOAc (3×300 mL). The combined organic layers were dried over Na$_2$SO$_4$ and concentrated under reduced pressure. The resulting residue was purified by column chromatography (15-75% EtOAc in Hex) to afford 7-((3S,4R,5R)-3,4-bis(benzyloxy)-S-((benzyloxy)methyl)tetrahydrofuran-2-yl)imidazo[2,1-f][1,2,4]triazin-4-amine. MS (ES, m/z)=538 [M+H]$^+$.

Step 3: (3R,4S,5R)-2-(4-aminoimidazo[2,1-f][1,2,4]triazin-7-yl)-S-(hydroxymethyl)-tetrahydrofuran-3,4-diol

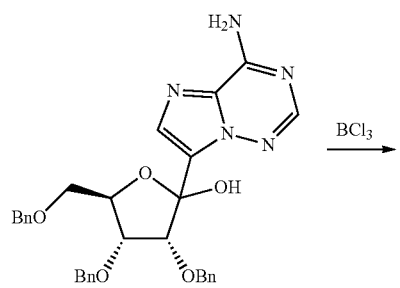

To a stirring mixture of 7-((3S,4R,5R)-3,4-bis(benzyloxy)-S-((benzyloxy)methyl)-tetrahydrofuran-2-yl)imidazo[2,1-f][1,2,4]triazin-4-amine (12 g, 22 mmol) in DCM (850 mL) at −78° C. was added BCl$_3$ (18 g, 0.16 mol) dropwise. Upon completion, the mixture was stirred at −78° C. for 3 h. After 3 h, the mixture was quenched with MeOH (50 mL) at −78° C., and the mixture was allowed to warm to 25° C. The mixture was concentrated under reduced pressure. The residue was purified by column chromatography (9-25% MeOH in DCM) to afford (3R,4S,5R)-2-(4-aminoimidazo[2,1-f][1,2,4]triazin-7-yl)-S-(hydroxymethyl)tetrahydrofuran-3,4-diol.

Step 4: (6aR,8S,9S,9aS)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-ol

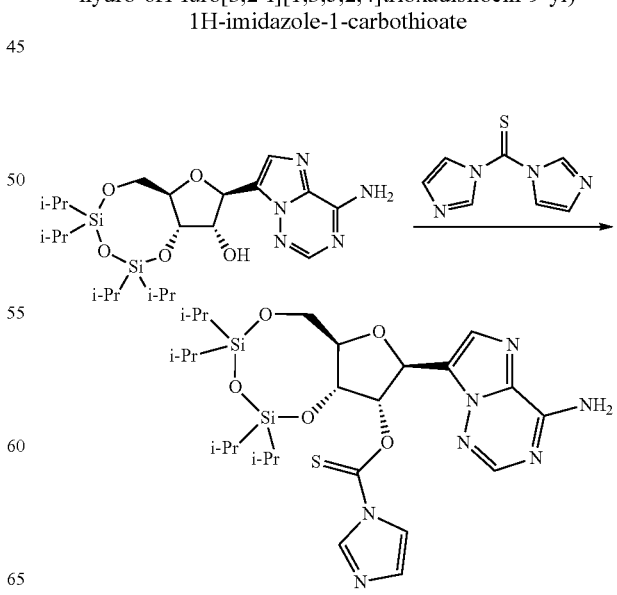

To a stirred mixture of (2S,3R,4S,5R)-2-(4-aminoimidazo[2,1-f][1,2,4]triazin-7-yl)-5-(hydroxymethyl)tetrahydrofuran-3,4-diol (4.0 g, 15 mmol) in Py (0.10 L) was added 1,3-dichloro-1,1,3,3-tetraisopropyldisiloxane (5.8 mL, 18 mmol). After 3 h, the mixture was diluted with toluene (50 mL) and then concentrated. The resulting mixture was taken up in DCM and MeOH, and then silica gel (40 g) was added. The mixture was concentrated, placed under vacuum for 1 h and then purified by column chromatography (0-80% EtOAc in Hex) to afford (6aR,8S,9S,9aS)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-ol. MS (ES, m/z)= 510 [M+H]$^+$.

Step 5: O-((6aR,8S,9S,9aR)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-yl) 1H-imidazole-1-carbothioate To a mixture of (6aR,8S,9S,9aS)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-ol (6.45 g, 12.7 mmol) in MeCN (63.0 mL) and Py (63.0 mL) was added 1,1'-thiocarbonyldiimidazole (2.71 g, 15.2 mmol). After 90 min, more 1,1'-thiocarbonyldiimidazole (2.71 g, 15.2 mmol) was added, and the mixture was stirred overnight. After stirring overnight, the mixture was concentrated and purified by column chromatography (0-100% EtOAc in Hex) to afford O-((6aR,8S,9S,9aR)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-yl) 1H-imidazole-1-carbothioate. MS (ES, m/z)=620 [M+H]$^+$.

Step 6: 7-((6aR,8R,9aS-2,2,4,4-tetraisopropyltetrahydro-6H-furo[3,2-f][1,3,5,2,4]trioxadisilocin-8-yl) imidazo[2,1-f][1,2,4]triazin-4-amine

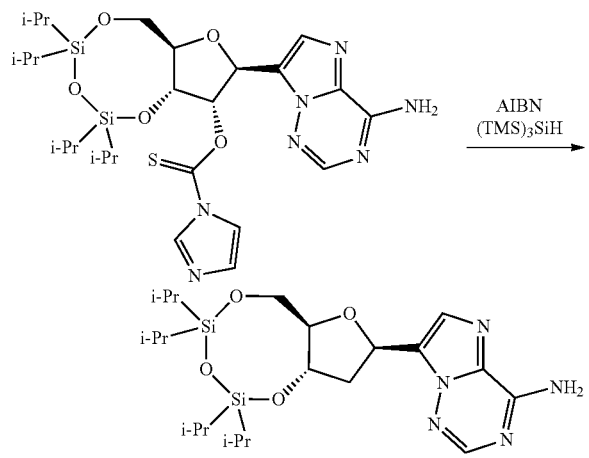

To a mixture of O-((6aR,8S,9S,9aR)-8-(4-aminoimidazo [2,1-f][1,2,4]triazin-7-yl)-2,2,4,4-tetraisopropyltetrahydro-6H-furo[3,2-f][1,3,5,2,4]trioxadisilocin-9-yl) (5.65 g, 9.11 mmol) in toluene (91.0 mL) was added 2,2'-azobis(2-methylpropionitrile) (0.300 g, 1.82 mmol) and (TMS)$_3$SiH (4.22 mL, 13.7 mmol). The mixture was heated to 85° C. for 30 min. After 30 min, the mixture was allowed to cool to RT, placed directly on the column, and purified (0-80% EtOAc in Hex) to afford 746aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-amine. MS (ES, m/z)=494 [M+H]$^+$.

Step 7: N-benzoyl-N-(7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-yl) benzamide

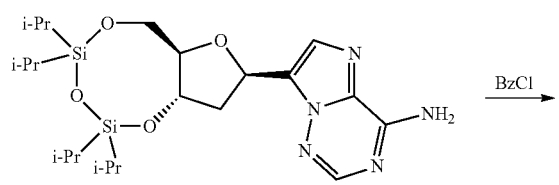

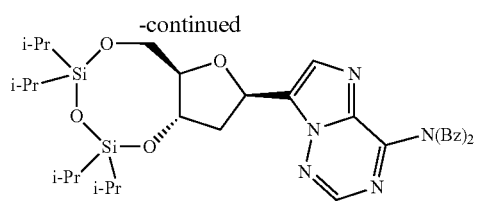

To a mixture of 746aR,8R,9aS)-2,2,4,4-tetraisopropyltetrahydro-6H-furo[3,2-j][1,3,5,2,4]trioxadisilocin-8-yl)imidazo[2,1-d][1,2,4]triazin-4-amine (15.7 g, 31.8 mmol) in Py (64.0 mL) was added BzCl (11.0 mL, 95.0 mmol), and the mixture was heated to 50° C. for 45 min. After 45 min, the mixture was allowed to cool to RT. After cooling, a precipitate formed and was filtered off. The filtrate was diluted with DCM (50 mL) and toluene (50 mL). The mixture was concentrated to about 50 mL. The mixture was filtered, and the solids were washed with DCM. The filtrate and washes were combined, loaded onto a column, and purified (0-50% EtOAc in Hex) to afford N-benzoyl-N-(7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-yl)benzamide. MS (ES, m/z)=702 [M+H]$^+$.

Step 8: N-(7-((2R,4S,5R)-4-hydroxy-S-(hydroxymethyl)tetrahydrofuran-2-yl)imidazo[2,1-f][1,2,4]triazin-4-yl)benzamide

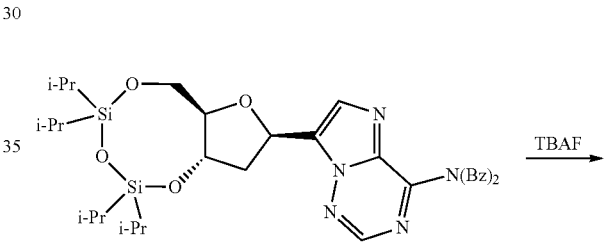

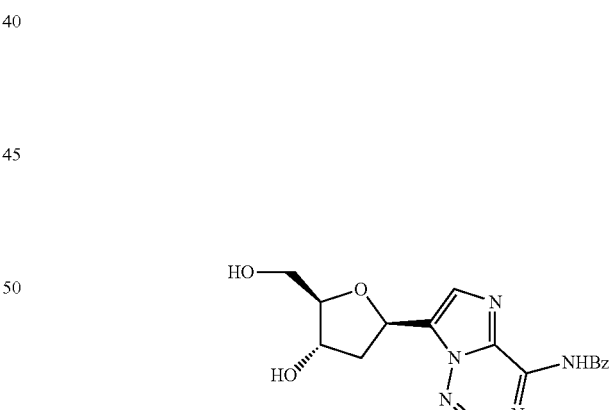

To a mixture of N-benzoyl-N-(746aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-yl)benzamide (10 g, 14 mmol) in THF (0.14 L) was added TBAF ((1.0M in THF, 29 mL, 29 mmol), and the mixture was stirred for 1 h. After 1 h, the mixture was concentrated and purified by column chromatography to afford N-(7-((2R,4S,5R)-4-hydroxy-S-(hydroxymethyl)tetrahydro-furan-2-yl)imidazo[2,1-f][1,2,4]triazin-4-yl)benzamide. MS (ES, m/z)=356 [M+H]$^+$.

Step 9: N-(7-((2R,4S,5R)—S-((bis(4-methoxyphenyl)(phenyl)methoxy)methyl)-4-hydroxytetrahydrofuran-2-yl)imidazo[2,1-f][1,2,4]triazin-4-yl)benzamide

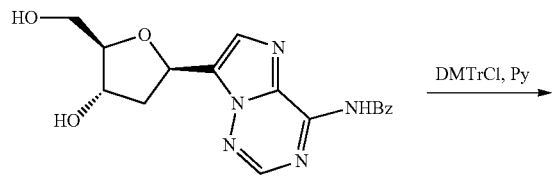

To a mixture of N-(7-((2R,4S,5R)-4-hydroxy-S-(hydroxymethyl)tetrahydrofuran-2-yl)imidazo[2,1-f][1,2,4]triazin-4-yl)benzamide (6.1 g, 17 mmol) in Py (86 mL) at 0° C. was added DMTrCl (5.8 g, 17 mmol), and the mixture was allowed to warm to RT overnight. After stirring overnight, the mixture was diluted with toluene and then concentrated under reduced pressure to afford the crude product residue. The crude product residue was purified by silica gel chromatography (0-100% EtOAc in Hex) to afford N-(7-((2R,4S,5R)—S-((bis(4-methoxyphenyl) (phenyl)-methoxy)methyl)-4-hydroxytetrahydrofuran-2-yl)imidazo[2,1-f][1,2,4]triazin-4-yl) benzamide. MS (ES, m/z)=658 [M+H]+.

Preparation 15: 4'-thioadenosine

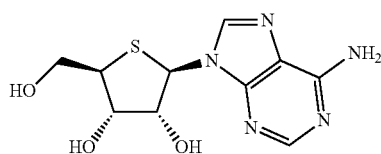 [SMILES: Nc1ncnc2c1ncn2[C@@H]1S[C@H](CO)[C@@H](O)[C@H]1O]

The title compound was prepared according to published procedures (*Journal of Medicinal Chemistry* 2006, 49(5), 1624-1634).

Preparation 16: triethylammonium 5'-O-[bis(4-methoxyphenyl)(phenyl) methyl]-3'-deoxy-3'-fluoro-2'-O-[hydroxy(oxido)-$\lambda^5$-phosphanyl]-N-(2-methylpropanoyl)guanosine

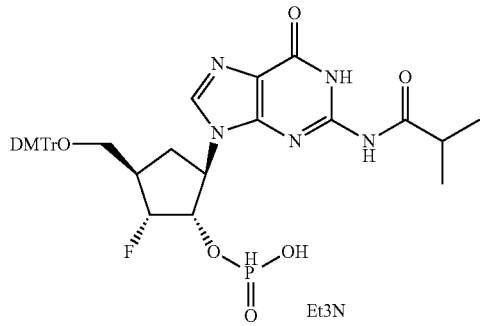

Step 1: (2R,3S,4R,5R)—S-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl phenyl phosphonate

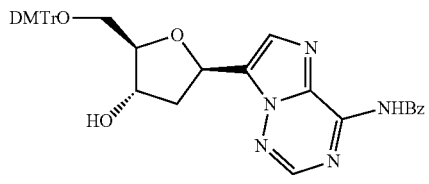

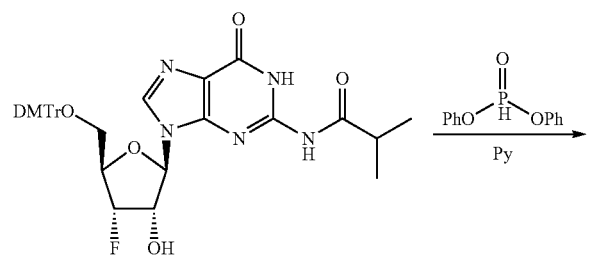

To a stirred solution of N-(9-((2R,3S,4S,5R)—S-((bis(4-methoxyphenyl)(phenyl) methoxy) methyl)-4-fluoro-3-hydroxytetrahydrofuran-2-yl)-6-oxo-6,9-dihydro-1H-purin-2-yl)isobutyramide (1 g, 1.520 mmol) in Py (7.6 mL) under Ar was added diphenyl phosphonate (1.068 g, 4.56 mmol), and it was stirred at RT for 20 min. The reaction mixture containing the product was used for the next reaction step without purification.

Step 2: (2R,3S,4R,5R)—S-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl phosphonate

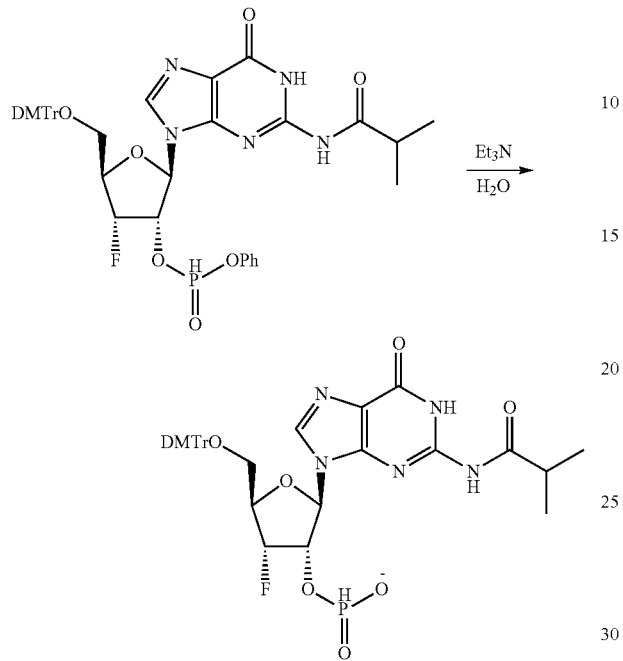

To the reaction mixture from Step 1 was added H$_2$O (1.5 mL) and Et$_3$N (1.5 mL). The mixture was stirred at RT for 20 min. Then, it was concentrated, and the residue was partitioned between CH$_2$Cl$_2$ (50 mL) and aq NaHCO$_3$ (5%, 20 mL). Layers were separated. The organic layer was washed with aq NaHCO$_3$ (5%, 2×20 mL), dried (Na$_2$SO$_4$), concentrated and purified by silica gel column chromatography using 0 to 7% MeOH in CH$_2$Cl$_2$ (1% Et$_3$N) to give the product. LCMS (ES, m/z): 722 [M+H]$^+$. $^{31}$P-NMR: (162 MHz, CD$_3$OD): δ 2.73 (s, 1P).

Preparation 17: triethylammonium 5'-O-[bis(4-methoxyphenyl)(phenyl) methyl]-3'-deoxy-3'-fluoro-2'-O-[hydroxy(oxido)-λ$^5$-phosphanyl]-N-(2-methylpropanoyl)guanosine

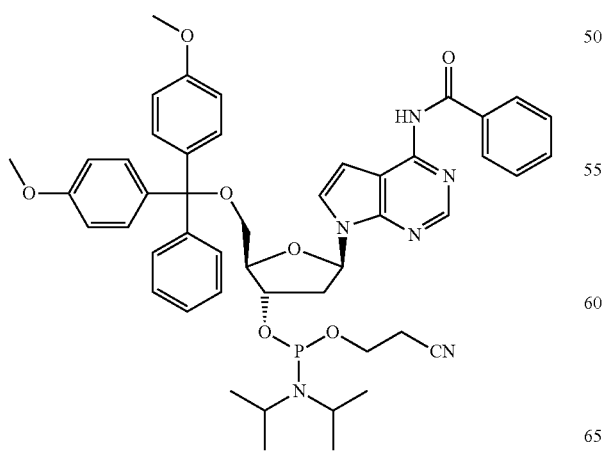

To a flask was added N-(7-((2R,4S,5R)—S-((bis(4-methoxyphenyl)(phenyl) methoxy)methyl)-4-hydroxytetrahydrofuran-2-yl)-7H-pyrrolo[2,3-d]pyrimidin-4-yl)benzamide (4 g, 6.09 mmol), DCM (71.7 mL), and 4,5-dicyanoimidazole (2.158 g, 18.27 mmol), and the solution was cooled to 0° C. 2-Cyanoethyl N,N,N',N'-tetraisopropylphosphorodiamidite (6.77 mL, 21.32 mmol) was added, and the mixture was stirred for 15 min at 0° C., after which time the mixture was concentrated under reduced pressure and purified by silica gel chromatography using a gradient of 30-100% EtOAc in Hex to yield (2R,3S,5R)—S-(4-benzamido-7H-pyrrolo[2,3-d]pyrimidin-7-yl)-2-((bis(4-methoxyphenyl)(phenyl)methoxy)methyl) tetrahydrofuran-3-yl (2-cyanoethyl) diisopropylphosphoramidite. LCMS (ES, m/z): 857 [M+H]$^+$.

Preparation 18: N-(3-((2R,3S,4S,5R)—S-((bis(4-methoxyphenyl)(phenyl) methoxy)methyl)-4-fluoro-3-hydroxytetrahydrofuran-2-yl)-7-oxo-6,7-dihydro-3H-[1,2,3]triazolo[4,5-d]pyrimidin-S-yl) isobutyramide

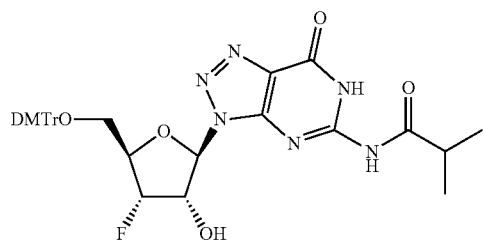

Step 1: ((2R,3R,4S,5R)—S-(5-amino-7-oxo-6,7-dihydro-3H-[1,2,3]triazolo[4,5-d]pyrimidin-3-yl)-4-(benzoyloxy)-3-fluorotetrahydrofuran-2-yl)methyl benzoate

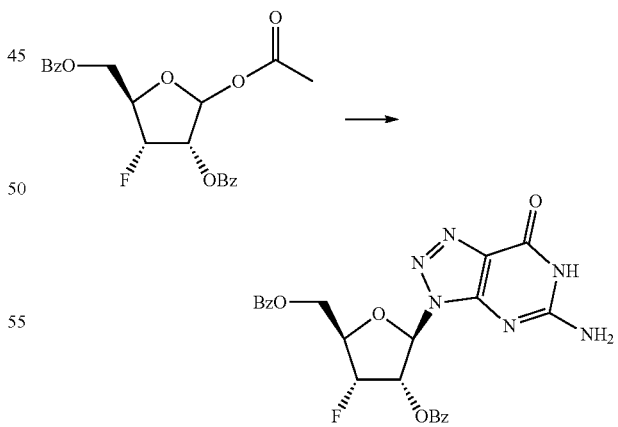

To a suspension of 8-azaguanine (5.14 g, 33.8 mmol) in anhydrous MeCN (100 mL) at RT was added dropwise (E)-trimethylsilyl N-(trimethylsilyl)acetimidate (16.53 mL, 67.6 mmol) then the mixture was stirred at 70° C. for 2 h. The reaction was cooled to rt, and a solution of ((2R,3R,4S)—S-acetoxy-4-(benzoyloxy)-3-fluorotetrahydrofuran-2-yl)methyl benzoate (6.8 g, 16.90 mmol) in anhydrous MeCN (20 mL) was added followed by dropwise addition of SnCl₄ (67.6 mL, 67.6 mmol). The homogeneous solution was stirred at 70° C. for 2 h. The reaction was cooled to RT and concentrated. The residue was dissolved in EtOAc (1000 mL) and neutralized by pouring into sat aq NaHCO₃ (500 mL). The organic layer was separated, and the aq layer was extracted with EtOAc (4×500 mL). The organic layers were combined and washed with H₂O (3×700 mL), brine, dried over anhydrous Na₂SO₄, filtered, and concentrated to afford title compound without further purification. LCMS (ES, m/z): 495.3 [M+H]⁺.

Step 2: ((2R,3R,4S,5R)-4-(benzoyloxy)-3-fluoro-S-(5-isobutyramido-7-oxo-6,7-dihydro-3H-[1,2,3]triazolo[4,5-d]pyrimidin-3-yl)tetrahydrofuran-2-yl) methyl benzoate

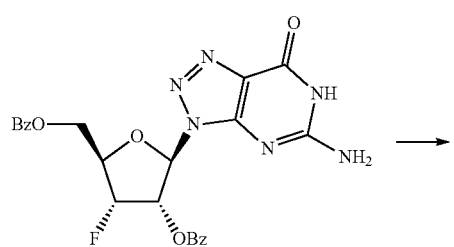

To a solution of ((2R,3R,4S,5R)—S-(5-amino-7-oxo-6,7-dihydro-3H-[1,2,3]triazolo[4,5-d]pyrimidin-3-yl)-4-(benzoyloxy)-3-fluorotetrahydrofuran-2-yl)methyl benzoate (8 g, 16.18 mmol) from Step 1 in anhydrous DMA (40 mL) at RT was added dropwise isobutyric anhydride (4.02 mL, 24.27 mmol). The mixture was stirred at 140° C. for 4 h. The reaction was cooled and diluted with EtOAc (600 mL), washed with sat aq NH₄Cl (4×500 mL), brine, dried over anhydrous Na₂SO₄, filtered and concentrated. The crude product was purified by MPLC (220 g silica gel, eluting with a gradient of 100% Hex to 100% EtOAc) to afford ((2R,3R,4S,5R)-4-(benzoyloxy)-3-fluoro-S-(5-isobutyramido-7-oxo-6,7-dihydro-3H-[1,2,3]triazolo[4,5-d]pyrimidin-3-yl)tetrahydrofuran-2-yl)methyl benzoate. LCMS (ES, m/z): 565.3 [M+H]⁺.

Step 3: N-(3-((2R,3S,4S,5R)-4-fluoro-3-hydroxy-S-(hydroxymethyl) tetrahydrofuran-2-yl)-7-oxo-6,7-dihydro-3H-[1,2,3]triazolo[4,5-d]pyrimidin-S-yl) isobutyramide

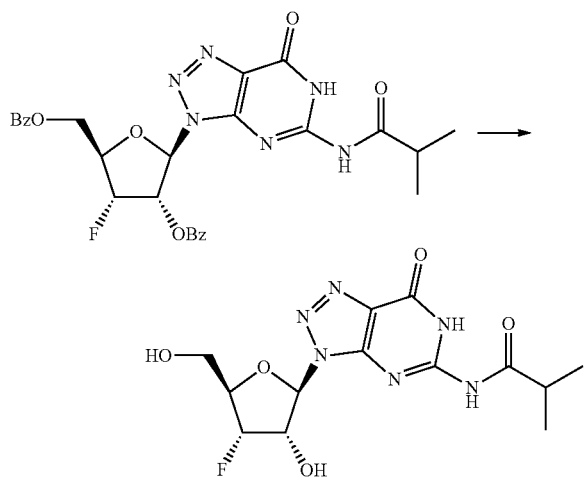

To a solution of ((2R,3R,4S,5R)-4-(benzoyloxy)-3-fluoro-S-(5-isobutyramido-7-oxo-6,7-dihydro-3H-[1,2,3]triazolo[4,5-d]pyrimidin-3-yl)tetrahydrofuran-2-yl)methyl benzoate (6 g, 10.63 mmol) in THF (20 mL), MeOH (16 mL), and H₂O (4 mL) at 0° C. was added 5N aq NaOH (4.89 mL, 24.45 mmol) and stirred for 1 h. The reaction was neutralized with formic acid (1.223 mL, 31.9 mmol). The solvent was removed, and the residue was purified by MPLC (120 g, silica gel, eluting with a gradient of 100% CH₂Cl₂ to 20% MeOH/CH₂Cl₂) to afford N-(3-((2R,3 S,4S,5R)-4-fluoro-3-hydroxy-S-(hydroxymethyl)tetrahydrofuran-2-yl)-7-oxo-6,7-dihydro-3H-[1,2,3]triazolo[4,5-d]pyrimidin-S-yl) isobutyramide. LCMS (ES, m/z): 357.2 [M+H]⁺.

Step 4: N-(3-((2R,3S,4S,5R)—S-((bis(4-methoxyphenyl)(phenyl)methoxy)methyl)-4-fluoro-3-hydroxytetrahydrofuran-2-yl)-7-oxo-6,7-dihydro-3H-[1,2,3]triazolo[4,5-d]pyrimidin-5-yl)isobutyramide

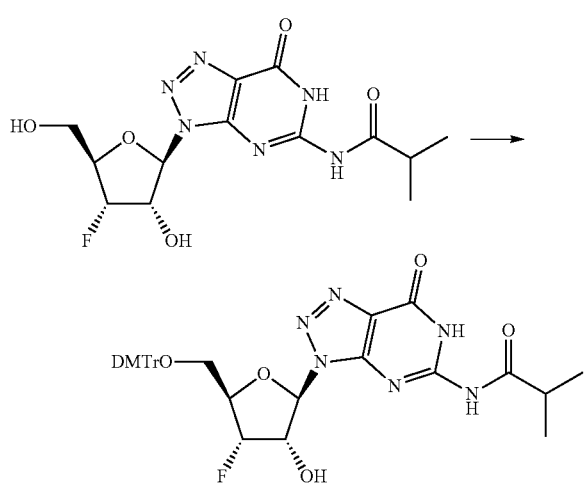

To a solution of N-(3-((2R,3S,4S,5R)-4-fluoro-3-hydroxy-S-(hydroxymethyl) tetrahydrofuran-2-yl)-7-oxo-6,7-dihydro-3H-[1,2,3]triazolo[4,5-d]pyrimidin-S-yl)isobutyramide (3 g, 8.42 mmol) in anhydrous Py (40 mL) at 0° C. was added 4,4'-dimethoxytrityl chloride (3.42 g, 10.10 mmol). The ice bath was removed, and the reaction mixture was allowed to reach RT and was stirred for 2 h. The mixture was diluted with EtOAc (400 mL), washed with sat aq NaHCO₃ (100 mL), H₂O (3×100 mL), brine, and dried over anhydrous Na₂SO₄, filtered, and concentrated. The crude product was purified by MPLC (120 g silica gel, eluting with a gradient of 100% DCM to 15% MeOH/DCM to afford N-(3-((2R,3S,4S,5R)—S-((bis(4-methoxyphenyl) (phenyl) methoxy)methyl)-4-fluoro-3-hydroxytetrahydrofuran-2-yl)-7-oxo-6,7-dihydro-3H-[1,2,3]triazolo[4,5-d]pyrimidin-S-yl) isobutyramide. LCMS (ES, m/z): 659.3 [M+H]⁺.

Preparation 19: N-(3-((2R,3S,4R,5R)—S-((bis(4-methoxyphenyl)(phenyl) methoxy)methyl)-4-fluoro-3-hydroxytetrahydrofuran-2-yl)-7-oxo-6,7-dihydro-3H-[1,2,3]triazolo[4,5-d]pyrimidin-S-yl) isobutyramide

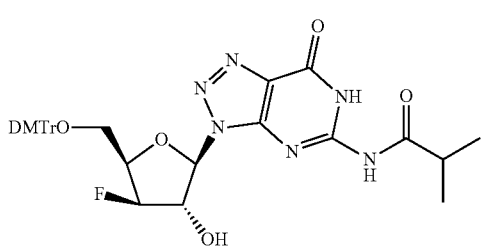

N-(3-((2R,3 S,4R,5R)—S-((bis(4-methoxyphenyl)(phenyl)methoxy)methyl)-4-fluoro-3-hydroxytetrahydrofuran-2-yl)-7-oxo-6,7-dihydro-3H-[1,2,3]triazolo[4,5-d]pyrimidin-S-yl) isobutyramide was prepared according to procedures analogous to those described for Preparation 18 using the appropriately substituted ribose in Step 1. LCMS (ES, m/z): 659.4 [M+H]⁺.

Preparation 20: N-(3-((2R,3R,5S)—S-((bis(4-methoxyphenyl)(phenyl)methoxy) methyl)-3-hydroxytetrahydrofuran-2-yl)-7-oxo-6,7-dihydro-3H-[1,2,3]triazolo[4,5-d]pyrimidin-S-yl)isobutyramide

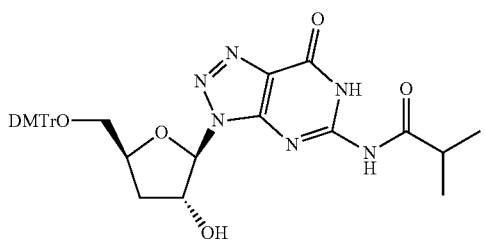

N-(3-((2R,3R,5S)—S-((bis(4-methoxyphenyl)(phenyl)methoxy)methyl)-3-hydroxy-tetrahydrofuran-2-yl)-7-oxo-6,7-dihydro-3H-[1,2,3]triazolo[4,5-d]pyrimidin-S-yl)isobutyramide was prepared according to procedures analogous to those described for Preparation 18 using the appropriately substituted ribose in Step 1. LCMS (ES, m/z): 641.2 [M+H]⁺.

Preparation 21: N-(9-((2R,3R,5S)—S-((bis(4-methoxyphenyl)(phenyl)methoxy) methyl)-3-hydroxytetrahydrothiophen-2-yl)-6-oxo-6,9-dihydro-1H-purin-2-yl) isobutyramide

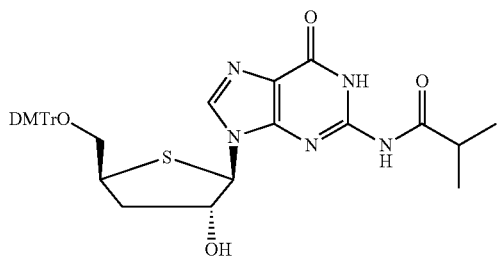

Step 1: (3R,4S,5R)-4-hydroxy-S-(hydroxymethyl) tetrahydrothiophen-3-yl 2,4-dimethoxybenzoate

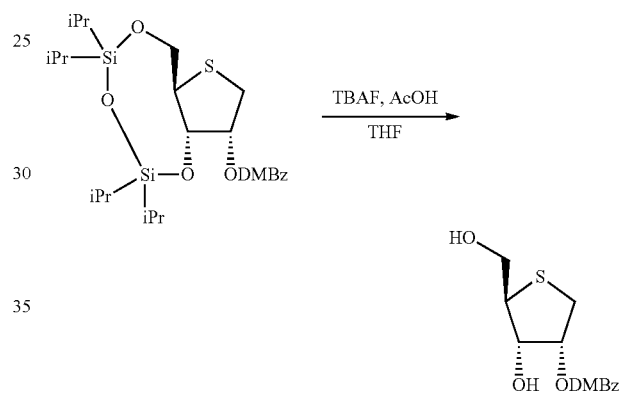

To a solution of (6aR,9R,9aS)-2,2,4,4-tetraisopropyltetrahydro-6H-thieno[3,2-f][1,3,5,2,4]trioxadisilocin-9-yl 2,4-dimethoxybenzoate (60 g, 108 mmol) in THF (500 mL) were added AcOH (13.59 g, 226 mmol) and TBAF in THF (1M, 226 mL, 226 mmol). After 1 h, it was concentrated under reduced pressure and purified by silica gel column chromatography eluting with 0-20% EtOAc in CH₂Cl₂ to give the product. LCMS (ES, m/z): 315.1 [M+H]⁺. ¹H-NMR (400 MHz, CDCl₃) δ 7.87 (d, J=8.7 Hz, 1H), 6.58-6.46 (m, 2H), 5.51 (dt, J=5.0, 3.7 Hz, 1H), 4.31 (td, J=6.9, 3.7 Hz, 1H), 3.88 (d, J=12.0 Hz, 8H), 3.58 (dt, J=7.1, 4.7 Hz, 1H), 3.26 (dd, J=12.2, 5.0 Hz, 1H), 3.15-3.01 (m, 2H), 2.31 (s, 1H).

Step 2: (3R,4S,5R)—S-(((tert-butyldiphenylsilyl)oxy)methyl)-4-hydroxytetrahydrothiophen-3-yl 2,4-dimethoxybenzoate

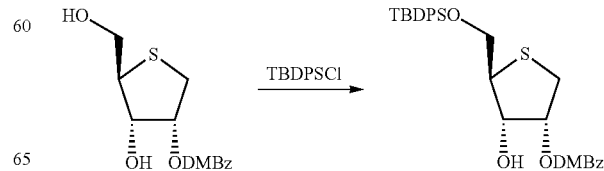

To a solution of (3R,4S,5R)-4-hydroxy-S-(hydroxymethyl)tetrahydrothiophen-3-yl 2,4-dimethoxybenzoate (33 g, 105 mmol) in Py (300 mL) was added TBDPSCl (43.3 g, 157 mmol). It was stirred at RT for 4 h. Then, H₂O (300 mL) was added. Layers were separated, and the aq layer was extracted with CH₂Cl₂ (3×300 mL). The combined organic layer was washed with brine (300 mL), dried (Na₂SO₄), concentrated, and purified by silica gel column chromatography eluting with 1 to 10% EtOAc in petroleum ether to give the product. LCMS (ES, m/z): 575.3 [M+Na]⁺. ¹H-NMR (400 MHz, DMSO-d₆) δ 7.83 (d, J=8.7 Hz, 1H), 7.68 (t, J=5.5 Hz, 5H), 7.54-7.38 (m, 6H), 6.69-6.60 (m, 2H), 5.40 (d, J=5.6 Hz, 1H), 5.35-5.29 (m, 1H), 4.12 (s, 1H), 4.05 (d, J=7.3 Hz, 1H), 3.85 (d, J=7.2 Hz, 6H), 3.78-3.66 (m, 1H), 3.55 (d, J=7.2 Hz, 1H), 3.14 (dd, J=11.0, 5.0 Hz, 1H), 2.86-2.77 (m, 1H), 1.03 (s, 9H).

Step 3: (3R,4S,5R)-4-((1H-imidazole-1-carbonothioyl)oxy)-S-(((tert-butyldiphenylsilyl)oxy)methyl)tetrahydrothiophen-3-yl 2,4-dimethoxybenzoate

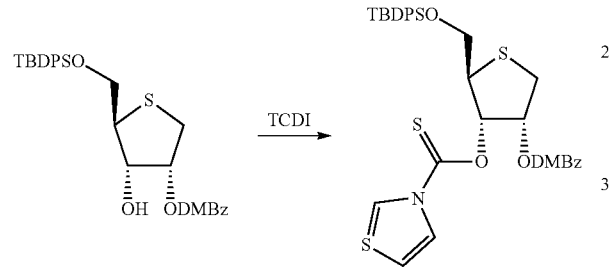

To a solution of (3R,4S,5R)—S-(((tert-butyldiphenylsilyl)oxy)methyl)-4-hydroxytetrahydrothiophen-3-yl 2,4-dimethoxybenzoate (48 g, 87 mmol) in DCE (500 mL) was added di(1H-imidazol-1-yl)methanethione (20.12 g, 113 mmol). It was heated at 85° C. under Ar for 1 h. Then, it was concentrated and used in the next step without purification. LCMS (ES, m/z): 663.2 [M+H]⁺.

Step 4: (3R,5S)—S-(((tert-butyldiphenylsilyl)oxy)methyl)tetrahydrothiophen-3-yl 2,4-dimethoxybenzoate

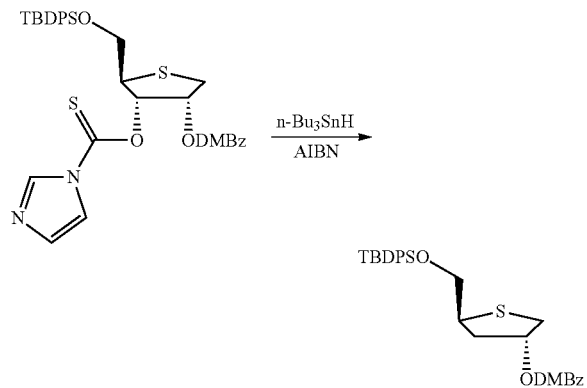

To a solution of (3R,4S,5R)-4-((1H-imidazole-1-carbonothioyl)oxy)-S-(((tert-butyldiphenylsilyl)oxy)methyl)tetrahydrothiophen-3-yl 2,4-dimethoxybenzoate (crude, 57.6 g, 87 mmol) in THF (40 mL) and toluene (200 mL) was added n-Bu₃SnH (139 g, 478 mmol). It was heated at 95° C., and 2,2'-(diazene-1,2-diyl)bis(2-methylpropanenitrile) (1.427 g, 8.69 mmol) in toluene (200 mL) was added over 30 min. After 1 h, the resulting mixture was concentrated and purified by silica gel column chromatography eluting with 0 to 10% EtOAc in petroleum ether to give the product. LCMS (ES, m/z): 537.3 [M+H]⁺. ¹H-NMR (400 MHz, CDCl₃) δ 7.88 (d, J=8.6 Hz, 1H), 7.77-7.67 (m, 4H), 7.50-7.36 (m, 6H), 6.58-6.48 (m, 2H), 5.70 (p, J=3.8 Hz, 1H), 3.95-3.74 (m, 10H), 3.28 (dd, J=12.0, 4.6 Hz, 1H), 3.10-3.02 (m, 1H), 2.49-2.39 (m, 1H), 1.92 (ddd, J=13.3, 8.6, 4.1 Hz, 1H), 1.09 (s, 9H).

Step 5: (1R,3R,5S)—S-(((tert-butyldiphenylsilyl)oxy)methyl)-1-oxidotetrahydrothiophen-3-yl 2,4-dimethoxybenzoate

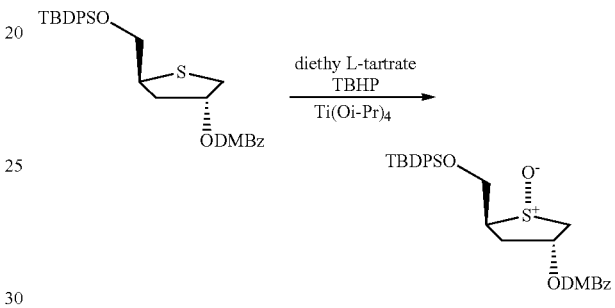

To a solution of Ti(OiPr)₄ (23.29 mL, 78 mmol) in CH₂Cl₂ (130 mL) under Ar was added diethyl (L)-tartrate (38.3 mL, 224 mmol) dropwise. After 10 min, the mixture was cooled to −20° C., and then TBHP in decane (~5.5M, 27.1 mL, 149 mmol) was added dropwise. After 5 min, a solution of (3R,5S)—S-(((tert-butyldiphenylsilyl)oxy)methyl)tetrahydrothiophen-3-yl 2,4-dimethoxybenzoate (40 g, 74.5 mmol) in CH₂Cl₂ (130 mL) was added to the reaction at −20° C. The resulting mixture was stirred at −20° C. for 16 h. It was quenched by the addition of ice water (300 mL) and allowed to warm up to RT. The precipitate was filtered off and washed with EtOAc (3×300 mL). The filtrate was washed with H₂O (3×200 mL). The aq layer was extracted with EtOAc (400 mL). The combined organic layer was dried (Na₂SO₄), concentrated and purified by flash chromatography eluting with 0 to 70% EtOAc in petroleum ether to give the product (mixture of two isomers). LCMS (ES, m/z): 553.2 [M+H]⁺. ¹H-NMR (400 MHz, DMSO-d₆) δ 7.81 (d, J=8.7 Hz, 1H), 7.75-7.61 (m, 4H), 7.54-7.39 (m, 6H), 6.67-6.56 (m, 2H), 5.66 (q, J=3.8 Hz, 1H), 4.12 (dt, J=10.5, 4.4 Hz, 1H), 3.92-3.79 (m, 8H), 3.58-3.42 (m, 1H), 3.20-3.09 (m, 1H), 2.97 (d, J=15.0 Hz, 1H), 2.05 (ddd, J=14.5, 10.5, 4.3 Hz, 1H), 1.02 (s, 9H).

Step 6: (3R,5S)-2-acetoxy-S-(((tert-butyldiphenylsilyl)oxy)methyl) tetrahydrothiophen-3-yl 2,4-dimethoxybenzoate

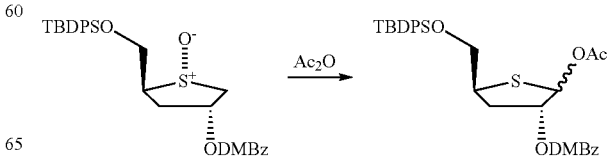

A solution of (3R,5S)-2-acetoxy-S-(((tert-butyldiphenyl-silyl)oxy)methyl)-tetrahydrothiophen-3-yl 2,4-dimethoxybenzoate (21 g, 34.2 mmol) in acetic anhydride (210 mL) was heated at 110° C. After stirring of 3.5 h, the reaction mixture was cooled to RT and concentrated. The residue was purified by silica gel column chromatography eluting with 0% to 20% EtOAc in petroleum ether to give the product. LCMS (ES, m/z): 535.3 [M-OAc]+. 1H-NMR (400 MHz, DMSO-d6) δ 7.76-7.61 (m, 5H), 7.46 (dq, J=7.6, 4.5, 3.7 Hz, 6H), 6.68-6.58 (m, 2H), 6.22 (d, J=4.3 Hz, 0.65H), 5.94 (s, 0.28H), 5.51-5.46 (m, 0.33H), 5.38 (ddd, J=11.1, 7.2, 4.3 Hz, 0.65H), 3.96-3.61 (m, 9H), 2.40-2.21 (m, 2H), 2.03 (d, J=1.6 Hz, 3H), 1.01 (s, 9H).

Step 7: (3R,5S)—S-(((tert-butyldiphenylsilyl)oxy)methyl)-2-(6-chloro-2-isobutyramido-9H-purin-9-yl)tetrahydrothiophen-3-yl 2,4-dimethoxybenzoate

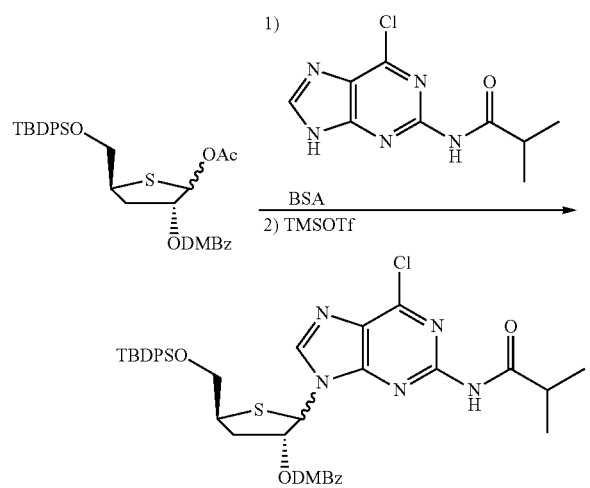

To a solution of N-(6-chloro-9H-purin-2-yl)isobutyramide (10.27 g, 42.9 mmol) in toluene (600 mL) at 0° C. was added trimethylsilyl N-(trimethylsilyl)acetimidate (23.26 g, 114 mmol). It was heated at 80° C. for 1 h and was cooled to 0° C. again. To the reaction was then added a solution of (3R,5S)-2-acetoxy-S-(((tert-butyldiphenylsilyl)oxy)methyl)-tetrahydro-thiophen-3-yl 2,4-dimethoxybenzoate (17 g, 28.6 mmol) in toluene (600 mL) and TMSOTf (19.06 g, 86 mmol). It was heated to 80° C. and stirred under Ar for 12 h. At that time, the reaction was cooled to RT, and sat aq NaHCO3 (400 mL) was added. Layers were separated, and the aq layer was extracted with EtOAc (4×1000 mL). The combined organic phase was dried (Na2SO4), concentrated and purified by silica gel column chromatography eluting with 10% to 40% EtOAc in petroleum ether to give the product (mixture of α and β isomers). LCMS (ES, m/z): 774.3 [M+H]+. 1H-NMR (400 MHz, CDCl3) δ 8.48 (s, 0.32H), 8.35 (s, 0.69H), 7.97-7.83 (m, 1.67H), 7.70 (dq, J=8.4, 1.5 Hz, 4H), 7.54 (d, J=8.7 Hz, 0.33H), 7.49-7.36 (m, 6H), 6.57-6.36 (m, 2.5H), 6.18 (d, J=2.4 Hz, 0.7H), 5.87-5.80 (m, 0.35H), 5.73 (q, J=3.3 Hz, 0.75H), 4.23-4.01 (m, 1.2H), 3.98-3.74 (m, 7.8H), 3.11 (s, 0.73H), 2.95 (s, 0.37H), 2.57-2.36 (m, 1.75H), 2.30-2.20 (m, 0.34H), 1.23 (d, J=6.8 Hz, 2.19H), 1.19 (dd, J=6.8, 3.5 Hz, 4.38H), 1.09 (d, J=1.7 Hz, 9H).

Step 8: (2R,3R,5S)-2-(6-chloro-2-isobutyramido-9H-purin-9-yl)-S-(hydroxymethyl)-tetrahydrothiophen-3-yl 2,4-dimethoxybenzoate

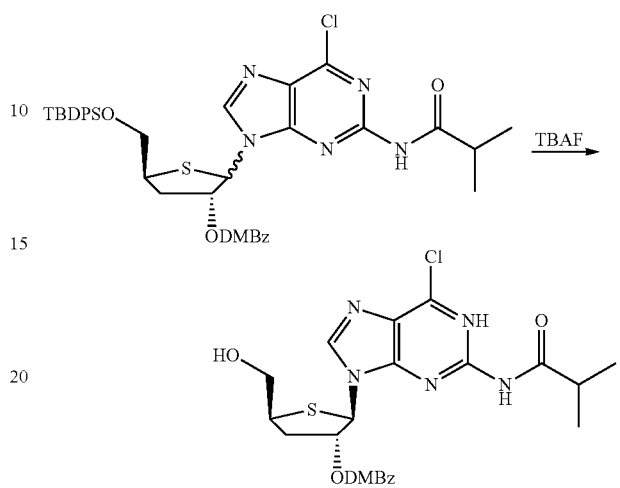

To a solution of (3R,5S)—S-(((tert-butyldiphenylsilyl)oxy)methyl)-2-(6-chloro-2-isobutyramido-9H-purin-9-yl)tetrahydrothiophen-3-yl 2,4-dimethoxybenzoate (20 g, 25.8 mmol) in THF (135 mL) was added TBAF in THF (1M, 31 mL, 31 mmol) dropwise. After 1 h, the reaction mixture was concentrated and purified by column chromatography using 1% to 10% MeOH in CH2Cl2 as the eluent to give a mixture of two isomers. It was re-purified by reverse phase (C18) chromatography eluting with 10 to 45% ACN in aq NH4CO3 (5 mM) to give the product. LCMS (ES, m/z): 536.2 [M+H]+. 1H-NMR (400 MHz, DMSO-d6) δ 10.80 (s, 1H), 8.83 (s, 1H), 7.72 (d, J=8.7 Hz, 1H), 6.65-6.55 (m, 2H), 6.18 (d, J=2.5 Hz, 1H), 5.80 (q, J=3.5 Hz, 1H), 5.22 (t, J=5.1 Hz, 1H), 3.93-3.67 (m, 9H), 2.85 (p, J=6.9 Hz, 1H), 2.70 (ddd, J=13.4, 8.5, 4.5 Hz, 1H), 2.36 (dt, J=14.1, 5.0 Hz, 1H), 1.06 (dd, J=6.8, 3.3 Hz, 6H).

Step 9: 2-amino-9-((2R,3R,5S)-3-hydroxy-S-(hydroxymethyl)tetrahydrothiophen-2-yl)-1,9-dihydro-6H-purin-6-one

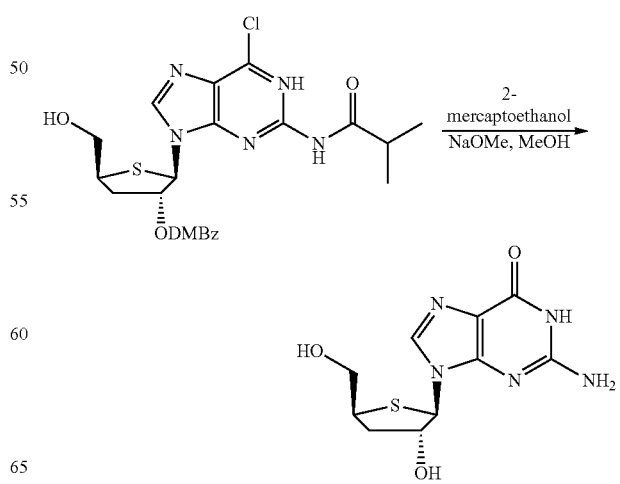

To a solution of (2R,3R,5S)-2-(6-chloro-2-isobutyramido-9H-purin-9-yl)-5-(hydroxymethyl)tetrahydrothiophen-3-yl 2,4-dimethoxybenzoate (6.0 g, 11.19 mmol) in MeOH (300 mL) were added 2-mercaptoethanol (3.50 g, 44.8 mmol) and NaOMe (10.08 g, 56 mmol, 30% in MeOH). It was heated at 60° C. for 16 h, cooled to rt, and concentrated HCl (4 mL) was added. The resulting mixture was concentrated, and H$_2$O (100 mL) and EtOAc (100 mL) were added. Layers were separated, and the aq layer was extracted with EtOAc (3×100 mL). The aq layer was basified with NaHCO$_3$ (solid) to pH 8 and stirred at RT for 1 h. The precipitate was filtered and kept under reduced pressure to give the product. LCMS (ES, m/z): 284.1 [M+H]$^+$. $^1$H-NMR (400 MHz, DMSO-d$_6$) δ 10.57 (s, 1H), 7.98 (s, 1H), 6.46 (s, 2H), 5.57 (dd, J=10.9, 3.9 Hz, 2H), 5.12 (t, J=5.4 Hz, 1H), 4.48 (p, J=4.1 Hz, 1H), 3.78-3.53 (m, 3H), 2.11-1.99 (m, 2H).

Step 10: N-(9-((2R,3R,5S)-3-hydroxy-S-(hydroxymethyl)tetrahydrothiophen-2-yl)-6-oxo-6,9-dihydro-1H-purin-2-yl)isobutyramide

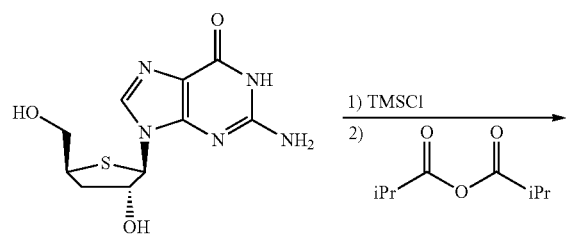

2-amino-9-((2R,3R,5S)-3-hydroxy-S-(hydroxymethyl)tetrahydrothiophen-2-yl)-1,9-dihydro-6H-purin-6-one (580 mg, 2.047 mmol) was co-evaporated with Py (3×20 mL) and then re-dissolved in Py (20 mL). The mixture was cooled to 0° C. and then treated with TMSCl (1557 mg, 14.33 mmol). It was warmed to RT and stirred for 2 h. Then, the reaction was cooled to 0° C., and isobutyric anhydride (486 mg, 3.07 mmol) was added dropwise. It was warmed to RT and stirred for 2 h. The reaction was quenched by the addition of MeOH (5 mL). After 5 min, NH$_4$OH (ca 29%, 10 mL) was added. The mixture was stirred at RT for 30 min. Then, it was concentrated and purified by column chromatography on silica gel eluting with 10% to 20% MeOH in CH$_2$Cl$_2$ to give the product. LCMS (ES, m/z): 354.1 [M+H]$^+$. $^1$H-NMR (300 MHz, CD$_3$OD) δ: 8.40 (s, 1H), 5.83-5.82 (m, 1H), 4.62-4.59 (m, 1H), 3.89-3.80 (m, 2H), 3.79-3.74 (m, 1H), 2.73-2.64 (m, 1H), 2.19-2.11 (m, 2H), 1.20 (d, J=6.8 Hz, 6H).

Step 11: N-(9-((2R,3R,5S)—S-((bis(4-methoxyphenyl)(phenyl)methoxy)methyl)-3-hydroxytetrahydrothiophen-2-yl)-6-oxo-6,9-dihydro-1H-purin-2-yl)isobutyramide

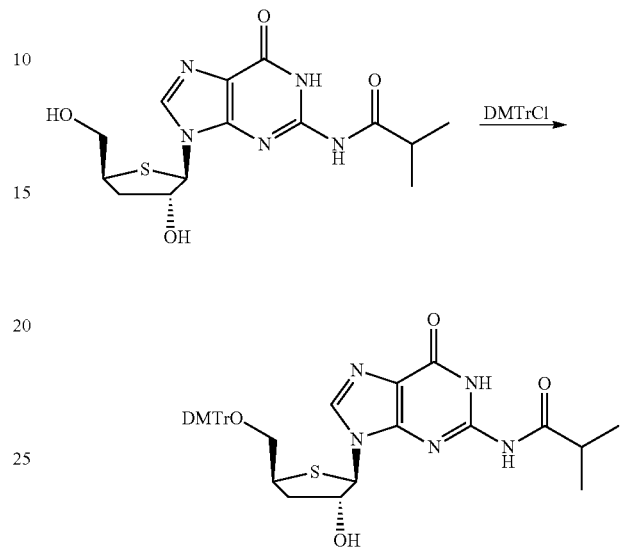

N-(9-((2R,3R,5S)-3-hydroxy-S-(hydroxymethyl)tetrahydrothiophen-2-yl)-6-oxo-6,9-dihydro-1H-purin-2-yl)isobutyramide (510 mg, 1.443 mmol) was co-evaporated with Py (3×5 mL) and then re-suspended in Py (7 mL). To the suspension was added DMTrCl (538 mg, 1.587 mmol), and the mixture was stirred at RT for 2 h. At that time, the mixture was concentrated under reduced pressure, and residue was purified by column chromatography on silica gel eluting with 1% to 4% MeOH in CH$_2$Cl$_2$ (containing 1% Et$_3$N) to give the product. LCMS (ES, m/z): 656.0 [M+H]$^+$. $^1$H-NMR (400 MHz, CD$_3$OD) δ: 8.02 (s, 1H), 7.51-7.43 (m, 2H), 7.40-7.17 (m, 7H), 6.91-6.82 (m, 4H), 5.85-5.84 (d, J=2.3 Hz, 1H), 4.59-4.57 (m, 1H), 4.02-3.95 (m, 1H), 3.78 (s, 6H), 3.52-3.34 (m, 3H), 2.72-2.68 (m, 1H), 1.95-191 (m, 1H), 1.38 (d, J=6.8 Hz, 6H).

Preparation 22: N-(3-((2R,3R,4S,5R)—S-((bis(4-methoxyphenyl)(phenyl)-methoxy)methyl)-4-fluoro-3-hydroxytetrahydrothiophen-2-yl)-7-oxo-6,7-dihydro-3H-[1,2,3]triazolo[4,5-d]pyrimidin-S-yl)isobutyramide

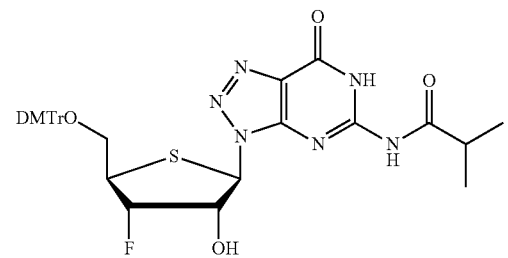

Step 1: N-(7-oxo-6,7-dihydro-3H-[1,2,3]triazolo[4,5-d]pyrimidin-5-yl)isobutyramide

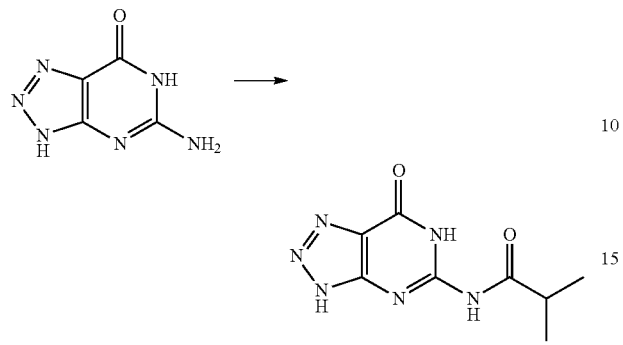

To a suspension of 5-amino-3,6-dihydro-7H-[1,2,3]triazolo[4,5-d]pyrimidin-7-one (5.0 g, 32.9 mmol) in anhydrous DMF (60 mL) was added isobutyric anhydride (12.5 mL, 76.0 mmol) dropwise. The reaction mixture was refluxed at 150° C. for 1 h. The reaction was quenched with MeOH (6.6 mL, 164 mmol) and concentrated in vacuo. The residue was taken up in DCM (50 mL)/Hex (100 mL) and was stirred at vigorously at RT for 15 min. The product was collected by filtration. LCMS (ES, m/z): 223.2 [M+H]$^+$. $^1$H NMR (500 MHz, DMSO-d$_6$) δ 16.04 (s, 1H), 12.19 (s, 1H), 11.78 (s, 1H), 2.78 (hept, J=6.7 Hz, 1H), 1.13 (d, J=6.8 Hz, 6H).

Step 2: ((2R,3S,4R,5R)-4-(benzoyloxy)-3-fluoro-S-(5-isobutyramido-7-oxo-6,7-dihydro-3H-[1,2,3]triazolo[4,5-d]pyrimidin-3-yl)tetrahydrothiophen-2-yl)methyl benzoate

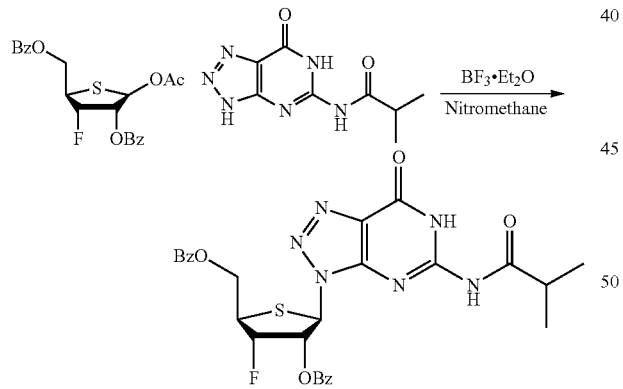

To a mixture of ((2R,3S,4R)—S-acetoxy-4-(benzoyloxy)-3-fluorotetrahydro-thiophen-2-yl)methyl benzoate (1.5 g, 3.6 mmol) and N-(7-oxo-6,7-dihydro-3H-[1,2,3]triazolo[4,5-d]pyrimidin-S-yl)isobutyramide (0.96 g, 4.3 mmol) in nitromethane (20 mL) was added BF$_3$.Et$_2$O (0.54 mL, 4.3 mmol), and the resulting mixture was heated at 100° C. under microwave irradiation for 1 h. The reaction mixture was cooled, diluted in 100 mL of EtOAc and washed with sat aq. NaHCO$_3$ (100 mL) and brine (100 mL). The organic portion was dried over Na$_2$SO$_4$ and concentrated in vacuo. The residue was purified by a silica gel column, eluting with 0-35% EtOAc/Hex. LCMS (ES, m/z): 581.4 [M+H]$^+$. $^1$H NMR (500 MHz, Chloroform-d) δ 12.24 (s, 1H), 9.70 (s, 1H), 8.06-8.03 (m, 2H), 7.99-7.96 (m, 2H), 7.67-7.62 (m, 1H), 7.61-7.56 (m, 1H), 7.53-7.46 (m, 2H), 7.46-7.40 (m, 2H), 6.73 (d, J=6.7 Hz, 1H), 6.55-6.45 (m, 1H), 5.76 (t, J=2.9 Hz, 0.5H), 5.66 (t, J=2.9 Hz, 0.5H), 5.55 (dd, J=11.5, 8.8 Hz, 1H), 4.86 (ddd, J=11.5, 7.8, 1.0 Hz, 1H), 4.23 (dtd, J=15.0, 8.4, 2.5 Hz, 1H), 2.93 (hept, J=6.9 Hz, 1H), 1.41-1.32 (m, 6H).

Step 3: N-(3-((2R,3R,4S,5R)-4-fluoro-3-hydroxy-S-(hydroxymethyl)tetrahydro-thiophen-2-yl)-7-oxo-6,7-dihydro-3H-[1,2,3]triazolo[4,5-d]pyrimidin-S-yl)isobutyramide

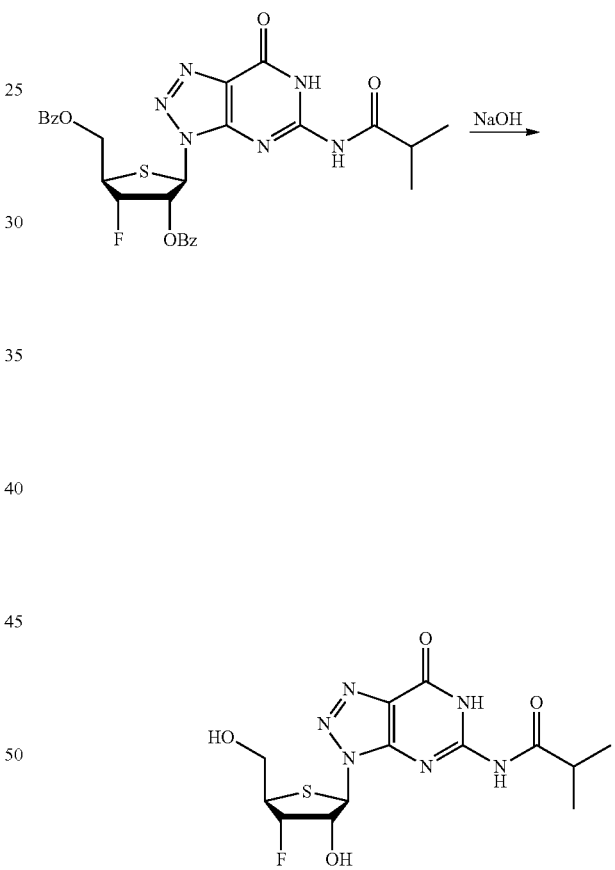

To a solution of ((2R,3S,4R,5R)-4-(benzoyloxy)-3-fluoro-S-(5-isobutyramido-7-oxo-6,7-dihydro-3H-[1,2,3]triazolo[4,5-d]pyrimidin-3-yl)tetrahydrothiophen-2-yl) methyl benzoate (4.5 g, 7.8 mmol) in THF (35 mL)/MeOH (28 mL)/H (7 mL) at 0° C. was added 2N NaOH (8.6 mL, 17.2 mmol). The reaction mixture was stirred at 0° C. for 1 h and then neutralized with AcOH (2.3 mL, 39.0 mmol). The product was collected by filtration and carried on to the next step without further purification. LCMS (ES, m/z): 373.3 [M+H]$^+$.

167

Step 4: N-(3-((2R,3R,4S,5R)—S-((bis(4-methoxy-phenyl)(phenyl)methoxy)methyl)-4-fluoro-3-hydroxytetrahydrothiophen-2-yl)-7-oxo-6,7-dihydro-3H-[1,2,3]triazolo[4,5-d]pyrimidin-S-yl)isobutyramide

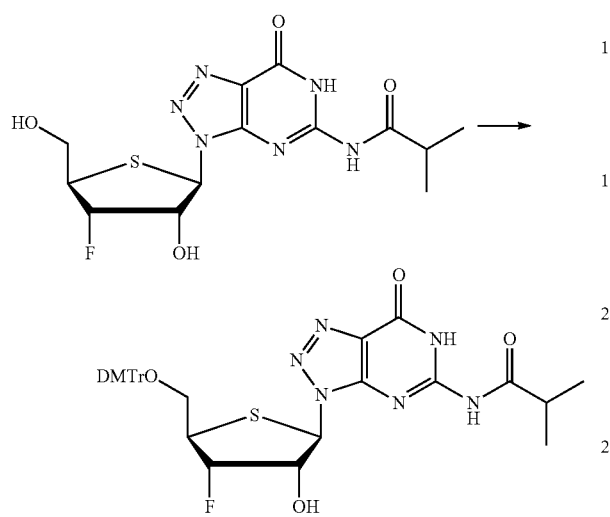

To a solution of N-(3-((2R,3R,4S,5R)-4-fluoro-3-hydroxy-S-(hydroxymethyl)-tetrahydrothiophen-2-yl)-7-oxo-6,7-dihydro-3H-[1,2,3]triazolo[4,5-d]pyrimidin-S-yl)isobutyramide (1.8 g, 4.8 mmol) in Py (30 mL) at 0° C. was added DMTrCl (1.8 g, 5.3 mmol). The reaction mixture was stirred at 0° C. for 1 h. The reaction was quenched with H$_2$O (1 mL), and the mixture was concentrated. The residue was diluted in 100 mL of EtOAc and washed with sat aq. NaHCO$_3$ (100 mL) and brine (100 mL). The separated organic layer was dried over anhydrous Na$_2$SO$_4$, filtered, and concentrated in vacuo. The residue was purified by a silica gel column, eluting with 0-100% EtOAc/Hex containing 0.1% Et$_3$N to give product. LCMS (ES, m/z): 675.5 [M+H]$^+$. $^1$H NMR (500 MHz, Chloroform-d) δ 12.13 (bs, 1H), 8.46 (bs, 1H), 7.54-7.48 (m, 2H), 7.38 (tt, J=6.8, 2.6 Hz, 4H), 7.31-7.27 (m, 2H), 7.24-7.18 (m, 1H), 6.83 (dd, J=9.0, 1.0 Hz, 4H), 6.16 (d, J=7.2 Hz, 1H), 5.36 (m, 1H), 5.33-5.24 (m, 1H), 3.79-3.76 (m, 1H), 3.78 (s, 3H), 3.72 (d, J=1.8 Hz, 1H), 3.70 (s, 3H), 3.43 (dd, J=10.2, 5.6 Hz, 1H), 3.34 (dd, J=10.2, 5.4 Hz, 1H), 2.14 (dt, J=13.7, 6.7 Hz, 1H), 1.05 (d, J=6.9 Hz, 3H), 1.00 (d, J=6.9 Hz, 3H).

Preparation 23: 7-(2-deoxy-β-D-erythro-pentofuranosyl)-S-fluoro-7H-pyrrolo[2,3-d]pyrimidin-4-amine

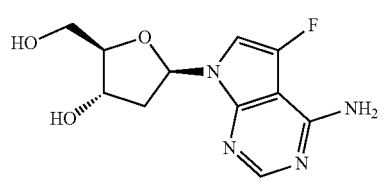 [SMILES: Nc1ncnc2c1c(F)cn2[C@H]1C[C@H](O)[C@@H](CO)O1]

The title compound was prepared according to published procedures (Synthesis 2006 (12), 2005-2012).

168

EXAMPLES

Examples 1 and 2: 8-[(2R,5R,7R,8R,10R,12aR,14R,15R,15aS,16R)-14-(6-amino-9H-purin-9-yl)-15,16-dihydroxy-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one (Diastereomer 1) and 8-[(2S,5R,7R,8R,10R,12aR,14R,15R,15aS,16R)-14-(6-amino-9H-purin-9-yl)-15,16-dihydroxy-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one (Diastereomer 2)

Diastereomer1

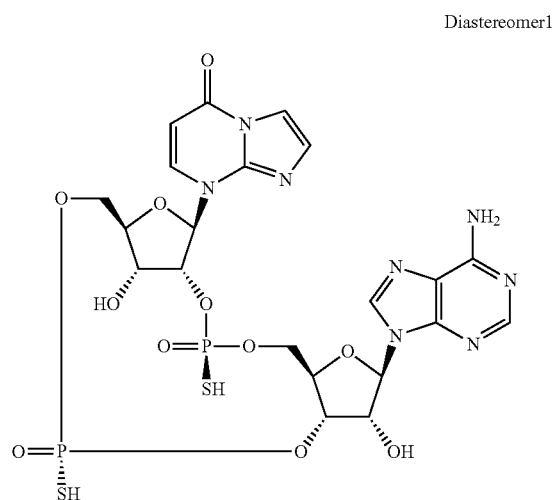

Diastereomer2

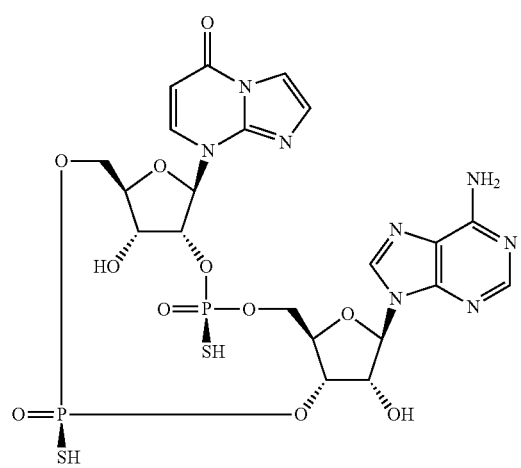

Step 1: 8-((2R,3R,4S,5R)—S-((bis(4-methoxyphenyl)(phenyl)methoxy)methyl)-3,4-dihydroxytetrahydrofuran-2-yl)imidazo[1,2-a]pyrimidin-5(8H)-one

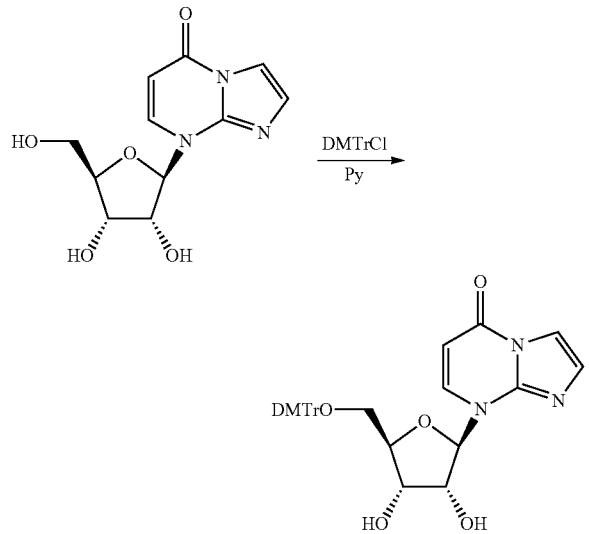

To a solution of 8-((2R,3R,4S,5R)-3,4-dihydroxy-S-(hydroxymethyl) tetrahydrofuran-2-yl)imidazo[1,2-a]pyrimidin-5(8H)-one (1.70 g, 6.36 mmol) in Py (25 mL) was added DMTrCl (2.37 g, 7.00 mmol). The resulting mixture was stirred at RT for 4 h. It was concentrated, and EtOAc (100 mL) and H₂O (40 mL) were added. Layers were separated, and the aq layer was extracted with EtOAc (2×50 mL). The combined organics were washed with brine (50 mL), dried (MgSO₄), and purified by column chromatography eluted with 0 to 10% MeOH in CH₂Cl₂ (0.2% of Et₃N) to give the product. LCMS (ES, m/z): 1137.5 [2M−H]⁻. ¹H-NMR (300 MHz, DMSO-d₆): δ 8.15 (d, J=7.9 Hz, 1H), 7.64 (s, 1H), 7.43-7.17 (m, 10H), 6.92-6.81 (m, 4H), 6.09 (d, J=3.2 Hz, 1H), 5.63 (d, J=5.1 Hz, 1H), 5.50 (d, J=7.8 Hz, 1H), 5.20 (d, J=6.2 Hz, 1H), 4.39-4.17 (m, 2H), 4.06 (dt, J=6.8, 3.5 Hz, 1H), 3.72 (s, 6H), 3.38-3.23 (m, 2H).

Step 2: 8-((2R,3R,4S,5R)—S-((bis(4-methoxyphenyl)(phenyl)methoxy)methyl)-4-((tert-butyldimethylsilyl)oxy)-3-hydroxytetrahydrofuran-2-yl)imidazo[1,2-a]pyrimidin-5(8H)-one

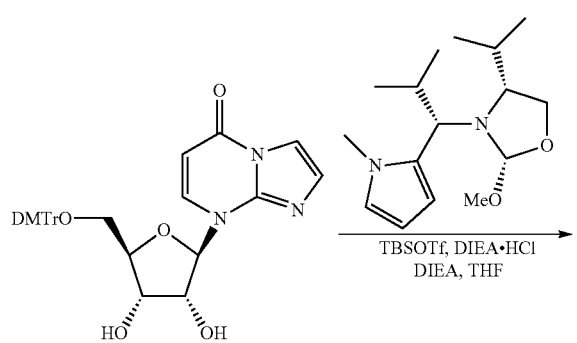

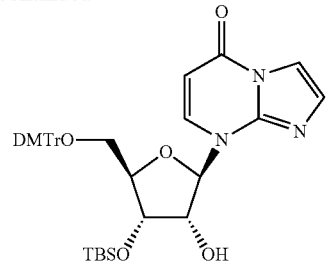

To a solution of 8-((2R,3R,4S,5R)—S-((bis(4-methoxyphenyl)(phenyl)methoxy) methyl)-3,4-dihydroxytetrahydrofuran-2-yl)imidazo[1,2-a]pyrimidin-5(8H)-one (5.0 g, 8.8 mmol), (2S,4R)-4-isopropyl-2-methoxy-3-((S)-2-methyl-1-(1-methyl-1H-imidazol-2-yl)propyl) oxazolidine (3.71 g, 13.2 mmol) and DIEA HCl (0.044 g, 0.263 mmol) in THF (90 mL) at 0° C. under Ar was added DIEA (3.40 g, 26.3 mmol) and TBSOTf (2.55 g, 9.66 mmol). The resulting mixture was stirred at RT for 1.5 h. Then, it was concentrated, and the residue was partitioned between EtOAc (200 mL) and H₂O (100 mL). The aq layer was extracted with EtOAc (2×200 mL), and the combined organic phase was dried (Na₂SO₄) and concentrated. The crude was purified by silica gel chromatography eluted with 0-40% EtOAc in Hex to give the product. LCMS (ES, m/z): 682.1 [M−H]⁻. ¹H-NMR (400 MHz, DMSO-d₆): δ 8.25 (d, J=7.9 Hz, 1H), 7.67 (t, J=1.4 Hz, 1H), 7.44-7.36 (m, 2H), 7.36-7.21 (m, 8H), 6.90 (dt, J=9.1, 1.2 Hz, 4H), 6.09 (d, J=3.7 Hz, 1H), 5.58 (dd, J=7.8, 1.0 Hz, 1H), 5.50 (d, J=5.9 Hz, 1H), 4.45 (q, J=4.9 Hz, 1H), 4.34 (t, J=5.4 Hz, 1H), 4.07 (dt, J=5.9, 4.1 Hz, 1H), 3.75 (s, 6H), 3.47 (dd, J=10.9, 3.5 Hz, 1H), 3.25 (dd, J=10.9, 4.3 Hz, 1H), 0.80 (s, 9H), 0.05 (s, 3H), −0.00 (s, 3H).

a. Step 3: 8-{5-O-[bis(4-methoxyphenyl)(phenyl)methyl]-3-O-[tert-butyl(dimethyl)silyl]-2-O-[hydroxy(oxido)-λ⁵-phosphanyl]-β-D-ribofuranosyl}imidazo[1,2-a]pyrimidin-5(8H)-one

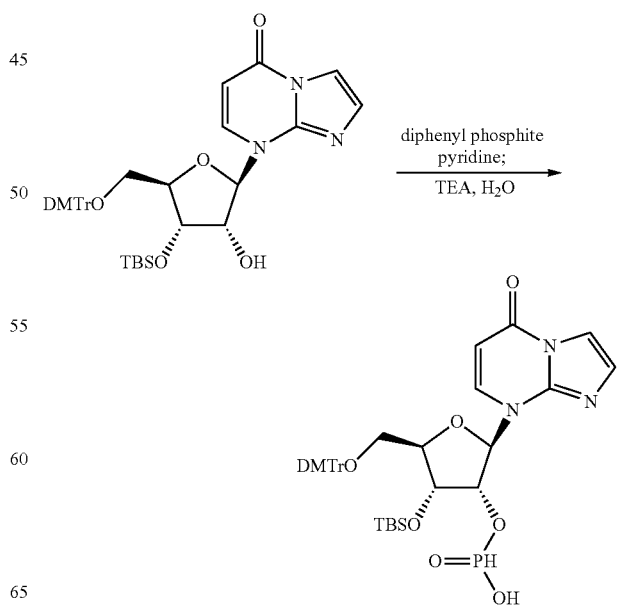

A solution of 8-((2R,3R,4S,5R)—S-((bis(4-methoxyphenyl)(phenyl)methoxy) methyl)-4-((tert-butyldimethylsilyl)oxy)-3-hydroxytetrahydrofuran-2-yl)imidazo[1,2-a]pyrimidin-5(8H)-one (1.0 g, 1.46 mmol) in Py (10 mL) was concentrated in vacuo. To the residue was added Py (9.3 mL) followed by dropwise addition of diphenyl phosphite (0.84 mL, 4.4 mmol). The mixture was left to stir for 5 h, treated with TEA (0.61 mL, 4.4 mmol) and H$_2$O (0.61 mL, 34 mmol), and left to stir for 30 min. The mixture was concentrated, and the residue was partitioned between DCM and 5% NaHCO$_3$ solution. The organic layer was separated, washed with 5% NaHCO$_3$ solution (2×), dried over Na$_2$SO$_4$, and purified by silica gel column chromatography eluted with 0-18% of MeOH in DCM with 0.5% TEA to afford the product as the triethylammonium salt. LCMS (ES, m/z): 746 [M−H]$^-$. $^1$H-NMR (600 MHz, DMSO-d$_6$): δ 9.94 (s, 1H), 8.21 (d, J=7.8 Hz, 1H), 7.66 (s, 1H), 7.4-6.78 (m, 15H), 6.19 (s, 1H), 5.69 (d, J=7.8 Hz, 1H), 5.07 (brs, 1H), 4.54 (s, 1H), 3.98 (m, 1H), 3.72 (s, 6H), 3.38 (m, 1H), 3.15 (m, 1H), 0.79 (s, 9H), 0.07 (s, 3H), 0.02 (s, 3H).

Step 4: (2R,3R,4R,5R)—S-((((((2R,3R,4R,5R)—S-(6-benzamido-9H-purin-9-yl)-4-((tert-butyldimethylsilyl)oxy)-2-(hydroxymethyl)tetrahydrofuran-3-yl)oxy)(2-cyanoethoxy) phosphorothioyl)oxy)methyl)-4-((tert-butyldimethylsilyl)oxy)-2-(5-oxoimidazo[1,2-a]pyrimidin-8(5H)-yl)tetrahydrofuran-3-yl hydrogen phosphonate

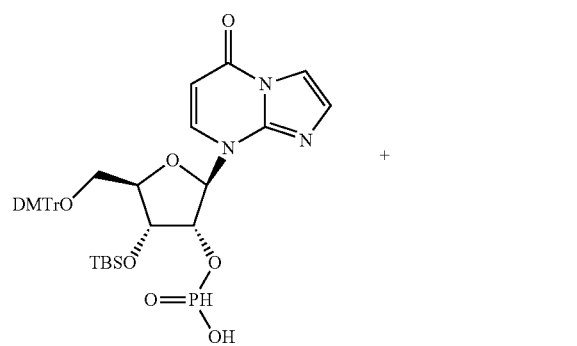

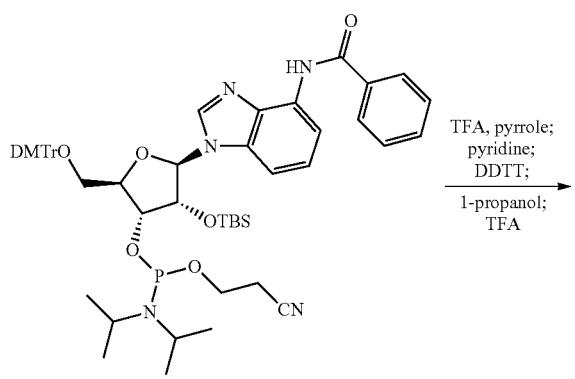

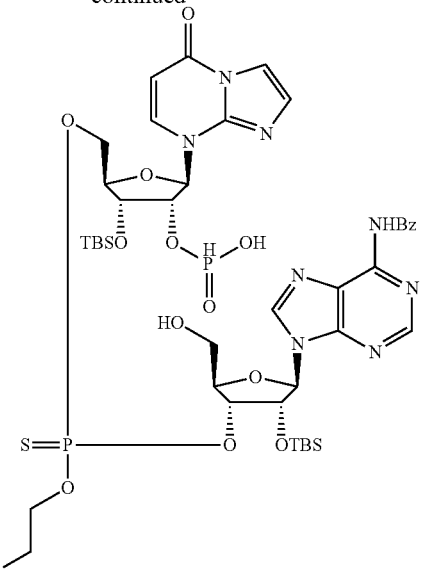

A solution of (2R,3R,4R,5R)—S-((bis(4-methoxyphenyl)(phenyl)methoxy)methyl)-4-((tert-butyldimethylsilyl)oxy)-2-(5-oxoimidazo[1,2-a]pyrimidin-8(5H)-yl)tetrahydrofuran-3-yl hydrogen phosphonate (0.64 g, 0.67 mmol) in MeCN (4.6 mL) was concentrated in vacuo. Addition of MeCN (4.6 mL) followed by concentration was repeated twice. The residue was taken up in MeCN (4.6 mL), cooled to 0° C., and treated with pyrrole (0.14 mL, 2.02 mmol) and TFA (0.16 mL, 2.02 mmol) over 1 min. The reaction mixture was allowed to warm to RT (1.5 h) and left to stir at RT for 0.5 h. The mixture was cooled to 0° C. and treated with Py (0.22 mL, 2.7 mmol).

A solution of (2R,3R,4R,5R)—S-(6-benzamido-9H-purin-9-yl)-2-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (0.886 g, 0.896 mmol) in ACN (4.6 mL) in a separate flask was concentrated in vacuo. Addition of MeCN (4.6 mL) followed by concentration was repeated twice. The residue was taken up in MeCN (1.6 mL) and transferred to the H-phosphonate solution over 1 min at 0° C. The mixture was left to stir at 0° C. for 20 min, treated with DDTT (0.166 g, 0.809 mmol), and left to stir at 0° C. for 20 min. The mixture was treated with 1-propanol (0.51 mL, 6.7 mmol), warmed to RT, and left to stir for 10 min. TFA (0.519 mL, 6.74 mmol) was added to the reaction mixture; the mixture was left to stir for 1 h and treated with pyridine (0.60 mL, 7.4 mmol). The mixture was concentrated to half the volume. The residue was added into rapidly stirring isopropyl acetate (46 mL). The precipitate was filtered and dried under vacuum overnight to afford the crude products. LCMS (ES, m/z): 1060 [M−H]$^-$.

Step 5: N-{9-[(5R,7R,8R,12aR,14R,15R,15aR,16R)-15,16-bis{[tert-butyl (dimethyl)silyl]oxy}-2-(2-cyanoethoxy)-10-oxido-7-(5-oxoimidazo[1,2-a]pyrimidin-8(5H)-yl)-10-sulfanyl-2-sulfidooctahydro-12H-5,8-methanofuro[3,2-l][1,3,6,9,11,2,10]pentaoxadiphosphacyclotetradecin-14-yl]-9H-purin-6-yl}benzamide

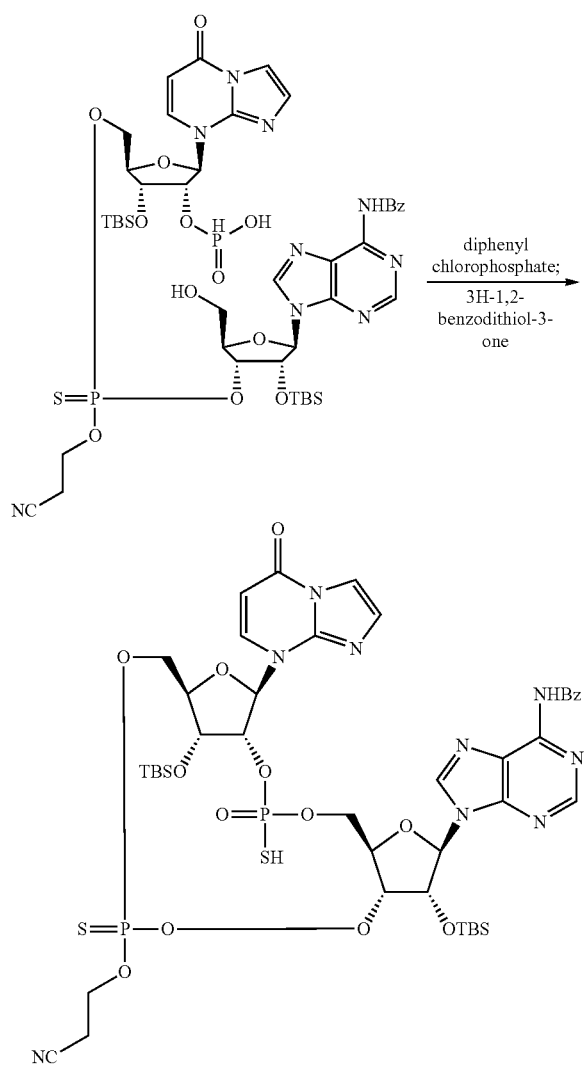

A solution of the crude (2R,3R,4R,5R)—S-(((((2R,3R,4R,5R)—S-(6-benzamido-9H-purin-9-yl)-4-((tert-butyldimethylsilyl)oxy)-2-(hydroxymethyl)tetrahydrofuran-3-yl)oxy)(2-cyanoethoxy)phosphorothioyl)oxy)methyl)-4-((tert-butyldimethylsilyl)oxy)-2-(5-oxoimidazo[1,2-a]pyrimidin-8(5H)-yl)tetrahydrofuran-3-yl hydrogen phosphonate in Py (4 mL) was concentrated in vacuo. Addition of Py (4 mL) followed by concentration was repeated once. The residue was taken up in Py (3.3 mL).

Into a separate flask were added MeCN (32 mL), Py (2.0 mL), and diphenyl chlorophosphate (0.699 mL, 3.37 mmol). The solution was cooled to −20° C., and the solution of the hydrogen phosphonate in Py was added dropwise. The residue was rinsed with Py (0.6 mL) and added to the reaction mixture. The mixture was left to stir at −23° C. to −20° C. for 20 min. 3H-1,2-benzodithiol-3-one (0.136 g, 0.809 mmol) and H$_2$O (0.243 mL, 13.5 mmol) were added, and the cooling bath was removed. After the mixture was warmed to RT, it was concentrated and purified by silica gel column chromatography eluted with 100% EtOAc, then 5-20% MeOH in DCM to give the products. LCMS (ES, m/z): 1074 [M−H]$^-$.

Step 6: 8-[(5R,7R,8R,12aR,14R,15R,15aR,16R)-14-(6-amino-9H-purin-9-yl)-15,16-bis{[tert-butyl(dimethyl)silyl]oxy}-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one

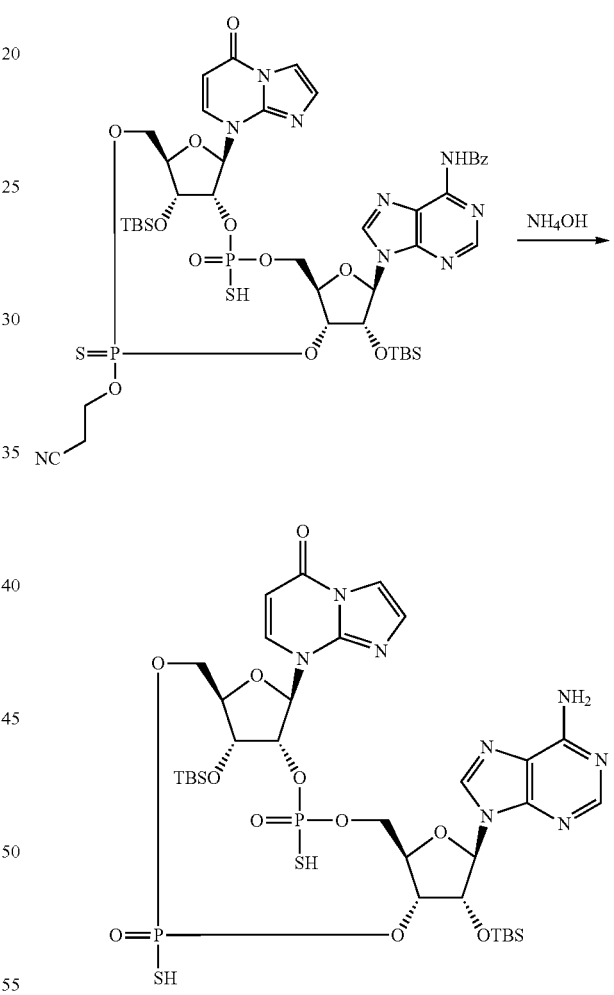

To a stirred solution of N-{9-[(5R,7R,8R,12aR,14R,15R,15aR,16R)-15,16-bis {[tert-butyl(dimethyl)silyl]oxy}-2-(2-cyanoethoxy)-10-oxido-7-(5-oxoimidazo[1,2-a]pyrimidin-8(5H)-yl)-10-sulfanyl-2-sulfidooctahydro-12H-5,8-methanofuro[3,2-l][1,3,6,9,11,2,10]pentaoxadiphosphacyclotetradecin-14-yl]-9H-purin-6-yl}benzamide (0.773 g, 0.718 mmol) in Py (8 mL) were added H$_2$O (2 mL) and NH$_4$OH (28%, 8 mL). The mixture was left to stir for 5 h, concentrated, and lyophilized to give the crude products. LCMS (ES, m/z): 917 [M−H]$^-$.

Step 7: 8-[(2R,5R,7R,8R,10R,12aR,14R,15R,15aS, 16R)-14-(6-amino-9H-purin-9-yl)-15,16-dihydroxy-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one (Diastereomer 1) and 8-[(2S,5R,7R,8R,10R,12aR,14R,15R,15aS,16R)-14-(6-amino-9H-purin-9-yl)-15,16-dihydroxy-2,10-dioxido-2,10-disulfanyloctahydro-12H-5,8-methano-furo[3,2-l][1,3,6,9,11,2,10]pentaoxadiphosphacyclotetradecin-7-yl]imidazo[1,2-a]pyrimidin-5(8H)-one (Diastereomer 2)

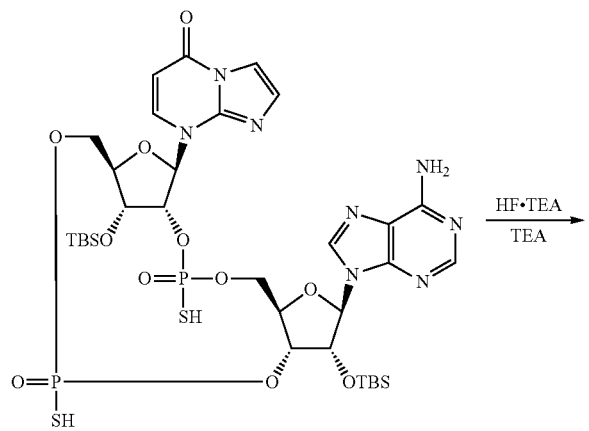

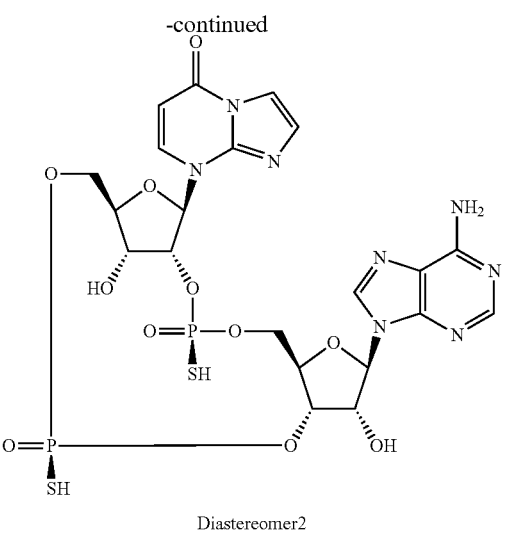

Diastereomer2

To a stirred solution of the crude 8-[(5R,7R,8R,12aR,14R,15R,15aR,16R)-14-(6-amino-9H-purin-9-yl)-15,16-bis{[tert-butyl(dimethyl)silyl]oxy}-2,10-dioxido-2,10-disulfanyloctahydro-12H-5,8-methanofuro[3,2-l][1,3,6,9,11,2,10]pentaoxadiphosphacyclo-tetradecin-7-yl]imidazo[1,2-a]pyrimidin-5(8H)-one (0.660 g, 0.718 mmol) in Py (1.5 mL) were added TEA (2 mL, 14.4 mmol) and HF.TEA (0.1 mL, 0.82 mmol). The mixture was heated to 50° C. for 6 h, cooled to RT, diluted with $H_2O$, lyophilized, and purified by reverse phase HPLC (eluted MeCN/$H_2O$ gradient with 100 mM TEAA modifier, linear gradient) to afford two diastereomers of the title compounds.

Example 1 (Diastereomer 1) (fast eluted): LCMS (ES, m/z): 689 [M–H]$^-$. $^1$H-NMR (600 MHz, $D_2O$): δ 8.48 (d, J=7.9 Hz, 1H), 8.26 (s, 1H), 8.18 (s, 1H), 7.67 (s, 1H), 7.28 (s, 1H), 6.50 (d, J=8.2 Hz, 1H), 6.12 (s, 1H), 5.41 (d, J=7.9 Hz, 1H), 5.09-5.06 (m, 2H), 5.00 (d, J=3.6 Hz, 1H), 4.76 (m, 1H), 4.56-4.46 (m, 3H), 4.32-4.20 (m, 3H).

Example 2 (Diastereomer 2) (slow eluted): LCMS (ES, m/z): 689 [M–H]$^-$. $^1$H-NMR (600 MHz, $D_2O$): δ 8.30 (d, J=7.9 Hz, 1H), 8.26 (s, 1H), 8.21 (s, 1H), 7.66 (s, 1H), 7.27 (s, 1H), 6.53 (d, J=8.2 Hz, 1H), 6.13 (s, 1H), 5.56 (d, J=7.8 Hz, 1H), 5.09 (td, J=8.7, 4.0 Hz, 1H), 4.93-4.89 (m, 2H), 4.80 (m, 1H), 4.56-4.53 (m, 2H), 4.42-4.37 (m, 2H), 4.29 (m, 1H), 4.16 (dd, J=11.9, 5.0 Hz, 1H).

Examples 3 through 9, as shown in Table 1 below, were prepared according to procedures analogous to those outlined in Examples 1 and 2 above using appropriate monomers, described as Preparations or as obtained from commercial sources, in the coupling step.

TABLE 1

| Ex. | Structure | Name | Mass [M + H]+ |
|---|---|---|---|
| 3 | 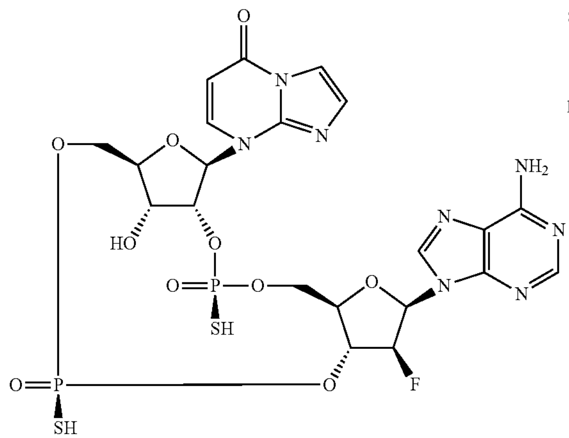 [SMILES: Nc1ncnc2c1ncn2[C@@H]1O[C@@H]2CO[P@@](=O)(S)O[C@@H]3[C@H](O)[C@@H](CO[P@](=O)(S)O[C@H]2[C@@H]1F)O[C@H]3n1ccc(=O)n2ccnc12] | 8-[(2S,5R,7R,8R,10R,12aR,14R,15S,15aR,16R)-14-(6-amino-9H-purin-9-yl)-15-fluoro-16-hydroxy-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one | 693 |
| 4 | 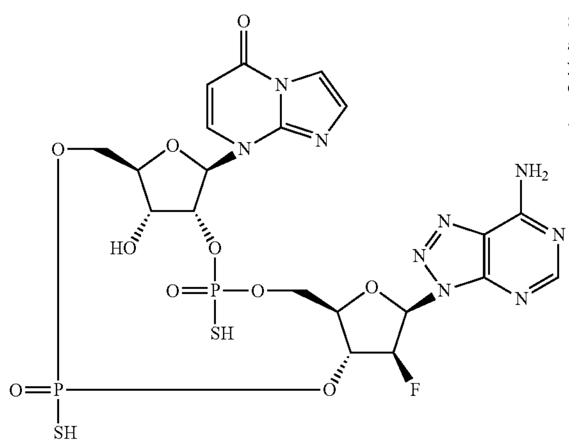 [SMILES: Nc1ncnc2c1nnn2[C@@H]1O[C@@H]2COP(=O)(S)O[C@@H]3[C@H](O)[C@@H](COP(=O)(S)O[C@H]2[C@@H]1F)O[C@H]3n1ccc(=O)n2ccnc12] | 8-[(5R,7R,8R,12aR,14R,15S,15aR,16R)-14-7-amino-3H-[1,2,3]triazolo[4,5-d]pyrimidin-3-yl)-15-fluoro-16-hydroxy-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one | 694 |
| 5 | 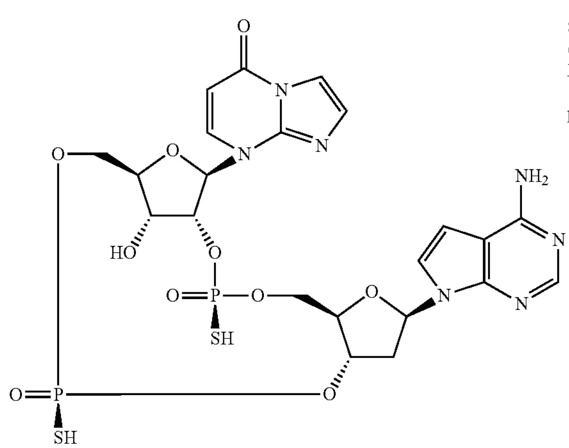 [SMILES: Nc1ncnc2c1ccn2[C@H]1C[C@@H]2O[P@@](=O)(S)OC[C@H]3O[C@@H](n4ccc(=O)n5ccnc45)[C@H](O[P@](=O)(S)OC[C@H]2O1)[C@@H]3O] | 8-[(2S,5R,7R,8R,10R,12aR,14R,15aS,16R)-14-(4-amino-7H-pyrrolo[2,3-d]pyrimidin-7-yl)-16-hydroxy-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one | 674 |

TABLE 1-continued

| Ex. | Structure | Name | Mass [M + H]+ |
|---|---|---|---|
| 6 | 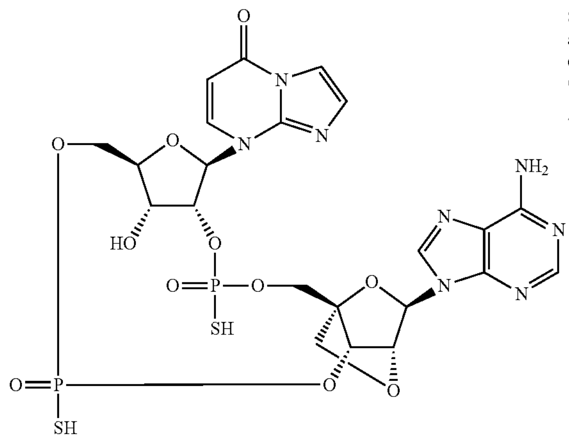 [SMILES: Nc1ncnc2c1ncn2[C@@H]1O[C@@]23CO[C@@H]1[C@@H]2OP(=O)(S)OC[C@H]1O[C@@H](n2ccc(=O)n4ccnc24)[C@H](OP(=O)(S)OC3)[C@@H]1O] | 8-[(5R,7R,8R,12aR,14R,15R,15aS,18R)-14-(6-amino-9H-purin-9-yl)-18-hydroxy-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]imidazo[1,2-a]pyrimidin-5(8H)-one | 703 |
| 7 | 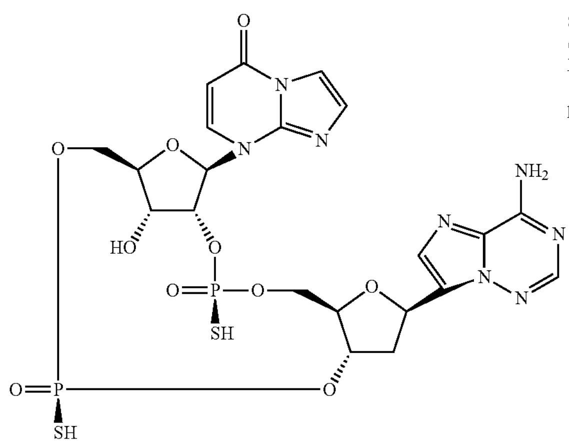 [SMILES: Nc1ncnn2c([C@H]3C[C@@H]4O[P@@](=O)(S)OC[C@H]5O[C@@H](n6ccc(=O)n7ccnc67)[C@H](O[P@](=O)(S)OC[C@H]4O3)[C@@H]5O)cnc12] | 8-[(2S,5R,7R,8R,10R,12aR,14R,15aS,16R)-14-(4-aminoimidazo[2,1-f][1,2,4]triazin-7-yl)-16-hydroxy-2,10-dioxido-2,10-disulfanyl-octahydro-12H-5,8-methanofuro[3,2-l][1,3,6,9,11,2,10]pentaoxadiphosphacyclotetradecin-7-yl]imidazo[1,2-a]pyrimidin-5(8H)-one | 675 |
| 8 | 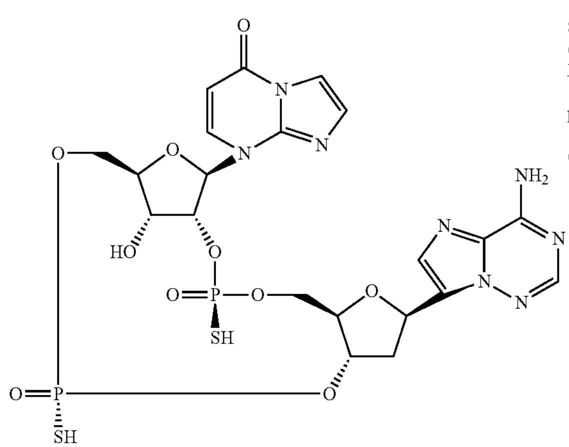 [SMILES: Nc1ncnn2c([C@H]3C[C@@H]4O[P@](=O)(S)OC[C@H]5O[C@@H](n6ccc(=O)n7ccnc67)[C@H](O[P@](=O)(S)OC[C@H]4O3)[C@@H]5O)cnc12] | 8-[(2R,5R,7R,8R,10R,12aR,14R,15aS,16R)-14-(4-aminoimidazo[2,1-f][1,2,4]triazin-7-yl)-16-hydroxy-2,10-dioxido-2,10-disulfanyl-octahydro-12H-5,8-methanofuro[3,2-l][1,3,6,9,11,2,10]pentaoxadiphosphacyclotetradecin-7-yl]imidazo[1,2-a]pyrimidin-5(8H)-one (Diastereomer 2) | 675 |

TABLE 1-continued

| Ex. | Structure | Name | Mass [M + H]+ |
|---|---|---|---|
| 9 | 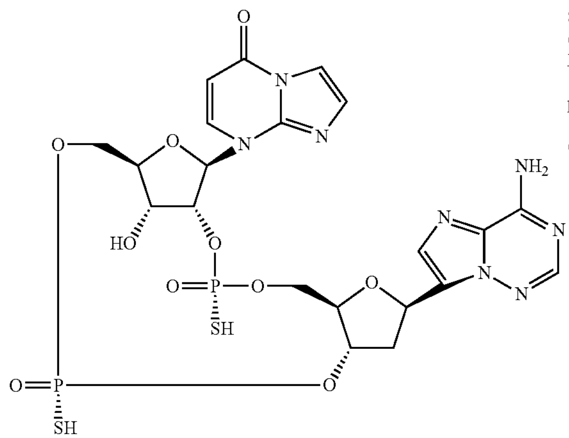 [SMILES: Nc1ncnn2c([C@H]3C[C@@H]4O[P@](=O)(S)OC[C@H]5O[C@@H](n6ccc(=O)n7ccnc67)[C@H](O[P@@](=O)(S)OC[C@H]4O3)[C@@H]5O)cnc12] | 8-[(2R,5R,7R,8R,10S,12aR,14R,15aS,16R)-14-(4-aminoimidazo[2,1-f][1,2,4]triazin-7-yl)-16-hydroxy-2,10-dioxido-2,10-disulfanyl-octahydro-12H-5,8-methanofuro[3,2-l][1,3,6,9,11,2,10]pentaoxadiphosphacyclotetradecin-7-yl]imidazo[1,2-a]pyrimidin-5(8H)-one (Diastereomer 3) | 675 |
| 10 | 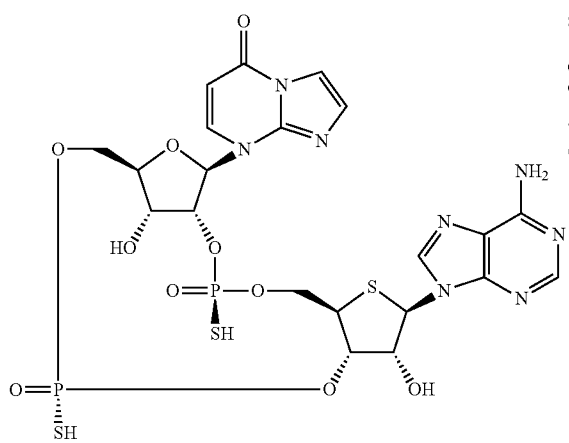 [SMILES: Nc1ncnc2c1ncn2[C@@H]1S[C@@H]2CO[P@@](=O)(S)O[C@@H]3[C@H](O)[C@@H](CO[P@@](=O)(S)O[C@H]2[C@H]1O)O[C@H]3n1ccc(=O)n2ccnc12] | 8-[(2R,5R,7R,8R,10R,12aR,14R,15R,15aS,16R)-14-(6-amino-9H-purin-9-yl)-15,16-dihydroxy-2,10-dioxido-2,10-disulfanyl-octahydro-12H-5,8-methanothieno[3,2-l][1,3,6,9,11,2,10]pentaoxadiphosphacyclotetradecin-7-yl]imidazo[1,2-a]pyrimidin-5(8H)-one (Diastereomer 1) | 707 |
| 11 | 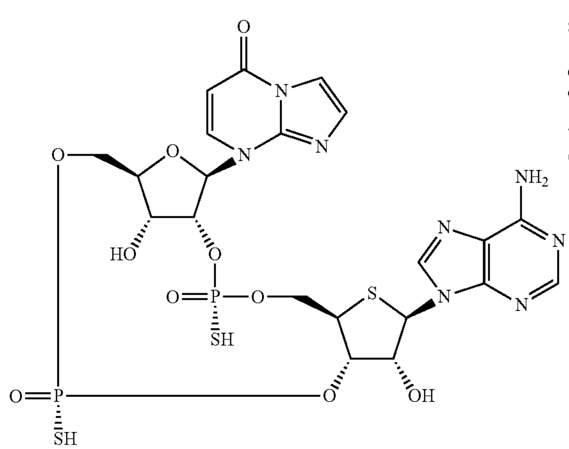 [SMILES: Nc1ncnc2c1ncn2[C@@H]1S[C@@H]2CO[P@](=O)(S)O[C@@H]3[C@H](O)[C@@H](CO[P@@](=O)(S)O[C@H]2[C@H]1O)O[C@H]3n1ccc(=O)n2ccnc12] | 8-[(2R,5R,7R,8R,10S,12aR,14R,15R,15aS,16R)-14-(6-amino-9H-purin-9-yl)-15,16-dihydroxy-2,10-dioxido-2,10-disulfanyl-octahydro-12H-5,8-methanothieno[3,2-l][1,3,6,9,11,2,10]pentaoxadiphosphacyclotetradecin-7-yl]imidazo[1,2-a]pyrimidin-5(8H)-one (Diastereomer 2) | 707 |

TABLE 1-continued

| Ex. | Structure | Name | Mass [M + H]+ |
|---|---|---|---|
| 12 | 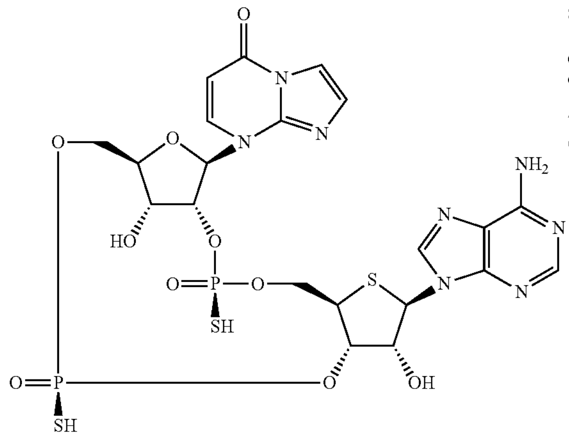 [SMILES: Nc1ncnc2c1ncn2[C@@H]1S[C@@H]2CO[P@@](=O)(S)O[C@@H]3[C@H](O)[C@@H](CO[P@](=O)(S)O[C@H]2[C@H]1O)O[C@H]3n1ccc(=O)n2ccnc12] | 8-[(2S,5R,7R,8R,10R,12aR,14R,15R,15aS,16R)-14-(6-amino-9H-purin-9-yl)-15,16-dihydroxy-2,10-dioxido-2,10-disulfanyl-octahydro-12H-5,8-methanothieno[3,2-l][1,3,6,9,11,2,10]pentaoxadiphosphacyclotetradecin-7-yl]imidazo[1,2-a]pyrimidin-5(8H)-one (Diastereomer 3) | 707 |
| 13 | 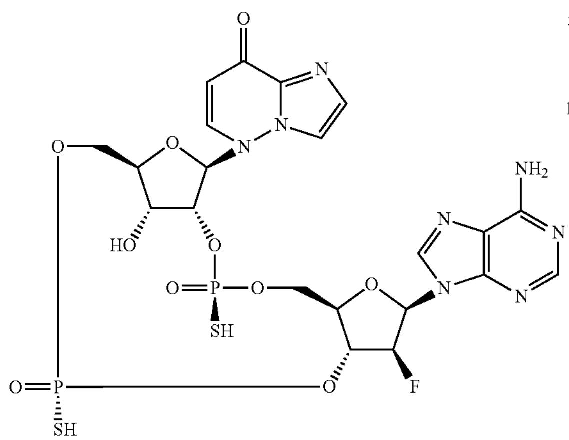 [SMILES: Nc1ncnc2c1ncn2[C@@H]1O[C@@H]2CO[P@@](=O)(S)O[C@@H]3[C@H](O)[C@@H](CO[P@@](=O)(S)O[C@H]2[C@@H]1F)O[C@H]3n1ccc(=O)c2nccn21] | 5-[(2R,5R,7R,8R,10R,12aR,14R,15S,15aR,16R)-14-(6-amino-9H-purin-9-yl)-15-fluoro-16-hydroxy-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-b]pyridazin-8(5H)-one | 693 |
| 14 | 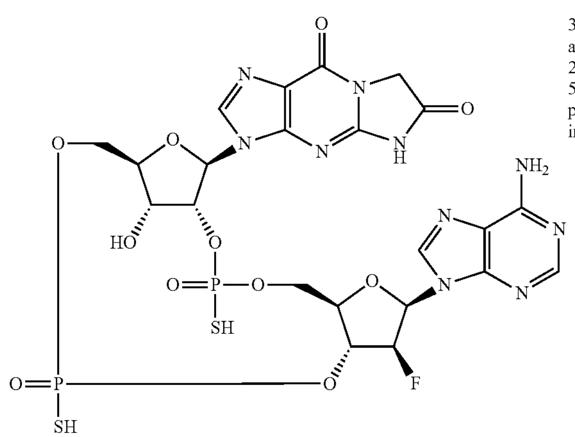 | 3-[(5R,7R,8R,12aR,14R,15S,15aR,16R)-14-(6-amino-9H-purin-9-yl)-15-fluoro-16-hydroxy-2,10-dioxido-2,10-disulfanyloctahydro-12H-5,8-methanofuro[3,2-l][1,3,6,9,11,2,10]pentaoxadiphosphacyclotetradecin-7-yl]-3H-imidazo[1,2-a]purine-6,9(5H,7H)-dione | 749 |

TABLE 1-continued

| Ex. | Structure | Name | Mass [M + H]+ |
|---|---|---|---|
| 15 | 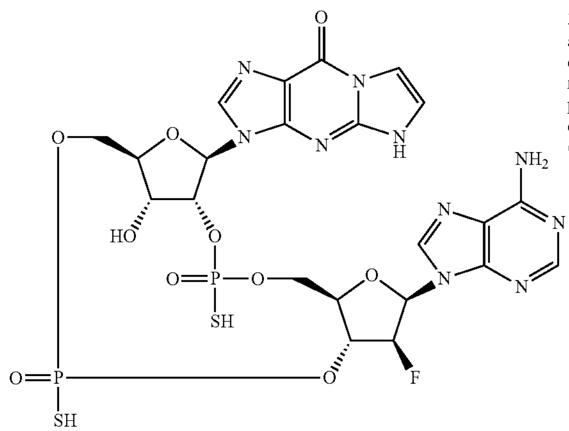 | 3-[(5R,7R,8R,12aR,14R,15S,15aR,16R)-14-(6-amino-9H-purin-9-yl)-15-fluoro-16-hydroxy-2,10-dioxido-2,10-disulfanyloctahydro-12H-5,8-methanofuro[3,2-l][1,3,6,9,11,2,10]pentaoxadiphosphacyclotetradecin-7-yl]-3,5-dihydro-9H-imidazo[1,2-a]purin-9-one (Diastereomer 1) | 733 |
| 16 | 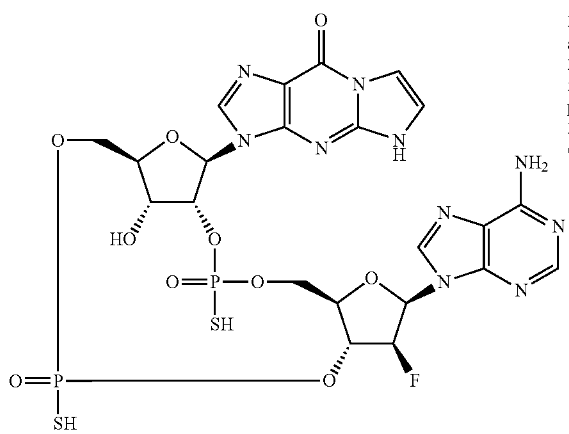 | 3-[(5R,7R,8R,12aR,14R,15S,15aR,16R)-14-(6-amino-9H-purin-9-yl)-15-fluoro-16-hydroxy-2,10-dioxido-2,10-disulfanyloctahydro-12H-5,8-methanofuro[3,2-l][1,3,6,9,11,2,10]pentaoxadiphosphacyclotetradecin-7-yl]-3,5-dihydro-9H-imidazo[1,2-a]purin-9-one (Diastereomer 2) | 733 |
| 17 | 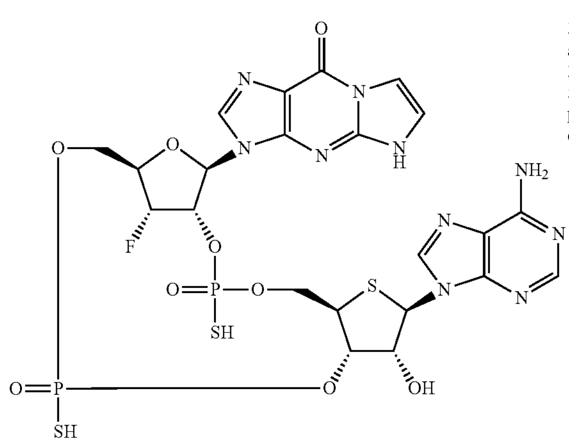 | 3-[(5R,7R,8R,12aR,14R,15S,15aR,16R)-14-(6-amino-9H-purin-9-yl)-16-fluoro-15-hydroxy-2,10-dioxido-2,10-disulfanyloctahydro-12H-5,8-methanothieno[3,2-l][1,3,6,9,11,2,10]pentaoxadiphosphacyclotetradecin-7-yl]-3,5-dihydro-9H-imidazo[1,2-a]purin-9-one | 749 |

Example 18: 8-[(5R,7R,8R,12aR,14R,15aS,16R)-14-(7-amino-3H-[1,2,3]triazolo[4,5-b]pyridin-3-yl)-16-hydroxy-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one

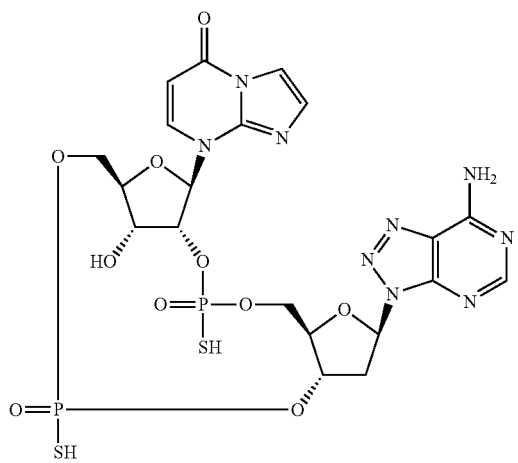 [SMILES: Nc1ncnc2c1nnn2[C@H]1C[C@@H]2OP(=O)(S)OC[C@H]3O[C@@H](n4ccc(=O)n5ccnc45)[C@H](OP(=O)(S)OC[C@H]2O1)[C@@H]3O]

Step 1: (2R,3R,4R,5R)-4-((tert-butyldimethylsilyl)oxy)-S-(hydroxymethyl)-2-(5-oxoimidazo[1,2-a]pyrimidin-8(5H)-yl)tetrahydrofuran-3-yl hydrogen phosphonate

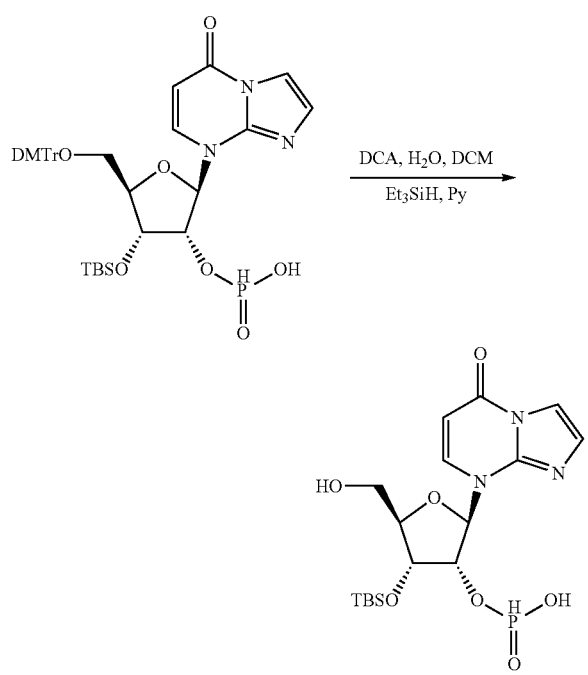

To a solution of (2R,3R,4R,5R)—S-((bis(4-methoxyphenyl)(phenyl)methoxy) methyl)-4-((tert-butyldimethylsilyl)oxy)-2-(5-oxoimidazo[1,2-a]pyrimidin-8(5H)-yl) tetrahydrofuran-3-yl hydrogen phosphonate (0.76 g, 0.9 mmol) in CH$_2$Cl$_2$ (13 mL) at RT was added H$_2$O (0.16 mL), and DCA in CH$_2$Cl$_2$ (6%, 13 mL, 8.1 mmol). The mixture was stirred for 30 min, and then Et$_3$SiH (16 mL) was added. After 40 min, Py (1.5 mL) was added, and it was stirred for 10 min. The solution was concentrated to give the crude product, which was used for the next reaction step without purification. LCMS (ES, m/z): 446.2 [M+H]$^+$.

Step 2: 2-(4-(tert-butyl)phenoxy)-N-(3-((2R,4S,5R)-4-hydroxy-5-(hydroxymethyl)tetrahydrofuran-2-yl)-3H-[1,2,3]triazolo[4,5-b]pyridin-7-yl)acetamide

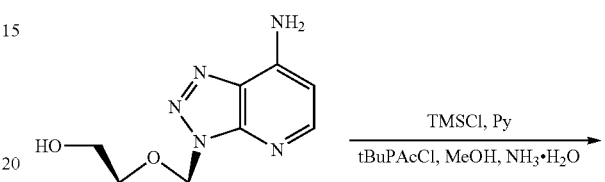

(2R,3S,5R)—S-(7-amino-3H-[1,2,3]triazolo[4,5-b]pyridin-3-yl)-2-(hydroxymethyl) tetrahydrofuran-3-ol (470 mg, 1.87 mmol) was co-evaporated with Py (3×5 mL) and then re-suspended in Py (14 mL). To the mixture under Ar at 0° C. was added TMSCl (1.66 mL, 13.1 mmol), and it was stirred at RT for 2 h. To the resulting mixture at 0° C. was added 2-(4-(tert-butyl)phenoxy) acetyl chloride (0.576 mL, 2.81 mmol) over 1 min. It was stirred at RT for 2 h. Then, H$_2$O (3.5 mL) was added, and it was stirred for 20 min. Then, NH$_4$OH (7 mL) was added, and it was stirred for 1 h. It was concentrated and purified by preparative-TLC eluted with 3% MeOH in CH$_2$Cl$_2$ to give the product. LCMS (ES, m/z): 442.3 [M+H]$^+$. $^1$H-NMR (400 MHz, DMSO-d$_6$): δ 11.37 (s, 1H), 8.63 (d, J=5.4 Hz, 1H), 8.21 (d, J=5.4 Hz, 1H), 7.38-7.29 (m, 2H), 6.96-6.87 (m, 2H), 6.81 (t, J=6.4 Hz, 1H), 5.42 (d, J=4.6 Hz, 1H), 4.99 (s, 2H), 4.83 (t, J=5.8 Hz, 1H), 4.66-4.55 (m, 1H), 3.96-3.92 (m, 1H), 3.60 (dt, J=11.1, 5.4 Hz, 1H), 3.42 (dt, J=11.8, 6.0 Hz, 1H), 3.18-3.10 (m, 1H), 2.51-2.45 (m, 1H), 1.26 (s, 9H).

Step 3: N-(3-((2R,4S,5R)—S-((bis(4-methoxyphenyl)(phenyl)methoxy)methyl)-4-hydroxytetrahydrofuran-2-yl)-3H-[1,2,3]triazolo[4,5-b]pyridin-7-yl)-2-(4-(tert-butyl)phenoxy)acetamide

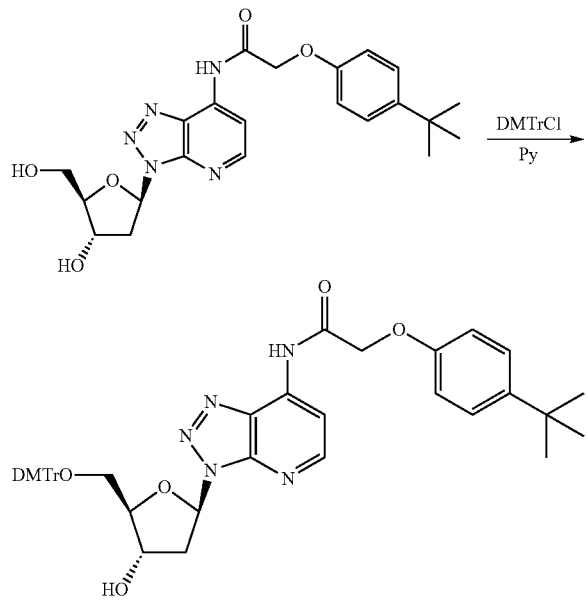

To a solution of 2-(4-(tert-butyl)phenoxy)-N-(3-((2R,4S,5R)-4-hydroxy-5-(hydroxymethyl) tetrahydrofuran-2-yl)-3H-[1,2,3]triazolo[4,5-b]pyridin-7-yl)acetamide (467 mg, 1.06 mmol) in Py (5 mL) at 0° C. under Ar was added 4,4'-(chloro(phenyl)methylene)bis (methoxybenzene) (394 mg, 1.16 mmol), and the mixture was stirred at RT for 2 h. Then, MeOH (3 mL) was added, and the volatile components were removed under reduced pressure. The residue was purified by chromatography on silica gel eluted with 0-2.8% MeOH in $CH_2Cl_2$ to the product. LCMS (ES, m/z): 744.3 $[M+H]^+$. $^1$H-NMR (300 MHz, DMSO-$d_6$): δ 11.31 (s, 1H), 8.57 (d, J=5.4 Hz, 1H), 8.18 (d, J=5.4 Hz, 1H), 7.34-7.25 (m, 2H), 7.20 (dd, J=6.8, 3.0 Hz, 2H), 7.11-7.06 (m, 7H), 6.92-6.78 (m, 3H), 6.73-6.65 (m, 2H), 6.65-6.58 (m, 2H), 5.42 (d, J=4.9 Hz, 1H), 4.94 (s, 2H), 4.72-4.58 (m, 1H), 4.03 (q, J=5.3 Hz, 1H), 3.65 (s, 3H), 3.63 (s, 3H), 3.18-2.93 (m, 3H), 2.56-2.48 (m, 1H), 1.22 (s, 9H).

Step 4: (2R,3S,5R)-2-((bis(4-methoxyphenyl)(phenyl)methoxy)methyl)-S-(7-(2-(4-(tert-butyl)phenoxy)acetamido)-3H-[1,2,3]triazolo[4,5-b]pyridin-3-yl)tetrahydrofuran-3-yl (2-cyanoethyl) diisopropylphosphoramidite

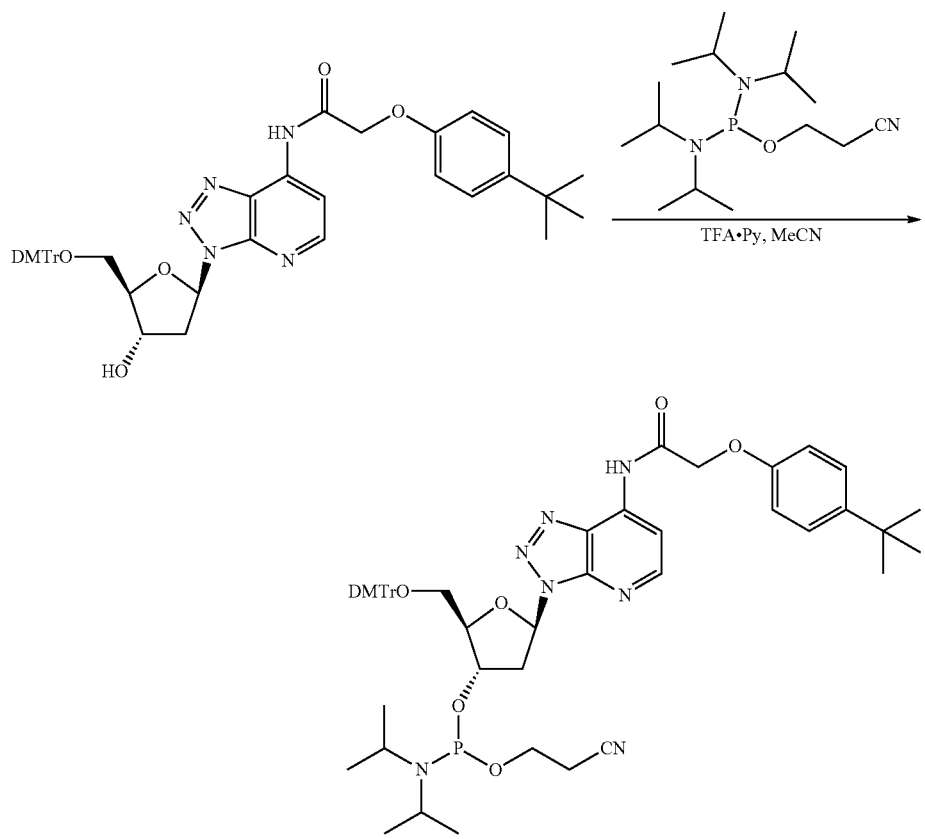

To a solution of 3-((bis(diisopropylamino)phosphino)oxy)propanenitrile (477 mg, 1.58 mol) in MeCN (8 mL) at rt under Ar was added pyridin-1-ium 2,2,2-trifluoroacetate (229 mg, 1.19 mmol) and a solution of dry N-(3-((2R,4S,5R)—S-((bis(4-methoxyphenyl)(phenyl)methoxy) methyl)-4-hydroxytetrahydrofuran-2-yl)-3H-[1,2,3]triazolo[4,5-b]pyridin-7-yl)-2-(4-(tert-butyl)phenoxy)acetamide (589 mg, 0.792 mmol) in MeCN (3.75 mL) over 2 min. After 1 h, the residue was dissolved in EtOAc (60 mL). It was washed with aq NaHCO$_3$ (1%, 2×40 mL), H$_2$O (40 mL), and brine (40 mL), dried (Na$_2$SO$_4$), concentrated and purified by reverse phase (C18) chromatography eluted with 0 to 95% ACN in H$_2$O to give the product. LCMS (ES, m/z): 944.5 [M+H]$^+$. $^1$H-NMR (300 MHz, DMSO-d$_6$): δ 11.35 (s, 1H), 8.58 (dd, 1.4 Hz, 1H), 8.18 (dd, J=5.4, 1.4 Hz, 1H), 7.32-7.24 (m, 2H), 7.18 (dd, 3.0 Hz, 2H), 7.14-7.00 (m, 7H), 6.91-6.80 (m, 3H), 6.72-6.57 (m, 4H), 5.03-4.89 (m, 3H), 4.17 (t, J=4.9 Hz, 1H), 3.79-3.37 (m, 10H), 3.27-3.06 (m, 2H), 2.97 (dd, J=10.4, 6.1 Hz, 1H), 2.78-2.58 (m, 3H), 1.21 (s, 9H), 1.14-1.06 (m, 9H), 0.98 (d, J=6.7 Hz, 3H). $^{31}$P NMR (121 MHz, DMSO-d$_6$): δ 147.79, 147.14.

Step 5: (2R,3R,4R,5R)—S-(((((2R,3S,5R)-2-((bis(4-methoxyphenyl)(phenyl) methoxy)methyl)-S-(7-(2-(4-(tert-butyl)phenoxy)acetamido)-3H-[1,2,3]triazolo[4,5-b]pyridin-3-yl)tetrahydrofuran-3-yl)oxy)(2-cyanoethoxy)phosphanyl)oxy)methyl)-4-((tert-butyldimethylsilyl) oxy)-2-(5-oxoimidazo[1,2-a]pyrimidin-8(5H)-yl)tetrahydrofuran-3-yl hydrogen phosphonate

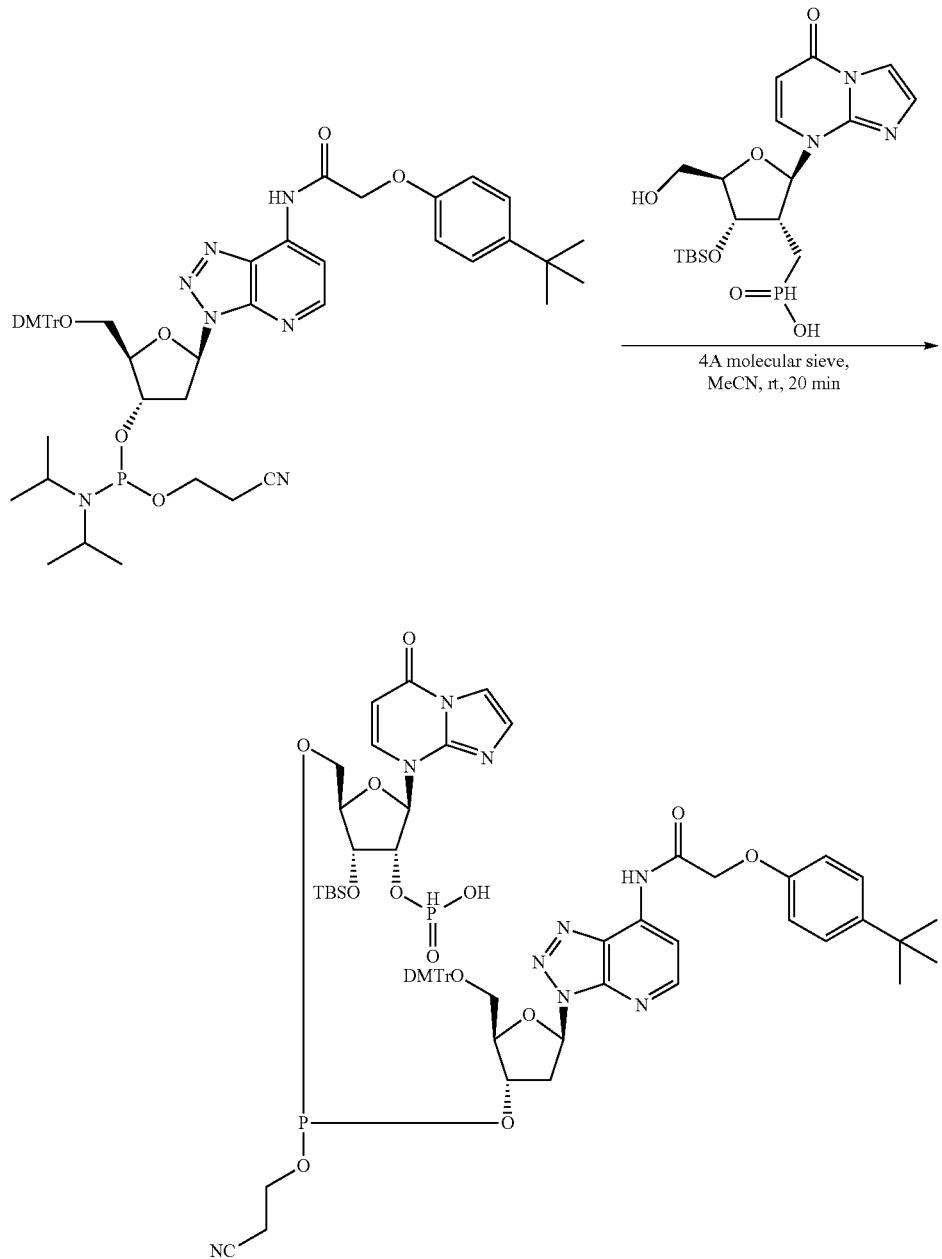

(2R,3R,4R,5R)-4-((tert-butyldimethylsilyl)oxy)-S-(hydroxymethyl)-2-(5-oxoimidazo[1,2a]-pyrimidin-8(5H)-yl) tetrahydrofuran-3-yl phosphonate (~290 mg, 0.56 mmol) was co-evaporated with MeCN (3×3 mL) and then re-dissolved in MeCN (2.5 mL). Activated 4 Å molecular sieve (200 mg) was added to the solution under Ar. (2R,3S,5R)-2-((bis(4-methoxy-phenyl)(phenyl)methoxy)methyl)-5-(7-(2-(4-(tert-butyl)phenoxy)acetamido)-3H[1,2,3]triazolo[4,5-b]pyridin-3-yl)tetrahydrofuran-3-yl(2-cyanoethyl) diisopropylphosphoramidite (480 mg, 0.508 mmol) was also co-evaporated with MeCN (3×3 mL), and then re-dissolved in MeCN (2.5 mL). Activated 4 Å molecular sieve (200 mg) was added to the solution under Ar. After 30 min, it was added to the (2R,3R,4R,5R)-4-((tert-butyldimethylsilyl) oxy)-S-(hydroxymethyl)-2-(5-oxoimidazo[1,2a]-pyrimidin-8(5H)-yl)tetrahydrofuran-3-yl phosphonate solution. The resulting mixture under Ar was stirred at RT for 30 min. The reaction mixture was used for the next reaction step without purification. LCMS (ES, m/z): 1288.6 [M+H]$^+$.

Step 6: (2R,3R,4R,5R)—S-(((((2R,3S,5R)-2-((bis(4-methoxyphenyl)(phenyl)methoxy) methyl)-S-(7-(2-(4-(tert-butyl)phenoxy)acetamido)-3H-[1,2,3] triazolo[4,5-b]pyridin-3-yl) tetrahydrofuran-3-yl) oxy)(2-cyanoethoxy)phosphorothioyl)oxy)methyl)-4-((tert-butyldimethyl-silyl)oxy)-2-(5-oxoimidazo[1,2-a]pyrimidin-8(5H)-yl)tetrahydrofuran-3-yl hydrogen phosphonate

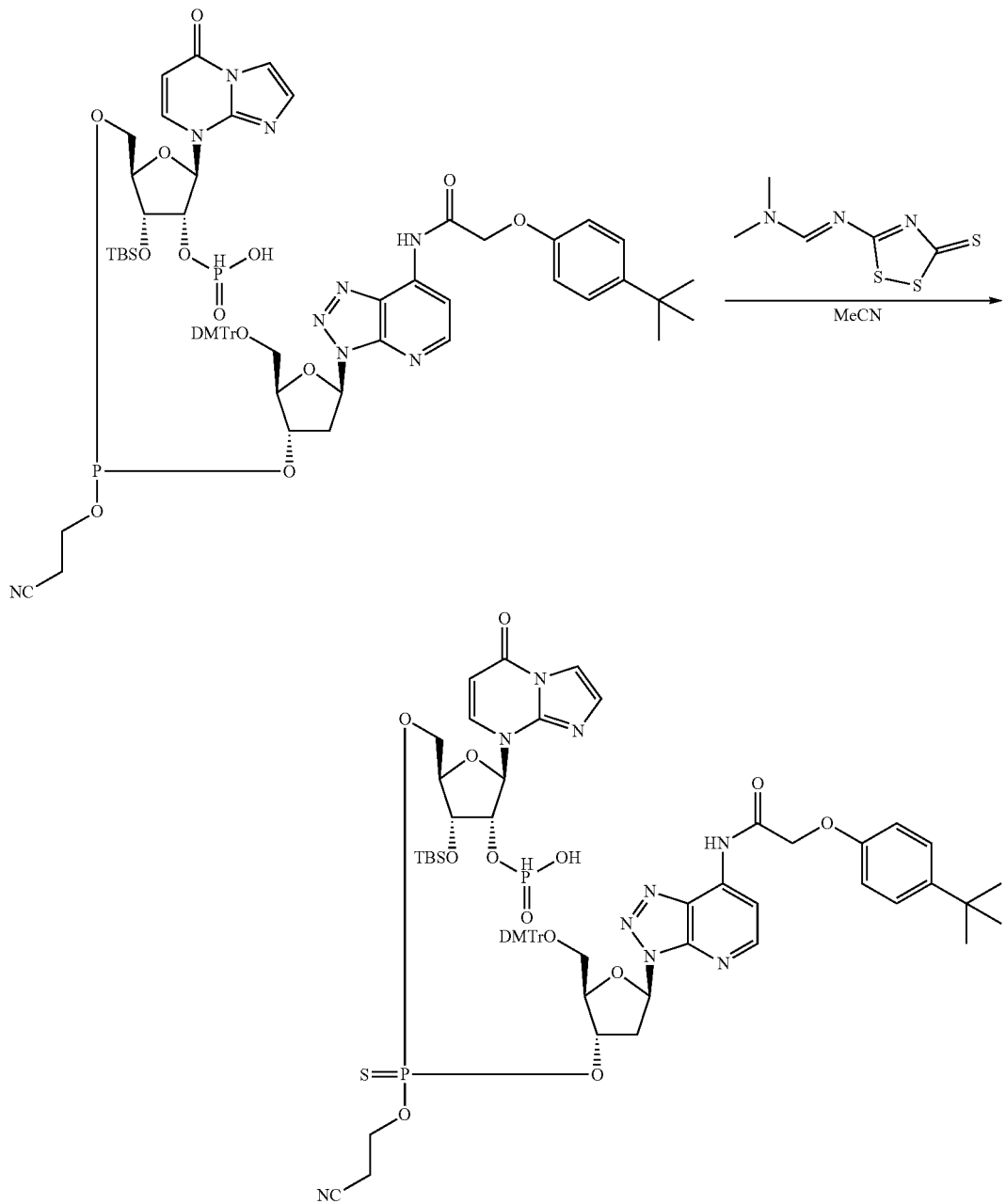

To the reaction mixture from Step 5 at RT was added (E)-N,N-dimethyl-N-(3-thioxo-3H-1,2,4-dithiazol-S-yl)formimidamide (0.115 g, 0.560 mmol), and the mixture was stirred for 1 h. Then, it was filtered, and the filtrate was concentrated to give the crude product, which was used for the next step without purification. LCMS (ES, m/z): 1318.5 [M–H]⁻.

Step 7: (2R,3R,4R,5R)—S-(((((2R,3S,5R)—S-(7-(2-(4-(tert-butyl)phenoxy) acetamido)-3H-[1,2,3]triazolo[4,5-b]pyridin-3-yl)-2-(hydroxymethyl)tetrahydrofuran-3-yl)oxy)(2-cyanoethoxy)phosphorothioyl)oxy)methyl)-4-((tert-butyldimethylsilyl)oxy)-2-(5-oxoimidazo[1,2-a]pyrimidin-8(5H)-yl)tetrahydrofuran-3-yl hydrogen phosphonate

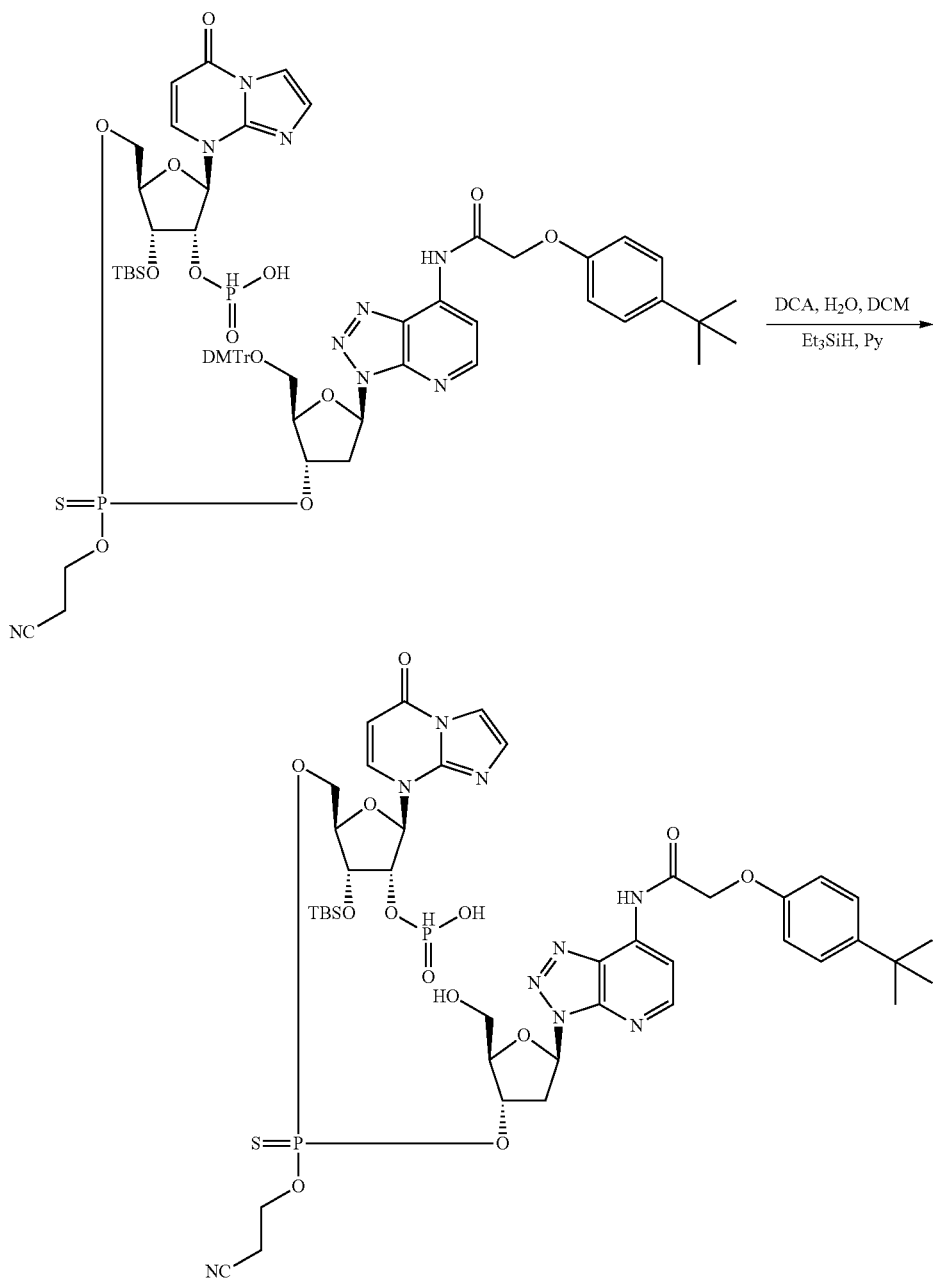

To a solution of the crude from Step 6 in CH$_2$Cl$_2$ (5.6 mL) at RT was added H$_2$O (0.1 mL) and DCA (6%, 7.3 mL, 4.6 mmol) in CH$_2$Cl$_2$. After 15 min, TES (59 mg, 0.51 mmol) was added, and it was stirred for 40 min. Then, Py (0.74 mL, 9.2 mmol) was added. After 5 min, the mixture was concentrated, and the residue was purified by reverse phase (C18) chromatography eluted with 0 to 95% ACN in aq NH$_4$HCO$_3$ (5 mM) to give the product. LCMS (ES, m/z): 1018.3 [M+H]$^+$. $^{31}$P NMR (121 MHz, CD$_3$OD): δ 66.89 (s), 66.81 (s); 2.96 (s), 2.87 (s).

Step 8: N-{3-[(5R,7R,8R,12aR,14R,15aS,16R)-16-{[tert-butyl(dimethyl)silyl]oxy}-2-(2-cyanoethoxy)-10-hydroxy-7-(5-oxoimidazo[1,2-a]pyrimidin-8(5H)-yl)-2-sulfidooctahydro-12H-5,8-methanofuro[3,2-l][1,3,6,9,11,2,10]pentaoxadiphosphacyclotetradecin-14-yl]-3H-[1,2,3]triazolo[4,5-b]pyridin-7-yl}-2-(4-tert-butylphenoxy)acetamide

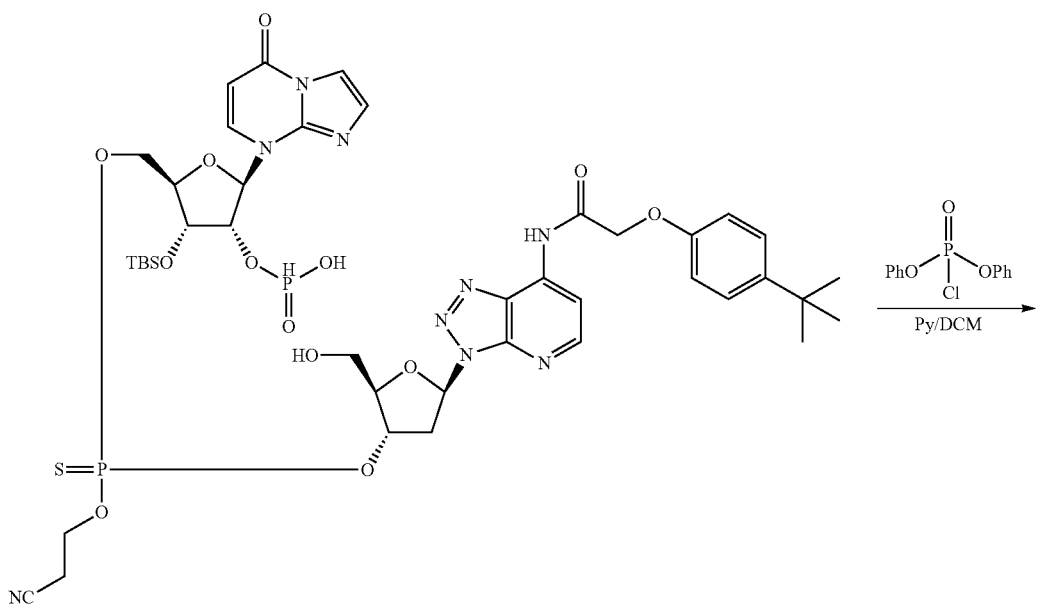

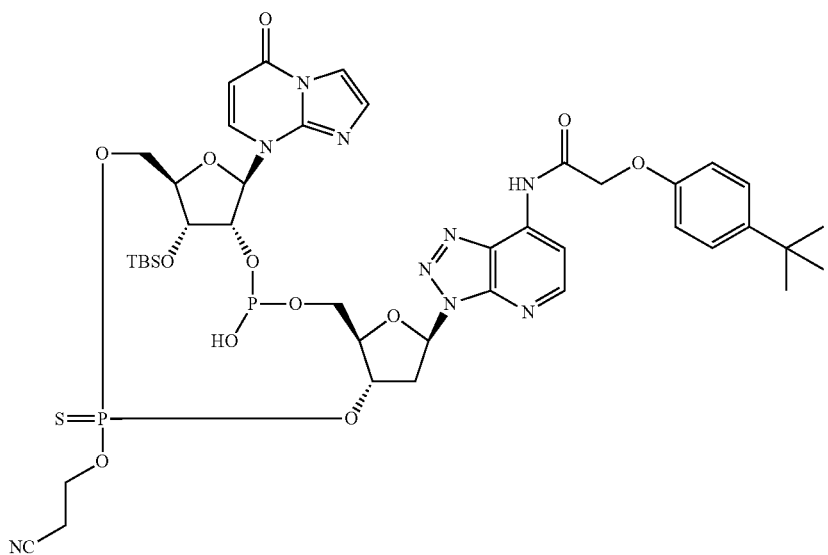

To a solution of (2R,3R,4R,5R)—S-(((((2R,3S,5R)—S-(7-(2-(4-(tert-butyl)phenoxy) acetamido)-3H-[1,2,3]triazolo[4,5-b]pyridin-3-yl)-2-(hydroxymethyl)tetrahydrofuran-3-yl)oxy) (2-cyanoethoxy)phosphorothioyl)oxy)methyl)-4-((tert-butyldimethylsilyl)oxy)-2-(5-oxoimidazo[1,2-a]pyrimidin-8(5H)-yl)tetrahydrofuran-3-yl phosphonate (300 mg, 0.290 mmol) in DCM (29 mL) and Py (29 mL) at −40° C. under Ar was added diphenyl phosphorochloridate (1.2 mL, 5.80 mmol) over 5 min. It was stirred at −40° C. for 20 min. The reaction mixture was used for the next reaction step immediately without purification. LCMS (ES, m/z): 1000.1 [M+H]⁺.

Step 9: N-{3-[(5R,7R,8R,12aR,14R,15aS,16R)-16-{[tert-butyl(dimethyl)silyl]oxy}-2-(2-cyanoethoxy)-10-oxido-7-(5-oxoimidazo[1,2-a]pyrimidin-8(5H)-yl)-10-sulfanyl-2-sulfidooctahydro-12H-5,8-methanofuro[3,2-l][1,3,6,9,11,2,10]pentaoxadiphosphacyclo-tetradecin-14-yl]-3H-[1,2,3]triazolo[4,5-b]pyridin-7-yl}-2-(4-tert-butylphenoxy)acetamide

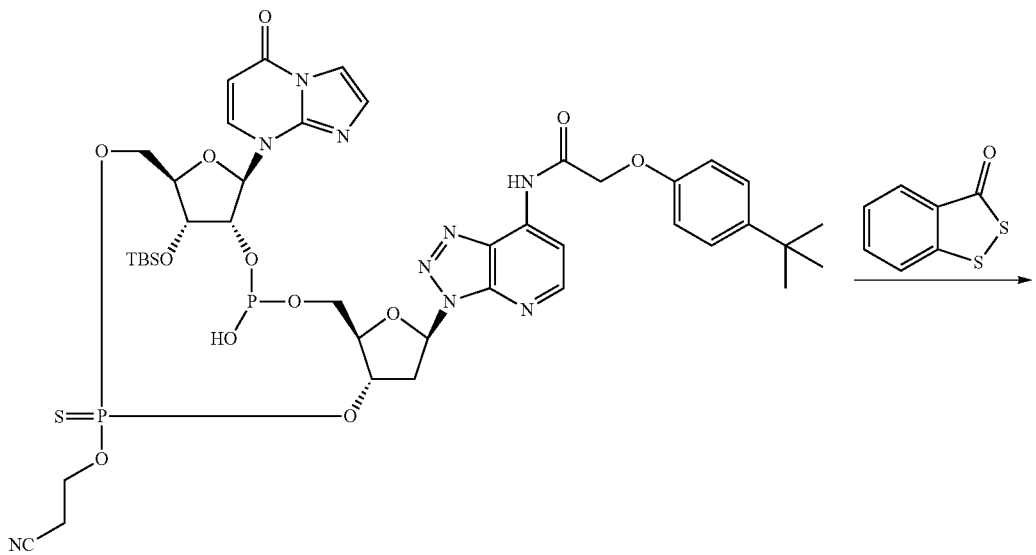

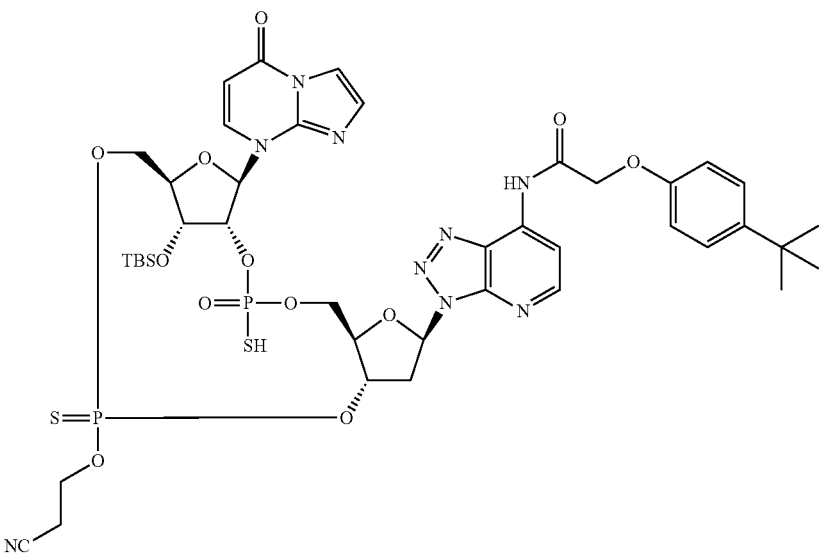

To the reaction mixture from Step 8 at −40° C. was added 3H-benzo[c][1,2]dithiol-3-one (0.073 g, 0.44 mmol) and H₂O (0.3 mL). It was stirred at RT for 40 min, and the mixture was concentrated under reduced pressure. The residue was purified by reverse phase (C18) chromatography eluted with 0 to 95% ACN in aq NH₄HCO₃ (5 mM) to give the product. LCMS (ES, m/z): 1032.3 [M+H]⁺. ¹H-NMR (300 MHz, CD₃OD): δ 8.60-8.57 (m, 1H), 8.45 (d, J=8.0 Hz, 0.5H), 8.29-8.27 (m, 1H), 8.16 (d, J=8.0 Hz, 0.5H), 7.62-7.61 (m, 1H), 7.41-7.29 (m, 2H), 7.27-7.13 (m, 1H), 7.09-6.90 (m, 3H), 6.56 (d, J=8.7 Hz, 1H), 6.04 (dd, J=36.6, 7.9 Hz, 1H), 5.76-5.74 (m, 1H), 5.17-5.13 (m, 1H), 4.82-4.79 (m, 2H), 4.68-4.63 (m, 1H), 4.60-4.11 (m, 5H), 3.97-3.70 (m, 2H), 3.00-2.94 (m, 3H), 1.27 (s, 9H), 0.97-0.96 (m, 9H), 0.28 (d, J=4.1 Hz, 3H), 0.23 (d, J=2.3 Hz, 3H). ³¹P NMR (121 MHz, CD₃OD): δ 66.05-64.43 (m, 1P), 57.93-57.39 (m, 1P).

Step 10: 8-[(5R,7R,8R,12aR,14R,15aS,16R)-14-(7-amino-3H-[1,2,3]triazolo[4,5-b]pyridin-3-yl)-16-{[tert-butyl(dimethyl)silyl]oxy}-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one

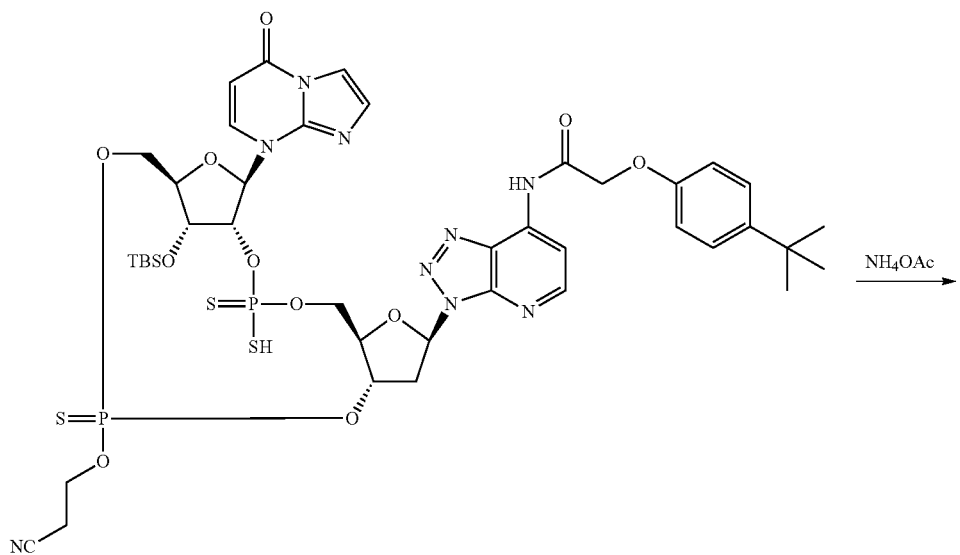

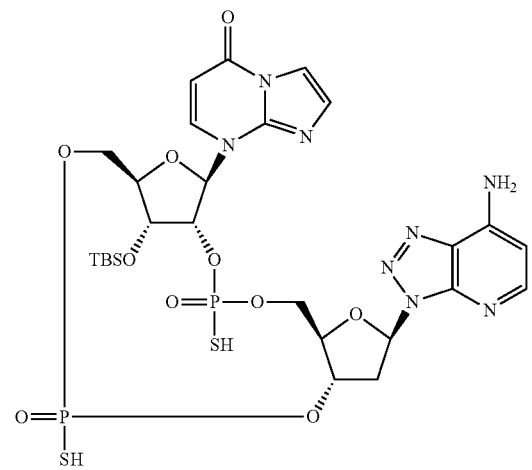

To a suspension of N-{3-[(5R,7R,8R,12aR,14R,15aS, 16R)-16-{[tert-butyl (dimethyl)silyl]oxy}-2-(2-cyanoethoxy)-10-oxido-7-(5-oxoimidazo[1,2-a]pyrimidin-8(5H)-yl)-10-sulfanyl-2-sulfidooctahydro-12H-5,8-methanofuro[3,2-l][1,3,6,9,11,2,10]pentaoxadiphospha-cyclotetradecin-14-yl]-3H-[1,2,3]triazolo[4,5-b]pyridin-7-yl}-2-(4-tert-butylphenoxy)acetamide (118 mg, 0.112 mmol) in NH$_4$OH (9.9 mL, 64 mmol) was added NH$_4$OAc (1.0 g, 13 mmol). The resulting mixture was stirred at rt for 16 h. Then, it was concentrated under reduced pressure, and the residue was purified by reverse phase (C18) chromatography eluted with 0 to 95% ACN in aq NH$_4$HCO$_3$ (5 mM) to give the product. LCMS (ES, m/z): 789.2 [M+H]$^+$. $^1$H-NMR (400 MHz, CD$_3$OD): δ 8.98 (d, J=7.9 Hz, 0.5H), 8.62 (dd, J=10.6, 7.9 Hz, 0.5H), 8.09 (dd, J=5.6, 1.9 Hz, 1H), 7.76-7.61 (m, 1H), 7.19 (d, J=1.7 Hz, 1H), 6.89-6.81 (m, 1H), 6.67 (dd, J=8.6, 3.5 Hz, 1H), 6.50 (dd, J=5.6, 1.3 Hz, 1H), 6.22-6.02 (m, 1H), 5.59-5.41 (m, 1H), 5.30 (tdd, J=11.9, 8.4, 4.0 Hz, 1H), 4.81-4.67 (m, 1.5H), 4.58-4.50 (m, 0.5H), 4.41-4.35 (m, 0.5H), 4.31-4.26 (m, 1.5H), 4.21-3.88 (m, 3H), 3.70-3.58 (m, 1H), 3.07-2.88 (m, 1H), 1.01 (s, 9H), 0.32 (d, J=5.5 Hz, 3H), 0.26 (s, 3H). $^{31}$P NMR (162 MHz, CD$_3$OD): δ 57.05-56.52 (m).

Step 11: 8-[(5R,7R,8R,12aR,14R,15aS,16R)-14-(7-amino-3H-[1,2,3]triazolo[4,5-b]pyridin-3-yl)-16-hydroxy-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one To a stirred suspension of 8-[(5R,7R,8R,12aR,14R,15aS, 16R)-14-(7-amino-3H-[1,2,3]triazolo[4,5-b]pyridin-3-yl)-16-{[tert-butyl(dimethyl)silyl]oxy}-2,10-dioxido-2,10-disulfanyloctahydro-12H-5,8-methanofuro[3,2-l][1,3,6,9,11,2,10]pentaoxadiphospha-cyclotetradecin-7-yl]imidazo[1,2-a]pyrimidin-5(8H)-one (68 mg, 0.083 mmol) in Py (0.22 mL) at RT was added TEA (1.15 mL, 8.26 mmol) and TEA.3HF (0.674 mL, 4.13 mmol). The mixture was stirred at 50° C. for 16 h. Then, the mixture was concentrated under reduced pressure, and acetone (1.1 mL) was added. Ethoxytrimethylsilane (3.9 mL, 25 mmol) was added to the mixture. The crude product crystallized out, and the mixture was maintained at 0° C. After 30 min, the crude product was collected by filtration, and it was washed with acetone. The crude product was purified by reverse phase (C18) chromatography eluted with 0 to 15% ACN in aq NH$_4$HCO$_3$ (30 mM) over 55 min (T$_R$: 41.2 min) and then, prep-HPLC (XBridge Shield RP18 OBD Column, 19 mm×250 mm) eluted with 10 to 11% ACN in aq NH$_4$HCO$_3$ (10 mM) over 11 min to afford the product (T$_R$: 8.33 min). LCMS (ES, m/z): 674.9 [M+H]$^+$. $^1$H-NMR (400 MHz, D$_2$O): δ 8.38 (d, J=7.9 Hz, 1H), 8.03 (d, J=5.7 Hz, 1H), 7.61 (d, J=1.9 Hz, 1H), 7.22 (d, J=1.9 Hz, 1H), 6.73 (t, J=6.3 Hz, 1H), 6.53 (d, J=8.2 Hz, 1H), 6.49 (d, J=5.7 Hz, 1H), 6.17 (d, J=7.9 Hz, 1H), 5.34 (dq, J=8.7, 4.0 Hz, 1H), 5.02 (ddd, J=10.0, 8.2, 4.3 Hz, 1H), 4.64 (d, J=4.2 Hz, 1H), 4.52-4.34 (m, 3H), 4.19-4.09 (m, 1H), 3.99-3.80 (m, 2H), 3.44 (dt, J=14.4, 6.0 Hz, 1H), 2.93 (ddd, J=14.5, 7.0, 4.3 Hz, 1H). $^{31}$P NMR (162 MHz, D$_2$O): δ 55.36 (s), 53.98 (s).

Examples 19 and 20: 8-[(2R,5S,7R,8R,10R,12aR, 14R,15S,15aR)-14-(6-amino-9H-purin-9-yl)-15-fluoro-2,10-dioxido-2,10-disulfanyloctahydro-12H-5,8-methanofuro[3,2-l][11,3,6,9,11,2,10]pentaoxadiphosphacyclotetradecin-7-yl]imidazo[1,2-a]pyrimidin-5(8H)-one (Diastereomer 1) and 8-[(2S,5S,7R,8R,10R,12aR,14R,15S,15aR)-14-(6-amino-9H-purin-9-yl)-15-fluoro-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one (Diastereomer 2

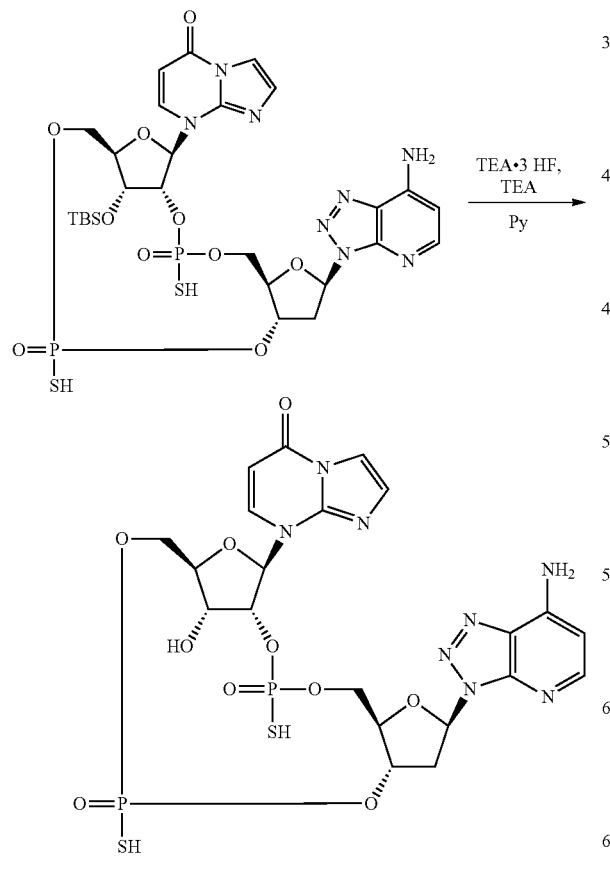

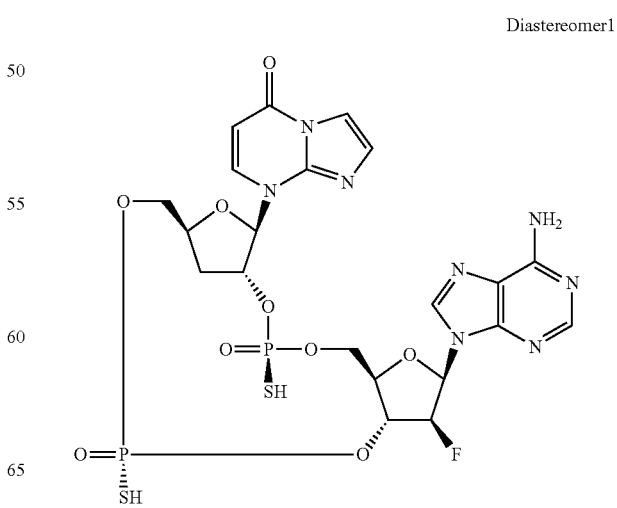

Diastereomer1

-continued

Diastereomer2

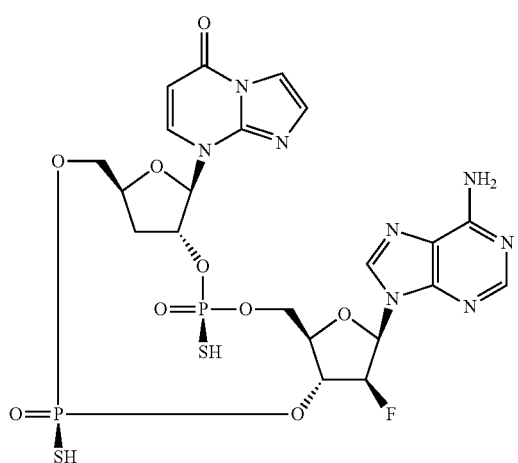

Step 1: 8-{5-O-[bis(4-methoxyphenyl)(phenyl)methyl]-2-O-[tert-butyl(dimethyl) silyl]-β-D-ribofuranosyl}imidazo[1,2-a]pyrimidin-5(8H)-one and 8-{5-O-[bis(4-methoxyphenyl) (phenyl)methyl]-3-O-[tert-butyl(dimethyl)silyl]-β-D-ribofuranosyl}imidazo[1,2-a]pyrimidin-5(8H)-one

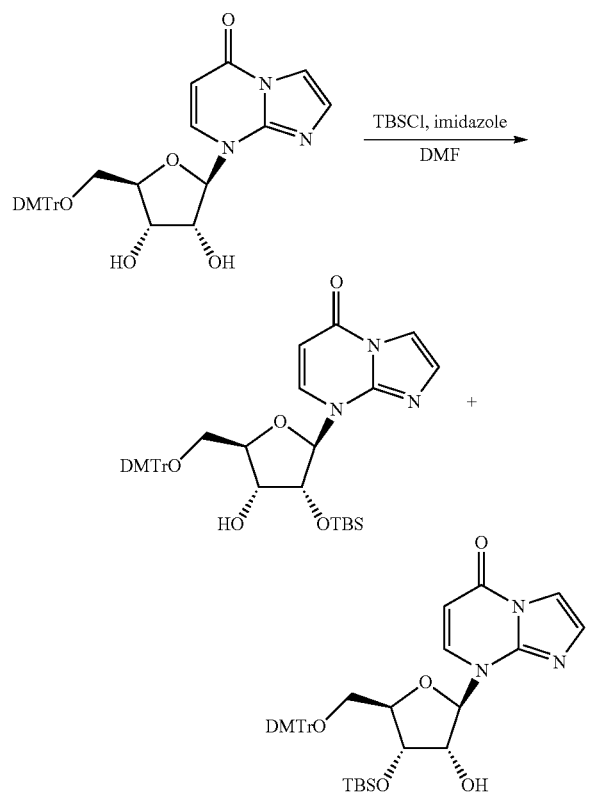

To a stirred solution of 8-{5-O-[bis(4-methoxyphenyl)(phenyl)methyl]-β-D-ribofuranosyl}imidazo[1,2-a]pyrimidin-5(8H)-one (1.64 g, 2.88 mmol) in DMF (6 mL) were added imidazole (0.49 g, 7.2 mmol) and TBSCl (0.521 g, 3.46 mmol). The mixture was left to stir overnight. The mixture was concentrated, and purified by silica gel column chromatography eluting with 10-80% of EtOAc in Hex with 1% TEA to give the products. For 8-{5-O-[bis(4-methoxyphenyl)(phenyl)methyl]-2-O-[tert-butyl(dimethyl)silyl]-β-D-ribofuranosyl}imidazo[1,2-a]pyrimidin-5(8H)-one (fast eluting): LCMS (ES, m/z): 706 [M+Na]$^+$. $^1$H-NMR (600 MHz, DMSO-d$_6$): δ 8.19 (d, J=7.8 Hz, 1H), 7.66 (s, 1H), 7.18-7.44 (m, 10H), 6.91 (d, J=8.5 Hz, 4H), 6.10 (d, J=2.8 Hz, 1H), 5.50 (d, J=7.8 Hz, 1H), 5.26 (d, J=6.0 Hz, 1H), 4.48 (brs, 1H), 4.22 (m, J=5.6 Hz, 1H), 4.11 (brs, 1H), 3.74 (s, 6H), 3.31-3.42 (m, 2H), 0.81 (s, 9H), 0.02 (s, 3H), 0.01 (s, 3H). For 8-{5-O-[bis(4-methoxyphenyl)(phenyl)methyl]-3-O-[tert-butyl(dimethyl)silyl]-β-D-ribofuranosyl}imidazo[1,2-a]pyrimidin-5(8H)-one (slow eluting): LCMS (ES, m/z): 706 [M+Na]$^+$. $^1$H-NMR (600 MHz, DMSO-d$_6$): δ 8.25 (d, J=7.8 Hz, 1H), 7.66 (s, 1H), 7.20-7.40 (m, 10H), 6.89 (d, J=7.5 Hz, 4H), 6.08 (d, J=3.3 Hz, 1H), 5.56 (d, J=7.8 Hz, 1H), 5.52 (d, J=5.8 Hz, 1H), 4.43 (m, J=4.8 Hz, 1H), 4.33 (t, J=5.3 Hz, 1H), 4.05 (m, 1H), 3.73 (s, 6H), 3.45 (dd, J=10.7, 2.8 Hz, 1H), 3.22 (dd, J=10.7, 3.9 Hz, 1H), 0.78 (s, 9H), 0.03 (s, 3H), −0.02 (s, 3H).

Step 2: 8-{5-O-[bis(4-methoxyphenyl)(phenyl)methyl]-2-O-[tert-butyl(dimethyl)silyl]-3-O-(1H-imidazol-1-ylcarbonothioyl)-β-D-ribofuranosyl}imidazo[1,2-a]pyrimidin-5(8H)-one

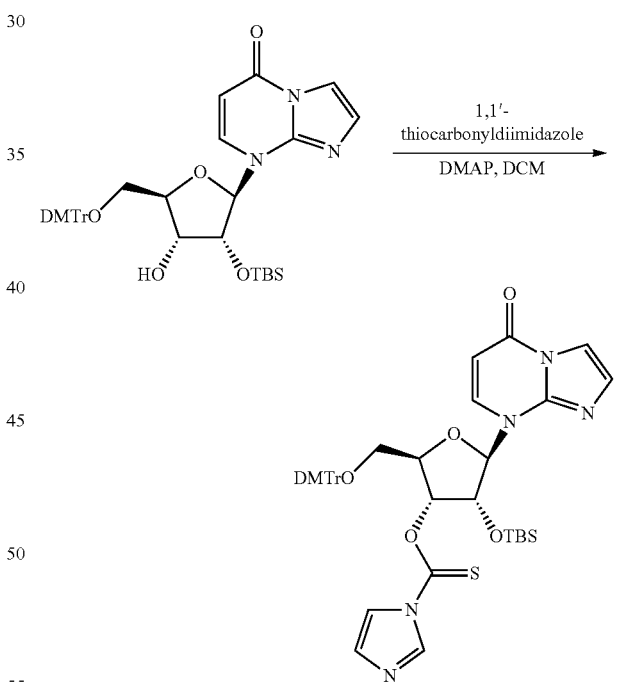

To a stirred solution of 8-{5-O-[bis(4-methoxyphenyl)(phenyl)methyl]-2-O-[tert-butyl(dimethyl)silyl]-β-D-ribofuranosyl}imidazo[1,2-a]pyrimidin-5(8H)-one (3.98 g, 5.82 mmol) in DCM (29 mL) was added DMAP (71 mg, 0.58 mmol). 1,1′-Thiocarbonyldiimidazole (1.245 g, 6.98 mmol) was added to the mixture in small portions. The mixture was left to stir overnight. The mixture was purified by silica gel column chromatography eluting with 10-80% EtOAc in Hex with 1% TEA to give the product. LCMS (ES, m/z): 816 [M+Na]$^+$. $^1$H-NMR (600 MHz, DMSO-d$_6$): δ 8.58 (s, 1H), 8.21 (d, J=7.9 Hz, 1H), 7.88 (s, 1H), 7.69 (s, 1H), 7.13-7.46 (m, 10H), 6.87 (m, 4H), 6.21 (d, J=5.9 Hz, 1H), 6.12 (m, 1H), 5.89 (d, J=7.8 Hz, 1H), 5.32 (t, J=5.6 Hz, 1H), 4.62 (d, J=3.8 Hz, 1H), 3.72 (s, 6H), 3.43-3.52 (m, 2H), 0.60 (s, 9H), −0.15 (s, 3H), −0.34 (s, 3H).

Step 3: 8-((2R,3R,5S)—S-((bis(4-methoxyphenyl)(phenyl)methoxy)methyl)-3-((tert-butyldimethylsilyl)oxy)tetrahydrofuran-2-yl)imidazo[1,2-a]pyrimidin-5(8H)-one

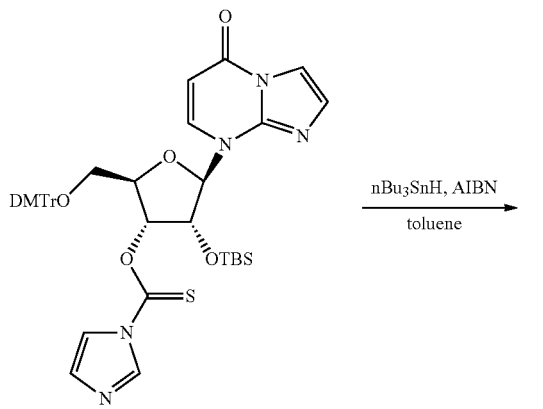

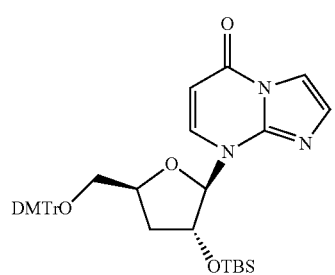

To a stirred solution of 8-{5-O-[bis(4-methoxyphenyl)(phenyl)methyl]-2-O-[tert-butyl(dimethyl)silyl]-3-O-(1H-imidazol-1-ylcarbonothioyl)-β-D-ribofuranosyl}imidazo[1,2-a]pyrimidin-5(8H)-one (4.23 g, 5.33 mmol) in toluene (152 mL) were added AIBN (1.05 g, 6.39 mmol) and nBu₃SnH (2.82 mL, 10.65 mmol). The reaction mixture was heated to 95° C. for 1 h, cooled to RT, concentrated, and purified by silica gel column chromatography eluting with 5-80% EtOAc in Hex with 1% TEA to give the product. LCMS (ES, m/z): 690 [M+Na]⁺. ¹H-NMR (600 MHz, DMSO-d₆): δ 8.19 (d, J=7.8 Hz, 1H), 7.65 (s, 1H), 7.44-6.87 (m, 14H), 6.03 (s, 1H), 5.37 (d, J=7.8 Hz, 1H), 4.65 (d, J=3.5 Hz, 1H), 4.52 (brs, 1H), 3.74 (s, 6H), 3.40 (m, 2H), 2.21 (m, 1H), 1.87 (dd, J=13.0, 4.8 Hz, 1H), 0.86 (s, 9H), 0.12 (s, 3H), 0.07 (s, 3H).

Step 4: 8-((2R,3R,5S)—S-((bis(4-methoxyphenyl)(phenyl)methoxy)methyl)-3-hydroxytetrahydrofuran-2-yl)imidazo[1,2-a]pyrimidin-5(8H)-one

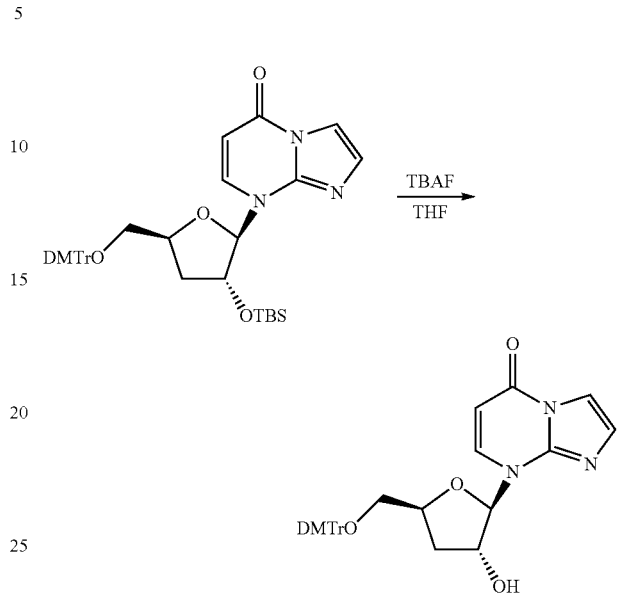

To a stirred solution of 8-((2R,3R,5S)—S-((bis(4-methoxyphenyl)(phenyl) methoxy)methyl)-3-((tert-butyldimethylsilyl)oxy)tetrahydrofuran-2-yl)imidazo[1,2-a]pyrimidin-5(8H)-one (2.54 g, 3.80 mmol) in THF (38 mL) at 0° C. was added TBAF (1.0M in THF, 7.61 mL, 7.61 mmol). The cooling bath was removed, and the mixture was left to stir at RT for 45 min. The mixture was cooled to 0° C., diluted with EtOAc, and treated with sat NaHCO₃ solution. The aq layer was extracted with EtOAc (3×). The combined organics were dried (Na₂SO₄), concentrated, and purified by silica gel column chromatography eluting with 5-70% EtOAc:EtOH (3:1) in Hex with 0.5% TEA to give the product. LCMS (ES, m/z): 576 [M+Na]⁺. ¹H-NMR (600 MHz, DMSO-d₆): δ 8.19 (d, J=7.8 Hz, 1H), 7.66 (s, 1H), 7.43-6.85 (m, 14H), 6.06 (s, 1H), 5.78 (d, J=3.5 Hz, 1H), 5.38 (d, J=7.7 Hz, 1H), 4.55 (brs, 1H), 4.49 (s, 1H), 3.74 (s, 6H), 3.36 (m, 2H), 2.20 (m, 1H), 1.88 (dd, J=13.0, 4.8 Hz, 1H).

Step 5: 8-{5-O-[bis(4-methoxyphenyl)(phenyl)methyl]-3-deoxy-2-O-[hydroxyl (oxido)-λ⁵-phosphanyl]-β-D-erythro-pentofuranosyl}imidazo[1,2-a]pyrimidin-5(8H)-one

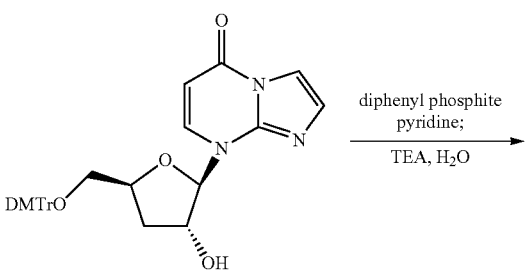

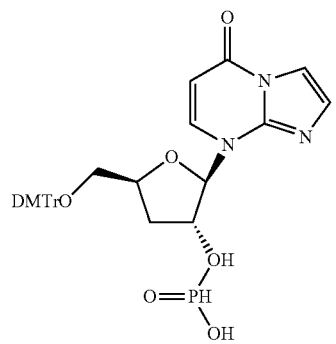

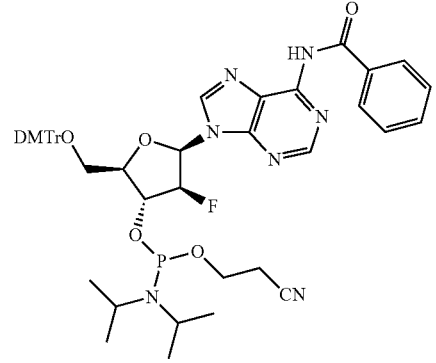

A solution of 8-((2R,3R,5S)—5-((bis(4-methoxyphenyl)(phenyl)methoxy)methyl)-3-hydroxytetrahydrofuran-2-yl)imidazo[1,2-a]pyrimidin-5(8H)-one (546 mg, 0.986 mmol) in Py (5 mL) was concentrated in vacuo. To the residue was added Py (6 mL) followed by dropwise addition of diphenyl phosphite (567 µL, 2.96 mmol). The mixture was left to stir for 5 h, treated with TEA (378 µl, 2.71 mmol) and H$_2$O (374 µl, 20.8 mmol), left to stir for 45 min and concentrated. The residue was partitioned between DCM and sat NaHCO$_3$ solution. The organic layer was washed with sat aq NaHCO$_3$ (2×), dried over Na$_2$SO$_4$, and purified by silica gel column chromatography eluting with 0-18% of MeOH in DCM with 0.5% TEA to give the product. LCMS (ES, m/z): 616 [M−H]$^−$. $^1$H-NMR (500 MHz, DMSO-d$_6$): δ 9.85 (brs, 1H), 8.17 (d, J=7.8 Hz, 1H), 7.65 (s, 1H), 7.42-6.81 (m, 14H), 6.14 (s, 1H), 5.47 (d, J=7.8 Hz, 1H), 4.91 (m, 1H), 4.48 (m, 1H), 3.73 (s, 6H), 3.30 (m, 2H), 2.34 (m, 1H), 2.13 (dd, J=13.2, 5.2 Hz, 1H).

Step 6: (2R,3R,5S)—S-(((((2R,3R,4S,5R)—S-(6-benzamido-9H-purin-9-yl)-4-fluoro-2-(hydroxymethyl)tetrahydrofuran-3-yl)oxy)(2-cyanoethoxy)phosphorothioyl)oxy)methyl)-2-(5-oxoimidazo[1,2-a]pyrimidin-8(5H)-yl)tetrahydrofuran-3-yl hydrogen phosphonate

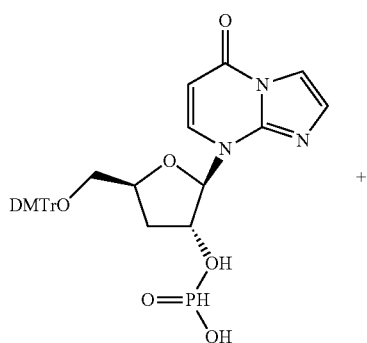

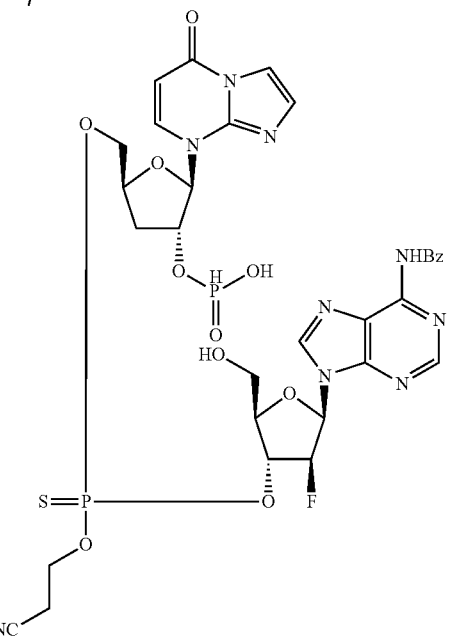

A solution of (2R,3R,5S)—S-((bis(4-methoxyphenyl)(phenyl)methoxy)methyl)-2-(5-oxoimidazo[1,2-a]pyrimidin-8(5H)-yl)tetrahydrofuran-3-yl hydrogen phosphonate (520 mg, 0.723 mmol) in MeCN (3 mL) was concentrated in vacuo. Addition of MeCN (3 mL) followed by concentration was repeated twice. The residue was taken up in MeCN (2.5 mL), cooled to 0° C., and treated with pyrrole (154 µl, 2.17 mmol) and TFA (167 µl, 2.17 mmol) over 1 min. The reaction mixture was allowed to warm to RT over 1.5 h. Then, the mixture was cooled to 0° C. and treated with pyridine (234 µl, 2.89 mmol).

A solution of (2R,3R,4S,5R)—S-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (0.842 g, 0.962 mmol) in ACN (4 mL) was concentrated in vacuo. The residue was taken up in ACN (1.6 mL) and transferred to the H-phosphonate solution at 0° C. over 1 min. The mixture was left to stir at 0° C. for 20 min, treated with (E)-N,N-dimethyl-N'-(3-thioxo-3H-1,2,4-dithiazol-5-yl)formimidamide (0.178 g, 0.868 mmol), and left to stir at 0° C. for 20 min. The mixture was treated with 1-propanol (0.543 mL, 7.23 mmol), warmed to RT, and left to stir for 10 min. TFA (0.557 mL, 7.23 mmol) was added to the mixture, and the reaction mixture was left to stir for 2 h and treated with Py (0.643 mL, 7.95 mmol). The mixture was concentrated to half the volume. The residue was added into rapidly stirring isopropyl acetate (50 mL). The precipitate was collected by filtration and kept under high vacuum overnight to give the crude products. LCMS (ES, m/z): 818 [M+H]$^−$.

Step 7: N-{9-[(5S,7R,8R,12aR,14R,15S,15aR)-2-(2-cyanoethoxy)-15-fluoro-10-oxido-7-(5-oxoimidazo[1,2-a]pyrimidin-8(5H)-yl)-10-sulfanyl-2-sulfidooctahydro-12H-5,8-methanofuro[3,2-l][1,3,6,9,11,2,10]pentaoxadiphosphacyclotetradecin-14-yl]-9H-purin-6-yl}benzamide

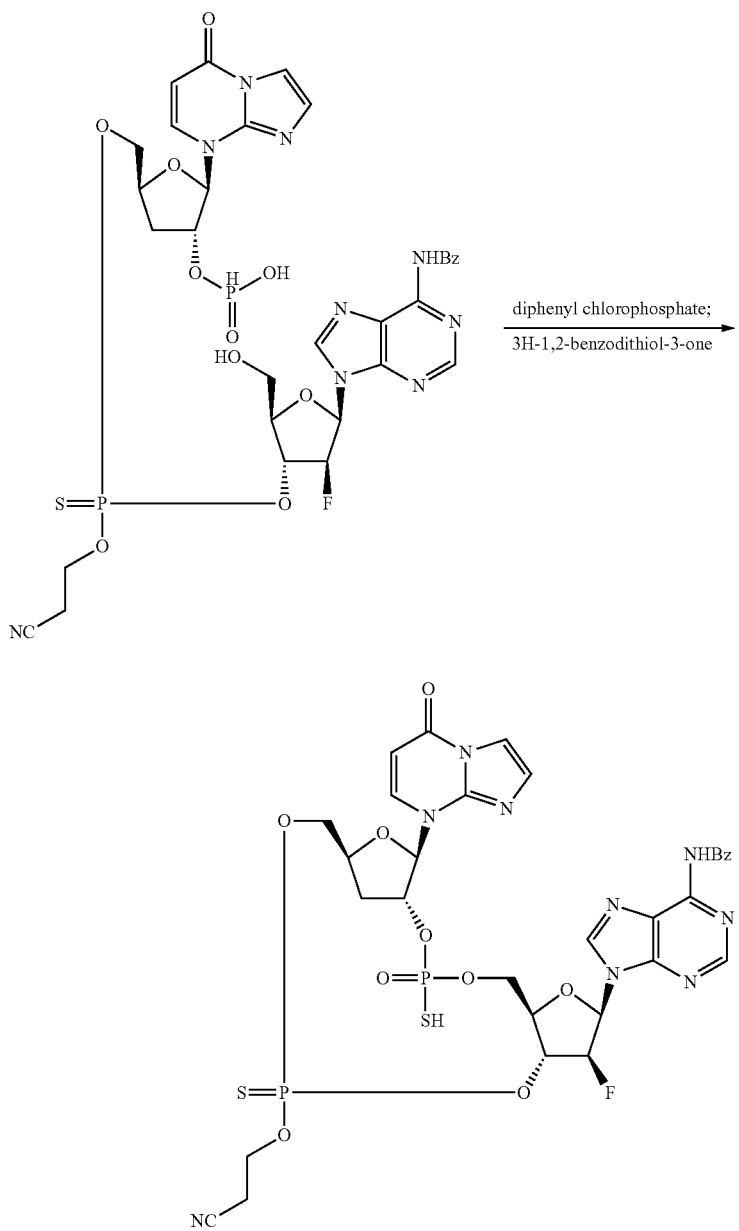

A solution of the crude (2R,3R,5S)—S-(((((2R,3R,4S,5R)—S-(6-benzamido-9H-purin-9-yl)-4-fluoro-2-(hydroxymethyl)tetrahydrofuran-3-yl)oxy)(2-cyanoethoxy)phosphorothioyl)oxy)methyl)-2-(5-oxoimidazo[1,2-a]pyrimidin-8(5H)-yl)tetrahydrofuran-3-yl hydrogen phosphonate from the previous step in Py (4 mL) was concentrated in vacuo. Addition of Py (4 mL) followed by concentration was repeated once. The residue was taken up in Py (3.6 mL). Into a separate flask were added MeCN (34 mL), Py (2.2 mL), and diphenyl chlorophosphate (0.749 mL, 3.62 mmol). The solution was cooled to −20° C., and the solution of the hydrogen phosphonate in Py was added dropwise. The residue was rinsed with Py (0.7 mL) and added to the reaction mixture. The mixture was left to stir at −23° C. to −20° C. for 20 min. 3H-1,2-benzodithiol-3-one (0.146 g, 0.868 mmol) and H₂O (0.26 mL, 14.5 mmol) were added, and the cooling bath was removed. After the mixture was warmed to RT, it was concentrated and purified by silica gel column chromatography eluting with 100% EtOAc, then 5-20% MeOH in DCM to give the products. LCMS (ES, m/z): 832 [M−H]⁻.

213

Step 8: 8-[(2R,5S,7R,8R,10R,12aR,14R,15S,15aR)-14-(6-amino-9H-purin-9-yl)-15-fluoro-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one (Diastereomers 1-2)

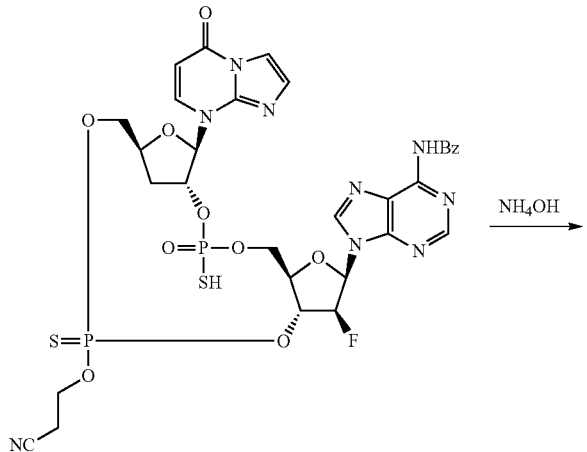

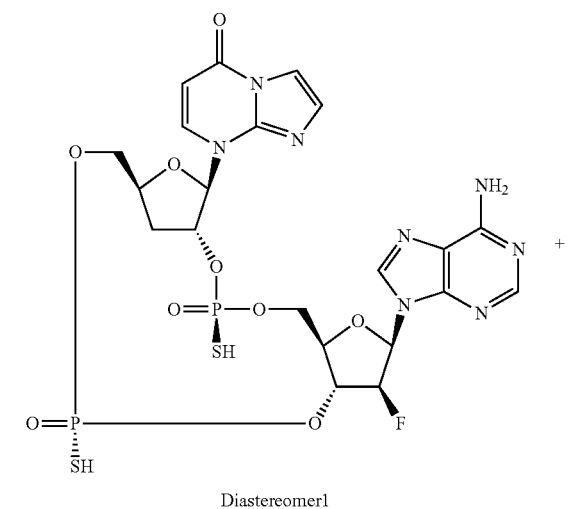

Diastereomer1

214

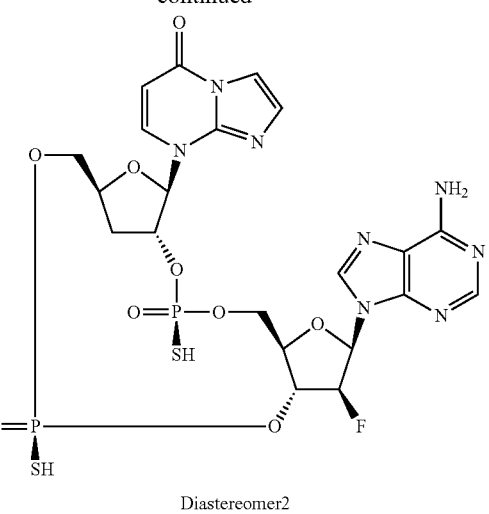

Diastereomer2

To a stirred solution of N-{9-[(5S,7R,8R,12aR,14R,15S,15aR)-2-(2-cyanoethoxy)-15-fluoro-10-oxido-7-(5-oxoimidazo[1,2-a]pyrimidin-8(5H)-yl)-10-sulfanyl-2-sulfidooctahydro-12H-5,8-methanofuro[3,2-l][1,3,6,9,11,2,10]pentaoxadiphosphacyclotetradecin-14-yl]-9H-purin-6-yl}benzamide (599 mg, 0.718 mmol) in Py (8 mL) were added $H_2O$ (2 mL) and $NH_4OH$ (28%, 8 mL). The mixture was left to stir for 5 h, concentrated, lyophilized, and purified by reverse phase HPLC (eluting MeCN/$H_2O$ gradient with 100 mM TEAA modifier, linear gradient) to afford the title compounds.

Example 19 (diastereomer 1) (fast eluted): LCMS (ES, m/z): 675 [M–H]⁻. $^1$H-NMR (600 MHz, $D_2O$): δ 8.48 (d, J=7.9 Hz, 1H), 8.31 (brs, 1H), 8.24 (s, 1H), 7.66 (s, 1H), 7.28 (s, 1H), 6.54 (dd, J=19.1, 3.0 Hz, 1H), 6.37 (d, J=6.4 Hz, 1H), 6.01 (d, J=7.9 Hz, 1H), 5.71 (d, J=49.8 Hz, 1H), 5.21-5.12 (m, 2H), 4.70 (d, J=7.7 Hz, 1H), 4.54 (m, 1H), 4.32-4.16 (m, 4H), 2.72 (m, 1H), 2.56 (m, 1H).

Example 20 (diastereomer 2) (slow eluted): LCMS (ES, m/z): 675 [M–H]⁻. $^1$H-NMR (600 MHz, $D_2O$): δ 8.30 (s, 1H), 8.22 (s, 1H), 8.16 (d, J=7.8 Hz, 1H), 7.65 (s, 1H), 7.26 (s, 1H), 6.54 (dd, J=16.2, 3.4 Hz, 1H), 6.33 (d, J=4.6 Hz, 1H), 5.93 (d, J=7.8 Hz, 1H), 5.62 (d, J=50.3 Hz, 1H), 5.09 (m, 2H), 4.66 (brs, 1H), 4.50 (t, J=11.3 Hz, 1H), 4.41 (brs, 1H), 4.29 (m, 1H), 4.23 (m, 1H), 4.14 (m, 1H), 2.76 (m, 1H), 2.42 (m, 1H).

Examples 21 through 28, as shown in Table 2 below, were prepared according to procedures analogous to those outlined in Examples 19 and 20 above using the appropriate monomers, described as Preparations or as obtained from commercial sources, in the coupling step.

TABLE 2

| Ex. | Structure | Name | Mass [M + H]+ |
|---|---|---|---|
| 21 | 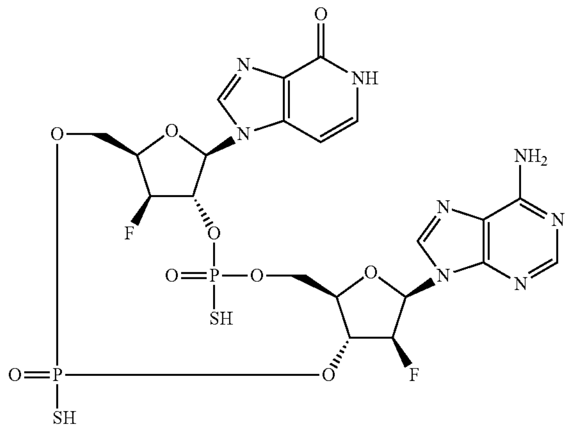 [SMILES: Nc1ncnc2c1ncn2[C@@H]1O[C@@H]2COP(=O)(S)O[C@@H]3[C@@H](F)[C@@H](COP(=O)(S)O[C@H]2[C@@H]1F)O[C@H]3n1cnc2c(=O)[nH]ccc21] | 1-[(5R,7R,8S,12aR,14R,15S,15aR,16S)-14-(6-amino-9H-purin-9-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-7-yl]-1,5-dihydro-4H-imidazo[4,5-c]pyridin-4-one | 695 |
| 22 | 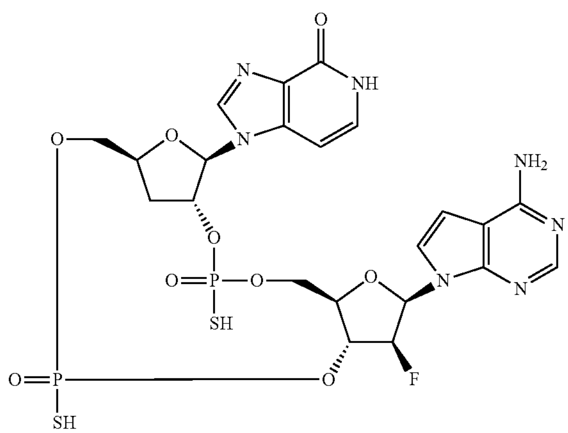 [SMILES: Nc1ncnc2c1ccn2[C@@H]1O[C@@H]2COP(=O)(S)O[C@@H]3C[C@@H](COP(=O)(S)O[C@H]2[C@@H]1F)O[C@H]3n1cnc2c(=O)[nH]ccc21] | 1-[(5S,7R,8R,12aR,14R,15S,15aR)-14-(4-amino-7H-pyrrolo[2,3-d]pyrimidin-7-yl)-15-fluoro-2,10-dioxido-2,10-disulfanyloctahydro-12H-5,8-methanofuro[3,2-l][1,3,6,9,11,2,10]pentaoxadiphosphacyclotetradecin-7-yl]-1,5-dihydro-4H-imidazo[4,5-c]pyridin-4-one | 676 |
| 23 | 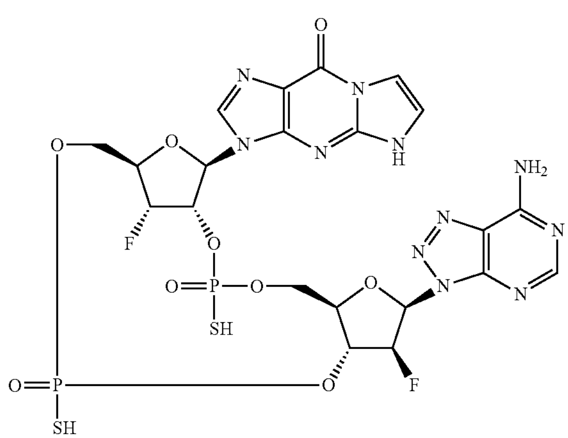 [SMILES: Nc1ncnc2c1nnn2[C@@H]1O[C@@H]2COP(=O)(S)O[C@@H]3[C@H](F)[C@@H](COP(=O)(S)O[C@H]2[C@@H]1F)O[C@H]3n1cnc2c(=O)n3cc[nH]c3nc21] | 3-[(5R,7R,8S,12aR,14R,15S,15aR,16R)-14-(7-amino-3H-[1,2,3]triazolo[4,5-d]pyrimidin-3-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-7-yl]-3,5-dihydro-9H-imidazo[1,2-a]purin-9-one (Diastereomer 1) | 736 |

TABLE 2-continued

| Ex. | Structure | Name | Mass [M + H]+ |
|---|---|---|---|
| 24 | 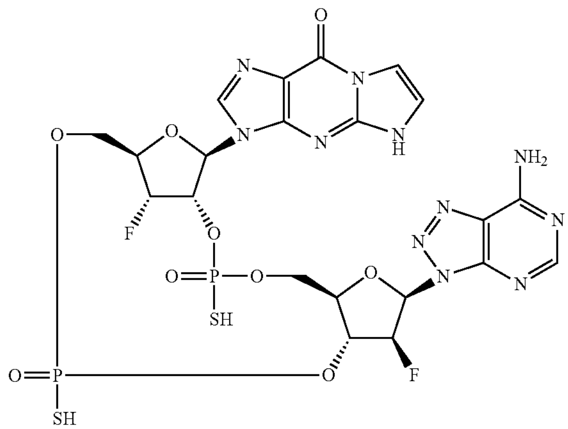 | 3-[(5R,7R,8S,12aR,14R,15S,15aR,16R)-14-(7-amino-3H-[1,2,3]triazolo[4,5-d]pyrimidin-3-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-7-yl]-3,5-dihydro-9H-imidazo[1,2-a]purin-9-one (Diastereomer 2) | 736 |
| 25 | 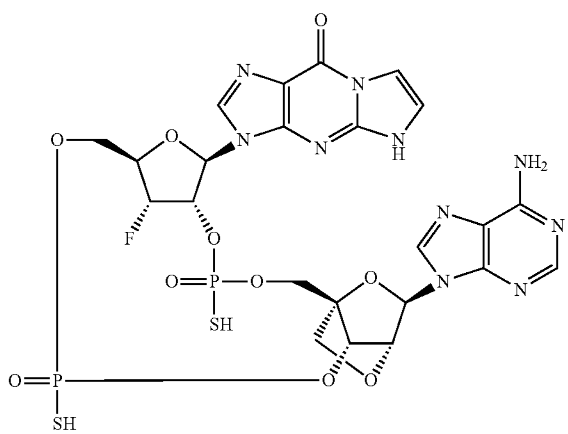 [SMILES: Nc1ncnc2c1ncn2[C@@H]1O[C@@]23CO[C@@H]1[C@@H]2OP(=O)(S)OC[C@H]1O[C@@H](n2cnc4c(=O)n5cc[nH]c5nc42)[C@H](OP(=O)(S)OC3)[C@@H]1F] | 3-[(5R,7R,8S,12aR,14R,15R,15aS,18R)-14-(6-amino-9H-purin-9-yl)-18-fluoro-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-3,5-dihydro-9H-imidazo[1,2-a]purin-9-one (Diastereomer 1) | 745 |
| 26 | 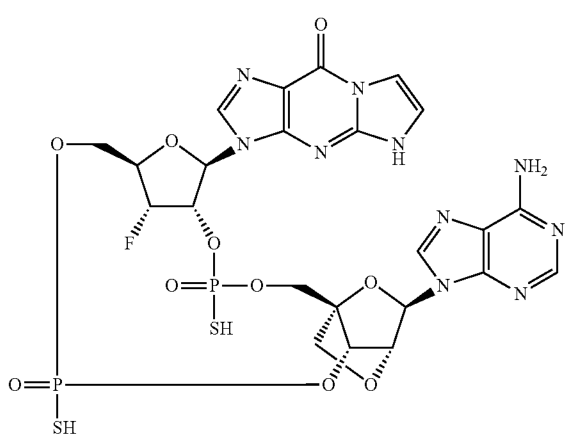 [SMILES: Nc1ncnc2c1ncn2[C@@H]1O[C@@]23CO[C@@H]1[C@@H]2OP(=O)(S)OC[C@H]1O[C@@H](n2cnc4c(=O)n5cc[nH]c5nc42)[C@H](OP(=O)(S)OC3)[C@@H]1F] | 3-[(5R,7R,8S,12aR,14R,15R,15aS,18R)-14-(6-amino-9H-purin-9-yl)-18-fluoro-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-3,5-dihydro-9H-imidazo[1,2-a]purin-9-one (Diastereomer 2) | 745 |

TABLE 2-continued

| Ex. | Structure | Name | Mass [M + H]+ |
|---|---|---|---|
| 27 | 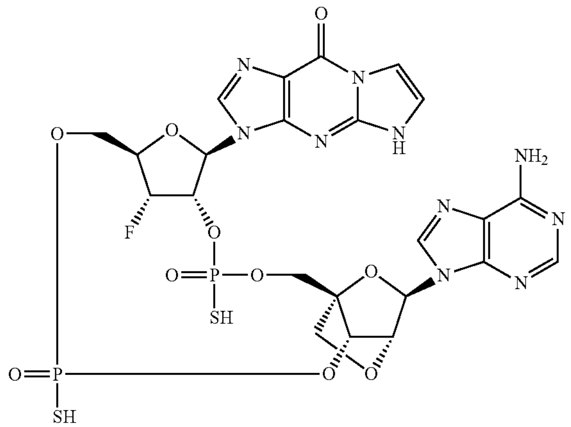 [SMILES: Nc1ncnc2c1ncn2[C@@H]1O[C@@]23CO[C@@H]1[C@@H]2OP(=O)(S)OC[C@H]1O[C@@H](n2cnc4c(=O)n5cc[nH]c5nc42)[C@H](OP(=O)(S)OC3)[C@@H]1F] | 3-[(5R,7R,8S,12aR,14R,15R,15aS,18R)-14-(6-amino-9H-purin-9-yl)-18-fluoro-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-3,5-dihydro-9H-imidazo[1,2-a]purin-9-one (Diastereomer 3) | 745 |
| 28 | 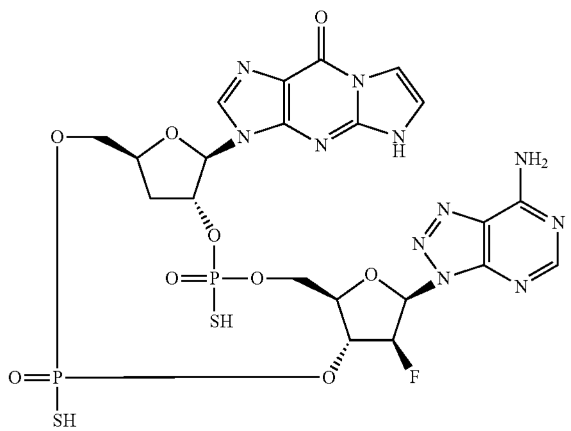 [SMILES: Nc1ncnc2c1nnn2[C@@H]1O[C@@H]2COP(=O)(S)O[C@@H]3C[C@@H](COP(=O)(S)O[C@H]2[C@@H]1F)O[C@H]3n1cnc2c(=O)n3cc[nH]c3nc21] | 3-[(5S,7R,8R,12aR,14R,15S,15aR)-14-(7-amino-3H-[1,2,3]triazolo[4,5-d]pyrimidin-3-yl)-15-fluoro-2,10-dioxido-2,10-disulfanyloctahydro-12H-5,8-methanofuro[3,2-l][1,3,6,9,11,2,10]pentaoxadiphosphacyclotetradecin-7-yl]-3,5-dihydro-9H-imidazo[1,2-a]purin-9-one | 718 |

Examples 29: 9-[(2R,5S,7R,8R,10R,12aR,14R,15S,15aR)-15-fluoro-2,10-dioxido-7-(5-oxoimidazo[1,2-a]pyrimidin-8(5H)-yl)-2,10-disulfanyloctahydro-12H-5,8-methanofuro[3,2-l][1,3,6,9,11,2,10]pentaoxadiphosphacyclotetradecin-14-yl]-1,9-dihydro-6H-purin-6-one To 8-[(2R,5S,7R,8R,10R,12aR,14R,15S,15aR)-14-(6-amino-9H-purin-9-yl)-15-fluoro-2,10-dioxido-2,10-disulfanyloctahydro-12H-5,8-methanofuro[3,24][1,3,6,9,11,2,10]pentaoxadiphosphacyclotetradecin-7-yl]imidazo[1,2-a]pyrimidin-5(8H)-one triethylammonium salt (16 mg, 18 µmol) were added sodium phosphate buffer (pH 6.8, 50 mM, 1.5 mL) and AMPDA (20 mg). The reaction mixture was left to stir overnight, filtered, and purified by reverse phase HPLC (eluting MeCN/H₂O gradient with 100 mM TEAA modifier, linear gradient) to afford the product. LCMS (ES, m/z): 676 [M−H]⁻. ¹H NMR (600 MHz, D₂O): δ 8.20 (m, 1H), 8.16 (d, J=7.9 Hz, 1H), 8.14 (s, 1H), 7.63 (s, 1H), 7.25 (s, 1H), 6.51 (dd, J=18.9, 3.4 Hz, 1H), 6.32 (d, J=4.4 Hz, 1H), 6.03 (d, J=7.8 Hz, 1H), 5.58 (d, J=50.2 Hz, 1H), 5.11-5.03 (m, 2H), 4.65 (brs, 1H), 4.53 (t, J=11.2 Hz, 1H), 4.39 (brs, 1H), 4.27 (m, 1H), 4.21-4.10 (m, 2H), 2.78 (dt, J=13.6, 7.0 Hz, 1H), 2.35 (m, 1H).

Example 30: 8,8'-[(5R,7R,8R,12aR,14R,15R,15aS,16R)-15,16-dihydroxy-2,10-dioxido-2,10-disulfanyloctahydro-12H-5,8-methanofuro[3,2-l][1,3,6,9,11,2,10]pentaoxadiphosphacyclo-tetradecine-7,14-diyl]bisimidazo[1,2-a]pyrimidin-5(8H)-one

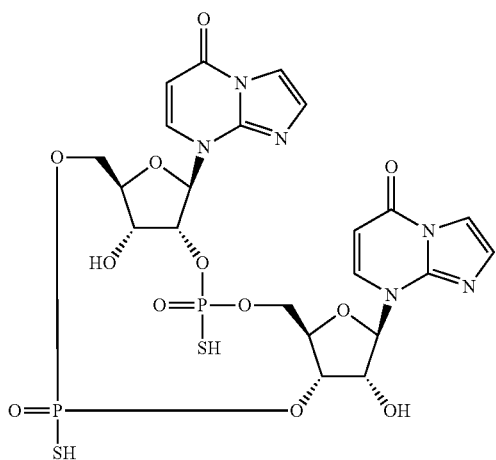 [SMILES: O=c1ccn([C@@H]2O[C@@H]3COP(=O)(S)O[C@@H]4[C@H](O)[C@@H](COP(=O)(S)O[C@H]3[C@H]2O)O[C@H]4n2ccc(=O)n3ccnc23)c2nccn12]

Step 1: (2R,3R,4R,5R)-2-((bis(4-methoxyphenyl)(phenyl)methoxy)methyl)-4-((tert-butyldimethylsilyl)oxy)-5-(5-oxoimidazo[1,2-a]pyrimidin-8(5H)-yl)tetrahydrofuran-3-yl (2-cyanoethyl)diisopropylphosphoramidite

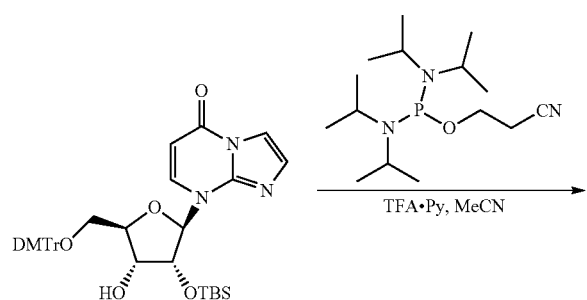

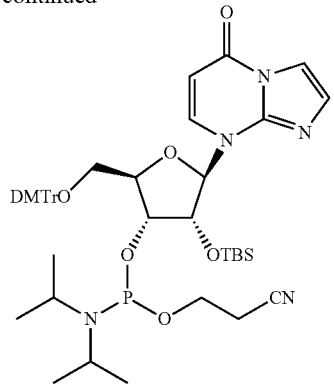

To a stirred solution of dry 3-((bis(diisopropylamino)phosphino)oxy) propanenitrile (643 mg, 2.14 mmol) in MeCN (4 mL) under Ar was added pyridin-1-ium 2,2,2-trifluoroacetate (309 mg, 1.60 mmol) and 8-((2R,3R,4R,5R)—S-((bis(4-methoxyphenyl)(phenyl) methoxy)methyl)-3-((tert-butyldimethylsilyl)oxy)-4-hydroxytetrahydrofuran-2-yl)imidazo[1,2-a]pyrimidin-5(8H)-one (730 mg, 1.07 mmol) in MeCN (4 mL). The resulting mixture was stirred at RT for 1 h, then concentrated. The residue was dissolved in EtOAc (100 mL), washed with aq NaHCO₃ (1%, 2×50 mL), H₂O (50 mL) and brine (50 mL), dried (Na₂SO₄) and purified by reverse phase (C18) chromatography eluted with 60 to 95% ACN in aq NH₄HCO₃ (5 mM) to give the product. LCMS (ES, m/z): 884.1 [M+H]⁺. ¹H NMR (300 MHz, DMSO-d₆): δ 8.14 (dd, J 7.9, 5.1 Hz, 1H), 7.65-7.60 (m, 1H), 7.40-7.35 (m, 2H), 7.33-7.21 (m, 7H), 7.18-7.15 (m, 1H), 6.99-6.77 (m, 4H), 6.13-5.93 (m, 1H), 5.58 (dd, 7.9 Hz, 1H), 4.76 (dt, 4.6 Hz, 1H), 4.39-4.15 (m, 2H), 3.74-3.69 (m, 7H), 3.66-3.31 (m, 5H), 2.73 (t, J=5.9 Hz, 1H), 2.55 (t, J=5.9 Hz, 1H), 1.15-0.92 (m, 12H), 0.73 (d, J=5.2 Hz, 9H), 0.06-0.34 (m, 6H). ³¹P NMR: (121 MHz, DMSO-d₆) δ 148.94 (s), 148.68 (s).

Step 2: (2R,3R,4R,5R)—S-((((((2R,3R,4R,5R)-2-((bis(4-methoxyphenyl)(phenyl) methoxy)methyl)-4-((tert-butyldimethylsilyl)oxy)-S-(5-oxoimidazo[1,2-a]pyrimidin-8(5H)-yl)tetrahydrofuran-3-yl)oxy)(2-cyanoethoxy)phosphanyl)oxy)methyl)-4-((tert-butyldimethylsilyl) oxy)-2-(5-oxoimidazo[1,2-a]pyrimidin-8(5H)-yl)tetrahydrofuran-3-yl hydrogen phosphonate

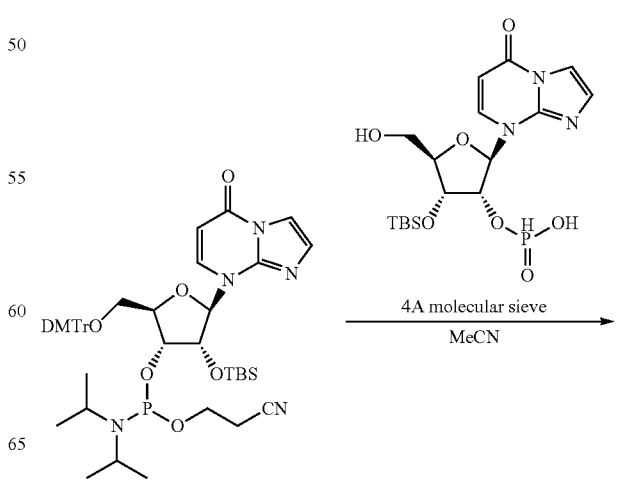

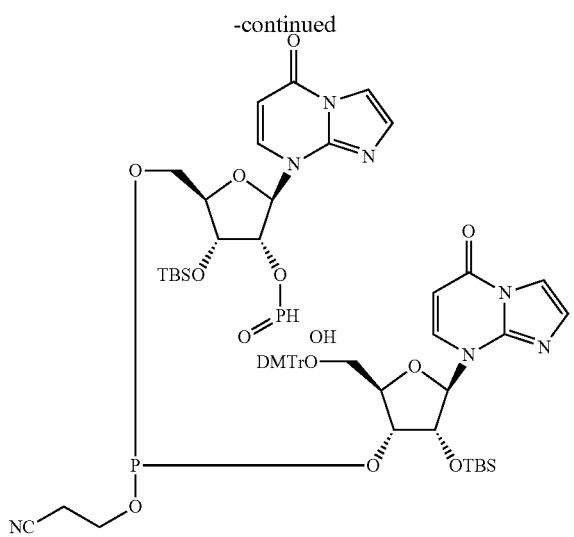

(2R,3R,4R,5R)-2-((bis(4-methoxyphenyl)(phenyl)methoxy)methyl)-4-((tert-butyl-dimethylsilyl)oxy)-5-(5-oxoimidazo[1,2-a]pyrimidin-8(5H)-yl)tetrahydrofuran-3-yl (2-cyanoethyl)diisopropylphosphoramidite (540 mg, 0.611 mmol) was co-evaporated with MeCN (3×6 mL) and re-dissolved in MeCN (5 mL). Activated 4 Å molecular sieve (300 mg) was added. (2R,3R,4R,5R)-4-((tert-butyldimethylsilyl)oxy)-5-(hydroxymethyl)-2-(5-oxoimidazo[1,2-a]pyrimidin-8(5H)-yl)tetrahydrofuran-3-yl hydrogen phosphonate (crude, 0.71 mmol) was co-evaporated with MeCN (3×8 mL) and re-dissolved in MeCN (4 mL) under Ar. Activated 4 Å molecular sieve (300 mg) was added. To this mixture was added the mixture containing (2R,3R,4R,5R)-2-((bis(4-methoxyphenyl)(phenyl)methoxy)methyl)-4-((tert-butyldimethylsilyl) oxy)-5-(5-oxoimidazo[1,2-a]pyrimidin-8(5H)-yl)tetrahydrofuran-3-yl (2-cyanoethyl)diisopropyl-phosphoramidite dropwise, and it was stirred for 30 min. The reaction mixture was used for the next reaction step directly without purification. LCMS (ES, m/z): 1228.4 [M+H]$^+$.

Step 3: (2R,3R,4R, 5R)—S-((((((2R,3R,4R, 5R)-2-((bis(4-methoxyphenyl) (phenyl) methoxy)methyl)-4-((tert-butyldimethylsilyl)oxy)-S-(5-oxoimidazo[1,2-a]pyrimidin-8(5H)-yl)tetrahydrofuran-3-yl)oxy)(2-cyanoethoxy)phosphorothioyl)oxy)methyl)-4-((tert-butyldimethylsilyl)oxy)-2-(5-oxoimidazo[1,2-a]pyrimidin-8(5H)-yl)tetrahydrofuran-3-yl hydrogen phosphonate

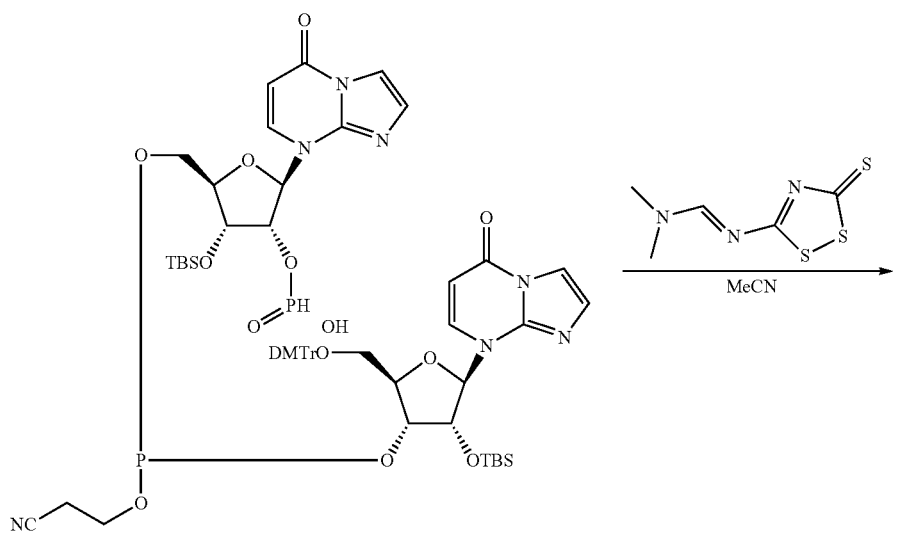

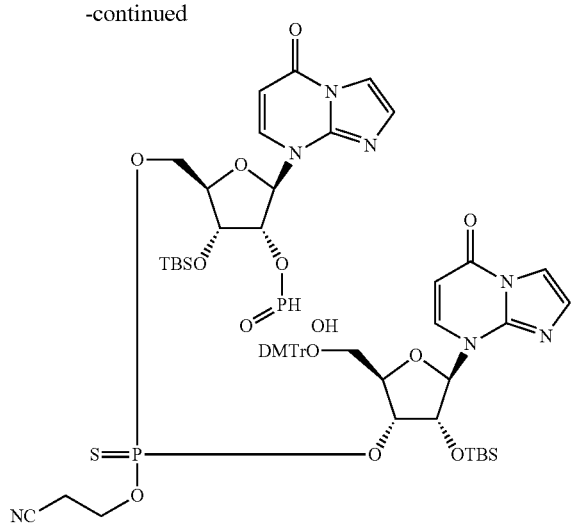

To the reaction mixture from Step 2 was added (E)-N,N-dimethyl-N-(3-thioxo-3H-1,2,4-dithiazol-S-yl)formimidamide (138 mg, 0.672 mmol), and the mixture was stirred at rt for 1 h. Then, it was concentrated to give the crude product, which was used for the next reaction step directly without purification. LCMS (ES, m/z): 1258.5 [M−H]⁻.

Step 4: (2R,3R,4R,5R)-4-((tert-butyldimethylsilyl)oxy)-S-((((((2R,3R,4R,5R)-4-((tert-butyldimethylsilyl)oxy)-2-(hydroxymethyl)-S-(5-oxoimidazo[1,2-a]pyrimidin-8(5H)-yl)tetrahydrofuran-3-yl)oxy)(2-cyanoethoxy)phosphorothioyl)oxy)methyl)-2-(5-oxoimidazo[1,2-a]pyrimidin-8(5H)-yl)tetrahydrofuran-3-yl hydrogen phosphonate

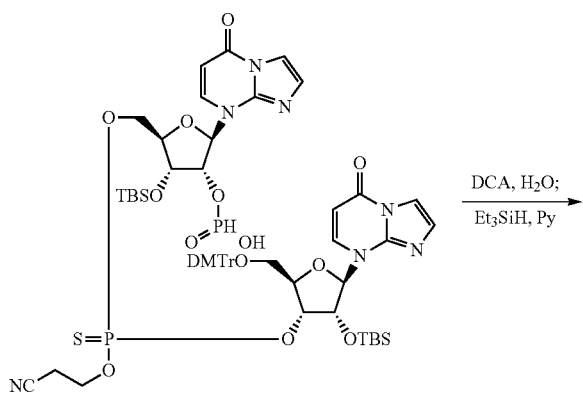

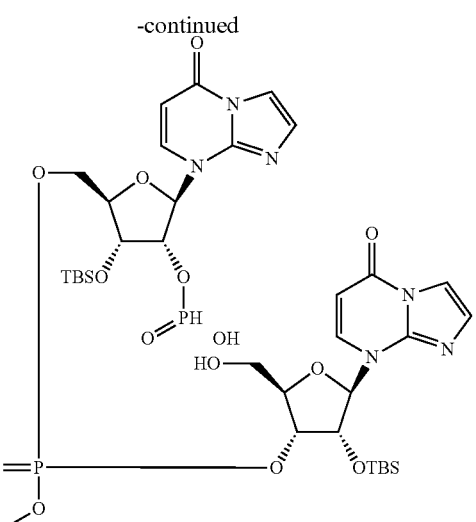

To a solution of crude from Step 4 in DCM (9 mL) was added H₂O (0.11 mL, 6.1 mmol) and DCA (8.8 mL, 5.58 mmol). The mixture was stirred at RT for 30 min and then, Et₃SiH (20 mL) was added. After 1 h, Py (0.90 mL, 11 mmol) was added, and the mixture was stirred for 10 min. It was concentrated, and the residue was purified by reverse phase (C18) chromatography eluted with 0 to 95% ACN in aq NH₄HCO₃ (5 mM) to give the product. LCMS (ES, m/z): 958.3 [M+H]⁺. ¹H NMR (300 MHz, CD₃OD): δ 8.25-8.20 (m, 1H), 8.10-8.05 (m, 1H), 7.86-7.84 (m, 0.5H), 7.72-7.68 (m, 1H), 7.65-7.58 (m, 1H), 7.25-7.22 (m, 2H), 6.26-6.21 (m, 1H), 6.04-5.84 (m, 4H), 5.77-5.75 (m, 0.5H), 5.32-5.17 (m, 1H), 5.16-4.97 (m, 2H), 4.63-4.18 (m, 6H), 4.09-3.52 (m, 4H), 1.05-0.90 (m, 9H), 0.85-0.63 (m, 9H), 0.27-0.23 (m, 6H), −0.06 to −0.09 (m, 3H), −0.2 to −0.30 (m, 3H). ³¹P-NMR: (121 MHz, CD₃OD) δ 67.88 (s), 67.65 (s); 3.23 (s), 3.12 (s).

227

Step 5: 3-{[(5R,7R,8R,12aR,14R,15R,15aR,16R)-15,16-bis{[tert-butyl(dimethyl) silyl]oxy}-10-hydroxy-7,14-bis(5-oxoimidazo[1,2-a]pyrimidin-8(5H)-yl)-2-sulfidooctahydro-12H-5,8-methanofuro[3,2-l][1,3,6,9,11,2,10]pentaoxadiphosphacyclotetradecin-2-yl]oxy}propanenitrile

228

Step 6: 3-{[(5R,7R,8R,12aR,14R,15R,15aR,16R)-15,16-bis{[tert-butyl(dimethyl)silyl]oxy}-10-oxido-7,14-bis(5-oxoimidazo[1,2-a]pyrimidin-8(5H)-yl)-10-sulfanyl-2-sulfidooctahydro-12H-5,8-methanofuro[3,24][1,3,6,9,11,2,10]pentaoxadiphosphacyclotetradecin-2-yl]oxy}propanenitrile

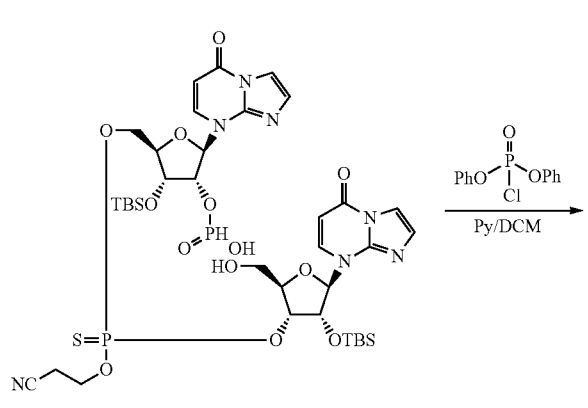

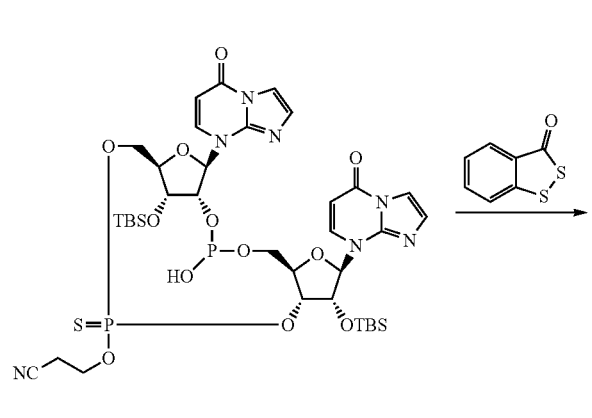

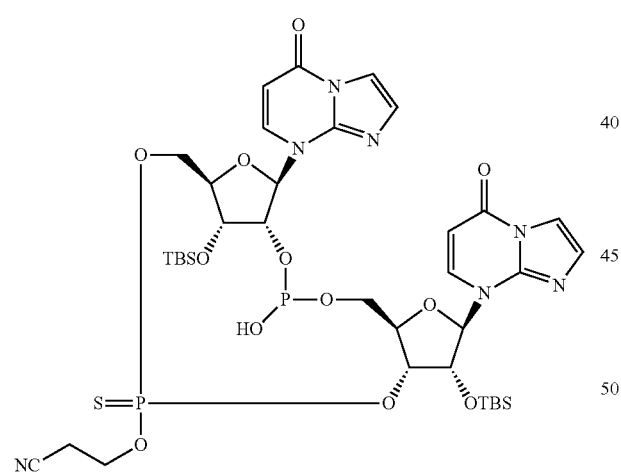

To Py (30 mL) at −40° C. under Ar was added diphenyl phosphorochloridate (1.65 g, 6.15 mmol) and a solution of (2R,3R,4R,5R)-4-((tert-butyldimethylsilyl)oxy)-S-((((((2R,3R,4R, 5R)-4-((tert-butyldimethylsilyl)oxy)-2-(hydroxymethyl)-S-(5-oxoimidazo[1,2-a]pyrimidin-8(5H)-yl)tetrahydrofuran-3-yl)oxy)(2-cyanoethoxy)phosphorothioyl)oxy)methyl)-2-(5-oxoimidazo[1,2-a]pyrimidin-8(5H)-yl)tetrahydrofuran-3-yl hydrogen phosphonate (0.30 g, 0.31 mmol) in DCM (30 mL) drop-wise over 5 min. It was stirred at −40° C. for 30 min. The reaction mixture was used for the next reaction step immediately without purification. LCMS (ES, m/z): 940.3 [M+H]⁺.

To the mixture from Step 5 at −40° C. was added 3H-benzo[c][1,2]dithiol-3-one (78 mg, 0.46 mmol). It was warmed to RT and stirred for 40 min. The mixture was concentrated and purified by reverse phase (C18) chromatography eluted with 0 to 95% ACN in aq NH₄HCO₃ (5 mM) to give the product. LCMS (ES, m/z): 972.3 [M+H]⁺. ³¹P-NMR: (121 MHz, CD₃OD) δ 67.71-64.65 (m), 62.22-53.56 (m).

Step 7: 8,8'-[(5R,7R,8R,12aR,14R,15R,15aR,16R)-15,16-bis{[tert-butyl(dimethyl) silyl]oxy}-2,10-dioxido-2,10-disulfanyloctahydro-12H-5,8-methanofuro[3,2-l][1,3,6,9,11,2,10] pentaoxadiphosphacyclotetradecine-7,14-diyl] bisimidazo[1,2-a]pyrimidin-5(8H)-one

Step 8: 8,8'-[(5R,7R,8R,12aR,14R,15R,15aS,16R)-15,16-dihydroxy-2,10-dioxido-2,10-disulfanyloctahydro-12H-5,8-methanofuro[3,2-l][1,3,6,9,11,2,10] pentaoxadiphosphacyclotetradecine-7,14-diyl] bisimidazo[1,2-a]pyrimidin-5(8H)-one

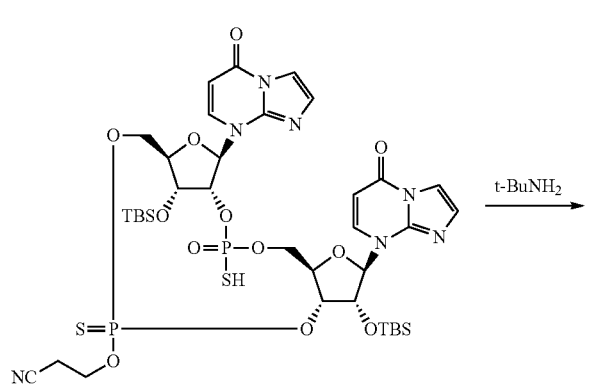

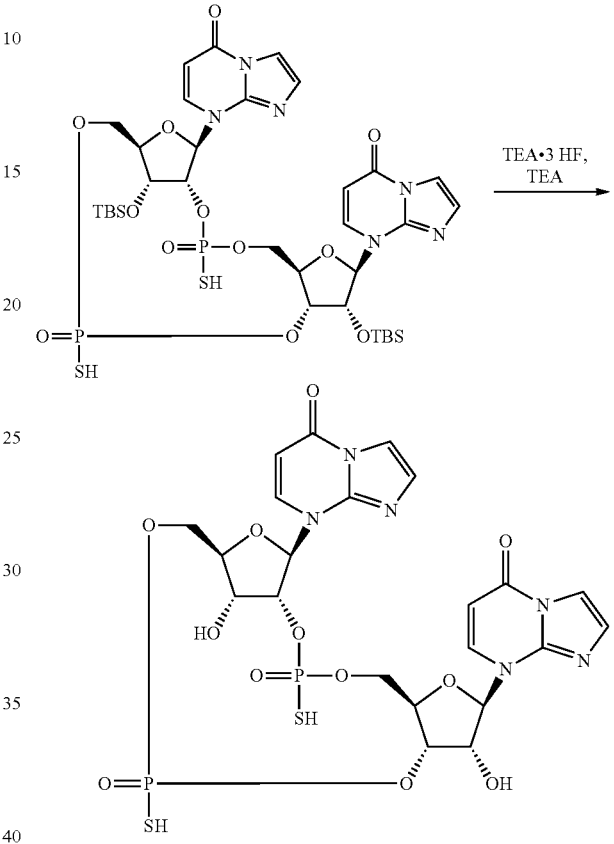

3-{[(5R,7R,8R,12aR,14R,15R,15aR,16R)-15,16-bis{[tert-butyl(dimethyl)silyl]oxy}-10-oxido-7,14-bis(5-oxo-imidazo[1,2-a]pyrimidin-8(5H)-yl)-10-sulfanyl-2-sulfi-doocta-hydro-12H-5,8-methanofuro[3,2-l][1,3,6,9,11,2,10]pentaoxadiphosphacyclotetra-decin-2-yl]oxy}propanenitrile (0.25 g, 0.21 mmol) was dissolved in MeCN (5 mL) and t-BuNH₂ (10 mL, 94 mmol) was added. It was stirred at RT for 1 h. Then, the solution was concentrated and the residue was purified by reverse phase (C18) chromatography eluted with 0 to 95% ACN in aq NH₄HCO₃ (5 mM) over 55 min to give the product ($T_R$=43 min). LCMS (ES, m/z): 919.3 [M+H]⁺. ¹H NMR (400 MHz, CD₃OD): δ 8.87 (d, J=7.9 Hz, 1H), 8.51 (d, J=7.8 Hz, 1H), 7.63 (dd, J=16.2, 1.7 Hz, 2H), 7.20 (dd, J=28.2, 1.7 Hz, 2H), 6.66 (d, J=8.3 Hz, 1H), 6.16 (d, J=3.2 Hz, 1H), 5.81 (dd, J=15.7, 7.9 Hz, 2H), 5.31-5.07 (m, 2H), 4.95-4.91 (m, 1H), 4.75-4.72 (m, 1H), 4.57-4.53 (m, 1H), 4.45-4.41 (m, 1H), 4.32-4.21 (m, 2H), 4.18-4.14 (m, 1H), 3.95-3.91 (m, 1H), 1.05-0.91 (m, 18H), 0.34-0.11 (m, 12H). ³¹P-NMR: (162 MHz, CD₃OD) δ 57.80 (s), 57.12 (s).

To a suspension of 8,8'-[(5R,7R,8R,12aR,14R,15R,15aR,16R)-15,16-bis{[tert-butyl(dimethyl)silyl]oxy}-2,10-dioxido-2,10-disulfanyloctahydro-12H-5,8-methanofuro[3,2-l][1,3,6,9,11,2,10]pentaoxadiphosphacyclotetradecine-7,14-diyl]bisimidazo[1,2-a]pyrimidin-5(8H)-one (38 mg, 0.040 mmol) in Py (0.2 mL) was added Et₃N.3HF (0.64 g, 4.0 mmol) and TEA (0.83 mL, 6.0 mmol). The mixture was heated at 50° C. for 3 h. Then, it was concentrated, and acetone (0.6 mL) and ethoxytrimethylsilane (3.7 mL) were added. The mixture was stirred at 0° C. for 30 min, and the resulting solid was collected by filtration and purified by reverse phase (AQ C18) chromatography eluted with 0 to 95% ACN in aq NH₄HCO₃ (5 mM) over 58 min to give the product ($T_R$=36 min). LCMS (ES, m/z): 690.8 [M+H]⁺. ¹H NMR (400 MHz, D₂O): δ 8.30 (d, J=7.9 Hz, 1H), 8.13 (d, J=7.9 Hz, 1H), 7.70-7.49 (m, 2H), 7.37-7.14 (m, 2H), 6.47 (d, J=8.1 Hz, 1H), 6.02 (s, 1H), 5.45 (d, J=7.8 Hz, 1H), 5.25 (d, J=7.9 Hz, 1H), 5.08-4.91 (m, 2H), 4.70-4.65 (m, 2H), 4.55-4.39 (m, 3H), 4.33-4.28 (m, 2H), 4.13-4.06 (m, 1H). ³¹P-NMR: (162 MHz, D₂O) δ 55.16 (s), 52.14 (s).

Example 31, as shown in Table 3 below, were prepared according to procedures analogous to those outlined in Example 30 above using the appropriate monomers, described as Preparations or as obtained from commercial sources, in the coupling step.

TABLE 3

| Ex. | Structure | Name | Mass [M + H]+ |
|---|---|---|---|
| 31 | 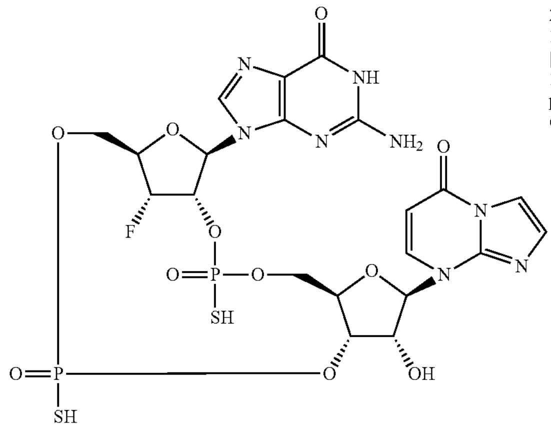 [SMILES: Nc1nc2c(ncn2[C@@H]2O[C@@H]3COP(=O)(S)O[C@H]4[C@@H](O)[C@H](n5ccc(=O)n6ccnc56)O[C@@H]4COP(=O)(S)O[C@@H]2[C@@H]3F)c(=O)[nH]1] | 2-amino-9-[(5R,7R,8S,12aR,14R,15R,15aS,16R)-16-fluoro-15-hydroxy-2,10-dioxido-14-(5-oxoimidazo[1,2-a]pyrimidin-8(5H)-yl)-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one | 709 |

Examples 32 and 33: 1-[(5R,7R,8S,12aR,14R,15R,15aS,16R)-7-(2-amino-6-oxo-1,6-dihydro-9H-purin-9-yl)-16-fluoro-15-hydroxy-2,10-dioxido-2,10-disulfanyl-octahydro-12H-5,8-methanofuro[3,2-l][1,3,6,9,11,2,10]pentaoxadiphosphacyclotetradecin-14-yl]-1H-imidazo[2,1-b]purin-4(5H)-one (Diastereomer 1) and 1-[(5R,7R,8S,12aR,14R,15R,15aS,16R)-7-(2-amino-6-oxo-1,6-dihydro-9H-purin-9-yl)-16-fluoro-15-hydroxy-2,10-dioxido-2,10-disulfanylocta-hydro-12H-5,8-methanofuro[3,2-l][1,3,6,9,11,2,10]pentaoxa-diphosphacyclotetradecin-14-yl]-1H-imidazo[2,1-b]purin-4(5H)-one (Diastereomer 2)

Diastereomer 1

Diastereomer 2

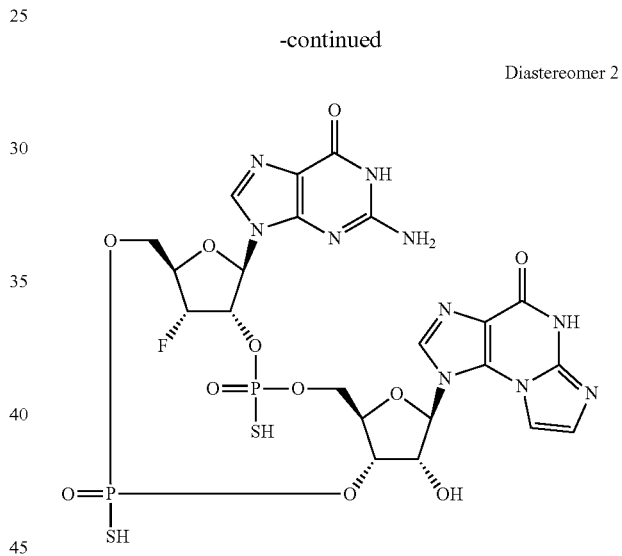

Step 1: (2R,3R,4S,5R)-2-(4-(benzyloxy)-1H-imidazo[2,1-b]purin-1-yl)-5-((bis(4-methoxyphenyl)(phenyl)methoxy)methyl)tetrahydrofuran-3,4-diol

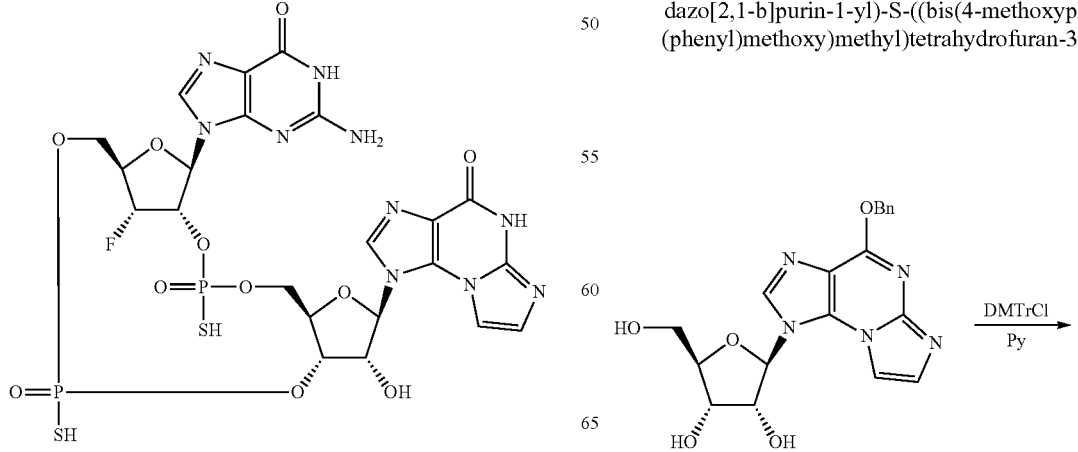

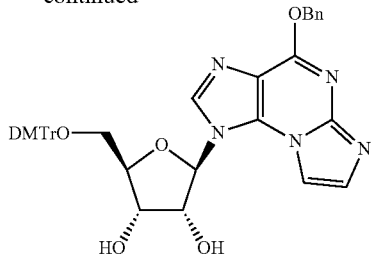

To a stirred solution of (2R,3R,4S,5R)-2-(4-(benzyloxy)-1H-imidazo[2,1-b]purin-1-yl)-5-(hydroxymethyl)tetrahydrofuran-3,4-diol (1.27 g, 3.20 mmol) in Py (25 mL) under Ar were added N-ethyl-N-isopropylpropan-2-amine (1.06 mL, 6.39 mmol) and DMTrCl (1.62 g, 4.79 mmol). The resulting mixture was stirred at RT for 2 h. Then, MeOH (2 mL) was added. It was concentrated and purified by silica gel column chromatography eluted with 0 to 5.6% MeOH in DCM to give the product. LCMS (ES, m/z): 700.4 [M+H]$^+$. $^1$H-NMR (400 MHz, DMSO-d$_6$): δ 8.35 (s, 1H), 8.07 (d, J=1.7 Hz, 1H), 7.58-7.48 (m, 3H), 7.45-7.33 (m, 3H), 7.14-7.06 (m, 5H), 7.04-6.95 (m, 4H), 6.73-6.62 (m, 4H), 6.30 (d, J=2.0 Hz, 1H), 5.98 (d, J=5.0 Hz, 1H), 5.61-5.47 (m, 2H), 5.28 (d, J=7.2 Hz, 1H), 4.90-4.81 (m, 1H), 4.39 (td, J=7.2, 4.5 Hz, 1H), 4.19 (dt, J=7.0, 3.3 Hz, 1H), 3.68, 3.67 (2 s, 6H), 3.25 (dd, J=11.1, 2.3 Hz, 1H), 2.95 (dd, J=10.8, 3.8 Hz, 1H).

Step 2: 1-((2R,3R,4S,5R)—5-((bis(4-methoxyphenyl)(phenyl)methoxy)methyl)-3,4-dihydroxytetrahydrofuran-2-yl)-1H-imidazo[2,1-b]purin-4(5H)-one

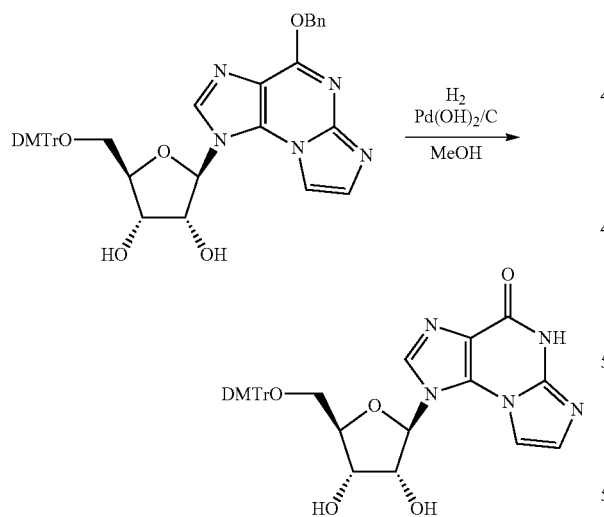

To a solution of (2R,3R,4S,5R)-2-(4-(benzyloxy)-1H-imidazo[2,1-b]purin-1-yl)-5-((bis(4-methoxyphenyl)(phenyl)methoxy)methyl)tetrahydrofuran-3,4-diol (1.00 g, 1.43 mmol) in MeOH (20 mL) and EtOAc (10 mL) was added Pd(OH)$_2$/C (0.22 g). The mixture was charged with H$_2$ (2 atm) and stirred at 40° C. for 30 h. It was filtered, and the filtrate was concentrated. The crude was purified by reverse phase (AQ-C18) chromatography eluted with 0 to 95% ACN in aq NH$_4$HCO$_3$ (5 mM) to give the product. LCMS (ES, m/z): 610.3 [M+H]$^+$. $^1$H-NMR (400 MHz, DMSO-d$_6$): δ 11.53 (br s, 1H), 8.22 (s, 1H), 7.79 (d, J=1.8 Hz, 1H), 7.26-7.11 (m, 6H), 7.09-7.01 (m, 4H), 6.80-6.66 (m, 4H), 6.18 (d, J=2.0 Hz, 1H), 5.99 (s, 1H), 5.29 (d, J=7.5 Hz, 1H), 4.82 (d, J=4.5 Hz, 1H), 4.38 (q, J=5.8, 5.3 Hz, 1H), 4.18 (dt, J=6.8, 3.1 Hz, 1H), 3.73 (s, 3H), 3.72 (s, 3H), 3.27 (dd, J=10.9, 2.5 Hz, 1H), 2.96 (dd, J=10.9, 3.8 Hz, 1H).

Step 3: 1-((2R,3R,4R,5R)—5-((bis(4-methoxyphenyl)(phenyl)methoxy)methyl)-4-hydroxy-3-((triisopropylsilyl)oxy)tetrahydrofuran-2-yl)-1H-imidazo[2,1-b]purin-4(5H)-one

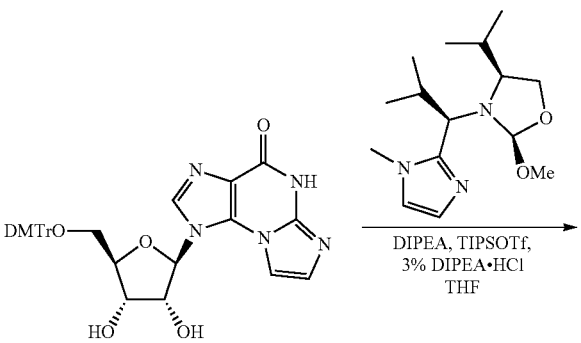

To a solution of 1-((2R,3R,4S,5R)—5-((bis(4-methoxyphenyl)(phenyl)methoxy) methyl)-3,4-dihydroxytetrahydrofuran-2-yl)-1H-imidazo[2,1-b]purin-4(5H)-one (0.37 g, 0.60 mmol) in THF (6 mL) were added (2R,4S)-4-isopropyl-2-methoxy-3-((R)-2-methyl-1-(1-methyl-1H-imidazol-2-yl)propyl)oxazolidine (0.068 g, 0.240 mmol), DiPEA.HCl (3.0 mg, 0.018 mmol), and DiPEA (0.491 mL, 2.82 mmol). The mixture was stirred at RT for 5 min and then cooled to 0° C. To the mixture was added TIPSOTf (0.70 mL, 2.6 mmol) over 2 min. It was stirred at RT for 2 h. Then, the mixture was concentrated, and EtOAc (50 mL) and aq NaHCO$_3$ (5%, 30 mL) were added. Layers were separated, and the organic layer was washed with aq NaHCO$_3$ (5%, 30 mL), dried (Na$_2$SO$_4$) and concentrated. The crude product was used for next step directly. LCMS (ES, m/z): 766.3 [M+H]$^+$.

Step 4: (2R,3R,4R,5R)-2-((bis(4-methoxyphenyl)(phenyl)methoxy)methyl)-S-(4-oxo-4,5-dihydro-1H-imidazo[2,1-b]purin-1-yl)-4-((triisopropylsilyl)oxy)tetrahydrofuran-3-yl phenyl phosphonate

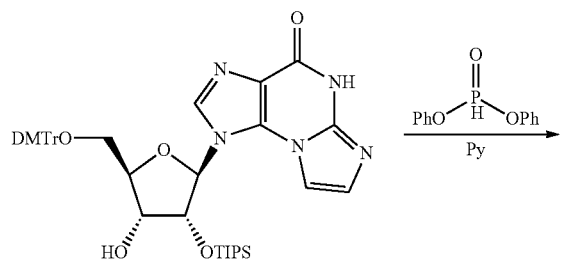

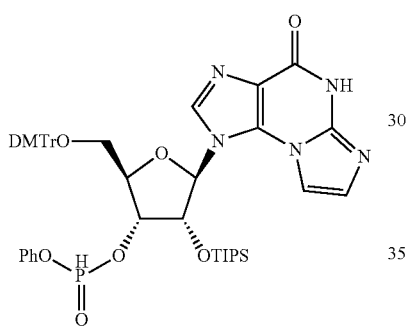

To a solution of crude from Step 3 in Py (4 mL) under Ar was added diphenyl phosphonate (0.58 mL, 3.0 mmol), and the reaction was stirred at RT for 20 min. It was used for the next reaction step without purification. LCMS (ES, m/z): 906.2 [M+H]⁺.

Step 5: (2R,3R,4R,5R)-2-((bis(4-methoxyphenyl)(phenyl)methoxy)methyl)-S-(4-oxo-4,5-dihydro-1H-imidazo[2,1-b]purin-1-yl)-4-((triisopropylsilyl)oxy)tetrahydrofuran-3-yl hydrogen phosphonate

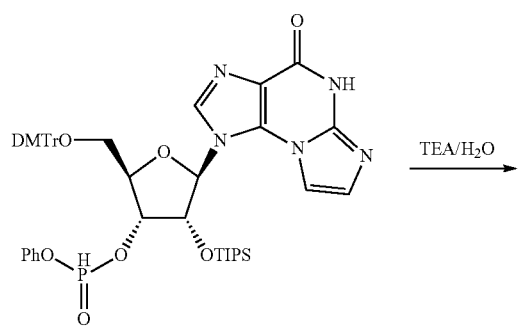

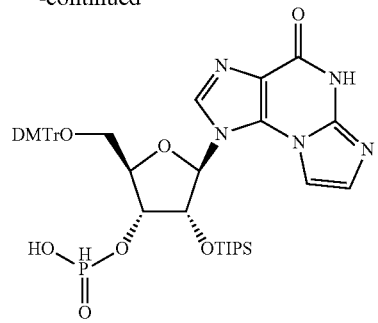

To the reaction mixture from Step 4 at 0° C. was added H₂O (2 mL) and TEA (2 mL). It was stirred at RT for 20 min. Then, it was concentrated, and the residue was purified by reverse phase (AQ-C18) chromatography eluted with 0 to 95% ACN in aq NH₄HCO₃ (5 mM) to give the product. LCMS (ES, m/z): 830.2 [M+H]⁺. ¹H-NMR (400 MHz, DMSO-d₆): δ 12.34 (br s, 1H), 7.99 (s, 1H), 7.69 (s, 1H), 7.34 (s, 0.5H), 7.20-7.12 (m, 6H), 7.06-7.02 (m, 4H), 6.75-6.71 (m, 4H), 6.14 (d, J=3.7 Hz, 1H), 5.88 (s, 0.5H), 4.99 (s, 1H), 4.89-4.74 (m, 1H), 4.37 (d, J=5.7 Hz, 1H), 3.70-3.69 (m, 6H), 3.30-3.28 (m, 1H), 3.06-3.02 (m, 1H), 1.10-0.84 (m, 21H). ³¹P-NMR: (162 MHz, DMSO-d₆) δ 1.13 (s, 1P).

Step 6: (2R,3R,4R,5R)-2-(hydroxymethyl)-S-(4-oxo-4,5-dihydro-1H-imidazo[2,1-b]purin-1-yl)-4-((triisopropylsilyl)oxy)tetrahydrofuran-3-yl hydrogen phosphonate

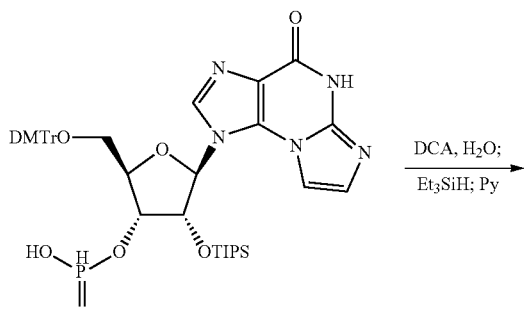

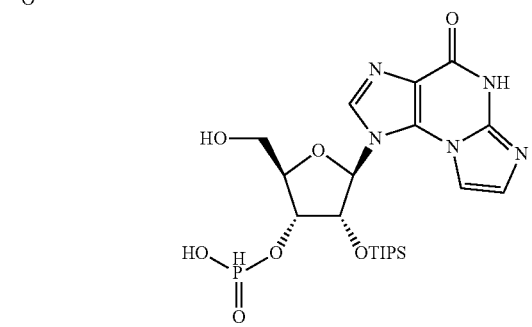

To a solution of (2R,3R,4R,5R)-2-((bis(4-methoxyphenyl)(phenyl)methoxy) methyl)-S-(4-oxo-4,5-dihydro-1H-imidazo[2,1-b]purin-1-yl)-4-((triisopropylsilyl)oxy) tetrahydrofuran-3-yl hydrogen phosphonate (290 mg, 0.342 mmol) in DCM (5.1 mL) at RT was added H₂O (62 mg, 3.4 mmol) and DCA in DCM (5%, 5.1 mL, 3.1 mmol). It was stirred for 15 min, and then Et₃SiH (5 mL) was added. After 1 h, Py (0.2 mL) was added, and the mixture was stirred for 5 min. Then, it was concentrated, and the residue was used for the next reaction step without purification. LCMS (ES, m/z): 528.2 [M+H]⁺.

Step 7: (2R,3R,4R,5R)-2-((((2-cyanoethoxy)(((2R, 3S,4R,5R)-4-fluoro-5-(hydroxymethyl)-2-(2-isobutyramido-6-oxo-1,6-dihydro-9H-purin-9-yl)tetrahydrofuran-3-yl)oxy)phosphanyl)oxy)methyl)-5-(4-oxo-4,5-dihydro-1H-imidazo[2,1-b]purin-1-yl)-4-((triisopropylsilyl)oxy)tetrahydrofuran-3-yl hydrogen phosphonate

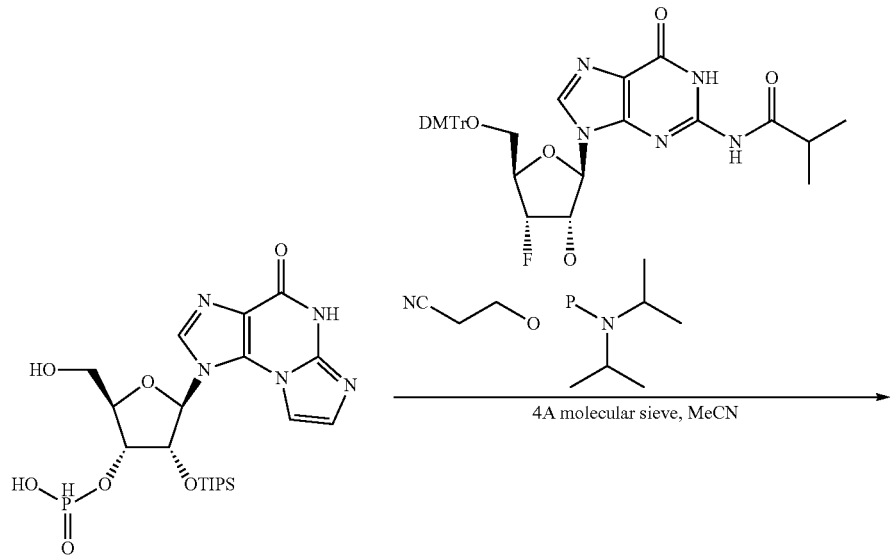

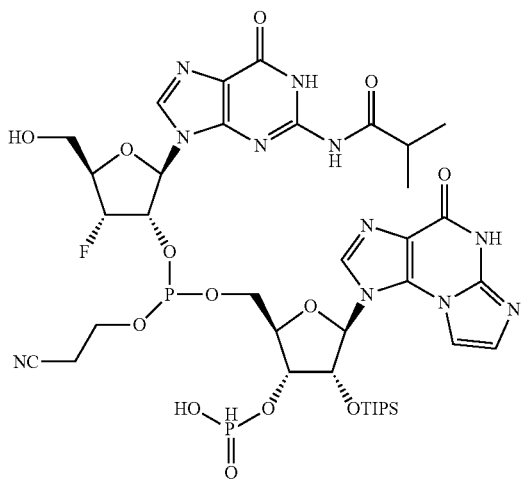

(2R,3S,4R,5R)—S-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl (2-cyanoethyl) diisopropyl-phosphoramidite (0.32 g, 0.38 mmol) was co-evaporated with MeCN (3×3 mL) and re-dissolved in MeCN (3 mL). Activated 4 Å molecular sieve (100 mg) was added. (2R,3R,4R,5R)-2-(hydroxyl-methyl)-5-(4-oxo-4,5-dihydro-1H-imidazo[2,1-b]purin-1-yl)-4-((triisopropylsilyl)oxy) tetrahydrofuran-3-yl hydrogen phosphonate (crude, 0.89 g, 0.34 mmol) was co-evaporated with MeCN (3×5 mL) and re-suspended in MeCN (8 mL) under Ar. Activated 4 Å molecular sieve (100 mg) was added. After 30 min, to the mixture was added the mixture containing (2R,3S,4R, 5R)—S-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl (2-cyanoethyl) diisopropylphosphoramidite, and it was stirred at RT for 15 min. Then, the reaction mixture was used for the next reaction step without purification. LCMS (ES, m/z): 980.1 [M−H]⁻.

Step 8: (2R,3R,4R,5R)-2-((((2-cyanoethoxy)(((2R,3S,4R,5R)-4-fluoro-5-(hydroxymethyl)-2-(2-isobutyramido-6-oxo-1,6-dihydro-9H-purin-9-yl)tetrahydrofuran-3-yl) oxy)phosphorothioyl)oxy)methyl)-5-(4-oxo-4,5-dihydro-1H-imidazo[2,1-b]purin-1-yl)-4-((triisopropylsilyl)oxy)tetrahydrofuran-3-yl hydrogen phosphonate

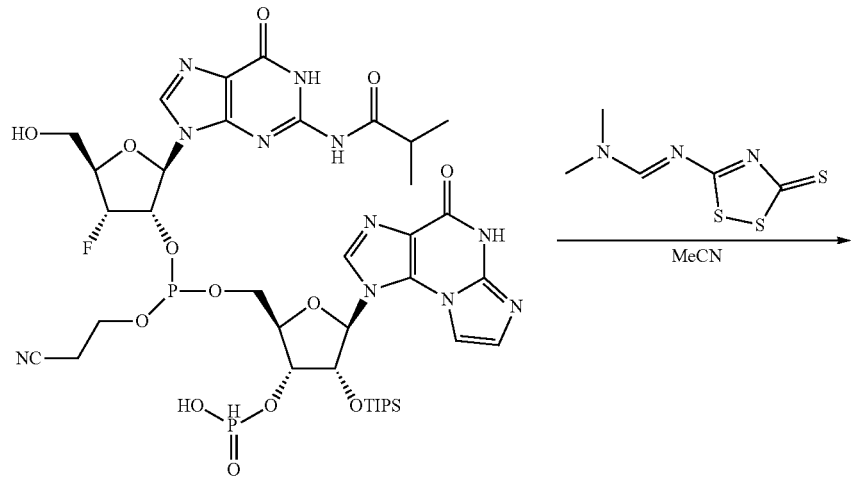

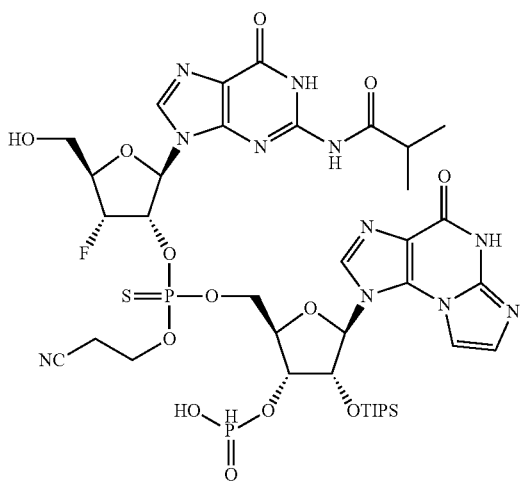

To the reaction mixture from Step 7 was added (E)-N,N-dimethyl-N'-(3-thioxo-3H-1,2,4-dithiazol-5-yl)formimidamide (77 mg, 0.38 mmol), and the mixture was stirred at RT for 1 h. It was concentrated, and the residue was purified by reverse phase (C18) chromatography eluted with 0 to 95% ACN in aq NH$_4$HCO$_3$ (5 mM) to give the product. LCMS (ES, m/z): 1014.3 [M+H]$^+$. $^1$H-NMR (400 MHz, CD$_3$OD): δ 8.35 (d, J=8.6 Hz, 1H), 8.23-8.06 (m, 1H), 7.86 (s, 0.5H), 7.76 (d, J=14.0 Hz, 1H), 7.23 (d, J=17.0 Hz, 1H), 6.44-6.11 (m, 2.5H), 5.59-5.55 (m, 1H), 5.50-5.26 (m, 1H), 4.71 (d, J=5.5 Hz, 1H), 4.62-4.17 (m, 5H), 4.12-3.75 (m, 3H), 3.08-2.51 (m, 3H), 1.29-1.13 (m, 6H), 0.98-0.88 (m, 21H). $^{31}$P-NMR: (162 MHz, CD$_3$OD) δ 67.45-66.89 (m); 3.97-3.90 (m).

Step 9: N-(9-{(5R,7R,8S,12aR,14R,15R,15aR,16R)-10-(2-cyanoethoxy)-16-fluoro-2-hydroxy-14-(4-oxo-4,5-dihydro-1H-imidazo[2,1-b]purin-1-yl)-10-sulfido-15-[(tripropan-2-yl)silyl)oxy]octahydro-12H-5,8-methanofuro[3,2-l][1,3,6,9,11,2,10]pentaoxadiphosphacyclo-tetradecin-7-yl}-6-oxo-6,9-dihydro-1ll-purin-2-yl)-2-methylpropanamide Step 10: N-(9-{(5R,7R,8S,12aR,14R,15R,15aR,16R)-10-(2-cyanoethoxy)-16-fluoro-2-oxido-14-(4-oxo-4,5-dihydro-1H-imidazo[2,1-b]purin-1-yl)-2-sulfanyl-10-sulfido-15-[(tripropan-2-ylsilyl)oxy]octahydro-12H-5,8-methanofuro[3,2-l][1,3,6,9,11,2,10]pentaoxa-diphosphacyclotetradecin-7-yl}-6-oxo-6,9-dihydro-1H-purin-2-yl)-2-methylpropanamide

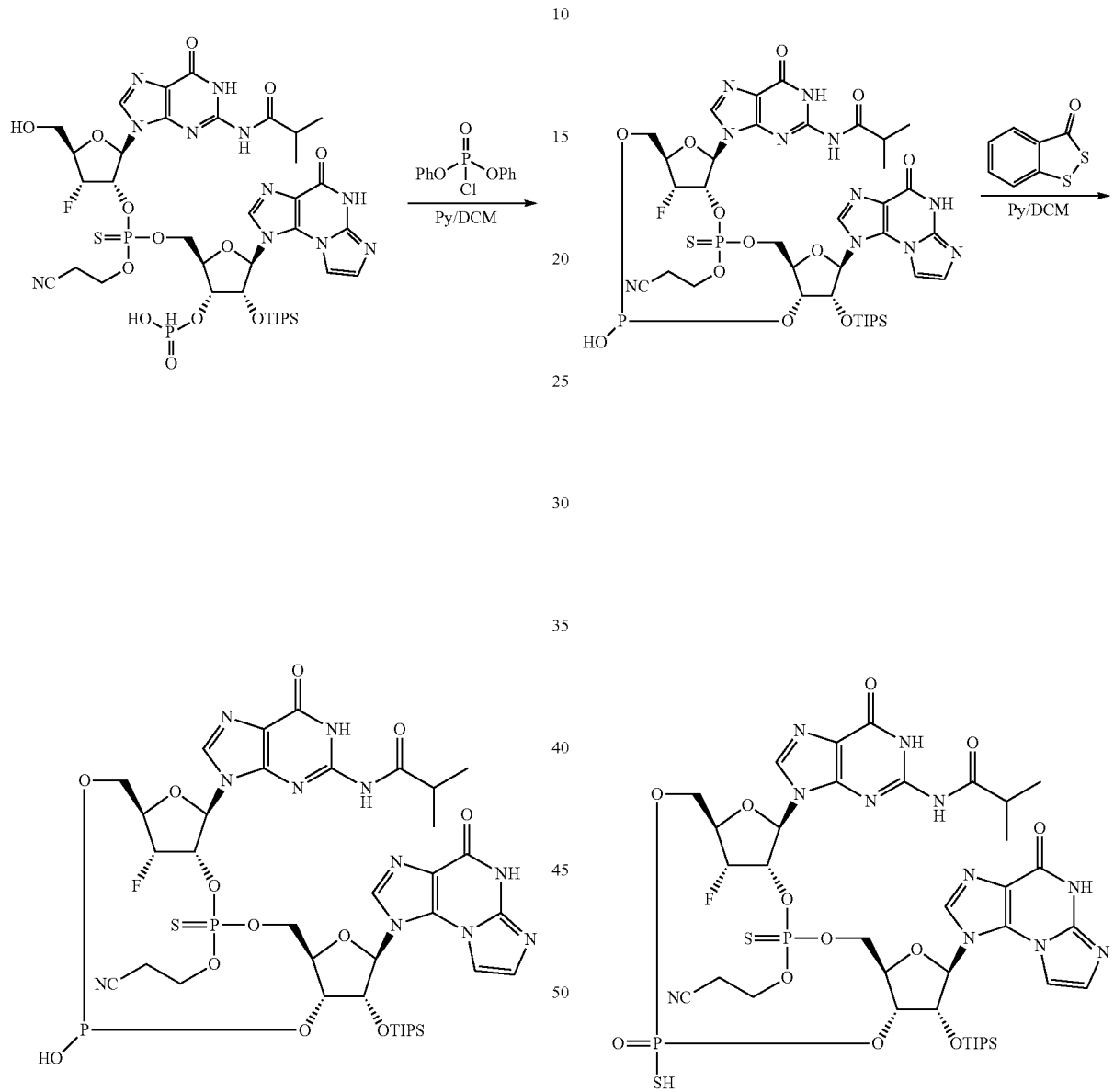

To Py (3.5 mL) and DCM (3.5 mL) at −40° C. under Ar was added diphenyl phosphorochloridate (0.285 mL, 1.38 mmol), and a solution of (2R,3R,4R,5R)-2-((((2-cyanoethoxy)(((2R,3 S,4R,5R)-4-fluoro-5-(hydroxymethyl)-2-(2-isobutyramido-6-oxo-1,6-dihydro-9H-purin-9-yl)tetrahydrofuran-3-yl)oxy)phosphorothioyl)oxy)methyl)-5-(4-oxo-4,5-dihydro-1H-imidazo[2,1-b]purin-1-yl)-4-((triisopropylsilyl)oxy)tetrahydrofuran-3-yl hydrogen phosphonate (71 mg, 0.069 mmol) in Py (3.5 mL) and DCM (3.5 mL). It was stirred at −40° C. for 30 min. Then, the reaction mixture was used for the next step without purification. LCMS (ES, m/z): 996.4 [M+H]+.

To the reaction mixture from Step 9 at −40° C. was added 3H-benzo[c][1,2]dithiol-3-one (17.4 mg, 0.104 mmol). The reaction was stirred at rt for 2 h, and then MeOH (1 mL) was added. It was concentrated and purified by reverse phase (AQ-C18) chromatography eluted with 0 to 95% ACN in aq $NH_4HCO_3$ (5 mM) to give the product. LCMS (ES, m/z): 1028.4 [M+H]+. $^1$H-NMR (400 MHz, $CD_3OD$): δ 8.57-8.02 (m, 2H), 7.99-7.55 (m, 1H), 7.56-7.12 (m, 7H), 6.50-6.08 (m, 2H), 5.65-4.95 (m, 6H), 4.72-4.18 (m, 5H), 4.13-3.56 (m, 3H), 2.95-2.65 (m, 3H), 1.45-0.73 (m, 24H). $^{31}$P-NMR: (162 MHz, $CD_3OD$) δ 67.53-63.91 (m), 58.62-55.15 (m).

Step 11: 1-{(5R,7R,8S,12aR,14R,15R,15aR,16R)-7-(2-amino-6-oxo-1,6-dihydro-9H-purin-9-yl)-16-fluoro-2,10-dioxido-2,10-disulfanyl-15-[(tripropan-2-ylsilyl)oxy]octahydro-12H-5,8-methanofuro[3,2-l][1,3,6,9,11,2,10]pentaoxadiphosphacyclotetradecin-14-yl}-1H-imidazo[2,1-b]purin-4(5H)-one Step 12: 1-[(5R,7R,8S,12aR,14R,15R,15aS,16R)-7-(2-amino-6-oxo-1,6-dihydro-9H-purin-9-yl)-16-fluoro-15-hydroxy-2,10-dioxido-2,10-disulfanyloctahydro-12H-5,8-methanofuro[3,2-l][1,3,6,9,11,2,10]pentaoxadiphosphacyclotetradecin-14-yl]-1H-imidazo[2,1-b]purin-4(5H)-one (Diastereomer 1-2)

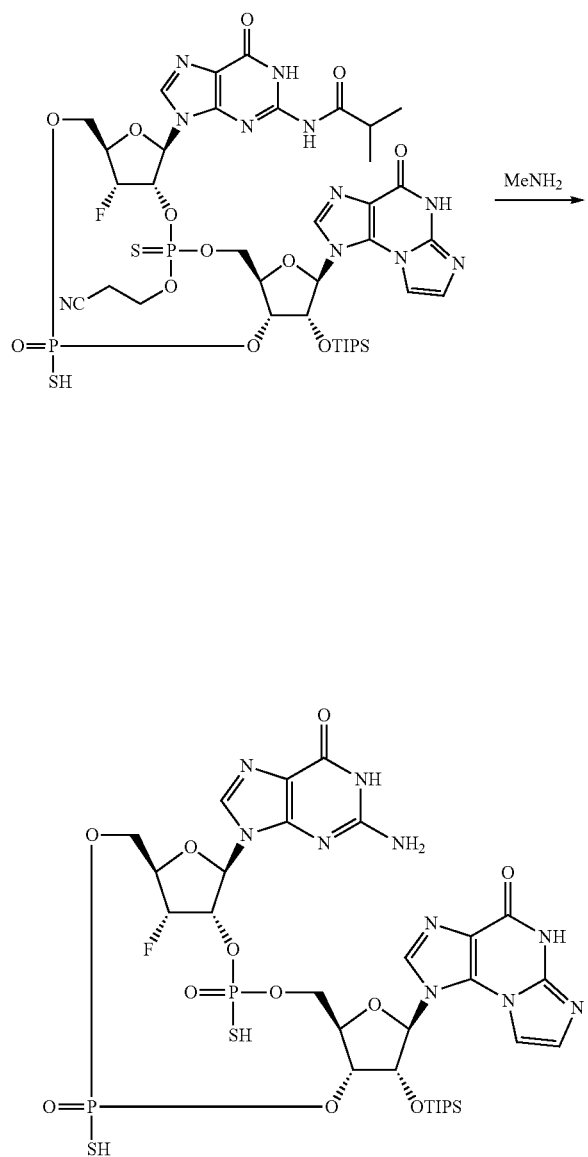

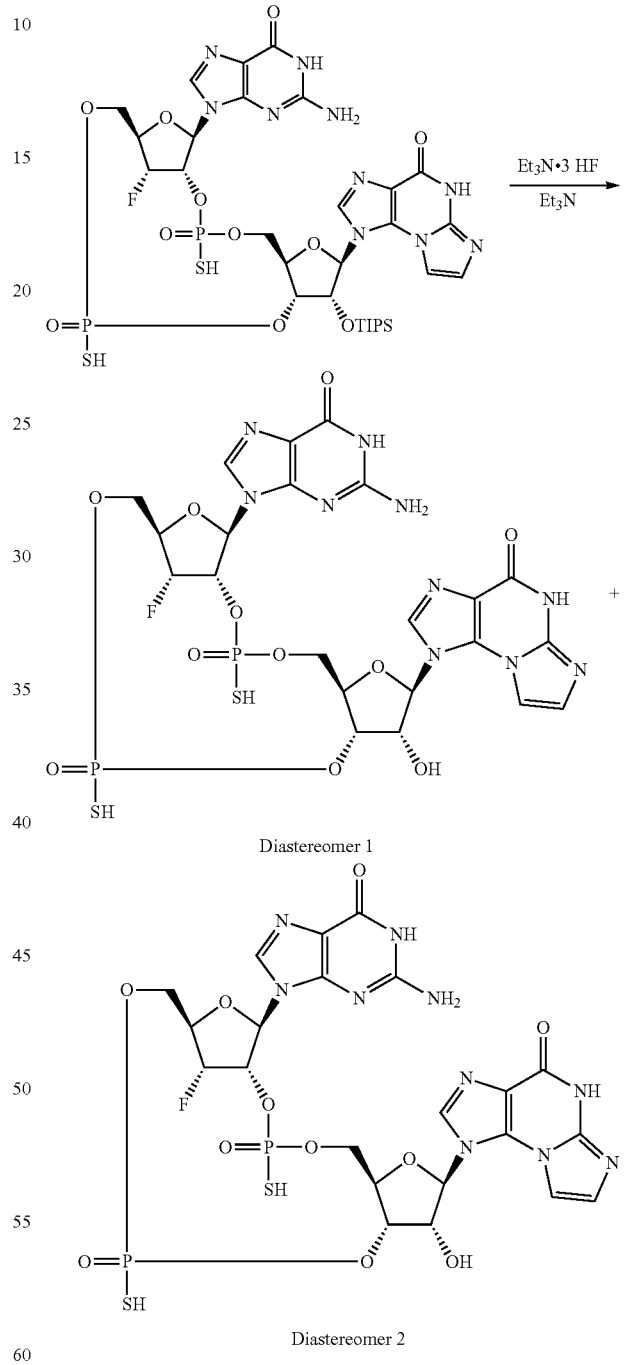

N-(9-{(5R,7R,8S,12aR,14R,15R,15aR,16R)-10-(2-cyanoethoxy)-16-fluoro-2-oxido-14-(4-oxo-4,5-dihydro-1H-imidazo[2,1-b]purin-1-yl)-2-sulfanyl-10-sulfido-15-[(tripropan-2-ylsilyl)oxy]octahydro-12H-5,8-methanofuro[3,2-l][1,3,6,9,11,2,10]pentaoxadi-phosphacyclotetradecin-7-yl}-6-oxo-6,9-dihydro-1H-purin-2-yl)-2-methylpropanamide (57 mg, 0.055 mmol) was dissolved in MeNH$_2$ in EtOH (30%, 3.2 mL, 22 mmol), and it was stirred at RT for 3 h. Then, it was concentrated, and the crude product was used for the next reaction step without purification. LCMS (ES, m/z): 905.3 [M+H]$^+$.

To a solution of the crude from Step 11 in Py (0.12 mL) under Ar were added TEA (0.76 mL, 5.5 mmol) and TEA.3HF (0.45 mL, 2.7 mmol). The mixture was stirred at 50° C. for 15 h. Then, it was cooled to RT, and acetone (5.5 mL) and ethoxytrimethylsilane (2.6 mL, 17 mmol) were added. After stirring for 30 min, precipitates formed, and the reaction mixture was purified by prep-HPLC (XBridge Shield RP18 OBD Column, 19 mm×250 mm) eluted with 5 to 15% ACN in aq NH$_4$HCO$_3$ (10 mM) over 20 min to provide two peaks (T$_R$: 13.53 and 16.58 min) with matching mass (LCMS (ES, m/z): 749.0 [M+H]$^+$). Fractions at T$_R$=13.53 were further purified by reverse phase chromatography (AQ-C18) eluted with 0 to 95% ACN in aq NH$_4$HCO$_3$ (5 mM) to give the product. Example 32 (diastereomer 1): LCMS (ES, m/z): 749.0 [M+H]$^+$. $^1$H-NMR: (400 MHz, D$_2$O): δ 8.12 (s, 1H), 7.86 (s, 1H), 7.61 (d, J=2.4 Hz, 1H), 7.22 (d, J=2.3 Hz, 1H), 6.35 (d, J=1.6 Hz, 1H), 5.99 (d, J=8.6 Hz, 1H), 5.88-5.72 (m, 1H), 5.46 (dd, J=53.5, 3.4 Hz, 1H), 5.19 (td, J=8.6, 4.7 Hz, 1H), 4.56-4.40 (m, 4H), 4.14-4.00 (m, 2H). $^{31}$P-NMR: (162 MHz, D$_2$O): δ 55.37 (s), 52.33 (s). Fractions at T$_R$=16.58 were further purified by reverse phase chromatography (AQ-C18) eluted with 0 to 95% ACN in aq NH$_4$HCO$_3$ (5 mM) to give the product. Example 33 (diastereomer 2): LCMS (ES, m/z): 749.0 [M+H]$^+$. $^1$H-NMR: (400 MHz, D$_2$O): δ 8.26 (s, 1H), 7.89 (s, 1H), 7.65 (d, J=2.4 Hz, 1H), 7.26 (d, J=2.4 Hz, 1H), 6.33 (d, J=2.5 Hz, 1H), 6.01 (d, J=8.5 Hz, 1H), 5.93-5.72 (m, 1H), 5.44-5.20 (m, 2H), 4.81 (dd, J=4.7, 2.6 Hz, 1H), 4.55-4.34 (m, 4H), 4.05 (t, J=12.7 Hz, 2H). $^{31}$P-NMR: (162 MHz, D$_2$O): δ 55.75 (s), 55.64 (s).

Example 34: 8-[(5R,7R,8R,12aR,14R,15aS,16R)-14-(4-amino-1H-pyrrolo[2,3-b]pyridin-1-yl)-16-hydroxy-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one

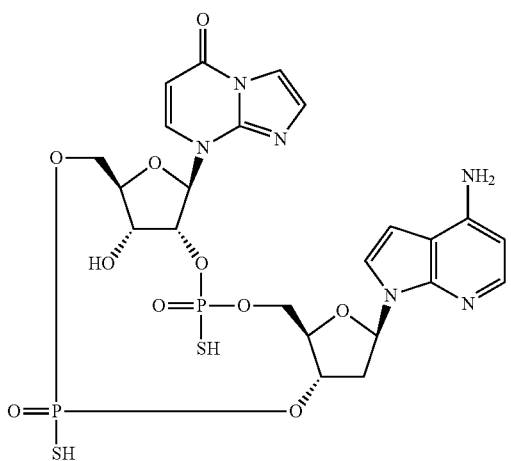 [SMILES: Nc1ccnc2c1ccn2[C@H]1C[C@@H]2OP(=O)(S)OC[C@H]3O[C@@H](n4ccc(=O)n5ccnc45)[C@H](OP(=O)(S)OC[C@H]2O1)[C@@H]3O]

Step 1: (Z)—N'-(1-((2R,4S,5R)-4-hydroxy-5-(hydroxymethyl)tetrahydrofuran-2-yl)-1H-pyrrolo[2,3-b]pyridin-4-yl)-N,N-dimethylformimidamide

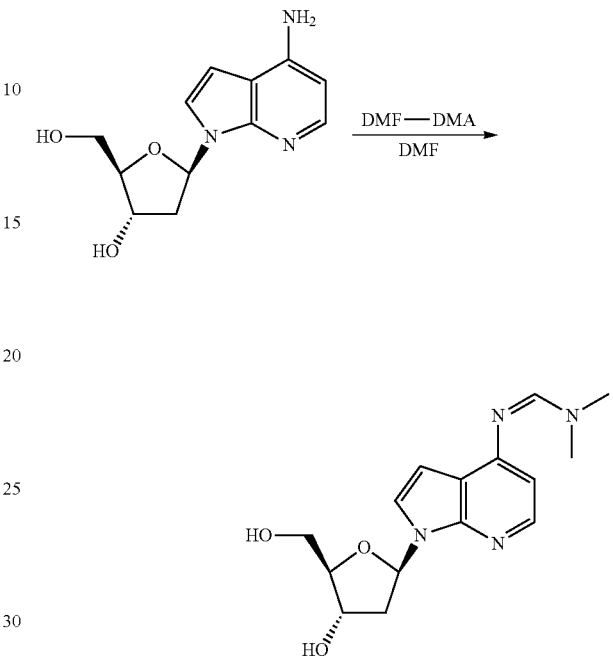

To a solution of (2R,3S,5R)—5-(4-amino-1H-pyrrolo[2,3-b]pyridin-1-yl)-2-(hydroxymethyl)tetrahydrofuran-3-ol (0.14 mg, 0.56 mmol) in DMF (2 mL) was added DMF-DMA (1.0 g, 8.4 mmol). The resulting mixture was stirred at 40° C. for 12 h. Then, it was concentrated and the residue was purified by column chromatography eluted with 0% to 10% MeOH in DCM to give the product. LCMS (ES, m/z): 305.2 [M+H]$^+$. $^1$H NMR (300 MHz, DMSO-d$_6$): δ 8.04-7.90 (m, 2H), 7.46 (d, J=3.7 Hz, 1H), 6.59 (dd, J=7.4, 5.5 Hz, 2H), 6.46 (d, J=3.6 Hz, 1H), 5.27-5.15 (m, 2H), 4.35-4.30 (m, 1H), 3.83-3.80 (m, 1H), 3.62-3.41 (m, 2H), 3.03 (d, J=17.3 Hz, 6H), 2.62-2.49 (m, 1H), 2.18-2.14 (m, 1H).

Step 2: (Z)—N'-(1-((2R,4S,5R)-5-((bis(4-methoxyphenyl)(phenyl)methoxy)methyl)-4-hydroxytetrahydrofuran-2-yl)-1H-pyrrolo[2,3-b]pyridin-4-yl)-N,N-dimethylformimidamide

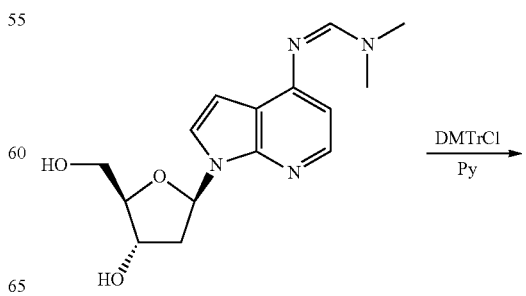

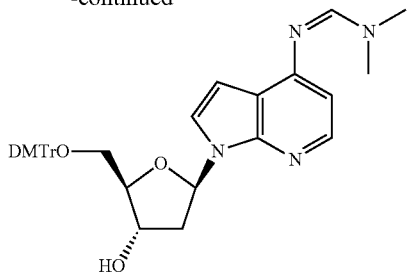

To a mixture of (Z)—N'-(1-((2R,4S,5R)-4-hydroxy-5-(hydroxymethyl) tetrahydrofuran-2-yl)-1H-pyrrolo[2,3-b]pyridin-4-yl)-N,N-dimethylformimidamide (100 mg, 0.33 mmol) in Py (1.8 mL) was added DMTrCl (122 mg, 0.361 mmol). After stirring at RT for 2 h, the mixture was concentrated, and the residue was purified by reverse phase chromatography (C18) eluted with 0 to 95% aq NH$_4$HCO$_3$ (5 mM) in MeCN to give the product. LCMS (ES, m/z): 607.3 [M+H]$^+$. $^1$H NMR (300 MHz, DMSO-d$_6$): δ 8.03-7.92 (m, 2H), 7.41-7.12 (m, 9H), 6.85-6.80 (m, 4H), 6.72-6.54 (m, 2H), 6.46 (d, J=3.7 Hz, 1H), 5.73 (s, 1H), 5.27 (d, J=4.4 Hz, 1H), 4.33 (dt, J=6.7, 3.6 Hz, 1H), 3.90 (q, J=4.4 Hz, 1H), 3.72 (s, 6H), 3.18-3.15 (m, 2H), 3.06 (s, 3H), 3.00 (s, 3H), 2.51-2.48 (m, 1H), 2.26-2.13 (m, 1H).

Step 3: (2R,3S,5R)-2-((bis(4-methoxyphenyl)(phenyl)methoxy)methyl)-5-(4-(((Z)-(dimethylamino)methylene)amino)-1H-pyrrolo[2,3-b]pyridin-1-yl)tetrahydrofuran-3-yl (2-cyanoethyl) diisopropylphosphoramidite

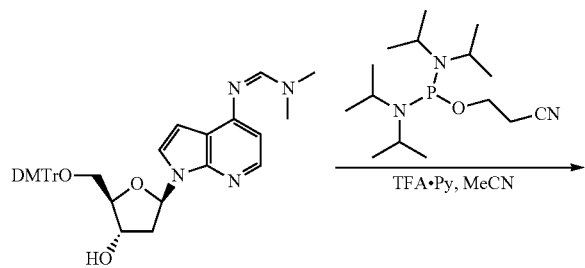

To a stirred solution of 3-((bis(diisopropylamino)phosphino)oxy)propanenitrile (129 mg, 0.429 mmol) in MeCN (2 mL) under Ar was added TFA.Py (62 mg, 0.32 mmol) and a solution of (Z)—N'-(1-((2R,4S,5R)—5-((bis(4-methoxyphenyl)(phenyl)methoxy) methyl)-4-hydroxytetrahydrofuran-2-yl)-1H-pyrrolo[2,3-b]pyridin-4-yl)-N,N-dimethylformimidamide in MeCN (4 mL) over 2 min. The resulting mixture was stirred at RT for 1 h. Then, it was concentrated, and DCM (40 mL) was added. The solution was washed with aq NaHCO$_3$ (1%, 2×20 mL), H$_2$O (20 mL), and brine (20 mL), dried (Na$_2$SO$_4$), and concentrated. The residue was purified by reverse phase chromatography (C18) eluted with 0 to 95% aq NH$_4$HCO$_3$ (5 mM) in MeCN to give the product. LCMS (ES, m/z): 807.5 [M+H]$^+$. $^1$H NMR (400 MHz, DMSO-d$_6$): δ 8.06-7.95 (m, 2H), 7.42-7.37 (m, 3H), 7.33-7.25 (m, 7H), 6.85-6.81 (m, 4H), 6.72-6.59 (m, 2H), 6.51 (dd, J=3.7, 1.5 Hz, 1H), 4.65 (m, 1H), 4.06 (dq, J=21.5, 4.3 Hz, 1H), 3.83-3.51 (m, 10H), 3.29-3.12 (m, 2H), 3.06 (d, J=24.2 Hz, 6H), 2.75-2.70 (m, 3H), 2.50-2.40 (m, 1H), 1.20-1.13 (m, 9H), 1.06 (d, J=6.7 Hz, 3H). $^{31}$P NMR (162 MHz, DMSO-d$_6$): δ 147.54 (s), 146.94 (s).

Step 4: (2R,3R,4R,5R)—5-((((((2R,3S,5R)-2-((bis(4-methoxyphenyl)(phenyl) methoxy)methyl)-5-(4-(((Z)-(dimethylamino)methylene)amino)-1H-pyrrolo[2,3-b]pyridin-1-yl)tetrahydrofuran-3-yl)oxy)(2-cyanoethoxy)phosphanyl)oxy)methyl)-4-((tert-butyldimethylsilyl) oxy)-2-(5-oxoimidazo[1,2-a]pyrimidin-8(5H)-yl)tetrahydrofuran-3-yl hydrogen phosphonate

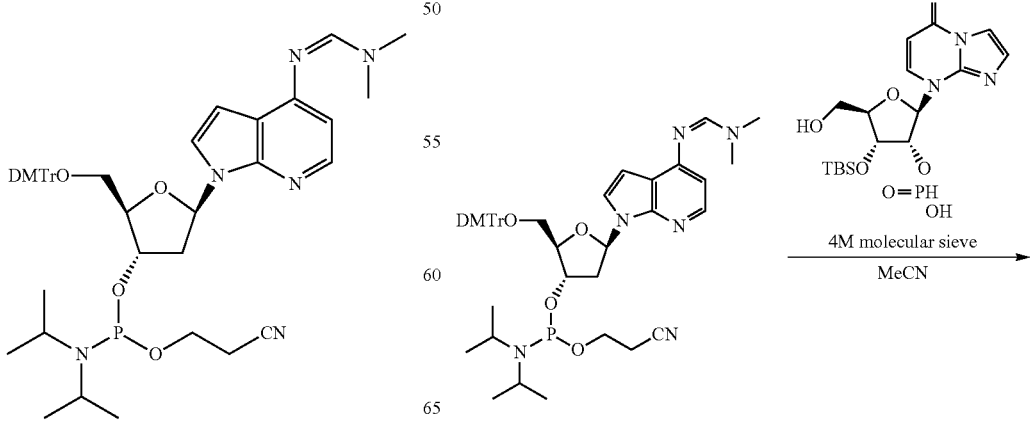

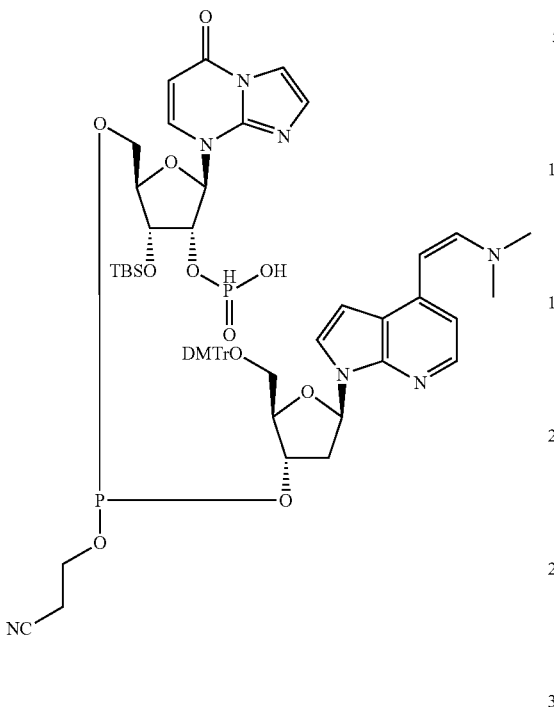

(2R,3R,4R,5R)-4-((tert-butyldimethylsilyl)oxy)-S-(hydroxymethyl)-2-(5-oxoimidazo[1,2-a]pyrimidin-8(5H)-yl)tetrahydrofuran-3-yl hydrogen phosphonate (crude, 0.24 g, ~0.130 mmol) was also co-evaporated with MeCN (3×3 mL), and then re-dissolved in MeCN (1 mL). Activated 4 Å molecular sieve (100 mg) was added to the solution under Ar. (2R,3S,5R)-2-((bis(4-methoxyphenyl)(phenyl)methoxy) methyl)-S-(4-(((Z)-(dimethylamino)methylene) amino)-1H-pyrrolo[2,3-b]pyridin-1-yl)tetrahydrofuran-3-yl (2-cyanoethyl)diisopropyl-phosphoramidite (0.115 g, 0.143 mmol) was co-evaporated with MeCN (3×3 mL) and re-dissolved in MeCN (1 mL). Activated 4 Å molecular sieve (100 mg) was added to the solution under Ar. After 30 min, it was added to the solution containing (2R,3R,4R,5R)-4-((tert-butyldimethylsilyl) oxy)-S-(hydroxymethyl)-2-(5-oxoimidazo[1,2-a]pyrimidin-8(5H)-yl)tetrahydrofuran-3-yl hydrogen phosphonate. The resulting mixture under Ar was stirred at RT for 30 min. It was used for the next reaction step without purification. LCMS (ES, m/z): 1151.5 [M+H]+.

Step 5: (2R,3R,4R,5R)—S-((((((2R,3S,5R)-2-((bis(4-methoxyphenyl)(phenyl)methoxy) methyl)-S-(4-(((Z)-(dimethylamino)methylene)amino)-1H-pyrrolo[2,3-b]pyridin-1-yl) tetra-hydrofuran-3-yl)oxy)(2-cyanoethoxy)phosphorothioyl)oxy)methyl)-4-((tert-butyldimethylsilyl) oxy)-2-(5-oxoimidazo[1,2-a]pyrimidin-8(5H)-yl)tetrahydrofuran-3-yl hydrogen phosphonate

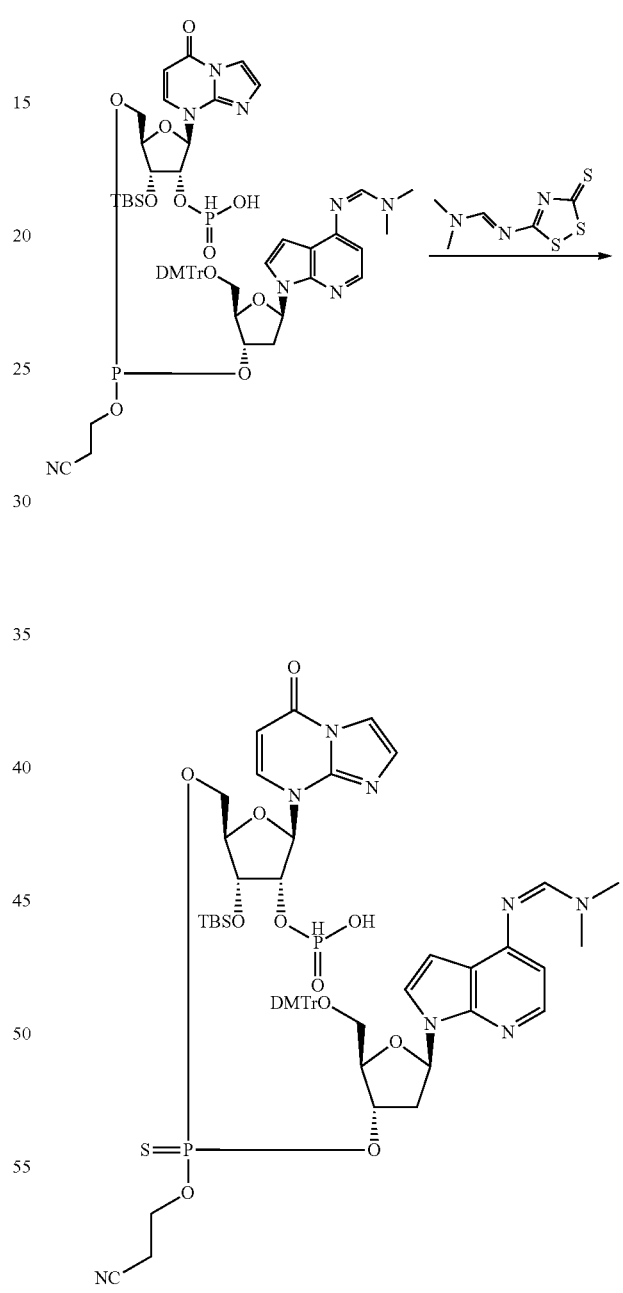

To the reaction mixture from Step 4 was added (E)-N,N-dimethyl-N'-(3-thioxo-3H-1,2,4-dithiazol-S-yl)formimidamide (0.029 g, 0.14 mmol), and it was stirred at RT for 30 min. Then, it was concentrated to give a crude containing the product, and it was used for the next reaction step without purification. LCMS (ES, m/z): 1183.5 [M+H]+.

Step 6: (2R,3R,4R,5R)-4-((tert-butyldimethylsilyl)oxy)-S-((((2-cyanoethoxy)(((2R,3S,5R)—S-(4-(((Z)-(dimethylamino)methylene)amino)-1H-pyrrolo[2,3-b]pyridin-1-yl)-2-(hydroxymethyl)tetrahydrofuran-3-yl)oxy)phosphorothioyl)oxy)methyl)-2-(5-oxoimidazo[1,2-a]pyrimidin-8(5H)-yl)tetrahydrofuran-3-yl hydrogen phosphonate

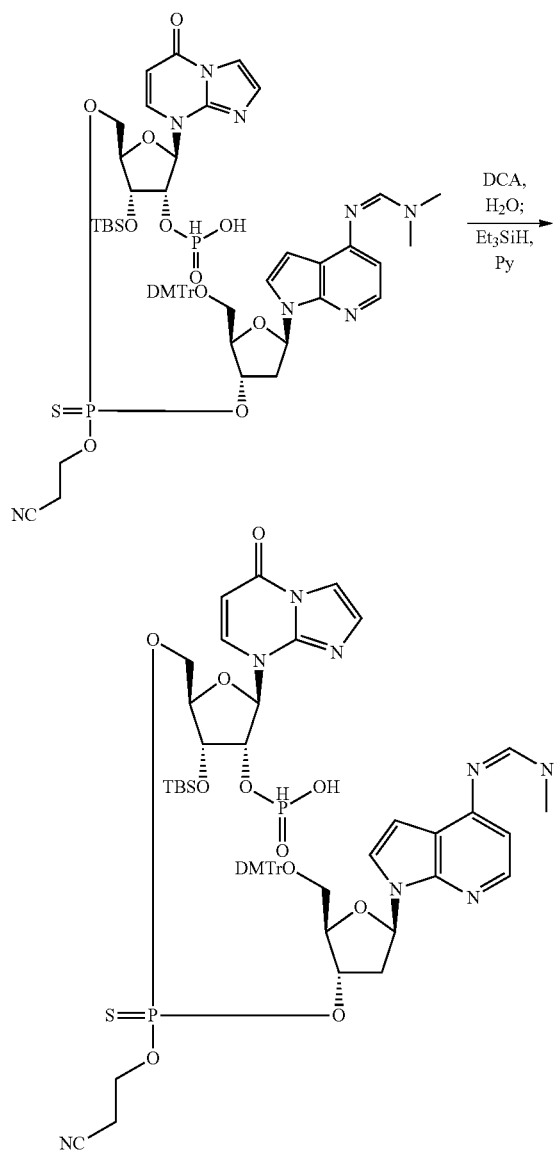

To a solution of the crude from Step 5 in DCM (1.8 mL) was added H₂O (23 mg, 1.3 mmol) and DCA in DCM (6%, 1.87 mL, 1.17 mmol). The reaction was stirred at RT for 30 min. Then, Et₃SiH (2.0 mL) was added to the reaction, and it was stirred for 1 h. Then, Py (185 mg, 2.34 mmol) was added, and the resulting solution was concentrated. The residue was purified by reverse phase chromatography (C18) eluted with 0 to 95% aq NH₄HCO₃ (5 mM) in MeCN to give the product. LCMS (ES, m/z): 881.3 [M+H]⁺. ¹H NMR (400 MHz, CD₃OD): δ 8.10-7.94 (m, 3H), 7.68-7.51 (m, 2H), 7.41-7.34 (m, 1H), 7.23-7.15 (m, 1H), 6.75-6.65 (m, 1H), 6.63-6.44 (m, 1.5H), 6.32-6.23 (m, 1H), 6.06-5.88 (m, 0.5H), 5.80-5.74 (m, 1H), 5.35-5.30 (m, 1H), 5.24-5.19 (m, 1H), 4.86-4.77 (m, 2H), 4.57-4.22 (m, 6H), 3.79-3.76 (m, 2H), 3.22-3.05 (m, 5H), 3.05-2.78 (m, 3H), 2.64-2.42 (m, 1H), 1.00 (d, J=6.8 Hz, 9H), 0.33-0.17 (m, 6H). ³¹P NMR (162 MHz, CD₃OD): δ 66.88 (s), 66.77 (s); 2.98 (s), 2.87 (s).

Step 7: N'-{1-[(5R,7R,8R,12aR,14R,15aS,16R)-16-{[tert-butyl(dimethyl)silyl]oxy}-2-(2-cyanoethoxy)-10-hydroxy-7-(5-oxoimidazo[1,2-a]pyrimidin-8(5H)-yl)-2-sulfidooctahydro-12H-5,8-methanofuro[3,2-l][1,3,6,9,11,2,10]pentaoxadiphosphacyclotetradecin-14-yl]-1H-pyrrolo[2,3-b]pyridin-4-yl}-N,N-dimethylimidoformamide

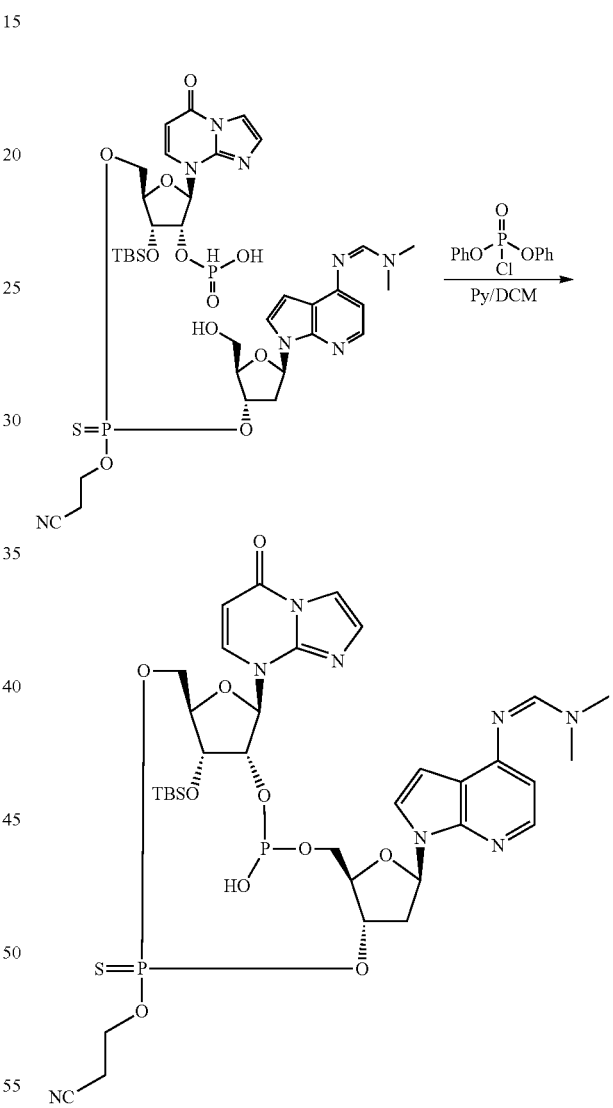

(2R,3R,4R,5R)-4-((tert-butyldimethylsilyl)oxy)-S-((((2-cyanoethoxy) (((2R,3 S,5R)-5-(4-(((Z)-(dimethylamino)methylene)amino)-1H-pyrrolo[2,3-b]pyridin-1-yl)-2-(hydroxyl-methyl)tetrahydrofuran-3-yl)oxy)phosphorothioyl)oxy)methyl)-2-(5-oxoimidazo[1,2-a]pyrimidin-8(5H)-yl)tetrahydrofuran-3-yl hydrogen phosphonate (40 mg, 0.045 mmol) was co-evaporated with Py (3×2 mL) and then dissolved in DCM (5 mL). To this solution at −40° C. was added a solution of diphenyl phosphorochloridate (239 mg, 0.891 mmol) in Py (5 mL) over 10 min. The resulting mixture was stirred at −40° C. for 20 min. Then, it was used for the next reaction step directly. LCMS (ES, m/z): 863.3 [M+H]+.

Step 8: N'-{1-[(5R,7R,8R,12aR,14R,15aS,16R)-16-{[tert-butyl(dimethyl)silyl]oxy}-2-(2-cyanoethoxy)-10-oxido-7-(5-oxoimidazo[1,2-a]pyrimidin-8(5H)-yl)-10-sulfanyl-2-sulfidooctahydro-12H-5,8-methanofuro[3,2-l][1,3,6,9,11,2,10]pentaoxadiphosphacyclotetradecin-14-yl]-1H-pyrrolo[2,3-b]pyridin-4-yl}-N,N-dimethylimidoformamide Step 9: 8-[(5R,7R,8R,12aR,14R,15aS,16R)-14-(4-amino-1H-pyrrolo[2,3-b]pyridin-1-yl)-16-{[tert-butyl(dimethyl)silyl]oxy}-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-a]pyrimidin-5(8H)-one

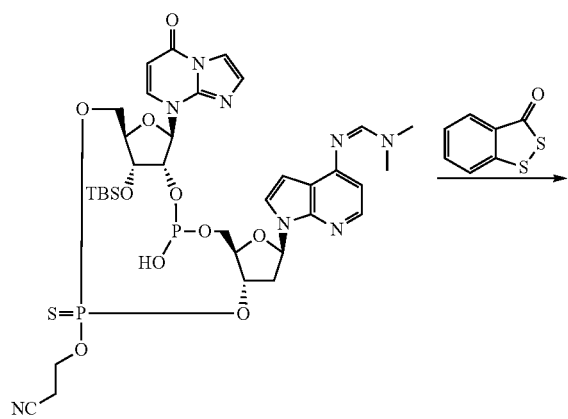

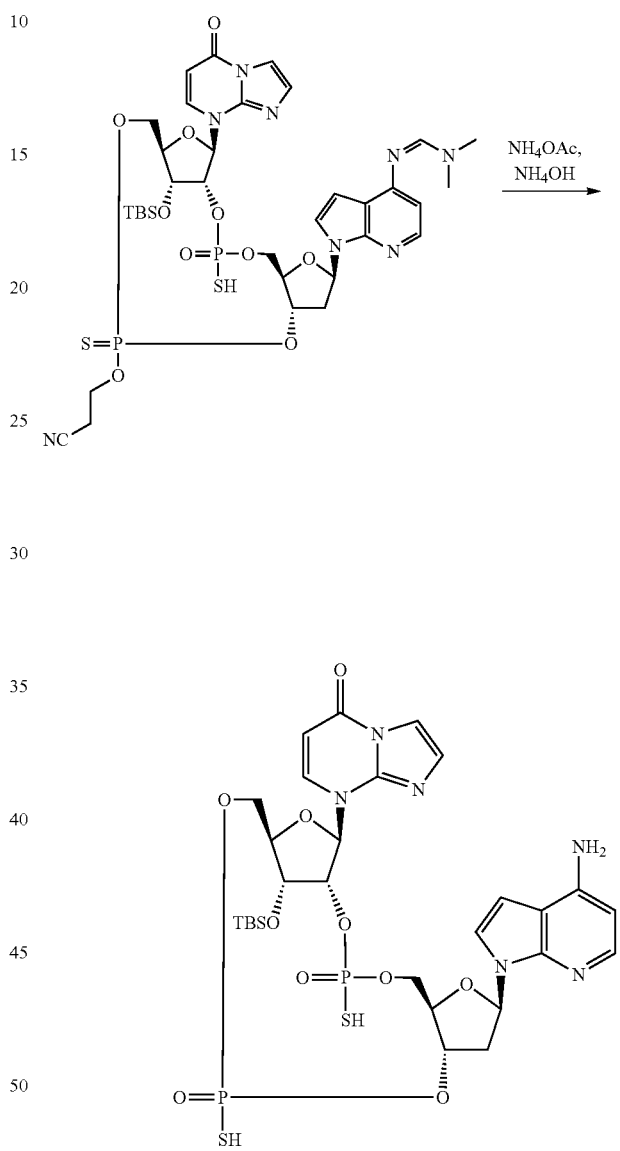

To the reaction mixture from Step 7 at −40° C. was added 3H-benzo[c][1,2]dithiol-3-one (11 mg, 0.068 mmol) and H₂O (0.05 mL). After stirring at RT for 40 min, the mixture was concentrated under reduced pressure. The residue was purified by reverse phase chromatography (C18) eluted with 0 to 95% aq NH₄HCO₃ (5 mM) in MeCN to give the product. LCMS (ES, m/z): 895.3 [M+H]+. ³¹P NMR (162 MHz, CD₃OD): δ 65.78-65.36 (m), 58.29-57.20 (m).

N'-{1-[(5R,7R,8R,12aR,14R,15aS,16R)-16-{[tert-butyl(dimethyl)silyl]oxy}-2-(2-cyanoethoxy)-10-oxido-7-(5-oxoimidazo[1,2-a]pyrimidin-8(5H)-yl)-10-sulfanyl-2-sulfido-octahydro-12H-5,8-methanofuro[3,2-l][1,3,6,9,11,2,10] pentaoxadiphosphacyclo-tetradecin-14-yl]-1H-pyrrolo[2,3-b]pyridin-4-yl}-N,N-dimethylimidoformamide (20 mg, 0.022 mmol) and NH₄OAc (1.0 g, 13 mmol) were dissolved in NH₄OH (10 mL, 260 mmol), and the resulting mixture was stirred at rt for 3 h. Then, it was concentrated, and the residue was purified by reverse phase chromatography (C18) eluted with 0 to 95% aq NH₄HCO₃ (5 mM) in MeCN over 51 min to give the product (T$_R$=32.5 min). LCMS (ES, m/z): 787.3 [M+H]+.

Step 10: 8-[(5R,7R,8R,12aR,14R,15aS,16R)-14-(4-amino-1H-pyrrolo[2,3-b]pyridin-1-yl)-16-hydroxy-2,10-dioxido-2,10-disulfanyloctahydro-12H-5,8-methanofuro[3,2-l][1,3,6,9,11,2,10]pentaoxadiphosphacyclotetradecin-7-yl]imidazo[1,2-c]pyrimidin-5(8H)-one

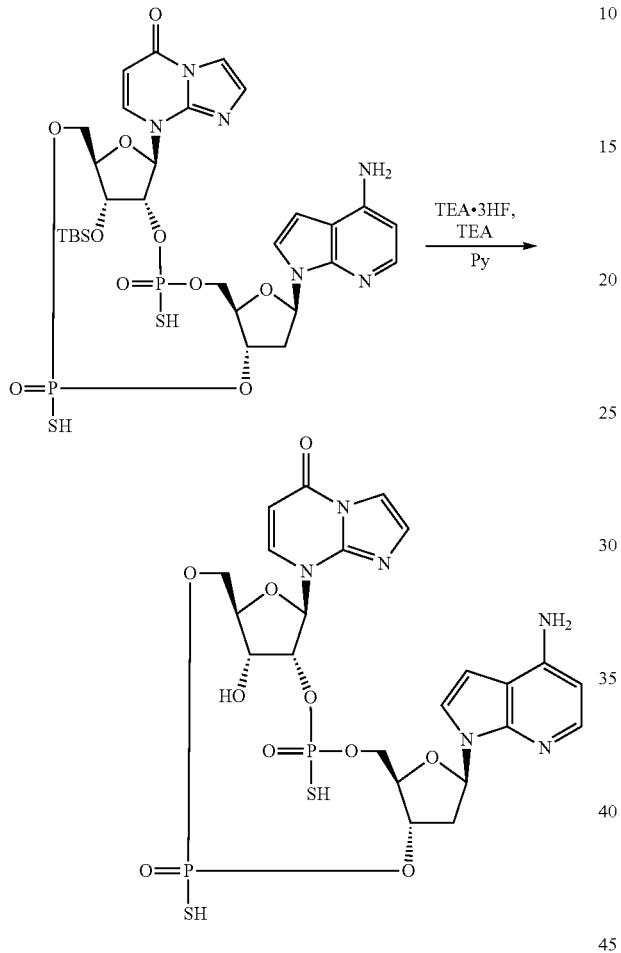

To a suspension of 8-[(5R,7R,8R,12aR,14R,15aS,16R)-14-(4-amino-1H-pyrrolo[2,3-b]pyridin-1-yl)-16-{[tert-butyl(dimethyl)silyl]oxy}-2,10-dioxido-2,10-disulfanyloctahydro-12H-5,8-methanofuro[3,2-l][1,3,6,9,11,2,10]pentaoxadiphosphacyclo-tetradecin-7-yl]imidazo[1,2-a]pyrimidin-5(8H)-one (10 mg, ~0.012 mmol) in Py (0.2 mL) were added TEA (62 mg, 0.61 mmol) and TEA.3HF (49 mg, 0.31 mmol). The mixture was stirred at 50° C. for 3 h. Then, it was concentrated, and acetone (1.1 mL) and ethoxytrimethylsilane (3.9 mL, 25 mmol) were added. After stirring for 30 min, precipitates were formed. The precipitates were purified by reverse phase chromatography (C18) eluted with 0 to 95% aq $NH_4HCO_3$ (30 mM) in MeCN to give the product. LCMS (ES, m/z): 672.9 [M+H]$^+$. $^1$H NMR (400 MHz, $D_2O$): δ 8.37 (d, J=7.9 Hz, 1H), 7.86-7.83 (m, 1H), 7.65 (s, 1H), 7.32-7.28 (m, 2H), 6.67-6.63 (m, 1H), 6.56 (d, J=8.3 Hz, 1H), 6.46-6.40 (m, 2H), 6.01 (d, J=7.9 Hz, 1H), 5.19-4.99 (m, 2H), 4.88-4.82 (m, 2H), 4.53-4.48 (m, 1H), 4.41-4.28 (m, 2H), 4.19-4.02 (m, 1H), 3.97-3.73 (m, 1H), 2.96-2.73 (m, 2H). $^{31}$P NMR (162 MHz, $D_2O$): δ 55.28 (s), 53.94 (s).

Example 35: 2-amino-9-[(5R,7R,8S,12aR,14R,15aS,16R)-16-fluoro-2,10-dioxido-14-(4-oxo-3,4-dihydro-7H-pyrrolo[2,3-d]pyrimidin-7-yl)-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1)

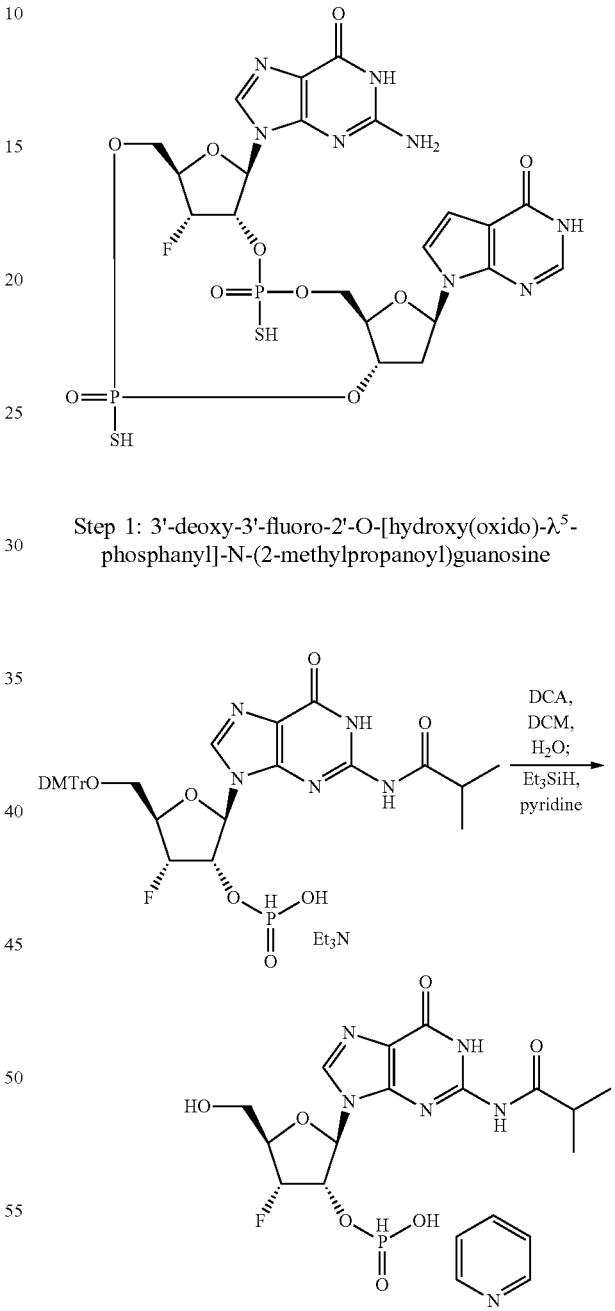

Step 1: 3'-deoxy-3'-fluoro-2'-O-[hydroxy(oxido)-λ$^5$-phosphanyl]-N-(2-methylpropanoyl)guanosine To a stirred solution of triethylammonium 5'-O-[bis(4-methoxyphenyl)(phenyl) methyl]-3'-deoxy-3'-fluoro-2'-O-[hydroxy(oxido)-λ$^5$-phosphanyl]-N-(2-methylpropanoyl) guanosine (1.35 g, 1.50 mmol) in DCM (22.5 mL) were added $H_2O$ (0.27 mL, 15 mmol) and 2,2-DCA in DCM solution (0.6M, 22.5 mL, 13.5 mmol) at RT. The mixture was stirred at RT for 15 min, treated with $Et_3SiH$ (5 mL), and left to stir for 1.5 h. Py (2.4 mL, 30 mmol) was added, and the mixture was stirred for 5 min and concentrated under reduced pressure to give the crude product as the pyridinium salt. LCMS (ES, m/z): 420 [M+H]$^+$.

Step 2: (2R,3S,4R,5R)—S-((((((2R,3S,5R)—S-(4-benzamido-7H-pyrrolo[2,3-d]pyrimidin-7-yl)-2-((bis (4-methoxyphenyl)(phenyl)methoxy)methyl)tetrahydrofuran-3-yl)oxy)(2-cyanoethoxy)phosphorothioyl) oxy)methyl)-4-fluoro-2-(2-isobutyramido-6-oxo-1,6-dihydro-9H-purin-9-yl)tetrahydrofuran-3-yl hydrogen phosphonate A solution of 7-{5-O-[bis(4-methoxyphenyl)(phenyl) methyl]-3-O-[(2-cyanoethoxy)(dipropan-2-ylamino)phosphanyl]-2-deoxy-β-D-erythro-pentofuranosyl}-N-(phenylcarbonyl)-7H-pyrrolo[2,3-d]pyrimidin-4-amine (1.41 g, 1.65 mmol) in MeCN (5 mL) was concentrated in vacuo. Addition of MeCN (5 mL) followed by concentration was repeated twice. To the residue were added MeCN (5 mL) and activated 4 Å molecular sieves (100 mg).

The crude pyridinium 3'-deoxy-3'-fluoro-2'-O-[hydroxy (oxido)-λ$^5$-phosphanyl]-N-(2-methylpropanoyl)guanosine was dissolved in MeCN (5 m) and concentrated in vacuo. Addition of MeCN (5 mL) followed by concentration was repeated twice. To the residue were added MeCN (5 mL) and activated 4 Å molecular sieves (100 mg). After 30 min, the phosphoramidite solution was added to the H-phosphonate solution over 5 min. The flask was rinsed with MeCN (1 mL), and the solution was transferred to the H-phosphonate solution (2×). The resulting mixture was charged with Ar and stirred at RT for 10 min, treated with DDTT (0.339 g, 1.65 mmol), and left to stir for 45 min. The mixture was concentrated to give the product as the pyridinium salt. LCMS (ES, m/z): 1205 [M−H]$^-$.

Step 3: (2R,3S,4R,5R)—S-((((((2R,3S,5R)—S-(4-benzamido-7H-pyrrolo[2,3-d]pyrimidin-7-yl)-2-(hydroxymethyl)tetrahydrofuran-3-yl)oxy)(2-cyanoethoxy)phosphorothioyl) oxy)methyl)-4-fluoro-2-(2-isobutyramido-6-oxo-1,6-dihydro-9H-purin-9-yl) tetrahydrofuran-3-yl hydrogen phosphonate

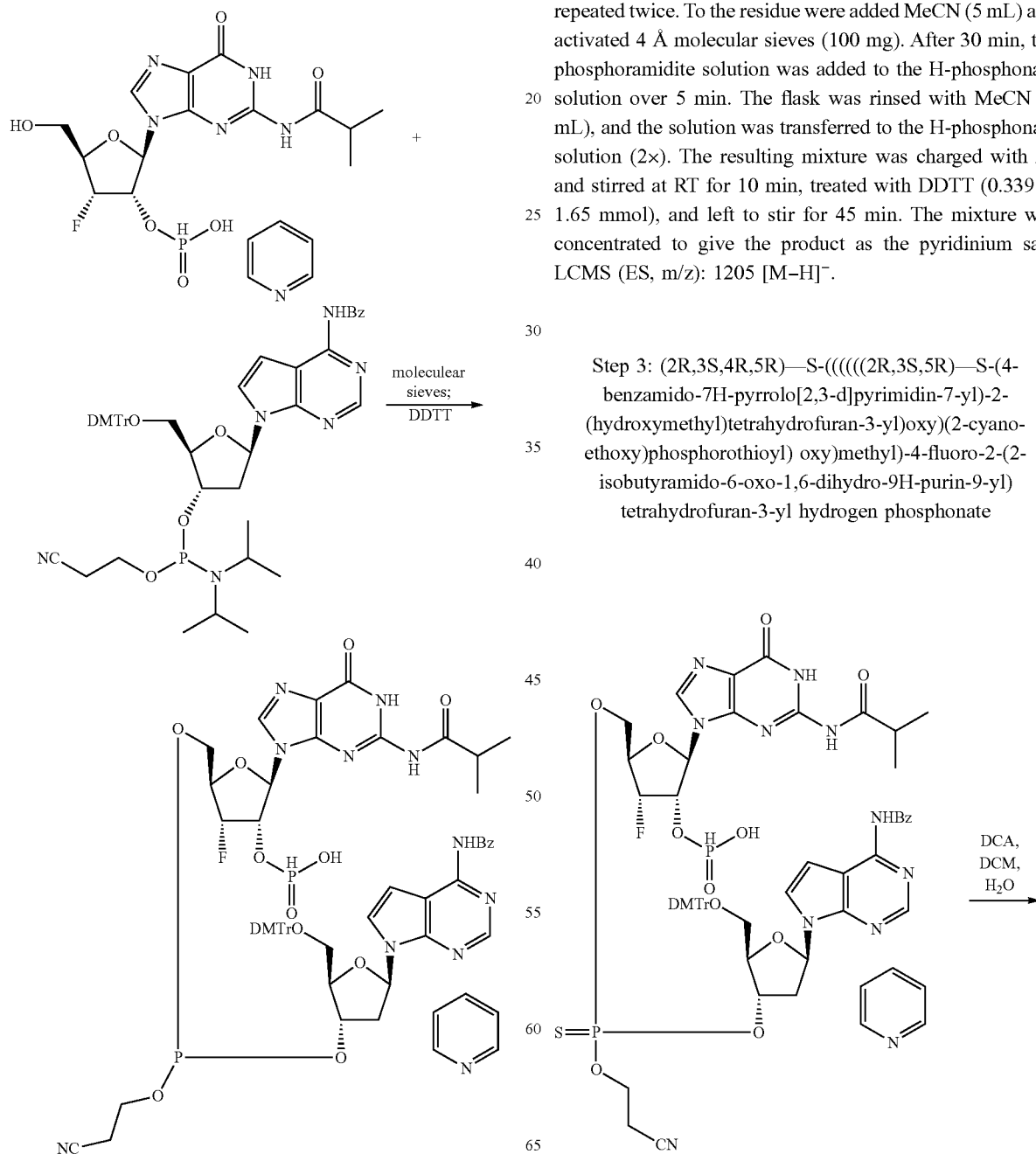

259
-continued

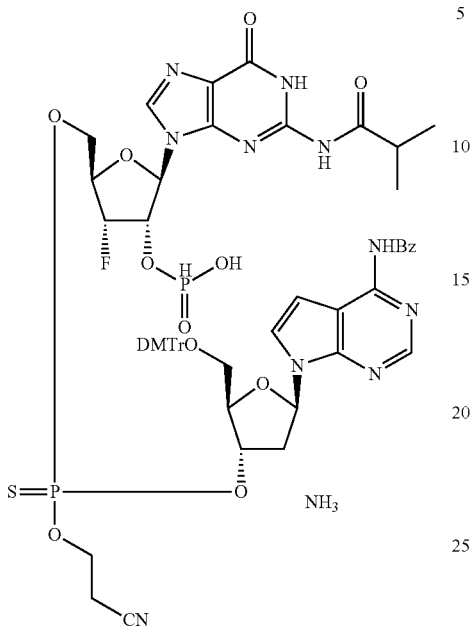

The crude pyridinium (2R,3S,4R,5R)—S-(((((((2R,3S,5R)—S-(4-benzamido-7H-pyrrolo[2,3-d]pyrimidin-7-yl)-2-((bis(4-methoxyphenyl)(phenyl)methoxy)methyl) tetrahydrofuran-3-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl hydrogen phosphonate was dissolved in DCM (22.5 mL) was treated with H$_2$O (0.27 mL, 15 mmol) and 2,2-DCA in DCM (0.6M, 22.5 mL, 13.5 mmol) at RT over 3 min. The mixture was left to stir for 15 min and cooled to 0° C. The mixture was treated with Hex (50 mL) and left to stir for 30 min. The supernatant was decanted, and DCM and Hex (30 mL each) were added to the residue. The supernatant was decanted, and the residue was dried under vacuum and purified by reverse phase (C18) chromatography eluting with 0 to 95% MeCN in 5 mM aq NH$_4$HCO$_3$ solution to give the product as the ammonium salt. LCMS (ES, m/z): 903 [M−H]$^-$.

260

Step 4: N-{7-[(5R,7R,8S,12aR,14R,15aS,16R)-2-(2-cyanoethoxy)-16-fluoro-10-hydroxy-7-{2-[(2-methylpropanoyl)amino]-6-oxo-1,6-dihydro-9H-purin-9-yl}-2,10-disulfido-octahydro-12H-5,8-methanofuro[3,2-l][1,3,6,9,11,2,10]pentaoxadiphosphacyclotetradecin-14-yl]-7H-pyrrolo[2,3-d]pyrimidin-4-yl}benzamide

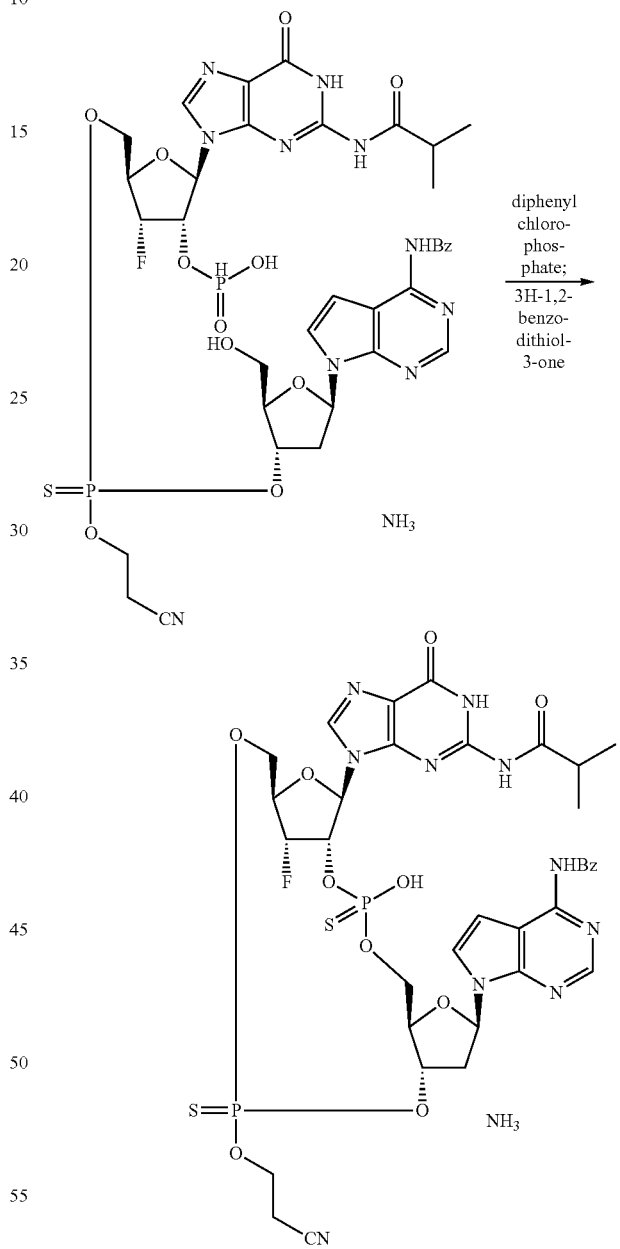

A solution of ammonium (2R,3S,4R,5R)—S-(((((((2R,3S,5R)—S-(4-benzamido-7H-pyrrolo[2,3-d]pyrimidin-7-yl)-2-(hydroxymethyl)tetrahydrofuran-3-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl hydrogen phosphonate (850 mg, 0.922 mmol) in Py (10 mL) was concentrated in vacuo. Addition of Py (10 mL) followed by concentration was repeated twice. The residue was taken up in DCM (92 mL) and Py (22 mL).

To a stirred Py (70 mL) in a separate flask was added diphenyl chlorophosphate (4954 mg, 18.44 mmol) under Ar at −40° C. over 5 min. To the solution was added hydrogen phosphonate solution dropwise at −40° C. over 20 min. The resulting mixture was stirred at −40° C. for 20 min and treated with 3H-1,2-benzodithiol-3-one (233 mg, 1.38 mmol) in one portion and H₂O (332 mg, 18.4 mmol) at −40° C. After stirring at RT for 40 min, the mixture was concentrated under reduced pressure. The residue was purified by reverse phase (C18) chromatography eluting with 0 to 95% MeCN in 5 mM aq NH₄HCO₃ solution to give the product as the ammonium salt (800 mg, 0.885 mmol). LCMS (ES, m/z): 917 [M−H]⁻.

Step 5: 2-amino-9-[(5R,7R,8S,12aR,14R,15aS, 16R)-14-(4-amino-7H-pyrrolo[2,3-d]pyrimidin-7-yl)-16-fluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one To ammonium N-{7-[(5R,7R,8S,12aR,14R,15aS,16R)-2-(2-cyanoethoxy)-16-fluoro-10-hydroxy-7-{2-[(2-methylpropanoyl)amino]-6-oxo-1,6-dihydro-9H-purin-9-yl}-2,10-disulfidooctahydro-12H-5,8-methanofuro[3,2-l][1,3,6,9,11,2,10]pentaoxadiphosphacyclo-tetradecin-14-yl]-7H-pyrrolo[2,3-d]pyrimidin-4-yl}benzamide (800 mg, 0.885 mmol) was added MeNH₂ in EtOH (30% w/w, 47 mL), and the resulting solution was left to stir at RT for 8 h and concentrated. The residue was taken up in acetone (30 mL), left to stir overnight, filtered, and washed with acetone (5 mL×2). The filter cake was dissolved in DMSO (8 mL) and then filtered. The filtrate was purified by reverse phase (C18) chromatography eluting with 0 to 100% MeCN in 30 mM aq NH₄HCO₃ solution to give the four phosphorus diastereomers as the diammonium salts. The second fastest eluting peak fractions were collected and lyophilized to give the product as the diammonium salt. LCMS (ES, m/z): 692 [M+H]⁺ ¹H-NMR: (400 MHz, D₂O): δ 8.28 (s, 1H), 8.03 (s, 1H), 7.17 (d, J=3.7 Hz, 1H), 6.33-6.32 (m, 2H), 5.97 (d, J=8.5 Hz, 1H), 5.48 (d, J=55.6 Hz, 1H), 5.26-5.14 (m, 1H), 4.91-4.87 (m, 1H), 4.66-4.64 (m, 1H), 4.19-4.13 (m, 4H), 4.02-3.99 (m, 1H), 2.71-2.68 (m, 2H). ³¹P-NMR: (162 MHz, D₂O): δ 54.14, 52.59.

Step 6: 2-amino-9-[(5R,7R,8S,12aR,14R,15aS, 16R)-16-fluoro-2,10-dioxido-14-(4-oxo-3,4-dihydro-7H-pyrrolo[2,3-d]pyrimidin-7-yl)-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one

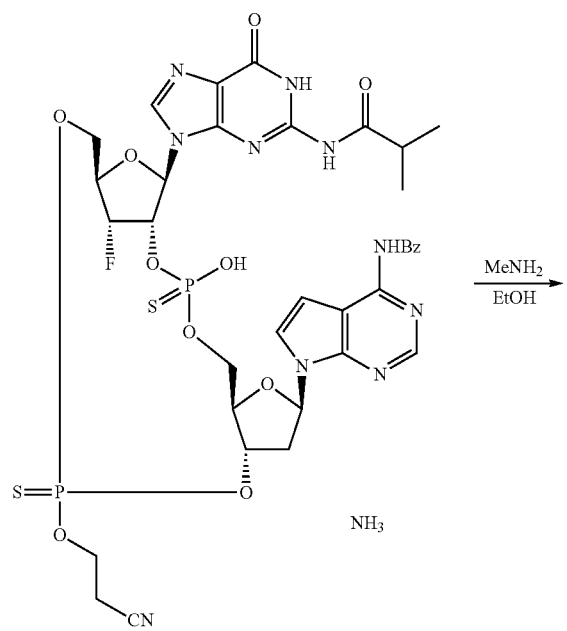

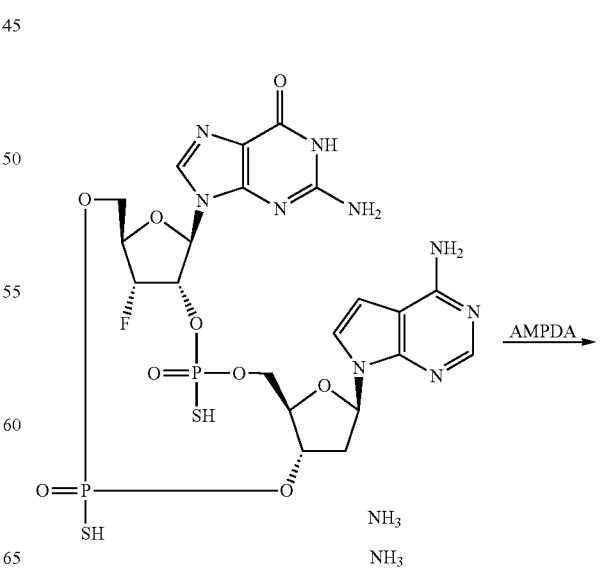

-continued

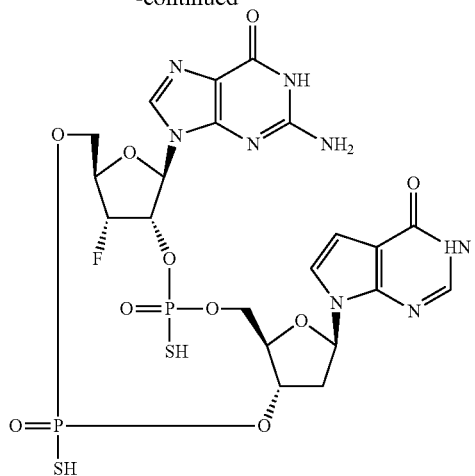

To diammonium 2-amino-9-[(5R,7R,8S,12aR,14R,15aS,16R)-14-(4-amino-7H-pyrrolo[2,3-d]pyrimidin-7-yl)-16-fluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (4.3 mg, 6.1 μmol) were added sodium phosphate buffer (pH 6.8, 50 mM, 8 mL) and AMPDA (200 mg). The reaction mixture was left to stir for 11 days, filtered, and purified by reverse phase HPLC (eluting MeCN/H$_2$O gradient with 100 mM TEAA modifier, linear gradient) to afford the product (Diastereomer 1) as the triethylammonium salt. LCMS (ES, m/z): 691 [M−H]$^-$. $^1$H NMR (600 MHz, D$_2$O): δ 8.39 (s, 1H), 8.07 (s, 1H), 7.28 (d, J=3.3 Hz, 1H), 6.62 (m, 2H), 6.11 (d, J=8.6 Hz, 1H), 5.58 (dd, J=53.1, 2.4 Hz, 1H), 5.45 (m, 1H), 5.21 (m, 1H), 4.41 (brs, 1H), 4.23-4.30 (m, 2H), 4.10 (m, 2H), 2.95-3.08 (m, 2H), 2.86 (m, 1H).

Examples 36 through 51, as shown in Table 5 below, were prepared according to procedures analogous to those outlined in Example 35 above.

TABLE 5

| Ex. | Structure | Name | Mass [M − H]$^-$ |
|---|---|---|---|
| 36 | 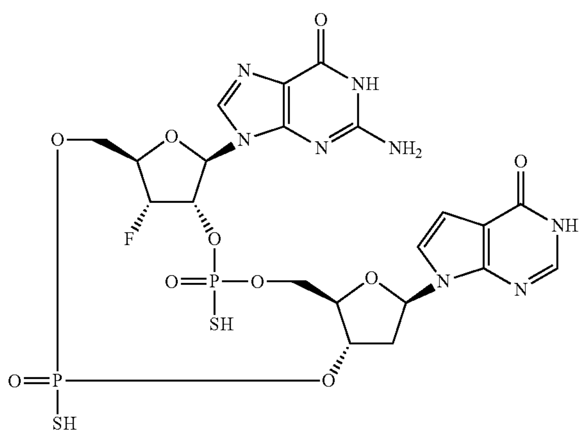 [SMILES: Nc1nc2c(ncn2[C@@H]2O[C@@H]3COP(=O)(S)O[C@H]4C[C@H](n5ccc6c(=O)[nH]cnc65)O[C@@H]4COP(=O)(S)O[C@@H]2[C@@H]3F)c(=O)[nH]1] | 2-amino-9-[(5R,7R,8S,12aR,14R,15aS,16R)-16-fluoro-2,10-dioxido-14-(4-oxo-3,4-dihydro-7H-pyrrolo[2,3-d]pyrimidin-7-yl)-2,10-disulfanyl-octahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 691 |
| 37 | 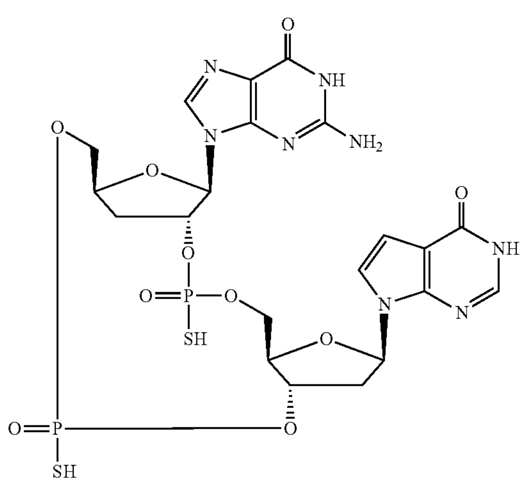 [SMILES: Nc1nc2c(ncn2[C@@H]2O[C@@H]3COP(=O)(S)O[C@H]4C[C@H](n5ccc6c(=O)[nH]cnc65)O[C@@H]4COP(=O)(S)O[C@@H]2C3)c(=O)[nH]1] | 2-amino-9-[(5S,7R,8R,12aR,14R,15aS)-2,10-dioxido-14-(4-oxo-3,4-dihydro-7H-pyrrolo[2,3-d]pyrimidin-7-yl)-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 673 |

TABLE 5-continued

| Ex. | Structure | Name | Mass [M − H]⁻ |
|---|---|---|---|
| 38 | 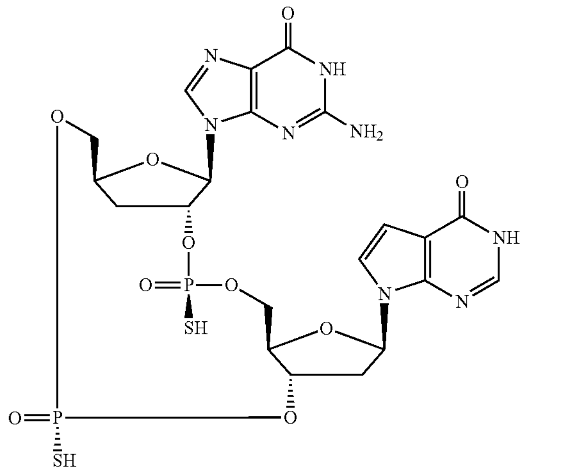 [SMILES: Nc1nc2c(ncn2[C@@H]2O[C@@H]3CO[P@@](=O)(S)O[C@H]4C[C@H](n5ccc6c(=O)[nH]cnc65)O[C@@H]4CO[P@@](=O)(S)O[C@@H]2C3)c(=O)[nH]1] | 2-amino-9-[(2R,5S,7R,8R,10R,12aR,14R,15aS)-2,10-dioxido-14-(4-oxo-3,4-dihydro-7H-pyrrolo[2,3-d]pyrimidin-7-yl)-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 673 |
| 39 | 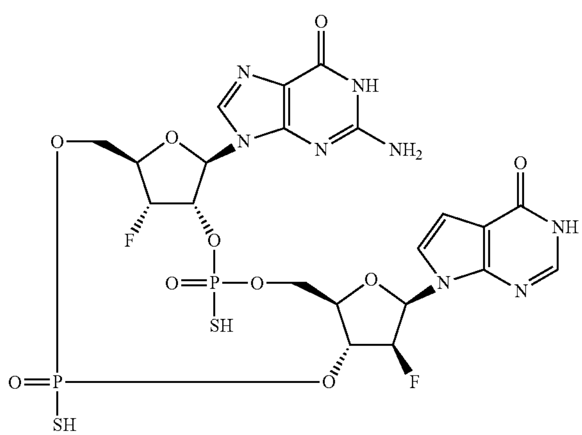 [SMILES: Nc1nc2c(ncn2[C@@H]2O[C@@H]3COP(=O)(S)O[C@H]4[C@H](F)[C@H](n5ccc6c(=O)[nH]cnc65)O[C@@H]4COP(=O)(S)O[C@@H]2[C@@H]3F)c(=O)[nH]1] | 2-amino-9-[(5R,7R,8S,12aR,14R,15S,15aR,16R)-15,16-difluoro-2,10-dioxido-14-(4-oxo-3,4-dihydro-7H-pyrrolo[2,3-d]pyrimidin-7-yl)-2,10-disulfanyl-octahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 709 |
| 40 | 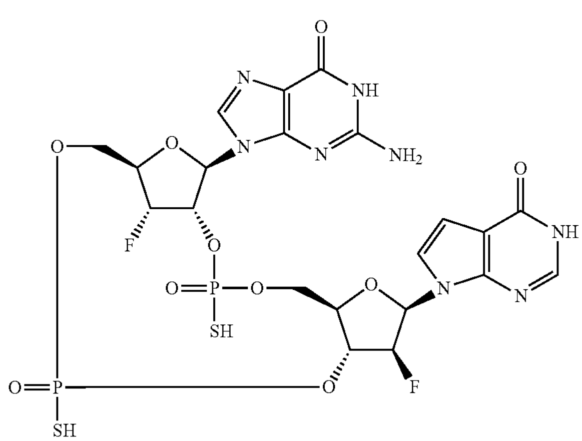 [SMILES: Nc1nc2c(ncn2[C@@H]2O[C@@H]3COP(=O)(S)O[C@H]4[C@H](F)[C@H](n5ccc6c(=O)[nH]cnc65)O[C@@H]4COP(=O)(S)O[C@@H]2[C@@H]3F)c(=O)[nH]1] | 2-amino-9-[(5R,1R,8S,12aR,14R,15S,15aR,16R)-15,16-difluoro-2,10-dioxido-14-(4-oxo-3,4-dihydro-7H-pyrrolo[2,3-d]pyrimidin-7-yl)-2,10-disulfanyl-octahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 709 |

TABLE 5-continued

| Ex. | Structure | Name | Mass [M − H]⁻ |
|---|---|---|---|
| 41 | 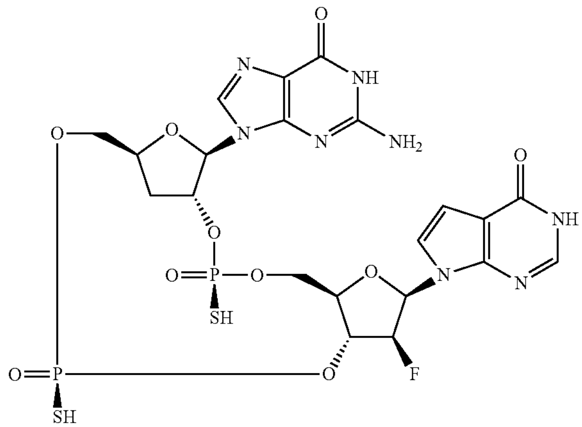 [SMILES: Nc1nc2c(ncn2[C@@H]2O[C@@H]3CO[P@](=O)(S)O[C@H]4[C@H](F)[C@H](n5ccc6c(=O)[nH]cnc65)O[C@@H]4CO[P@@](=O)(S)O[C@@H]2C3)c(=O)[nH]1] | 2-amino-9-[(2R,5S,7R,8R,10R,12aR,14R,15S,15aR)-15-fluoro-2,10-dioxido-14-(4-oxo-3,4-dihydro-7H-pyrrolo[2,3-d]pyrimidin-7-yl)-2,10-disulfanyl-octahydro-12H-5,8-methanofuro[3,2-l][1,3,6,9,11,2,10]pentaoxadiphosphacyclotetradecin-7-yl]-1,9-dihydro-6H-purin-6-one | 691 |
| 42 | 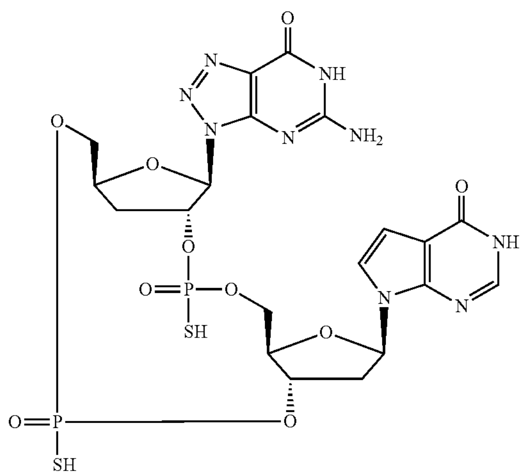 [SMILES: Nc1nc2c(nnn2[C@@H]2O[C@@H]3COP(=O)(S)O[C@H]4C[C@H](n5ccc6c(=O)[nH]cnc65)O[C@@H]4COP(=O)(S)O[C@@H]2C3)c(=O)[nH]1] | 5-amino-3-[(5S,7R,8R,12aR,14R,15aS)-2,10-dioxido-14-(4-oxo-3,4-dihydro-7H-pyrrolo[2,3-d]pyrimidin-7-yl)-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 674 |
| 43 | 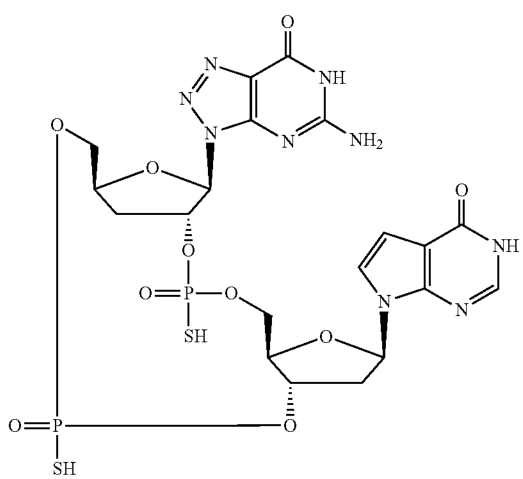 [SMILES: Nc1nc2c(nnn2[C@@H]2O[C@@H]3COP(=O)(S)O[C@H]4C[C@H](n5ccc6c(=O)[nH]cnc65)O[C@@H]4COP(=O)(S)O[C@@H]2C3)c(=O)[nH]1] | 5-amino-3-[(5S,7R,8R,12aR,14R,15aS)-2,10-dioxido-14-(4-oxo-3,4-dihydro-7H-pyrrolo[2,3-d]pyrimidin-7-yl)-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 674 |

TABLE 5-continued

| Ex. | Structure | Name | Mass [M − H]⁻ |
|---|---|---|---|
| 44 | 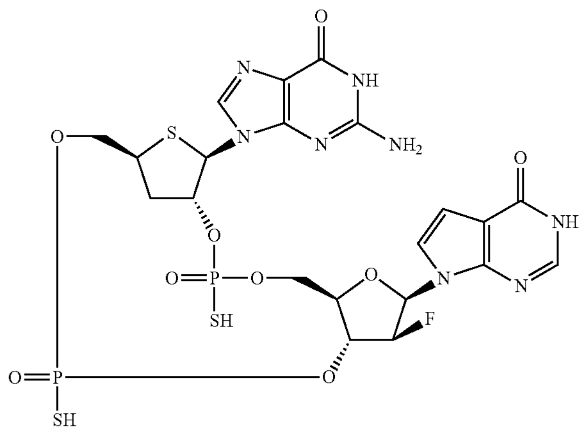 [SMILES: Nc1nc2c(ncn2[C@@H]2S[C@@H]3COP(=O)(S)O[C@H]4[C@H](F)[C@H](n5ccc6c(=O)[nH]cnc65)O[C@@H]4COP(=O)(S)O[C@@H]2C3)c(=O)[nH]1] | 2-amino-9-[(5S,7R,8R,12aR,14R,15S,15aR)-15-fluoro-2,10-dioxido-14-(4-oxo-3,4-dihydro-7H-pyrrolo[2,3-d]pyrimidin-7-yl)-2,10-disulfanyl-octahydro-12H-5,8-methanofuro[3,2-l][1,3,9,11,6,2,10]tetraoxathiadiphosphacyclotetradecin-7-yl]-1,9-dihydro-6H-purin-6-one | 707 |
| 45 | 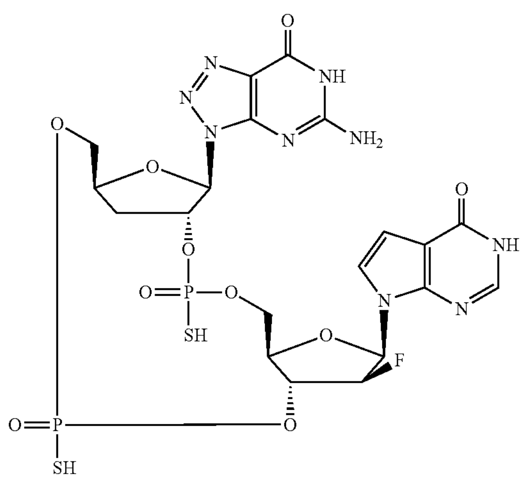 [SMILES: Nc1nc2c(nnn2[C@@H]2O[C@@H]3COP(=O)(S)O[C@H]4[C@H](F)[C@H](n5ccc6c(=O)[nH]cnc65)O[C@@H]4COP(=O)(S)O[C@@H]2C3)c(=O)[nH]1] | 5-amino-3-[(5S,7R,8R,12aR,14R,15S,15aR)-15-fluoro-2,10-dioxido-14-(4-oxo-3,4-dihydro-7H-pyrrolo[2,3-d]pyrimidin-7-yl)-2,10-disulfanyl-octahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one | 692 |
| 46 | 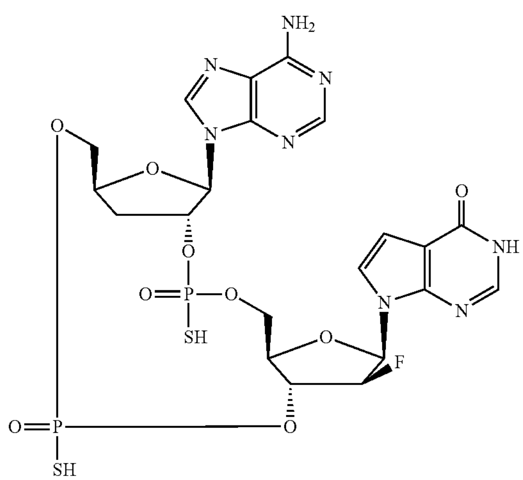 [SMILES: Nc1ncnc2c1ncn2[C@@H]1O[C@@H]2COP(=O)(S)O[C@H]3[C@H](F)[C@H](n4ccc5c(=O)[nH]cnc54)O[C@@H]3COP(=O)(S)O[C@@H]1C2] | 7-[(5S,7R,8R,12aR,14R,15S,15aR)-7-(6-amino-9H-purin-9-yl)-15-fluoro-2,10-dioxido-2,10-disulfanyloctahydro-12H-5,8-methanofuro[3,2-l][1,3,6,9,11,2,10]pentaoxadiphosphacyclotetradecin-14-yl]-3,7-dihydro-4H-pyrrolo[2,3-d]pyrimidin-4-one (Diastereomer 1) | 675 |

TABLE 5-continued

| Ex. | Structure | Name | Mass [M − H]⁻ |
|---|---|---|---|
| 47 | 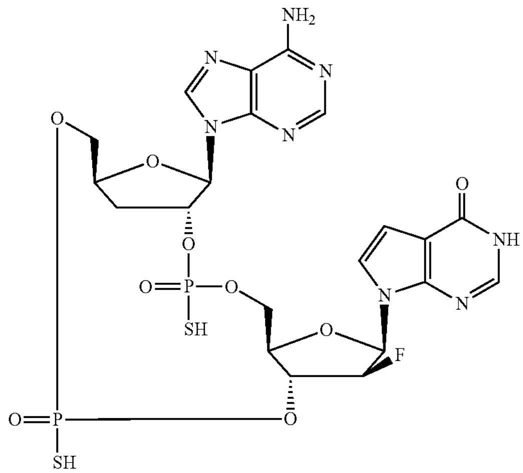 [SMILES: Nc1ncnc2c1ncn2[C@@H]1O[C@@H]2COP(=O)(S)O[C@H]3[C@H](F)[C@H](n4ccc5c(=O)[nH]cnc54)O[C@@H]3COP(=O)(S)O[C@@H]1C2] | 7-[(5S,7R,8R,12aR,14R,15S,15aR)-7-(6-amino-9H-purin-9-yl)-15-fluoro-2,10-dioxido-2,10-disulfanyloctahydro-12H-5,8-methanofuro[3,2-l][1,3,6,9,11,2,10]pentaoxadiphosphacyclotetradecin-14-yl]-3,7-dihydro-4H-pyrrolo[2,3-d]pyrimidin-4-one (Diastereomer 2) | 675 |
| 48 | 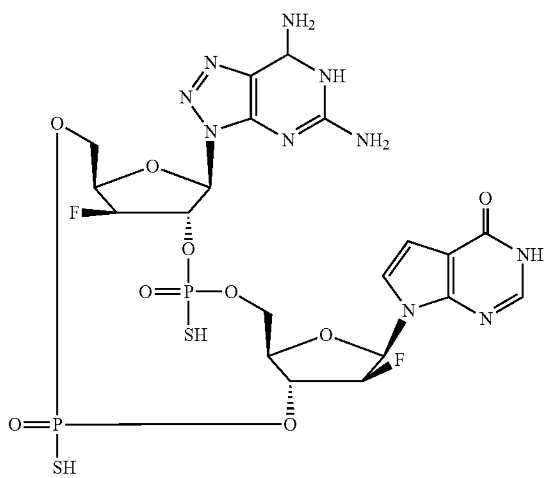 [SMILES: NC1=Nc2c(nnn2[C@@H]2O[C@@H]3COP(=O)(S)O[C@H]4[C@H](F)[C@H](n5ccc6c(=O)[nH]cnc65)O[C@@H]4COP(=O)(S)O[C@@H]2[C@H]3F)C(N)N1] | 5-amino-3-[(5R,7R,8S,12aR,14R,15S,15aR,16S)-15,16-difluoro-2,10-dioxido-14-(4-oxo-3,4-dihydro-7H-pyrrolo[2,3-d]pyrimidin-7-yl)-2,10-disulfanyl-octahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one | 710 |
| 49 | 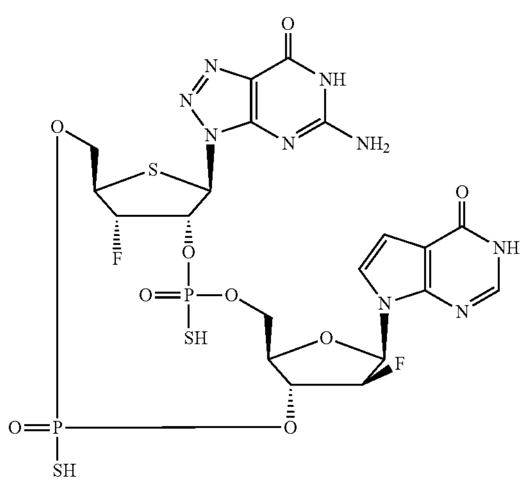 [SMILES: Nc1nc2c(nnn2[C@@H]2S[C@@H]3COP(=O)(S)O[C@H]4[C@H](F)[C@H](n5ccc6c(=O)[nH]cnc65)O[C@@H]4COP(=O)(S)O[C@@H]2[C@@H]3F)c(=O)[nH]1] | 5-amino-3-[(5R,7R,8R,12aR,14R,15S,15aR,16S)-15,16-difluoro-2,10-dioxido-14-(4-oxo-3,4-dihydro-7H-pyrrolo[2,3-d]pyrimidin-7-yl)-2,10-disulfanyl-octahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 1) | 726 |

TABLE 5-continued

| Ex. | Structure | Name | Mass [M − H]− |
|---|---|---|---|
| 50 | 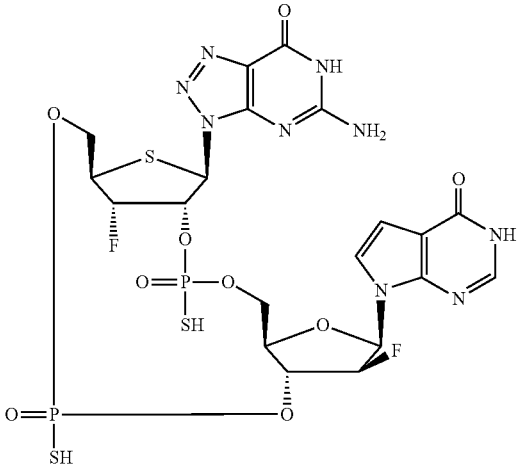 [SMILES: Nc1nc2c(nnn2[C@@H]2S[C@@H]3COP(=O)(S)O[C@H]4[C@H](F)[C@H](n5ccc6c(=O)[nH]cnc65)O[C@@H]4COP(=O)(S)O[C@@H]2[C@@H]3F)c(=O)[nH]1] | 5-amino-3-[(5R,7R,8R,12aR,14R,15S,15aR,16S)-15,16-difluoro-2,10-dioxido-14-(4-oxo-3,4-dihydro-7H-pyrrolo[2,3-d]pyrimidin-7-yl)-2,10-disulfanyl-octahydro-1277-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 2) | 726 |
| 51 | 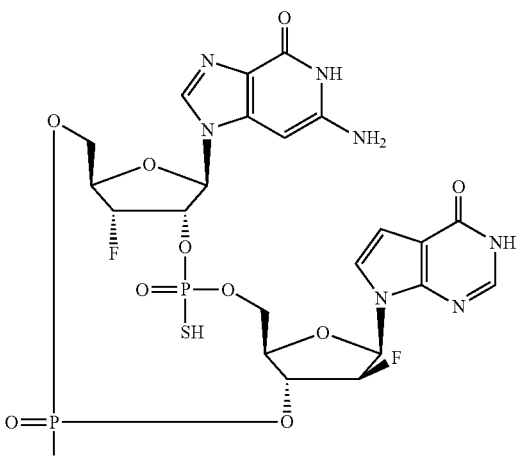 | 6-amino-1-[(5R,7R,8S,12aR,14R,15S,15aR,16R)-15,16-difluoro-2,10-dioxido-14-(4-oxo-3,4-dihydro-7H-pyrrolo[2,3-d]pyrimidin-7-yl)-2,10-disulfanyl-octahydro-12H-5,8-methanofuro[3,2-l][1,3,6,9,11,2,10]pentaoxadiphosphacyclotetradecin-7-yl]-1,5-dihydro-4H-imidazo[4,5-c]pyridin-4-one | 708 |

Example 52: 2-amino-9-[(5R,7R,8S,12aR,14R,15aS, 16R)-14-(4-amino-5-fluoro-7H-pyrrolo[2,3-d]pyrimidin-7-yl)-16-fluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one

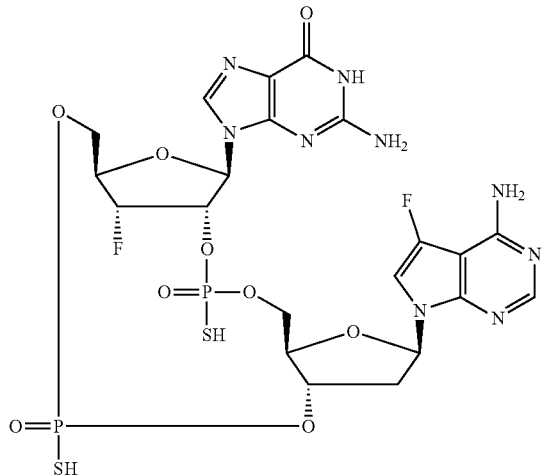 [SMILES: Nc1nc2c(ncn2[C@@H]2O[C@@H]3COP(=O)(S)O[C@H]4C[C@H](n5cc(F)c6c(N)ncnc65)O[C@@H]4COP(=O)(S)O[C@@H]2[C@@H]3F)c(=O)[nH]1]

Step 1: N-{5-fluoro-7-[(6aR,8R,9a5)-2,2,4,4-tetra)propan-2-yl)tetrahydro-6H-furo[3,2-f][1,3,5,2,4]trioxadisilocin-8-yl]-7H-pyrrolo[2,3-d]pyrimidin-4-yl}benzamide

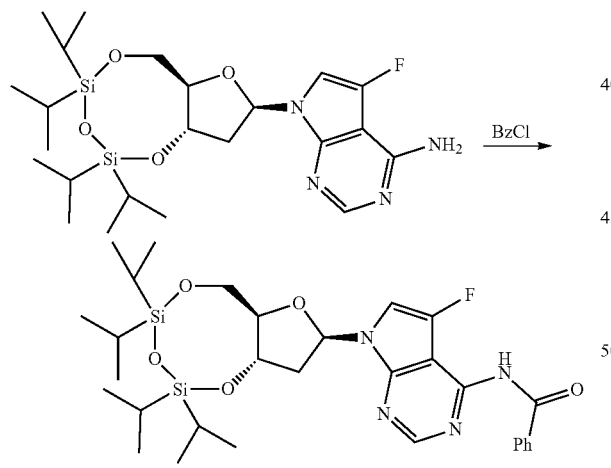

BzCl (1.2 mL, 10.3 mmol) was added to a stirring solution of 5-fluoro-7-[(6aR,8R,9aS)-2,2,4,4-tetra(propan-2-yl)tetrahydro-6H-furo[3,2-f][1,3,5,2,4]trioxadisilocin-8-yl]-7H-pyrrolo[2,3-d]pyrimidin-4-amine (3.3 g, 6.5 mmol) in Py (32 mL) at 0° C. The reaction mixture was allowed to warm to RT and stir for 1 h. MeOH (10 mL) was added, and the reaction mixture was allowed to stir for 30 min. The reaction mixture was concentrated in vacuo. The residue was purified by flash column chromatography on silica eluting with Hex, EtOAc, and EtOH to give the titled compound. LCMS (ES, m/z): 615 [M+H]$^+$.

Step 2: 7-(2-deoxy-β-D-erythro-pentofuranosyl)-5-fluoro-N-(phenylcarbonyl)-7H-pyrrolo[2,3-d]pyrimidin-4-amine

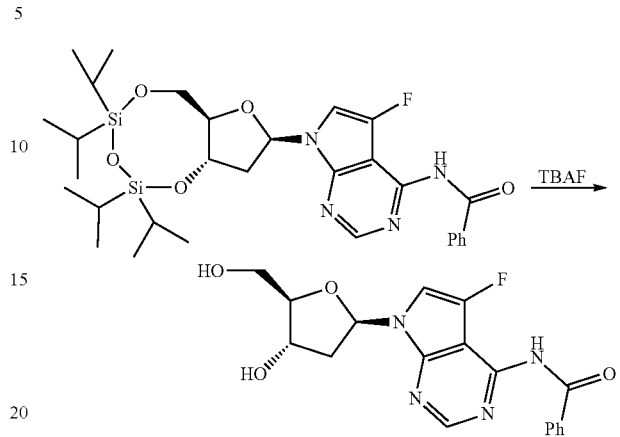

To N-{5-fluoro-7-[(6aR,8R,9aS)-2,2,4,4-tetra(propan-2-yl)tetrahydro-6H-furo[3,2-f][1,3,5,2,4]trioxadisilocin-8-yl]-7H-pyrrolo[2,3-d]pyrimidin-4-yl}benzamide (2.8 g, 4.60 mmol) in THF (46 mL) at RT was added TBAF (1M, 14 mL, 14 mmol). The reaction mixture was stirred overnight. The reaction mixture was concentrated in vacuo. The residue was purified by flash column chromatography on silica eluting with hexane, EtOAc, and EtOH to give the titled compound. LCMS (ES, m/z): 373 [M+H]$^+$.

Step 3: 7-{5-O-[bis(4-methoxyphenyl)(phenyl)methyl]-2-deoxy-β-D-erythro-pentofuranosyl}-5-fluoro-N-(phenylcarbonyl)-7H-pyrrolo[2,3-d]pyrimidin-4-amine

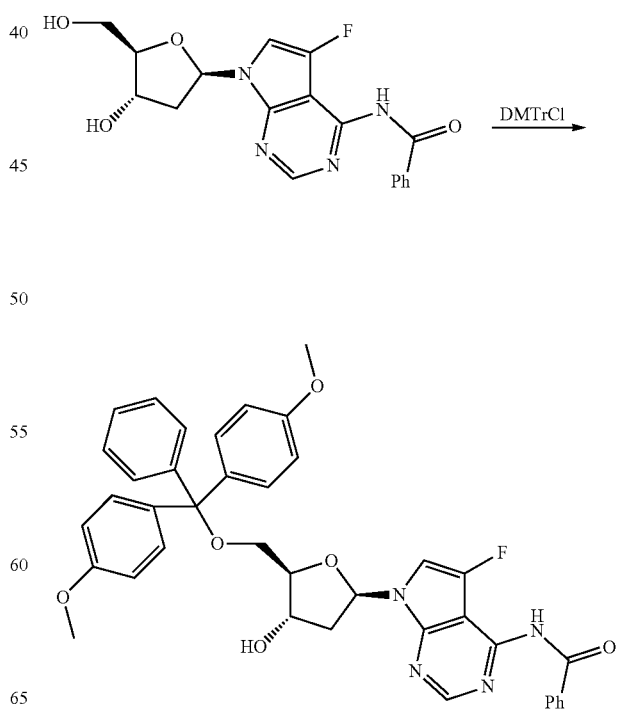

DMTrCl (1.33 g, 3.93 mmol) was added to 7-(2-deoxy-β-D-erythro-pentofuranosyl)-5-fluoro-N-(phenylcarbonyl)-7H-pyrrolo[2,3-d]pyrimidin-4-amine (1.2 g, 3.3 mmol) in Py (12 mL) at 0° C. The reaction mixture was allowed to warm to RT and stir overnight. Additional DMTrCl (1.33 g, 3.93 mmol) was added, and the reaction mixture was stirred for 4 h. DMAP (0.040 g, 0.33 mmol) was added, and the reaction mixture was stirred for 2 h. The reaction mixture was concentrated in vacuo. The residue was purified by flash column chromatography on silica eluting with MeOH and DCM with 1% TEA additive to give the title compound. LCMS (ES, m/z): 675 [M+H]⁺.

Step 4: 7-{5-O-[bis(4-methoxyphenyl)(phenyl)methyl]-3-O-[(2-cyanoethoxy) (dipropan-2-ylamino) phosphanyl]-2-deoxy-β-D-erythro-pentofuranosyl}-S-fluoro-N-(phenylcarbonyl)-7H-pyrrolo[2,3-d]pyrimidin-4-amine

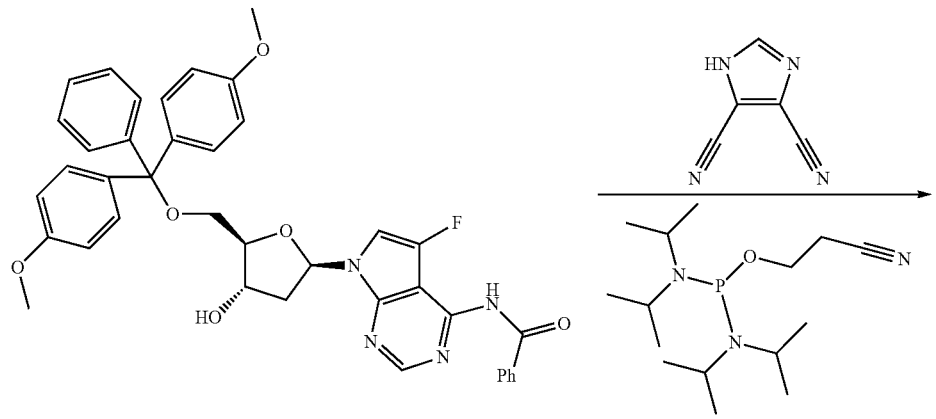

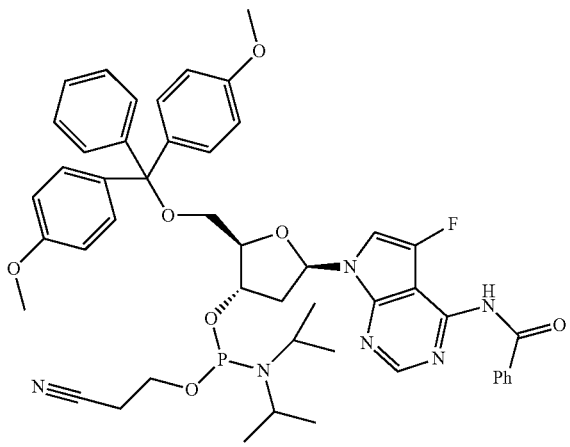

To 7-{5-O-[bis(4-methoxyphenyl)(phenyl)methyl]-2-deoxy-β-D-erythro-pentofuranosyl}-S-fluoro-N-(phenylcarbonyl)-7H-pyrrolo[2,3-d]pyrimidin-4-amine (1.5 g, 2.2 mmol) in DCM (22 mL) was added 4,5-dicyanoimidazole (0.8 g, 6.7 mmol) followed by 2-cyanoethyl N,N,N',N'-tetraisopropylphosphorodiamidite (2.1 mL, 6.7 mmol) at 0° C. The reaction mixture was stirred overnight. The reaction mixture was concentrated in vacuo. The product was purified by flash column chromatography on silica eluting with EtOAc and Hex with 1% TEA additive to the title compound. LCMS (ES, m/z): 875 [M+H]⁺.

Step 5: (2R,3S,4R,5R)—S-((((((2R,3S,5R)—S-(4-benzamido-5-fluoro-7H-pyrrolo[2,3-d]pyrimidin-7-yl)-2-(hydroxymethyl)tetrahydrofuran-3-yl)oxy)(2-cyanoethoxy)phosphorothioyl) oxy)methyl)-4-fluoro-2-(2-isobutyramido-6-oxo-1,6-dihydro-9H-purin-9-yl)tetrahydrofuran-3-yl hydrogen phosphonate
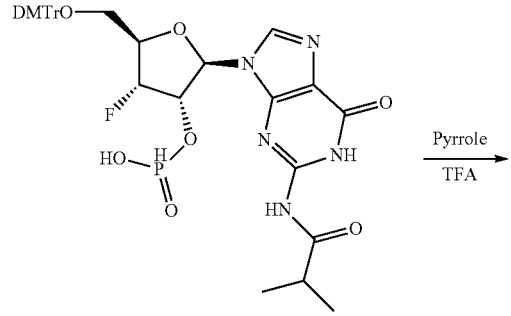
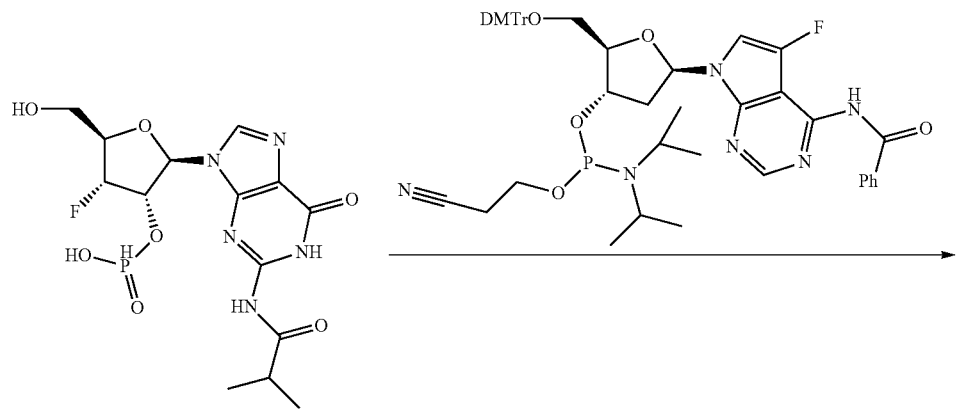
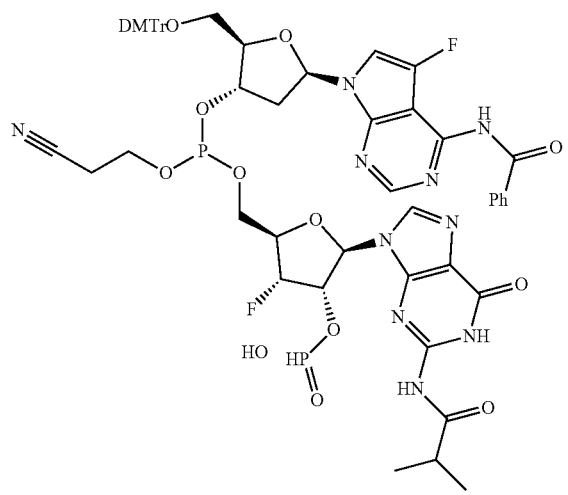

-continued

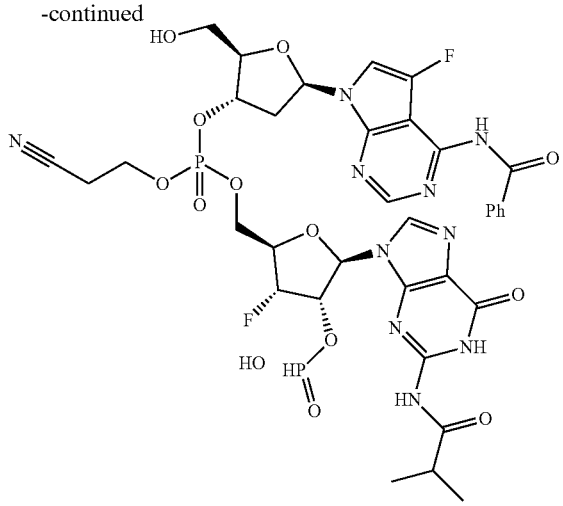

Pyrrole (0.277 mL, 3.96 mmol) was added to a stirring solution of 5'-O-[bis(4-methoxyphenyl)(phenyl)methyl]-3'-deoxy-3'-fluoro-2'-O-[hydroxy(oxido)-λ~5~-phosphanyl]-N-(2-methylpropanoyl)guanosine (1.2 g, 1.3 mmol) in MeCN (4.5 mL) at 0° C. followed by TFA (0.3 mL, 4.0 mmol). The reaction mixture was stirred at 0° C. for 2 h. 7-{5-O-[bis(4-methoxy-phenyl)(phenyl)methyl]-3-O-[(2-cyanoethoxy)(dipropan-2-ylamino)phosphanyl]-2-deoxy-β-D-erythro-pentofuranosyl}-5-fluoro-N-(phenylcarbonyl)-7H-pyrrolo[2,3-d] pyrimidin-4-amine (1.2 g, 1.3 mmol) in MeCN (4.50 mL) was added at 0° C. The reaction mixture was allowed to stir for 30 min. (E)-N,N-dimethyl-N'-(3-thioxo-3H-1,2,4-dithiazol-5-yl) formimidamide (0.33 g, 1.6 mmol) was added at 0° C. The reaction mixture was allowed to stir for 30 min. 1-propanol (1 mL, 13 mmol) was added at 0° C., and the reaction mixture was allowed to stir for 10 min and warmed to RT. TFA (1.0 mL, 13 mmol) was added, and the reaction mixture stirred at RT for 30 min. Py (1.3 mL, 16 mmol) was added, and the reaction mixture was stirred for 20 min. The reaction mixture was concentrated to half volume, diluted with isopropyl acetate (15 mL), and left to stir overnight. The precipitate was isolated by filtration to give the title compound that was used in the next step without further purification.

Step 6: 2-amino-9-[(5R,7R,8S,12aR,14R,15aS,16R)-14-(4-amino-5-fluoro-7H-pyrrolo[2,3-d]pyrimidin-7-yl)-16-fluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one

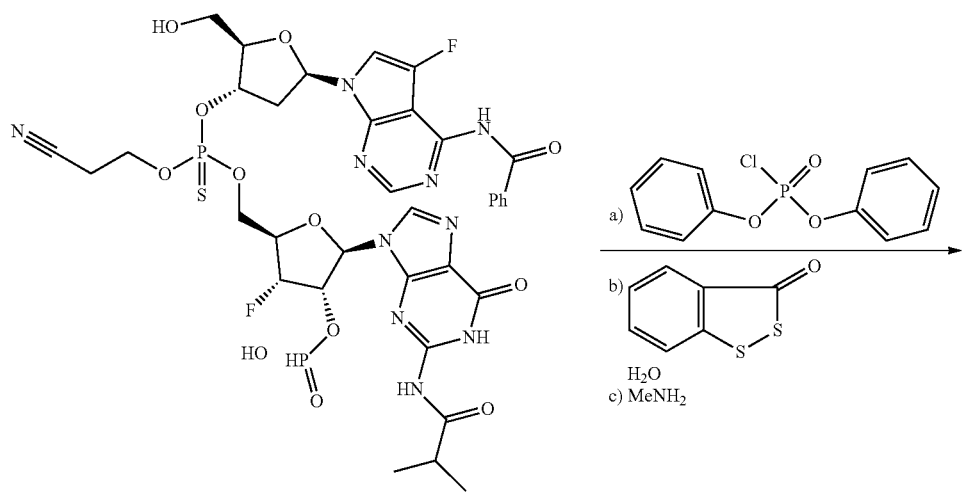

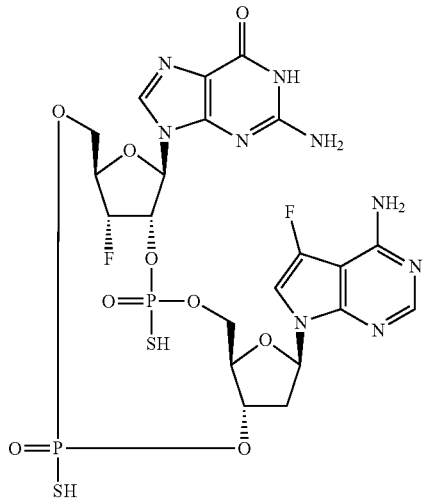

Diphenyl chlorophosphate (1.4 mL, 6.6 mmol) was added to degassed MeCN (60 mL) and Py (5 mL) at RT. A solution of the crude (2R,3S,4R,5R)—S-(((((2R,3S,5R)—S-(4-benzamido-5-fluoro-7H-pyrrolo[2,3-d]pyrimidin-7-yl)-2-(hydroxymethyl)tetrahydrofuran-3-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl hydrogen phosphonate in Py (8 mL) was added dropwise while maintaining the internal temperature below −20° C. The reaction mixture was stirred for 30 min. 3H-1,2-Benzodithiol-3-one (0.3 g, 1.6 mmol) followed by H$_2$O (0.5 mL, 26 mmol) were added, and the reaction mixture was allowed to warm to RT and stir for 30 min. The reaction mixture was concentrated in vacuo and azeotroped with Py. The residue was dissolved in Py (8 mL) and cooled to 0° C. MeNH$_2$ (12.16 mL, 98 mmol, 33% v/v in EtOH) was added, and the reaction mixture was allowed to warm to RT and stir overnight. The reaction mixture was concentrated in vacuo, and purified by reverse phase HPLC (eluted MeCN/H$_2$O gradient with 100 mM TEAA modifier, linear gradient) to give the four phosphorus diastereomers as triethylammonium salts. The slowest eluting peak fractions were collected and lyophilized to give the product as the triethylammonium salt. LCMS (ES, m/z): 708 [M−H]$^-$. $^1$H NMR (600 MHz, D$_2$O) δ 8.14 (s, 1H), 7.97 (s, 1H), 7.15 (s, 1H), 6.63 (m, 1H), 6.07 (d, J=8.5 Hz, 1H), 5.77 (m, 1H), 5.53 (dd, 2.4 Hz, 1H), 5.35 (m, 1H), 4.75 (m, 1H), 4.48 (m, 1H), 4.31-4.08 (m, 4H), 2.80 (m, 2H).

Step 7: 2-amino-9-[(5R,7R,8S,12aR,14R,15aS,16R)-16-fluoro-14-(5-fluoro-4-oxo-3,4-dihydro-7H-pyrrolo[2,3-d]pyrimidin-7-yl)-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1)

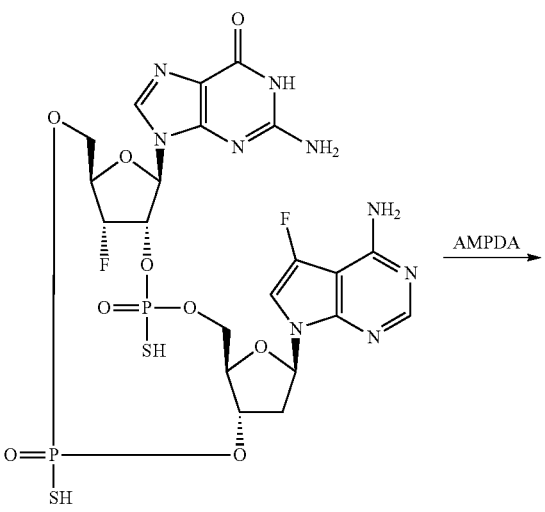

-continued

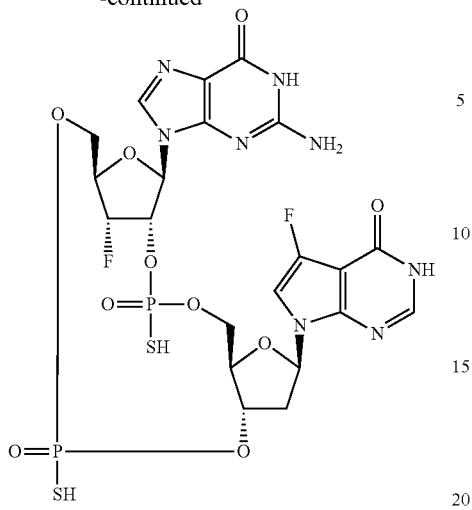

To triethylammonium 2-amino-9-[(5R,7R,8S,12aR,14R,15aS,16R)-14-(4-amino-5-fluoro-7H-pyrrolo[2,3-d]pyrimidin-7-yl)-16-fluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (4.6 mg, 5.7 μmol) were added sodium phosphate buffer (pH 6.8, 50 mM, 8 mL) and AMPDA (200 mg). The reaction mixture was left to stir for 4 days, filtered, and purified by reverse phase HPLC (eluting MeCN/H$_2$O gradient with 100 mM TEAA modifier, linear gradient) to afford the product (Diastereomer 1) as the triethylammonium salt. LCMS (ES, m/z): 709 [M−H]$^-$. $^1$H NMR (600 MHz, D$_2$O) δ 8.02 (s, 1H), 7.99 (s, 1H), 7.04 (s, 1H), 6.66 (m, 1H), 6.07 (d, J=8.5 Hz, 1H), 5.76 (m, 1H), 5.49 (d, J=55.8 Hz, 1H), 5.34 (m, 1H), 4.74 (m, 1H), 4.47 (m, 1H), 4.31 (brs, 1H), 4.22-4.13 (m, 2H), 4.06 (m, 1H), 2.80 (m, 3H).

Example 53, as shown in Table 6 below, was prepared according to procedures analogous to those outlined in Example 52 above.

TABLE 6

| Ex. | Structure | Name | Mass [M − H]$^-$ |
|---|---|---|---|
| 53 | 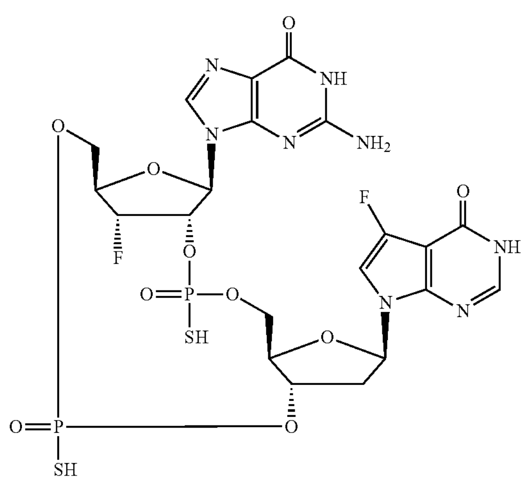 [SMILES: Nc1nc2c(ncn2[C@@H]2O[C@@H]3COP(=O)(S)O[C@H]4C[C@H](n5cc(F)c6c(=O)[nH]cnc65)O[C@@H]4COP(=O)(S)O[C@@H]2[C@@H]3F)c(=O)[nH]1] | 2-amino-9-[(5R,7R,8S,12aR,14R,15aS,16R)-16-fluoro-14-(5-fluoro-4-oxo-3,4-dihydro-7H-pyrrolo[2,3-d]pyrimidin-7-yl)-2,10-dioxido-2,10-disulfanyl-octahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 709 |

287

Example 54: 2-amino-9-[(5S,7R,8R,12aR,14R, 15aS)-2-hydroxy-2,10-dioxido-14-(4-oxo-3,4-dihydro-7H-pyrrolo[2,3-d]pyrimidin-7-yl)-10-sulfanyloctahydro-12H-5,8-methanofuro[3,2-l][1,3,6,9,11,2,10]pentaoxadiphosphacyclotetradecin-7-yl]-1,9-dihydro-6H-purin-6-one Step 1: 3'-deoxy-2'-O-[hydroxy(oxido)-λ⁵-phosphanyl]-N-(2-methylpropanoyl)guanosine

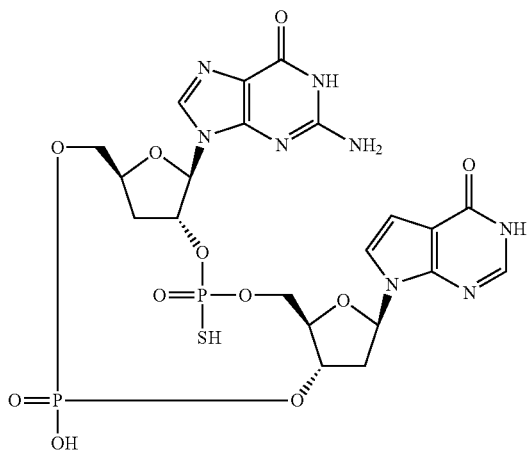 [SMILES: Nc1nc2c(ncn2[C@@H]2O[C@@H]3COP(=O)(O)O[C@H]4C[C@H](n5ccc6c(=O)[nH]cnc65)O[C@@H]4COP(=O)(S)O[C@@H]2C3)c(=O)[nH]1]

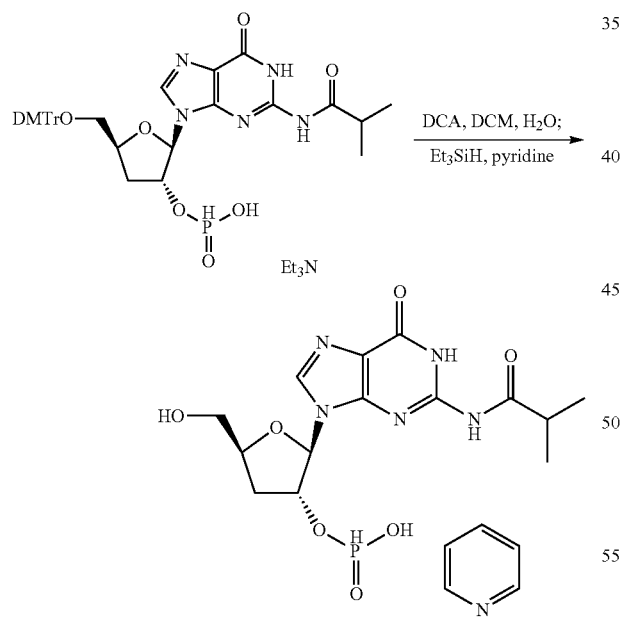

To a stirred solution of triethylammonium 5'-O-[bis(4-methoxyphenyl)(phenyl) methyl]-3'-deoxy-2'-O-[hydroxy (oxido)-λ⁵-phosphanyl]-N-(2-methylpropanoyl)guanosine (1.28 g, 1.59 mmol) in DCM (24 mL) were added H₂O (0.287 g, 15.9 mmol) and DCA in DCM solution (0.6M, 23.85 mL, 14.31 mmol) at RT. The mixture was stirred at RT for 10 min, treated with Et₃SiH (32 mL), and left to stir for 1 h. Py (2.264 g, 28.6 mmol) was added, and the mixture was concentrated under reduced pressure to give the crude product as the pyridinium salt. LCMS (ES, m/z): 402 [M+H]+.

Step 2: (2R,3R,5S)—S-((((((2R,3S,5R)—S-(4-benzamido-7H-pyrrolo[2,3-d]pyrimidin-7-yl)-2-((bis(4-methoxyphenyl)(phenyl)methoxy)methyl)tetrahydrofuran-3-yl)oxy)(2-cyanoethoxy)phosphoryl)oxy) methyl)-2-(2-isobutyramido-6-oxo-1,6-dihydro-9H-purin-9-yl)tetrahydrofuran-3-yl hydrogen phosphonate

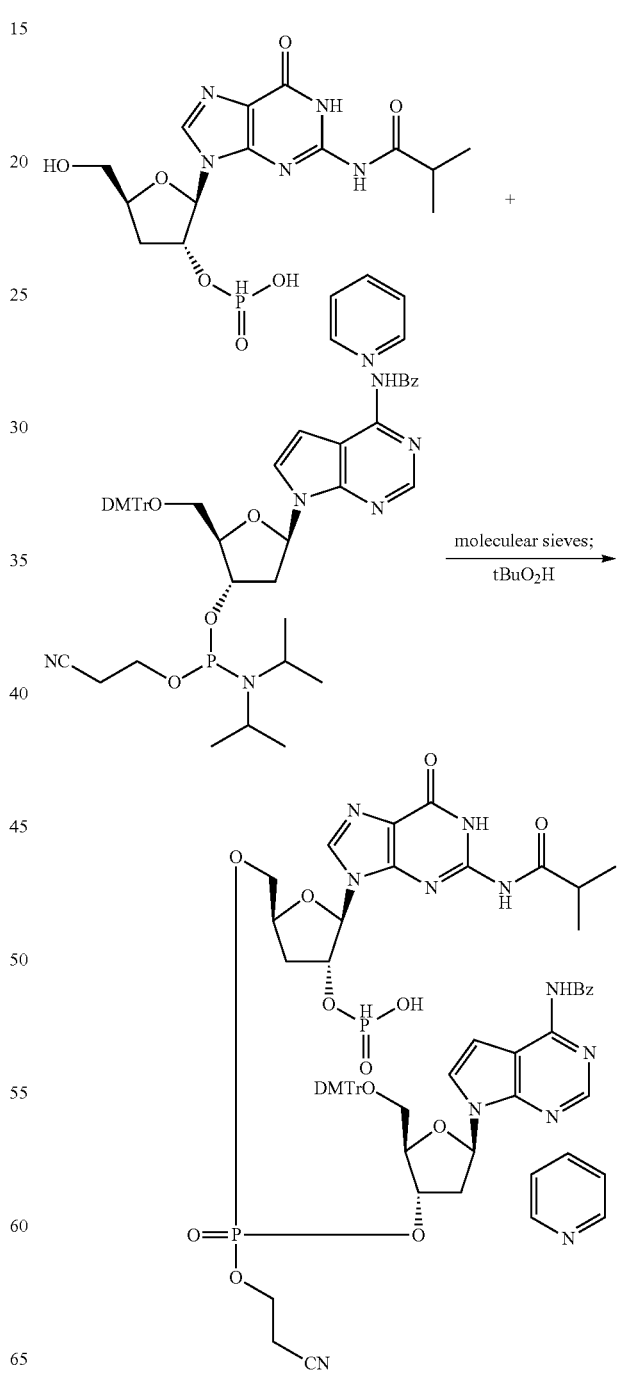

A solution of 7-{5-O-[bis(4-methoxyphenyl)(phenyl)methyl]-3-O-[(2-cyanoethoxy)(dipropan-2-ylamino)phosphanyl]-2-deoxy-β-D-erythro-pentofuranosyl}-N-(phenylcarbonyl)-7H-pyrrolo[2,3-d]pyrimidin-4-amine (1.43 g, 1.67 mmol) in MeCN (5 mL) was concentrated in vacuo. Addition of MeCN (5 mL) followed by concentration was repeated twice. To the residue were added MeCN (12 mL) and activated 4 Å molecular sieves (150 mg).

The crude pyridinium 3'-deoxy-3'-fluoro-2'-O-[hydroxy(oxido)-λ⁵-phosphanyl]-N-(2-methylpropanoyl)guanosine was dissolved in MeCN (5 m) and concentrated in vacuo. Addition of MeCN (5 mL) followed by concentration was repeated twice. To the residue were added MeCN (12 mL) and activated 4 Å molecular sieves (150 mg). After 30 min, the phosphoramidite solution was added to the H-phosphonate solution. The flask was rinsed with MeCN (1 mL), and the solution was transferred to the H-phosphonate solution (2×). The resulting mixture was charged with Ar and stirred at RT for 30 min, treated with tBuO$_2$H (5.5M in decane, 1.0 mL, 5.5 mmol) over 1 min, and left to stir for 1 h. The mixture was cooled to 0° C., treated with aq Na$_2$S$_2$O$_3$ solution (18 g in 3 mL H$_2$O) slowly. The mixture was left to stir at RT for 5 min and concentrated to give the crude product as the pyridinium salt. LCMS (ES, m/z): 1171 [M−H]⁻.

Step 3: (2R,3R,5S)—S-((((((2R,3S,5R)—S-(4-benzamido-7H-pyrrolo[2,3-d]pyrimidin-7-yl)-2-(hydroxymethyl)tetrahydrofuran-3-yl)oxy)(2-cyanoethoxy)phosphoryl) oxy)methyl)-2-(2-isobutyramido-6-oxo-1,6-dihydro-9H-purin-9-yl)tetrahydrofuran-3-yl hydrogen phosphonate

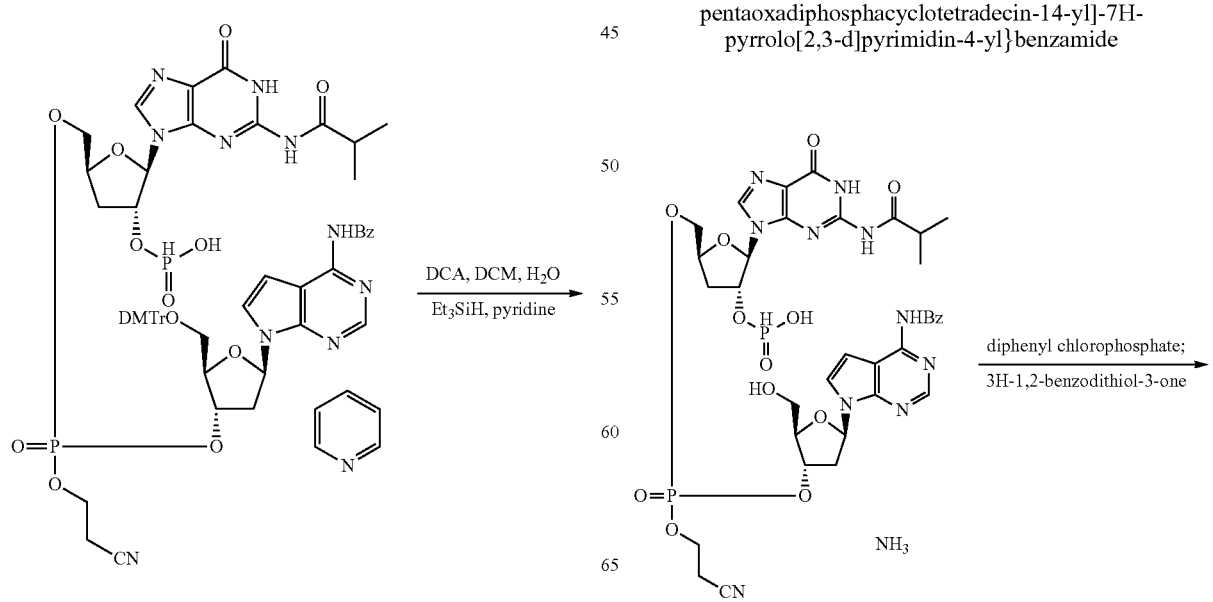

The crude pyridinium (2R,3R,5S)—S-((((((2R,3S,5R)—S-(4-benzamido-7H-pyrrolo[2,3-d]pyrimidin-7-yl)-2-((bis(4-methoxyphenyl)(phenyl)methoxy)methyl)tetrahydrofuran-3-yl)oxy)(2-cyanoethoxy)phosphoryl)oxy)methyl)-2-(2-isobutyramido-6-oxo-1,6-dihydro-9H-purin-9-yl)tetrahydrofuran-3-yl hydrogen phosphonate was dissolved in DCM (24 mL) was treated with H$_2$O (286 mg, 15.9 mmol) and DCA in DCM (0.6M, 23.9 mL, 14.3 mmol) at RT. The mixture was left to stir for 10 min, treated with Et$_3$SiH (20 mL), left to stir for 1 h, and treated with Py (2.26 g, 28.6 mmol). The mixture was concentrated and purified by reverse phase (C18) chromatography eluting with 0 to 95% MeCN in 5 mM aq NH$_4$HCO$_3$ solution to give the product as the ammonium salt. LCMS (ES, m/z): 871 [M+H]⁺.

Step 4: N-{7-[(5S,7R,8R,12aR,14R,15aS)-2-(2-cyanoethoxy)-10-hydroxy-7-{2-[(2-methylpropanoyl)amino]-6-oxo-1,6-dihydro-9H-purin-9-yl}-2-oxido-10-sulfidooctahydro-12H-5,8-methanofuro[3,2-l][1,3,6,9,11,2,10]pentaoxadiphosphacyclotetradecin-14-yl]-7H-pyrrolo[2,3-d]pyrimidin-4-yl}benzamide

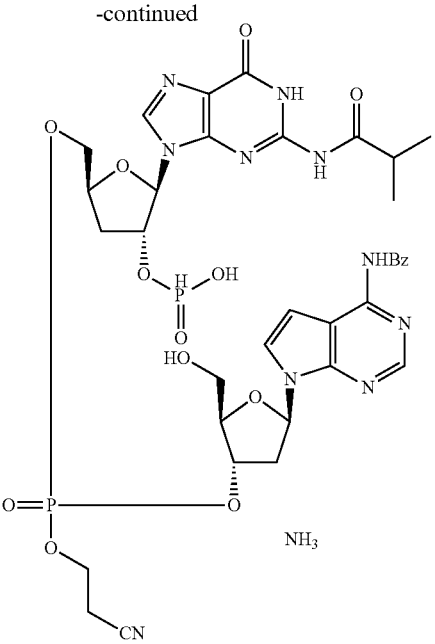

291 -continued

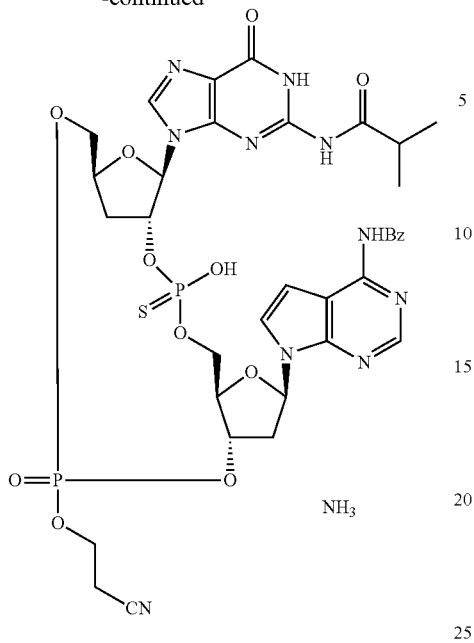

A solution of ammonium (2R,3R,5S)—S-(((((2R,3S,5R)—S-(4-benzamido-7H-pyrrolo[2,3-d]pyrimidin-7-yl)-2-(hydroxymethyl)tetrahydrofuran-3-yl)oxy)(2-cyanoethoxy)phosphoryl)oxy)methyl)-2-(2-isobutyramido-6-oxo-1,6-dihydro-9H-purin-9-yl)tetrahydrofuran-3-yl hydrogen phosphonate (803 mg, 0.923 mmol) in Py (5 mL) was concentrated in vacuo. Addition of Py (5 mL) followed by concentration was repeated twice. The residue was taken up in DCM (70 mL) and Py (20 mL).

To a stirred Py (72 mL) and DCM (20 mL) in a separate flask was added diphenyl chlorophosphate (4961 mg, 18.47 mmol) under Ar at −40° C. To the solution was added the hydrogen phosphonate solution dropwise at −40° C. over 30 min. The resulting mixture was left to stir at −40° C. for 40 min and treated with 3H-1,2-benzodithiol-3-one (255 mg, 1.384 mmol) in one portion and H$_2$O (416 mg, 23.1 mmol) at −40° C. After stirring at RT for 1 h, the mixture was concentrated under reduced pressure. The residue was purified by reverse phase (C18) chromatography eluting with 0 to 95% MeCN in 5 mM aq NH$_4$HCO$_3$ solution to give the product as the ammonium salt. LCMS (ES, m/z): 885 [M+H]$^+$.

292

Step 5: 2-amino-9-[(5S,7R,8R,12aR,14R,15aS)-14-(4-amino-7H-pyrrolo[2,3-d]pyrimidin-7-yl)-2-hydroxy-2,10-dioxido-10-sulfanyloctahydro-12H-5,8-methanofuro[3,2-l][1,3,6,9,11,2,10]pentaoxadiphosphacyclotetradecin-7-yl]-1,9-dihydro-6H-purin-6-one

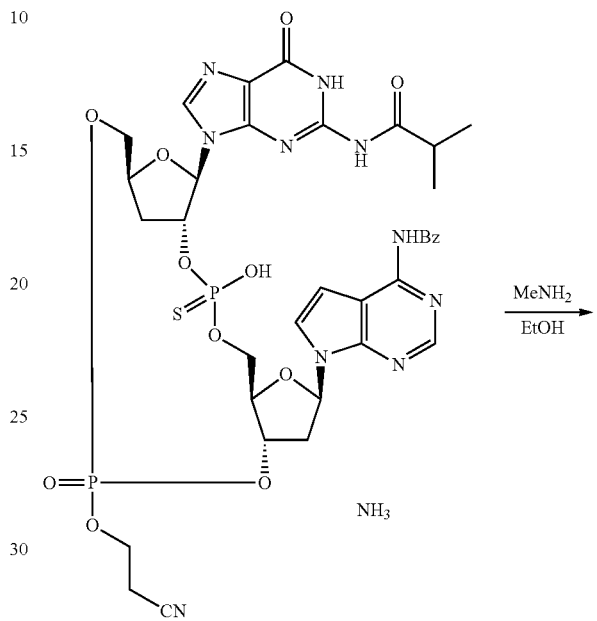

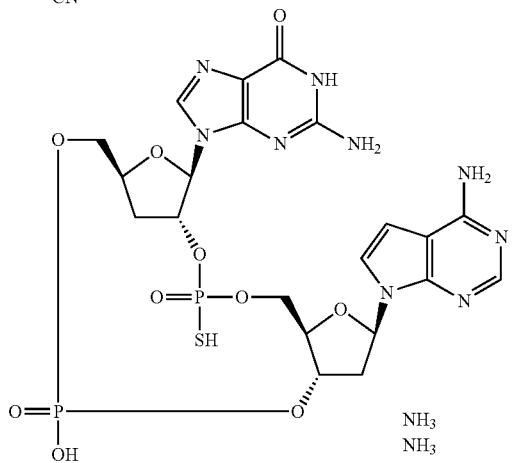

To ammonium N-{7-[(5S,7R,8R,12aR,14R,15aS)-2-(2-cyanoethoxy)-10-hydroxy-7-{2-[(2-methylpropanoyl)amino]-6-oxo-1,6-dihydro-9H-purin-9-yl}-2-oxido-10-sulfidooctahydro-12H-5,8-methanofuro[3,2-l][1,3,6,9,11,2,10]pentaoxadiphospha-cyclotetradecin-14-yl]-7H-pyrrolo[2,3-d]pyrimidin-4-yl}benzamide (580 mg, 0.656 mmol) was added MeNH$_2$ in EtOH (33% w/w, 38 mL), and the resulting solution was left to stir at RT for 3 h and concentrated. The residue was purified by Prep-HPLC (Atlantis Prep T3 OBD Column) eluting with 4 to 13% MeCN in 10 mM aq NH$_4$HCO$_3$ solution to give the two phosphorus diastereomers as the diammonium salts. The slower eluting peak fractions were collected and lyophilized to give the product as the diammonium salt. LCMS (ES, m/z): 658 [M+H]$^+$. $^1$H-NMR: (400 MHz, D$_2$O): δ 8.07 (s, 1H), 7.86 (s, 1H), 7.35 (d, J=3.8 Hz, 1H), 6.52 (dd, J=6.8, 4.4 Hz, 1H), 6.48 (d, J=3.7 Hz, 1H), 5.78 (d, J=6.0 Hz, 1H), 5.47-5.37 (m, 1H), 5.10-5.04 (m, 1H), 4.56-48 (m, 1H), 4.23-4.21 (m, 1H), 4.15-4.00 (m, 4H), 2.83-2.76 (m, 1H), 2.74-2.67 (m, 1H), 2.63-2.55 (m, 1H), 2.47-2.41 (m, 1H). $^{31}$P-NMR: (162 MHz, D$_2$O): δ 53.18, −0.86.

Step 6: 2-amino-9-[(5S,7R,8R,12aR,14R,15a5)-2-hydroxy-2,10-dioxido-14-(4-oxo-3,4-dihydro-7H-pyrrolo[2,3-d]pyrimidin-7-yl)-10-sulfanyloctahydro-12H-5,8-methanofuro [3,2-l][1,3,6,9,11,2,10] pentaoxadiphosphacyclotetradecin-7-yl]-1,9-dihydro-6H-purin-6-one

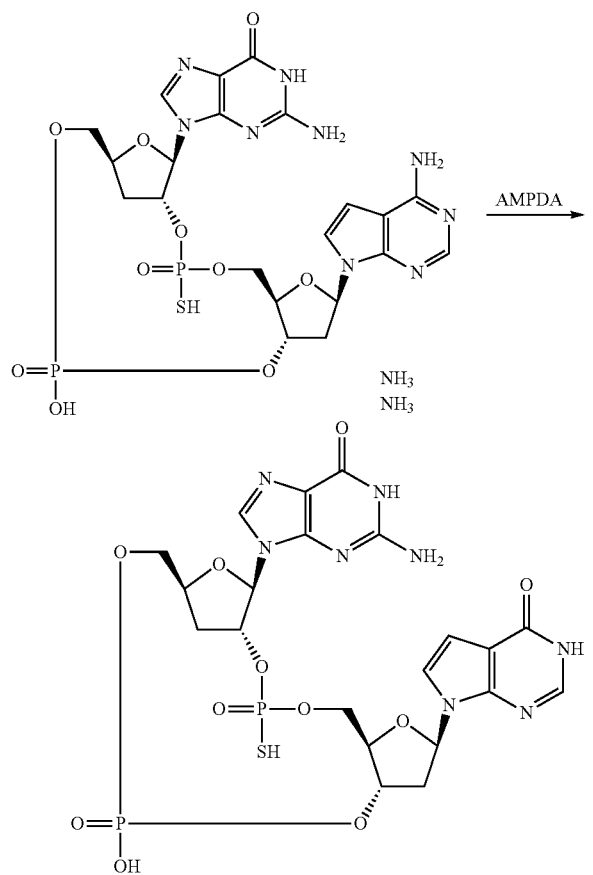

To diammonium 2-amino-9-[(5S,7R,8R,12aR,14R,15aS)-14-(4-amino-7H-pyrrolo[2,3-d]pyrimidin-7-yl)-2-hydroxy-2,10-dioxido-10-sulfanyl octahydro-12H-5,8-methanofuro [3,2-l][1,3,6,9,11,2,10] pentaoxadiphosphacyclotetradecin-7-yl]-1,9-dihydro-6H-purin-6-one (2.7 mg, 4.0 μmol) were added sodium phosphate buffer (pH 6.8, 50 mM, 8 mL) and AMPDA (200 mg). The reaction mixture was left to stir for 11 days and filtered. The filtrate was treated with AMPDA (200 mg) and left to stir for 2 weeks. The mixture was purified by reverse phase HPLC (eluting ACN/H$_2$O gradient with 100 mM TEAA modifier, linear gradient) to afford the product as the triethylammonium salt. LCMS (ES, m/z): 657 [M−H]$^−$. $^1$H NMR (500 MHz, D$_2$O): δ 8.07 (s, 1H), 7.98 (s, 1H), 7.35 (s, 1H), 6.68-6.61 (m, 2H), 5.92 (d, J=4.6 Hz, 1H), 5.45 (m, 1H), 5.13 (brs, 1H), 4.62 (brs, 1H), 4.33 (s, 1H), 4.23-4.08 (m, 4H), 3.08-2.66 (m, 3H), 2.53 (m, 1H).

Biological Evaluation

The individual compounds described in the Examples herein are defined as STING agonists by (i) binding to the STING protein as evidenced by a reduction in binding of tritiated cGAMP ligand to the SITING protein by at least 20% at 20 uM (concentration of compound being tested) in a STING Biochemical [3H]cGAMP Competition Assay and (ii) demonstrating interferon production with a 6% or greater induction of IFN-β secretion at 30 uM in the THP1 cell assay (where induction caused by cGAMP at 30 uM was set at 100%).

[$^3$H]-cGAMP Synthesis 2.3 mL of buffer solution containing 80 mM TrisCl, 200 mM MgCl$_2$, and 20 mM NaCl followed by 0.32 mL of 10 mM aq solution of GTP was added to a plastic 50 mL AMICON tube. A solution of [$^3$H]ATP (21 Ci/mmol, 45 mCi) in 0.5 mL H$_2$O was then added followed by 1 mL of 1 mg/mL solution of DNA (Herring testes activator DNA, Sigma, #D6898) and 53 uL of 47 mM solution of cGAS enzyme. Additional H$_2$O was added to bring the total volume to 10 mL.

The reaction was stirred for 2 h at 37° C. and then added directly to an Amicon Ultra-15 10K centrifuge tube and spun for 1 h at 4,000 g. The collected solution was then purified on a semi-prep Mono Q column using the following mobile phases:

A: 0.05M TrisCl pH 8.5 adjusted with 1M NaOH
B: 0.05M TrisCl, 0.5M NaCl pH 8.5 adjusted with 1M NaOH Gradient: 100% A for 5 min followed by a linear gradient to 50:50 (A:B) over 25 min, 3 mL/min, 254 nm.

The collected product fractions were pooled and adjusted to a total volume of 30 mL with buffer A. A total yield of 15.5 mCi of [$^3$H]cGAMP was isolated at a radiochemical purity of 98.0% at a specific activity of 21.5 Ci/mmol.

cGAS Enzyme

A recombinant DNA vector was chemically synthesized to express the truncated human cGAS enzyme (residues 161-522). To aid in expression and purification, the amino terminus contains a hexahistidine tag, SUMO tag and TEV cleavage site. The recombinant enzyme was overexpressed in R$_{OSETTA}$™ 2(DE3) Single Competent Cells (Novagen). Affinity purification was carried out using HIS-Select HF Nickel Affinity Gel (Sigma) followed by size exclusion chromatography using a Hi-Load 26/60 S$_{UPERDEX}$200 prep grade column (GE Healthcare). Fractions were pooled, concentrated, flash-frozen in liquid nitrogen and stored at −80° C. until needed.

Example 55: $^3$H-cGAMP Filtration Binding Assay (HAQ STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* cell membranes (*T. ni*; Expression Systems, cat #94-002F, www.expressionsystems.com) overexpressing full-length HAQ STING and tritiated cGAMP ligand.

The basic HAQ STING filtration assay protocol is as follows:

The compounds were serially titrated by the Hamilton STARPlus CORE in a 96-well plate (Greiner, #651201) using a 1:3 ten-point dose response format. After compound preparation, a 2.2 ug/ml working concentration of STING membrane (SEQ. ID. No. 1) was prepared by diluting concentrated membrane into assay buffer (lx PBS; Invitrogen #SH30028.02) and douncing 7× using a manual tissue homogenizer (Wheaton, #357546). 148 uL of prepared membrane was then manually added to each well of a 96-well deep-well polypropylene plate (Fisher Scientific, #12-566-121). Following membrane addition, 2 uL of either titrated test compound, DMSO control (Sigma #276855), or cold cGAMP control was added to the appropriate wells using a BIOMEK FX. Compound and membrane then preincubated for 60 min at RT to allow compound binding to equilibrate. Following equilibration, 8 nM of [$^3$H] c-GAMP ligand was prepared by diluting into assay buffer, and 50 uL of this working stock was then manually added to each well of the assay plate. Plates were then incubated at RT for 60 min, and the contents of each assay plate were then filtered through a 96-well GF/B filter plate (PerkinElmer, #6005250) using a TOMTEC MACH III Cell Harvester equipped with 20 mM HEPES buffer (Fisher Scientific, #BP299500). The filter plates were then dried at 55° C. for 30 min using a pressurized oven before 30 uL of ULTIMA GOLD F scintillate was added to each well. Tritium levels for each reaction well were then measured using a PerkinElmer TopCount plate reader.

After normalization to controls, the percent activity for each compound concentration was calculated by measuring the amount of remaining radioactivity. The plot of percent activity versus the log of compound concentration was fit with a 4-parameter dose response equation to calculate $EC_{50}$ values.

The final reaction conditions were:

| Component | Volume (uL) | Final Concentration |
| --- | --- | --- |
| STING membrane | 148 | 1.5 ug/ml |
| $^3$H-cGAMP | 50 | 2.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.001 µM with 1.0% residual DMSO.

Full-Length STING (HAQ) Virus Generation

STING virus was generated using an insect cell baculovirus system. *Spodoptera frugiperda* Sf21 cells (Kempbio, Inc.) were diluted to 5e5 cells/ml in Sf-900II SFM media (LifeTechnologies #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of HAQ STING [STING(1-379)R71H,G230A,H232R,R293Q-GG-AviTag-GS-HRV3C-HIS8/pBAC1] DNA (Genewiz custom synthesis) with 1 mL Sf-900II SFM media containing 10 µL Cellfectin® II Reagent (Invitrogen #10362100) and 100 ng viral backbone BestBac 2.0, v-cath/chiA Deleted Linearized Baculovirus DNA (Expression Systems #91-002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, 1 mL Sf-900II SFM media (no antibiotics) was added to each well of the 6-well plate. After media addition, the cells were allowed to incubate with DNA (SEQ. ID. No. 2) at 27° C. for 5-7 days to generate the P0 viral stock. To generate P1 viral stocks, 0.5 mL of P0 viral supernatant was added to 50 mL uninfected Sf21 cells (seeded the day prior to infection at a density of 5×10$^5$ cells/mL to allow for one overnight doubling) in Sf-900II SFM media containing 5 µg/mL gentamicin (Invitrogen #15710072). The infected cells were then incubated at 27° C. for 3 days while shaking at 110 rpm (ATR Biotech Multitron Infors HT #AJ118). On day 3, P1 cultures were counted using a ViCell XR (Beckman Coulter Life Sciences #383556) to confirm infection had occurred (cell size ≥3 µm larger than uninfected cells and viability approximately 85-95%). Cultures were harvested in 50 mL conical tubes and centrifuged at 2000×g for 10 min at 4° C. The P1 viral supernatants were poured off into clean 50 ml centrifuge tubes, and the remaining P1 cell pellets were used to generate Baculovirus Infected Insect Cells (BIICs). Cryopreservation media containing Sf-900II SFM media with 10% heat inactivated FBS, 10% DMSO (Sigma #D2650), and 5 µg/ml gentamicin was prepared and sterilized through 0.22 µM filter immediately prior to use. P1 cell pellets were resuspended to a density of 2e7 cells/ml and aliquoted into cryovials (1 mL per vial). Cryovials were placed in MR. FROSTY™ cell freezers O/N at −80° C. and transferred to liquid nitrogen for long term storage the following day. To generate P2 viral stock, 0.5 mL of the P1 viral supernatant was added to 50 mL uninfected Sf21 cells (seeded the day prior to infection at a density of 5×10$^5$ cells/mL to allow for one overnight doubling) in Sf-900II SFM media containing 5 µg/mL gentamicin. These cells were incubated at 27° C. for 3 days while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cells/mL×100 pfu/cell).

Full-Length STING (HAQ) Expression

To generate STING membranes, P1/P2 BIICs were amplified overnight by adding thawed BIICs to Sf21 cells seeded at a density of 1.0×10$^6$ cells/mL. The volume of BIIC used to infect the culture was calculated using an assumed BIIC titer of 2e9 pfu/ml to achieve an MOI of 10 in the overnight amplification. After culturing overnight, the cells were counted on a ViCell XR to confirm infection had occurred (cell size ≥3 µm larger than uninfected cells and viability approximately 80-90%). The volume of infected Sf21 cells from the overnight amplification used to infect the large-scale expression of *Trichoplusia ni* (*T. ni*; Expression Systems, cat #94-002F, www.expressionsystems.com) seeded at a density of 1.0×10$^6$ in cell media (ESF921 SFM containing 5 µg/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. *T. ni* cells were counted on a ViCell XR to confirm infection had occurred (cell size ≥3 µm larger than uninfected cells and viability approximately 80-90%) prior to harvest.

Full-Length STING (HAQ) Membrane Generation

Buffer stock reagents:
1) 1M HEPES pH 7.5, Teknova, Cat #H1035
2) 5M NaCl, Sigma Aldrich, Cat #55150-1L
3) KCl, Sigma Aldrich, Cat #319309-500ML
4) Complete EDTA-free protease inhibitor tablets, Roche Diagnostics, Cat #11873580001
5) Benzonase, Universal Nuclease, Pierce, Cat #88702

Lysis buffer [25 mM HEPES pH 7.5, 10 mM MgCl$_2$, 20 mM KCl, (Benzonase 1:5000, Complete Protease Inhibitor tab/50 mL)] was added to the pellet of cells expressing full-length STING (HAQ) prepared above at 5 mL Lysis buffer per g of cell pellet. The pellet was resuspended and dounced twenty times using a Wheaton Dounce Homogenizer to disrupt the cell membrane. Homogenized lysate was then passed through the EMULSIFLEX-05 microfluidizer at a pressure close to 5000PSI. The resuspended pellet was centrifuged at 36,000 rpm (100,000×g) in a 45Ti rotor ultra-high speed centrifuge for 45 min, 4° C. The supernatant was removed. The pellet then was resuspended in wash buffer [(25 mM HEPES pH7.5, 1 mM $MgCl_2$, 20 mM KCl, 1M NaCl (Complete Protease Inhibitor tab/50 mL)] at a volume of 50 mL pellet/centrifuge tube. The pellet/wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (1 tablet/50 mL). The protein concentration was measured by Bradford assay (Bio-Rad Protein Assay, Cat #500-0006), and protein enrichment was determined by SDS-PAGE and confirmed by Western blot. The resuspended membranes were stored at −80° C.

```
Full-Length HAQ STING [STING(1-379) R71H, G230A, H232R, R293Q-GG-AviTag-
GS-HRV3C-HIS8] Amino Acid Sequence:
                                                           (SEQ. ID. No. 1)
MPHSSLHPSIPCPRGHGAQKAALVLLSACLVTLWGLGEPPEHTLRYLVLHLASLQLGLL

LNGVCSLAEELHHIHSRYRGSYWRTVRACLGCPLRRGALLLLSIYFYYSLPNAVGPPFT

WMLALLGLSQALNILLGLKGLAPAEISAVCEKGNFNVAHGLAWSYYIGYLRLILPELQA

RIRTYNQHYNNLLRGAVSQRLYILLPLDCGVPDNLSMADPNIRFLDKLPQQTADRAGIK

DRVYSNSIYELLENGQRAGTCVLEYATPLQTLFAMSQYSQAGFSREDRLEQAKLFCQTL

EDILADAPESQNNCRLIAYQEPADDSSFSLSQEVLRHLRQEEKEEVTVGSLKTSAVPSTST

MSQEPELLISGMEKPLPLRTDFSGGGLNDIFEAQKIEWHEGSLEVLFQGPHHHHHHHH

Full-length HAQ [STING(1-379) R71H, G230A, H232R, R293Q-GG-AviTag-GS-
HRV3C-HIS8/pBAC1] PlasmidDNA Sequence:
                                                           (SEQ. ID. No. 2)
GGAACGGCTCCGCCCACTATTAATGAAATTAAAAATTCCAATTTTAAAAAACGCAGC

AAGAGAAACATTTGTATGAAAGAATGCGTAGAAGGAAAGAAAAATGTCGTCGACAT

GCTGAACAACAAGATTAATATGCCTCCGTGTATAAAAAAAATATTGAACGATTTGA

AAGAAAACAATGTACCGCGCGGCGGTATGTACAGGAAGAGGTTTATACTAAACTGT

TACATTGCAAACGTGGTTTCGTGTGCCAAGTGTGAAAACCGATGTTTAATCAAGGCT

CTGACGCATTTCTACAACCACGACTCCAAGTGTGTGGGTGAAGTCATGCATCTTTTA

ATCAAATCCCAAGATGTGTATAAACCACCAAACTGCCAAAAAATGAAAACTGTCGA

CAAGCTCTGTCCGTTTGCTGGCAACTGCAAGGGTCTCAATCCTATTTGTAATTATTGA

ATAATAAAACAATTATAAATGCTAAATTTGTTTTTTATTAACGATACAAACCAAACG

CAACAAGAACATTTGTAGTATTATCTATAATTGAAAACGCGTAGTTATAATCGCTGA

GGTAATATTTAAAATCATTTTCAAATGATTCACAGTTAATTTGCGACAATATAATTTT

ATTTTCACATAAACTAGACGCCTTGTCGTCTTCTTCTTCGTATTCCTTCTCTTTTTCAT

TTTTCTCTTCATAAAAATTAACATAGTTATTATCGTATCCATATATGTATCTATCGTA

TAGAGTAAATTTTTTGTTGTCATAAATATATATGTCTTTTTTAATGGGGTGTATAGTA

CCGCTGCGCATAGTTTTTCTGTAATTTACAACAGTGCTATTTTCTGGTAGTTCTTCGG

AGTGTGTTGCTTTAATTATTAAATTTATATAATCAATGAATTTGGGATCGTCGGTTTT

GTACAATATGTTGCCGGCATAGTACGCAGCTTCTTCTAGTTCAATTACACCATTTTTT

AGCAGCACCGGATTAACATAACTTTCCAAAATGTTGTACGAACCGTTAAACAAAAA

CAGTTCACCTCCCTTTTCTATACTATTGTCTGCGAGCAGTTGTTTGTTGTTAAAAATA

ACAGCCATTGTAATGAGACGCACAAACTAATATCACAAACTGGAAATGTCTATCAA

TATATAGTTGCTGATCAGATCTGATCATGGAGATAATTAAAATGATAACCATCTCGC

AAATAAATAAGTATTTTACTGTTTTCGTAACAGTTTTGTAATAAAAAAACCTATAAA

TATAGGATCCATGCCCCACTCCAGCCTGCATCCATCCCGTGTCCCAGGGGTCA
```

-continued

```
CGGGGCCCAGAAGGCAGCCTTGGTTCTGCTGAGTGCCTGCCTGGTGACCCTTTGGGG

GCTAGGAGAGCCACCAGAGCACACTCTCCGGTACCTGGTGCTCCACCTAGCCTCCCT

GCAGCTGGGACTGCTGTTAAACGGGGTCTGCAGCCTGGCTGAGGAGCTGCACCACA

TCCACTCCAGGTACCGGGGCAGCTACTGGAGGACTGTGCGGGCCTGCCTGGGCTGC

CCCCTCCGCCGTGGGGCCCTGTTGCTGCTGTCCATCTATTTCTACTACTCCCTCCCAA

ATGCGGTCGGCCCGCCCTTCACTTGGATGCTTGCCCTCCTGGGCCTCTCGCAGGCAC

TGAACATCCTCCTGGGCCTCAAGGGCCTGGCCCCAGCTGAGATCTCTGCAGTGTGTG

AAAAAGGGAATTTCAACGTGGCCCATGGGCTGGCATGGTCATATTACATCGGATATC

TGCGGCTGATCCTGCCAGAGCTCCAGGCCCGGATTCGAACTTACAATCAGCATTACA

ACAACCTGCTACGGGGTGCAGTGAGCCAGCGGCTGTATATTCTCCTCCCATTGGACT

GTGGGGTGCCTGATAACCTGAGTATGGCTGACCCCAACATTCGCTTCCTGGATAAAC

TGCCCCAGCAGACCGCTGACCGTGCTGGCATCAAGGATCGGGTTTACAGCAACAGC

ATCTATGAGCTTCTGGAGAACGGGCAGCGGGCGGGCACCTGTGTCCTGGAGTACGC

CACCCCCTTGCAGACTTTGTTTGCCATGTCACAATACAGTCAAGCTGGCTTTAGCCG

GGAGGATAGGCTTGAGCAGGCCAAACTCTTCTGCCAGACACTTGAGGACATCCTGG

CAGATGCCCCTGAGTCTCAGAACAACTGCCGCCTCATTGCCTACCAGGAACCTGCAG

ATGACAGCAGCTTCTCGCTGTCCCAGGAGGTTCTCCGGCACCTGCGGCAGGAGGAA

AAGGAAGAGGTTACTGTGGGCAGCTTGAAGACCTCAGCGGTGCCCAGTACCTCCAC

GATGTCCCAAGAGCCTGAGCTCCTCATCAGTGGAATGGAAAAGCCCCTCCCTCTCCG

CACGGATTTCTCTGGCGGTGGCCTGAACGACATCTTCGAAGCCCAGAAAATCGAATG

GCATGAAGGCAGCCTGGAAGTGCTGTTCCAGGGCCCACACCACCATCATCACCATC

ACCATTAATGAGCGGCCGCACTCGAGCACCACCACCACCACCACTAACCTAGGTAG

CTGAGCGCATGCAAGCTGATCCGGGTTATTAGTACATTTATTAAGCGCTAGATTCTG

TGCGTTGTTGATTTACAGACAATTGTTGTACGTATTTTAATAATTCATTAAATTTATA

ATCTTTAGGGTGGTATGTTAGAGCGAAAATCAAATGATTTTCAGCGTCTTTATATCT

GAATTTAAATATTAAATCCTCAATAGATTTGTAAAATAGGTTTCGATTAGTTTCAAA

CAAGGGTTGTTTTTCCGAACCGATGGCTGGACTATCTAATGGATTTTCGCTCAACGC

CACAAAACTTGCCAAATCTTGTAGCAGCAATCTAGCTTTGTCGATATTCGTTTGTGTT

TTGTTTTGTAATAAAGGTTCGACGTCGTTCAAAATATTATGCGCTTTTGTATTTCTTT

CATCACTGTCGTTAGTGTACAATTGACTCGACGTAAACACGTTAAATAGAGCTTGGA

CATATTTAACATCGGGCGTGTTAGCTTTATTAGGCCGATTATCGTCGTCGTCCCAACC

CTCGTCGTTAGAAGTTGCTTCCGAAGACGATTTTGCCATAGCCACACGACGCCTATT

AATTGTGTCGGCTAACACGTCCGCGATCAAATTTGTAGTTGAGCTTTTTGGAATTATT

TCTGATTGCGGGCGTTTTTGGGCGGGTTTCAATCTAACTGTGCCCGATTTTAATTCAG

ACAACACGTTAGAAAGCGATGGTGCAGGCGGTGGTAACATTTCAGACGGCAAATCT

ACTAATGGCGGCGGTGGTGGAGCTGATGATAAATCTACCATCGGTGGAGGCGCAGG

CGGGGCTGGCGGCGGAGGCGGAGGCGGAGGTGGTGGCGGTGATGCAGACGGCGGT

TTAGGCTCAAATGTCTCTTTAGGCAACACAGTCGGCACCTCAACTATTGTACTGGTTT

CGGGCGCCGTTTTTGGTTTGACCGGTCTGAGACGAGTGCGATTTTTTCGTTTCTAAT

AGCTTCCAACAATTGTTGTCTGTCGTCTAAAGGTGCAGCGGGTTGAGGTTCCGTCGG

CATTGGTGGAGCGGGCGGCAATTCAGACATCGATGGTGGTGGTGGTGGTGGAGGCG
```

```
CTGGAATGTTAGGCACGGGAGAAGGTGGTGGCGGCGGTGCCGCCGGTATAATTTGT

TCTGGTTTAGTTTGTTCGCGCACGATTGTGGGCACCGGCGCAGGCGCCGCTGGCTGC

ACAACGGAAGGTCGTCTGCTTCGAGGCAGCGCTTGGGGTGGTGGCAATTCAATATTA

TAATTGGAATACAAATCGTAAAAATCTGCTATAAGCATTGTAATTTCGCTATCGTTT

ACCGTGCCGATATTTAACAACCGCTCAATGTAAGCAATTGTATTGTAAAGAGATTGT

CTCAAGCTCGGATCGATCCCGCACGCCGATAACAAGCCTTTTCATTTTTACTACAGC

ATTGTAGTGGCGAGACACTTCGCTGTCGTCGAGGTTTAAACGCTTCCTCGCTCACTG

ACTCGCTGCGCTCGGTCGTTCGGCTGCGGCGAGCGGTATCAGCTCACTCAAAGGCGG

TAATACGGTTATCCACAGAATCAGGGGATAACGCAGGAAAGAACATGTGAGCAAAA

GGCCAGCAAAAGGCCAGGAACCGTAAAAAGGCCGCGTTGCTGGCGTTTTTCCATAG

GCTCCGCCCCCCTGACGAGCATCACAAAAATCGACGCTCAAGTCAGAGGTGGCGAA

ACCCGACAGGACTATAAAGATACCAGGCGTTTCCCCCTGGAAGCTCCCTCGTGCGCT

CTCCTGTTCCGACCCTGCCGCTTACCGGATACCTGTCCGCCTTTCTCCCTTCGGGAAG

CGTGGCGCTTTCTCATAGCTCACGCTGTAGGTATCTCAGTTCGGTGTAGGTCGTTCGC

TCCAAGCTGGGCTGTGTGCACGAACCCCCCGTTCAGCCCGACCGCTGCGCCTTATCC

GGTAACTATCGTCTTGAGTCCAACCCGGTAAGACACGACTTATCGCCACTGGCAGCA

GCCACTGGTAACAGGATTAGCAGAGCGAGGTATGTAGGCGGTGCTACAGAGTTCTT

GAAGTGGTGGCCTAACTACGGCTACACTAGAAGGACAGTATTTGGTATCTGCGCTCT

GCTGAAGCCAGTTACCTTCGGAAAAAGAGTTGGTAGCTCTTGATCCGGCAAACAAA

CCACCGCTGGTAGCGGTGGTTTTTTTGTTTGCAAGCAGCAGATTACGCGCAGAAAAA

AAGGATCTCAAGAAGATCCTTTGATCTTTTCTACGGGGTCTGACGCTCAGTGGAACG

AAAACTCACGTTAAGGGATTTTGGTCATGAGATTATCAAAAAGGATCTTCACCTAGA

TCCTTTTAAATTAAAAATGAAGTTTTAAATCAATCTAAAGTATATATGAGTAAACTT

GGTCTGACAGTTACCAATGCTTAATCAGTGAGGCACCTATCTCAGCGATCTGTCTAT

TTCGTTCATCCATAGTTGCCTGACTCCCCGTCGTGTAGATAACTACGATACGGGAGG

GCTTACCATCTGGCCCCAGTGCTGCAATGATACCGCGAGACCCACGCTCACCGGCTC

CAGATTTATCAGCAATAAACCAGCCAGCCGGAAGGGCCGAGCGCAGAAGTGGTCCT

GCAACTTTATCCGCCTCCATCCAGTCTATTAATTGTTGCCGGGAAGCTAGAGTAAGT

AGTTCGCCAGTTAATAGTTTGCGCAACGTTGTTGCCATTGCTACAGGCATCGTGGTG

TCACGCTCGTCGTTTGGTATGGCTTCATTCAGCTCCGGTTCCCAACGATCAAGGCGA

GTTACATGATCCCCCATGTTGTGCAAAAAAGCGGTTAGCTCCTTCGGTCCTCCGATC

GTTGTCAGAAGTAAGTTGGCCGCAGTGTTATCACTCATGGTTATGGCAGCACTGCAT

AATTCTCTTACTGTCATGCCATCCGTAAGATGCTTTTCTGTGACTGGTGAGTACTCAA

CCAAGTCATTCTGAGAATAGTGTATGCGGCGACCGAGTTGCTCTTGCCCGGCGTCAA

TACGGGATAATACCGCGCCACATAGCAGAACTTTAAAAGTGCTCATCATTGGAAAA

CGTTCTTCGGGGCGAAAACTCTCAAGGATCTTACCGCTGTTGAGATCCAGTTCGATG

TAACCCACTCGTGCACCCAACTGATCTTCAGCATCTTTTACTTTCACCAGCGTTTCTG

GGTGAGCAAAAACAGGAAGGCAAAATGCCGCAAAAAAGGGAATAAGGGCGACACG

GAAATGTTGAATACTCATACTCTTCCTTTTTCAATATTATTGAAGCATTTATCAGGGT

TATTGTCTCATGAGCGGATACATATTTGAATGTATTTAGAAAAATAAACAAATAGGG
```

-continued
```
GTTCCGCGCACATTTCCCCGAAAAGTGCCACCTGACGCGCCCTGTAGCGGCGCATTA

AGCGCGGCGGGTGTGGTGGTTACGCGCAGCGTGACCGCTACACTTGCCAGCGCCCT

AGCGCCCGCTCCTTTCGCTTTCTTCCCTTCCTTTCTCGCCACGTTCGCCGGCTTTCCCC

GTCAAGCTCTAAATCGGGGGCTCCCTTTAGGGTTCCGATTTAGTGCTTTACGGCACC

TCGACCCCAAAAAACTTGATTAGGGTGATGGTTCACGTAGTGGGCCATCGCCCTGAT

AGACGGTTTTTCGCCCTTTGACGTTGGAGTCCACGTTCTTTAATAGTGGACTCTTGTT

CCAAACTGGAACAACACTCAACCCTATCTCGGTCTATTCTTTTGATTTATAAGGGATT

TTGCCGATTTCGGCCTATTGGTTAAAAAATGAGCTGATTTAACAAAAATTTAACGCG

AATTTTAACAAAATATTAACGTTTACAATTTCCCATTCGCCATTCAGGCTGCGCAACT

GTTGGGAAGGGCGATCGGTGCGGGCCTCTTCGCTATTACGCCA
```

Certain compounds of the disclosure were evaluated in HAQ STING in vitro binding assay as described above. Table 7 tabulates the biological data for these compounds as $EC_{50}$ values.

TABLE 7

$^3$H-cGAMP filtration binding assay for HAQ STING

| Compound | $EC_{50}$ (nM) |
| --- | --- |
| Example 1 | 77 |
| Example 2 | 2 |
| Example 3 | 140 |
| Example 4 | 59 |
| Example 5 | 563 |
| Example 6 | 28 |
| Example 7 | 2 |
| Example 8 | 23 |
| Example 9 | 23 |
| Example 10 | 3 |
| Example 11 | 1742 |
| Example 12 | 156 |
| Example 13 | 238 |
| Example 17 | 3 |
| Example 18 | 126 |
| Example 19 | 208 |
| Example 20 | 15 |
| Example 22 | 146 |
| Example 23 | 28 |
| Example 24 | 411 |
| Example 25 | 1 |
| Example 26 | 19 |
| Example 27 | 61 |
| Example 28 | 41 |
| Example 29 | 45 |
| Example 30 | 37 |
| Example 31 | 16 |
| Example 32 | 14 |
| Example 33 | 90 |
| Example 34 | 1123 |
| Example 35 | 11 |
| Example 36 | 2 |
| Example 37 | 49 |
| Example 38 | 1 |
| Example 39 | 1 |
| Example 40 | 5 |
| Example 41 | 2 |
| Example 42 | 1 |
| Example 43 | 37 |
| Example 44 | 1 |
| Example 45 | 3 |
| Example 46 | 16 |
| Example 47 | 460 |
| Example 48 | 2 |
| Example 49 | 1 |
| Example 50 | 4 |
| Example 51 | 13 |

TABLE 7-continued $^3$H-cGAMP filtration binding assay for HAQ STING

| Compound | $EC_{50}$ (nM) |
| --- | --- |
| Example 52 | 14 |
| Example 53 | 167 |
| Example 54 | 12 |

Example 56: $^3$H-cGAMP Filtration Binding Assay (WT STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* cell membranes (*T. ni*; Expression Systems, cat #94-002F, www.expressionsystems.com) overexpressing full-length WT STING and tritiated cGAMP ligand.

The basic WT STING filtration assay protocol is as follows:

16 nM of [$^3$H] c-GAMP ligand was prepared by diluting into assay buffer, and 50 uL of this working stock was manually added to each well of the assay plate. After ligand addition, 2 uL of either titrated test compound, DMSO control (Sigma #276855), or cold cGAMP control was added to the appropriate wells using a BIOMEK FX. The serially titrated compound was prepared on a Hamilton STARPlus CORE in a 96-well plate (Greiner, #651201) using a 1:3 ten-point dose response format. Following compound addition, a 2.2 ug/ml working concentration of STING membrane (SEQ. ID. No. 3) was prepared by diluting concentrated membrane into assay buffer (1×PBS; Invitrogen #SH30028.02) and douncing 7× using a manual tissue homogenizer (Wheaton, #357546). 148 uL of this prepared membrane was then manually added to each well of a 96-well deep-well polypropylene plate (Fisher Scientific, #12-566-121). Compound, ligand, and membrane then incubated for 60 min at RT before the contents of each assay plate were filtered through a 96-well GF/B filter plate (PerkinElmer, #6005250) using a TOMTEC MACH III Cell Harvester equipped with 20 mM HEPES buffer (Fisher Scientific, #BP299500). The filter plates were then dried at 55° C. for 30 min using a pressurized VWR oven before 30 uL of ULTIMA GOLD F scintillate was added to each well. Tritium levels for each reaction well were then measured using a PerkinElmer TopCount plate reader.

After normalization to controls, the percent activity for each compound concentration was calculated by measuring the amount of remaining radioactivity. The plot of percent activity versus the log of compound concentration was fit with a 4-parameter dose response equation to calculate $EC_{50}$ values.

The final reaction conditions were:

| Component | Volume (uL) | Final Concentration |
| --- | --- | --- |
| STING membrane | 148 | 1.5 ug/ml |
| $^3$H-cGAMP | 50 | 4.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.001 µM with 1.0% residual DMSO.

Full-Length STING (WT) Virus Generation

STING virus was generated using an insect cell baculovirus system. *Spodoptera frugiperda* Sf21 cells (Kempbio, Inc.) were diluted to 5e5 cells/ml in Sf-900II SFM media (LifeTechnologies #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of WT STING[STING(1-379)H232R-gg-AviTag-gs-HRV3C-HIS8/pBAC1] (Genewiz custom synthesis) with 1 mL Sf-900II SFM media containing 10 µL CELLFECTIN® II Reagent (Invitrogen #10362100) and 100 ng viral backbone BestBac 2.0, v-cath/chiA Deleted Linearized Baculovirus DNA (Expression Systems #91-002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, 1 mL Sf-900II SFM media (no antibiotics) was added to each well of the 6-well plate. After media addition, the cells were allowed to incubate with DNA [(SEQ. ID. No. 4) and linearized viral backbone BestBac 2.0] at 27° C. for 5-7 days to generate the P0 viral stock. To generate P1 viral stocks, 0.5 mL of P0 viral supernatant was added to 50 mL uninfected Sf21 cells (seeded the day prior to infection at a density of $5\times10^5$ cells/mL to allow for one overnight doubling) in Sf-900II SFM media containing 5 µg/mL gentamicin (Invitrogen #15710072). The infected cells were then incubated at 27° C. for 3 days while shaking at 110 rpm (ATR Biotech Multitron Infors HT #AJ118). On day 3, P1 cultures were counted using a ViCell XR (Beckman Coulter Life Sciences #383556) to confirm infection had occurred (cell size ≥3 µm larger than uninfected cells and viability approximately 85-95%). Cultures were harvested in 50 mL conical tubes and centrifuged at 2000×g for 10 min at 4° C. The P1 viral supernatants were poured off into clean 50 ml centrifuge tubes, and the remaining P1 cell pellets were used to generate Baculovirus Infected Insect Cells (BIICs). Cryopreservation media containing Sf-900II SFM media with 10% heat inactivated FBS, 10% DMSO (Sigma #D2650), and 5 µg/ml gentamicin was prepared and sterilized through 0.22 µM filter immediately prior to use. P1 cell pellets were resuspended to a density of 2e7 cells/ml and aliquoted into cryovials (1 mL per vial). Cryovials were placed in MR. FROSTY™ cell freezers O/N at −80° C. and transferred to liquid nitrogen for long term storage the following day. To generate P2 viral stock, 0.5 mL of the P1 viral supernatant was added to 50 mL uninfected Sf21 cells (seeded the day prior to infection at a density of $5\times10^5$ cells/mL to allow for one overnight doubling) in Sf-900II SFM media containing 5 µg/mL gentamicin. These cells were incubated at 27° C. for 3 days while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cell s/mL×100 pfu/cell).

Full-Length STING (WT) Expression

To generate STING membranes, P1/P2 BIICs were amplified overnight by adding thawed BIICs to Sf21 cells seeded at a density of $1.0\times10^6$ cells/mL. The volume of BIIC used to infect the culture was calculated using an assumed BIIC titer of 2e9 pfu/ml to achieve an MOI of 10 in the overnight amplification. After culturing overnight, the cells were counted on a ViCell XR to confirm infection had occurred (cell size ≥3 µm larger than uninfected cells and viability approximately 80-90%). The volume of infected Sf21 cells from the overnight amplification used to infect the large-scale expression of *Trichoplusia ni* (*T. ni*; Expression Systems, cat #94-002F, www.expressionsystems.com) seeded at a density of $1.0\times10^6$ in cell media (ESF921 SFM containing 5 µg/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. *T. ni* cells were counted on a ViCell XR to confirm infection had occurred (cell size ≥3 µm larger than uninfected cells and viability approximately 80-90%) prior to harvest.

Full-Length STING (WT) Membrane Generation

Buffer stock reagents:
1) 1 M HEPES pH 7.5, Teknova, Cat #H1035
2) 5 M NaCl, Sigma Aldrich, Cat #55150-1L
3) KCl, Sigma Aldrich, Cat #319309-500ML
4) Complete EDTA-free protease inhibitor tablets, Roche Diagnostics, Cat #11873580001
5) Benzonase, Universal Nuclease, Pierce, Cat #88702

Lysis buffer [25 mM HEPES pH 7.5, 10 mM $MgCl_2$, 20 mM KCl, (Benzonase 1:5000, Complete Protease Inhibitor tab/50 mL)] was added to the pellet of cells expressing full-length STING (WT) prepared above at 5 mL Lysis buffer per g of cell pellet. The pellet was resuspended and dounced twenty times using a Wheaton Dounce Homogenizer to disrupt the cell membrane. Homogenized lysate was then passed through the emulsiflex-05 microfluidizer at a pressure close to 5000PSI. The resuspended pellet was centrifuged at 36,000 rpm (100,000× g) in a 45Ti rotor ultra-high speed centrifuge for 45 min, 4° C. The supernatant was removed. The pellet then was resuspended in wash buffer [(25 mM HEPES pH 7.5, 1 mM $MgCl_2$, 20 mM KCl, 1M NaCl (Complete Protease Inhibitor tab/50 mL)] at a volume of 50 mL/pellet/centrifuge tube. The pellet/wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (1 tablet/50 mL). The protein concentration was measured by Bradford assay (Bio-Rad Protein Assay, Cat #500-0006), and protein enrichment was determined by SDS-PAGE and confirmed by Western blot. The resuspended membranes were stored at −80° C.

[0590] Full-Length STING WT[STING(1-379)H232R-gg-AviTag-gs-HRV3C-HIS8] Amino Acid Sequence:
MPHSSLHPSIPCPRGHGAQKAALVLLSACLVTLWGLGEPPEHTLRYLVLHLASLQLGLL
LNGVCSLAEELRHIHSRYRGSYWRTVRACLGCPLRRGALLLLSIYFYYSLPNAVGPPFT
WMLALLGLSQALNILLGLKGLAPAEISAVCEKGNFNVAHGLAWSYYIGYLRLILPELQA
RIRTYNQHYNNLLRGAVSQRLYILLPLDCGVPDNLSMADPNIRFLDKLPQQTGDRAGIK
DRVYSNSIYELLENGQRAGTCVLEYATPLQTLFAMSQYSQAGFSREDRLEQAKLFCRTL
EDILADAPESQNNCRLIAYQEPADDSSFSLSQEVLRHLRQEEKEEVTVGSLKTSAVPSTST
MSQEPELLISGMEKPLPLRTDFSGGGLNDIFEAQKIEWHEGSLEVLFQGPHHHHHHHH
(SEQ. ID. No. 3)

[0591] Full-length WTSTING [STING(1-379)H232R-gg-AviTag-gs-HRV3C-HIS8/pBAC1] plasmid sequence:
GGAACGGCTCCGCCCACTATTAATGAAATTAAAAATTCCAATTTTAAAAAACGCAGC
AAGAGAAACATTTGTATGAAAGAATGCGTAGAAGGAAAGAAAAATGTCGTCGACAT
GCTGAACAACAAGATTAATATGCCTCCGTGTATAAAAAAAATATTGAACGATTTGA
AAGAAAACAATGTACCGCGCGGCGGTATGTACAGGAAGAGGTTTATACTAAACTGT
TACATTGCAAACGTGGTTTCGTGTGCCAAGTGTGAAAACCGATGTTTAATCAAGGCT
CTGACGCATTTCTACAACCACGACTCCAAGTGTGTGGGTGAAGTCATGCATCTTTTA
ATCAAATCCCAAGATGTGTATAAACCACCAAACTGCCAAAAAATGAAAACTGTCGA
CAAGCTCTGTCCGTTTGCTGGCAACTGCAAGGGTCTCAATCCTATTTGTAATTATTGA
ATAATAAAACAATTATAAATGTCAAATTTGTTTTTTATTAACGATACAAACCAAACG
CAACAAGAACATTTGTAGTATTATCTATAATTGAAAACGCGTAGTTATAATCGCTGA
GGTAATATTTAAAATCATTTTCAAATGATTCACAGTTAATTTGCGACAATATAATTTT
ATTTTCACATAAACTAGACGCCTTGTCGTCTTCTTCTTCGTATTCCTTCTCTTTTTCAT
TTTTCTCTTCATAAAAATTAACATAGTTATTATCGTATCCATATATGTATCTATCGTA
TAGAGTAAATTTTTTGTTGTCATAAATATATATGTCTTTTTTAATGGGGTGTATAGTA
CCGCTGCGCATAGTTTTTCTGTAATTTACAACAGTGCTATTTTCTGGTAGTTCTTCGG
AGTGTGTTGCTTTAATTATTAAATTTATATAATCAATGAATTTGGGATCGTCGGTTTT
GTACAATATGTTGCCGGCATAGTACGCAGCTTCTTCTAGTTCAATTACACCATTTTTT
AGCAGCACCGGATTAACATAACTTTCCAAAATGTTGTACGAACCGTTAAACAAAAA
CAGTTCACCTCCCTTTTCTATACTATTGTCTGCGAGCAGTTGTTTGTTGTTAAAAATA
ACAGCCATTGTAATGAGACGCACAAACTAATATCACAAACTGGAAATGTCTATCAA
TATATAGTTGCTGATCAGATCTGATCATGGAGATAATTAAAATGATAACCATCTCGC
AAATAAATAAGTATTTTACTGTTTTCGTAACAGTTTTGTAATAAAAAAACCTATAAA
TATAGGATCCATGCCCCACTCCAGCCTGCATCCATCCATCCCGTGTCCCAGGGGTCA
CGGGGCCCAGAAGGCAGCCTTGGTTCTGCTGAGTGCCTGCCTGGTGACCCTTTGGGG
GCTAGGAGAGCCACCAGAGCACACTCTCCGGTACCTGGTGCTCCACCTAGCCTCCT
GCAGCTGGGACTGCTGTTAAACGGGGTCTGCAGCCTGGCTGAGGAGCTGCGCCACA
TCCACTCCAGGTACCGGGGCAGCTACTGGAGGACTGTGCGGGCCTGCCTGGGCTGC
CCCCTCCGCCGTGGGGCCCTGTTGCTGCTGTCCATCTATTTCTACTACTCCCTCCCAA
ATGCGGTCGGCCCGCCCTTCACTTGGATGCTTGCCCTCCTGGGCCTCTCGCAGGCAC
TGAACATCCTCCTGGGCCTCAAGGGCCTGGCCCCAGCTGAGATCTCTGCAGTGTGTG
AAAAAGGGAATTTCAACGTGGCCCATGGGCTGGCATGGTCATATTACATCGGATATC
TGCGGCTGATCCTGCCAGAGCTCCAGGCCCGGATTCGAACTTACAATCAGCATTACA
ACAACCTGCTACGGGGTGCAGTGAGCCAGCGGCTGTATATTCTCCTCCCATTGGACT
GTGGGGTGCCTGATAACCTGAGTATGGCTGACCCCAACATTCGCTTCCTGGATAAAC
TGCCCCAGCAGACCGGTGACCGTGCTGGCATCAAGGATCGGGTTTACAGCAACAGC
ATCTATGAGCTTCTGGAGAACGGGCAGCGGGCGGGCACCTGTGTCCTGGAGTACGC
CACCCCCTTGCAGACTTTGTTTGCCATGTCACAATACAGTCAAGCTGGCTTTAGCCG
GGAGGATAGGCTTGAGCAGGCCAAACTCTTCTGCCGGACACTTGAGGACATCCTGG
CAGATGCCCCTGAGTCTCAGAACAACTGCCGCCTCATTGCCTACCAGGAACCTGCAG
ATGACAGCAGCTTCTCGCTGTCCCAGGAGGTTCTCCGGCACCTGCGGCAGGAGGAA
AAGGAAGAGGTTACTGTGGGCAGCTTGAAGACCTCAGCGGTGCCCAGTACCTCCAC
GATGTCCCAAGAGCCTGAGCTCCTCATCAGTGGAATGGAAAAGCCCCTCCCTCTCCG
CACGGATTTCTCTGGCGGTGGCCTGAACGACATCTTCGAAGCCCAGAAAATCGAATG
GCATGAAGGCAGCCTGGAAGTGCTGTTCCAGGGCCCACACCACCATCATCACCATC
ACCATTAATGAGGCCGCGCACTCGAGCACCACCACCACCACCACTAACCTAGGTAG
CTGAGCGCATGCAAGCTGATCCGGGTTATTAGTACATTTATTAAGCGCTAGATTCTG
TGCGTTGTTGATTTACAGACAATTGTTGTACGTATTTTAATAATTCATTAAATTTATA
ATCTTTAGGGTGGTATGTTAGAGCGAAAATCAAATGATTTTCAGCGTCTTTATATCT
GAATTTAAATATTAAATCCTCAATAGATTTGTAAAATAGGTTTCGATTAGTTTCAAA
CAAGGGTTGTTTTTCCGAACCGATGGCTGGACTATCTAATGGATTTTCGCTCAACGC
CACAAAACTTGCCAAATCTTGTAGCAGCAATCTAGCTTTGTCGATATTCGTTTGTGTT
ttgttttgtaataaaggttcgacgtcgttcaaaatattatgcgcttttgtatttcttt
CATCACTGTCGTTAGTGTACAATTGACTCGACGTAAACACGTTAAATAGAGCTTGGA
CATATTTAACATCGGGCGTGTTAGCTTTATTAGGCCGATTATCGTCGTCGTCCCAACC
CTCGTCGTTAGAAGTTGCTTCCGAAGACGATTTTGCCATAGCCACACGACGCCTATT
AATTGTGTCGGCTAACACGTCCGCGATCAAATTTGTAGTTGAGCTTTTTGGAATTATT
TCTGATTGCGGGCGTTTTTGGGCGGGTTTCAATCTAACTGTGCCCGATTTTAATTCAG
ACAACACGTTAGAAAGCGATGGTCAGGCGGTGGTAACATTTCAGACGGCAAATCT
ACTAATGGCGGCGGTGGTGGAGCTGATGATAAATCTACCATCGGTGGAGGCGCAGG
CGGGGCTGGCGGCGGAGGCGGAGGCGGAGGTGGTGGCGGTGATGCAGACGGCGGT
TTAGGCTCAAATGTCTCTTTAGGCAACACAGTCGGCACCTCAACTATTGTACTGGTTT
CGGGCGCCGTTTTGGTTTGACCGGTCTGAGACGAGTGCGATTTTTTCGTTTCTAAT
AGCTTCCAACAATTGTTGTCTGTCGTCTAAAGGTGCAGCGGGTTGAGGTTCCGTCGG
CATTGGTGGAGCGGGCGGCAATTCAGACATCGATGGTGGTGGTGGTGGAGGGCG
CTGGAATGTTAGGCACGGGAGAAGGTGGTGGCGGCGGTGCCGCCGGTATAATTTGT
TCTGGTTTAGTTTGTTCGCGCACGATTGTGGGCACCGGCGCAGGCGCCGCTGGCTGC
ACAACGGAAGGTCGTCTGCTTCGAGGCAGCGCTTGGGTGGTGGCAATTCAATATTA
TAATTGGAATACAAATCGTAAAAATCTGCTATAAGCATTGTAATTTCGCTATCGTTT
ACCGTGCCGATATTTAACAACCGCTCAATGTAAGCAATTGTATTGTAAAGAGATTGT -continued

```
CTCAAGCTCGGATCGATCCCGCACGCCGATAACAAGCCTTTTCATTTTTACTACAGC
ATTGTAGTGGCGAGACACTTCGCTGTCGTCGAGGTTTAAACGCTTCCTCGCTCACTG
ACTCGCTGCGCTCGGTCGTTCGGCTGCGGCGAGCGGTATCAGCTCACTCAAAGGCGG
TAATACGGTTATCCACAGAATCAGGGGATAACGCAGGAAAGAACATGTGAGCAAAA
GGCCAGCAAAAGGCCAGGAACCGTAAAAAGGCCGCGTTGCTGGCGTTTTTCCATAG
GCTCCGCCCCCCTGACGAGCATCACAAAAATCGACGCTCAAGTCAGAGGTGGCGAA
ACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCC
GGTAACTATCGTCTTGAGTCCAACCCGGTAAGACACGACTTATCGCCACTGGCAGCA
GCCACTGGTAACAGGATTAGCAGAGCGAGGTATGTAGGCGGTGCTACAGAGTTCTT
GAAGTGGTGGCCTAACTACGGCTACACTAGAAGGACAGTATTTGGTATCTGCGCTCT
GCTGAAGCCAGTTACCTTCGGAAAAAGAGTTGGTAGCTCTTGATCCGGCAAACAAA
CCACCGCTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGTGGAACG
AAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTAT
TTCGTTCATCCATAGTTGCCTGACTCCCCGTCGTGTAGATAACTACGATACGGGAGG
GCTTACCATCTGGCCCCAGTGCTGCAATGATACCGCGAGACCCACGCTCACCGGCTC
CAGATTTATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAGAGTAAGT
AGTTCGCCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCAAGGCGA
GTTACATGATCCCCATGTTGTGCAAAAAAGCGGTTAGCTCCTTCGGTCCTCCGATC
GTTGTCAGAAGTAAGTTGGCCGCAGTGTTATCACTCATGGTTATGGCAGCACTGCAT
AATTCTCTTACTGTCATGCCATCCGTAAGATGCTTTTCTGTGACTGGTGAGTACTCAA
CCAAGTCATTCTGAGAATAGTGTATGCGGCGACCGAGTTGCTCTTGCCCGGCGTCAA
TACGGGATAATACCGCGCCACATAGCAGAACTTTAAAAGTGCTCATCATTGGAAAA
CGTTCTTCGGGGCGAAAACTCTCAAGGATCTTACCGCTGTTGAGATCCAGTTCGATG
TAACCCACTCGTGCACCCAACTGATCTTCAGCATCTTTTACTTTCACCAGCGTTTCTG
GGTGAGCAAAAACAGGAAGGCAAATGCCGCAAAAAAGGGAATAAGGGCGACACG
GAAATGTTGAATACTCATACTCTTCCTTTTTCAATATTATTGAAGCATTTATCAGGGT
TATTGTCTCATGAGCGGATACATATTTGAATGTATTTAGAAAAATAAACAAATAGGG
GTTCCGCGCACATTTCCCCGAAAAGTGCCACCTGACGCGCCCTGTAGCGGCGCATTA
AGCGCGGCGGGTGTGGTGGTTACGCGCAGCGTGACCGCTACACTTGCCAGCGCCCT
AGCGCCCGCTCCTTTCGCTTTCTTCCCTTCCTTTCTCGCCACGTTCGCCGGCTTTCCCC
GTCAAGCTCTAAATCGGGGGCTCCCTTTAGGGTTCCGATTTAGTGCTTTACGGCACC
TCGACCCCAAAAAACTTGATTAGGGTGATGGTTCACGTAGTGGGCCATCGCCCTGAT
AGACGGTTTTTCGCCCTTTGACGTTGGAGTCCACGTTCTTTAATAGTGGACTCTTGTT
CCAAACTGGAACAACACTCAACCCTATCTCGGTCTATTCTTTTGATTTATAAGGGATT
TTGCCGATTTCGGCCTATTGGTTAAAAAATGAGCTGATTTAACAAAAATTTAACGCG
AATTTTAACAAAATATTAACGTTTACAATTTCCCATTCGCCATTCAGGCTGCGCAACT
GTTGGGAAGGGCGATCGGTGCGGGCCTCTTCGCTATTACGCCA (SEQ. ID. No. 4)
```

Certain compounds of the disclosure were evaluated in WT STING in vitro binding assay as described above. The following table tabulates the biological data for these compounds as $EC_{50}$ values.

TABLE 8

$^3$H-cGAMP filtration binding assay for WT STING

| Compound | $EC_{50}$ (nM) |
|---|---|
| Example 1 | 1642 |
| Example 2 | 32 |
| Example 3 | 1856 |
| Example 4 | 1764 |
| Example 5 | 10260 |
| Example 13 | 1960 |
| Example 14 | 433 |
| Example 15 | 43 |
| Example 16 | 90 |
| Example 19 | 902 |
| Example 20 | 83 |
| Example 21 | 832 |
| Example 29 | 136 |
| Example 38 | 393 |
| Example 40 | 2830 |
| Example 41 | 124 |
| Example 42 | 46 |
| Example 43 | 148 |
| Example 45 | 85 |

TABLE 8-continued $^3$H-cGAMP filtration binding assay for WT STING

| Compound | $EC_{50}$ (nM) |
|---|---|
| Example 46 | 2402 |
| Example 48 | 205 |
| Example 49 | 756 |
| Example 50 | 9133 |
| Example 52 | 21 |
| Example 53 | 253 |
| Example 55 | 212 |
| Example 56 | 1985 |

Example 57: IFN-β Secretion in THP1 Cell Culture (5 h)

The ability of compounds to stimulate the secretion of interferon-beta from THP1 cells was measured using a human IFN-β AlphaLISA kit (Perkin Elmer, Cat. No. AL265F). The basic protocol is as follows:

A Labcyte Echo 550 acoustic dispenser was used to transfer 120 nL of compound dissolved in DMSO into the wells of an empty, sterile 384-well microplate, (Corning, Cat. No. 3712). THP1 cells (American Type Culture Collection, Cat. No. TIB202) previously frozen in Recovery Medium (Life Technologies, Cat. No. 12648-010) were thawed and immediately diluted 10-fold into 37° C. assay medium (RPMI 1640+L-Glutamine & phenol red, Life Technologies, Cat. No. 11875-085; 0.5% heat inactivated fetal bovine serum, Sigma Aldrich, Cat. No. F4135; 1 mM Sodium Pyruvate, Life Technologies, Cat. No. 11360-070; 1× non-essential amino acids; Life Technologies, Cat. No. 11140-050). The cell viability and count was ascertained using a Beckman Coulter V-Cell XR cell counter. The cell suspension was centrifuged at 200×g for 5 min at RT. Cells were resuspended to a density of $0.8×10^6$/mL in 37° C. assay medium. Subsequent liquid transfers were performed using either a Matrix electronic multichannel pipette or an Agilent Bravo Automated Liquid Handling Platform.

The assay was started by dispensing 40 μL of the previously prepared cell suspension into the wells of the plate containing compounds. After 5 h incubation at 37° C., 5% $CO_2$ in a humidified atmosphere, the plate of cells and compounds was centrifuged at 200×g for 5 min at RT. From each well, 5 μL of supernatant was transferred into corresponding wells of a white 384-well plate (Perkin Elmer, Cat. No. 6005620). To these supernatant-containing wells was added 10 μL of 5× Anti-Analyte Acceptor beads (50 μg/mL of AlphaLISA HiBlock Buffer) and incubated for 30 min at RT while shaking on an orbital plate shaker. To each well was added 10 μL of 5× Biotinylated Antibody Anti-analyte (5 nM in AlphaLISA HiBlock Buffer) and incubated on an orbital plate shaker for 60 min at RT or overnight at 4° C. To each well was added 25 μL of 2× SA-Donor beads (80 μg/mL in AlphaLISA HiBlock Buffer) and incubated for 30-45 min at RT in the dark while shaking on an orbital plate shaker. The plate was then read on a Perkin Elmer Envision ($\lambda_{ex}$ 680 nm, $\lambda_{em}$=570 nm). The percent effect of the AlphaLISA signal at each compound concentration was calculated based on 30 uM cGAMP positive controls and 0.3% DMSO negative controls. The plot of percent effect versus the log of compound concentration was fit with a 4-parameter concentration response equation to calculate $EC_{50}$ values. The test compounds were tested at concentrations 30000, 10000, 3333, 1111, 370.4, 123.4, 41.2, 13.7, 4.6, and 1.5 nM with 0.3% residual DMSO. The control compound, cGAMP was tested at concentrations 100000, 33333, 11111, 3704, 1235, 412, 137, 46, and 15 nM with 0.3% residual DMSO.

Compounds of the disclosure were evaluated for IFN-β secretion in THP1 cell culture as described above. The following table tabulates the biological data for these compounds as percent activation relative to 2'3'-cGAMP at the 30 μM concentration.

TABLE 9

IFN-β secretion in THP1 cell culture (5 h)

| Compound | % Effect at 30 μM relative to 2'3'-cGAMP |
| --- | --- |
| Example 1 | 143 |
| Example 2 | 44 |
| Example 3 | 20 |
| Example 4 | 139 |
| Example 5 | 39 |
| Example 6 | 145 |
| Example 7 | 140 |
| Example 8 | 128 |
| Example 9 | 80 |
| Example 10 | 183 |
| Example 11 | 5 |
| Example 12 | 123 |
| Example 13 | 334 |
| Example 14 | 12 |
| Example 15 | 318 |
| Example 16 | 281 |
| Example 17 | 122 |
| Example 18 | 124 |
| Example 19 | 7 |
| Example 20 | 169 |
| Example 21 | 143 |
| Example 22 | 100 |
| Example 23 | 123 |
| Example 23 | 36 |
| Example 25 | 131 |
| Example 26 | 153 |
| Example 27 | 143 |
| Example 28 | 143 |
| Example 29 | 150 |
| Example 30 | 127 |
| Example 31 | 28 |
| Example 32 | 141 |
| Example 33 | 83 |
| Example 34 | 157 |
| Example 35 | 98 |
| Example 36 | 94 |
| Example 37 | 102 |
| Example 38 | 109 |
| Example 39 | 166 |
| Example 40 | 150 |
| Example 41 | 156 |
| Example 42 | 72 |
| Example 43 | 120 |
| Example 44 | 164 |
| Example 45 | 135 |
| Example 46 | 166 |
| Example 47 | 13 |
| Example 48 | 159 |
| Example 49 | 163 |
| Example 50 | 109 |
| Example 51 | 113 |
| Example 52 | 53 |
| Example 53 | 85 |
| Example 54 | 68 |

It will be appreciated that various of the above-discussed and other features and functions, or alternatives thereof, may be desirably combined into many other different systems or applications. It also will be appreciated that various presently unforeseen or unanticipated alternatives, modifications, variations or improvements therein may be subsequently made by those skilled in the art and are also intended to be encompassed by the following claims.

What is claimed is:
1. A compound of formula (I):
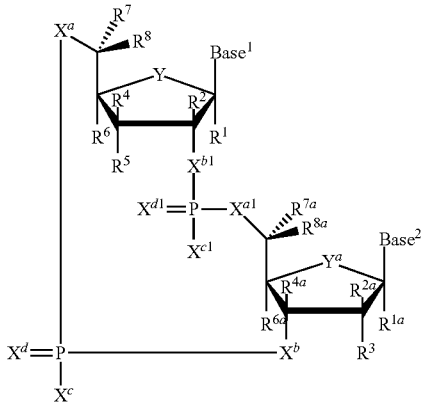
or a pharmaceutically acceptable salt thereof, wherein
Base¹ and Base² are each independently selected from the group consisting of
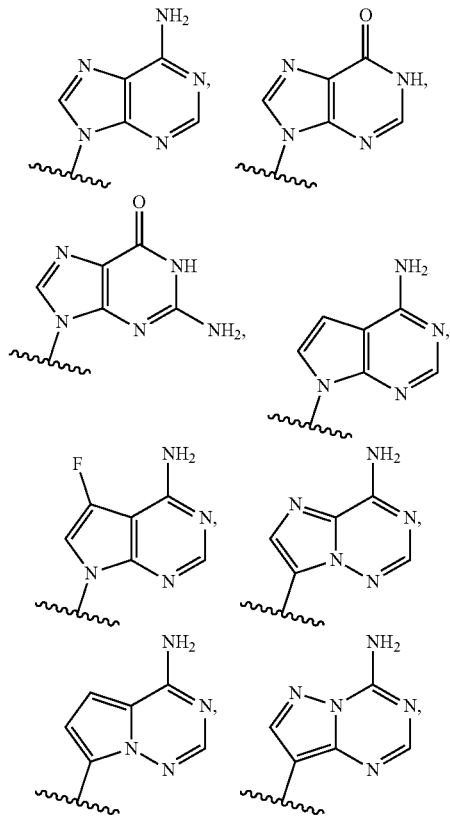
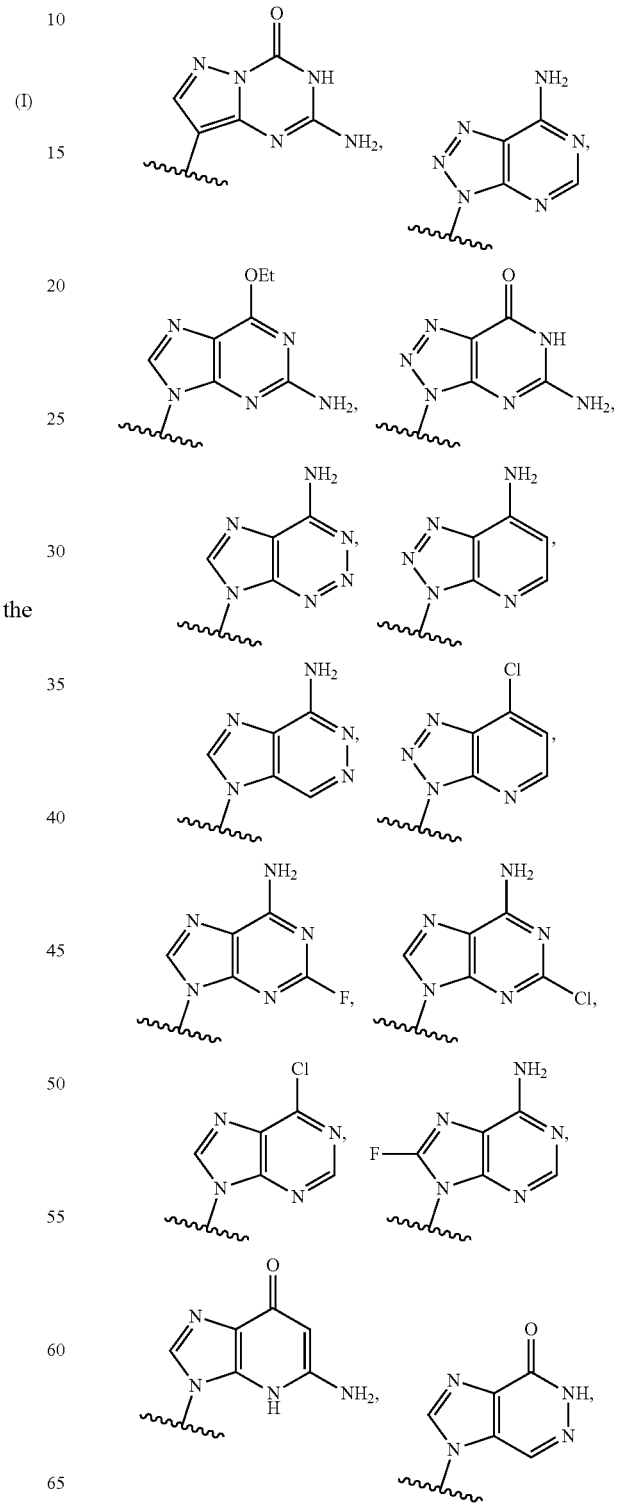

331
-continued
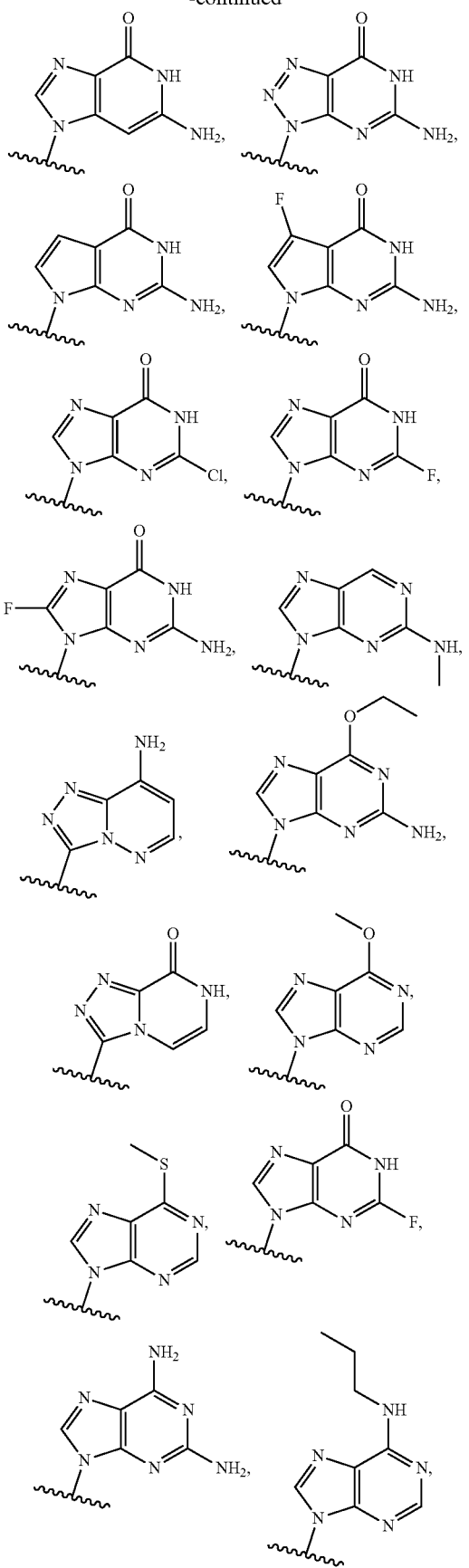
332
-continued
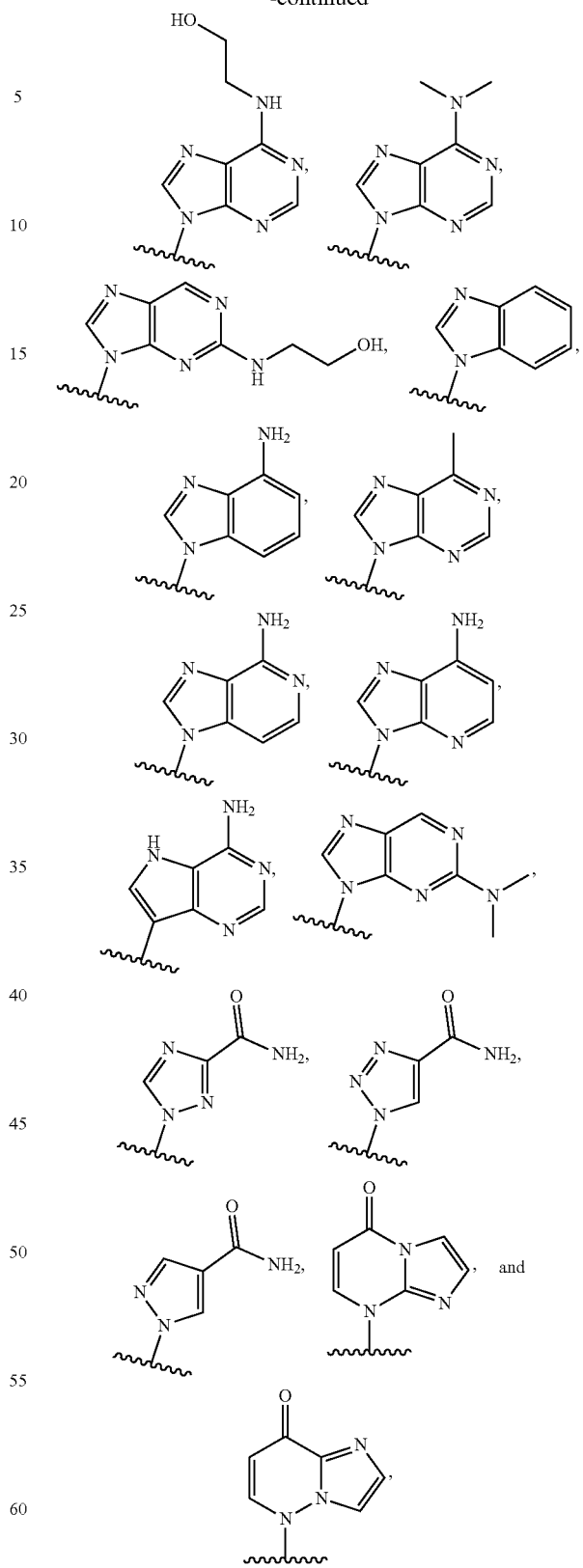
wherein
at least one of Base[1] and Base[2] is each independently selected from the group consisting of

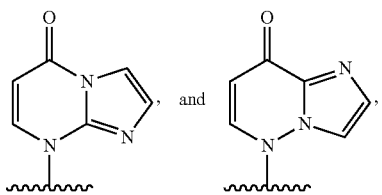 [SMILES: *n1ccc(=O)n2ccnc12 ; *n1ccc(=O)c2nccn21]

and

Base[1] and Base[2] each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$;

Y and $Y^a$ are each independently selected from the group consisting of —S—, —$SO_2$—, —$CH_2$—, and —$CF_2$—;

$X^a$ and $X^{a1}$ are each independently selected from the group consisting of —O—, —S—, and —$CH_2$—;

$X^b$ and $X^{b1}$ are each independently selected from the group consisting of —O—, —S—, and —$CH_2$—;

$X^c$ and $X^{c1}$ are each independently selected from the group consisting of —$SR^9$, —$OR^9$, and —$NR^9R^9$, $X^d$ and $X^{d1}$ are each independently selected from the group consisting of O and S;

$R^1$ and $R^{1a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^1$ and $R^{1a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^2$ and $R^{2a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^2$ and $R^{2a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^3$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^3$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^4$ and $R^{4a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^4$ and $R^{4a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^5$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^5$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^6$ and $R^{6a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^6$ and $R^{6'}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^7$ and $R^{7a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^7$ and $R^{7a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^8$ and $R^{8a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^8$ and $R^{8a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

each $R^9$ is independently selected from the group consisting of H, $C_1$-$C_{20}$ alkyl,

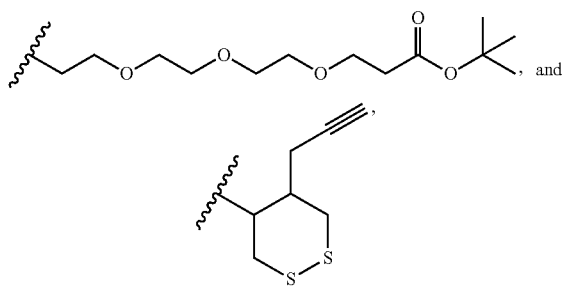

where each $R^9$ $C_1$-$C_{20}$ alkyl is optionally substituted by 0 to 3 substituents independently selected from the group consisting of OH, —O—$C_1$-$C_{20}$ alkyl, —S—$C(O)C_1$-$C_6$ alkyl, and $C(O)OC_1$-$C_6$ alkyl;

optionally $R^{1a}$ and $R^3$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^{1a}$ and $R^3$ are connected to form —O—$C_1$-$C_6$ alkylene, or —O—$C_2$-$C_6$ alkenylene, said O is bound at the $R^3$ position;

optionally $R^{2a}$ and $R^3$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^{2a}$ and $R^3$ are connected to form —O—$C_1$-$C_6$ alkylene, or —O—$C_2$-$C_6$ alkenylene, said O is bound at the $R^3$ position;

optionally $R^3$ and $R^{6'}$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^3$ and $R^{6'}$ are connected to form —O—$C_1$-$C_6$ alkylene, or —O—$C_2$-$C_6$ alkenylene, said O is bound at the $R^3$ position;

optionally $R^4$ and $R^5$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^4$ and $R^5$ are connected to form —O—$C_1$-$C_6$ alkylene, or —O—$C_2$-$C_6$ alkenylene, said O is bound at the $R^5$ position;

optionally $R^5$ and $R^6$ are connected to form —O—$C_1$-$C_6$ alkylene, —O—$C_2$-$C_6$ alkenylene, or —O—$C_2$-$C_6$ alkynylene, such that where $R^5$ and $R^6$ are connected to form $C_1$-$C_6$ alkylene, —O—$C_2$-$C_6$ alkenylene, or —O—$C_2$-$C_6$ alkynylene, said O is bound at the $R^5$ position;

optionally $R^7$ and $R^8$ are connected to form $C_1$-$C_6$ alkylene or $C_2$-$C_6$ alkenylene; and optionally $R^{7a}$ and $R^{8a}$ are connected to form $C_1$-$C_6$ alkylene or $C_2$-$C_6$ alkenylene.

2. The compound according to claim 1, or a pharmaceutically acceptable salt thereof, wherein $Y$ and $Y^a$ are each independently selected from the group consisting of —O— and —S—;

$X^a$ and $X^{a1}$ are each independently selected from the group consisting of —O— and —S—;

$X^b$ and $X^{b1}$ are each independently selected from the group consisting of —O and —S—;

$X^c$ and $X^{c1}$ are each independently selected from the group consisting of —S$R^9$, —O$R^9$, and —N$R^9R^9$;

$X^d$ and $X^{d1}$ are each independently selected from the group consisting of O and S;

$R^1$ and $R^{1a}$ are each H;

$R^2$ and $R^{2a}$ are each independently selected from the group consisting of H, F, Cl, Br, I, OH, CN, N$_3$, $C_1$-$C_6$ alkyl, and $C_1$-$C_6$ haloalkyl, where said $R^2$ and $R^{2a}$ $C_1$-$C_6$ alkyl or $C_1$-$C_6$ haloalkyl are substituted by 0 to 3 substituents selected from the group consisting of OH, CN, and N$_3$;

$R^3$ is selected from the group consisting of H, F, Cl, Br, I, OH, CN, N$_3$, $C_1$-$C_6$ alkyl, and $C_1$-$C_6$ haloalkyl, where said $R^3$ $C_1$-$C_6$ alkyl or $C_1$-$C_6$ haloalkyl are substituted by 0 to 3 substituents selected from the group consisting of OH, CN, and N$_3$;

$R^4$ and $R^{4a}$ are each independently selected from the group consisting of H, F, Cl, I, Br, CN, OH, N$_3$, $C_1$-$C_6$ alkyl, and $C_1$-$C_6$ haloalkyl, where said $R^4$ and $R^{4a}$ $C_1$-$C_6$ alkyl or $C_1$-$C_6$ haloalkyl are substituted by 0 to 3 substituents selected from the group consisting of OH, CN, and N$_3$;

$R^5$ is selected from the group consisting of H, F, Cl, Br, I, OH, N$_3$, $C_1$-$C_6$ alkyl, and $C_1$-$C_6$ haloalkyl, where said $R^5$ $C_1$-$C_6$ alkyl or $C_1$-$C_6$ haloalkyl are substituted by 0 to 3 substituents selected from the group consisting of F, Cl, Br, I, OH, CN, and N$_3$;

$R^6$ and $R^{6a}$ are each independently selected from the group consisting of H, F, Cl, I, Br, OH, CN, N$_3$, $C_1$-$C_6$ alkyl, $C_2$-$C_6$ alkenyl, and $C_2$-$C_6$ alkynyl, where said $R^6$ and $R^{6a}$ $C_1$-$C_6$ alkyl, $C_2$-$C_6$ alkenyl, and $C_2$-$C_6$ alkynyl are substituted by 0 to 3 substituents selected from the group consisting of F, Cl, Br, I, OH, CN, and N$_3$;

$R^7$ and $R^{7a}$ are each independently selected from the group consisting of H, $C_1$-$C_6$ alkyl, and $C_1$-$C_6$ haloalkyl, where said $R^7$ and $R^{7a}$ $C_1$-$C_6$ alkyl or $C_1$-$C_6$ haloalkyl are substituted by 0 to 3 substituents selected from the group consisting of OH, CN, and N$_3$;

$R^8$ and $R^{8a}$ are each independently selected from the group consisting of H, $C_1$-$C_6$ alkyl, and $C_1$-$C_6$ haloalkyl, where said $R^7$ and $R^{8a}$ $C_1$-$C_6$ alkyl or $C_1$-$C_6$ haloalkyl are substituted by 0 to 3 substituents selected from the group consisting of OH, CN, and N$_3$;

each $R^9$ is independently selected from the group consisting of H, $C_1$-$C_6$ alkyl,

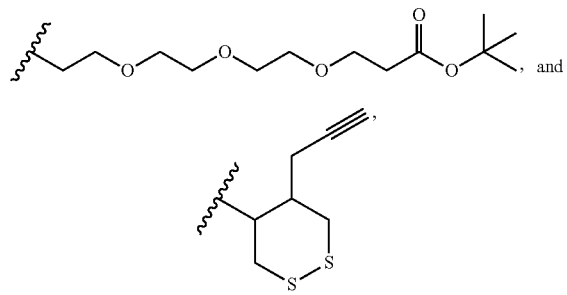, and where each $R^9$ $C_1$-$C_6$ alkyl is optionally substituted by 1 to 2 substituents independently selected from the group consisting of OH, —O—$C_1$-$C_{20}$ alkyl, —S—C(O)$C_1$-$C_6$ alkyl, and —C(O)O$C_1$-$C_6$ alkyl;

optionally $R^3$ and $R^{6'}$ are connected to form $C_2$-$C_6$ alkylene, $C_2$-$C_6$ alkenylene, —O—$C_1$-$C_6$ alkylene, or —O—$C_2$-$C_6$ alkenylene, such that where $R^3$ and $R^{6a}$ are connected to form —O—$C_1$-$C_6$ alkylene or —O—$C_2$-$C_6$ alkenylene, said O is bound at the $R^3$ position; and optionally $R^5$ and $R^6$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^5$ and $R^6$ are connected to form —O—$C_1$-$C_6$ alkylene or —O—$C_2$-$C_6$ alkenylene, said O is bound at the $R^5$ position.

3. The compound according to claim 1, or a pharmaceutically acceptable salt thereof, wherein Base$^1$ and Base$^2$ are each independently selected from the group consisting of

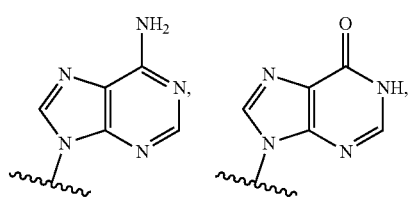

337
-continued
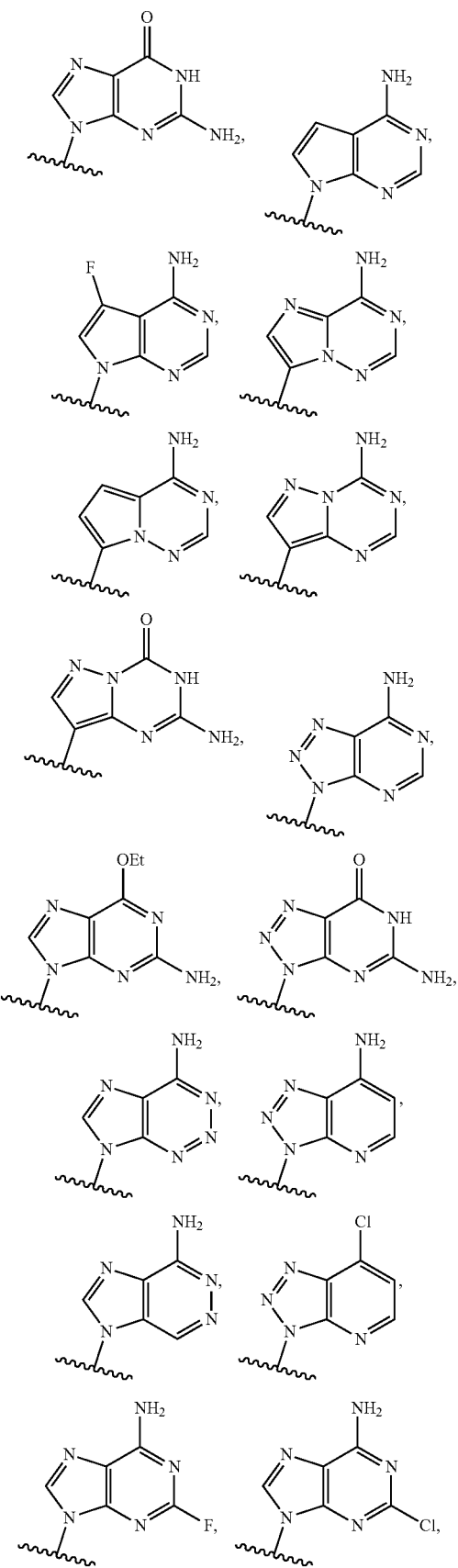
338
-continued
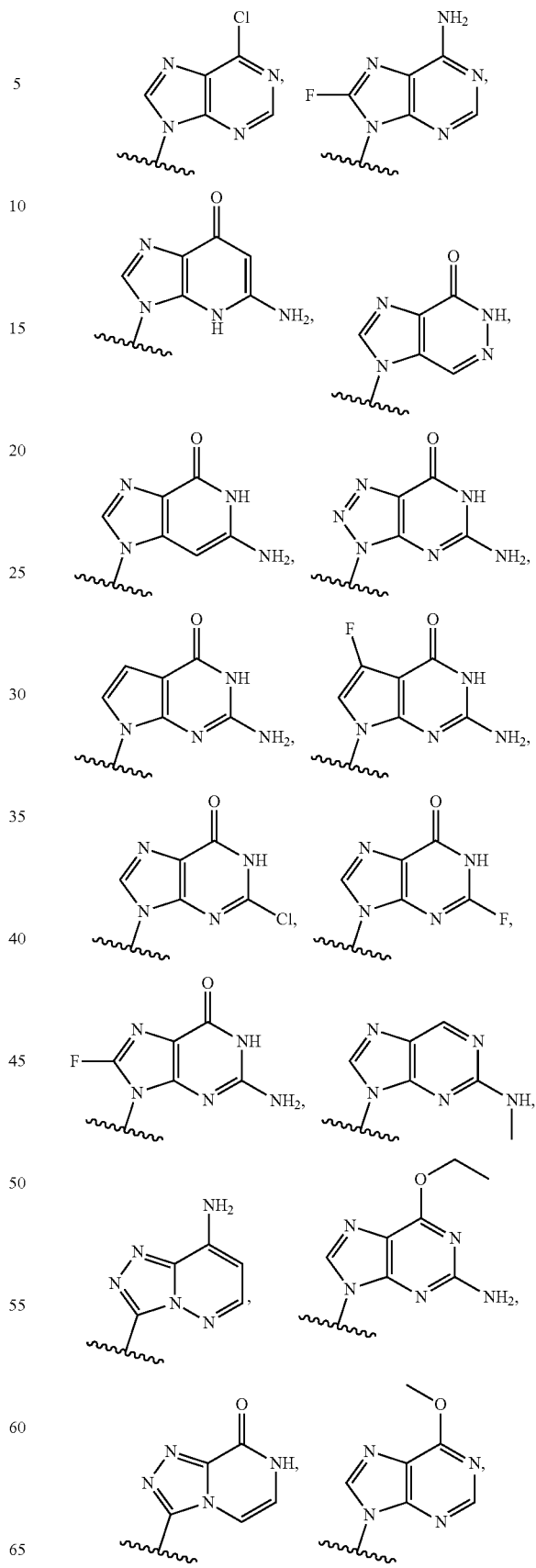

-continued

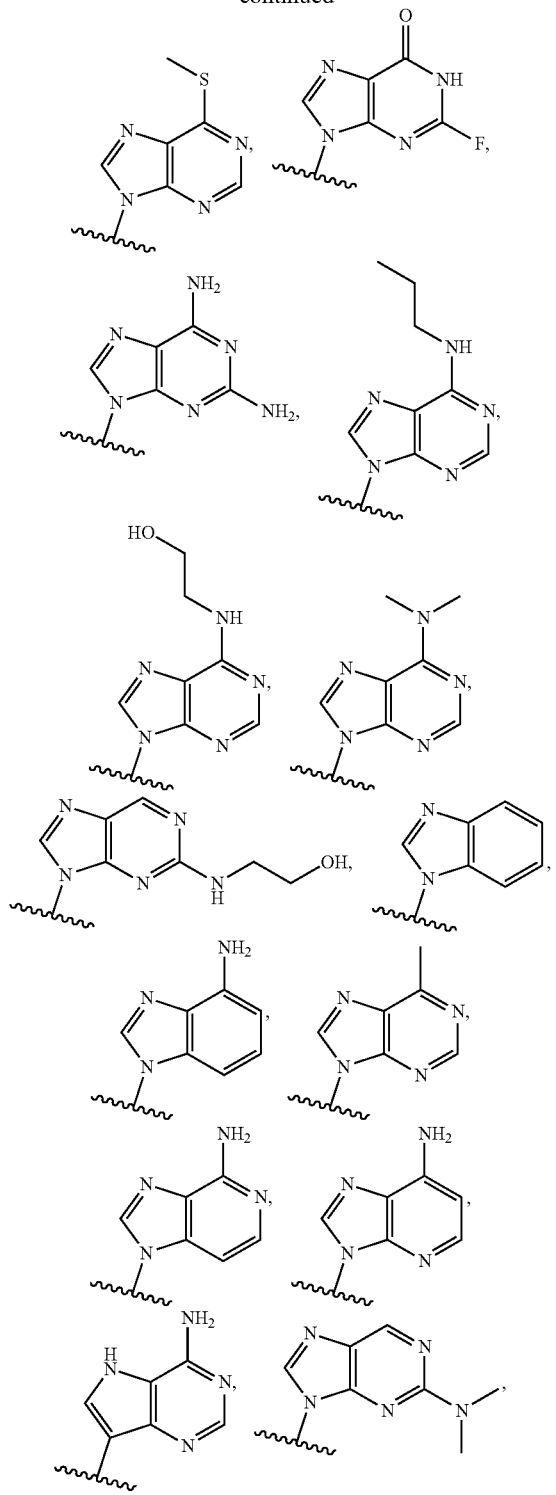

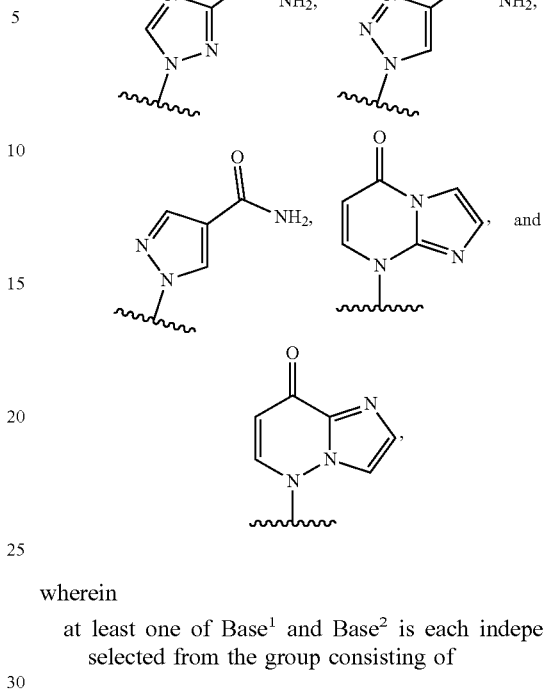

wherein
at least one of Base¹ and Base² is each independently selected from the group consisting of

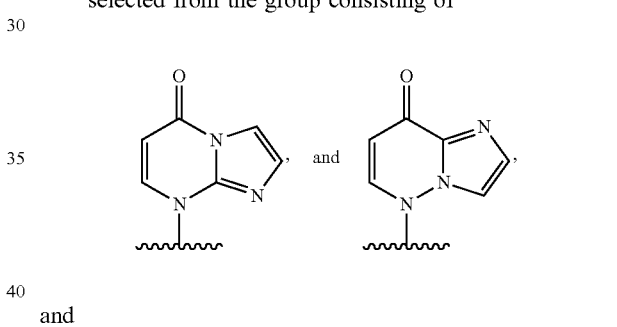

and

Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$;

Y and $Y^a$ are each independently selected from the group consisting of —O— and —S—;

$X^a$ and $X^{a1}$ are each independently selected from the group consisting of —O— and —S—;

$X^b$ and $X^{b1}$ are each independently selected from the group consisting of —O— and —S—;

$X^c$ and $X^{c1}$ are each independently selected from the group consisting of —OH, —SH,

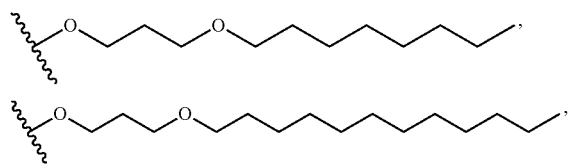

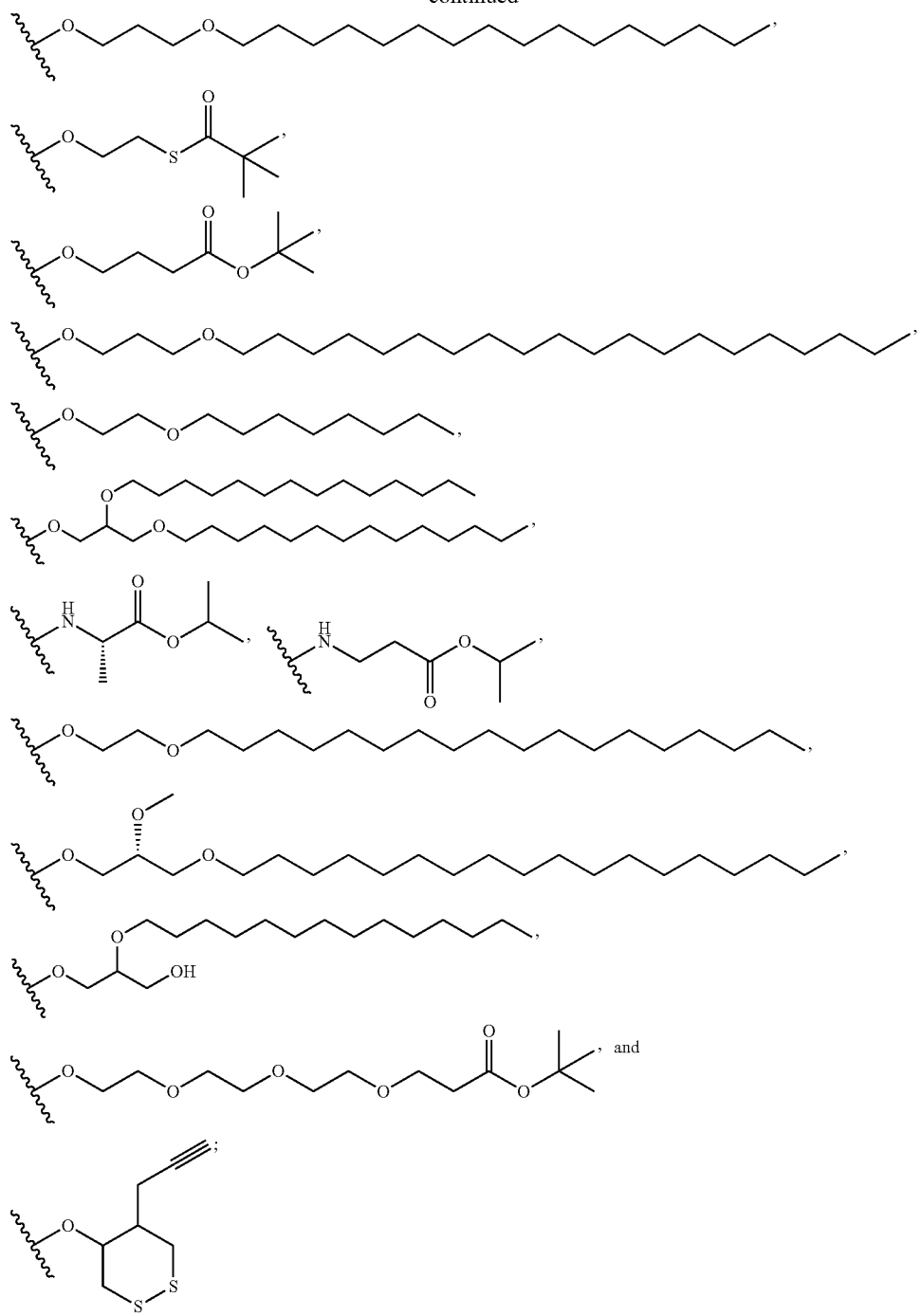

$X^d$ and $X^{d1}$ are each independently selected from the group consisting of O and S;

$R^1$ and $R^{1a}$ are each H;

$R^2$ and $R^{2a}$ are each independently selected from the group consisting of H, F, Cl, I, Br, OH, CN, $N_3$, —$CF_3$, —$CH_3$, —$CH_2OH$, and —$CH_2CH_3$;

$R^3$ is selected from the group consisting of H, F, Cl, I, Br, OH, CN, $N_3$, —$CF_3$, —$CH_3$, —$CH_2OH$, and —$CH_2CH_3$;

$R^4$ and $R^{4a}$ are each independently selected from the group consisting of H, F, Cl, I, Br, OH, CN, $N_3$, —$CF_3$, —$CH_3$, —$CH_2OH$, and —$CH_2CH_3$;

$R^5$ is selected from the group consisting of H, F, Cl, I, Br, OH, CN, $N_3$, —$CF_3$, —$CH_3$, —$CH_2OH$, and —$CH_2CH_3$;

$R^6$ and $R^{6a}$ are each independently selected from the group consisting of H, F, Cl, I, Br, OH, CN, $N_3$, —$CF_3$, —$CH_3$, —$CH_2OH$, —$CH_2CH_3$, —$CH{=}CH_2$, —$C{\equiv}CH$, and —$C{\equiv}C$—$CH$;

$R^7$ and $R^{7a}$ are each independently selected from the group consisting of H, —$CF_3$, —$CH_3$, and —$CH_2CH_3$;

$R^8$ and $R^{8a}$ are each independently selected from the group consisting of H, —$CF_3$, —$CH_3$, and —$CH_2CH_3$;

optionally R³ and R⁶ᵃ are connected to C₂-C₆ alkylene, C₂-C₆ alkenylene, —O—C₁-C₆ alkylene, or —O—C₂-C₆ alkenylene, such that where R³ and R⁶ᵃ are connected to form —O—C₁-C₆ alkylene or —O—C₂-C₆ alkenylene, said O is bound at the R³ position; and optionally R⁵ and R⁶ are connected to form C₁-C₆ alkylene, C₂-C₆ alkenylene, —O—C₁-C₆ alkylene, or —O—C₂-C₆ alkenylene, such that where R⁵ and R⁶ are connected to form —O—C₁-C₆ alkylene or —O—C₂-C₆ alkenylene, said O is bound at the R⁵ position.

4. The compound according to claim 1, or a pharmaceutically acceptable salt thereof, wherein Base¹ and Base² are each independently selected from the group consisting of

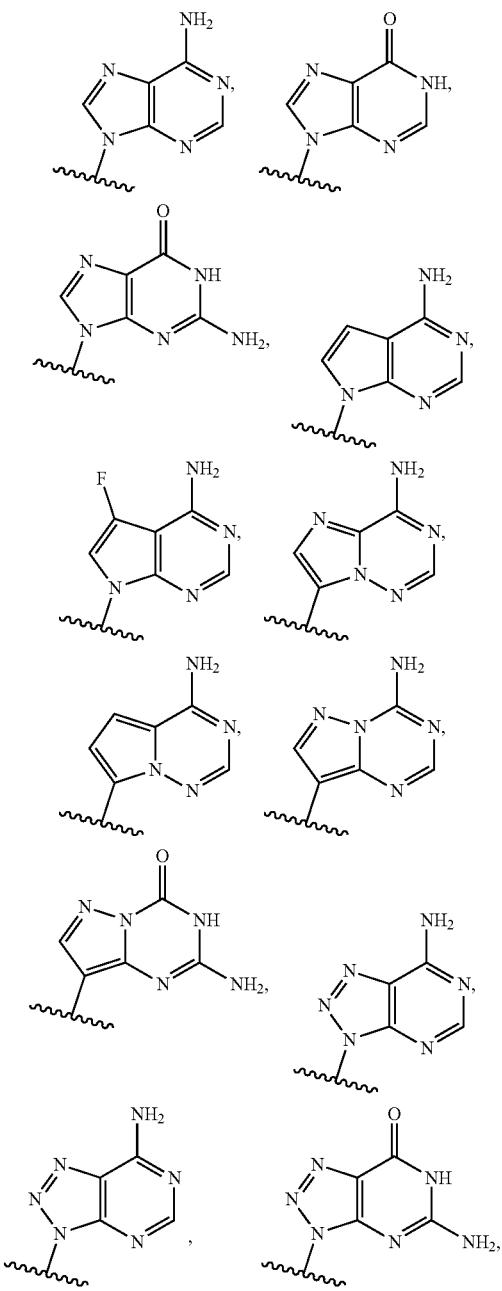
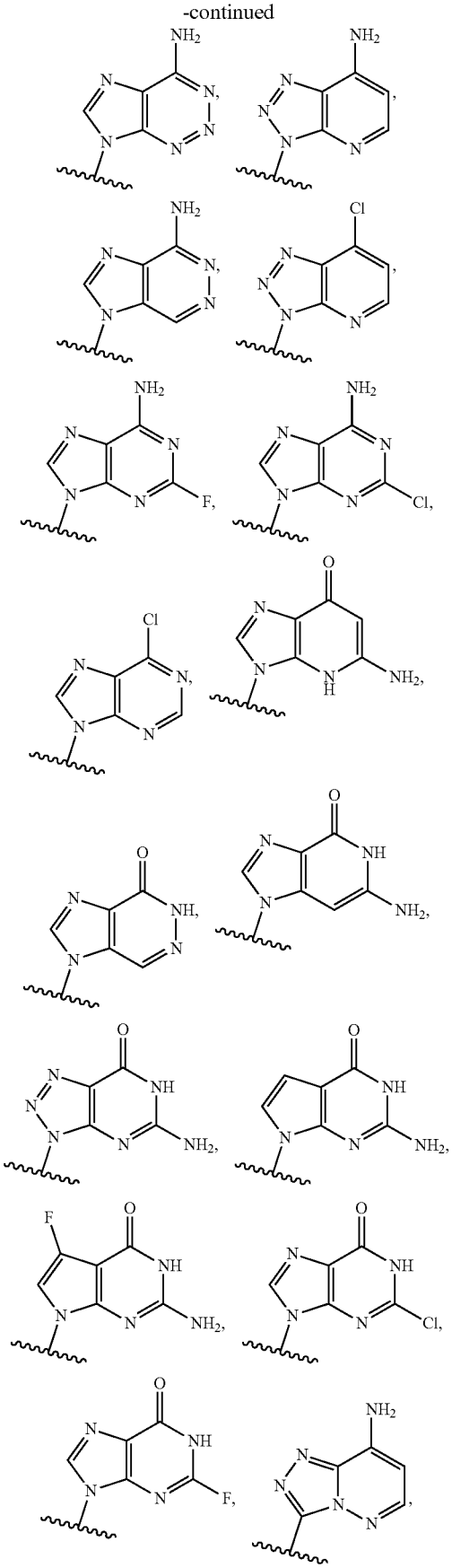

-continued

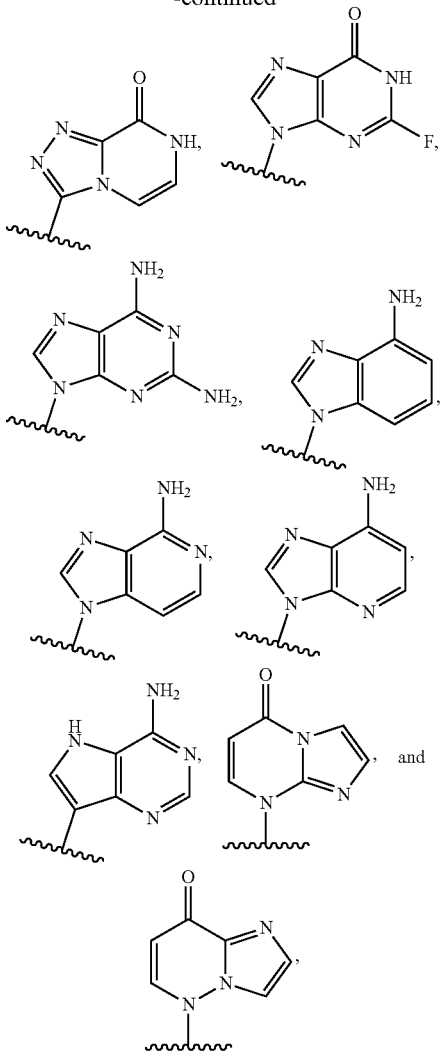

wherein
at least one of Base¹ and Base² is each independently selected from the group consisting of

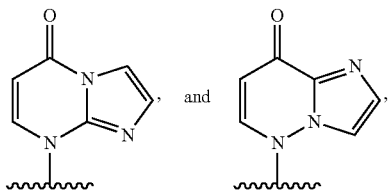 [SMILES: *n1ccc(=O)n2ccnc12 ; *n1ccc(=O)c2nccn21]

and
Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$;
Y and $Y^a$ are each independently selected from the group consisting of —O— and —S—;
$X^a$ and $X^{a1}$ are each —O—;
$X^b$ and $X^{b1}$ are each —O—;
$X^c$ and $X^{c1}$ are each independently selected from the group consisting of —OH and —SH;
$X^d$ and $X^{d1}$ are each independently selected from the group consisting of O and S;
$R^1$ and $R^{1a}$ are each H;
$R^2$ and $R^{2a}$ are each independently selected from the group consisting of H, F, Cl, OH, CN, $N_3$, and —$CH_3$;
$R^3$ is selected from the group consisting of H, F, Cl, OH, CN, $N_3$, and —$CH_3$;
$R^4$ and $R^{4a}$ are each independently selected from the group consisting of H, F, Cl, OH, CN, $N_3$, and —$CH_3$;
$R^5$ is selected from the group consisting of H, F, Cl, OH, CN, $N_3$, and —$CH_3$;
$R^6$ and $R^{6a}$ are each independently selected from the group consisting of H, F, CN, $N_3$, —$CH_3$, —CH=$CH_2$, and —C≡CH;
$R^7$ and $R^{7a}$ are each H;
$R^8$ and $R^{8a}$ are each H;
optionally $R^3$ and $R^{6a}$ are connected to form —O—$C_1$-$C_6$ alkylene or —O—$C_2$-$C_6$ alkenylene, such that O is bound at the $R^3$ position; and
optionally $R^5$ and $R^6$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^5$ and $R^6$ are connected to form —O—$C_1$-$C_6$ alkylene or —O—$C_2$-$C_6$ alkenylene, said O is bound at the $R^5$ position.

5. The compound according to claim 1, or a pharmaceutically acceptable salt thereof, wherein
Base¹ and Base² are each independently selected from the group consisting of

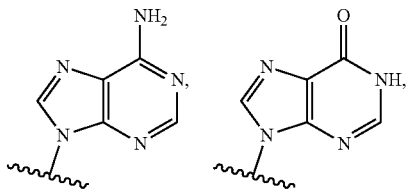

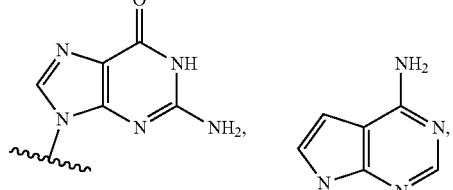

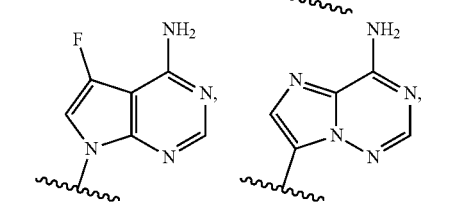

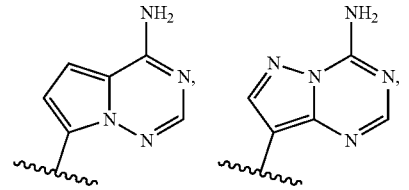

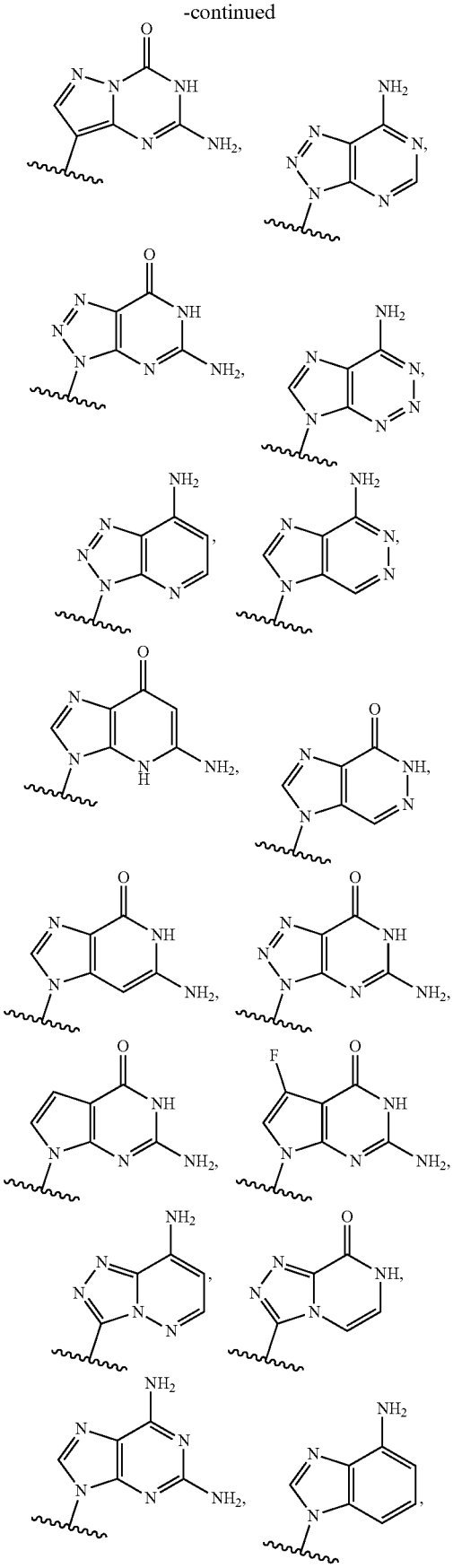

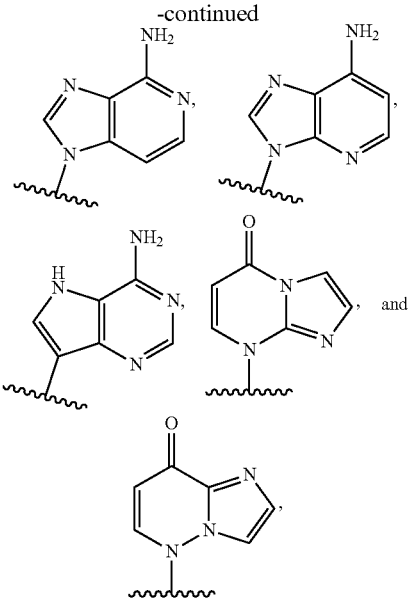

wherein
at least one of Base¹ and Base² is each independently selected from the group consisting of

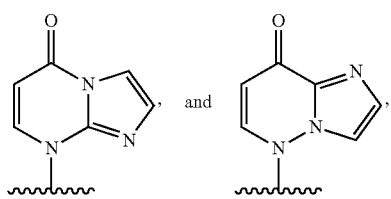 [SMILES: *n1ccc(=O)n2ccnc12 ; *n1ccc(=O)c2nccn21]

and

Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$;

Y and $Y^a$ are each independently selected from the group consisting of —O— and —S—;

$X^a$ and $X^{a1}$ are each O;

$X^b$ and $X^{b1}$ are each O;

$X^c$ and $X^{c1}$ are each independently selected from the group consisting of —OH and —SH;

$X^d$ and $X^{d1}$ are each independently selected from the group consisting of O and S;

$R^1$ and $R^{1a}$ are each H;

$R^2$ and $R^{2a}$ are each independently selected from the group consisting of H, F, Cl, OH, CN, $N_3$, and —$CH_3$;

$R^3$ is selected from the group consisting of H, F, Cl, OH, CN, $N_3$, and —$CH_3$;

$R^4$ and $R^{4a}$ are each independently selected from the group consisting of H, F, Cl, OH, CN, $N_3$, and $CH_3$;

$R^5$ is selected from the group consisting of H, F, Cl, OH, CN, $N_3$, and —$CH_3$;

$R^6$ and $R^{6a}$ are each independently selected from the group consisting of H, F, CN, $N_3$, —$CH_3$, —CH=$CH_2$, and —C≡CH;

$R^7$ and $R^{7a}$ are each H;

$R^8$ and $R^{8a}$ are each H;

optionally $R^3$ and $R^{6a}$ are connected to form —O—$C_1$-$C_6$ alkylene or —O—$C_2$-$C_6$ alkenylene, such that where $R^3$ and $R^{6'}$ are connected to form —O—$C_1$-$C_6$ alkylene or —O—$C_2$-$C_6$ alkenylene, said O is bound at the $R^3$ position; and optionally $R^5$ and $R^6$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^5$ and $R^6$ are connected to form —O—$C_1$-$C_6$ alkylene or —O—$C_2$-$C_6$ alkenylene, said O is bound at the $R^5$ position.

6. The compound according to claim 1, or a pharmaceutically acceptable salt thereof, wherein Base$^1$ and Base$^2$ are each independently selected from the group consisting of

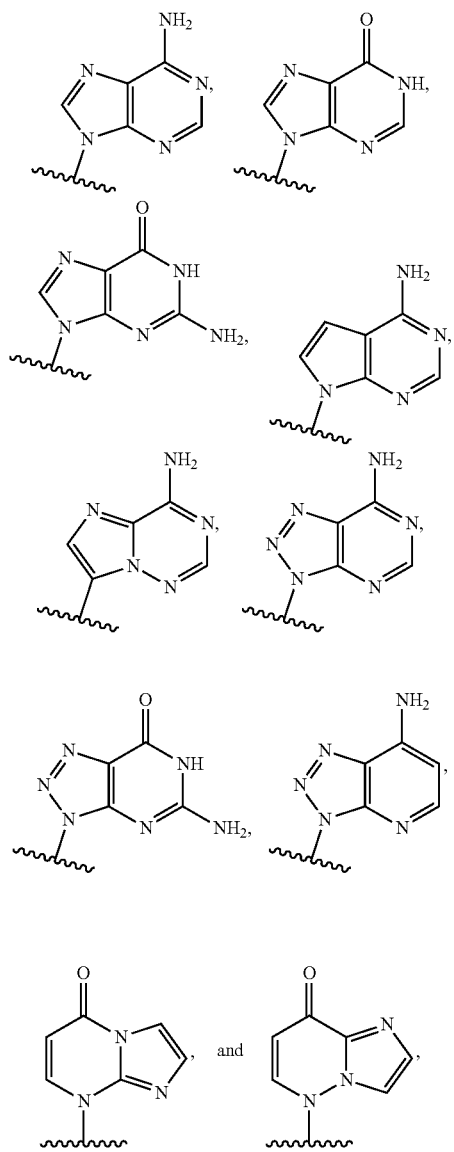

wherein at least one of Base$^1$ and Base$^2$ is each independently selected from the group consisting of

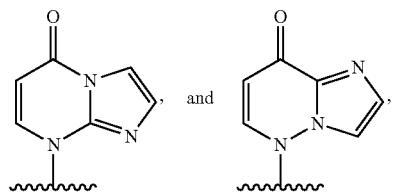 [SMILES: *n1ccc(=O)n2ccnc12 ; *n1ccc(=O)c2nccn21]

and

Base$^1$ and Base$^2$ each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$;

Y and $Y^a$ are each independently selected from the group consisting of —O— and —S—;

$X^a$ and $X^{a1}$ are each —O—;

$X^b$ and $X^{b1}$ are each —O—;

$X^c$ and $X^{c1}$ are each independently selected from the group consisting of —SH and —OH;

$X^d$ and $X^{d1}$ are each independently selected from the group consisting of O and S;

$R^1$ and $R^{1a}$ are each H;

$R^2$ and $R^{2a}$ are each independently selected from the group consisting of H, F, and OH;

$R^3$ is selected from the group consisting of H, F, and OH;

$R^4$ and $R^{4a}$ are each independently selected from the group consisting of H, F, and OH;

$R^5$ is selected from the group consisting of H, F, and OH;

$R^6$ and $R^{6a}$ are each H;

$R^7$ and $R^{7a}$ are each H;

$R^8$ and $R^{8a}$ are each H; and optionally $R^3$ and $R^{6a}$ are connected to form —O—$C_1$-$C_6$ alkylene or —O—$C_2$-$C_6$ alkenylene, such that where $R^3$ and $R^{6a}$ are connected to form —O—$C_1$-$C_6$ alkylene or —O—$C_2$-$C_6$ alkenylene, said O is bound at the $R^3$ position.

7. The compound according to claim 1, or a pharmaceutically acceptable salt thereof, wherein Base$^1$ and Base$^2$ are each independently selected from the group consisting of

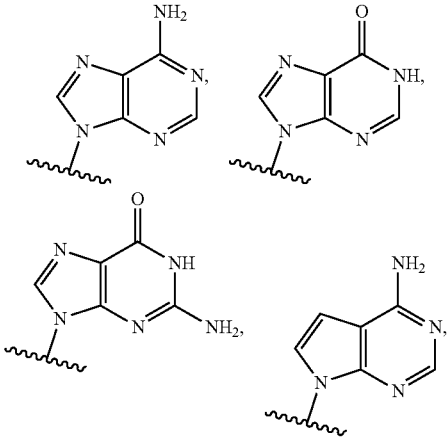

351

-continued

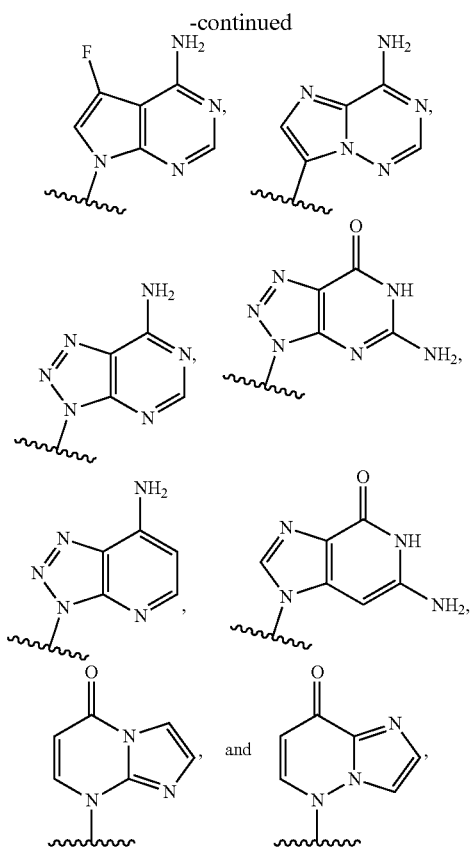

wherein
at least one of Base¹ and Base² is each independently selected from the group consisting of

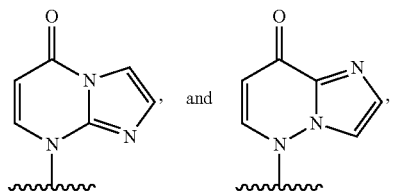 [SMILES: *n1ccc(=O)n2ccnc12 ; *n1ccc(=O)c2nccn21]

and
Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl$)_2$, and $N(C_{3-6}$ cycloalkyl$)_2$;
Y and $Y^a$ are each independently selected from the group consisting of —O— and —S—;
$X^a$ and $X^{a1}$ are each —O—;
$X^b$ and $X^{b1}$ are each —O—;
$X^c$ and $X^{c1}$ are each independently selected from the group consisting of —SH and —OH;
$X^d$ and $X^{d1}$ are each independently selected from the group consisting of O and S;
$R^1$ and $R^{1a}$ are each H;
$R^2$ is H;
$R^{2a}$ is selected from the group consisting of H, F, and OH;
$R^3$ is selected from the group consisting of H, F, and OH;

352

$R^4$ is selected from the group consisting of H, F, and OH;
$R^{4a}$ is H;
$R^5$ is selected from the group consisting of H, F, and OH;
$R^6$ and $R^{6a}$ are each H;
$R^7$ and $R^{7a}$ are each H;
$R^8$ and $R^{8a}$ are each H; and
optionally $R^3$ and $R^{6a}$ are connected to form —O—$C_1$-$C_6$ alkylene, such that where $R^3$ and $R^{6a}$ are connected to form —O—$C_1$-$C_6$ alkylene, said O is bound at the $R^3$ position.

8. The compound according to claim 1, or a pharmaceutically acceptable salt thereof, wherein
Base¹ and Base² are each independently selected from the group consisting of

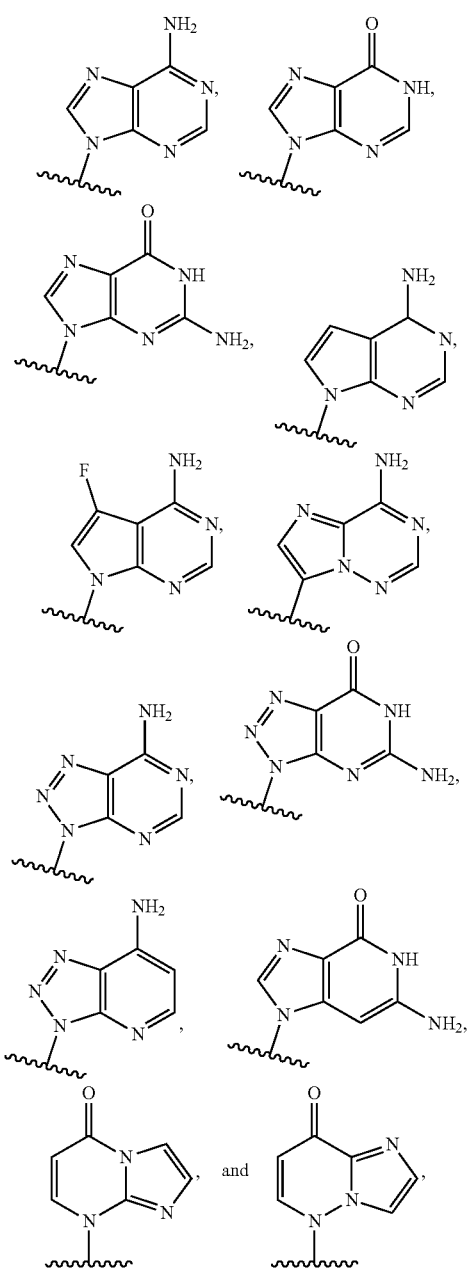

wherein
at least one of Base¹ and Base² is each independently selected from the group consisting of

353

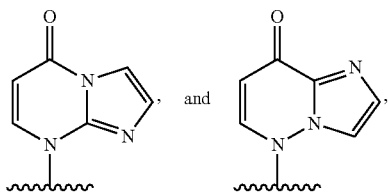 [SMILES: *n1ccc(=O)n2ccnc12 ; *n1ccc(=O)c2nccn21]

and

Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$;

Y and $Y^a$ are each independently selected from the group consisting of —O— and —S—;

$X^a$ and $X^{a1}$ are each —O—;

$X^b$ and $X^{b1}$ are each —O—;

$X^c$ and $X^{c1}$ are each independently selected from the group consisting of —SH and —OH;

$X^d$ and $X^{d1}$ are each independently selected from the group consisting of O and S;

$R^1$ and $R^{1a}$ are each H;

$R^2$ is H;

$R^{2a}$ is selected from the group consisting of H, F, and OH;

$R^3$ is selected from the group consisting of H, F, and OH;

$R^4$ is selected from the group consisting of H, F, and OH;

$R^{4a}$ is H;

$R^5$ is selected from the group consisting of H, F, and OH;

$R^6$ and $R^{6a}$ are each H;

$R^7$ and $R^{7a}$ are each H; and $R^8$ and $R^{8a}$ are each H.

9. The compound according to claim 1, or a pharmaceutically acceptable salt thereof, wherein Base¹ is selected from the group consisting of

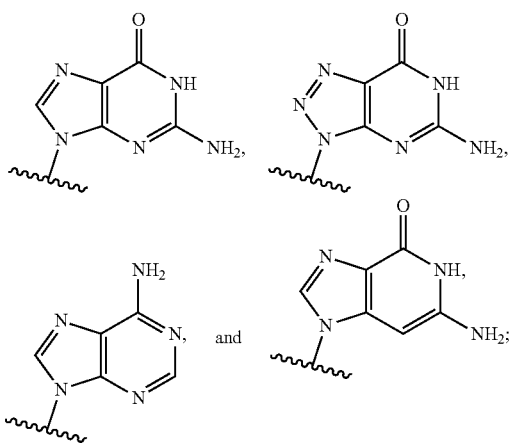

354

Base² is selected from the group consisting of

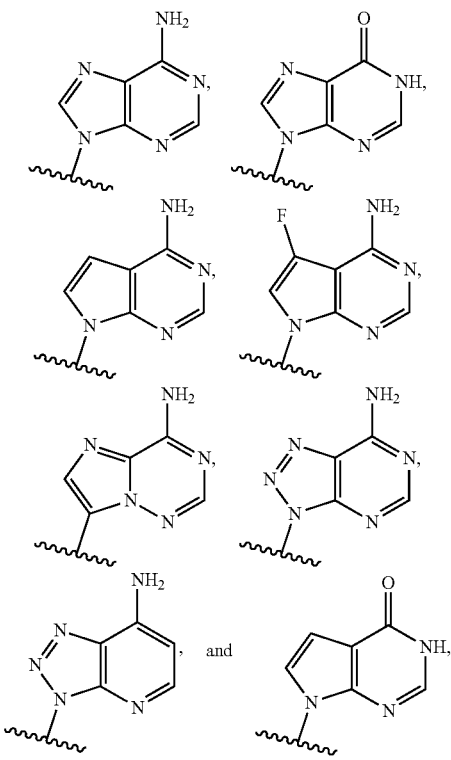

at least one of Base¹ and Base² is each independently selected from the group consisting of

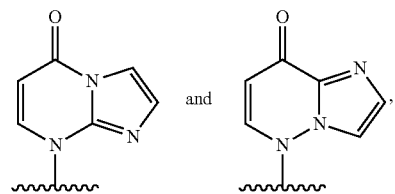 [SMILES: *n1ccc(=O)n2ccnc12 ; *n1ccc(=O)c2nccn21]

and Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$;

Y and $Y^a$ are each independently selected from the group consisting of —O— and —S—;

$X^a$ and $X^{a1}$ are each —O—;

$X^b$ and $X^{b1}$ are each —O—;

$X^c$ and $X^{c1}$ are each independently selected from the group consisting of —SH and —OH;

$X^d$ and $X^{d1}$ are each independently selected from the group consisting of O and S;

$R^1$ and $R^{1a}$ are each H;

$R^2$ is H;

$R^{2a}$ is selected from the group consisting of H, F, and OH;

$R^3$ is selected from the group consisting of H, F, and OH;

$R^4$ is selected from the group consisting of H, F, and OH;

$R^{4a}$ is H;

$R^5$ is selected from the group consisting of H, F, and OH;

$R^6$ and $R^{6a}$ are each H;

$R^7$ and $R^{7a}$ are each H;

$R^8$ and $R^{8a}$ are each H; and $R^3$ and $R^{6a}$ are connected to form —O—$C_1$-$C_6$ alkylene, such that where $R^3$ and $R^{6a}$ are connected to form —O—$C_1$-$C_6$ alkylene, said O is bound at the $R^3$ position.

10. The compound according to claim 1, or a pharmaceutically acceptable salt thereof, wherein Base$^1$ is selected from the group consisting of

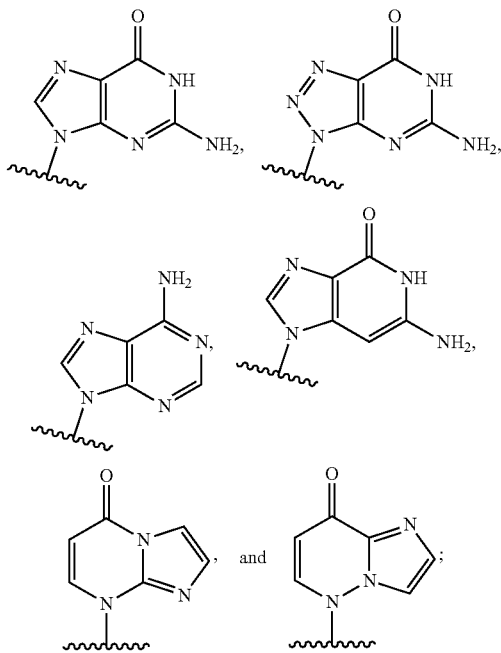

Base$^2$ is selected from the group consisting of

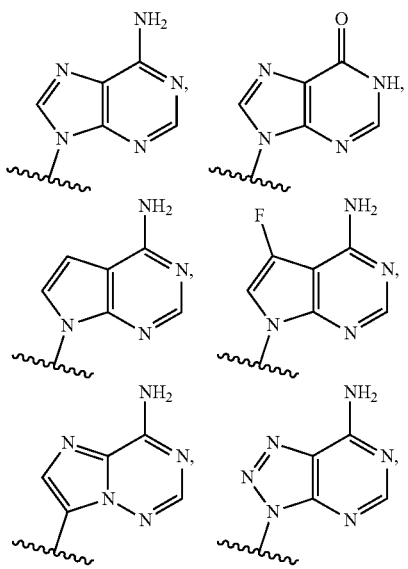

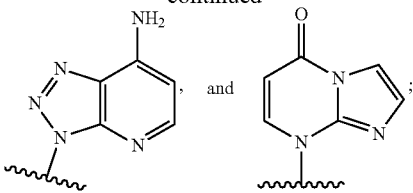

at least one of Base$^1$ and Base$^2$ is each independently selected from the group consisting of

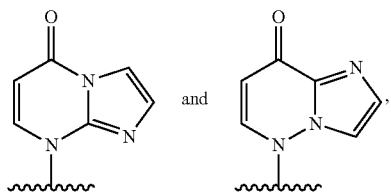 [SMILES: *n1ccc(=O)n2ccnc12 ; *n1ccc(=O)c2nccn21]

and Base$^1$ and Base$^2$ each may be independently substituted by 0-3 substituents $R^{10}$, where each $R^{10}$ is independently selected from the group consisting of F, Cl, I, Br, OH, SH, NH$_2$, $C_{1-3}$ alkyl, $C_{3-6}$ cycloalkyl, O($C_{1-3}$ alkyl), O($C_{3-6}$ cycloalkyl), S($C_{1-3}$ alkyl), S($C_{3-6}$ cycloalkyl), NH($C_{1-3}$ alkyl), NH($C_{3-6}$ cycloalkyl), N($C_{1-3}$ alkyl)$_2$, and N($C_{3-6}$ cycloalkyl)$_2$;

Y and Y$^a$ are each independently selected from the group consisting of and —S—;

$X^a$ and $X^{a1}$ are each —O—;

$X^b$ and $X^{b1}$ are each —O—;

$X^c$ and $X^{c1}$ are each independently selected from the group consisting of —SH and —OH;

$X^d$ and $X^{d1}$ are each independently selected from the group consisting of O and S;

$R^1$ and $R^{1a}$ are each H;

$R^2$ is H;

$R^{2a}$ is selected from the group consisting of H, F, and OH;

$R^3$ is selected from the group consisting of H, F, and OH;

$R^4$ is selected from the group consisting of H, F, and OH;

$R^{4a}$ is H;

$R^5$ is selected from the group consisting of H, F, and OH;

$R^6$ and $R^{6a}$ are each H;

$R^7$ and $R^{7a}$ are each H; and $R^8$ and $R^{8a}$ are each H.

11. A compound selected from the group consisting of:

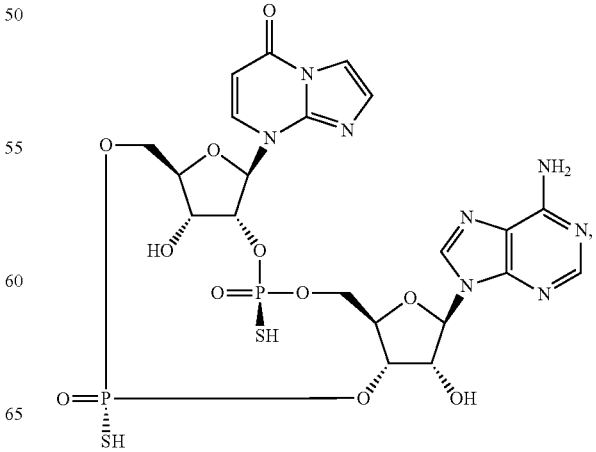

357
-continued
358
-continued
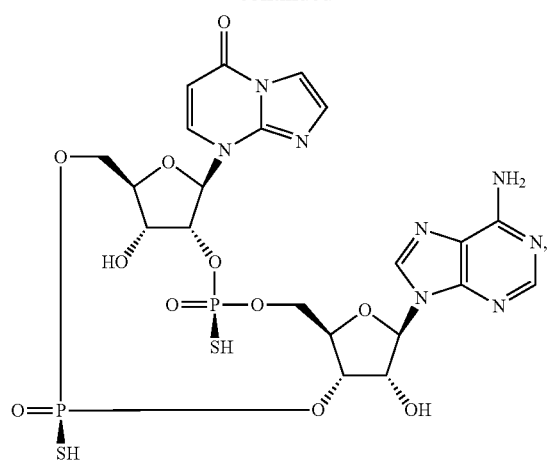
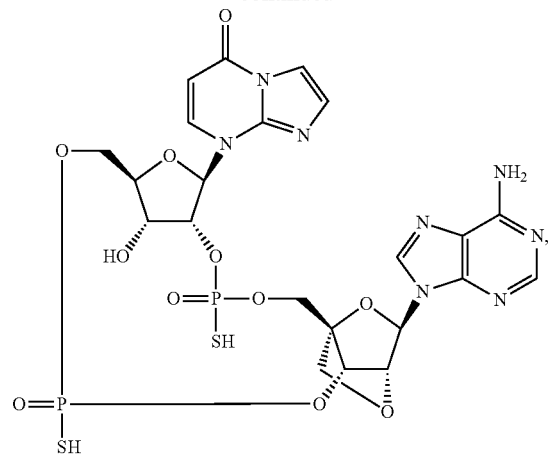
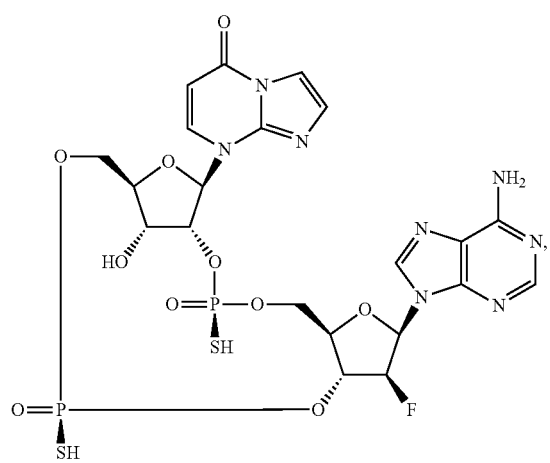
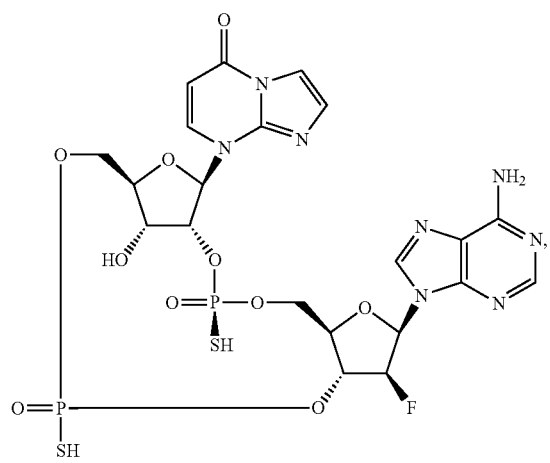
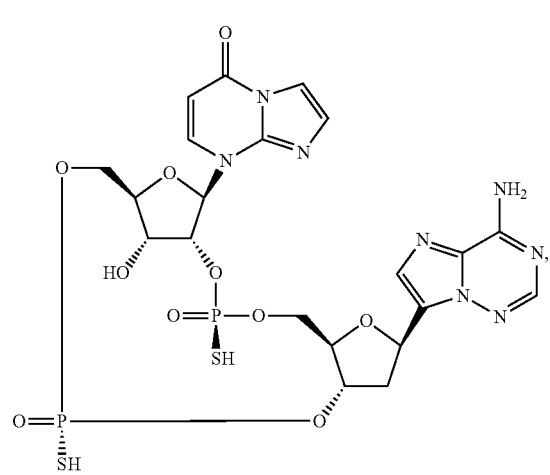

359
-continued
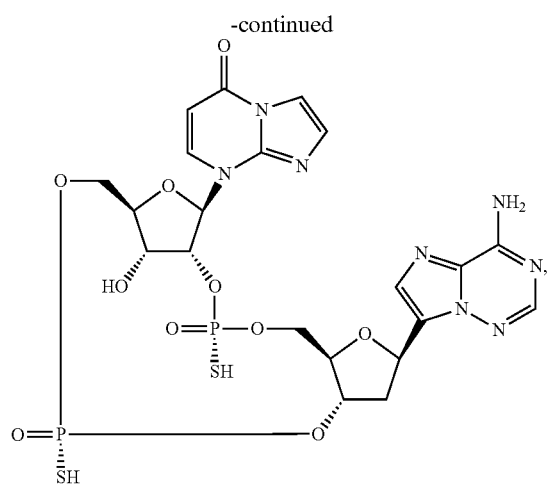
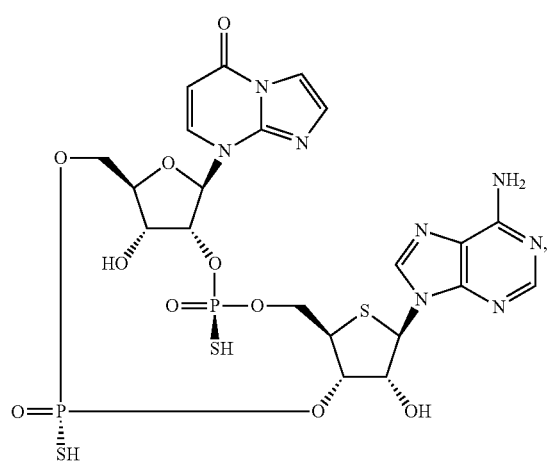
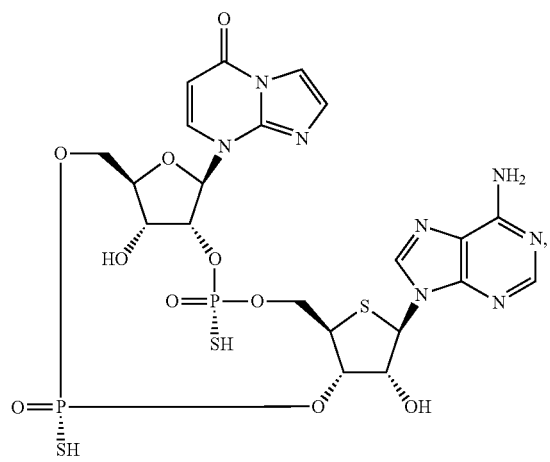
360
-continued
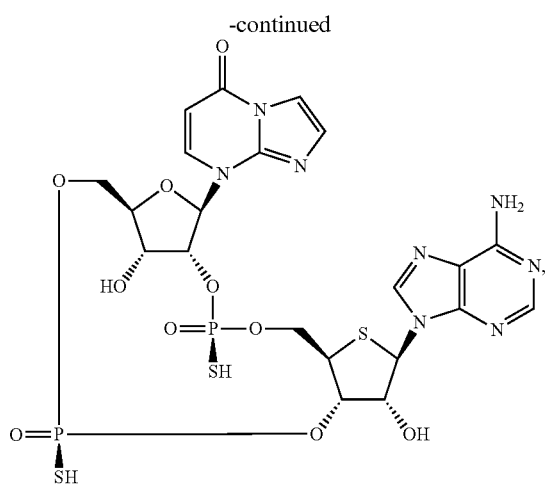
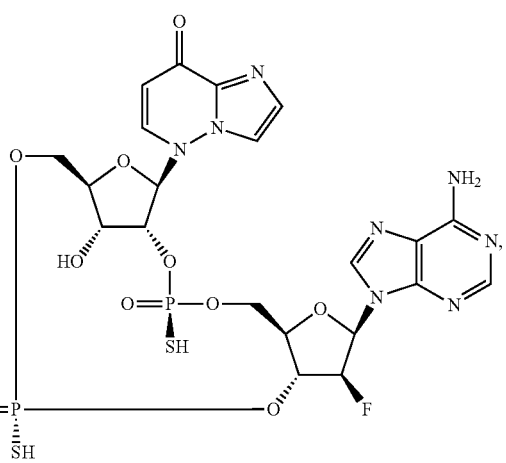
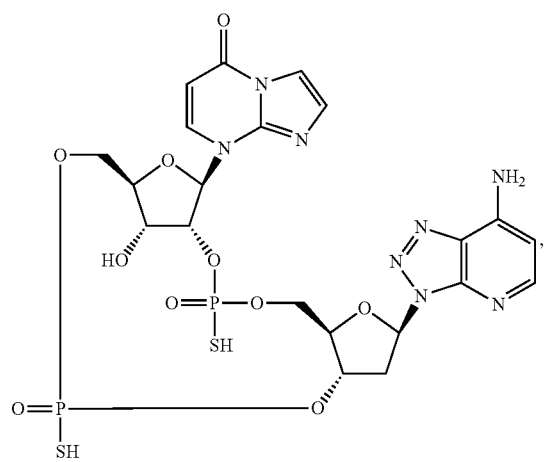

-continued

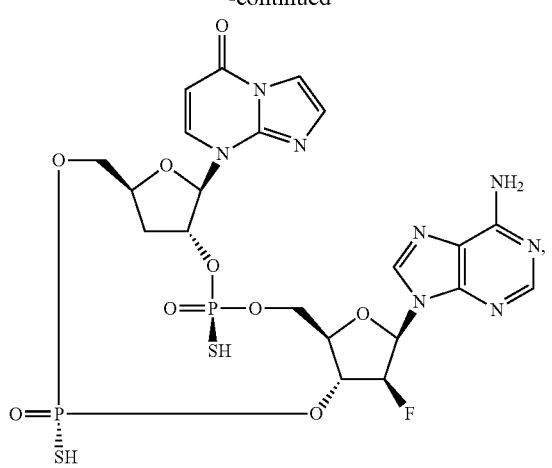

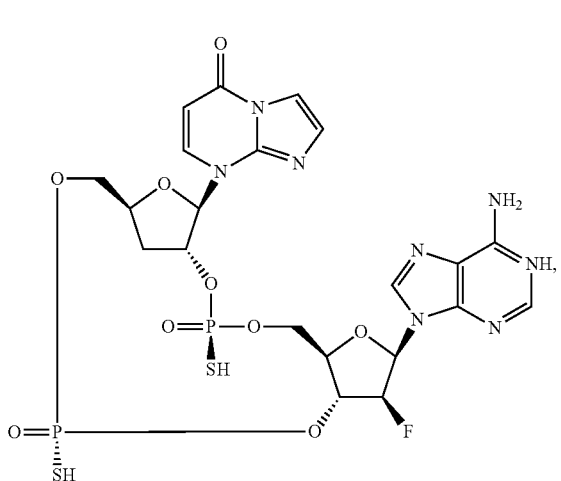

-continued

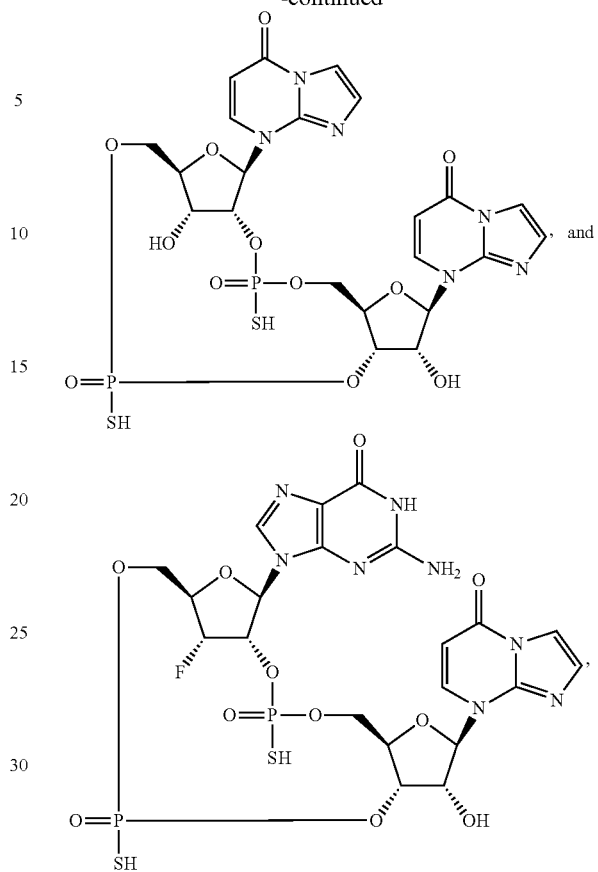

or a pharmaceutically acceptable salt thereof.

12. A pharmaceutical composition, said pharmaceutical composition comprising:
   (a) a compound according to claim 1 or a pharmaceutically acceptable salt thereof; and
   (b) a pharmaceutically acceptable carrier.

13. A method of inducing an immune response in a subject, said method comprising administering to the subject in need thereof a therapeutically effective amount of a compound according to claim 1, or a pharmaceutically acceptable salt thereof.

14. A method of inducing an immune response in a subject, said method comprising administering to the subject in need thereof a therapeutically effective amount of a pharmaceutical composition according to claim 12.

15. A method of inducing a STING-dependent type I interferon production in a subject, said method comprising administering to the subject in need thereof a therapeutically effective amount of a compound according to claim 1, or a pharmaceutically acceptable salt thereof.

16. A method of inducing a STING-dependent type I interferon production in a subject, said method comprising administering to the subject in need thereof a therapeutically effective amount of a pharmaceutical composition according to claim 12.

17. A method of treating a cell proliferation disorder in a subject, said method comprising administering to the subject in need thereof a therapeutically effective amount of a compound according to claim 1, or a pharmaceutically acceptable salt thereof.

18. The method of claim 17, wherein the cell proliferation disorder is cancer.

19. A method of treating a cell proliferation disorder in a subject, said method comprising administering to the subject in need thereof a therapeutically effective amount of a pharmaceutical composition according to claim 12.

20. The method of claim 19, wherein the cell proliferation disorder is cancer.

* * * * *

SEQUENCE LISTING

<160> NUMBER OF SEQ ID NOS: 4

<210> SEQ ID NO 1

```
<211> LENGTH: 414
<212> TYPE: PRT
<213> ORGANISM: Artificial Sequence
<220> FEATURE:
<223> OTHER INFORMATION: Full-Length HAQ STING
     [STING(1-379)R71H,G230A,H232R,R293Q-GG-AviTag-GS-HRV3C-HIS8]

<400> SEQUENCE: 1
```

| | | | | | | | | | | | | | | |
|---|---|---|---|---|---|---|---|---|---|---|---|---|---|---|
|Met|Pro|His|Ser|Ser|Leu|His|Pro|Ser|Ile|Pro|Cys|Pro|Arg|Gly|His|
|1| | | |5| | | | |10| | | | |15|
|Gly|Ala|Gln|Lys|Ala|Ala|Leu|Val|Leu|Leu|Ser|Ala|Cys|Leu|Val|Thr|
| | | |20| | | | |25| | | | |30| | |
|Leu|Trp|Gly|Leu|Gly|Glu|Pro|Pro|Glu|His|Thr|Leu|Arg|Tyr|Leu|Val|
| | |35| | | | |40| | | | |45| | | |
|Leu|His|Leu|Ala|Ser|Leu|Gln|Leu|Gly|Leu|Leu|Leu|Asn|Gly|Val|Cys|
| |50| | | | |55| | | | |60| | | | |
|Ser|Leu|Ala|Glu|Glu|Leu|His|His|Ile|His|Ser|Arg|Tyr|Arg|Gly|Ser|
|65| | | | |70| | | | |75| | | | |80|
|Tyr|Trp|Arg|Thr|Val|Arg|Ala|Cys|Leu|Gly|Cys|Pro|Leu|Arg|Arg|Gly|
| | | | |85| | | | |90| | | | |95| |
|Ala|Leu|Leu|Leu|Leu|Ser|Ile|Tyr|Phe|Tyr|Tyr|Ser|Leu|Pro|Asn|Ala|
| | | | |100| | | | |105| | | | |110| |
|Val|Gly|Pro|Pro|Phe|Thr|Trp|Met|Leu|Ala|Leu|Leu|Gly|Leu|Ser|Gln|
| | | |115| | | | |120| | | | |125| | |
|Ala|Leu|Asn|Ile|Leu|Leu|Gly|Leu|Lys|Gly|Leu|Ala|Pro|Ala|Glu|Ile|
| | |130| | | | |135| | | | |140| | | |
|Ser|Ala|Val|Cys|Glu|Lys|Gly|Asn|Phe|Asn|Val|Ala|His|Gly|Leu|Ala|
|145| | | | |150| | | | |155| | | | |160|
|Trp|Ser|Tyr|Tyr|Ile|Gly|Tyr|Leu|Arg|Leu|Ile|Leu|Pro|Glu|Leu|Gln|
| | | | |165| | | | |170| | | | |175| |
|Ala|Arg|Ile|Arg|Thr|Tyr|Asn|Gln|His|Tyr|Asn|Asn|Leu|Leu|Arg|Gly|
| | | |180| | | | |185| | | | |190| | |
|Ala|Val|Ser|Gln|Arg|Leu|Tyr|Ile|Leu|Leu|Pro|Leu|Asp|Cys|Gly|Val|
| | |195| | | | |200| | | | |205| | | |
|Pro|Asp|Asn|Leu|Ser|Met|Ala|Asp|Pro|Asn|Ile|Arg|Phe|Leu|Asp|Lys|
| |210| | | | |215| | | | |220| | | | |
|Leu|Pro|Gln|Gln|Thr|Ala|Asp|Arg|Ala|Gly|Ile|Lys|Asp|Arg|Val|Tyr|
|225| | | | |230| | | | |235| | | | |240|
|Ser|Asn|Ser|Ile|Tyr|Glu|Leu|Leu|Glu|Asn|Gly|Gln|Arg|Ala|Gly|Thr|
| | | | |245| | | | |250| | | | |255| |
|Cys|Val|Leu|Glu|Tyr|Ala|Thr|Pro|Leu|Gln|Thr|Leu|Phe|Ala|Met|Ser|
| | | |260| | | | |265| | | | |270| | |
|Gln|Tyr|Ser|Gln|Ala|Gly|Phe|Ser|Arg|Glu|Asp|Arg|Leu|Glu|Gln|Ala|
| | |275| | | | |280| | | | |285| | | |
|Lys|Leu|Phe|Cys|Gln|Thr|Leu|Glu|Asp|Ile|Leu|Ala|Asp|Ala|Pro|Glu|
| |290| | | | |295| | | | |300| | | | |
|Ser|Gln|Asn|Asn|Cys|Arg|Leu|Ile|Ala|Tyr|Gln|Glu|Pro|Ala|Asp|Asp|
|305| | | | |310| | | | |315| | | | |320|
|Ser|Ser|Phe|Ser|Leu|Ser|Gln|Glu|Val|Leu|Arg|His|Leu|Arg|Gln|Glu|
| | | | |325| | | | |330| | | | |335| |
|Glu|Lys|Glu|Glu|Val|Thr|Val|Gly|Ser|Leu|Lys|Thr|Ser|Ala|Val|Pro|
| | | |340| | | | |345| | | | |350| | |
|Ser|Thr|Ser|Thr|Met|Ser|Gln|Glu|Pro|Glu|Leu|Leu|Ile|Ser|Gly|Met|
| | |355| | | | |360| | | | |365| | | |
|Glu|Lys|Pro|Leu|Pro|Leu|Arg|Thr|Asp|Phe|Ser|Gly|Gly|Gly|Leu|Asn|

```
              370                 375                 380
Asp Ile Phe Glu Ala Gln Lys Ile Glu Trp His Gly Ser Leu Glu
385                 390                 395                 400

Val Leu Phe Gln Gly Pro His His His His His His His
                405                 410
```

<210> SEQ ID NO 2
<211> LENGTH: 6482
<212> TYPE: DNA
<213> ORGANISM: Artificial Sequence
<220> FEATURE:
<223> OTHER INFORMATION: Full-length HAQ
    [STING(1-379)R71H,G230A,H232R,R293Q-GG-AviTag-GS-HRV3C-HIS8/pBAC1]

<400> SEQUENCE: 2

```
ggaacggctc cgcccactat taatgaaatt aaaaattcca attttaaaaa acgcagcaag    60
agaaacattt gtatgaaaga atgcgtagaa ggaaagaaaa atgtcgtcga catgctgaac   120
aacaagatta tatgcctcc gtgtataaaa aaaatattga acgatttgaa agaaaacaat   180
gtaccgcgcg gcggtatgta caggaagagg tttatactaa actgttacat tgcaaacgtg   240
gtttcgtgtg ccaagtgtga aaaccgatgt ttaatcaagg ctctgacgca tttctacaac   300
cacgactcca gtgtgtgggg tgaagtcatg catcttttaa tcaaatccca agatgtgtat   360
aaaccaccaa actgccaaaa aatgaaaact gtcgacaagc tctgtccgtt tgctggcaac   420
tgcaagggtc tcaatcctat ttgtaattat tgaataataa aacaattata aatgctaaat   480
ttgtttttta ttaacgatac aaaccaaacg caacaagaac atttgtagta ttatctataa   540
ttgaaaacgc gtagttataa tcgctgaggt aatatttaaa atcattttca aatgattcac   600
agttaatttg cgacaatata attttatttt cacataaact agacgccttg tcgtcttctt   660
cttcgtattc cttctctttt tcattttct cttcataaaa attaacatag ttattatcgt   720
atccatatat gtatctatcg tatagagtaa atttttgtt gtcataaata tatatgtctt   780
ttttaatggg gtgtatagta ccgctgcgca tagttttct gtaatttaca acagtgctat   840
tttctggtag ttcttcggag tgtgttgctt taattattaa atttatataa tcaatgaatt   900
tgggatcgtc ggttttgtac aatatgttgc cggcatagta cgcagcttct tctagttcaa   960
ttacaccatt ttttagcagc accggattaa cataactttc caaaatgttg tacgaaccgt  1020
taaacaaaaa cagttcacct cccttttcta tactattgtc tgcgagcagt tgtttgttgt  1080
taaaaataac agccattgta atgagacgca caaactaata tcacaaactg gaaatgtcta  1140
tcaatatata gttgctgatc agatctgatc atggagataa ttaaaatgat aaccatctcg  1200
caaataaata agtatttac tgttttcgta acagttttgt aataaaaaaa cctataaata  1260
taggatccat gccccactcc agcctgcatc catccatccc gtgtcccagg ggtcacgggg  1320
cccagaaggc agccttggtt ctgctgagtg cctgcctggt gacccttggg ggctaggag  1380
agccaccaga gcacactctc cggtacctgg tgctccacct agcctccctg cagctgggac  1440
tgctgttaaa cggggtctgc agcctggctg aggagctgca ccacatccac tccaggtacc  1500
ggggcagcta ctggaggact gtgcgggcct gcctggctg ccccctccgc cgtggggccc  1560
tgttgctgct gtccatctat ttctactact cccctcccaaa tgcggtcggc ccgcccttca  1620
cttggatgct tgcccctcctg ggcctctcgc aggcactgaa catcctcctg ggcctcaagg  1680
gcctggcccc agctgagatc tctgcagtgt gtgaaaaagg gaattcaac gtggcccatg  1740
ggctggcatg gtcatattac atcggatatc tgcggctgat cctgccagag ctccaggccc  1800
```

-continued

```
ggattcgaac ttacaatcag cattacaaca acctgctacg gggtgcagtg agccagcggc   1860
tgtatattct cctcccattg gactgtgggg tgcctgataa cctgagtatg gctgacccca   1920
acattcgctt cctggataaa ctgccccagc agaccgctga ccgtgctggc atcaaggatc   1980
gggtttacag caacagcatc tatgagcttc tggagaacgg gcagcgggcg ggcacctgtg   2040
tcctggagta cgccaccccc ttgcagactt tgtttgccat gtcacaatac agtcaagctg   2100
gctttagccg ggaggatagg cttgagcagg ccaaactctt ctgccagaca cttgaggaca   2160
tcctggcaga tgcccctgag tctcagaaca actgccgcct cattgcctac caggaacctg   2220
cagatgacag cagcttctcg ctgtcccagg aggttctccg gcacctgcgg caggaggaaa   2280
aggaagaggt tactgtgggc agcttgaaga cctcagcggt gcccagtacc tccacgatgt   2340
cccaagagcc tgagctcctc atcagtggaa tggaaaagcc cctccctctc cgcacggatt   2400
tctctggcgg tggcctgaac gacatcttcg aagcccagaa aatcgaatgg catgaaggca   2460
gcctggaagt gctgttccag ggcccacacc accatcatca ccatcaccat taatgagcgg   2520
ccgcactcga gcaccaccac caccaccact aacctaggta gctgagcgca tgcaagctga   2580
tccgggttat tagtacattt attaagcgct agattctgtg cgttgttgat ttacagacaa   2640
ttgttgtacg tattttaata attcattaaa tttataatct ttagggtggt atgttagagc   2700
gaaaatcaaa tgattttcag cgtctttata tctgaattta aatattaaat cctcaataga   2760
tttgtaaaat aggtttcgat tagtttcaaa caagggttgt ttttccgaac cgatggctgg   2820
actatctaat ggattttcgc tcaacgccac aaaacttgcc aaatcttgta gcagcaatct   2880
agctttgtcg atattcgttt gtgttttgtt ttgtaataaa ggttcgacgt cgttcaaaat   2940
attatgcgct tttgtatttc tttcatcact gtcgttagtg tacaattgac tcgacgtaaa   3000
cacgttaaat agagcttgga catatttaac atcgggcgtg ttagctttat taggccgatt   3060
atcgtcgtcg tcccaaccct cgtcgttaga agttgcttcc gaagacgatt ttgccatagc   3120
cacacgacgc ctattaattg tgtcggctaa cacgtccgcg atcaaatttg tagttgagct   3180
ttttggaatt atttctgatt gcgggcgttt ttgggcgggt ttcaatctaa ctgtgcccga   3240
ttttaattca gacaacacgt tagaaagcga tggtgcaggc ggtggtaaca tttcagacgg   3300
caaatctact aatggcggcg gtggtggagc tgatgataaa tctaccatcg gtggaggcgc   3360
aggcgggggct ggcggcggag gcggaggcgg aggtggtggc ggtgatgcag acggcggttt   3420
aggctcaaat gtctctttag gcaacacagt cggcacctca actattgtac tggtttcggg   3480
cgccgttttt ggtttgaccg gtctgagacg agtgcgattt ttttcgtttc taatagcttc   3540
caacaattgt tgtctgtcgt ctaaaggtgc agcgggttga ggttccgtcg gcattggtgg   3600
agcgggcggc aattcagaca tcgatggtgg tggtggtggt ggaggcgctg gaatgttagg   3660
cacgggagaa ggtggtggcg gcggtgccgc cggtataatt tgttctggtt tagtttgttc   3720
gcgcacgatt gtgggcaccg gcgcaggcgc cgctggctgc acaacggaag gtcgtctgct   3780
tcgaggcagc gcttggggtg gtggcaattc aatattataa ttggaataca aatcgtaaaa   3840
atctgctata agcattgtaa tttcgctatc gtttaccgtg ccgatattta acaaccgctc   3900
aatgtaagca attgtattgt aaagagattg tctcaagctc ggatcgatcc cgcacgccga   3960
taacaagcct tttcattttt actacagcat tgtagtggcg agacacttcg ctgtcgtcga   4020
ggtttaaacg cttcctcgct cactgactcg ctgcgctcgg tcgttcggct gcggcgagcg   4080
gtatcagctc actcaaaggc ggtaatacgg ttatccacag aatcagggga taacgcagga   4140
aagaacatgt gagcaaaagg ccagcaaaag gccaggaacc gtaaaaaggc cgcgttgctg   4200
```

-continued

```
gcgttttcc ataggctccg cccccctgac gagcatcaca aaaatcgacg ctcaagtcag    4260
aggtggcgaa acccgacagg actataaaga taccaggcgt ttccccctgg aagctccctc    4320
gtgcgctctc ctgttccgac cctgccgctt accggatacc tgtccgcctt tctcccttcg    4380
ggaagcgtgg cgctttctca tagctcacgc tgtaggtatc tcagttcggt gtaggtcgtt    4440
cgctccaagc tgggctgtgt gcacgaaccc cccgttcagc ccgaccgctg cgccttatcc    4500
ggtaactatc gtcttgagtc caacccggta agacacgact tatcgccact ggcagcagcc    4560
actggtaaca ggattagcag agcgaggtat gtaggcggtg ctacagagtt cttgaagtgg    4620
tggcctaact acggctacac tagaaggaca gtatttggta tctgcgctct gctgaagcca    4680
gttaccttcg gaaaaagagt tggtagctct tgatccggca acaaaccac cgctggtagc     4740 ggtggttttt tgtttgcaa gcagcagatt acgcgcagaa aaaaggatc tcaagaagat     4800 cctttgatct tttctacggg gtctgacgct cagtggaacg aaaactcacg ttaagggatt    4860
ttggtcatga gattatcaaa aaggatcttc acctagatcc ttttaaatta aaaatgaagt    4920
tttaaatcaa tctaaagtat atatgagtaa acttggtctg acagttacca atgcttaatc    4980
agtgaggcac ctatctcagc gatctgtcta tttcgttcat ccatagttgc ctgactcccc    5040
gtcgtgtaga taactacgat acgggagggc ttaccatctg gccccagtgc tgcaatgata    5100
ccgcgagacc cacgctcacc ggctccagat ttatcagcaa taaaccagcc agccggaagg    5160
gccgagcgca gaagtggtcc tgcaacttta tccgcctcca tccagtctat taattgttgc    5220
cgggaagcta gagtaagtag ttcgccagtt aatagtttgc gcaacgttgt tgccattgct    5280
acaggcatcg tggtgtcacg ctcgtcgttt ggtatggctt cattcagctc cggttcccaa    5340
cgatcaaggc gagttacatg atcccccatg ttgtgcaaaa aagcggttag ctccttcggt    5400
cctccgatcg ttgtcagaag taagttggcc gcagtgttat cactcatggt tatggcagca    5460
ctgcataatt ctcttactgt catgccatcc gtaagatgct tttctgtgac tggtgagtac    5520
tcaaccaagt cattctgaga atagtgtatg cggcgaccga gttgctcttg cccggcgtca    5580
atacgggata taccgcgcc acatagcaga actttaaaag tgctcatcat tggaaaacgt    5640
tcttcggggc gaaaactctc aaggatctta ccgctgttga tccagttc gatgtaaccc     5700 actcgtgcac ccaactgatc ttcagcatct tttactttca ccagcgtttc tgggtgagca    5760
aaaacaggaa ggcaaaatgc cgcaaaaaag ggaataaggg cgacacggaa atgttgaata    5820
ctcatactct tccttttca atattattga agcatttatc agggttattg tctcatgagc     5880
ggatacatat ttgaatgtat ttagaaaaat aaacaaatag gggttccgcg cacatttccc    5940
cgaaaagtgc cacctgacgc gccctgtagc ggcgcattaa gcgcggcggg tgtggtggtt    6000
acgcgcagcg tgaccgctac acttgccagc gccctagcgc ccgctccttt cgctttcttc    6060
ccttcctttc tcgccacgtt cgccggcttt ccccgtcaag ctctaaatcg ggggctccct    6120
ttagggttcc gatttagtgc tttacggcac ctcgacccca aaaaacttga ttagggtgat    6180
ggttcacgta gtgggccatc gccctgatag acggtttttc gccctttgac gttggagtcc    6240
acgttcttta atagtggact cttgttccaa actggaacaa cactcaaccc tatctcggtc    6300 tattctttg atttataagg gatttttgccg atttcggcct attggttaaa aaatgagctg    6360
atttaacaaa aatttaacgc gaattttaac aaaatattaa cgtttacaat ttcccattcg    6420
ccattcaggc tgcgcaactg ttgggaaggg cgatcggtgc gggcctcttc gctattacgc    6480
ca                                                                    6482
```

```
<210> SEQ ID NO 3
<211> LENGTH: 414
<212> TYPE: PRT
<213> ORGANISM: Artificial Sequence
<220> FEATURE:
<223> OTHER INFORMATION: Full-Length STING WT [STING(1-379)H232R-gg-
      AviTag-gs-HRV3C-HIS8]

<400> SEQUENCE: 3

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
                20                  25                  30

Leu Trp Gly Leu Gly Glu Pro Pro Glu His Thr Leu Arg Tyr Leu Val
            35                  40                  45

Leu His Leu Ala Ser Leu Gln Leu Gly Leu Leu Leu Asn Gly Val Cys
        50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
                100                 105                 110

Val Gly Pro Pro Phe Thr Trp Met Leu Ala Leu Leu Gly Leu Ser Gln
            115                 120                 125

Ala Leu Asn Ile Leu Leu Gly Leu Lys Gly Leu Ala Pro Ala Glu Ile
        130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
                180                 185                 190

Ala Val Ser Gln Arg Leu Tyr Ile Leu Leu Pro Leu Asp Cys Gly Val
            195                 200                 205

Pro Asp Asn Leu Ser Met Ala Asp Pro Asn Ile Arg Phe Leu Asp Lys
210                 215                 220

Leu Pro Gln Gln Thr Gly Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
                260                 265                 270

Gln Tyr Ser Gln Ala Gly Phe Ser Arg Glu Asp Arg Leu Glu Gln Ala
            275                 280                 285

Lys Leu Phe Cys Arg Thr Leu Glu Asp Ile Leu Ala Asp Ala Pro Glu
        290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
                340                 345                 350

Ser Thr Ser Thr Met Ser Gln Glu Pro Glu Leu Leu Ile Ser Gly Met
            355                 360                 365
```

Glu Lys Pro Leu Pro Leu Arg Thr Asp Phe Ser Gly Gly Gly Leu Asn
    370                 375                 380

Asp Ile Phe Glu Ala Gln Lys Ile Glu Trp His Glu Gly Ser Leu Glu
385                 390                 395                 400

Val Leu Phe Gln Gly Pro His His His His His His His His
                405                 410

<210> SEQ ID NO 4
<211> LENGTH: 6482
<212> TYPE: DNA
<213> ORGANISM: Artificial Sequence
<220> FEATURE:
<223> OTHER INFORMATION: Full-length WT STING
      [STING(1-379)H232R-gg-AviTag-gs-HRV3C-HIS8/pBAC1]

<400> SEQUENCE: 4

| | | | | | |
|---|---|---|---|---|---|
| ggaacggctc | cgcccactat | taatgaaatt | aaaaattcca | attttaaaaa | acgcagcaag | 60 |
| agaaacattt | gtatgaaaga | atgcgtagaa | ggaaagaaaa | atgtcgtcga | catgctgaac | 120 |
| aacaagatta | atatgcctcc | gtgtataaaa | aaaatattga | acgatttgaa | agaaaacaat | 180 |
| gtaccgcgcg | gcggtatgta | caggaagagg | tttatactaa | actgttacat | tgcaaacgtg | 240 |
| gtttcgtgtg | ccaagtgtga | aaaccgatgt | taatcaagg | ctctgacgca | tttctacaac | 300 |
| cacgactcca | agtgtgtggg | tgaagtcatg | catcttttaa | tcaaatccca | agatgtgtat | 360 |
| aaaccaccaa | actgccaaaa | aatgaaaact | gtcgacaagc | tctgtccgtt | tgctggcaac | 420 |
| tgcaagggtc | tcaatcctat | ttgtaattat | tgaataataa | aacaattata | aatgtcaaat | 480 |
| ttgttttta | ttaacgatac | aaaccaaacg | caacaagaac | atttgtagta | ttatctataa | 540 |
| ttgaaaacgc | gtagttataa | tcgctgaggt | aatatttaaa | atcatttca | aatgattcac | 600 |
| agttaatttg | cgacaatata | attttatttt | cacataaact | agacgccttg | tcgtcttctt | 660 |
| cttcgtattc | cttctctttt | tcattttct | cttcataaaa | attaacatag | ttattatcgt | 720 |
| atccatatat | gtatctatcg | tatagagtaa | atttttttgtt | gtcataaata | tatatgtctt | 780 |
| ttttaatggg | gtgtatagta | ccgctgcgca | tagttttttct | gtaatttaca | acagtgctat | 840 |
| tttctggtag | ttcttcggag | tgtgttgctt | taattattaa | atttatataa | tcaatgaatt | 900 |
| tgggatcgtc | ggttttgtac | aatatgttgc | cggcatagta | cgcagcttct | tctagttcaa | 960 |
| ttacaccatt | ttttagcagc | accggattaa | cataactttc | caaaatgttg | tacgaaccgt | 1020 |
| taaacaaaaa | cagttcacct | cccttttcta | tactattgtc | tgcgagcagt | tgtttgttgt | 1080 |
| taaaaataac | agccattgta | atgagacgca | caaactaata | tcacaaactg | aaatgtcta | 1140 |
| tcaatatata | gttgctgatc | agatctgatc | atggagataa | ttaaaatgat | aaccatctcg | 1200 |
| caaataaata | agtattttac | tgttttcgta | acagttttgt | aataaaaaaa | cctataaata | 1260 |
| taggatccat | gccccactcc | agcctgcatc | catccatccc | gtgtcccagg | ggtcacgggg | 1320 |
| cccagaaggc | agccttggtt | ctgctgagtg | cctgcctggt | gacccttggg | gggctaggag | 1380 |
| agccaccaga | gcacactctc | cggtacctgg | tgctccacct | agcctccctg | cagctgggac | 1440 |
| tgctgttaaa | cggggtctgc | agcctggctg | aggagctgcg | ccacatccac | tccaggtacc | 1500 |
| ggggcagcta | ctggaggact | gtgcgggcct | gctgggctg | ccccctccgc | cgtgggccc | 1560 |
| tgttgctgct | gtccatctat | ttctactact | ccctcccaaa | tgcggtcggc | ccgcccttca | 1620 |
| cttggatgct | tgcccctctg | ggcctctcgc | aggcactgaa | catcctcctg | ggcctcaagg | 1680 |
| gcctggcccc | agctgagatc | tctgcagtgt | gtgaaaaagg | gaatttcaac | gtggcccatg | 1740 |

```
ggctggcatg gtcatattac atcggatatc tgcggctgat cctgccagag ctccaggccc    1800
ggattcgaac ttacaatcag cattacaaca acctgctacg gggtgcagtg agccagcggc    1860
tgtatattct cctcccattg gactgtgggg tgcctgataa cctgagtatg gctgacccca    1920
acattcgctt cctggataaa ctgccccagc agaccggtga ccgtgctggc atcaaggatc    1980
gggtttacag caacagcatc tatgagcttc tggagaacgg gcagcgggcg gcacctgtg     2040
tcctggagta cgccaccccc ttgcagactt tgtttgccat gtcacaatac agtcaagctg    2100
gctttagccg ggaggatagg cttgagcagg ccaaactctt ctgccggaca cttgaggaca    2160
tcctggcaga tgcccctgag tctcagaaca actgccgcct cattgcctac caggaacctg    2220
cagatgacag cagcttctcg ctgtcccagg aggttctccg gcacctgcgg caggaggaaa    2280
aggaagaggt tactgtgggc agcttgaaga cctcagcggt gcccagtacc tccacgatgt    2340
cccaagagcc tgagctcctc atcagtggaa tggaaaagcc cctccctctc cgcacggatt    2400
tctctggcgg tggcctgaac gacatcttcg aagcccagaa aatcgaatgg catgaaggca    2460
gcctggaagt gctgttccag ggcccacacc accatcatca ccatcaccat taatgagcgg    2520
ccgcactcga gcaccaccac caccaccact aacctaggta gctgagcgca tgcaagctga    2580
tccgggttat tagtacattt attaagcgct agattctgtg cgttgttgat ttacagacaa    2640
ttgttgtacg tattttaata attcattaaa tttataatct ttagggtggt atgttagagc    2700
gaaaatcaaa tgattttcag cgtctttata tctgaattta atattaaat cctcaataga     2760
tttgtaaaat aggtttcgat tagtttcaaa caagggttgt ttttccgaac cgatggctgg    2820
actatctaat ggattttcgc tcaacgccac aaaacttgcc aaatcttgta gcagcaatct    2880
agctttgtcg atattcgttt gtgtttttgtt ttgtaataaa ggttcgacgt cgttcaaaat    2940
attatgcgct tttgtatttc tttcatcact gtcgttagtg tacaattgac tcgacgtaaa    3000
cacgttaaat agagcttgga catatttaac atcgggcgtg ttagctttat taggccgatt    3060
atcgtcgtcg tcccaacccct cgtcgttaga agttgcttcc gaagacgatt tgccatagc    3120
cacacgacgc ctattaattg tgtcggctaa cacgtccgcg atcaaatttg tagttgagct    3180
ttttggaatt atttctgatt gcgggcgttt ttgggcgggt tcaatctaa ctgtgcccga    3240
ttttaattca gacaacacgt tagaaagcga tggtgcaggc ggtggtaaca tttcagacgg    3300
caaatctact aatggcggcg gtggtggagc tgatgataaa tctaccatcg gtggaggcgc    3360
aggcggggct ggcggcggag gcggaggcgg aggtggtggc ggtgatgcag acggcggttt    3420
aggctcaaat gtctctttag gcaacacagt cggcacctca actattgtac tggtttcggg    3480
cgccgttttt ggtttgaccg gtctgagacg agtgcgattt ttttcgtttc taatagcttc    3540
caacaattgt tgtctgtcgt ctaaaggtgc agcgggttga ggttccgtcg gcattggtgg    3600
agcgggcggc aattcagaca tcgatggtgg tggtggtggt ggaggcgctg gaatgttagg    3660
cacgggagaa ggtggtggcg gcggtgccgc cggtataatt tgttctggtt tagtttgttc    3720
gcgcacgatt gtgggcaccg gcgcaggcgc cgctggctgc acaacggaag gtcgtctgct    3780
tcgaggcagc gcttggggtg gtggcaattc aatattataa ttggaataca aatcgtaaaa    3840
atctgctata agcattgtaa tttcgctatc gtttaccgtg ccgatattta acaaccgctc    3900
aatgtaagca attgtattgt aaagagattg tctcaagctc ggatcgatcc cgcacgccga    3960
taacaagcct tttcatttt actacagcat tgtagtggcg agacacttcg ctgtcgtcga    4020
ggtttaaacg cttcctcgct cactgactcg ctgcgctcgg tcgttcggct gcggcgagcg    4080
gtatcagctc actcaaaggc ggtaatacgg ttatccacag aatcagggga taacgcagga    4140
```

```
aagaacatgt gagcaaaagg ccagcaaaag gccaggaacc gtaaaaaggc cgcgttgctg    4200
gcgtttttcc ataggctccg ccccctgac gagcatcaca aaaatcgacg ctcaagtcag    4260
aggtggcgaa acccgacagg actataaaga taccaggcgt ttcccctgg aagctccctc    4320 gtgcgctctc ctgttccgac cctgccgctt accggatacc tgtccgcctt tctcccttcg    4380
ggaagcgtgg cgctttctca tagctcacgc tgtaggtatc tcagttcggt gtaggtcgtt    4440
cgctccaagc tgggctgtgt gcacgaaccc cccgttcagc ccgaccgctg cgccttatcc    4500
ggtaactatc gtcttgagtc caacccggta agacacgact tatcgccact ggcagcagcc    4560
actggtaaca ggattagcag agcgaggtat gtaggcggtg ctacagagtt cttgaagtgg    4620
tggcctaact acggctacac tagaaggaca gtatttggta tctgcgctct gctgaagcca    4680
gttaccttcg gaaaagagt tggtagctct tgatccggca aacaaaccac cgctggtagc    4740
ggtggttttt ttgtttgcaa gcagcagatt acgcgcagaa aaaaggatc tcaagaagat    4800 cctttgatct tttctacggg gtctgacgct cagtggaacg aaaactcacg ttaagggatt    4860
ttggtcatga gattatcaaa aaggatcttc acctagatcc ttttaaatta aaaatgaagt    4920
tttaaatcaa tctaaagtat atatgagtaa acttggtctg acagttacca atgcttaatc    4980
agtgaggcac ctatctcagc gatctgtcta tttcgttcat ccatagttgc ctgactcccc    5040
gtcgtgtaga taactacgat acgggagggc ttaccatctg gccccagtgc tgcaatgata    5100
ccgcgagacc cacgctcacc ggctccagat ttatcagcaa taaaccagcc agccggaagg    5160
gccgagcgca gaagtggtcc tgcaacttta tccgcctcca tccagtctat taattgttgc    5220
cgggaagcta gagtaagtag ttcgccagtt aatagtttgc gcaacgttgt tgccattgct    5280
acaggcatcg tggtgtcacg ctcgtcgttt ggtatggctt cattcagctc cggttcccaa    5340
cgatcaaggc gagttacatg atcccccatg ttgtgcaaaa aagcggttag ctccttcggt    5400
cctccgatcg ttgtcagaag taagttggcc gcagtgttat cactcatggt tatggcagca    5460
ctgcataatt ctcttactgt catgccatcc gtaagatgct tttctgtgac tggtgagtac    5520
tcaaccaagt cattctgaga atagtgtatg cggcgaccga gttgctcttg cccggcgtca    5580
atacgggata taccgcgcc acatagcaga actttaaaag tgctcatcat tggaaaacgt    5640 tcttcgggc gaaaactctc aaggatctta ccgctgttga tccagttc gatgtaaccc       5700 actcgtgcac ccaactgatc ttcagcatct tttactttca ccagcgtttc tgggtgagca    5760
aaaacaggaa ggcaaaatgc cgcaaaaag ggaataaggg cgacacggaa atgttgaata    5820
ctcatactct ccttttttca atattattga agcatttatc agggttattg tctcatgagc    5880
ggatacatat ttgaatgtat ttagaaaaat aaacaaatag gggttccgcg cacatttccc    5940
cgaaaagtgc cacctgacgc gccctgtagc ggcgcattaa gcgcggcggg tgtggtggtt    6000
acgcgcagcg tgaccgctac acttgccagc gccctagcgc ccgctccttt cgctttcttc    6060
ccttcctttc tcgccacgtt cgccggcttt ccccgtcaag ctctaaatcg ggggctccct    6120
ttagggttcc gatttagtgc tttacggcac ctcgacccca aaaaacttga ttagggtgat    6180
ggttcacgta gtgggccatc gccctgatag acggttttc gccctttgac gttggagtcc    6240
acgttcttta atagtggact cttgttccaa actggaacaa cactcaaccc tatctcggtc    6300 tattctttg atttataagg gattttgccg atttcggcct attggttaaa aaatgagctg    6360
atttaacaaa aatttaacgc gaattttaac aaaatattaa cgtttacaat ttcccattcg    6420
```

```
ccattcaggc tgcgcaactg ttgggaaggg cgatcggtgc gggcctcttc gctattacgc    6480
ca                                                                  6482
```